US010131655B2

(12) United States Patent
Sasmal et al.

(10) Patent No.: US 10,131,655 B2
(45) Date of Patent: *Nov. 20, 2018

(54) SUBSTITUTED HETEROCYCLIC ACETAMIDES AS KAPPA OPIOID RECEPTOR (KOR) AGONISTS

(71) Applicant: Dr. Reddy's Laboratories Ltd., Hyderabad, Telangana (IN)

(72) Inventors: Pradip Kumar Sasmal, Hyderabad (IN); Chintakunta Vamseekrishna, Hyderabad (IN); Vijay Potluri, Hyderabad (IN); Ashok Tehim, Ridgewood, NJ (US); Yonghua Gai, Irvine, CA (US); Hang Zhang, Beijing (CN)

(73) Assignee: DR. REDDY'S LABORATORIES, LTD., Hyderabad, Telangana (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,267

(22) Filed: Sep. 19, 2016

(65) Prior Publication Data

US 2017/0001998 A1 Jan. 5, 2017

Related U.S. Application Data

(63) Continuation of application No. 14/382,645, filed as application No. PCT/CN2013/000230 on Mar. 5, 2013, now Pat. No. 9,487,510.

(Continued)

(51) Int. Cl.

| | |
|---|---|
| A61K 31/428 | (2006.01) |
| A61K 31/404 | (2006.01) |
| A61K 31/423 | (2006.01) |
| A61K 31/4704 | (2006.01) |
| A61K 31/4709 | (2006.01) |
| A61K 31/498 | (2006.01) |
| A61K 31/538 | (2006.01) |
| A61K 31/5415 | (2006.01) |
| C07D 417/14 | (2006.01) |
| C07D 241/52 | (2006.01) |
| C07D 403/12 | (2006.01) |
| C07D 413/14 | (2006.01) |
| C07D 401/12 | (2006.01) |
| C07D 403/14 | (2006.01) |
| C07D 413/12 | (2006.01) |

(Continued)

(52) U.S. Cl.
CPC .......... *C07D 417/14* (2013.01); *A61K 31/404* (2013.01); *A61K 31/423* (2013.01); *A61K 31/428* (2013.01); *A61K 31/4704* (2013.01); *A61K 31/4709* (2013.01); *A61K 31/498* (2013.01); *A61K 31/538* (2013.01); *A61K 31/5415* (2013.01); *C07D 209/34* (2013.01); *C07D 215/227* (2013.01); *C07D 241/52* (2013.01); *C07D 263/58* (2013.01); *C07D 265/36* (2013.01); *C07D 275/06* (2013.01); *C07D 277/68* (2013.01); *C07D 279/16* (2013.01); *C07D 401/12* (2013.01); *C07D 403/12* (2013.01); *C07D 403/14* (2013.01); *C07D 413/12* (2013.01); *C07D 413/14* (2013.01); *C07D 417/12* (2013.01)

(58) Field of Classification Search
CPC .. A61K 31/428; A61K 31/404; A61K 31/423; A61K 31/4704; A61K 31/4709; A61K 31/498; A61K 31/538; A61K 31/5415
See application file for complete search history.

(56) References Cited

U.S. PATENT DOCUMENTS

| 5,472,961 A | 12/1995 | Gottschlich | |
|---|---|---|---|
| 9,487,510 B2 * | 11/2016 | Sasmal | ................ C07D 403/12 |

FOREIGN PATENT DOCUMENTS

WO  2012-012410 A2  1/2012

OTHER PUBLICATIONS

Delvaux et al., Alimentary Pharmacology and Therapeutics, 2004, 20, pp. 237-246.*

(Continued)

*Primary Examiner* — Laura L Stockton
(74) *Attorney, Agent, or Firm* — Stites & Harbison, PLLC; Mandy Wilson Decker; Sean P. Ritchie

(57) ABSTRACT

The present invention relates to a series of substituted compounds having the general formula (I), including their stereoisomers and/or their pharmaceutically acceptable salts.

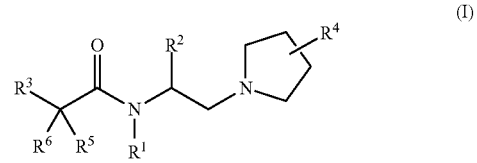

wherein $R^1$, $R^2$, $R^3$, $R^4$, $R^5$, and $R^6$ are as defined herein. This invention also relates to methods of making these compounds including intermediates. The compounds of this invention are effective at the kappa (κ) opioid receptor (KOR) site. Therefore, the compounds of this invention are useful as pharmaceutical agents, especially in the treatment and/or prevention of a variety of central nervous system disorders (CNS), including but not limited to acute and chronic pain, and associated disorders, particularly functioning peripherally at the CNS.

9 Claims, No Drawings

Related U.S. Application Data

(60) Provisional application No. 61/606,632, filed on Mar. 5, 2012.

(51) Int. Cl.
*C07D 417/12* (2006.01)
*C07D 215/227* (2006.01)
*C07D 263/58* (2006.01)
*C07D 265/36* (2006.01)
*C07D 275/06* (2006.01)
*C07D 277/68* (2006.01)
*C07D 209/34* (2006.01)
*C07D 279/16* (2006.01)

(56) References Cited

OTHER PUBLICATIONS

Fajardo, MD et al., Current Gastroenterology Reports 2005, 7, pp. 289-296.*
State Intellectual Property Office, P.R. China, Third Office Action issued in corresponding Application No. 201380023425.8, dated Nov. 8, 2016.
Japan Patent Office, Office Action issued in corresponding Application No. 2014-560224, dated Dec. 14, 2016.
Korean Intellectual Property Office, Notice of Request for Submission of Argument issued in corresponding Application No. 10-2014-7025946, dated Jan. 9, 2017.

* cited by examiner

SUBSTITUTED HETEROCYCLIC ACETAMIDES AS KAPPA OPIOID RECEPTOR (KOR) AGONISTS

RELATED APPLICATIONS

This application is a continuation of U.S. patent application Ser. No. 14/382,645, which is a 371 of International Patent Application No. PCT/CN2013/000230 filed Mar. 5, 2013, which claims priority from U.S. Provisional Patent Application No. 61/606,632 filed Mar. 5, 2012, the entire disclosures of which are incorporated herein by this reference.

TECHNICAL FIELD

The present application relates to novel compounds of formula (I), stereoisomers thereof or pharmaceutically acceptable salts thereof as κ (kappa) opioid receptor (KOR) agonists. The present application also describes method of making such compounds and pharmaceutical compositions comprising such compounds.

BACKGROUND

The endogenous opioid system comprises of three principal opioid receptor types in the central nervous system and in the periphery designated as μ (Mu), κ (Kappa) and δ (Delta). The pharmacological response is elicited by binding of a multitude of endogenous opioid ligands to these receptors, the principal ligands being—the enkephalins, endorphins, and dynorphins. The exogenous opioids/opiates exert their activity by mimicking and/or antagonizing the activity of the endogenous opioid ligands at these receptors. Since the anatomical location, distribution and function of the opioid receptors is wide and varied (Neuropharmacology, 21, 487-497; Med. Res. Rev., 11, 357-374), the pharmacological effects elicited by their agonism and antagonism are diverse as well.

The μ receptors which bind morphine and its derivatives are responsible for analgesia, respiratory and gastrointestinal functions, sedation, neuroendocrine functions and mediate opiate dependence. The δ receptors are abundant in the CNS and mediate analgesia, feeding and various hormonal functions. The κ receptors have a wide distribution in the CNS and the PNS; for example, centrally, these receptors are expressed in caudateputamen, nucleus accumbens, amygdale, neural lobe of the pituitary gland, etc., and peripherally, they are expressed in the sensory neuron DRG, stomach, duodenum, jejunum, oleum, proximal and distal colon (Acta Neurobiol Exp., 71: 129-138). The κ receptors are responsible for functions including analgesia, gastrointestinal functions like food intake, gut motility; water balance, thermoregulation and various neuroendocrine functions. (J. Pharmacol. Exp. Ther. 234, 463-469; Peptides 4, 797-800; Goodman and Gilman's The Pharmacological Basis of Therapeutics (11th Edition) Chapter 21, Pp 547-590).

Pharmacologic studies with receptor selective ligands have shown that analgesia can be produced by selective activation of each of the three types of opioid receptors. Most clinically used opioid analgesics such as morphine and codeine act as μ receptor agonists. These opioids have well-known, undesirable and potentially dangerous dependence forming side effects associated with their CNS activity. κ opioid receptors, on the other hand, have attracted special attention due to their ability to act peripherally and produce analgesia without causing dependence and respiratory depression that is typically associated with μ receptor activation by morphine (Pharmaceutica Acta Helvetiae, 74, 2-3, Pp 337-344).

The opioid receptors are members of the superfamily of G-protein-coupled receptors (GPCRs). Agonist binding to the κ receptor activates the intracellularly associated G protein, which decreases $Ca^{2+}$ channel conductance or inhibits adenylyl cyclase (AC). In addition to analgesia, potential applications of κ selective agonists include the areas of diuresis (Pharmacology Biochemistry and Behavior, 65, 1, Pp 53-59), eating disorders, motion sickness, and neuroprotection (Peptides 29, 12, Pp 2292-2375). Therefore, the κ receptors represent important therapeutic targets. Ligands selective for the κ receptors can serve as important pharmacologic tools. For example, such compounds can be used in competition assays to determine the relative specificity and selectivity of other compounds for the κ receptor, as well as for μ and δ receptors.

A large number of classes of compounds which act as KOR agonists have been described in the art including the following illustrative classes of compounds.

U.S. Pat. No. 7,112,598 describes KOR agonist comprising 2-phenylbenzothiazoline derivatives.

U.S. Pat. No. 5,681,830 describes diarylmethyl piperazine compounds having utility as exogenous receptor combinant species for binding with opioid receptors such as kappa receptors.

EP663401 describes morphinan derivatives as selective KOR agonists and their application as an analgesic, diuretic, antitussive and brain cell protective agent.

κ opioid receptor (commonly known as KOR) modulation has also been reported to be useful in the treatment of arthritis (Life Sciences, 57, 4, Pp 371-378), hypertension, pain, particularly pain which is inflammatory in origin and post-operative pain, (European Journal of Pharmacology, 429, 1-3, Pp 79-91) inflammation, migraine, inflammatory disorders of the gastrointestinal tract, psoriasis, and irritable bowel syndrome (IBS), Parkinsonism, (European Journal of Pharmacology, 396, 2-3, Pp 101-107, Molecular Brain Research, 44, 1, Pp 12-20) and stroke.

Accordingly, it is an object of the application to provide compounds as KOR agonists.

SUMMARY

The present application relates to compounds of formula (I),

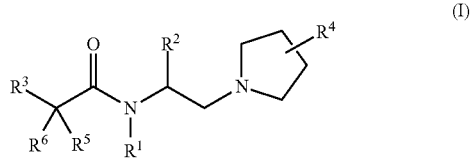

stereoisomers thereof or pharmaceutically acceptable salts thereof;
wherein,
$R^1$ represents hydrogen, alkyl, haloalkyl or —$(CH_2)_m$-cycloalkyl;
$R^2$ represents (1) cycloalkyl, (2) an group selected from heterocyclyl, heteroaryl or aryl, wherein such group is optionally substituted with 1 to 3 substituents selected independently from cyano, hydroxyl, alkyl, alkynyl, alkoxy, halogen, haloalkyl, haloalkoxy, —COOR$^a$, —CONR$^e$R$^f$, —O—(CH$_2$)—R$^7$ or R$^{11}$;

R$^3$ is an optionally substituted group selected from

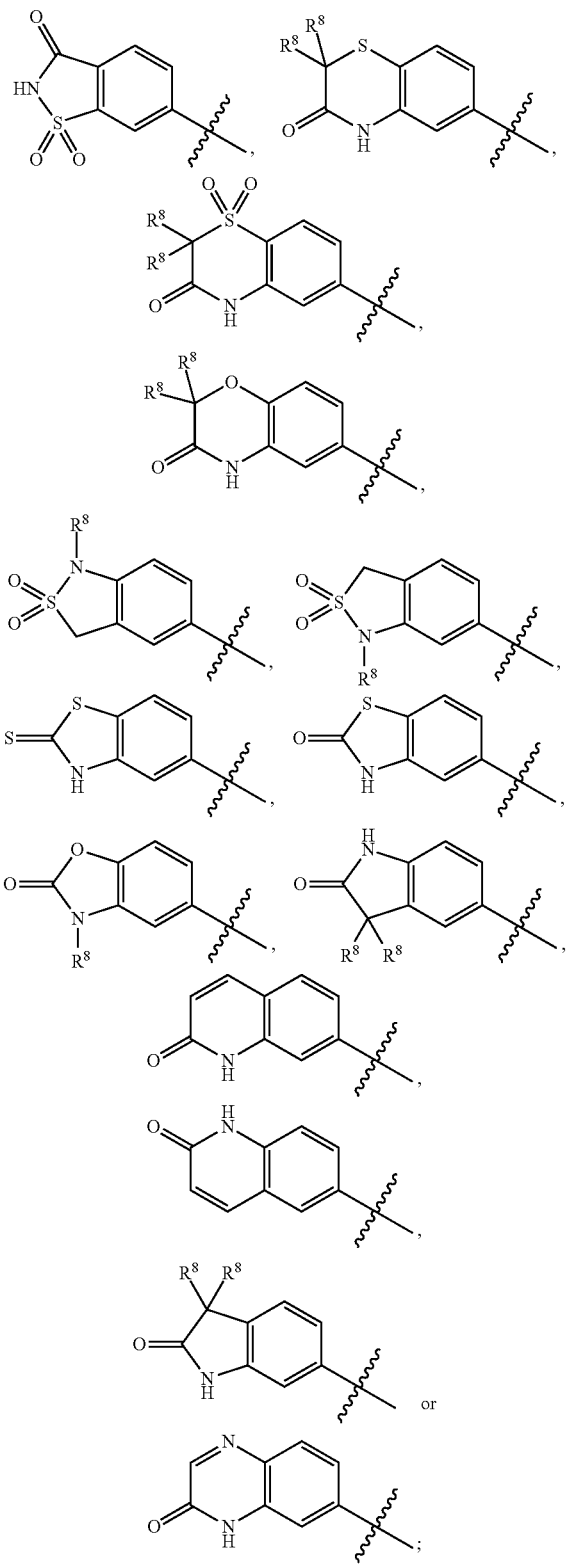

Optional substituent on R$^3$, in each occurrence, independently selected from halogen, alkyl or haloalkyl;

R$^4$ is selected from hydrogen, hydroxyl, halogen, alkyl, alkoxy, or haloalkyl;

R$^5$ and R$^6$, each are independently selected from hydrogen or alkyl;

R$^7$ is selected from cyano, tetrazolyl, —COOR$^a$, —CONR$^e$R$^f$ or

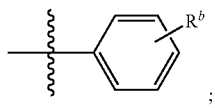

R$^8$, in each occurrence, is independently selected from hydrogen, halogen, alkyl or —(CH$_2$)$_q$—R$^9$;

R$^9$ is —COOR$^a$ or

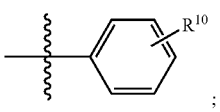

R$^{10}$ is selected from hydrogen, cyano, —COOR$^c$, —CONR$^e$R$^f$ or tetrazolyl;

R$^{11}$ is selected from (1) (C$_3$-C$_6$)cycloalkyl, benzyl,

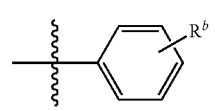

or (2) 5-6 membered heteroaryl optionally substituted with 1 to 2 substituents selected independently from alkyl, haloalkyl, haloalkoxy or —(CH$_2$)$_m$—(C$_3$-C$_6$)cycloalkyl;

R$^a$ and R$^c$, in each occurrence, independently selected from hydrogen, alkyl, heterocyclyl or heteroaryl;

R$^b$, in each occurrence, independently selected from hydrogen, alkyl or alkoxy;

R$^e$, in each occurrence, independently selected from hydrogen, alkyl, haloalkyl or —S(O)$_2$-alkyl;

R$^f$, in each occurrence, independently selected from hydrogen or alkyl;

m is selected from 0, 1, 2, 3 or 4;

n and q, each independently selected from 1 or 2;

provided that when R$^2$ is phenyl optionally substituted with alkyl, alkoxy or halogen, R$^1$ is alkyl and one of R$^5$ and R$^6$ represents hydrogen, then R$^3$ does not represent the following rings

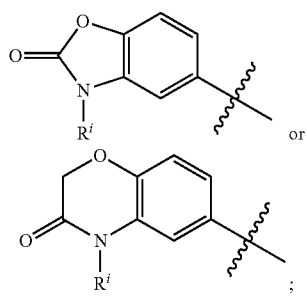

wherein $R^i$, in each occurrence, represents hydrogen or alkyl.

In another embodiment, the application is directed to pharmaceutical compositions comprising a pharmaceutically acceptable carrier and an effective amount of a compound of formula (I), stereoisomer thereof or pharmaceutically acceptable salt thereof.

In one embodiment, the application is directed to novel compounds of formula (I), stereoisomers thereof or pharmaceutically acceptable salts thereof as κ opioid receptor (KOR) agonists.

In other embodiment, the application is directed to a method for binding opioid receptor, in a patient in need thereof, comprising administering to said patient a composition comprising an effective amount of a compound of formula (I) or a stereoisomer thereof or a pharmaceutically acceptable salt thereof.

In another embodiment, the application is directed to a method of treating or preventing gastrointestinal dysfunction, in a patient in need thereof, comprising administering to said patient a composition comprising an effective amount of a compound of formula (I), a stereoisomer thereof or a pharmaceutically acceptable salt thereof.

In another embodiment, the application is directed to a method of treating or preventing pain, to a patient in need thereof, comprising administering to said patient a composition comprising an effective amount of a compound of formula (I), a stereoisomer thereof or a pharmaceutically acceptable salt thereof.

In another embodiment, the application is directed to a method of administering KOR agonists in a subject, which comprises administering to the subject a therapeutically effective amount of a compound of formula (I), a stereoisomer thereof or a pharmaceutically acceptable salt thereof.

DETAILED DESCRIPTION

'Halogen represents fluorine, chlorine, bromine, or iodine.

'Hydroxyl' represents —OH.

'Alkyl' group refers to linear or branched alkyl group with 1 to 10 carbon atoms. Exemplary alkyl group includes, but is not limited to, methyl, ethyl, n-propyl, iso-propyl, n-butyl, iso-butyl, t-butyl, n-pentyl, iso-pentyl, hexyl, heptyl, octyl and the like.

'Alkynyl' group refers to linear or branched alkynyl group with 1 to 10 carbon atoms. Exemplary alkyl group includes, but is not limited to, ethynyl, prop-1-ynyl, but-2-ynyl, 4-methylpent-2-ynyl and the like.

'Alkoxy' group refers to an —O(alkyl) group, wherein alkyl group is as defined above. Exemplary alkoxy groups include methoxy, ethoxy, n-propoxy, iso-propoxy, n-butoxy, iso-butoxy, t-butoxy, and the like. Unless otherwise specified, an alkoxy group has from 1 to 10 carbon atoms.

'Aryl' is a monocyclic or polycyclic aromatic ring system. Exemplary aryl groups include, but are not limited to, phenyl, naphthyl, and the like. Unless otherwise specified, an aryl group typically has from 6 to about 14 carbon atoms but the application is not limited in that respect.

'Cycloalkyl' group refers to a cyclic alkyl group which may be mono, bicyclic, polycyclic, or a fused/bridged ring system. Exemplary cycloalkyl groups include, but are not limited to, cyclopropyl, cyclobutyl, cyclopentyl, cyclohexyl, cycloheptyl, cyclooctyl, and the like. Unless otherwise specified, a cycloalkyl group typically has from 3 to about 10 carbon atoms. Typical bridged cycloalkyls include, but are not limited to adamantyl, noradamantyl, bicyclo[1.1.0] butanyl, norbornyl(bicyclo[2.2.1]heptanyl), and the like. '($C_3$-$C_6$)cycloalkyl' refers to cycloalkyl group having 3 to 6 carbon atoms.

'Haloalkyl' means at least one halogen atom is substituted on an alkyl group. Both halogen and alkyl have the meaning as defined above. Representative examples of haloalkyl groups include, but are not limited to, fluoromethyl, chloromethyl, fluoroethyl, chloroethyl, difluoromethyl, difluoroethyl, trifluoromethyl, dichloroethyl, trichloroethyl and the like. Unless otherwise specified, a haloalkyl group typically has from 1 to 10 carbon atoms.

'Haloalkoxy' means at least one halogen atom is substituted on an alkoxy group, wherein alkoxy and halogen groups are as defined above. Exemplary haloalkoxy groups include, but not limited to, fluoromethoxy, chloromethoxy, trifluoromethoxy, difluoromethoxy, trichloroethoxy, fluoroethoxy, chloroethoxy, difluoroethoxy, trifloroethoxy, perfluoroethoxy (—$OCF_2CF_3$), trifluoro-t-butoxy, hexafluoro-t-butoxy, perfluoro-t-butoxy (—$OC(CF_3)_3$), and the like. Unless otherwise specified, an haloalkoxy group typically has from 1 to 10 carbon atoms.

'Heterocyclyl' is a saturated monocyclic or polycyclic ring system of 3 to 10 members having at least one heteroatom or heterogroup selected from one or more of —O—, —N—, —S—, —$SO_2$, or —CO. Exemplary heterocyclyl groups include one or more of, but not limited to, azetidinyl, pyrrolidinyl, piperidinyl, piperazinyl, morpholinyl, tetrahydro-2H-pyranyl, thiomorpholinyl, thiomorpholine-1,1-dioxide, thiazolidinyl, 1,3-dioxolanyl, 1,4-dioxanyl, and the like. Unless otherwise specified, a heterocyclyl group typically has from 3 to about 10 carbon atoms but the application is not limited in that respect.

'Heteroaryl' is an unsaturated, aromatic or non-aromatic, monocyclic or polycyclic ring system of 3 to 10 members having at least one heteroatom or heterogroup selected from one or more of —O—, —N—, —S—, —$SO_2$, or —CO where $R_a$ is H, alkyl or a bond. Exemplary heteroaryl groups include one or more of, but not limited to, pyridinyl, thiazinyl, pyrazinyl, pyrazolyl, thiazolyl, tetrazolyl, 1,3,4-oxadiazolyl, imidazolyl, 1,3,4-thiadiazolyl, imidazothiazolyl, indolizidinyl, indolyl, quinolinyl, quinoxalinyl, 2-oxoindolinyl, 1H-benzo[d]imidazol-2 (3H)-onyl, benzo[d] oxazol-2 (3H)-onyl, benzo[d]thiazol-2 (3H)-only, quinolin-2 (1H)-only, 1,3-dihydrobenzo[c]isothiazole 2,2-dioxide-yl, 2H-benzo[b][1,4]thiazin-3(4H)-one 1,1-dioxide-yl, benzo [d]isothiazol-3(2H)-one1,1-dioxide-yl, benzo[d]thiazole-2 (3H)-thionyl, 2H-benzo[b][1,4]thiazin-3(4H)-onyl, quinoxalin-2 (1H)-onyl, 2H-benzo[b][1,4]oxazin-3(4H)-onyl, and the like. Unless otherwise specified, a heteroaryl group typically has from 3 to about 10 carbon atoms.

'5-6 membered heteroaryl' is a heteroaryl group as defined above, having 5 to 6 ring atoms and is monocyclic. Exemplary heteroaryl groups include one or more of, but not limited to, pyridinyl, thiazinyl, pyrazinyl, pyrazolyl, thiazolyl, tetrazolyl, 1,3,4-oxadiazolyl, imidazolyl and the like.

The KOR may be an animal or a mammalian or non-mammalian receptor, such as a human receptor 'Optionally substituted' means that the substitution is optional and therefore it is possible for the designated atom or group to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is oxo (i.e., =O), then two hydrogens on the atom are replaced and when the substitution is fluoro, then one hydrogen on the atom is replaced and the like. When more than one substituent is present on an atom or group, the chosen substituents are independent of each other (i.e same or different).

As used herein and in the appended claims, the singular forms "a", "an", and "the" include plural reference unless the context clearly indicates otherwise.

As used herein, the term 'subject' or 'patient' means mammals, such as humans and other animals, including horses, dogs, cats, rats, mice, sheep, pigs, etc. In exemplary embodiments, the subject may include subjects for which treatment and/or prevention of the conditions described herein would be beneficial.

The terms 'treating' or 'to treat' means to alleviate symptoms, eliminate the causation either on a temporary or permanent basis, or to prevent or slow the appearance of symptoms.

The term 'treatment' includes alleviation, elimination of causation of or prevention of any of the diseases or disorders described below. Besides being useful for human treatment, these combinations are also useful for treatment of other mammals, including horses, dogs, cats, rats, mice, sheep, pigs, etc.

The compounds described herein are typically administered in admixture with one or more pharmaceutically acceptable excipients or carriers in the form of a pharmaceutical composition. A 'composition' may comprise one compound or a mixture of compounds. A 'pharmaceutical composition' is any composition useful in producing at least one physiological response in a subject to which such pharmaceutical composition is administered.

For ease of reference, in this application it will be described in terms of administration to human subjects. It will be understood, however, that such descriptions are not limited to administration to humans, but will also include administration to other animals unless explicitly stated otherwise.

A 'therapeutically effective amount' is the amount of compound of the present application that is effective in generating biological or medical response of a subject, for example, reduction or inhibition of an enzyme or a protein activity, or ameliorate symptoms, alleviate conditions, slow or delay disease progression, or prevent a disease.

In one embodiment, the term 'a therapeutically effective amount' refers to the amount of the compound of formula (I) of the present application that, when administered to a subject, is effective in at least partially alleviating, inhibiting, preventing and/or ameliorating a condition, or a disorder or a disease associated with KOR.

Unless defined otherwise, all technical and scientific terms used herein have the same meaning as commonly understood to one of ordinary skill in the art.

One or more compounds of formula (I) can be supplied in the form of a therapeutic composition that is within the scope of the present application.

One or more compounds of formula (I) can be supplied in the form of a novel therapeutic composition that is within the scope of the present application.

One or more compounds of formula (I) can be supplied in the form of a therapeutic composition that is within the scope of the present application.

The term 'Pharmaceutically acceptable salts' refers to any acid or base salt, pharmaceutically acceptable solvates, or any complex of the compound that, when administered to a recipient, is capable of providing (directly or indirectly) a compound as described herein. It should be appreciated, however, salts that are not pharmaceutically acceptable also lie within the scope of the application. The preparation of salts can be carried out using known methods.

For example, pharmaceutically acceptable salts of compound of formula (I) contemplated refers to salts prepared from acids or bases including inorganic or organic acids and inorganic or organic bases by conventional chemical methods using a compound of formula (I). Generally, such salts may be prepared, for example, by making free base of the compounds and reacting with a stoichiometric quantity of the appropriate acid and vice-versa in water or in an organic solvent, or in a mixture of the two. Generally, non-aqueous media such as one or more of ether, ethyl acetate, methanol, ethanol, isopropanol or acetonitrile may be utilized.

When the compound of formula (I) is basic, salts may be prepared from acids, including inorganic or organic acids (acid addition salts). Examples of such acids include, but not limited to formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), nitric, hydrochloride, hydrobromide, isoethionic, hydroiodide, phosphoric, sulfuric, succinic, tartaric, methanesulfonic, ethanesulfonic, benzenesulfonic, benzoic, mucic, pantothenic, p-toluenesulfonic, camphorsulfonic, 2-hydroxyethanesulfonic, sulfanilic, cyclohexylaminosulfonic, algenic, β-hydroxybutyric, galactaric, and galacturonic acid, and the like.

Salts formed from inorganic bases include sodium, potassium, lithium, calcium, copper, magnesium, manganic salts, manganous, zinc, aluminum, ammonium, ferric, ferrous and the like.

Salts derived from organic bases include salts of primary, secondary, and tertiary amines, substituted amines including naturally occurring substituted amines, cyclic amines, and basic ion exchange resins, such as arginine, betaine, caffeine, choline, N,N-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperide, polyamine resins, procaine, purines, theobromine, triethylamine, trimethylamine, tripropylamine, tromethamine, and the like.

'Pharmaceutically acceptable salts' in the solid form may exist in more than one crystal structure, and may also be in the form of hydrates.

Pharmaceutically acceptable solvates of compound of formula (I) may be hydrates or comprising other solvents of crystallization such as alcohols. Pharmaceutically acceptable solvates of compound of formula (I) may be prepared by conventional methods such as dissolving the compounds of formula (I) in solvents such as water, methanol, ethanol etc., preferably water and recrystallizing by using different crystallization techniques.

The term 'stereoisomers' is a general term used for all isomers of an individual molecule that differ only in the orientation of their atoms in space. Where the compounds according to the present application possess one or more asymmetric centers and compounds with asymmetric centers give rise to enantiomers, diastereomers or both as pure or partially purified compounds. It is to be understood that all stereoisomeric forms of the compounds of the invention, including but not limited to, diastereomers, enantiomers and atropsiomers, as well as mixtures thereof such as forms, are included in the scope of the present application. Preparation of such stereoisomeric forms of compound of formula (I), may be achieved by appropriate modification of the methodology known in the art. Their absolute stereochemistry may be determined by the suitable methods. If required, racemic mixtures of the compound of formula (I) may be separated to isolate individual enantiomers or diastereomers. Such separation can be carried out by methods known in the art, such as the coupling of a racemic mixture of compound of formula (I) to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer or diastereomer of a compound may be obtained by stereoselective synthesis using optically pure starting materials or known reagents.

For any particular compound disclosed herein, wherein the stereochemistry of any particular chiral atom is not specified, then all stereoisomers are contemplated and included as the compounds of the application. Where stereochemistry is specified by a solid wedge or a dashed wedge bond or dashed line representing a particular configuration then that stereoisomer is so specified and defined. Following the standard chemical literature description practice and as used herein, a full wedge bond means above the ring plane, and a dashed wedge bond or dashed line means below the ring plane.

Furthermore the configuration of a chiral atom may be denoted as (R) or (S) by the symbols (R) and (S) written next to the chiral atom. For example, a compound (S)-2-(2-oxo-2,3-dihydrobenzo[d]thiazol-5-yl)-N-(1-phenyl-2-(pyrrolidin-1-yl)ethyl)acetamide may be represented as provided below.

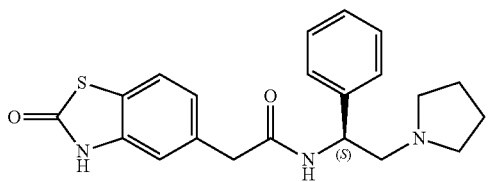

Further certain individual molecules may exist as geometric isomers (cis/trans). Similarly, certain compounds of this application may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present application.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

For any particular compound disclosed herein, any general structure presented also encompasses all conformational isomers, regioisomers and tautomers that may arise from a particular set of substituents.

Compounds of the application, such as a compound of formula (I) and salts thereof, also include other forms, such as their stereoisomers (except where specifically indicated), prodrugs, hydrates, solvates, acid salt hydrates, or any isomorphic crystalline forms thereof.

Compounds employed in the methods and compositions of the present application may exist in prodrug form. As used herein, "prodrug" is intended to include any covalently bonded carriers which release the active parent drug, for example, the compound of Formula (I), or other formulas or compounds employed in the present methods and compositions in vivo when such prodrug is administered to a mammalian subject. The term "prodrug" also includes compounds which may be specifically designed to maximize the amount of active species that reaches the desired site of reaction and which themselves may be inactive or minimally active for the activity desired, but through biotransformation are converted into biologically active metabolites. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present application contemplates methods of delivering prodrugs. Prodrugs of the compounds employed in the present application, for example a compound of Formula (I), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

'Pain' refers to the perception or condition of unpleasant sensory or emotional experience, associated with actual or potential tissue damage or described in terms of such damage. 'Pain' includes, but is not limited to, two broad categories of pain: acute and chronic pain. Buschmann, H.; Christoph, T; Friderichs, E.; Maul, C.; Sundermann, B; eds.; Analgesics, Wiley-VCH, Verlag GMbH & Co. KgaA, Weinheim; 2002; Jain, K. K., 'A Guide to Drug Evaluation for Chronic Pain'; Emerging Drugs, 5(2), 241-257 (2000), the disclosures of which are hereby incorporated herein by reference in their entireties. Non-limiting examples of pain include, for example, nociceptive pain, inflammatory pain, visceral pain, somatic pain, neuralgias, neuropathic pain, AIDS pain, cancer pain, phantom pain, and psychogenic pain, and pain resulting from hyperalgesia, pain caused by rheumatoid arthritis, migraine, allodynia and the like.

The term 'gastrointestinal dysfunction', as used herein, refers collectively to maladies of the gastrointestinal system, particularly the stomach and small and large intestines. Non-limiting examples of gastrointestinal dysfunction include, for example, diarrhea, nausea, emesis, post-operative emesis, opioid-induced emesis, irritable bowel syndrome, opioid-bowel dysfunction, opioid induced constipation, ileus, including post-operative ileus, post-partum ileus and opioid-induced ileus, colitis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, distension, abdominal or epigastric pain and discomfort, non-ulcerogenic dyspepsia, gastritis, constipation, or delayed absorption of orally administered medications or nutritive substances.

The term 'peripheral' designates that the compound acts primarily on physiological systems and components external to the central nervous system (CNS). In preferred form, the compounds of the present application employed in the methods of the present application exhibit high levels of activity with respect to peripheral tissue, such as, gastrointestinal tissue, while exhibiting reduced, and preferably substantially no CNS activity at therapeutically relevant doses.

The phrase 'does not substantially cross,' as used herein, means that less than about 20% by weight of the compound employed in the present methods crosses the blood-brain barrier, preferably less than about 15% by weight, more preferably less than about 10% by weight, even more preferably less than about 5% by weight and still more preferably a non-detectible, de minimus, or even 0% by weight of the compound crosses the blood-brain barrier at therapeutically relevant doses. Selected compounds can be evaluated for CNS penetration by determining plasma and brain levels following i.v., oral, subcutaneous or intraperitoneal administration.

The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful or potentially useful in producing at least one physiological response in a subject to which such pharmaceutical composition is administered.

The pharmaceutical compositions of compounds of formula (I) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present application may be administered in a wide variety of different dosage forms. For example, they may be combined with various pharmaceutically acceptable inert carriers in the form of one or more of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include one or more of solid diluents or fillers, sterile aqueous media, and various nontoxic organic solvents, etc. Moreover, oral pharmaceutical compositions may be sweetened and/or flavored. In general, the compounds of the application may be present in such dosage forms at concentration levels ranging from about 0.1% to about 90% by weight.

For oral administration, tablets may contain various excipients such as one or more of microcrystalline cellulose, sodium citrate, calcium carbonate, dicalcium phosphate, and glycine, along with various disintegrants such as starch (such as corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulphate and talc may be employed. Solid compositions of a similar type may also be employed as fillers in gelatin capsules; exemplary materials in this connection may also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents, together with diluents such as water, ethanol, propylene glycol, glycerin, and various combinations thereof.

For parenteral administration (including intraperitoneal subcutaneous, intravenous, intradermal or intramuscular injection), solutions of compounds of the present application in, for example, either sesame or peanut oil or in aqueous propylene glycol may be employed. The aqueous solutions may be buffered, if necessary or desirable, and the liquid diluent first rendered isotonic. These aqueous solutions may be suitable for intravenous injection purposes. The oily solutions may be suitable for intraarticular, intramuscular, and/or subcutaneous injection purposes. The synthesis of such solutions under sterile conditions may be accomplished by standard pharmaceutical techniques known to those having ordinary skill in the art. For parenteral administration, examples of suitable preparations may include solutions, such as oily or aqueous or non-aqueous solutions, as well as suspensions, emulsions, and/or implants, including suppositories. Compounds of the present application may be formulated in sterile form in multiple or single dose formats. For example, the compounds of the present application may be dispersed in a fluid carrier such as sterile saline and/or 5% saline dextrose solutions commonly used with injectables.

In another embodiment, the compounds of the present application may be administered topically. For example, it may be desirable to administer the compounds of the present application topically when treating inflammatory conditions of the skin. Non-limiting examples of methods of topical administration include transdermal, buccal, or sublingual application. For topical applications, therapeutic compounds may be suitably admixed in a pharmacologically inert topical carrier such as a gel, an ointment, a lotion, and/or a cream. Such topical carriers may include water, glycerol, alcohol, propylene glycol, fatty alcohols, triglycerides, fatty acid esters, and/or mineral oils. Other possible topical carriers may include liquid petrolatum, isopropylpalmitate, polyethylene glycol, ethanol 95%, polyoxyethylene monolaurate 5% in water, sodium lauryl sulphate 5% in water, and the like, and combinations thereof. In addition, materials such as surfactants, anti-oxidants, humectants, viscosity stabilizers, and the like, and combinations thereof, also may be added if desired.

It will be appreciated by those having ordinary skill in the art that the exemplary amounts of active compounds used in a given therapy will vary according to the specific compound being utilized, the particular compositions formulated, the mode of application, the particular site of administration, etc. Optimal administration rates for a given protocol of administration may be ascertained by those having ordinary skill in the art using conventional dosage determination tests conducted with regard to the foregoing guidelines.

In general, compounds of the present application for treatment may be administered to a subject in a suitable effective dose of one or more compounds of the present application may be in the range of from about 0.01 to about 100 milligrams per kilogram of body weight of recipient per day, in some embodiments, in the range of from about 0.5 to about 50 milligrams per kilogram body weight of recipient per day, in still other embodiments, in the range of from about 0.1 to about 20 milligrams per kilogram body weight of recipient per day. The exemplary dose may be suitably administered once daily, or several sub-doses, e.g. 2 to 5 sub-doses, may be administered at appropriate intervals through the day, or on other appropriate schedules.

Reference will now be made in detail to the embodiments of the application, one or more examples of which are set forth below. Each example is provided by way of explanation of the application, and not by way of limitation of the application. In fact, it will be apparent to those skilled in the art that various modification and variations can be made in the present application without departing from the scope or spirit of the application. For instance, features illustrated or described as part of one embodiment can be used on another embodiment to yield a still further embodiment. Thus it is intended that the present application cover such modifications and variations as come within the scope of the appended claims and their equivalents. Other objects, features, and aspects of the present application are disclosed in, or are obvious from, the following detailed description. It is to be understood by one of ordinary skill in the art that the present discussion is a description of exemplary embodiments only, and is not to be construed as limiting the broader aspects of the present application.

The present application relates to compounds of formula (I),

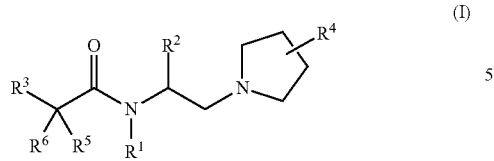

stereoisomers thereof or pharmaceutically acceptable salts thereof;
wherein, $R^1$ represents hydrogen, alkyl, haloalkyl or —$(CH_2)_m$-cycloalkyl;

$R^2$ represents (1) cycloalkyl, (2) an group selected from heterocyclyl, heteroaryl or aryl, wherein such group is optionally substituted with 1 to 3 substituents selected independently from cyano, hydroxyl, alkyl, alkynyl, alkoxy, halogen, haloalkyl, haloalkoxy, —$COOR^a$, —$CONR^eR^f$, —O—$(CH_2)_n$—$R^7$ or $R^{11}$;

$R^3$ is an optionally substituted group selected from

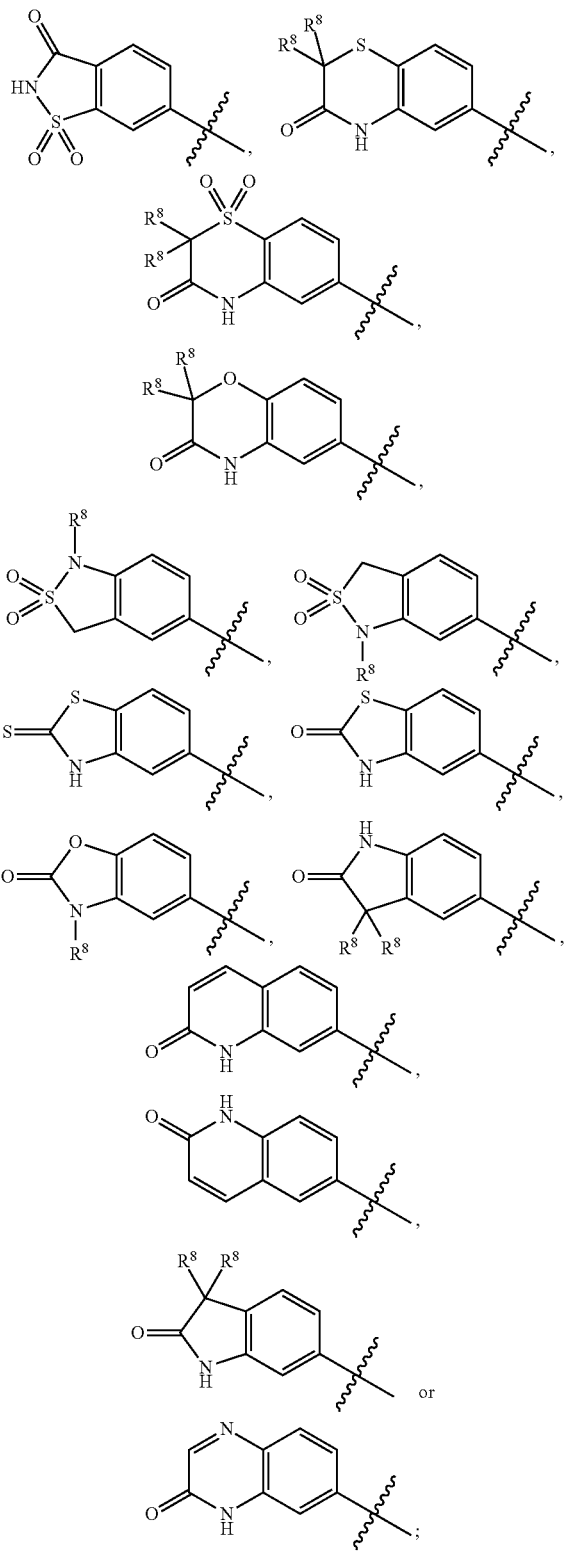

Optional substituent on $R^3$, in each occurrence, independently selected from halogen, alkyl or haloalkyl;

$R^4$ is selected from hydrogen, hydroxyl, halogen, alkyl, alkoxy, or haloalkyl;

$R^5$ and $R^6$, each are independently selected from hydrogen or alkyl;

$R^7$ is selected from cyano, tetrazolyl, —COOR$^a$, —CONR$^e$R$^f$ or

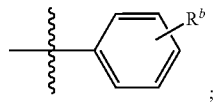
;

$R^8$, in each occurrence, is independently selected from hydrogen, halogen, alkyl or —(CH$_2$)$_q$—R$^9$;

$R^9$ is —COOR$^a$ or

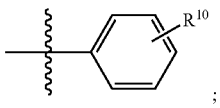
;

$R^{10}$ is selected from hydrogen, cyano, —COOR$^c$, —CONR$^e$R$^f$ or tetrazolyl;

$R^{11}$ is selected from (1) (C$_3$-C$_6$)cycloalkyl, benzyl,

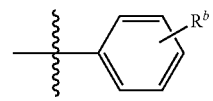

or (2) 5-6 membered heteroaryl optionally substituted with 1 to 2 substituents selected independently from alkyl, haloalkyl, haloalkoxy or —(CH$_2$)$_m$—(C$_3$-C$_6$)cycloalkyl;

$R^a$ and $R^c$, in each occurrence, independently selected from hydrogen, alkyl, heterocyclyl or heteroaryl;

$R^b$, in each occurrence, independently selected from hydrogen, alkyl or alkoxy;

$R^e$, in each occurrence, independently selected from hydrogen, alkyl, haloalkyl or —S(O)$_2$-alkyl;

$R^f$, in each occurrence, independently selected from hydrogen or alkyl;

m is selected from 0, 1, 2, 3 or 4;

n and q, each independently selected from 1 or 2;

provided that when $R^2$ is phenyl optionally substituted with alkyl, alkoxy or halogen, $R^1$ is alkyl and one of $R^5$ and $R^6$ represents hydrogen, then $R^3$ does not represent the following rings

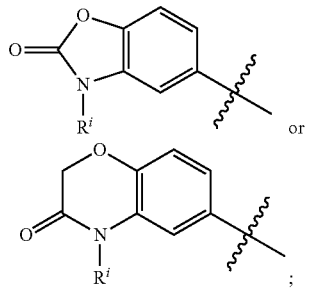

wherein $R^i$, in each occurrence, represents hydrogen or alkyl.

One embodiment of formula (I) includes compounds of formula (Ib),

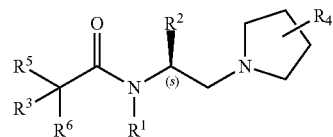

stereoisomers thereof or pharmaceutically acceptable salts thereof.

Another embodiment of formula (I) includes compounds of formula (Ib$^i$),

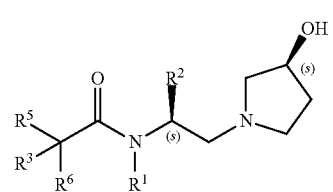

stereoisomers thereof or pharmaceutically acceptable salts thereof.

Another embodiment of formula (I) includes compounds of formula (Ic),

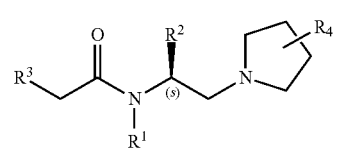

stereoisomers thereof or pharmaceutically acceptable salts thereof.

Another embodiment of formula (I) includes compounds of formula (Ic$^i$),

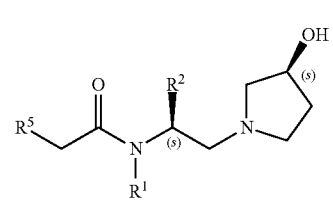

stereoisomers thereof or pharmaceutically acceptable salts thereof.

Another embodiment of formula (I) includes compounds of formula (Id),

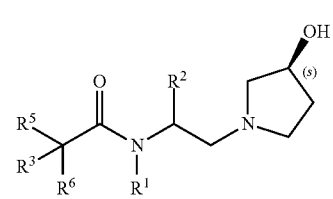

stereoisomers thereof or pharmaceutically acceptable salts thereof.

Another embodiment of formula (I) includes compounds of formula (Id'),

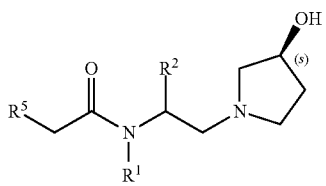
(Id$^i$)

stereoisomers thereof or pharmaceutically acceptable salts thereof.

Another embodiment of formula (I) includes compounds of formula (I), stereoisomers thereof or pharmaceutically acceptable salts thereof, wherein R$^3$ is selected from,

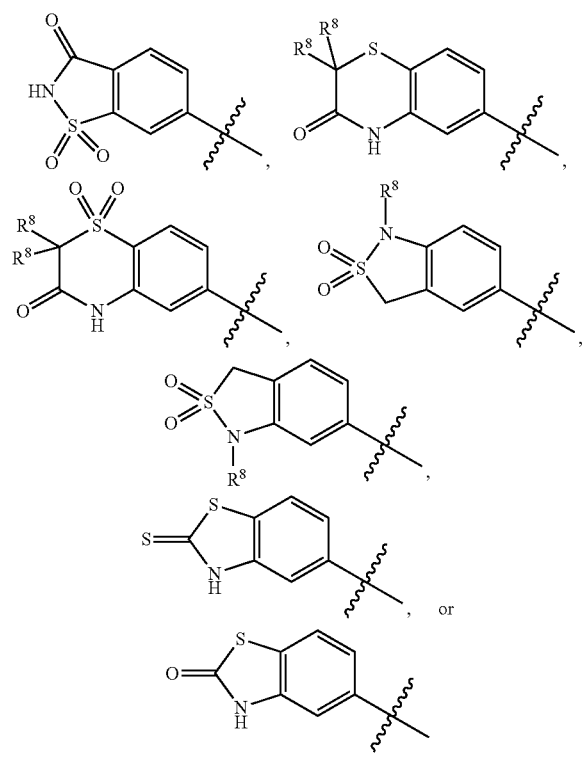

and R$^8$ is as defined in formula (I).

Another embodiment of formula (I) includes compounds of formula (I), stereoisomers thereof or pharmaceutically acceptable salts thereof, wherein R$^3$ is selected from,

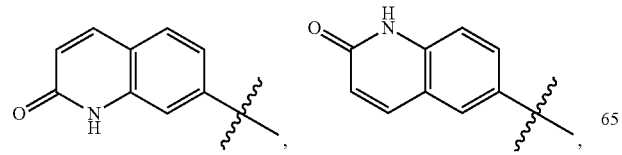

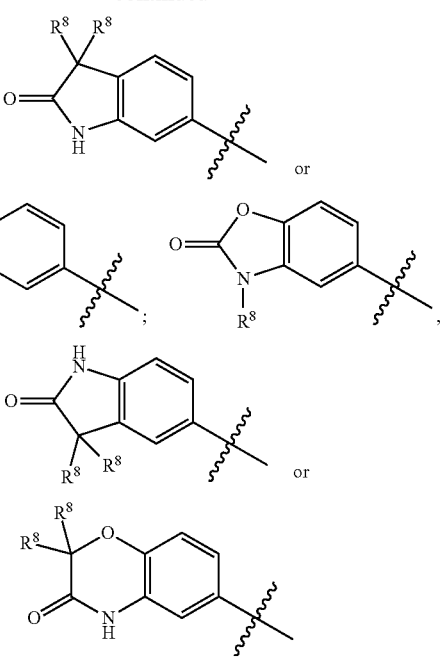

and R$^8$ is as defined in formula (I).

Another embodiment of formula (I), (Ib), (Ibi), (Ic), (Ici), (Id) or (Idi), wherein R$^2$ is phenyl optionally substituted with 1 to 3 groups independently selected from cyano, hydroxyl, alkyl, alkynyl, alkoxy, halogen, haloalkyl, haloalkoxy, —COOR$^a$, —CONR$^e$R$^f$, —O—(CH$_2$)—R$^7$ or R$^{11}$ and all other groups are as defined in formula (I); provided that when R$^2$ is phenyl optionally substituted with alkyl, alkoxy or halogen, R$^1$ is alkyl and R$^5$ and R$^6$ independently represents alkyl, then R$^3$ does not represent the following rings wherein, in each occurrence, R$^i$ represents hydrogen or alkyl.

In one aspect of the above embodiment R$^3$ represents

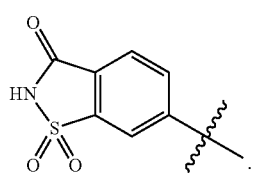 [SMILES: *c1ccc2c(c1)S(=O)(=O)NC2=O]

In another aspect of the above embodiment R³ represents

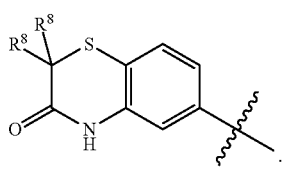

In another aspect of the above embodiment R³ represents

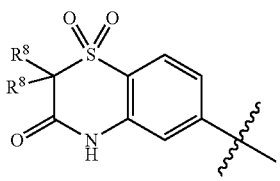

In another aspect of the above embodiment R³ represents

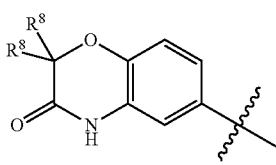

In another aspect of the above embodiment R³ represents

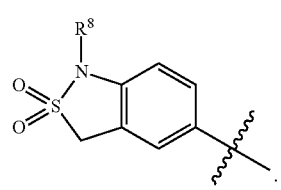

In another aspect of the above embodiment R³ represents

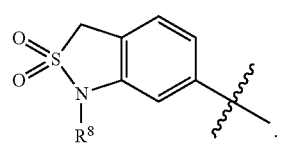

In another aspect of the above embodiment R³ represents

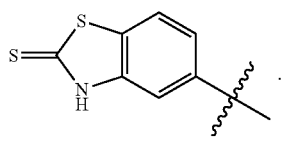 [SMILES: *c1ccc2sc(=S)[nH]c2c1]

In another aspect of the above embodiment R³ represents

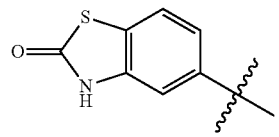

In another aspect of the above embodiment R³ represents

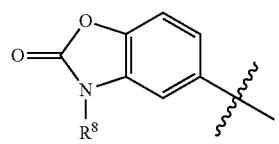

In another aspect of the above embodiment R³ represents

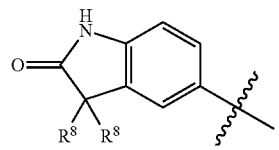

In another aspect of the above embodiment R³ represents

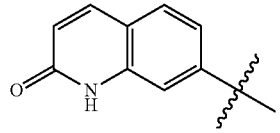

In another aspect of the above embodiment R³ represents

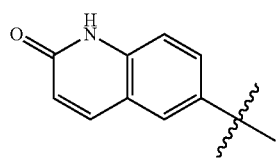

In another aspect of the above embodiment R³ represents

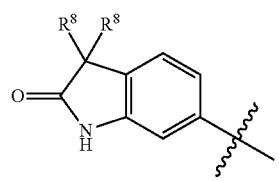

In another aspect of the above embodiment R³ represents

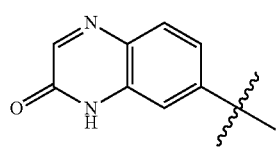

In an embodiment, specific compounds of formula (I) without any limitation are enumerated in Table (1):

Table (1)

N—((S)-2-((S)-3-hydroxypyrrolidin-1-yl)-1-phenylethyl)-N-methyl-2-(2-oxoindolin-6-yl)acetamide;
N-[(1S)-2-[(3S)-3-hydroxypyrrolidin-1-yl]-1-phenylethyl]-2-(3-oxo-3,4-dihydro-2H-1,4-benzoxazin-6-yl)acetamide;
N—((S)-2-((S)-3-hydroxypyrrolidin-1-yl)-1-phenylethyl)-N-methyl-2-(3-oxo-3,4-dihydroquinoxalin-6-yl)acetamide;
(S)-2-(2-oxo-2,3-dihydrobenzo[d]thiazol-5-yl)-N-(1-phenyl-2-(pyrrolidin-1-yl)ethyl)acetamide;
2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;
N—((S)-1-(3-cyanophenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;
N—((S)-2-((S)-3-hydroxypyrrolidin-1-yl)-1-phenylethyl)-N-methyl-2-(3-oxo-3,4-dihydro-2H-benzo[b][1,4]thiazin-6-yl)acetamide;
2-(1,1-dioxido-3-oxo-2,3-dihydrobenzo[d]isothiazol-6-yl)-N—((S)-2-((S)-3-hydroxypyrrolidin-1-yl)-1-phenylethyl)-N-methylacetamide;
2-(2,2-dioxido-1,3-dihydrobenzo[c]isothiazol-6-yl)-N—((S)-2-((S)-3-hydroxypyrrolidin-1-yl)-1-(3-(trifluoromethyl)phenyl)ethyl)-N-methylacetamide;
5-(2-(((S)-2-((S)-3-hydroxypyrrolidin-1-yl)-1-phenylethyl)(methyl)amino)-2-oxoethyl)-1,3-dihydrobenzo[c]isothiazol-1-ium 2,2-dioxide 2,2,2-trifluoroacetate;
N—((S)-1-(3-(difluoromethoxy)phenyl)-2-((S)-3-hydroxypyrrolidin-1-yl)ethyl)-2-(1,1-(S)-1-(3-(difluoromethoxy)phenyl)-2-((S)-3-dioxido-3-oxo-3,4-dihydro-2H-benzo[b][1,4]thiazin-6-yl)-N-methylacetamide;
2-(3,3-difluoro-2-oxoindolin-6-yl)-N—((S)-2-((S)-3-hydroxypyrrolidin-1-yl)-1-phenylethyl)-N-methylacetamide;
2-(3,3-difluoro-2-oxoindolin-6-yl)-N—((S)-2-((S)-3-hydroxypyrrolidin-1-yl)-1-phenylethyl)acetamide;
2-(1,1-dioxido-3-oxo-3,4-dihydro-2H-benzo[b][1,4]thiazin-6-yl)-N-ethyl-N—((S)-2-((S)-3-hydroxypyrrolidin-1-yl)-1-(3-(trifluoromethoxy)phenyl)ethyl)acetamide;
2-(1,1-dioxido-3-oxo-3,4-dihydro-2H-benzo[b][1,4]thiazin-6-yl)-N—((S)-2-((S)-3-methoxypyrrolidin-1-yl)-1-(3-(trifluoromethoxy)phenyl)ethyl)-N-methylacetamide
2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-(2,2,2-trifluoroethyl)acetamide 2,2,2-trifluoroacetate;
2-(1,1-dioxido-3-oxo-3,4-dihydro-2H-benzo[b][1,4]thiazin-6-yl)-N-(2-((S)-3-hydroxypyrrolidin-1-yl)-1-(tetrahydro-2H-pyran-4-yl)ethyl)-N-methylacetamide-2,2,2-trifluoroacetate;
3-((S)-2-((S)-3-hydroxypyrrolidin-1-yl)-1-(N-methyl-2-(2-oxo-2,3-dihydrobenzo[d]thiazol-5-yl)acetamido)ethyl) benzoic acid;
3-((S)-2-((S)-3-hydroxypyrrolidin-1-yl)-1-(N-methyl-2-(2-oxo-2,3-dihydrobenzo[d]thiazol-5-yl)acetamido)ethyl) benzamide;
(S)-2-(3-benzyl-2-oxo-2,3-dihydrobenzo[d]oxazol-5-yl)-N-(1-(3-hydroxyphenyl)-2-(pyrrolidin-1-yl)ethyl)acetamide;
N—((S)-1-(3-(1H-tetrazol-5-yl)phenyl)-2-((S)-3-hydroxypyrrolidin-1-yl)ethyl)-N-methyl-2-(1-methyl-2,2-dioxido-1,3-dihydrobenzo[c]isothiazol-6-yl)acetamide;
2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetic acid;
3-((S)-2-((S)-3-hydroxypyrrolidin-1-yl)-1-(N-methyl-2-(2-oxoindolin-6-yl)acetamido)ethyl) benzoic acid;
3-((S)-2-((S)-3-hydroxypyrrolidin-1-yl)-1-(N-methyl-2-(2-oxoindolin-6-yl)acetamido)ethyl) benzamide;
N—((S)-1-(3-cyanophenyl)-2-((S)-3-fluoropyrrolidin-1-yl)ethyl)-N-methyl-2-(2-oxoindolin-6-yl)acetamide;
N—((S)-1-(3-(2-amino-2-oxoethoxy)phenyl)-2-((S)-3-hydroxypyrrolidin-1-yl)ethyl)-N-methyl-2-(2-oxoindolin-6-yl)acetamide;
N—((S)-2-((S)-3-hydroxypyrrolidin-1-yl)-1-(3-(2-(methylsulfonamido)-2-oxoethoxy)phenyl)ethyl)-N-methyl-2-(2-oxoindolin-6-yl)acetamide;
3-((S)-2-((S)-3-fluoropyrrolidin-1-yl)-1-(N-methyl-2-(2-oxoindolin-6-yl)acetamido)ethyl) benzoic acid;
2-(3-((S)-2-((S)-3-fluoropyrrolidin-1-yl)-1-(N-methyl-2-(2-oxoindolin-6-yl)acetamido)ethyl) phenoxy)acetic acid;
N—((S)-1-(3-(2-amino-2-oxoethoxy)phenyl)-2-((S)-3-fluoropyrrolidin-1-yl)ethyl)-N-methyl-2-(2-oxoindolin-6-yl)acetamide;
3-((S)-2-((S)-3-hydroxypyrrolidin-1-yl)-1-(N-methyl-2-(3-oxo-3,4-dihydroquinoxalin-6-yl)acetamido)ethyl)benzoic acid;
3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzamide;
N—((S)-1-(3-ethynylphenyl)-2-((S)-3-hydroxypyrrolidin-1-yl)ethyl)-N-methyl-2-(2-oxo-2,3-dihydrobenzo[d]thiazol-5-yl)acetamide;
N—((S)-2-((S)-3-hydroxypyrrolidin-1-yl)-1-(3-(5-(trifluoromethyl)-1,2,4-oxadiazol-3-yl)phenyl)ethyl)-N-methyl-2-(3-oxo-3,4-dihydroquinoxalin-6-yl)acetamide;
N—((S)-2-((S)-3-hydroxypyrrolidin-1-yl)-1-(3-(5-methyl-1,2,4-oxadiazol-3-yl)phenyl)ethyl)-N-methyl-2-(2-oxoindolin-6-yl)acetamide;
N—((S)-2-((S)-3-hydroxypyrrolidin-1-yl)-1-(3-(thiazol-2-yl)phenyl)ethyl)-N-methyl-2-(2-oxoindolin-6-yl)acetamide;
N—((S)-1-(3-(but-1-yn-1-yl)phenyl)-2-((S)-3-hydroxypyrrolidin-1-yl)ethyl)-2-(2,2-dioxido-1,3-dihydrobenzo[c]isothiazol-6-yl)-N-methylacetamide;
3-((S)-2-((S)-3-hydroxypyrrolidin-1-yl)-1-(N-methyl-2-(2-oxoindolin-6-yl)acetamido)ethyl)-N-(2,2,2-trifluoroethyl)benzamide;
N,N-diethyl-3-((S)-2-((S)-3-hydroxypyrrolidin-1-yl)-1-(N-methyl-2-(2-oxoindolin-6-yl)acetamido)ethyl)benzamide;
3-((S)-2-((S)-3-hydroxypyrrolidin-1-yl)-1-(N-methyl-2-(2-oxo-2,3-dihydrobenzo[d]thiazol-5-yl)acetamido)ethyl)-N,N-dimethylbenzamide 2,2,2-trifluoroacetate;
N—((S)-1-(3-(2-(diethylamino)-2-oxoethoxy)phenyl)-2-((S)-3-hydroxypyrrolidin-1-yl)ethyl)-N-methyl-2-(2-oxoindolin-6-yl)acetamide;
N—((S)-1-(3-(2-(diethylamino)-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide;
N—((S)-1-(3-fluoro-5-(thiazol-2-yl)phenyl)-2-((S)-3-hydroxypyrrolidin-1-yl)ethyl)-N-methyl-2-(2-oxoindolin-6-yl)acetamide;
N—((S)-2-((S)-3-hydroxypyrrolidin-1-yl)-1-(3-(2-methyl-2H-tetrazol-5-yl)phenyl)ethyl)-N-methyl-2-(2-oxoindolin-6-yl)acetamide;

N—((S)-2-((S)-3-hydroxypyrrolidin-1-yl)-1-phenylethyl)-2-(3-methyl-2-oxo-2,3-dihydrobenzo[d]oxazol-5-yl)acetamide;

(S)-2-(3-(3-cyanobenzyl)-2-oxo-2,3-dihydrobenzo[d]oxazol-5-yl)-N-(1-phenyl-2-(pyrrolidin-1-yl)ethyl)acetamide;

(S)—N-methyl-2-(2-oxo-1,2-dihydroquinolin-6-yl)-N-(1-phenyl-2-(pyrrolidin-1-yl)ethyl)acetamide;

N—((S)-2-((S)-3-hydroxypyrrolidin-1-yl)-1-phenylethyl)-N-methyl-2-(2-oxo-1,2-dihydroquinolin-6-yl)acetamide;

(S)—N-methyl-2-(2-oxo-1,2-dihydroquinolin-7-yl)-N-(1-phenyl-2-(pyrrolidin-1-yl)ethyl)acetamide;

(S)—N-methyl-2-(3-methyl-2,2-dioxido-1,3-dihydrobenzo[c]isothiazol-5-yl)-N-(1-phenyl-2-(pyrrolidin-1-yl)ethyl)acetamide;

N—((S)-2-((R)-3-hydroxypyrrolidin-1-yl)-1-phenylethyl)-2-(2-oxo-1,2-dihydroquinolin-6-yl)acetamide;

N—((S)-2-((S)-3-hydroxypyrrolidin-1-yl)-1-phenylethyl)-N-methyl-2-(2-oxo-1,2-dihydroquinolin-7-yl)acetamide;

N—((S)-2-((S)-3-hydroxypyrrolidin-1-yl)-1-phenylethyl)-N-2-dimethyl-2-(2-oxo-2,3-dihydrobenzo[d]oxazol-5-yl)propanamide;

N—((S)-2-((S)-3-hydroxypyrrolidin-1-yl)-1-phenylethyl)-2-(2-oxo-1,2-dihydroquinolin-7-yl)acetamide;

N—((S)-2-((S)-3-hydroxypyrrolidin-1-yl)-1-phenylethyl)-2-methyl-2-(2-oxo-2,3-dihydrobenzo[d]oxazol-5-yl)propanamide;

(S)-2-(2-oxo-2,3-dihydrobenzo[d]oxazol-5-yl)-N-(1-phenyl-2-(pyrrolidin-1-yl)ethyl) acetamide;

N—((S)-2-((S)-3-hydroxypyrrolidin-1-yl)-1-phenylethyl)-2-(2-oxo-2,3-dihydrobenzo[d]oxazol-5-yl)acetamide;

(S)-2-(3-benzyl-2-oxo-2,3-dihydrobenzo[d]oxazol-5-yl)-N-(1-(3-(4-methoxybenzyloxy)phenyl)-2-(pyrrolidin-1-yl)ethyl)acetamide;

2-(3-(4-cyanobenzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-2-((S)-3-hydroxypyrrolidin-1-yl)-1-phenylethyl)-2-(2-oxoindolin-6-yl)acetamide (S)-2-(3-methyl-2-oxo-2,3-dihydrobenzo[d]oxazol-5-yl)-N-(1-phenyl-2-(pyrrolidin-1-yl)ethyl)acetamide;

N-(1-(1-benzyl-1H-pyrazol-4-yl)-2-(pyrrolidin-1-yl)ethyl)-2-(2-oxo-2,3-dihydrobenzo[d]oxazol-5-yl)acetamide;

(S)-t-butyl-2-(3-(1-(2-(3-benzyl-2-oxo-2,3-dihydrobenzo[d]oxazol-5-yl)acetamido)-2-(pyrrolidin-1-yl)ethyl)phenoxy)acetate;

(S)-2-(3-benzyl-2-oxo-2,3-dihydrobenzo[d]oxazol-5-yl)-N-(1-(3-(benzyloxy)phenyl)-2-(pyrrolidin-1-yl)ethyl)-N-methylacetamide;

N—((S)-1-cyclohexyl-2-((S)-3-hydroxypyrrolidin-1-yl)ethyl)-N-methyl-2-(2-oxoindolin-6-yl)acetamide;

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide;

N—((S)-1-cyclohexyl-2-((S)-3-hydroxypyrrolidin-1-yl)ethyl)-2-(2-oxo-2,3-dihydrobenzo[d]oxazol-5-yl)acetamide;

(S)-tert-butyl-2-(3-(1-(2-(3-benzyl-2-oxo-2,3-dihydrobenzo[d]oxazol-5-yl)-N-methyl acetamido)-2-(pyrrolidin-1-yl)ethyl)phenoxy)acetate;

N—((S)-1-cyclohexyl-2-((S)-3-hydroxypyrrolidin-1-yl)ethyl)-2-(2-oxoindolin-6-yl)acetamide N—((S)-1-cyclohexyl-2-((S)-3-hydroxypyrrolidin-1-yl)ethyl)-N-methyl-2-(2-oxo-2,3-dihydrobenzo[d]oxazol-5-yl)acetamide;

(S)—N-(1-(3-cyanophenyl)-2-(pyrrolidin-1-yl)ethyl)-N-methyl-2-(2-oxo-2,3-dihydrobenzo[d]oxazol-5-yl)acetamide;

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

(S)-tert-butyl 2-(3-(2-(3-hydroxypyrrolidin-1-yl)-1-(2-(2-oxo-2,3-dihydro benzo[d]oxazol-5-yl)acetamido)ethyl)phenoxy)acetate;

2-(3-(4-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide;

N-(1-(3-(cyanomethoxy)phenyl)-2-(3-hydroxypyrrolidin-1-yl)ethyl)-N-methyl-2-(2-oxo-2,3-dihydrobenzo[d]oxazol-5-yl)acetamide;

tert-butyl 2-(3-((S)-2-((R)-3-hydroxypyrrolidin-1-yl)-1-(N-methyl-2-(2-oxo-2,3-dihydrobenzo[d]oxazol-5-yl)acetamido)ethyl)phenoxy)acetate;

N—((S)-1-(3-cyanophenyl)-2-((S)-3-hydroxypyrrolidin-1-yl)ethyl)-N-methyl-2-(3-methyl-2-oxo-2,3-dihydrobenzo[d]oxazol-5-yl)acetamide;

N—((S)-1-(3-(1H-tetrazol-5-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(3-((S)-2-((S)-3-hydroxypyrrolidin-1-yl)-1-(N-methyl-2-(1-methyl-2,2-dioxido-1,3-dihydrobenzo[c]isothiazol-6-yl)acetamido)ethyl)phenoxy) acetic acid;

(S)-methyl 3-((2-oxo-5-(2-oxo-2-(1-phenyl-2-(pyrrolidin-1-yl)ethylamino)ethyl)benzo[d]oxazol-3(2H)-yl)methyl)benzoate;

(S)-tert-butyl 2-(2-oxo-5-(2-oxo-2-(1-phenyl-2-(pyrrolidin-1-yl)ethylamino)ethyl)benzo[d]oxazol-3(2H)-yl)acetate;

(S)-2-(2-oxo-5-(2-oxo-2-(1-phenyl-2-(pyrrolidin-1-yl)ethylamino)ethyl) benzo[d]oxazol-3(2H)-yl)acetic acid hydrochloride;

(S)—N-(1-(3-hydroxyphenyl)-2-(pyrrolidin-1-yl)ethyl)-2-(2-oxo-2,3-dihydrobenzo[d]oxazol-5-yl)acetamide;

(S)-2-(3-(1-(2-(2-oxo-2,3-dihydrobenzo[d]oxazol-5-yl)acetamido)-2-(pyrrolidin-1-yl)ethyl)phenoxy)acetic acid hydrochloride;

2-(5-(2-(((S)-2-((S)-3-hydroxypyrrolidin-1-yl)-1-phenylethyl)(methyl)amino)-2-oxoethyl)-2-oxobenzo[d]oxazol-3(2H)-yl)acetic acid;

2-(3-(1-(N-methyl-2-(2-oxoindolin-6-yl)acetamido)-2-(pyrrolidin-1-yl)ethyl)phenoxy)acetic acid hydrochloride;

3-((5-(2-(((S)-2-((S)-3-hydroxypyrrolidin-1-yl)-1-phenylethyl)(methyl)amino)-2-oxoethyl)-2-oxobenzo[d]oxazol-3(2H)-yl)methyl)benzamide;

(S)-2-(3-benzyl-2-oxo-2,3-dihydrobenzo[d]oxazol-5-yl)-N-(1-(3-hydroxyphenyl)-2-(pyrrolidin-1-yl)ethyl)-N-methylacetamide;

(R)-2-(3-(1-(N-methyl-2-(2-oxo-2,3-dihydrobenzo[d]oxazol-5-yl)acetamido)-2-(pyrrolidin-1-yl)ethyl)phenoxy)acetic acid;

(S)-3-((2-oxo-5-(2-oxo-2-(1-phenyl-2-(pyrrolidin-1-yl)ethylamino)ethyl)benzo[d]oxazol-3(2H)-yl)methyl)benzamide;

2-(3-(1-(2-(2-oxoindolin-6-yl)acetamido)-2-(pyrrolidin-1-yl)ethyl)phenoxy)acetic acid;

(S)—N-(1-(3-(2H-tetrazol-5-yl)phenyl)-2-(pyrrolidin-1-yl)ethyl)-N-methyl-2-(2-oxo-2,3-dihydrobenzo[d]oxazol-5-yl)acetamide;

(S)-2-(3-(2-(3-hydroxypyrrolidin-1-yl)-1-(N-methyl-2-(2-oxo-2,3-dihydrobenzo[d]oxazol-5-yl)acetamido)ethyl)phenoxy)acetic acid triflouro acetate;

(S)-2-(3-(2-(3-hydroxypyrrolidin-1-yl)-1-(N-methyl-2-(2-oxoindolin-6-yl) acetamido)ethyl)phenoxy)acetic acid hydrochloride;

2-(3-((S)-2-((R)-3-hydroxypyrrolidin-1-yl)-1-(N-methyl-2-(2-oxo-2,3-dihydrobenzo[d]oxazol-5-yl)acetamido)ethyl)phenoxy)acetic acid;

2-(5-(2-(((S)-1-cyclohexyl-2-((S)-3-hydroxypyrrolidin-1-yl)ethyl)(methyl)amino)-2-oxoethyl)-2-oxobenzo[d]oxazol-3(2H)-yl)acetic acid;

Methyl 4-((5-(2-(((S)-2-((S)-3-hydroxypyrrolidin-1-yl)-1-phenylethyl)(methyl)amino)-2-oxoethyl)-2-oxobenzo[d]oxazol-3(2H)-yl)methyl)benzoate;

N—((S)-1-(3-(2H-tetrazol-5-yl)phenyl)-2-((S)-3-hydroxypyrrolidin-1-yl)ethyl)-N-methyl-2-(2-oxo-2,3-dihydrobenzo[d]oxazol-5-yl)acetamide;

(S)-2-(3-(2-(3-hydroxypyrrolidin-1-yl)-1-(2-(2-oxoindolin-6-yl)acetamido)ethyl)phenoxy)acetic acid hydrochloride;

(S)-2-(3-(2-(3-hydroxypyrrolidin-1-yl)-1-(2-(2-oxo-2,3-dihydrobenzo[d]oxazol-5-yl)acetamido)ethyl)phenoxy)acetic acid;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

(R)—N-(1-(3-((2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-1-(3-(2H-tetrazol-5-yl)phenyl)-2-((S)-3-hydroxypyrrolidin-1-yl)ethyl)-N-methyl-2-(3-methyl-2-oxo-2,3-dihydrobenzo[d]oxazol-5-yl)acetamide;

N—((S)-1-(3-cyanophenyl)-2-((S)-3-fluoropyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-fluoropyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-hydroxypyrrolidin-1-yl)ethyl)-N-methyl-2-(2-oxoindolin-6-yl)acetamide;

N—((S)-1-(3-(2H-tetrazol-5-yl)phenyl)-2-((S)-3-hydroxypyrrolidin-1-yl)ethyl)-N-methyl-2-(1-methyl-2-oxoindolin-6-yl)acetamide;

(R)—N-(1-(3-((2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-fluoropyrrolidin-1-yl)ethyl)-N-methyl-2-(2-oxoindolin-6-yl)acetamide;

(S)-2-(3-oxo-3,4-dihydro-2H-benzo[b][1,4]oxazin-6-yl)-N-(1-phenyl-2-(pyrrolidin-1-yl)ethyl)acetamide;

(S)—N-methyl-2-(2-oxo-2,3-dihydrobenzo[d]thiazol-5-yl)-N-(1-phenyl-2-(pyrrolidin-1-yl)ethyl)acetamide;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

N—((S)-2-((S)-3-hydroxypyrrolidin-1-yl)-1-phenylethyl)-N-methyl-2-(2-oxo-2,3-dihydrobenzo[d]thiazol-5-yl)acetamide;

N—((S)-2-((S)-3-hydroxypyrrolidin-1-yl)-1-phenylethyl)-2-(2-thioxo-2,3-dihydrobenzo[d]thiazol-5-yl)acetamide;

N—((S)-2-((S)-3-hydroxypyrrolidin-1-yl)-1-phenylethyl)-N-methyl-2-(2-thioxo-2,3-dihydrobenzo[d]thiazol-5-yl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)-N-methylacetamide;

(S)-2-(1,1-dioxido-3-oxo-3,4-dihydro-2H-benzo[b][1,4]thiazin-6-yl)-N-(1-phenyl-2-(pyrrolidin-1-yl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethyl)phenyl)ethyl)-N-methylacetamide;

2-(1,1-dioxido-3-oxo-3,4-dihydro-2H-benzo[b][1,4]thiazin-6-yl)-N—((S)-1-(3-fluorophenyl)-2-((S)-3-hydroxypyrrolidin-1-yl)ethyl)-N-methylacetamide;

N—((S)-1-cyclohexyl-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-methoxyphenyl)ethyl)-N-methylacetamide;

(S)-2-(3-oxo-3,4-dihydro-2H-benzo[b][1,4]thiazin-6-yl)-N-(1-phenyl-2-(pyrrolidin-1-yl)ethyl)acetamide;

N—((S)-2-((S)-3-hydroxypyrrolidin-1-yl)-1-phenylethyl)-2-(3-oxo-3,4-dihydro-2H-benzo[b][1,4]thiazin-6-yl)acetamide;

(S)—N-methyl-2-(3-oxo-3,4-dihydro-2H-benzo[b][1,4]thiazin-6-yl)-N-(1-phenyl-2-(pyrrolidin-1-yl)ethyl)acetamide;

N-(2-((S)-3-hydroxypyrrolidin-1-yl)-1-(tetrahydro-2H-pyran-4-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-methoxyphenyl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethyl)phenyl)ethyl)-N-methyl-2-(3-oxo-3,4-dihydro-2H-benzo[b][1,4]thiazin-6-yl)acetamide;

N—((S)-1-(3-fluorophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethoxy)phenyl)ethyl)-N-methyl-2-(3-oxo-3,4-dihydro-2H-benzo[b][1,4]thiazin-6-yl)acetamide;

2-(1-benzyl-2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-propylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isopropylacetamide;

N-cyclopropyl-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isobutylacetamide;

N-(cyclopropylmethyl)-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(4-(trifluoromethoxy)phenyl)ethyl)-N-methylacetamide;

2-(2,2-dimethyl-3-oxo-3,4-dihydro-2H-benzo[1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2,2,2-trifluoroethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(m-tolyl)ethyl)-N-methylacetamide;

2-(1,1-dioxido-3-oxo-3,4-dihydro-2H-benzo[b][1,4]thiazin-6-yl)-N—((S)-1-(4-fluoro-3-(trifluoromethoxy)phenyl)-2-((S)-3-hydroxypyrrolidin-1-yl)ethyl)-N-methylacetamide;

N—((S)-1-(3,5-dimethylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(2,2-dimethyl-1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-1-(3-fluoro-5-(2,2,2-trifluoroethoxy)phenyl)-2-((S)-3-hydroxypyrrolidin-1-yl)ethyl)-N-methylacetamide;

N—((S)-1-(3-cyclopropylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

N—((S)-1-(3-cyanophenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]oxazin-6-yl)acetamide;

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzoic acid;

3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)benzoic acid;

N—((S)-1-(3-cyanophenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-phenylethyl)-2-(2-oxoindolin-5-yl)acetamide;

N—((S)-1-(3-cyanophenyl)-2-((S)-3-hydroxypyrrolidin-1-yl)ethyl)-N-methyl-2-(3-oxo-3,4-dihydroquinoxalin-6-yl)acetamide;

2-(3-((S)-2-((S)-3-hydroxypyrrolidin-1-yl)-1-(N-methyl-2-(2-oxoindolin-6-yl)acetamido)ethyl)phenoxy)acetic acid;

3-((S)-2-((S)-3-hydroxypyrrolidin-1-yl)-1-(N-methyl-2-(2-oxo-2,3-dihydrobenzo[d]oxazol-5-yl)acetamido)ethyl)benzamide;

N—((S)-2-((S)-3-hydroxypyrrolidin-1-yl)-1-phenylethyl)-N-methyl-2-(2-oxoindolin-5-yl)acetamide;

N—((S)-2-((S)-3-fluoropyrrolidin-1-yl)-1-(3-(2-(methylsulfonamido)-2-oxoethoxy)phenyl)ethyl)-N-methyl-2-(2-oxoindolin-6-yl)acetamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

3-((S)-2-((S)-3-hydroxypyrrolidin-1-yl)-1-(N-methyl-2-(3-oxo-3,4-dihydroquinoxalin-6-yl)acetamido)ethyl)benzamide;

3-((S)-2-((S)-3-fluoropyrrolidin-1-yl)-1-(N-methyl-2-(2-oxoindolin-6-yl)acetamido)ethyl)benzamide;

2-(3-((S)-2-((S)-3-hydroxypyrrolidin-1-yl)-1-(N-methyl-2-(2-oxo-2,3-dihydrobenzo[d]thiazol-5-yl)acetamido)ethyl)phenoxy)acetic acid;

2-(3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)phenoxy)acetic acid;

N—(S)-1-(3-(2-amino-2-oxoethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(3-((S)-2-((S)-3-hydroxypyrrolidin-1-yl)-1-(N-methyl-2-(2-oxoindolin-5-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide;

2-(3-((S)-2-((S)-3-hydroxypyrrolidin-1-yl)-1-(N-methyl-2-(3-oxo-3,4-dihydroquinoxalin-6-yl)acetamido)ethyl)phenoxy)acetic acid;

2-(3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]oxazin-6-yl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2-(methylsulfonamido)-2-oxoethoxy)phenyl)ethyl)-N-methylacetamide;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]thiazin-6-yl)acetamide;

3-((S)-2-((S)-3-hydroxypyrrolidin-1-yl)-1-(N-methyl-2-(2-oxo-2,3-dihydrobenzo[d]oxazol-5-yl)acetamido)ethyl)benzoic acid;

3-((S)-2-((S)-3-hydroxypyrrolidin-1-yl)-1-(N-methyl-2-(2-oxoindolin-6-yl)acetamido)ethyl)-N-(methylsulfonyl)benzamide;

N—((S)-1-(3-ethynylphenyl)-2-((S)-3-hydroxypyrrolidin-1-yl)ethyl)-N-methyl-2-(3-oxo-3,4-dihydroquinoxalin-6-yl)acetamide;

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxoindolin-6-yl)acetamide;

N—((S)-1-(3-ethynylphenyl)-2-((S)-3-hydroxypyrrolidin-1-yl)ethyl)-N-methyl-2-(2-oxoindolin-6-yl)acetamide;

2-(2,2-dioxido-1,3-dihydrobenzo[c]isothiazol-6-yl)-N—((S)-2-((S)-3-hydroxypyrrolidin-1-yl)-1-(3-(5-methyl-1,2,4-oxadiazol-3-yl)phenyl)ethyl)-N-methylacetamide;

2-(2,2-dioxido-1,3-dihydrobenzo[c]isothiazol-6-yl)-N—((S)-1-(3-ethynylphenyl)-2-((S)-3-hydroxypyrrolidin-1-yl)ethyl)-N-methylacetamide;

N—((S)-2-((S)-3-hydroxypyrrolidin-1-yl)-1-(3-(5-methyl-1,2,4-oxadiazol-3-yl)phenyl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxo-2,3-dihydrobenzo[d]thiazol-5-yl)acetamide;

N—((S)-1-(3-(1,2,4-oxadiazol-3-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-(1,2,4-oxadiazol-3-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(5-(trifluoromethyl)-1,2,4-oxadiazol-3-yl)phenyl)ethyl)-N-methylacetamide 2,2,2-trifluoroacetate;

N,N-diethyl-3-((S)-2-((S)-3-hydroxypyrrolidin-1-yl)-1-(N-methyl-2-(2-oxo-2,3-dihydrobenzo[d]thiazol-5-yl)acetamido)ethyl)benzamide;

N—((S)-1-(3-(1,2,4-oxadiazol-3-yl)phenyl)-2-((S)-3-hydroxypyrrolidin-1-yl)ethyl)-N-methyl-2-(2-oxo-2,3-dihydrobenzo[d]thiazol-5-yl)acetamide 2,2,2-trifluoroacetate;

N—((S)-1-(3-(1,2,4-oxadiazol-3-yl)phenyl)-2-((S)-3-hydroxypyrrolidin-1-yl)ethyl)-N-methyl-2-(3-oxo-3,4-dihydroquinoxalin-6-yl)acetamide 2,2,2-trifluoroacetate;

N—((S)-1-(3-(1H-imidazol-2-yl)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(thiazol-2-yl)phenyl)ethyl)-N-methyl-2-(2-oxo-2,3-dihydrobenzo[d]thiazol-5-yl)acetamide;

N—((S)-1-(3-cyano-5-fluorophenyl)-2-((S)-3-hydroxypyrrolidin-1-yl)ethyl)-N-methyl-2-(2-oxo-2,3-dihydrobenzo[d]thiazol-5-yl)acetamide hydrochloride;

N—((S)-2-((S)-3-hydroxypyrrolidin-1-yl)-1-(3-(5-methyl-1,2,4-oxadiazol-3-yl)phenyl)ethyl)-N-methyl-2-(3-oxo-3,4-dihydroquinoxalin-6-yl)acetamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N-(2,2,2-trifluoroethyl)benzamide;

3-((S)-2-((S)-3-hydroxypyrrolidin-1-yl)-1-(N-methyl-2-(3-oxo-3,4-dihydroquinoxalin-6-yl)acetamido)ethyl)-N-(2,2,2-trifluoroethyl)benzamide;

N—((S)-1-(3-cyano-5-fluorophenyl)-2-((S)-3-hydroxypyrrolidin-1-yl)ethyl)-N-methyl-2-(2-oxoindolin-6-yl)acetamide;

N—((S)-1-(3-(1H-imidazol-2-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-cyano-5-fluorophenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-cyano-5-fluorophenyl)-2-((S)-3-hydroxypyrrolidin-1-yl)ethyl)-N-methyl-2-(3-oxo-3,4-dihydroquinoxalin-6-yl)acetamide;

2-(1,1-dioxido-3-oxo-3,4-dihydro-2H-benzo[b][1,4]thiazin-6-yl)-N—((S)-1-(3-ethynylphenyl)-2-((S)-3-hydroxypyrrolidin-1-yl)ethyl)-N-methylacetamide;

N—((S)-1-(3-(1H-imidazol-2-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-cyanophenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-(but-1-yn-1-yl)phenyl)-2-((S)-3-hydroxypyrrolidin-1-yl)ethyl)-N-methyl-2-(2-oxoindolin-6-yl)acetamide;

N—((S)-1-(3-(but-1-yn-1-yl)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-(but-1-yn-1-yl)phenyl)-2-((S)-3-hydroxypyrrolidin-1-yl)ethyl)-N-methyl-2-(3-oxo-3,4-dihydroquinoxalin-6-yl)acetamide;

3-((S)-2-((S)-3-hydroxypyrrolidin-1-yl)-1-(N-methyl-2-(2-oxoindolin-6-yl)acetamido)ethyl)-N,N-dimethylbenzamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-diethylbenzamide;

N,N-diethyl-3-((S)-2-((S)-3-hydroxypyrrolidin-1-yl)-1-(N-methyl-2-(3-oxo-3,4-dihydroquinoxalin-6-yl)acetamido)ethyl)benzamide 2,2,2-trifluoroacetate;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-dimethylbenzamide;

3-((S)-2-((S)-3-hydroxypyrrolidin-1-yl)-1-(N-methyl-2-(3-oxo-3,4-dihydroquinoxalin-6-yl)acetamido)ethyl)-N,N-dimethylbenzamide;

N—((S)-1-(3-(1,2,4-oxadiazol-3-yl)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide 2,2,2-trifluoroacetate;

N—((S)-2-((S)-3-hydroxypyrrolidin-1-yl)-1-(3-(1-methyl-1H-imidazol-2-yl)phenyl)ethyl)-N-methyl-2-(2-oxoindolin-6-yl)acetamide;

N—((S)-1-(3-(5-ethyl-1,2,4-oxadiazol-3-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(thiazol-5-yl)phenyl)ethyl)-N-methyl-2-(2-oxoindolin-6-yl)acetamide;

N—((S)-2-((S)-3-hydroxypyrrolidin-1-yl)-1-(3-(thiazol-4-yl)phenyl)ethyl)-N-methyl-2-(2-oxoindolin-6-yl)acetamide;

N—((S)-2-((S)-3-hydroxypyrrolidin-1-yl)-1-(3-(4-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(2-methylthiazol-5-yl)phenyl)ethyl)-N-methyl-2-(2-oxoindolin-6-yl)acetamide;

N—((S)-2-((S)-3-hydroxypyrrolidin-1-yl)-1-(3-(2-methylthiazol-4-yl)phenyl)ethyl)-N-methyl-2-(2-oxoindolin-6-yl)acetamide;

N—((S)-2-((S)-3-hydroxypyrrolidin-1-yl)-1-(3-(5-methyl-1,3,4-thiadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-5-yl)phenyl)ethyl)-N-methyl-2-(2-oxoindolin-6-yl)acetamide;

N—((S)-1-(3-(1,3,4-oxadiazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methyl-1,3,4-oxadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-4-yl)phenyl)ethyl)-N-methyl-2-(2-oxoindolin-6-yl)acetamide;

N—((S)-1-(3-(1-(cyclopropylmethyl)-1H-imidazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(3-methyl-1,2,4-oxadiazol-5-yl)phenyl)ethyl)-N-methyl-2-(2-oxoindolin-6-yl)acetamide; and 3-((S)-2-((S)-3-hydroxypyrrolidin-1-yl)-1-(N-methyl-2-(2-oxo-2,3-dihydrobenzo[d]thiazol-5-yl)acetamido)ethyl)-N-(2,2,2-trifluoroethyl)benzamide;

or stereoisomers thereof or pharmaceutically acceptable salts thereof.

In one embodiment, compounds of formula (I) are 2-(3,3-difluoro-2-oxoindolin-6-yl)-N—((S)-2-((S)-3-hydroxypyrrolidin-1-yl)-1-phenylethyl)-N-methylacetamide;

2-(3,3-difluoro-2-oxoindolin-6-yl)-N—((S)-2-((S)-3-hydroxypyrrolidin-1-yl)-1-phenylethyl) acetamide;

3-((S)-2-((S)-3-hydroxypyrrolidin-1-yl)-1-(N-methyl-2-(2-oxoindolin-6-yl)acetamido)ethyl) benzoic acid;

3-((S)-2-((S)-3-hydroxypyrrolidin-1-yl)-1-(N-methyl-2-(2-oxoindolin-6-yl)acetamido)ethyl) benzamide;

N—((S)-1-(3-(2-amino-2-oxoethoxy)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(2-(methylsulfonamido)-2-oxoethoxy)phenyl)ethyl)-N-methyl-2-(2-oxoindolin-6-yl)acetamide;

3-((S)-2-((S)-3-fluoropyrrolidin-1-yl)-1-(N-methyl-2-(2-oxoindolin-6-yl)acetamido)ethyl) benzoic acid;

N—((S)-2-((S)-3-hydroxypyrrolidin-1-yl)-1-(3-(5-methyl-1,2,4-oxadiazol-3-yl)phenyl)ethyl)-N-methyl-2-(2-oxoindolin-6-yl)acetamide;

N—((S)-2-((S)-3-hydroxypyrrolidin-1-yl)-1-(3-(thiazol-2-yl)phenyl)ethyl)-N-methyl-2-(2-oxoindolin-6-yl)acetamide;

3-((S)-2-((S)-3-hydroxypyrrolidin-1-yl)-1-(N-methyl-2-(2-oxoindolin-6-yl)acetamido)ethyl)-N-(2,2,2-trifluoroethyl)benzamide;

N,N-diethyl-3-((S)-2-((S)-3-hydroxypyrrolidin-1-yl)-1-(N-methyl-2-(2-oxoindolin-6-yl)acetamido)ethyl)benzamide;

N—((S)-1-(3-(2-(diethylamino)-2-oxoethoxy)phenyl)-2-((S)-3-hydroxypyrrolidin-1-yl)ethyl)-N-methyl-2-(2-oxoindolin-6-yl)acetamide;

N—((S)-1-(3-fluoro-5-(thiazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(2-methyl-2H-tetrazol-5-yl)phenyl)ethyl)-N-methyl-2-(2-oxoindolin-6-yl)acetamide;

N—((S)-2-((S)-3-hydroxypyrrolidin-1-yl)-1-phenylethyl)-2-(2-oxoindolin-6-yl)acetamide;

N—((S)-1-cyclohexyl-2-((S)-3-hydroxypyrrolidin-1-yl)ethyl)-N-methyl-2-(2-oxoindolin-6-yl)acetamide;

N—((S)-1-cyclohexyl-2-((S)-3-hydroxypyrrolidin-1-yl)ethyl)-2-(2-oxoindolin-6-yl)acetamide;

2-(3-(1-(N-methyl-2-(2-oxoindolin-6-yl)acetamido)-2-(pyrrolidin-1-yl)ethyl)phenoxy)acetic acid hydrochloride;

2-(3-(1-(2-(2-oxoindolin-6-yl)acetamido)-2-(pyrrolidin-1-yl)ethyl)phenoxy)acetic acid;

(S)-2-(3-(2-(3-hydroxypyrrolidin-1-yl)-1-(N-methyl-2-(2-oxoindolin-6-yl) acetamido)ethyl)phenoxy)acetic acid hydrochloride;

(S)-2-(3-(2-(3-hydroxypyrrolidin-1-yl)-1-(2-(2-oxoindolin-6-yl)acetamido)ethyl)phenoxy)acetic acid hydrochloride;

N—((S)-1-(3-(2H-tetrazol-5-yl)phenyl)-2-((S)-3-hydroxypyrrolidin-1-yl)ethyl)-N-methyl-2-(2-oxoindolin-6-yl)acetamide;

N—((S)-1-(3-(2H-tetrazol-5-yl)phenyl)-2-((S)-3-hydroxypyrrolidin-1-yl)ethyl)-N-methyl-2-(1-methyl-2-oxoindolin-6-yl)acetamide;

N—((S)-1-(3-(2H-tetrazol-5-yl)phenyl)-2-((S)-3-fluoropyrrolidin-1-yl)ethyl)-N-methyl-2-(2-oxoindolin-6-yl)acetamide;

N—((S)-1-(3-cyanophenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-phenylethyl)-2-(2-oxoindolin-5-yl)acetamide;

2-(3-((S)-2-((S)-3-hydroxypyrrolidin-1-yl)-1-(N-methyl-2-(2-oxoindolin-6-yl)acetamido)ethyl)phenoxy)acetic acid;

N—((S)-2-((S)-3-hydroxypyrrolidin-1-yl)-1-phenylethyl)-N-methyl-2-(2-oxoindolin-5-yl)acetamide;

N—((S)-2-((S)-3-fluoropyrrolidin-1-yl)-1-(3-(2-(methylsulfonamido)-2-oxoethoxy)phenyl)ethyl)-N-methyl-2-(2-oxoindolin-6-yl)acetamide;

3-((S)-2-((S)-3-fluoropyrrolidin-1-yl)-1-(N-methyl-2-(2-oxoindolin-6-yl)acetamido)ethyl) benzamide;

2-(3-((S)-2-((S)-3-hydroxypyrrolidin-1-yl)-1-(N-methyl-2-(2-oxoindolin-5-yl)acetamido)ethyl)phenoxy)acetic acid;

3-((S)-2-((S)-3-hydroxypyrrolidin-1-yl)-1-(N-methyl-2-(2-oxoindolin-6-yl)acetamido)ethyl)-N-(methylsulfonyl) benzamide;

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxoindolin-6-yl)acetamide;

N—((S)-1-(3-ethynylphenyl)-2-((S)-3-hydroxypyrrolidin-1-yl)ethyl)-N-methyl-2-(2-oxoindolin-6-yl)acetamide;

N—((S)-1-(3-(1,2,4-oxadiazol-3-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-cyano-5-fluorophenyl)-2-((S)-3-hydroxypyrrolidin-1-yl)ethyl)-N-methyl-2-(2-oxoindolin-6-yl)acetamide;

N—((S)-1-(3-(1H-imidazol-2-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-(but-1-yn-1-yl)phenyl)-2-((S)-3-hydroxypyrrolidin-1-yl)ethyl)-N-methyl-2-(2-oxoindolin-6-yl)acetamide;

3-((S)-2-((S)-3-hydroxypyrrolidin-1-yl)-1-(N-methyl-2-(2-oxoindolin-6-yl)acetamido)ethyl)-N,N-dimethylbenzamide;

N—((S)-1-(3-(1-methyl-1H-imidazol-2-yl)phenyl)-2-((S)-3-hydroxypyrrolidin-1-yl)ethyl)-N-methyl-2-(2-oxoindolin-6-yl)acetamide;

N—((S)-1-(3-(5-ethyl-1,2,4-oxadiazol-3-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(thiazol-5-yl)phenyl)ethyl)-N-methyl-2-(2-oxoindolin-6-yl)acetamide;

N—((S)-2-((S)-3-hydroxypyrrolidin-1-yl)-1-(3-(thiazol-4-yl)phenyl)ethyl)-N-methyl-2-(2-oxoindolin-6-yl)acetamide;

N—((S)-2-((S)-3-hydroxypyrrolidin-1-yl)-1-(3-(4-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(2-methylthiazol-5-yl)phenyl)ethyl)-N-methyl-2-(2-oxoindolin-6-yl)acetamide;

N—((S)-2-((S)-3-hydroxypyrrolidin-1-yl)-1-(3-(2-methyl-thiazol-4-yl)phenyl)ethyl)-N-methyl-2-(2-oxoindolin-6-yl)acetamide;

N—((S)-2-((S)-3-hydroxypyrrolidin-1-yl)-1-(3-(5-methyl-1,3,4-thiadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-5-yl)phenyl)ethyl)-N-methyl-2-(2-oxoindolin-6-yl)acetamide;

N—((S)-1-(3-(1,3,4-oxadiazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methyl-1,3,4-oxadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-4-yl)phenyl)ethyl)-N-methyl-2-(2-oxoindolin-6-yl)acetamide;

N—((S)-1-(3-(1-(cyclopropylmethyl)-1H-imidazol-2-yl)phenyl)-2-((S)-3-hydroxypyrrolidin-1-yl)ethyl)-N-methyl-2-(2-oxoindolin-6-yl)acetamide; and N—((S)-2-((S)-3-hydroxypyrrolidin-1-yl)-1-(3-(3-methyl-1,2,4-oxadiazol-5-yl)phenyl)ethyl)-N-methyl-2-(2-oxoindolin-6-yl)acetamide;

stereoisomers thereof or pharmaceutically acceptable salts thereof.

In one embodiment, compounds of formula (I) are

N—((S)-1-(3-cyanophenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

N—((S)-1-(3-(difluoromethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(1,1-dioxido-3-oxo-3,4-dihydro-2H-benzo[b][1,4]thiazin-6-yl)-N-ethyl-N—((S)-2-((S)-3-hydroxypyrrolidin-1-yl)-1-(3-(trifluoromethoxy)phenyl)ethyl)acetamide;

N—((S)-2-((S)-3-hydroxypyrrolidin-1-yl)-1-phenylethyl)-N-methyl-2-(3-oxo-3,4-dihydro-2H-benzo[b][1,4]thiazin-6-yl)acetamide;

N—((S)-1-(3-(1,2,4-oxadiazol-3-yl)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide2,2,2-trifluoroacetate;

2-(1,1-dioxido-3-oxo-3,4-dihydro-2H-benzo[b][1,4]thiazin-6-yl)-N—((S)-2-((S)-3-methoxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-(2,2,2-trifluoroethyl)acetamide 2,2,2-trifluoroacetate;

2-(1,1-dioxido-3-oxo-3,4-dihydro-2H-benzo[b][1,4]thiazin-6-yl)-N-(2-((S)-3-hydroxy pyrrolidin-1-yl)-1-(tetrahydro-2H-pyran-4-yl)ethyl)-N-methylacetamide-2,2,2-trifluoroacetate;

2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetic acid;

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)-N-methylacetamide;

(S)-2-(1,1-dioxido-3-oxo-3,4-dihydro-2H-benzo[b][1,4]thiazin-6-yl)-N-(1-phenyl-2-(pyrrolidin-1-yl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethyl)phenyl)ethyl)-N-methylacetamide;

2-(1,1-dioxido-3-oxo-3,4-dihydro-2H-benzo[b][1,4]thiazin-6-yl)-N—((S)-1-(3-fluorophenyl)-2-((S)-3-hydroxypyrrolidin-1-yl)ethyl)-N-methylacetamide;

N—((S)-1-cyclohexyl-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-methoxyphenyl)ethyl)-N-methylacetamide;

(S)-2-(3-oxo-3,4-dihydro-2H-benzo[b][1,4]thiazin-6-yl)-N-(1-phenyl-2-(pyrrolidin-1-yl)ethyl)acetamide;

N—((S)-2-((S)-3-hydroxypyrrolidin-1-yl)-1-phenylethyl)-2-(3-oxo-3,4-dihydro-2H-benzo[b][1,4]thiazin-6-yl)acetamide;

(S)—N-methyl-2-(3-oxo-3,4-dihydro-2H-benzo[b][1,4]thiazin-6-yl)-N-(1-phenyl-2-(pyrrolidin-1-yl)ethyl)acetamide;

N-(2-((S)-3-hydroxypyrrolidin-1-yl)-1-(tetrahydro-2H-pyran-4-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-methoxyphenyl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethyl)phenyl)ethyl)-N-methyl-2-(3-oxo-3,4-dihydro-2H-benzo[b][1,4]thiazin-6-yl)acetamide;

N—((S)-1-(3-fluorophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethoxy)phenyl)ethyl)-N-methyl-2-(3-oxo-3,4-dihydro-2H-benzo[b][1,4]thiazin-6-yl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-propylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isopropylacetamide;

N-cyclopropyl-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isobutylacetamide;

N-(cyclopropylmethyl)-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(4-(trifluoromethoxy)phenyl)ethyl)-N-methylacetamide;

2-(2,2-dimethyl-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2,2,2-trifluoroethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(m-tolyl)ethyl)-N-methylacetamide;

2-(1,1-dioxido-3-oxo-3,4-dihydro-2H-benzo[b][1,4]thiazin-6-yl)-N—((S)-1-(4-fluoro-3-(trifluoromethoxy)phenyl)-2-((S)-3-hydroxypyrrolidin-1-yl)ethyl)-N-methylacetamide;

N—((S)-1-(3,5-dimethylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(2,2-dimethyl-1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-1-(3-fluoro-5-(2,2,2-trifluoroethoxy)phenyl)-2-((S)-3-hydroxypyrrolidin-1-yl)ethyl)-N-methylacetamide;

N—((S)-1-(3-cyclopropylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzoic acid;

N—((S)-1-(3-(2-amino-2-oxoethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)phenoxy)acetic acid;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2-(methylsulfonamido)-2-oxoethoxy)phenyl)ethyl)-N-methylacetamide;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]thiazin-6-yl)acetamide;

2-(1,1-dioxido-3-oxo-3,4-dihydro-2H-benzo[b][1,4]thiazin-6-yl)-N—((S)-1-(3-ethynylphenyl)-2-((S)-3-hydroxypyrrolidin-1-yl)ethyl)-N-methylacetamide;

stereoisomers thereof or pharmaceutically acceptable salts thereof.

In one embodiment, compounds of formula (I) are
2-(1,1-dioxido-3-oxo-2,3-dihydrobenzo[d]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(trifluoromethyl)phenyl)ethyl)-N-methylacetamide;

5-(2-(((S)-2-((S)-3-hydroxypyrrolidin-1-yl)-1-phenylethyl)(methyl)amino)-2-oxoethyl)-1,3-dihydrobenzo[c]isothiazol-1-ium 2,2-dioxide 2,2,2-trifluoroacetate;

N—((S)-1-(3-(1H-tetrazol-5-yl)phenyl)-2-((S)-3-hydroxypyrrolidin-1-yl)ethyl)-N-methyl-2-(1-methyl-2,2-dioxido-1,3-dihydrobenzo[c]isothiazol-6-yl)acetamide;

N—((S)-1-(3-(but-1-yn-1-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

(S)—N-methyl-2-(3-methyl-2,2-dioxido-1,3-dihydrobenzo[c]isothiazol-5-yl)-N-(1-phenyl-2-(pyrrolidin-1-yl)ethyl)acetamide;

N—((S)-1-(3-(1H-tetrazol-5-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(3-((S)-2-((S)-3-hydroxypyrrolidin-1-yl)-1-(N-methyl-2-(1-methyl-2,2-dioxido-1,3-dihydrobenzo[c]isothiazol-6-yl)acetamido)ethyl)phenoxy) acetic acid;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(1-benzyl-2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(5-methyl-1,2,4-oxadiazol-3-yl)phenyl)ethyl)-N-methylacetamide;

2-(2,2-dioxido-1,3-dihydrobenzo[c]isothiazol-6-yl)-N—((S)-1-(3-ethynylphenyl)-2-((S)-3-hydroxypyrrolidin-1-yl)ethyl)-N-methylacetamide;

N—((S)-1-(3-(1,2,4-oxadiazol-3-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(5-(trifluoromethyl)-1,2,4-oxadiazol-3-yl)phenyl)ethyl)-N-methylacetamide 2,2,2-trifluoroacetate;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N-(2,2,2-trifluoroethyl)benzamide;

N—((S)-1-(3-(1H-imidazol-2-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-cyanophenyl)-2-((S)-3-hydroxypyrrolidin-1-yl)ethyl)-2-(2,2-dioxido-1,3-dihydrobenzo[c]isothiazol-6-yl)-N-methylacetamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-diethylbenzamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-dimethylbenzamide;

N—((S)-1-(3-cyano-5-fluorophenyl)-2-((S)-3-hydroxypyrrolidin-1-yl)ethyl)-2-(2,2-dioxido-1,3-dihydrobenzo[c]isothiazol-6-yl)-N-methylacetamide;

stereoisomers thereof or pharmaceutically acceptable salts thereof.

In one embodiment, compounds of formula (I) are
3-((S)-2-((S)-3-hydroxypyrrolidin-1-yl)-1-(N-methyl-2-(2-oxo-2,3-dihydrobenzo[d]thiazol-5-yl)acetamido)ethyl) benzoic acid;

(S)—N-methyl-2-(2-oxo-2,3-dihydrobenzo[d]thiazol-5-yl)-N-(1-phenyl-2-(pyrrolidin-1-yl)ethyl)acetamide;

N—((S)-2-((S)-3-hydroxypyrrolidin-1-yl)-1-phenylethyl)-N-methyl-2-(2-oxo-2,3-dihydrobenzo[d]thiazol-5-yl)acetamide;

N,N-diethyl-3-((S)-2-((S)-3-hydroxypyrrolidin-1-yl)-1-(N-methyl-2-(2-oxo-2,3-dihydrobenzo[d]thiazol-5-yl)acetamido)ethyl)benzamide;

N—((S)-1-(3-(1,2,4-oxadiazol-3-yl)phenyl)-2-((S)-3-hydroxypyrrolidin-1-yl)ethyl)-N-methyl-2-(2-oxo-2,3-dihydrobenzo[d]thiazol-5-yl)acetamide 2,2,2-trifluoroacetate;

N—((S)-1-(3-(but-1-yn-1-yl)phenyl)-2-((S)-3-hydroxypyrrolidin-1-yl)ethyl)-N-methyl-2-(2-oxo-2,3-dihydrobenzo[d]thiazol-5-yl)acetamide;

3-((S)-2-((S)-3-hydroxypyrrolidin-1-yl)-1-(N-methyl-2-(2-oxo-2,3-dihydrobenzo[d]thiazol-5-yl)acetamido)ethyl)-N-(2,2,2-trifluoroethyl)benzamide;

N—((S)-1-(3-(1H-imidazol-2-yl)phenyl)-2-((S)-3-hydroxy-pyrrolidin-1-yl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(thiazol-2-yl)phenyl)ethyl)-N-methyl-2-(2-oxo-2,3-dihydrobenzo[d]thiazol-5-yl)acetamide;

N—((S)-1-(3-cyano-5-fluorophenyl)-2-((S)-3-hydroxypyrrolidin-1-yl)ethyl)-N-methyl-2-(2-oxo-2,3-dihydrobenzo[d]thiazol-5-yl)acetamide hydrochloride stereoisomers thereof or pharmaceutically acceptable salts thereof.

In another embodiment, compounds of formula (I) are 3-((S)-2-((S)-3-hydroxypyrrolidin-1-yl)-1-(N-methyl-2-(3-oxo-3,4-dihydroquinoxalin-6-yl)acetamido)ethyl)-N-(2,2,2-trifluoroethyl)benzamide;

N—((S)-1-(3-cyanophenyl)-2-((S)-3-hydroxypyrrolidin-1-yl)ethyl)-N-methyl-2-(3-oxo-3,4-dihydroquinoxalin-6-yl)acetamide;

3-((S)-2-((S)-3-hydroxypyrrolidin-1-yl)-1-(N-methyl-2-(3-oxo-3,4-dihydroquinoxalin-6-yl)acetamido)ethyl)benzamide;

2-(3-((S)-2-((S)-3-hydroxypyrrolidin-1-yl)-1-(N-methyl-2-(3-oxo-3,4-dihydroquinoxalin-6-yl)acetamido)ethyl)phenoxy)acetic acid;

N—((S)-1-(3-ethynylphenyl)-2-((S)-3-hydroxypyrrolidin-1-yl)ethyl)-N-methyl-2-(3-oxo-3,4-dihydroquinoxalin-6-yl)acetamide;

N—((S)-1-(3-(1,2,4-oxadiazol-3-yl)phenyl)-2-((S)-3-hydroxypyrrolidin-1-yl)ethyl)-N-methyl-2-(3-oxo-3,4-dihydroquinoxalin-6-yl)acetamide 2,2,2-trifluoroacetate;

N—((S)-2-((S)-3-hydroxypyrrolidin-1-yl)-1-(3-(5-methyl-1,2,4-oxadiazol-3-yl)phenyl)ethyl)-N-methyl-2-(3-oxo-3,4-dihydroquinoxalin-6-yl)acetamide;

N—((S)-1-(3-cyano-5-fluorophenyl)-2-((S)-3-hydroxypyrrolidin-1-yl)ethyl)-N-methyl-2-(3-oxo-3,4-dihydroquinoxalin-6-yl)acetamide;

N—((S)-1-(3-(but-1-yn-1-yl)phenyl)-2-((S)-3-hydroxypyrrolidin-1-yl)ethyl)-N-methyl-2-(3-oxo-3,4-dihydroquinoxalin-6-yl)acetamide;

N,N-diethyl-3-((S)-2-((S)-3-hydroxypyrrolidin-1-yl)-1-(N-methyl-2-(3-oxo-3,4-dihydroquinoxalin-6-yl)acetamido)ethyl)benzamide 2,2,2-trifluoroacetate;

3-((S)-2-((S)-3-hydroxypyrrolidin-1-yl)-1-(N-methyl-2-(3-oxo-3,4-dihydroquinoxalin-6-yl)acetamido)ethyl)-N,N-dimethylbenzamide;

stereoisomers thereof or pharmaceutically acceptable salts thereof.

In another embodiment, compounds of formula (I) are (S)—N-methyl-2-(2-oxo-1,2-dihydroquinolin-7-yl)-N-(1-phenyl-2-(pyrrolidin-1-yl)ethyl) acetamide;

N—((S)-2-((R)-3-hydroxypyrrolidin-1-yl)-1-phenylethyl)-2-(2-oxo-1,2-dihydroquinolin-6-yl)acetamide;

N—((S)-2-((S)-3-hydroxypyrrolidin-1-yl)-1-phenylethyl)-N-methyl-2-(2-oxo-1,2-dihydroquinolin-7-yl)acetamide;

stereoisomers thereof or pharmaceutically acceptable salts thereof.

In another embodiment, compounds of formula (I) are

N—((S)-2-((S)-3-hydroxypyrrolidin-1-yl)-1-phenylethyl)-2-(3-methyl-2-oxo-2,3-dihydrobenzo[d]oxazol-5-yl)acetamide;

(S)-2-(3-methyl-2-oxo-2,3-dihydrobenzo[d]oxazol-5-yl)-N-(1-phenyl-2-(pyrrolidin-1-yl)ethyl)acetamide;

N-(1-(1-benzyl-1H-pyrazol-4-yl)-2-(pyrrolidin-1-yl)ethyl)-2-(2-oxo-2,3-dihydrobenzo[d]oxazol-5-yl)acetamide;

(S)-t-butyl-2-(3-(1-(2-(3-benzyl-2-oxo-2,3-dihydrobenzo[d]oxazol-5-yl)acetamido)-2-(pyrrolidin-1-yl)ethyl)phenoxy)acetate;

(S)-2-(3-benzyl-2-oxo-2,3-dihydrobenzo[d]oxazol-5-yl)-N-(1-(3-(benzyloxy)phenyl)-2-(pyrrolidin-1-yl)ethyl)-N-methylacetamide;

N—((S)-2-((S)-3-hydroxypyrrolidin-1-yl)-1-phenylethyl)-2-(2-oxo-2,3-dihydrobenzo[d]oxazol-5-yl)acetamide;

(S)-2-(3-benzyl-2-oxo-2,3-dihydrobenzo[d]oxazol-5-yl)-N-(1-(3-(4-methoxybenzyloxy)phenyl)-2-(pyrrolidin-1-yl)ethyl)acetamide;

2-(3-(4-cyanobenzyl)-2-oxo-2,3-dihydrobenzo[d]oxazol-5-yl)-N—((S)-2-((S)-3-hydroxy pyrrolidin-1-yl)-1-phenylethyl)acetamide;

2-(3-(3-cyanobenzyl)-2-oxo-2,3-dihydrobenzo[d]oxazol-5-yl)-N—((S)-2-((S)-3-hydroxy pyrrolidin-1-yl)-1-phenylethyl)-N-methylacetamide;

N—((S)-1-cyclohexyl-2-((S)-3-hydroxypyrrolidin-1-yl)ethyl)-2-(2-oxo-2,3-dihydrobenzo[d]oxazol-5-yl)acetamide;

(S)-tert-butyl-2-(3-(1-(2-(3-benzyl-2-oxo-2,3-dihydrobenzo[d]oxazol-5-yl)-N-methyl acetamido)-2-(pyrrolidin-1-yl)ethyl)phenoxy)acetate;

N—((S)-1-cyclohexyl-2-((S)-3-hydroxypyrrolidin-1-yl)ethyl)-N-methyl-2-(2-oxo-2,3-dihydrobenzo[d]oxazol-5-yl)acetamide;

(S)—N-(1-(3-cyanophenyl)-2-(pyrrolidin-1-yl)ethyl)-N-methyl-2-(2-oxo-2,3-dihydrobenzo[d]oxazol-5-yl)acetamide;

2-(3-(3-cyanobenzyl)-2-oxo-2,3-dihydrobenzo[d]oxazol-5-yl)-N—((S)-2-((S)-3-hydroxy pyrrolidin-1-yl)-1-phenylethyl)acetamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

(S)-tert-butyl 2-(3-(2-(3-hydroxypyrrolidin-1-yl)-1-(2-(2-oxo-2,3-dihydro benzo[d]oxazol-5-yl)acetamido)ethyl)phenoxy)acetate;

2-(3-(4-cyanobenzyl)-2-oxo-2,3-dihydrobenzo[d]oxazol-5-yl)-N—((S)-2-((S)-3-hydroxy pyrrolidin-1-yl)-1-phenylethyl)-N-methylacetamide;

N-(1-(3-(cyanomethoxy)phenyl)-2-(3-hydroxypyrrolidin-1-yl)ethyl)-N-methyl-2-(2-oxo-2,3-dihydrobenzo[d]oxazol-5-yl)acetamide;

tert-butyl 2-(3-((S)-2-((R)-3-hydroxypyrrolidin-1-yl)-1-(N-methyl-2-(2-oxo-2,3-dihydro benzo[d]oxazol-5-yl)acetamido)ethyl)phenoxy)acetate;

N—((S)-1-(3-cyanophenyl)-2-((S)-3-hydroxypyrrolidin-1-yl)ethyl)-N-methyl-2-(3-methyl-2-oxo-2,3-dihydrobenzo[d]oxazol-5-yl)acetamide;

(S)-methyl 3-((2-oxo-5-(2-oxo-2-(1-phenyl-2-(pyrrolidin-1-yl)ethylamino)ethyl)benzo[d]oxazol-3(2H)-yl)methyl)benzoate;

(S)-tert-butyl-2-(2-oxo-5-(2-oxo-2-(1-phenyl-2-(pyrrolidin-1-yl)ethylamino)ethyl)benzo[d]oxazol-3(2H)-yl)acetate;

(S)-2-(2-oxo-5-(2-oxo-2-(1-phenyl-2-(pyrrolidin-1-yl)ethylamino)ethyl) benzo[d]oxazol-3(2H)-yl)acetic acid hydrochloride;

3-((5-(2-(((S)-2-((S)-3-hydroxypyrrolidin-1-yl)-1-phenylethyl)(methyl)amino)-2-oxoethyl)-2-oxobenzo[d]oxazol-3(2H)-yl)methyl)benzamide;

(S)-2-(3-benzyl-2-oxo-2,3-dihydrobenzo[d]oxazol-5-yl)-N-(1-(3-hydroxyphenyl)-2-(pyrrolidin-1-yl)ethyl)-N-methylacetamide;

2-(3-((S)-2-((R)-3-hydroxypyrrolidin-1-yl)-1-(N-methyl-2-(2-oxo-2,3-dihydrobenzo[d]oxazol-5-yl)acetamido)ethyl)phenoxy)acetic acid;

2-(5-(2-(((S)-1-cyclohexyl-2-((S)-3-hydroxypyrrolidin-1-yl)ethyl)(methyl)amino)-2-oxoethyl)-2-oxobenzo[d]oxazol-3(2H)-yl)acetic acid;

Methyl 4-((5-(2-(((S)-2-((S)-3-hydroxypyrrolidin-1-yl)-1-phenylethyl)(methyl)amino)-2-oxoethyl)-2-oxobenzo[d]oxazol-3(2H)-yl)methyl)benzoate;

N—((S)-1-(3-(2H-tetrazol-5-yl)phenyl)-2-((S)-3-hydroxypyrrolidin-1-yl)ethyl)-N-methyl-2-(2-oxo-2,3-dihydrobenzo[d]oxazol-5-yl)acetamide;

(S)-2-(3-(2-(3-hydroxypyrrolidin-1-yl)-1-(2-(2-oxo-2,3-dihydrobenzo[d]oxazol-5-yl)acetamido)ethyl)phenoxy)acetic acid;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

(R)—N-(1-(3-((2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-1-(3-(2H-tetrazol-5-yl)phenyl)-2-((S)-3-hydroxypyrrolidin-1-yl)ethyl)-N-methyl-2-(3-methyl-2-oxo-2,3-dihydrobenzo[d]oxazol-5-yl)acetamide;

N—((S)-1-(3-cyanophenyl)-2-((S)-3-fluoropyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-fluoropyrrolidin-1-yl)ethyl)-N-methyl-2-(2-oxo-2,3-dihydrobenzo[d]oxazol-5-yl)acetamide;

(R)—N-(1-(3-((2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide;

3-((S)-2-((S)-3-hydroxypyrrolidin-1-yl)-1-(N-methyl-2-(2-oxo-2,3-dihydrobenzo[d]oxazol-5-yl)acetamido)ethyl)benzamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

3-((S)-2-((S)-3-hydroxypyrrolidin-1-yl)-1-(N-methyl-2-(2-oxo-2,3-dihydrobenzo[d]oxazol-5-yl)acetamido)ethyl)benzoic acid;

stereoisomers thereof or pharmaceutically acceptable salts thereof.

In another embodiment, compounds of formula (I) are
(S)-2-(3-oxo-3,4-dihydro-2H-benzo[b][1,4]oxazin-6-yl)-N-(1-phenyl-2-(pyrrolidin-1-yl)ethyl)acetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]oxazin-6-yl)acetamide;

3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)benzoic acid;

2-(3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]oxazin-6-yl)acetamide;

stereoisomers thereof or pharmaceutically acceptable salts thereof.

In one embodiment, the present application provides compounds of formula (I) as κ opioid receptor (KOR) agonists.

In another embodiment, the application is directed to pharmaceutical compositions comprising a pharmaceutically acceptable carrier and an effective amount of a compound of formula (I), stereoisomer thereof or pharmaceutically acceptable salt thereof.

In another embodiment, the application is directed to a method for binding opioid receptor, in a patient in need thereof, comprising administering to said patient a composition comprising an effective amount of a compound of formula (I) or stereoisomer thereof or pharmaceutically acceptable salt thereof.

In other embodiment, the application is directed to a method of treating or preventing gastrointestinal dysfunction, in a patient in need thereof, comprising administering to said patient a composition comprising an effective amount of a compound of formula (I), stereoisomer thereof or pharmaceutically acceptable salt thereof.

In other embodiment, the application is directed to a method of treating or preventing pain, to a patient in need thereof, comprising administering to said patient a composition comprising an effective amount of a compound of formula (I), stereoisomer thereof or pharmaceutically acceptable salt thereof.

In another embodiment, the pain is selected from chronic pain or acute pain.

In another embodiment, the pain is selected from the group consisting of nociceptive pain, inflammatory pain, visceral pain, somatic pain, neuralgia, neuropathic pain, AIDS pain, cancer pain, phantom pain, psychogenic pain, pain resulting from hyperalgesia, pain caused by rheumatoid arthritis, migraine and allodynia.

In another embodiments, the application is directed to a method of treating or preventing ileus, in a patient in need thereof, comprising administering to said patient a composition comprising an effective amount of a compound of formula (I), stereoisomer thereof or pharmaceutically acceptable salt thereof.

In another embodiment, the compounds of formula (I), stereoisomers thereof or pharmaceutically acceptable salt thereof, are directed to the use in treating or preventing diseases or disorders that may be associated with and/or modulated by opioid receptors.

In another embodiment, the compounds of formula (I), stereoisomer thereof or pharmaceutically acceptable salt thereof, are directed to the use in treating or preventing diseases or disorders that may be associated with and/or modulated by KOR agonists.

Another embodiment provides a method, wherein the compound of formula (I), stereoisomer thereof or pharmaceutically acceptable thereof, binds κ opioid receptors.

Another embodiment provides a method, wherein the κ opioid receptors are located in the central nervous system.

Another embodiment provides a method, wherein the κ opioid receptors are located peripherally.

In other embodiments, the compounds of the present application act peripherally.

In yet another embodiment, the application is directed to a method of treating or preventing arthritis, hypertension, post-operative pain, inflammation, migraine, disorders of gastrointestinal tract, psoriasis, Parkinsonism and stroke, comprising administering to a patient in need thereof, a composition comprising an effective amount of a compound of formula (I), stereoisomer thereof or pharmaceutically acceptable salt thereof.

In another embodiment, the compounds of the present application 'does not substantially cross' the blood-brain barrier.

In other embodiment, the compounds of the application may be used in methods for preventing or treating post-operative or opioid-induced ileus.

Unless defined otherwise, all technical and scientific terms used herein have the same meaning as commonly understood to one of ordinary skill in the art at the time this application was made.

All publications, patent applications and patents mentioned herein are incorporated herein by reference for the purpose of describing and disclosing, for example, the constructs and methodologies that are described in the publications, which might be used in connection with the presently described application. An embodiment of the present application provides the process for preparing compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present application claimed herein. All temperatures are in degrees Celsius unless otherwise noted.

EXAMPLES

The following acronyms, abbreviations, terms and definitions have been used throughout the reaction scheme and experimental section.

AD-mix-alpha [Mixture containing Hydroquinine 1,4-phthalazinediyl diether (0.0016 mole), Boc$_2$O (Di-tert-butyl dicarbonate), BSA (Bovine serum albumin), BOP (Benzotriazole-1-yl-oxy-tris-(dimethylamino)-phosphonium-hexafluorophosphate), Bn (Benzyl), BnBr (Benzyl bromide), cDNA (complementary DNA), DCC (N,N'-Dicyclohexylcarbodiimide), DIEA or DIPEA [(N,N-diisopropylethylamine) (Hünig's base)], DMF (N,N-dimethylformamide), DMSO (dimethyl sulfoxide), DCM (Dichloromethane), DMAP (Dimethyl amino pyridine), EC$_{50}$ (half maximal effective concentration), EtOAc (Ethyl acetate), Ether/Et$_2$O (diethyl ether), EDCI (1-ethyl-3-(3-dimethylaminopropyl) carbodiimide hydrochloride, HOBt (1-hydroxybenzotriazole), HCl (hydrochloric acid), HATU [O-(−7-azabenzotriazol-1-yl)-N,N,N',N'-tetramethyluronium hexafluorophosphate], HEPES (4-(2-hydroxyethyl)-1-piperazineethanesulfonic acid), HTRF (homogeneous time resolved fluorescence), i-Pr$_2$NEt (Diisopropyl-ethylamine) MeOH (Methanol), MsCl (Methanesulfonyl chloride), n-BuLi (n-butyl lithium), OTBDMS (tertiary butyldimethylsilyloxy), PyBOP (benzotriazol-1-yl-oxytripyrrolidinophosphonium hexafluorophosphate), Q-Phos (pentaphenyl (di-tert-butylphosphino)ferrocene), Pd$_2$(dba)$_3$ (Tris(dibenzylideneacetone) dipalladium(0)), PMB (p-methoxybenzyl), PE (Petroleum ether), Pd(PPh$_3$)$_4$ (Tetrakis(triphenylphosphine)palladium(0)), SEM-Cl ((2-Trimethyl silyl)ethoxymethyl chloride), P(OMe)$_3$ (Trimethylphosphite), TBAI (Tetrabutylammonium iodide), TBAF (Tetrabutyl ammonium Fluoride), TEA (Triethylamine), THF (tetrahydrofuran), TMS-Cl (Trimethylsilyl chloride), TFA (Trifluoroacetic acid), h (hour), min (minute), X-Phos (2-Dicyclohexylphosphino-2',4',6'-triisopropylbiphenyl), TLC (thin layer chromatography), MS (mass spectroscopy), NMR (nuclear magnetic resonance), IR (Infrared Spectroscopy), Mp/mp (melting point), aq (aqueous), psi (pound per square inch).

NMR abbreviations: MHz (Megahertz), br (broad), apt (apparent), s (singlet), d (doublet), t (triplet), q (quartet), dd (doublet of doublets), m (multiplet).

Room temperature is defined as an ambient temperature range, typically from about 20° C. to about 35° C. An ice bath (crushed ice and water) temperature is defined as a range, typically from about −5° C. to about 0° C. Temperature at reflux is defined as ±15° C. of the boiling point of the primary reaction solvent. Overnight is defined as a time range of from about 8 to about 16 hours. 'Dried/concentrated in vacuo' or 'dried/concentrated under reduced pressure' is defined as using a high vacuum pump at a range of pressures, typically from about 0.1 mm Hg to about 5 mm Hg. Brine is defined as a saturated aqueous sodium chloride. Nitrogen atmosphere is defined as positive static pressure of nitrogen gas passed through a Drierite™ column with an oil bubbler system. Melting points were measured against a mercury thermometer and are not corrected.

All eluents for column or thin layer chromatography were prepared and reported as volume:volume (v:v) solutions. The solvents, reagents, and the quantities of solvents and/or reagents used for reaction work-up or product isolation can be those that typically would be used by one of ordinary skill in organic chemical synthesis, as would be determined for the specific reaction or product to be isolated. For example: 1) crushed ice quantity typically ranged from about 10 g to about 1000 g depending on reaction scale; 2) silica gel quantity used in column chromatography depended on material quantity, complexity of mixture, and size of chromatography column employed and typically ranged from about 5 g to about 1000 g; 3) extraction solvent volume typically ranged from about 10 mL to about 500 mL, depending upon the reaction size; 4) washes employed in compound isolation ranged from about 10 mL to about 100 mL of solvent or aqueous reagent, depending on scale of reaction; and 5) drying reagents (potassium carbonate, sodium carbonate or magnesium sulfate) ranged from about 5 g to about 100 g depending on the amount of solvent to be dried and its water content.

The following general schemes and examples describe various embodiments of the present application. Other embodiments within the scope of the claims herein will be apparent to one skilled in the art from consideration of the specification or practice of the application as disclosed herein. It is intended that the specification, together with the examples, be considered to be exemplary only, with the scope and spirit of the application being indicated by the claims which follow the examples.

The compound of formula (I) can be synthesized by following the processes explained in following general schemes, wherein all symbols/variables are as defined earlier unless otherwise stated:

General Scheme (1) for synthesis of compounds of formula (I)

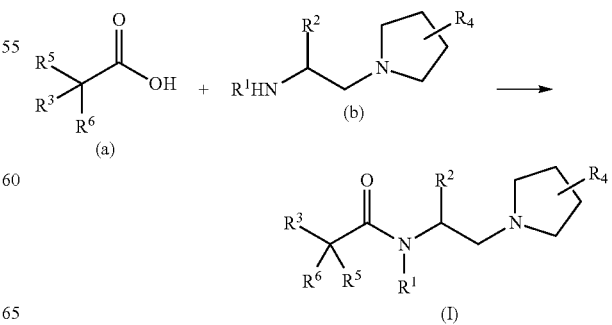

Condensation of reactant (a) with reactant (b) using suitable coupling agents such as EDCI/HOBt, HATU, BOP, PyBOP, DCC/HOBt, and the like in a suitable solvent like DCM, DMF and the like in the presence or absence of base like DMAP, DIPEA, triethylamine and the like can yield a deprotected to the corresponding hydroxyl group by using general procedures known in the art. When $R^4$ represents hydroxyl group, it can be further converted to the corresponding fluoro derivatives by following general procedures known in the art.

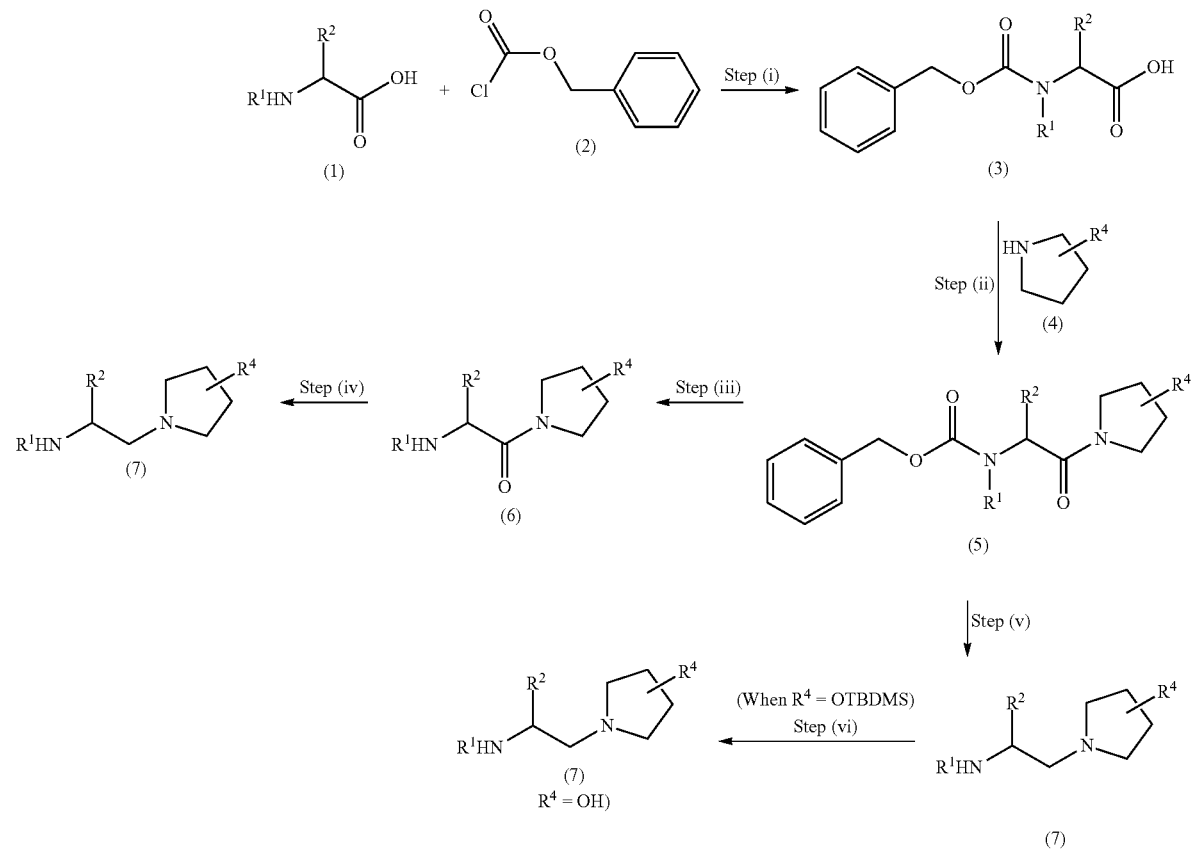

General Scheme (2) for Synthesis of the Reactant (b)

compound of general formula (I) wherein $R^1$, $R^2$, $R^3$, $R^4$, $R^5$ and $R^6$ are as defined in the specification.

The compounds of general formula (I), wherein optional substitutions on $R^2$ and $R^3$ independently contains cyano, can be further converted to the corresponding tetrazolyl, amide and or carboxylic acid group(s) by using general procedures known in the art. When the optional substitutions on $R^2$ and $R^3$ independently contains an ester functionality, the same can be further converted to the corresponding carboxylic acid group by using general procedures known in the art. When the optional substitutions on $R^2$ and $R^3$ independently contains a carboxylic acid moiety, the same can be further converted to the corresponding carboxamides, N-acylsulfonamides and related derivatives by following general procedures known in the art. The compounds of general formula (I), wherein optional substitutions on $R^2$ and $R^3$ independently contains a benzyl group like Bn, PMB etc and or benzyl ether (OBn, OPMB), the benzyl group can be hydrogenolytically removed by using general procedures known in the art. Similarly NBn or NPMB can be hydrogenolytically converted to their NH groups. When $R^4$ is a silyloxy group for example, OTBDMS, it can be further Step (i): The protection of nitrogen in the compound of general formula (1), wherein $R^1$ and $R^2$ are as described in the compound of general formula (I) in the specification, can be effected by reacting with a protecting agent such as benzyl chloroformate (2) in presence of a mild base such as sodium bicarbonate under suitable conditions of solvent and temperature, to yield a compound of general formula (3).

Step (ii): Condensation of the compound (3) with a compound of general formula (4) which represents a nitrogen containing saturated heterocycle substituted with $R^4$, using suitable coupling agents such as EDCI/HOBt, HATU, BOP, PyBOP, DCC/HOBt, and the like in a suitable solvent like DCM, DMF and the like in the presence or absence of base like DMAP, DIPEA and the like can yield a compound of general formula (5). $R^4$ is as defined in the general formula (I) in the specification.

Step (iii): Deprotection of the nitrogen i.e removal of the benzyloxycarbonyl (Cbz) group can be effected under hydrogenolytic conditions by treating the compound of general formula (5) with hydrogen in presence of a suitable catalyst such as Pd/C under suitable conditions of solvent and temperature to obtain a compound of formula (6).

Step (iv): A compound of general formula (7) can be obtained by reduction of the compound of formula (6) using suitable reducing agents such as LiAlH$_4$, NaBH$_4$ and the like under suitable conditions of solvent and temperature.
Step (v): A compound of general formula (7) can be obtained by reduction of the compound of formula (5) using suitable reducing agents such as LiAlH$_4$, and the like under suitable conditions of solvent and temperature.

Step (i): A compound of general formula (13) can be obtained from a compound of formula (12) wherein R$_2$ is as described in the compound of general formula (I) in the specification by using a suitable brominating agent as known in the literature.

General Scheme (3) for Synthesis of the Reactant (b)

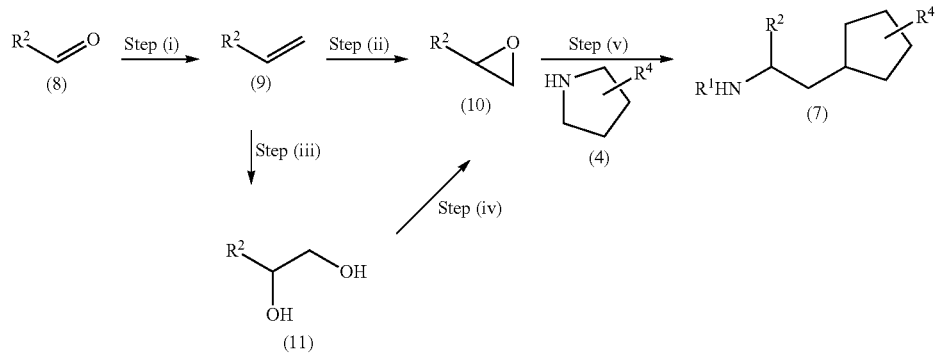

Step (i): A compound of general formula (9) can be obtained from a compound of formula (8) wherein R$^2$ is as described in the compound of general formula (I) in the specification by the treatment with NaH, and methyltriphenylphosphonium bromide in a suitable solvent like THF, ether and the like at a suitable temperature of 0-25° C.
Step (ii): A compound of formula (10) can be synthesized by reacting compound of formula (9) with m-chloroperbenzoic acid and NaHCO$_3$ in a suitable solvent like DCM and the like.
Step (iii): A compound of formula (11) can be synthesized from compound of formula (10) by following standard procedure of Sharpless' dihydroxylation method known in the art.
Step (iv): A compound of formula (10) can also be obtained from various diols of formula (11) by standard procedures.
Step (v): A compound of formula (7) can be obtained by the reaction of compound of formula (10) with compound of formula (4) and R$^1$NH$_2$, wherein R$^1$ is described as before, under suitable reaction conditions.

Step (ii): A compound of formula (14) can be synthesized from compound of formula (13) by following standard procedure of CBS reduction method known in the art.
Step (iii): A compound of formula (15) can be synthesized from compound of formula (14) by following standard procedures.
Step (iv): A compound of formula (16) can be obtained from compound of formula (15) by the treatment with compound of formula (4) under suitable reactions conditions.
Step (v): A compound of formula (18) can be obtained by the reaction of compound of formula (16) with mesyl chloride and the like under suitable condition followed by the treatment of various amines of formula (17) using suitable reaction conditions as known in the art.

The R$^2$ and R$^4$ in general formula (7) or general formula (18) can be further converted to the Reactant (b) with different functional groups. For example when R$^2$ is a bromophenyl moiety, the bromo group can be concerted to (a) acetylenic derivatives following Sonogashira reactions; (b) a cyano group or borate compounds which can be further General Scheme (4) for Synthesis of the Reactant (b)

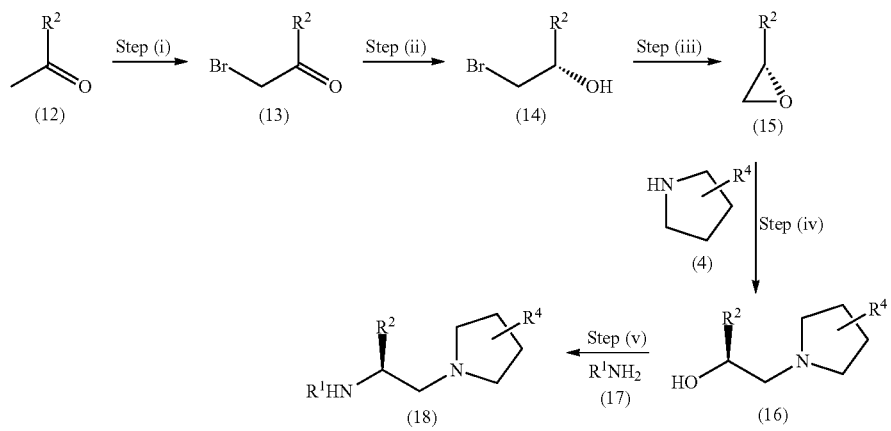

converted to various 5-membered heteroaryl compounds following standard procedures known in the art. When the optional substitutions on $R^2$ in the compounds of general formula (7 or 18) independently contains an ester functionality, the same can be converted to the corresponding carboxylic acids, amides, hydrazide, N-acylsulfonamides and the related compounds followed by further modifications as desired by using general procedures known in the art. A compound of general formula (7) or general formula (18) wherein $R^4$ represent a silyl ether such as OTBDMS group can be converted to the corresponding hydroxyl group by following standard deprotection protocol of silyl ethers.

EXAMPLES

Following are the non-limiting examples of the reactant of formula (a):

Example 1-a 2-(2-oxoindolin-6-yl) acetic acid

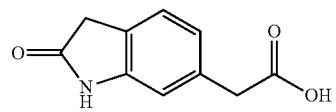

Step (i): Synthesis of 2-(4-fluoro-3-nitrophenyl) acetic acid

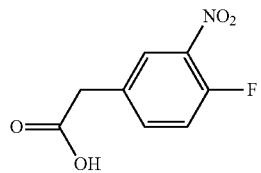 [SMILES: O=C(O)Cc1ccc(F)c([N+](=O)[O-])c1]

To a suspension of 2-(4-fluorophenyl) acetic acid (100 g, 0.648 mol) in $H_2SO_4$ (750 ml); $KNO_3$ (65.5 g, 0.648 mol) was added portion wise and stirred for 1.5 hr at 0° C. The reaction mixture was quenched with ice and filtered. The solid residue obtained was dried to get 2-(4-fluoro-3-nitrophenyl) acetic acid (80 g).

$^1$H-NMR (400 MHz, DMSO-$d_6$): δ 12.30 (bs, 1H), 8.10-8.08 (d, 1H), 7.73-7.71 (m, 1H), 7.56-7.51 (m, 1H), 3.76 (s, 2H); MS (ES): m/z 200 (M+1).

Step (ii): Synthesis of ethyl 2-(4-fluoro-3-nitrophenyl)acetate

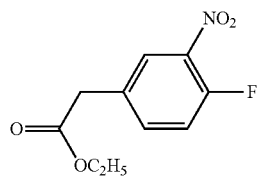 [SMILES: CCOC(=O)Cc1ccc(F)c([N+](=O)[O-])c1]

To a suspension of 2-(4-fluoro-3-nitrophenyl)acetic acid (80 g, 0.402 mol) in ethanol (560 ml), $SOCl_2$ (142.3 g, 1.206 mol) was added drop wise at 0° C. and stirred overnight at room temperature. The reaction mixture was concentrated under reduced pressure and the crude was dissolved in EtOAc (500 ml), washed with 5% $NaHCO_3$ solution (100 ml), water (100 ml), brine (100 ml) sequentially, dried over $Na_2SO_4$, filtered and concentrated to get ethyl 2-(4-fluoro-3-nitrophenyl)acetate (85 g).

$^1$H-NMR (400 MHz, DMSO-$d_6$): δ 8.01-7.99 (d, 1H), 7.58-7.56 (m, 1H), 7.28-7.23 (m, 1H), 4.21-4.19 (m, 2H), 3.67-3.58 (s, 2H), 1.29-1.25 (m, 3H); MS (ES): m/z 226 (M−1).

Step (iii): Synthesis of diethyl 2-(4-(2-ethoxy-2-oxoethyl)-2-nitrophenyl) malonate

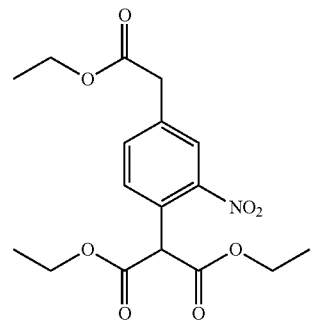 [SMILES: CCOC(=O)Cc1ccc(C(C(=O)OCC)C(=O)OCC)c([N+](=O)[O-])c1]

A suspension of ethyl 2-(4-fluoro-3-nitrophenyl) acetate (50 g, 0.220 mol), $K_2CO_3$ (45.6 g, 0.336 mol), diethyl malonate (42.3 g, 0.264 mol) in DMF (350 ml) was heated to 60° C. and stirred for 4 hours. The reaction mixture was concentrated under reduced pressure and the crude was dissolved in EtOAc (500 ml) and washed with water (100 ml), brine (100 ml) dried over $Na_2SO_4$, filtered and concentrated to diethyl 2-(4-(2-ethoxy-2-oxoethyl)-2-nitrophenyl) malonate. The crude compound was purified by column chromatography using 100-200 silica gel as stationary phase and 10% EtOAc in n-hexane as eluent (38 g).

$^1$H-NMR (400 MHz, DMSO-$d_6$): δ 8.07-8.07 (s, 1H), 7.70-7.67 (d, 1H), 7.48-7.46 (d, 1H), 5.38 (s, 1H), 4.20-4.08 (m, 6H), 3.88 (s, 2H), 1.25-1.18 (m, 9H); MS (ES): m/z 368 (M+1).

Step (iv): Synthesis of 2,2'-(2-nitro-1,4-phenylene)diacetic acid

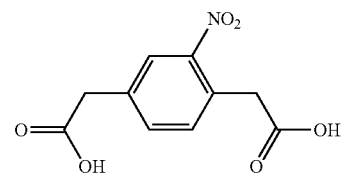 [SMILES: O=C(O)Cc1ccc(CC(=O)O)c([N+](=O)[O-])c1]

A suspension of diethyl 2-(4-(2-ethoxy-2-oxoethyl)-2-nitrophenyl) malonate (38 g, 0.103 mol) in 6N Aq.HCl (380 ml) was stirred overnight at 120° C. The reaction mixture was dissolved in EtOAc (500 ml); washed with water (100 ml) and brine (100 ml); dried over $Na_2SO_4$; filtered and concentrated to get 2,2'-(2-nitro-1,4-phenylene)diacetic acid (17 g).

¹H-NMR (400 MHz, DMSO-d₆): δ 12.53 (bs, 1H), 8.01 (s, 1H), 7.60-7.58 (d, 1H), 7.49-7.47 (d, 1H), 3.97 (s, 2H), 3.75 (s, 2H); MS (ES): m/z 262 (M+23).

Step (v): Synthesis of dimethyl 2,2'-(2-nitro-1,4-phenylene) diacetate

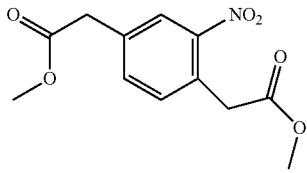 [SMILES: COC(=O)Cc1ccc(CC(=O)OC)c([N+](=O)[O-])c1]

To a suspension of 2,2'-(2-nitro-1,4-phenylene)diacetic acid (17 g, 0.071 mol) in methanol (170 ml) at 0° C., SOCl₂ (25 g, 1.20 mol) was added drop wise and stirred for 8 hours at room temperature. The reaction mixture was concentrated under reduced pressure, the residue was dissolved in EtOAc (400 ml); washed with water (100 ml) and brine (100 ml); dried over Na₂SO₄; filtered and concentrated to obtain the titled compound (17.5 g).

¹H-NMR (400 MHz, DMSO-d₆): δ 8.06 (s, 1H), 7.64-7.62 (d, 1H), 7.53-7.51 (d, 1H), 4.06-4.02 (s, 2H), 3.87 (s, 2H), 3.64 (s, 3H), 3.61 (s, 3H); MS (ES): m/z 266 (M−1).

Step (vi): Synthesis of methyl 2-(2-oxoindolin-6-yl)acetate

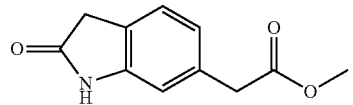

To a suspension of diethyl dimethyl 2,2'-(2-nitro-1,4-phenylene)diacetate (17 g, 0.063 mol) in acetic acid (170 ml), Pd/C was added and hydrogen gas pressure was applied to the reaction mixture and it was stirred overnight at room temperature. The reaction mass was filtered through celite plug; extracted with EtOAc (400 ml); washed with 5% NaHCO₃ solution (100 ml), water (100 ml), brine (100 ml); dried over Na₂SO₄; filtered and concentrated to get methyl 2-(2-oxoindolin-6-yl)acetate (10 g).

¹H-NMR (400 MHz, DMSO-d₆): δ10.36 (s, 1H), 7.13-7.11 (d, 1H), 6.81-6.79 (d, 1H), 6.72 (s, 1H), 3.63 (s, 3H), 3.60 (s, 2H), 3.43 (s, 2H); MS (ES): m/z 206 (M+1).

Step (vii): Synthesis of 2-(2-oxoindolin-6-yl) acetic acid

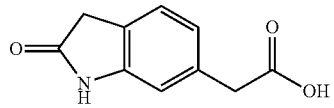 [SMILES: O=C(O)Cc1ccc2c(c1)NC(=O)C2]

A suspension of methyl 2-(2-oxoindolin-6-yl) acetate (10 g, 0.048 mol) in 6N Aq.HCl (180 ml) was stirred for 2 hours at 90° C. The reaction mixture was cooled to room temperature and filtered to obtain a solid residue which was dried to obtain 2-(2-oxoindolin-6-yl) acetic acid (6.5 g).

¹H-NMR (400 MHz, DMSO-d₆): δ12.30 (bs, 1H), 10.34 (s, 1H), 7.12-7.10 (d, 1H), 6.80-6.78 (m, 1H), 6.73 (s, 1H), 3.51 (s, 2H), 3.42 (s, 2H); MS (ES): m/z 192 (M+1).

Example 2-a 2-(1-methyl-2-oxoindolin-6-yl) acetic acid

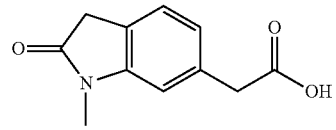

Step (i) Synthesis of dimethyl 2,2'-(2-amino-1,4-phenylene)diacetate

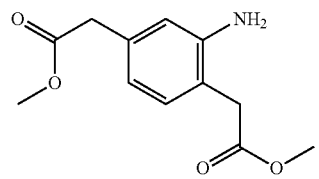 [SMILES: COC(=O)Cc1ccc(CC(=O)OC)c(N)c1]

Dimethyl 2,2'-(2-nitro-1,4-phenylene)diacetate (5 g, 0.018 mol), obtained in Step (iv) of Example (1-a), was dissolved in methanol (50 ml) and 10% Pd—C (3 g) was added to it. Thereafter hydrogen gas was introduced in it and the reaction mixture was stirred for 16 hours at room temperature. The reaction mixture was then filtered through celite, washed with methanol and concentrated under reduced pressure to get dimethyl 2,2'-(2-amino-1,4-phenylene)diacetate (4 g).

¹H-NMR (400 MHz, DMSO-d₆): δ 6.88-6.86 (m, 1H), 6.50-6.54 (m, 1H), 6.39-6.40 (m, 1H), 4.91 (s, 2H), 3.60 (s, 6H), 3.50 (s, 4H); MS (ES): m/z 238 (M+1).

Step (ii) Synthesis of methyl 2-(1-methyl-2-oxoindolin-6-yl)acetate

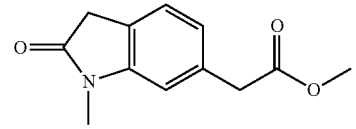 [SMILES: COC(=O)Cc1ccc2c(c1)N(C)C(=O)C2]

Propanol (40 ml) was added to a mixture of 10% Pd/C (1 g) ammoniumformate (10.7 g, 0.168 mol) dissolved in water (4 ml) and the mixture was stirred for about a minute to activate palladium carbon. Dimethyl 2,2'-(2-amino-1,4-phenylene)diacetate compound (4 g, 0.016 moles) and formaldehyde (4 ml, 0.033 moles) were added to the reaction mixture. The reaction mixture was stirred at room temperature, then filtered through celite bed, washed with methanol, removed the solvent in vacuo to obtain a residue which was dissolved in ethyl acetate, washed, dried, purified by column chromatography using 230-400 silica gel as stationary phase and 35% ethyl acetate in n-hexane as eluent to get methyl 2-(1-methyl-2-oxoindolin-6-yl)acetate (1.8 g).

$^1$H-NMR (400 MHz, DMSO-d$_6$): δ 7.26 (s, 1H), 6.94-6.95 (m, 1H), 6.76 (s, 1H), 3.71 (s, 6H), 3.50 (s, 2H), 3.20 (s, 3H); MS (ES): m/z 220 (M+1).

Step (iii) Synthesis of 2-(1-methyl-2-oxoindolin-6-yl) acetic acid

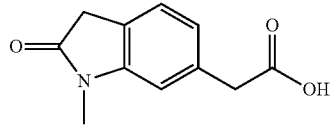

A suspension of methyl 2-(1-methyl-2-oxoindolin-6-yl) acetate (1.8 g, 0.008 moles) in 6N Aq.HCl (25 ml) was heated at 100° C. for 8 hours. Thereafter the reaction mixture was allowed to cool to room temperature. The mixture was filtered to obtain a solid which was dried well to get 2-(1-methyl-2-oxoindolin-6-yl) acetic acid (1.2 g).

$^1$H-NMR (400 MHz, DMSO-d$_6$): δ 12.40 (s, 1H), 7.17 (s, 1H), 6.87-6.90 (m, 2H), 3.71 (s, 2H), 3.50 (s, 2H), 3.10 (s, 3H); MS (ES): m/z 206 (M+1).

Example 3-a 2-(2-oxo-2,3-dihydrobenzo[d]oxazol-5-yl)acetic acid

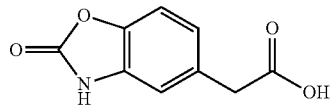

Step (i) Synthesis of methyl 2-(4-methoxyphenyl)acetate

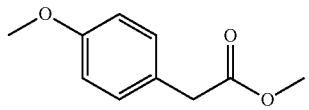

To a solution of 2-(4-methoxyphenyl)acetic acid (30 g, 0.180 mol) in methanol (350 ml), thionyl chloride was added drop-wise at 0° C.; and the mixture was refluxed for 1.5 hours. The reaction mixture was concentrated and treated with saturated sodium bicarbonate, extracted with ethyl acetate. The organic layer was separated, washed, dried and concentrated to get methyl 2-(4-methoxyphenyl)acetate (38 g of crude).

$^1$H-NMR (400 MHz, DMSO-d$_6$): δ 7.19 (d, J=8.6 Hz, 1H), 6.89 (d, J=8.6 Hz, 1H), 3.73 (s, 2H), 3.60 (s, 6H); MS (ES): m/z 266 (M+1).

Step (ii) Synthesis of methyl 2-(4-methoxy-3-nitrophenyl) acetate

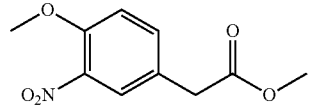

A mixture of nitric acid (9 ml) and acetic acid (83 ml) was added drop-wise to a solution of methyl 2-(4-methoxyphenyl)acetate (33 g) in acetic anhydride (50 ml) at −30° C. The reaction mixture was stirred and the temperature of the mixture was gradually raised from −30 to room temperature in a period of 2 hours. Ice-cold water was added portion-wise to the reaction mixture to obtain a yellow solid which was filtered and dried to get methyl 2-(4-methoxy-3-nitrophenyl) acetate (42 g).

$^1$H-NMR (400 MHz, DMSO-d$_6$): δ 7.80 (s, 2H), 7.58 (d, J=8.6 Hz, 1H), 7.33 (d, J=8.8 Hz, 1H), 3.75 (s, 2H), 3.75 (s, 3H), 3.62 (s, 3H); MS (ES): m/z 226 (M+1).

Step (iii) Synthesis of methyl 2-(4-hydroxy-3-nitrophenyl)acetate

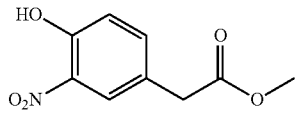

Fresh boron tribromide (27 ml, 70 g, 0.28 mol) was added drop-wise to a solution of methyl 2-(4-methoxy-3-nitrophenyl)acetate (42 gm, 0.186 mol) in DCM (200 ml) at −70° C. on dry ice bath. The temperature of the mixture was gradually raised from −30° C. to room temperature with stirring in a period of 4 hours. Thereafter the solvent was evaporated, the residue obtained was treated with ice-cold water and the precipitate thus obtained was dissolved in ethyl acetate. This organic layer was washed with brine, concentrated under reduced pressure and purified by column chromatography to obtain methyl 2-(4-hydroxy-3-nitrophenyl) acetate (23 g).

$^1$H-NMR (400 MHz, DMSO-d$_6$): δ 10.88 (bs, 1H), 7.82 (s, 1H), 7.46 (d, J=8.5 Hz, 1H), 7.01 (d, J=8.5 Hz, 1H), 3.70 (s, 2H), 3.62 (s, 3H); MS (ES): m/z 212 (M+1).

Step (iv) Synthesis of methyl 2-(3-amino-4-hydroxyphenyl) acetate

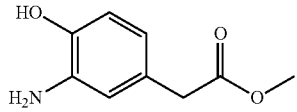

Raney nickel (20 g) was added to a suspension of methyl 2-(4-hydroxy-3-nitrophenyl)acetate in methanol (250 ml) at room temperature and the reaction mixture was stirred for 12 hours under hydrogen gas. Thereafter the reaction mixture was filtered through celite bed, washed with methanol and concentrated to get methyl 2-(3-amino-4-hydroxyphenyl)acetate (19.7 g) as a black solid.

¹H-NMR (400 MHz, DMSO-d₆): δ 9.00 (bs, 1H), 6.56 (d, J=7.6 Hz, 1H), 6.47 (s, 1H) 6.27 (d, J=7.6 Hz, 1H), 3.70 (s, 2H), 3.62 (s, 3H); MS (ES): m/z 182 (M+1).

Step (v) Synthesis of methyl 2-(2-oxo-2,3-dihydrobenzo[d]oxazol-5-yl)acetate

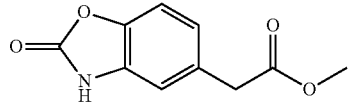

To methyl 2-(3-amino-4-hydroxyphenyl)acetate (19.5 g, 0.107 moles) in THF, was added triphosgene (45 g, 0.15 moles) portionwise at about 0° C. in an hour. Thereafter the solvent was vaporised, the residue was treated with ice-cold water. The solid precipitate thus obtained was filtered, dried in vacuo to obtain methyl 2-(2-oxo-2,3-dihydrobenzo[d]oxazol-5-yl)acetate (10 g).

¹H-NMR (400 MHz, DMSO-d₆): δ 11.60 (bs, 1H), 7.21 (d, J=8.0 Hz, 1H), 6.97 (d, J=8.0 Hz, 1H), 3.70 (s, 2H), 3.62 (s, 3H); MS (ES): m/z 208 (M+1).

Step (vi) Synthesis of 2-(2-oxo-2,3-dihydrobenzo[d]oxazol-5-yl)acetic acid

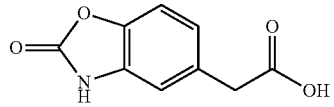

150 ml of 5% sodium hydroxide was added drop wise to methyl 2-(2-oxo-2,3-dihydrobenzo[d]oxazol-5-yl)acetate (10 g, 0.05 moles) in methanol (75 ml), and the resultant mixture was stirred for about an hour. The solvent was vaporized and the residue was treated with 3N aq.HCl. The mixture was filtered in vacuo and dried to obtain 2-(2-oxo-2,3-dihydrobenzo[d]oxazol-5-yl)acetic acid (7 g).

¹H-NMR (400 MHz, DMSO-d₆): δ 11.60 (bs, 1H), 7.20 (d, J=8.3 Hz, 1H), 7.00 (s, 1H), 6.96 (d, J=8.5 Hz, 1H), 3.60 (s, 2H); MS (ES): m/z 192 (M+1).

Example 4-a 2-(3-methyl-2-oxo-2,3-dihydrobenzo[d]oxazol-5-yl)acetic acid

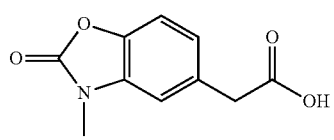

Step (i) Synthesis of methyl 2-(3-methyl-2-oxo-2,3-dihydrobenzo[d]oxazol-5-yl)acetate

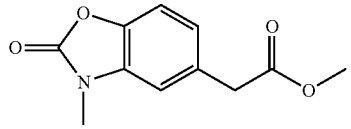 [SMILES: COC(=O)Cc1ccc2oc(=O)n(C)c2c1]

To methyl 2-(2-oxo-2,3-dihydrobenzo[d]oxazol-5-yl)acetate obtained in Step (v) of example 4-a, (500 mg, 2.26 moles) in DMF (10 ml), was added potassium carbonate (936 mg, 6.78 moles) at room temperature and the mixture was stirred for 10-15 minutes. The reaction mixture was then cooled to 0° C.; methyl iodide (168 μl, 2.71 moles) was added drop wise to it and the resultant mixture was stirred for 3 hours at room temperature. After completion of the reaction, the reaction mixture was poured into ice-cold water and extracted with ethyl acetate twice. Combined ethyl acetate layer was washed once with brine and water each respectively, dried over sodium sulphate and concentrated in vacuo to give the crude methyl 2-(3-methyl-2-oxo-2,3-dihydrobenzo[d]oxazol-5-yl)acetate which was purified by flash chromatography using 230-400 mesh silica gel as stationary phase and 20% ethyl acetate in hexane as eluent to obtain the titled product (311 mg).

¹H-NMR (400 MHz, DMSO-d₆): δ 7.26 (d, J=7.8 Hz, 1H), 7.16 (bs, 1H), 7.03-7.01 (m, 1H), 4.11-4.05 (q, 2H), 3.70 (s, 2H), 3.32 (s, 3H), 1.20-1.17 (t, 3H); MS (ES): m/z 236 (M+1).

Step (ii) Synthesis of 2-(3-methyl-2-oxo-2,3-dihydrobenzo[d]oxazol-5-yl)acetic acid

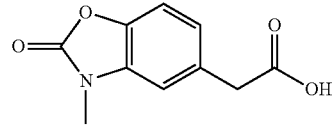

6N aq.HCl was added to methyl 2-(3-methyl-2-oxo-2,3-dihydrobenzo[d]oxazol-5-yl)acetate (311 mg, 1.32 moles) at room temperature and the mixture was refluxed for 2 hours. After completion of the reaction, the reaction mixture was extracted twice with ethyl acetate. Combined ethyl acetate layer washed with brine and water once each respectively, dried over sodium sulphate and concentrated in vacuo to give the pure 2-(3-methyl-2-oxo-2,3-dihydrobenzo[d]oxazol-5-yl)acetic acid. (200 mg).

¹H-NMR (400 MHz, DMSO-d₆): δ 12.50 (bs, 1H), 7.23 (d, J=8.3 Hz, 1H), 7.10 (bs, 1H), 6.99 (d, J=8.3 Hz, 1H), 3.60 (s, 2H), 3.29 (s, 3H); MS (ES): m/z 208 (M+1).

Example 5-a 2-(2-oxo-2,3-dihydrobenzo[d]thiazol-5-yl)acetic acid

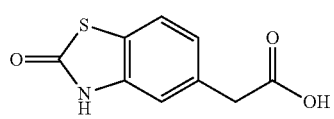

Step (i) Synthesis of 2-(4-chloro-3-nitrophenyl)acetic acid

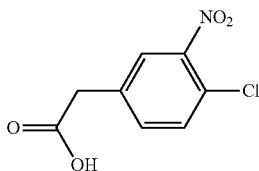 [SMILES: O=C(O)Cc1ccc(Cl)c([N+](=O)[O-])c1]

KNO₃ (18.7 g, 0.185 mol) was added portion-wise to a suspension of 2-(4-chlorophenyl)acetic acid (30 g, 0.176 mol) in $H_2SO_4$ (150 ml) at 0° C. and the resultant mixture was stirred for 1.5 hour maintaining the temperature at 0° C. The reaction mixture was quenched with ice and filtered. The solid residue was dried to get the titled compound (26 g).

$^1$H-NMR (400 MHz, DMSO-$d_6$): δ 8.0 (s, 1H), 7.73 (d, J=8.4 Hz, 1H), 7.62 (d, J=6.4 Hz, 1H), 3.76 (s, 2H); MS (ES): m/z 200 (M+18).

Step (ii): Synthesis of ethyl 2-(4-chloro-3-nitrophenyl)acetate

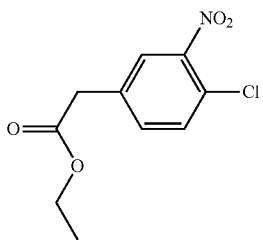 [SMILES: CCOC(=O)Cc1ccc(Cl)c([N+](=O)[O-])c1]

$H_2SO_4$ (25 ml) was added drop wise to a suspension of 2-(4-chloro-3-nitrophenyl)acetic acid (25 g, 0.116 mol) in ethanol (125 ml) at 0° C. and the reaction mixture was stirred for 4 hrs at 85° C. The reaction mixture was then cooled to room temperature and concentrated under reduced pressure. The crude product was dissolved in EtOAc (500 ml), dried over Na₂SO₄, filtered and concentrated to get the titled compound (27 g).

$^1$H-NMR (400 MHz, DMSO-$d_6$): δ 7.83 (s, 1H), 7.52-7.44 (m, 2H), 4.26-4.15 (m, 2H), 3.72 (s, 2H), 1.27-1.23 (m, 3H); MS (ES): m/z 242 (M−1).

Step (iii): Synthesis of ethyl 2-(2-oxo-2,3-dihydrobenzo[d]thiazol-5-yl)acetate

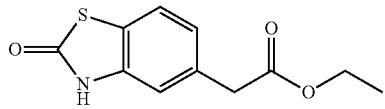

A suspension of ethyl 2-(4-chloro-3-nitrophenyl)acetate (27 g, 0.111 mol), sulfur powder (17.8 g, 0.555 mol), triethylamine (44.9 g, 0.44 mol), water (12 ml, 0.66 mol) in THF (135 ml) was loaded in autoclave; CO Gas pressure of up to 10 kg was applied and the mixture was stirred overnight at 80° C. The reaction mixture was cooled to room temperature, concentrated under reduced pressure, dissolved in EtOAc (600 ml), washed with brine (100 ml), dried over Na₂SO₄, filtered and concentrated to get the crude compound. The crude compound was purified by column chromatography using 100-200 silica gel as stationary phase and 15% EtOAc in n-hexane as eluent to afford the titled compound (10 g).

$^1$H-NMR (400 MHz, DMSO-$d_6$): δ 11.88 (s, 1H), 11.86 (s, 1H), 7.50 (d, J=8.0 Hz, 1H), 7.04-7.01 (m, 2H), 4.10-4.05 (m, 2H), 3.69 (s, 2H), 1.20-1.16 (m, 3H); MS (ES): m/z 238 (M+1).

Step (iv): Synthesis of 2-(2-oxo-2,3-dihydrobenzo[d]thiazol-5-yl)acetic acid

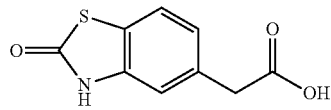

5% aq.NaOH solution (5 ml) was added to a suspension of ethyl 2-(2-oxo-2,3-dihydrobenzo[d]thiazol-5-yl)acetate (10 g, 0.042 mol) in methanol (50 ml) and the mixture was stirred for about an hour at room temperature. The reaction mixture was concentrated under reduced pressure. Water (10 ml) was added to the reaction mixture and it was adjusted to a pH 2-3 with 6N Aq.HCl; the solid precipitate thus obtained was filtered and dried to get title compound (8 g).

$^1$H-NMR (400 MHz, DMSO-$d_6$): δ 12.37 (bs, 1H), 11.86 (s, 1H), 7.49 (d, J=7.6 Hz, 1H), 7.03-7.03 (m, 2H), 3.59 (s, 2H); MS (ES): m/z 209.9 (M+1).

Example 6-a 2-(2-oxo-1,2-dihydroquinolin-6-yl)acetic acid

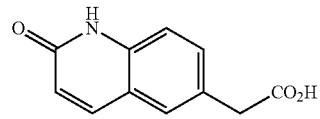 [SMILES: O=C(O)Cc1ccc2[nH]c(=O)ccc2c1]

Step (i) Synthesis of methyl 2-(4-aminophenyl)acetate

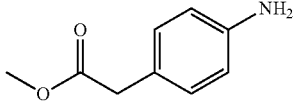

Thionyl chloride (1 ml) was added dropwise to a mixture of 2-(4-aminophenyl)acetic acid (1 g, 0.0062 moles) in MeOH (20 ml) at 0° C. The reaction was then stirred for 12 hours raising the temperature gradually from 0° C. to room temperature. After completion of the reaction, the reaction mixture was concentrated under reduced pressure, quenched with water, basified with saturated aqueous sodium bicarbonate solution and extracted 2-3 times with ethyl acetate.

Combined ethyl acetate layer was washed twice with brine and water each respectively, dried over sodium sulphate and concentrated in vacuo to give the title compound (0.9 g).

¹H-NMR (400 MHz, DMSO-d₆): δ 6.88 (d, J=8.4 Hz, 2H), 6.49 (d, J=8.3 Hz, 2H), 4.96 (s, 2H), 3.57 (s, 3H), 3.43 (s, 2H).

Step (ii) Synthesis of (E)-methyl 2-(4-cinnamamidophenyl)acetate

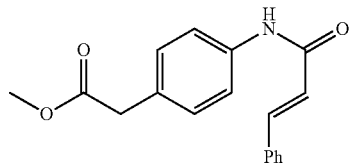 [SMILES: COC(=O)Cc1ccc(NC(=O)/C=C/c2ccccc2)cc1]

To methyl 2-(4-aminophenyl)acetate (1.88 g, 0.0109 moles) in dichloromethane (30 ml), pyridine (1.6 ml) was added slowly in portions at 0° C. under inert nitrogen atmosphere. To the reaction mixture at the same temperature, cinnamoyl chloride (2.7 g, 0.0163 moles) was added. The reaction mixture was then stirred at room temperature for 2 hours. After completion of the reaction, the reaction mixture was diluted with dichloromethane (60 ml), washed with saturated aqueous sodium bicarbonate solution, brine and water once respectively, dried over sodium sulphate and concentrated in vacuo to give the crude product which was then purified by flash chromatography using 40% ethyl acetate in n-hexane as eluent to obtain the titled compound (4.0 g).

¹H-NMR (400 MHz, DMSO-d₆): δ 10.19 (s, 1H), 7.65-7.56 (m, 5H), 7.45-7.42 (m, 3H), 7.23-7.21 (m, 2H), 6.85-6.81 (m, 1H), 3.63 (s, 2H), 3.61 (s, 3H); MS (ES): m/z 296 (M+1).

Step (iii) Synthesis of methyl 2-(2-oxo-1,2-dihydroquinolin-6-yl)acetate

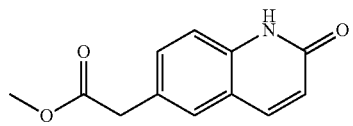 [SMILES: COC(=O)Cc1ccc2[nH]c(=O)ccc2c1]

Anhydrous and freshly sublimed AlCl₃ (4.5 g, 0.0338 moles) was added to (E)-methyl 2-(4-cinnamamidophenyl)acetate (2 g, 0.0067 moles) at room temperature under inert nitrogen atmosphere. The reaction mixture was then heated at 90-100° C. for 2-3 hours. After completion of the reaction, the reaction mixture was poured into ice-cold water at 0° C. and stirred for 30 min. A solid precipitate was obtained which was filtered in vacuo, washed 3-4 times with ethyl acetate. This organic layer washed once with brine and water each respectively, dried over sodium sulphate and concentrated in vacuo to give the titled compound (0.28 g).

¹H-NMR (400 MHz, DMSO-d₆): δ 11.67 (bs, 1H), 7.85 (d, J=9.3 Hz, 1H), 7.50 (s, 1H), 7.37 (d, J=7.9 Hz, 1H), 7.22 (d, J=8.3 Hz, 1H), 6.46 (d, J=9.3 Hz, 1H), 3.50 (s, 3H); MS (ES): m/z 218 (M+1).

Step (iv) Synthesis of 2-(2-oxo-1,2-dihydroquinolin-6-yl)acetic acid

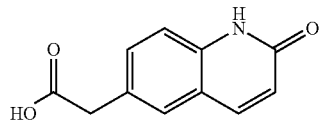 [SMILES: O=C(O)Cc1ccc2[nH]c(=O)ccc2c1]

10% aqueous sodium hydroxide solution (10 ml) was added to methyl 2-(2-oxo-1,2-dihydroquinolin-6-yl)acetate (0.5 g, 2.46 moles) in MeOH (10 ml) at 0° C. The reaction mixture was then stirred at room temperature for 2 hours. After completion of the reaction, the solvent was removed in vacuo and the reaction mixture (aqueous layer) was washed twice with ethyl acetate. The aqueous layer was then cooled to 0° C. and acidified to pH 2 with 3N Aq.HCl to obtain a solid precipitate. This precipitate was filtered in vacuo, washed with water and dried to obtain get pure 2-(2-oxo-1,2-dihydroquinolin-6-yl)ethaneperoxoic acid product. (0.35 g).

¹H-NMR (400 MHz, DMSO-d₆): δ 12.33 (bs, 1H), 11.70 (bs, 1H), 7.86 (d, J=9.3 Hz, 1H), 7.52 (s, 1H), 7.38 (d, J=8.4 Hz, 1H), 7.24 (d, J=8.3 Hz, 1H), 6.48 (d, J=9.3 Hz, 1H), 3.60 (s, 2H); MS (ES): m/z 204 (M+1).

Example 7-a 2-(2-oxo-1,2,3,4-tetrahydroquinolin-7-yl)ethaneperoxoic acid

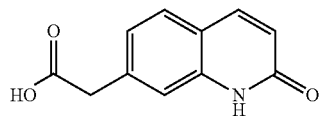

Step (i) Synthesis of methyl 2-(3-nitrophenyl)acetate

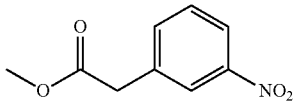

To 2-(3-nitrophenyl)ethaneperoxoic acid (1 g, 0.0055 moles) in MeOH (20 ml), thionyl chloride (1 ml) was added slowly dropwise at 0° C. The reaction was then stirred for 12 hours at 0° C.-RT. After completion of the reaction, the volatiles were removed under reduced pressure and the reaction mixture was quenched with water, basified with saturated aqueous sodium bicarbonate solution and extracted with ethyl acetate 2-3 times. Combined ethyl acetate layer was washed twice with brine and water each respectively, dried over sodium sulphate and concentrated in vacuo to give the pure methyl 2-(3-nitrophenyl)acetate. (0.9 g)

¹H-NMR (400 MHz, DMSO-d₆): δ 8.20 (s, 1H), 8.16-8.13 (m, 1H), 7.77-7.75 (m, 1H), 7.65-7.61 (m, 1H), 3.92 (s, 2H), 3.65 (s, 3H)

Step (ii) Synthesis of methyl 2-(3-aminophenyl)acetate

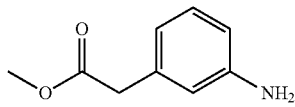

To methyl 2-(3-nitrophenyl)acetate (13 g, 0.978 moles) in MeOH (250 ml), 10% Pd/C (6 g) was added under inert nitrogen atmosphere. The reaction mixture was then subjected to hydrogen gas pressure at 60 psi by using par apparatus for 1 hour. After completion of the reaction, the reaction mixture was filtered through celite in vacuo, the celite bed was washed with little excess of MeOH and the filtrate was concentrated in vacuo to give the crude methyl 2-(3-aminophenyl)acetate. (10.5 g)

Step (iii) Synthesis of (E)-methyl 2-(3-cinnamamidophenyl)acetate

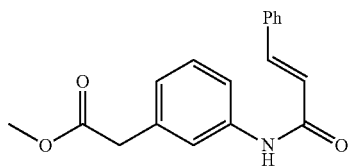 [SMILES: COC(=O)Cc1cccc(NC(=O)/C=C/c2ccccc2)c1]

To methyl 2-(3-aminophenyl)acetate (1.88 g, 0.0109 moles) in dichloromethane (30 ml), pyridine (1.6 ml) was added slowly portionwise at 0° C. under inert nitrogen atmosphere. To the reaction mixture at same temperature, cinnamoyl chloride (2.7 g, 0.0163 moles) was added. The reaction mixture was then stirred at room temperature for 2 hours. After completion of the reaction, the reaction mixture was diluted with dichloromethane (60 ml), washed with saturated aqueous sodium bicarbonate solution, brine and water once respectively, dried over sodium sulphate and concentrated under vacuo to give crude (E)-methyl 2-(3-cinnamamidophenyl)acetate product which was then purified by flash chromatography using 40% ethyl acetate in n-hexane as eluent. (4.0 g)

Step (iv) Synthesis of methyl 2-(2-oxo-1,2-dihydroquinolin-7-yl)acetate

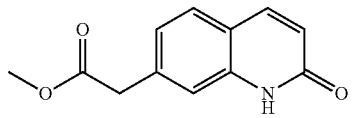

To (E)-methyl 2-(3-cinnamamidophenyl)acetate (2 g, 0.0067 moles) was added anhydrous and freshly sublimed AlCl$_3$ (4.5 g, 0.0338 moles) at room temperature under inert nitrogen atmosphere. The reaction mixture (neat reaction) was then heated at 90-100° C. for 2-3 hours. After completion of the reaction, the reaction mixture was poured into ice-cold water at 0° C. and stirred for half an hour. A solid precipitated out which was filtered in vacuo. The cake (solid bed) was washed with ethyl acetate 3-4 times. The aqueous layer was separated from ethyl acetate. The organic layer was washed with brine and water once respectively, dried over sodium sulphate and concentrated under vacuo to give pure methyl 2-(2-oxo-1,2,3,4-tetrahydroquinolin-7-yl)acetate. (0.280 g).

$^1$H-NMR (400 MHz, DMSO-d$_6$): δ 11.72 (bs, 1H), 7.87 (d, J=9.5 Hz, 1H), 7.58 (d, J=8.0 Hz, 1H), 7.18 (s, 1H), 7.07-7.05 (m, 1H), 6.45 (d, J=9.5 Hz, 1H), 3.64 (s, 3H), 3.68 (s, 2H).

Step (v) Synthesis of 2-(2-oxo-12-dihydroquinolin-7-yl)acetic acid

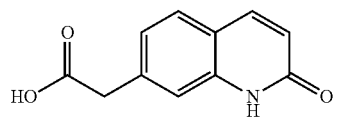

To methyl 2-(2-oxo-1,2,3,4-tetrahydroquinolin-7-yl)acetate (0.5 g, 2.46 moles), in MeOH (10 ml), was added 10% aqueous sodium hydroxide solution (10 ml) at 0° C. The reaction mixture was then stirred at room temperature for 2 hours. After completion of the reaction, solvent was removed in vacuo and the reaction mixture (aqueous layer) was washed twice with ethyl acetate. The aqueous layer was then cooled to 0° C. and acidified to pH 2 with 3N Aq. HCl. A Solid precipitated out which was filtered in vacuo, washed with water and dried to obtain pure 2-(2-oxo-1,2,3,4-tetrahydroquinolin-7-yl)ethaneperoxoic acid (0.35 g).

$^1$H-NMR (400 MHz, DMSO-d$_6$): δ 12.43 (bs, 1H), 11.72 (bs, 1H), 7.87 (d, J=9.5 Hz, 1H), 7.58 (d, J=8.0 Hz, 1H), 7.18 (s, 1H) 7.07-7.05 (m, 1H), 6.45 (d, J=9.5 Hz, 1H), 3.64 (s, 2H); MS (ES): m/z 204 (M+1).

Example 8-a 2-(2,2-dioxido-1,3-dihydrobenzo[c]isothiazol-6-yl) acetic acid

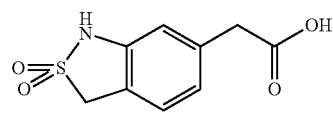 [SMILES: O=C(O)Cc1ccc2c(c1)NS(=O)(=O)C2]

Step (i) Synthesis of methyl 4-methyl-3-nitrobenzoate

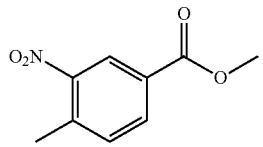

Thionyl chloride (33 ml, 0.447 moles) was added dropwise to 4-methyl-3-nitrobenzoic acid (27 g, 0.149 moles) in MeOH (500 ml) at 0° C. and the reaction mixture was then stirred for 12 hours in the temperature range of 0° C.-room temperature. Thereafter the reaction mixture was concentrated in vacuo, quenched with water, basified with saturated aqueous sodium bicarbonate solution and extracted 2-3 times with ethyl acetate. Combined ethyl acetate layer was washed twice with brine and water each respectively, dried over sodium sulphate and concentrated in vacuo to afford the titled product (29.7 g).

$^1$H-NMR (400 MHz, DMSO-$d_6$): δ 8.43 (s, 1H), 8.16-8.13 (m, 1H), 7.68 (d, J=7.9 Hz, 1H), 3.90 (s, 3H), 2.60 (s, 3H).

Step (ii) Synthesis of methyl 4-(bromomethyl)-3-nitrobenzoate

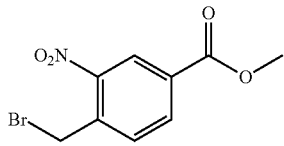

To the methyl 4-methyl-3-nitrobenzoate (29.7 g, 0.152 moles) in CCl$_4$ (450 ml), was added benzoyl peroxide (2 g, 0.0091 moles) and N-bromosuccinimide (32.5 g, 0.182 moles) at room temperature. The reaction mixture was then kept for refluxing at 90-100° C. for 15 hours. After completion of the reaction, the reaction mixture was cooled to room temperature, filtered in vacuo to remove succinimide precipitate. The filtrate was then concentrated in vacuo to give crude product which was purified by column chromatography using silica gel 230-400 mesh as stationary phase and 5% ethyl acetate in n-hexane as eluent to afford the titled product (23 g).

$^1$H-NMR (400 MHz, DMSO-$d_6$): δ 8.48 (s, 1H), 8.27-8.25 (m, 1H), 7.93-7.91 (m, 1H), 4.98 (s, 2H), 3.92 (s, 3H).

Step (iii) Synthesis of sodium (4-(methoxycarbonyl)-2-nitrophenyl)methanesulfonate

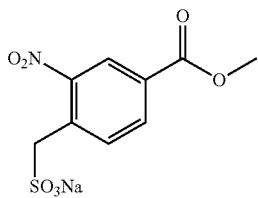

Tetrabutylammonium bromide (0.3 g, 0.00087 moles) was added to a mixture of sodium sulphite (14.5 g, 0.113 moles) in water (150 ml) at room temperature. To this reaction mixture, methyl 4-(bromomethyl)-3-nitrobenzoate (24 g, 0.087 moles) in MeOH (30 ml) was added at room temperature. The resultant mixture was then refluxed at 90-100° C. for 3 hours. After completion of the reaction, water and methanol were removed in vacuo. The residual water was then azeotrophed with toluene 3-4 times and the reaction mixture was dried thoroughly to obtain a crude solid product which was triturated twice with each of acetone, ethyl acetate and diethyl ether respectively, decanted and dried to obtain sodium (4-(methoxycarbonyl)-2-nitrophenyl)methanesulfonate (27 g) to be used as such for the next reaction without further purification.

$^1$H-NMR (400 MHz, DMSO-$d_6$): δ 8.28 (s, 1H), 8.14-8.12 (m, 1H), 7.66 (d, J=8.3 Hz, 1H), 4.27 (s, 2H), 3.90 (s, 3H).

Step (iv) Synthesis of sodium (2-amino-4-(methoxycarbonyl)phenyl)methanesulfonate

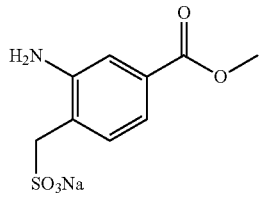

10% Pd/C (30% w/w, 3.6 g) was added to sodium (4-(methoxycarbonyl)-2-nitrophenyl)methanesulfonate (12 g, 0.040 moles) in MeOH (100 ml) under inert nitrogen atmosphere. The reaction mixture was then subjected to hydrogen gas pressure at 60 psi by using hydrogen bladder for 12 hours. After completion of the reaction, the reaction mixture was filtered through celite in vacuo. The filtrate was concentrated in vacuo to give the crude product which was triturated twice with each of ethyl acetate and diethyl ether respectively, decanted and dried to obtain sodium (2-amino-4-(methoxycarbonyl)phenyl)methanesulfonate as such for the next reaction without further purification (9 g).

$^1$H-NMR (400 MHz, DMSO-$d_6$): δ 7.31 (s, 1H), 7.14-7.12 (m, 1H), 7.04 (d, J=7.8 Hz, 1H), 5.42 (s, 2H), 3.80 (s, 3H), 3.74 (s, 2H).

Step (v) Synthesis of methyl 1,3-dihydrobenzo[c]isothiazole-6-carboxylate 2,2-dioxide

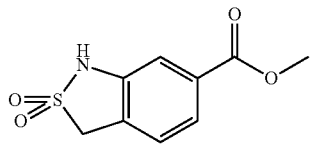

POCl$_3$ (55 ml) was added to sodium (2-amino-4-(methoxycarbonyl)phenyl) methanesulfonate (11 g, 0.041 moles) at room temperature and the reaction mixture was then heated to reflux at 140-150° C. for 2-3 hours. After completion of the reaction, the reaction mixture was allowed to cool to room temperature. POCl$_3$ was then distilled off under vacuo. Traces of POCl$_3$ were then removed by co-distilling with dichloromethane and diethyl ether respectively. The crude product thus obtained, was purified by flash chromatography using silica gel 230-400 mesh as stationary phase and 1% methanol in dichloromethane as eluent to afford methyl 1,3-dihydrobenzo[c]isothiazole-6-carboxylate 2,2-dioxide (3 g).

$^1$H-NMR (400 MHz, DMSO-$d_6$): δ 10.8 (s, 1H), 7.58 (d, J=7.9 Hz, 1H), 7.43 (d, J=7.8 Hz, 1H), 7.32 (s, 1H), 4.66 (s, 2H), 3.85 (s, 3H); MS (ES): m/z 226 (M−1).

Step (vi) Synthesis of methyl 1-benzyl-1,3-dihydrobenzo[c]isothiazole-6-carboxylate 2,2-dioxide

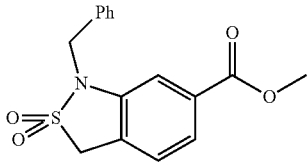 [SMILES: COC(=O)c1ccc2c(c1)N(Cc1ccccc1)S(=O)(=O)C2]

To methyl 1,3-dihydrobenzo[c]isothiazole-6-carboxylate 2,2-dioxide (1.8 g, 0.0079 moles) in DMF (15 ml), was added potassium carbonate (2.2 g, 0.0158 moles) at room temperature and stirred for 10 minutes. Benzyl bromide (1.36 g, 0.0079 moles) was then added at 0° C. and reaction mixture was stirred at room temperature for 2 hours. After completion of the reaction, ice-cold water was added to the reaction mixture and the aqueous layer was extracted with ethyl acetate (3×100 ml). Combined organic layer was washed twice with each of brine and water respectively, dried over sodium sulphate and concentrated in vacuo to give crude methyl 1-benzyl-1,3-dihydrobenzo[c]isothiazole-6-carboxylate 2,2-dioxide which was then triturated with petroleum ether to removes traces of benzyl bromide (1.92 g).

$^1$H-NMR (400 MHz, DMSO-$d_6$): δ 7.60 (s, 1H), 7.58 (s, 1H), 7.49-7.45 (m, 2H), 7.40-7.36 (m, 2H), 7.31 (d, J=7.3 Hz, 1H), 7.16 (s, 1H), 4.91 (s, 2H), 4.84 (s, 2H), 4.27-4.21 (q, 2H), 1.26 (t, 3H).

Step (vii) Synthesis of 1-benzyl-1,3-dihydrobenzo[c]isothiazole-6-carboxylic acid 2,2-dioxide

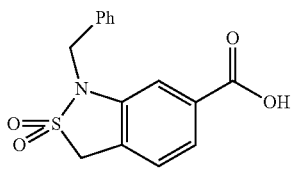 [SMILES: O=C(O)c1ccc2c(c1)N(Cc1ccccc1)S(=O)(=O)C2]

To methyl 1-benzyl-1,3-dihydrobenzo[c]isothiazole-6-carboxylate-2,2-dioxide (1.92 g, 0.068 moles) in MeOH (15 ml), was added 10% aqueous sodium hydroxide solution (15 ml) at 0° C. The reaction mixture was then heated at 50° C. for 2 hours. After completion of the reaction, the solvent was removed in vacuo and the reaction mixture (aqueous layer) was washed twice with ethyl acetate. The aqueous layer was then cooled to 0° C. and acidified to pH 2 with 3N Aq.HCl to obtain a solid precipitate which was filtered in vacuo, washed with water and dried to get 1-benzyl-1,3-dihydrobenzo[c]isothiazole-6-carboxylic acid 2,2-dioxide (1.2 g).

$^1$H-NMR (400 MHz, DMSO-$d_6$): δ 13.0 (bs, 1H), 7.59 (s, 1H), 7.57 (s, 1H), 7.46-7.40 (m, 2H), 7.38-7.32 (m, 2H), 7.29 (d, J=7.3 Hz, 1H), 7.15 (s, 1H), 4.89 (s, 2H), 4.83 (s, 2H).

Step (viii) Synthesis of 1-(1-benzyl-2,2-dioxido-1,3-dihydrobenzo[c]isothiazol-6-yl)-2-diazoethanone

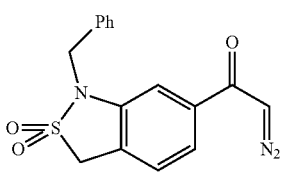

To benzyl-1,3-dihydrobenzo[c]isothiazole-6-carboxylic acid-2,2-dioxide (0.8 g, 0.0026 moles), SOCl$_2$ (20 ml) was added at room temperature under inert atmosphere. The reaction mixture was then refluxed for 6-8 hours. After complete conversion of acid into acid chloride, the reaction mixture was cooled to room temperature. SOCl$_2$ was distilled off completely in vacuo under inert nitrogen atmosphere. The reaction mixture was then cooled to 0° C. and diethyl ether (10 ml) was added to the crude acid chloride at 0° C. under inert atmosphere. A freshly prepared ethereal diazomethane solution (45 ml) (prepared from N-nitrosoN-methyl urea (1.5 g), 40% aq KOH solution (15 ml) was added slowly to the reaction mixture at 0° C. under inert nitrogen atmosphere. Finally, THF (10 ml) was added and reaction mixture was then kept for stirring at room temperature for 12 hours. After completion of the reaction, ether and THF were removed in vacuo at low temperature to give the crude product which was then purified by flash chromatography using 30% ethyl acetate in n-hexane as eluent to give 1-(1-benzyl-2,2-dioxido-1,3-dihydrobenzo[c]isothiazol-6-yl)-2-diazoethanone (0.7 g)

$^1$H-NMR (400 MHz, DMSO-$d_6$): δ 7.46-7.39 (m, 5H), 7.37-7.35 (m, 2H), 7.11 (s, 1H), 6.88 (s, 1H), 4.88 (s, 2H), 4.85 (s, 2H).

Step (ix) Synthesis of methyl 2-(1-benzyl-2,2-dioxido-1,3-dihydrobenzo[c]isothiazol-6-yl)acetate

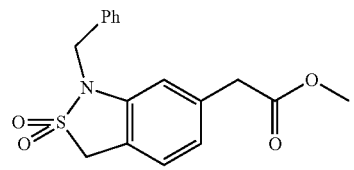 [SMILES: COC(=O)Cc1ccc2c(c1)N(Cc1ccccc1)S(=O)(=O)C2]

To 1-(1-benzyl-2,2-dioxido-1,3-dihydrobenzo[c]isothiazol-6-yl)-2-diazoethanone (0.8 g, 0.0024 moles) in methanol (15 ml), was added silver benzoate solution in triethylamine (3.5 ml) (prepared by dissolving 400 mg of silver benzoate in 4 ml of triethylamine) at room temperature. The reaction mixture was then heated at 50° C. for 1 hour. After completion of the reaction, the reaction mixture was cooled to room temperature and diluted with methanol, filtered through celite bed in vacuo. The filterate was concentrated in vacuo at low temperature to give crude solid which was then purified by purified by flash chromatography using silica gel 230-400 mesh as stationary phase and 20% ethyl acetate in n-hexane as eluent to give methyl 2-(1-benzyl-2,2-dioxido-1,3-dihydrobenzo[c]isothiazol-6-yl)acetate (0.53 g).

$^1$H-NMR (400 MHz, DMSO-$d_6$): δ 7.45-7.43 (m, 2H), 7.38-7.35 (m, 2H), 7.29-7.26 (m, 2H), 6.87 (d, J=8.0 Hz, 1H), 6.64 (s, 1H), 4.73 (s, 4H), 3.58 (s, 2H), 3.53 (s, 3H).

Step (x) Synthesis of methyl 2-(2,2-dioxido-1,3-dihydrobenzo[c]isothiazol-6-yl)acetate

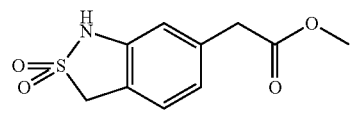 [SMILES: COC(=O)Cc1ccc2c(c1)NS(=O)(=O)C2]

To methyl 2-(1-benzyl-2,2-dioxido-1,3-dihydrobenzo[c]isothiazol-6-yl)acetate (0.5 g, 1.51 moles) in MeOH (10 ml), was added 10% Pd/C (50% w/w, 0.25 g) under inert nitrogen atmosphere. The reaction mixture was then subjected to hydrogen gas pressure at 70 psi for 6-8 hours. After completion of the reaction, the reaction mixture was filtered through celite in vacuo, and the filtrate was concentrated in vacuo to give the crude solid. The crude product was then purified by flash chromatography using silica gel 230-400 mesh as stationary phase and 30% ethyl acetate in n-hexane as eluent to afford methyl 2-(2,2-dioxido-1,3-dihydrobenzo[c]isothiazol-6-yl)acetate. (0.270 g)

$^1$H-NMR (400 MHz, DMSO-$d_6$): δ 10.48 (s, 1H), 7.21 (d, J=7.8 Hz, 1H), 6.85 (d, J=7.8 Hz, 1H), 6.73 (s, 1H), 4.49 (s, 2H), 3.66 (s, 2H), 3.60 (s, 3H).

Step (xi) Synthesis of 2-(2,2-dioxido-1,3-dihydrobenzo[c]isothiazol-6-yl)acetic acid

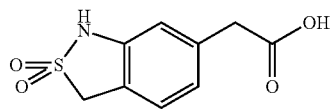 [SMILES: O=C(O)Cc1ccc2c(c1)NS(=O)(=O)C2]

To methyl 2-(2,2-dioxido-1,3-dihydrobenzo[c]isothiazol-6-yl)acetate (2.5 g, 0.011 moles) in MeOH (25 ml) was added 10% aqueous sodium hydroxide solution (25 ml) at 0° C. The reaction mixture was then heated at 50° C. for 2 hours. After completion of the reaction, the solvent was removed in vacuo and the reaction mixture (aqueous layer) washed with ethyl acetate. The aqueous layer was then cooled to 0° C., acidified to pH 2 with 3N aq.HCl to obtain a solid precipitate which was filtered in vacuo, washed with water and dried to afford 2-(2,2-dioxido-1,3-dihydrobenzo[c]isothiazol-6-yl)acetic acid (2 g).

$^1$H-NMR (400 MHz, DMSO-$d_6$): δ 13.10 (bs, 1H), 10.80 (bs, 1H), 7.57-7.55 (m, 1H), 7.40 (d, J=7.8 Hz, 1H), 7.31 (s, 1H), 4.64 (s, 2H).

Example 9-a 2-(1-methyl-2,2-dioxido-1,3-dihydrobenzo[c]isothiazol-6-yl)acetic acid

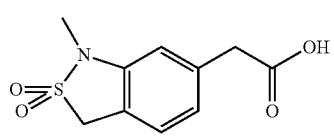 [SMILES: CN1c2cc(CC(=O)O)ccc2CS1(=O)=O]

Step (i) Synthesis of 1,3-dihydrobenzo[c]isothiazole-6-carboxylic acid 2,2-dioxide

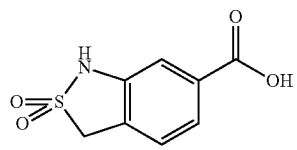 [SMILES: O=C(O)c1ccc2c(c1)NS(=O)(=O)C2]

To methyl 1,3-dihydrobenzo[c]isothiazole-6-carboxylate 2,2-dioxide (2.5 g, 0.011 moles) in MeOH (25 ml) was added 10% aqueous sodium hydroxide solution (25 ml) at 0° C. The reaction mixture was then heated at 50° C. for 2 hours. After completion of the reaction, the solvent was removed in vacuo and the reaction mixture (aqueous layer) was washed twice with ethyl acetate. The aqueous layer was then cooled to 0° C. and acidified to pH 2 with 3N Aq.HCl. The precipitated solid was filtered, washed with water and dried to get pure 1,3-dihydrobenzo[c]isothiazole-6-carboxylic acid 2,2-dioxide (2 g).

$^1$H-NMR (400 MHz, DMSO-$d_6$): δ 13.10 (bs, 1H), 10.8 (bs, 1H), 7.57-7.55 (m, 1H), 7.40 (d, J=7.8 Hz, 1H), 7.31 (s, 1H), 4.64 (s, 2H).

Step (ii) Synthesis of 2-diazo-1-(1-methyl-2,2-dioxido-1,3-dihydrobenzo[c]isothiazol-6-yl)ethanone

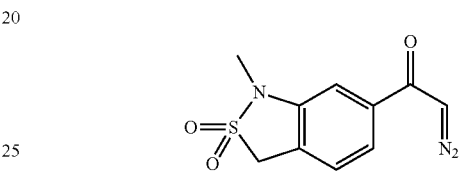

To 1,3-dihydrobenzo[c]isothiazole-6-carboxylic acid 2,2-dioxide (1 g, 0.0046 moles), was added SOCl$_2$ (20 ml) at room temperature under inert nitrogen atmosphere. The reaction mixture was then refluxed for 6-8 hours and cooled to room temperature. The SOCl$_2$ was distilled off in vacuo under inert nitrogen atmosphere. The reaction mixture was then cooled to 0° C. and diethyl ether (10 ml) was added to the crude acid chloride at 0° C. under inert atmosphere. A freshly prepared ethereal diazomethane solution (45 ml) (prepared from N-nitrosoN-methyl urea (1.5 g), 40% aq KOH solution (15 ml) was added slowly to the reaction mixture at 0° C. under inert nitrogen atmosphere. Finally, THF (10 ml) was added and reaction mixture was then stirred at room temperature for 12 hours. After completion of the reaction, ether and THF were removed in vacuo at low temperature to give the crude product which was then purified by flash chromatography using 30% ethyl acetate in n-hexane as eluent to give 2-diazo-1-(1-methyl-2,2-dioxido-1,3-dihydrobenzo[c]isothiazol-6-yl)ethanone. (0.8 g).

$^1$H-NMR (400 MHz, DMSO-$d_6$): δ 7.52-7.45 (m, 2H), 7.33 (s, 1H), 7.04 (s, 1H), 4.76 (s, 2H), 3.11 (s, 3H).

Step (iii) Synthesis of methyl 2-(1-methyl-2,2-dioxido-1,3-dihydrobenzo[c]isothiazol-6-yl)acetate

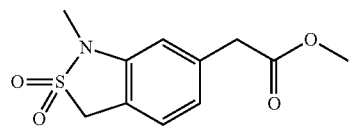 [SMILES: COC(=O)Cc1ccc2c(c1)N(C)S(=O)(=O)C2]

To 2,2-diazo-1-(1-methyl-2,2-dioxido-1,3-dihydrobenzo[c]isothiazol-6-yl)ethanone, (0.8 g, 0.0032 moles) in methanol (15 ml) was added 4.6 ml of silver benzoate solution in triethylamine (prepared by dissolving 500 mg of silver benzoate in 5 ml of triethylamine). The reaction mixture was heated at 50° C. for 1 hour. After completion of the reaction, the reaction mixture was cooled to room temperature and diluted with little excess of methanol. The solid was filtered through a short pad of celite and washed with excess of methanol. The filterate was then concentrated under vacuo at low temperature to give crude solid which was purified using column chromatography over silica gel using 25% ethyl acetate in n-hexane as eluent to give methyl 2-(1-methyl-2,2-dioxido-1,3-dihydrobenzo[c]isothiazol-6-yl)acetate (0.60 g).

¹H-NMR (400 MHz, DMSO-$d_6$): δ 7.26 (d, J=7.3 Hz, 1H), 6.92-6.90 (m, 1H), 6.85 (s, 1H), 4.62 (s, 2H), 3.69 (s, 2H), 3.61 (s, 3H), 3.01 (s, 3H).

Step (iv) Synthesis of 2-(1-methyl-2,2-dioxido-1,3-dihydrobenzo[c]isothiazol-6-yl)acetic acid

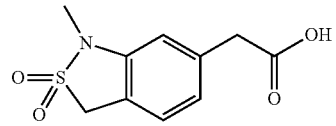 [SMILES: CN1c2cc(CC(=O)O)ccc2CS1(=O)=O]

To a solution of methyl 2-(1-methyl-2,2-dioxido-1,3-dihydrobenzo[c]isothiazol-6-yl)acetate (0.42 g, 0.0016 moles) in MeOH (15 ml) was added 10% aqueous sodium hydroxide solution (15 ml) at 0° C. The reaction mixture was then stirred at room temperature for 2 hours. After completion of the reaction, the solvent was removed in vacuo, the residue was dissolved in water and extracted with ethyl acetate twice. The aqueous layer was cooled to 0° C. and acidified to pH 2 with 3N Aq.HCl. The precipitated solid was filtered and washed with water and dried get pure 2-(2,2-dioxido-1,3-dihydrobenzo[c]isothiazol-6-yl)acetic acid (0.27 g).

¹H-NMR (400 MHz, DMSO-$d_6$): δ 12.37 (bs, 1H), 7.25 (d, J=7.8 Hz, 1H), 6.92-6.89 (m, 1H), 6.83 (s, 1H), 4.61 (s, 2H), 3.58 (s, 2H), 3.01 (s, 3H).

Example 10-a 2-(2,2-dioxido-1,3-dihydrobenzo[c]isothiazol-5-yl)acetic acid

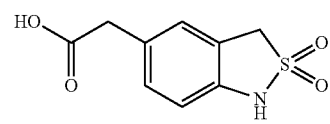 [SMILES: O=C(O)Cc1ccc2c(c1)CS(=O)(=O)N2]

Step (i) Synthesis of sodium (2-nitrophenyl)methanesulfonate

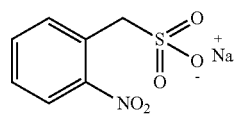

A mixture of Na$_2$SO$_3$ (25.6 g, 1.30 equiv), TBAI (600 mg, 1.62 mmol, 0.01 equiv), 1-(bromomethyl)-2-nitrobenzene (33.8 g, 1.00 equiv) and water (250 mL) was stirred for 15 h at 90° C. in an oil bath. The reaction mixture was cooled to room temperature and concentrated in vacuo. The residue was washed once with each of acetone, ethyl acetate and diethyl ether respectively. The solid was dried in an oven under reduced pressure to obtain 34 g (90%) of the title compound as a light yellow solid.

Step (ii) Synthesis of sodium (2-aminophenyl)methanesulfonate

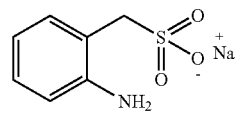

In an inert atmosphere of nitrogen, a solution of sodium (2-nitrophenyl)methanesulfonate (3 g, 12.54 mmol, 1.00 equiv) in methanol (50 mL) was treated with Palladium carbon hydrogen (0.5 g). The reaction mixture was then stirred under a hydrogen atmosphere for 16 h at 25° C., filtered, concentrated in vacuo to obtain 2 g (76%) of the title compound as a white solid.

LC-MS: (ES, m/z): 188 (M+1).

Step (iii) Synthesis of 1,3-dihydrobenzo[c]isothiazole 2,2-dioxide

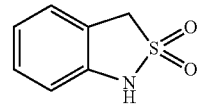

A solution of sodium (2-aminophenyl)methanesulfonate (5.2 g, 24.86 mmol, 1.00 equiv) in POCl$_3$ (148.2 g) was heated to reflux for 2 hr. The resulting mixture was concentrated in vacuo, quenched by the addition of 2N sodium hydroxide and the resulting basic solution was extracted with ethyl acetate and the aqueous layers were combined. The pH value of the solution was adjusted to 2 with 2N HCl. The solids were filtered, dried in an oven under reduced pressure to obtain 1.5 g (36%) of the title compound as a white solid.

Step (iv) Synthesis of 5-bromo-1,3-dihydrobenzo[c]isothiazole 2,2-dioxide

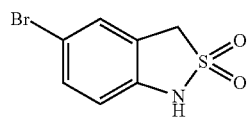

To a solution of 1,3-dihydrobenzo[c]isothiazole 2,2-dioxide (1.7 g, 10.05 mmol, 1.00 equiv) in acetic acid (15 mL) was added a solution of Br$_2$ (1.69 g, 10.56 mmol, 1.05 equiv) in acetic acid (1 mL) dropwise with stirring. The resulting solution was stirred for 2 h at 25° C. The resulting mixture was concentrated in vacuo followed by purification with column chromatography with silica gel as stationary phase and ethyl acetate/hexane (1:10) as eluent. This resulted in 1.6 g (64%) of the titled compound as a light yellow solid.

Step (v) Synthesis of 1-benzyl-5-bromo-1,3-dihydrobenzo[c]isothiazole-2,2-dioxide

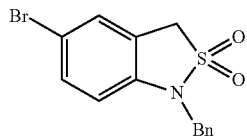 [SMILES: O=S1(=O)Cc2cc(Br)ccc2N1Cc1ccccc1]

To a suspension of 5-bromo-1,3-dihydrobenzo[c]isothiazole 2,2-dioxide (1.5 g, 6.05 mmol, 1.00 equiv) and potassium carbonate (1.67 g, 12.08 mmol, 2.00 equiv) in N,N-dimethylformamide (15 mL) was added BnBr (1.08 g, 6.31 mmol, 1.05 equiv) dropwise with stirring at 0° C. The resulting solution was stirred for 1 h at 25° C. and then diluted with water. The resulting solution was extracted with 3×50 mL of ethyl acetate and the combined organic layers were washed with brine, dried over anhydrous sodium sulfate and concentrated in vacuo. The residue was purified by column chromatography using silica gel as stationary phase and ethyl acetate/petroleum ether (1:15) as eluent. This resulted in 1.6 g (78%) of the titled compound as a white solid.

Step (vi) Synthesis of tert-butyl 2-(1-benzyl-2,2-dioxido-1,3-dihydrobenzo[c]isothiazol-5-yl)acetate

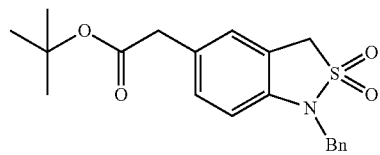 [SMILES: CC(C)(C)OC(=O)Cc1ccc2c(c1)CS(=O)(=O)N2Cc1ccccc1]

In an inert atmosphere of nitrogen, a solution of 1-benzyl-5-bromo-1,3-dihydrobenzo[c]isothiazole-2,2-dioxide (600 mg, 1.77 mmol, 1.00 equiv), X-Phos (170 mg, 0.36 mmol, 0.20 equiv), $Pd_2(dba)_3$ (160 mg, 0.17 mmol, 0.10 equiv) and tert-butyl 2-(bromozincio)acetate (1.62 g, 6.22 mmol, 3.50 equiv) in tetrahydrofuran (40 mL) was stirred for 16 h at 72° C. The reaction was then quenched by the addition of 40 mL of water, filtered, extracted with 3×50 mL of ethyl acetate and the combined organic layers were washed with brine, dried over anhydrous sodium sulfate and concentrated in vacuo. The residue was purified by column chromatography using silica gel as stationary phase and ethyl acetate/petroleum ether (1:20) as eluent to obtain 0.37 g (56%) of the titled compound as an off-white solid.

Step (vii) Synthesis of tert-butyl 2-(2,2-dioxido-1,3-dihydrobenzo[c]isothiazol-5-yl)acetate

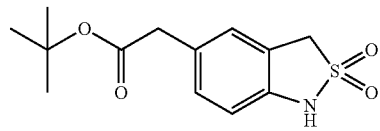 [SMILES: CC(C)(C)OC(=O)Cc1ccc2c(c1)CS(=O)(=O)N2]

In an inert atmosphere of nitrogen, to a solution of tert-butyl 2-(1-benzyl-2,2-dioxido-1,3-dihydrobenzo[c]isothiazol-5-yl)acetate (370 mg, 0.99 mmol, 1.00 equiv) in methanol (20 mL) was added palladium carbon (50 mg). The reaction was stirred under a hydrogen atmosphere for 1.5 h at 25° C. and then filtered, concentrated in vacuo to obtain the titled compound (360 mg) as yellow oil.

Step (viii) Synthesis of 2-(2,2-dioxido-1,3-dihydrobenzo[c]isothiazol-5-yl)acetic acid

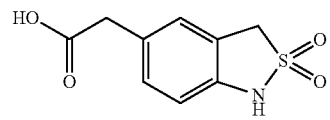 [SMILES: O=C(O)Cc1ccc2c(c1)CS(=O)(=O)N2]

A solution of tert-butyl 2-(2,2-dioxido-1,3-dihydrobenzo[c]isothiazol-5-yl)acetate (360 mg, 1.27 mmol, 1.00 equiv) and trifluoroacetic acid (5 mL) in dichloromethane (5 mL) was stirred for 2 h at 25° C. The resulting mixture was concentrated in vacuo. The residue was dissolved in water. Then the solution was lyophilized to yield 0.29 g of the title compound as an off-white solid.

Example 11-a 2-(3-oxo-3,4-dihydro-2H-benzo[b][1,4]thiazin-6-yl)acetic acid

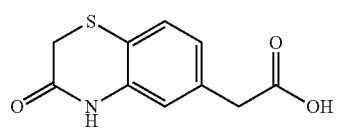 [SMILES: O=C(O)Cc1ccc2c(c1)NC(=O)CS2]

Step (i) Synthesis of methyl 2-(4-fluoro-3-nitrophenyl)acetate

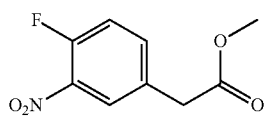

A solution of 2-(4-fluoro-3-nitrophenyl)acetic acid (90 g, 452.26 mmol, 1.00 equiv) in methanol (400 mL) and conc. $H_2SO_4$ (10 mL) was refluxed for 4 h in an oil bath. The reaction was then quenched by the addition of 1200 mL of ice-cold water. The resulting solution was extracted with ethyl acetate (3×500 mL). The combined organic layers were washed with sat. $NaHCO_3$ (2×400 mL), dried over anhydrous sodium sulfate and concentrated in vacuo to obtain methyl 2-(4-fluoro-3-nitrophenyl)acetate (90 g) as brown oil.

Step (ii) Synthesis of ethyl 2-((4-(2-methoxy-2-oxoethyl)-2-nitrophenyl)thio)acetate

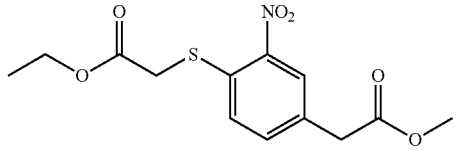 [SMILES: CCOC(=O)CSc1ccc(CC(=O)OC)cc1[N+](=O)[O-]]

A solution of methyl 2-(4-fluoro-3-nitrophenyl)acetate (90 g, 422.54 mmol, 1.00 equiv) in tetrahydrofuran (400 mL), triethylamine (85 g, 841.58 mmol, 2.01 equiv) and ethyl 2-mercaptoacetate (65 g, 541.67 mmol, 1.28 equiv) was stirred for 12-16 h at 15° C. and concentrated in vacuo. The solids were collected by filtration. This resulted in 80 g (crude) of methyl 2-(4-(2-ethoxy-2-oxoethylthio)-3-nitrophenyl)acetate as a yellow solid.

Step (iii) Synthesis of methyl 2-(3-oxo-3,4-dihydro-2H-benzo[b][1,4]thiazin-6-yl)acetate

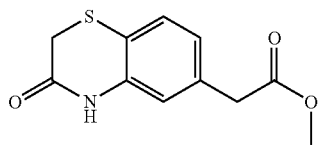 [SMILES: COC(=O)Cc1ccc2c(c1)NC(=O)CS2]

A solution of methyl 2-(4-(2-ethoxy-2-oxoethylthio)-3-nitrophenyl)acetate (5 g, 15.97 mmol, 1.00 equiv) in methanol (100 mL) and Zn (5 g, 76.92 mmol, 4.82 equiv), acetic acid (5 mL) was heated under reflux for 2 h in an oil bath. The solids were filtered out. The resulting mixture was concentrated in vacuo, diluted with 400 mL of sat. NaHCO$_3$. The resulting solution was extracted with 3×200 mL of ethyl acetate. The combined organic layers were washed with 2×200 mL of brine, dried over sodium sulfate and concentrated in vacuo. The crude product was purified by re-crystallization from ethyl acetate to obtain methyl 2-(3-oxo-3,4-dihydro-2H-benzo[b][1,4]thiazin-6-yl)acetate (2.8 g) as a white solid.

MS (ESI) m/z: 238 (M+1).

Step (iv) Synthesis of 2-(3-oxo-3,4-dihydro-2H-benzo[b][1,4]thiazin-6-yl)acetic acid

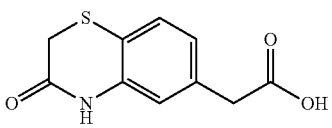

A solution of methyl 2-(3-oxo-3,4-dihydro-2H-benzo[b][1,4]thiazin-6-yl)acetate (7.8 g, 32.91 mmol, 1.00 equiv) in methanol:water (3:1) (160 mL) and LiOH·H$_2$O (7 g, 166.67 mmol, 5.06 equiv) was stirred for 2 h at 25° C. and then diluted with 100 mL of water. The pH value of the solution was adjusted to 3-4 with 2N HCl to obtain a solid precipitate which was collected by filtration. The crude product was purified by re-crystallization from methanol. This resulted in 2-(3-oxo-3,4-dihydro-2H-benzo[b][1,4]thiazin-6-yl)acetic acid (7 g) as a white solid.

MS (ESI) m/z: 224 (M+1).

Example 12-a

2-(1,1-dioxido-3-oxo-3,4-dihydro-2H-benzo[b][1,4]thiazin-6-yl)acetic acid

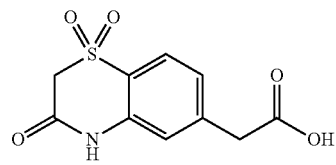 [SMILES: O=C(O)Cc1ccc2c(c1)NC(=O)CS2(=O)=O]

Step (i) Synthesis of methyl 2-(1,1-dioxido-3-oxo-3,4-dihydro-2H-benzo[b][1,4]thiazin-6-yl)acetate

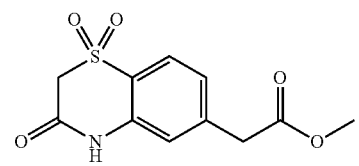 [SMILES: COC(=O)Cc1ccc2c(c1)NC(=O)CS2(=O)=O]

A solution of methyl 2-(3-oxo-3,4-dihydro-2H-benzo[b][1,4]thiazin-6-yl)acetate (5 g, 21.10 mmol, 1.00 equiv) in dichloromethane (120 mL) and m-CPBA (11 g, 63.95 mmol, 3.03 equiv) was stirred for 20 h at 25° C., diluted with 300 mL of dichloromethane, washed with 2×250 mL of sat.NaHCO$_3$. The aqueous phase was extracted with 2×150 mL of dichloromethane. The combined organic layers were dried over anhydrous sodium sulfate and concentrated in vacuo. The residue was purified by column chromatography using silica gel as stationary phase and ethyl acetate: petroleum ether (1:3) as eluent to obtain 4.5 g of methyl 2-(3-oxo-3,4-dihydro-2H-benzo[b][1,4]thiazin 1,1-dioxide-6-yl) acetate as a white solid.

MS (ESI) m/z: 270 (M+1).

Step (ii) Synthesis of 2-(1,1-dioxido-3-oxo-3,4-dihydro-2H-benzo[b][1,4]thiazin-6-yl)acetic acid

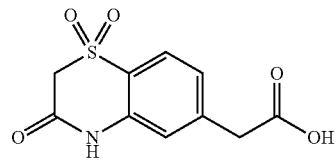 [SMILES: O=C(O)Cc1ccc2c(c1)NC(=O)CS2(=O)=O]

A solution of methyl 2-(3-oxo-3,4-dihydro-2H-benzo[b][1,4]thiazin 1,1-dioxide-6-yl)acetate (6.5 g, 24.16 mmol, 1.00 equiv) in tetrahydrofuran:MeOH:H$_2$O (4:1:1) (120 mL) and LiOH.H$_2$O (5 g, 119.05 mmol, 4.93 equiv) was stirred for 2 h at 20° C. The resulting mixture was concentrated in vacuo. The reaction was then quenched by the addition of 150 mL of ice-cold water. The pH of the solution was adjusted to 3-4 with 2N HCl. The solution was filtered to obtain 2-(3-oxo-3,4-dihydro-2H-benzo[b][1,4]thiazin 1,1-dioxide-6-yl)acetic acid (5.5 g) as a white solid.

MS (ESI) m/z: 256 (M+1).

Example 13-a 2-(1,1-dioxido-3-oxo-2,3-dihydrobenzo[d]isothiazol-6-yl)acetic acid

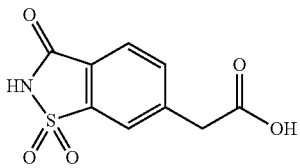 [SMILES: O=C(O)Cc1ccc2c(c1)S(=O)(=O)NC2=O]

Step (i) Synthesis of 5-bromo-2-methylbenzene-1-sulfonyl chloride

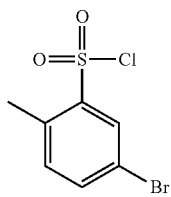

To 1-bromo-4-methylbenzene (40 g, 233.92 mmol, 1.00 equiv) was added sulfurochloridic acid (53.8 g) dropwise with stirring at about 30° C. The resulting solution was stirred for 3 h at 60° C. in an oil bath and then poured into 300 g of ice-cold water, The resulting solution was extracted with 3×200 mL of ethyl acetate. The combined organic layers were dried over anhydrous sodium sulfate and concentrated in vacuo. This resulted in 5-bromo-2-methylbenzene-1-sulfonyl chloride (30 g) as light yellow oil.

Step (ii) Synthesis of 5-bromo-2-methylbenzenesulfonamide

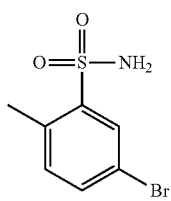

A solution of 5-bromo-2-methylbenzene-1-sulfonyl chloride (14 g, 51.85 mmol, 1.00 equiv) in dioxane (300 mL) and NH$_4$OH (600 mL) was stirred overnight at 0-10° C. The solids were filtered out. The resulting mixture was concentrated in vacuo to obtain 5-bromo-2-methylbenzenesulfonamide (9 g) as a white solid.

Step (iii) Synthesis of 4-bromo-2-sulfamoylbenzoic acid

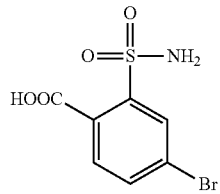 [SMILES: NS(=O)(=O)c1cc(Br)ccc1C(=O)O]

A solution of 5-bromo-2-methylbenzenesulfonamide (9 g, 36.00 mmol, 1.00 equiv) and KMnO$_4$ (29 g, 183.54 mmol, 4.98 equiv) in sodium hydroxide (10%) (60 mL) was stirred for 5 h at 40° C. The reaction was then quenched by the addition of NaHSO$_3$ (5 g). The solids were filtered out. The pH value of the filtrate was adjusted to 2 which resulted in precipitation of the product 4-bromo-2-sulfamoylbenzoic acid (10 g) as a white solid.

LC-MS (ES, m/z): 278, 280 (M−1)⁻

Step (iv) Synthesis of 6-bromobenzo[d]isothiazol-3(2H)-one-1,1-dioxide

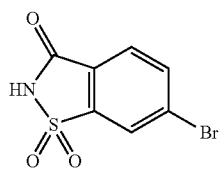 [SMILES: O=C1NS(=O)(=O)c2cc(Br)ccc21]

A solution of 4-bromo-2-sulfamoylbenzoic acid (4 g, 14.29 mmol, 1.00 equiv) in polyphosphoric acid (200 mL) was stirred for 4 h at 100° C. The reaction was then quenched by the addition of ice-cold water (100 mL). The resulting solution was extracted with 3×100 mL of ethyl acetate. The combined organic layers were dried over sodium sulfate and concentrated in vacuo. This resulted in 6-bromobenzo[d]isothiazol-3(2H)-one 1,1-dioxide (3.5 g) as a white solid.

Step (v) Synthesis of 6-bromo-2-((2-(trimethylsilyl)ethoxy)methyl)benzo[d]isothiazol-3(2H)-one 1,1-dioxide

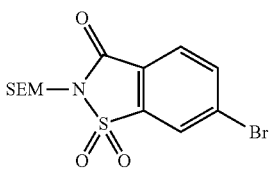 [SMILES: C[Si](C)(C)CCOCN1C(=O)c2ccc(Br)cc2S1(=O)=O]

In an inert atmosphere of nitrogen, to a solution of 6-bromobenzo[d]isothiazol-3(2H)-one 1,1-dioxide (1 g, 3.83 mmol, 1.00 equiv) in THF (10 mL) was added sodium hydride (310 mg, 12.92 mmol, 1.54 equiv) at 0° C. After 30 min, SEM-Cl (890 mg, 7.63 mmol, 1.50 equiv) was added. The resulting solution was stirred overnight at 20-35° C. The reaction was then quenched by the addition of 10 mL of water. The resulting solution was extracted with 3×30 mL of ethyl acetate. The combined organic layers were dried over anhydrous sodium sulfate and concentrated in vacuo. The residue was purified by column chromatography using silica gel as stationary phase and ethyl acetate/petroleum ether (1:50) as eluent to obtain the titled compound (0.8 g) as a white solid.

Step (vi) Synthesis of tert-butyl 2-(1,1-dioxido-3-oxo-2-((2-(trimethylsilyl)ethoxy)methyl)-2,3-dihydrobenzo[d]isothiazol-6-yl)acetate

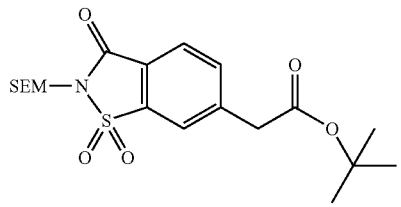 [SMILES: CC(C)(C)OC(=O)Cc1ccc2c(c1)S(=O)(=O)N(COCC[Si](C)(C)C)C2=O]

In an inert atmosphere of nitrogen, a solution of 6-bromo-2-((2-(trimethylsilyl)ethoxy)methyl)benzo[d]isothiazol-3(2H)-one 1,1-dioxide (500 mg, 1.28 mmol, 1.00 equiv), (2-tert-butoxy-2-oxoethyl)zinc(II) bromide (1180 mg, 4.54 mmol, 2.56 equiv), Pd$_2$(dba)$_3$ (40 mg, 0.04 mmol, 0.23 equiv) and Q-phos (28 mg, 0.04 mmol, 0.40 equiv) in THF (10 mL), was stirred for 5 h at 70° C. The resulting solution was then concentrated in vacuo. The residue was purified by column chromatography using silica gel as stationary phase and ethyl acetate/petroleum ether (1:15) as eluent to obtain the titled compound (200 mg) as a light yellow solid.

Step (vii) Synthesis of 2-(1,1-dioxido-3-oxo-2,3-dihydrobenzo[d]isothiazol-6-yl)acetic acid

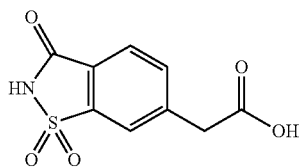 [SMILES: O=C(O)Cc1ccc2c(c1)S(=O)(=O)NC2=O]

A solution of tert-butyl 2-(1,1-dioxido-3-oxo-2-((2-(trimethylsilyl)ethoxy)methyl)-2,3-dihydrobenzo[d]isothiazol-6-yl)acetate (500 mg, 1.17 mmol, 1.00 equiv) in dichloromethane (8 mL) and CF$_3$COOH (800 mg, 7.02 mmol, 5.99 equiv) was stirred for 24 h at room temperature. The resulting mixture was then concentrated in vacuo to obtain the crude product which was further purified by Prep-HPLC to result in the title compound (170 mg) as a white solid.

LC-MS (ES, m/z): 240 (M−1)$^-$; $^1$H-NMR: (CD$_3$OD, 400 MHz) δ 7.961-7.989 (m, 2H), 7.830-7.890 (m, 1H), 3.929 (s, 2H).

Example 14-a 2-(3-oxo-3,4-dihydroquinoxalin-6-yl)acetic acid

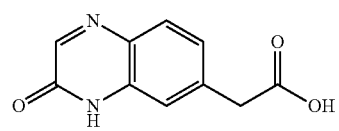 [SMILES: O=C(O)Cc1ccc2ncc(=O)[nH]c2c1]

Step (i) Synthesis of methyl 2-((4-(2-methoxy-2-oxoethyl)-2-nitrophenyl)amino)acetate

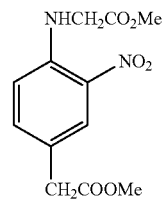

A solution of methyl 2-(4-fluoro-3-nitrophenyl)acetate (6 g, 28.15 mmol, 1.00 equiv), NH$_2$CH$_2$CO$_2$Me HCl (3.9 g, 30.95 mmol, 1.10 equiv) and i-Pr$_2$NEt (10.8 g, 83.72 mmol, 3.00 equiv) in N,N-dimethylformamide (100 mL) was stirred overnight at 30° C. The reaction was then quenched by the addition of 50 mL of water. The resulting solution was extracted with 3×100 mL of ethyl acetate. The combined organic layers were washed with 6×100 mL of brine, dried over Na$_2$SO$_4$ and concentrated under vacuum. The residue was applied onto a silica gel column and eluted with ethyl acetate/petroleum ether (1:5). This resulted in 4 g of methyl 2-(4-(2-methoxy-2-oxoethyl)-2-nitrophenylamino)acetate as a yellow solid.

Step (ii) Synthesis of methyl 2-(3-oxo-1,2,3,4-tetrahydroquinoxalin-6-yl)acetate

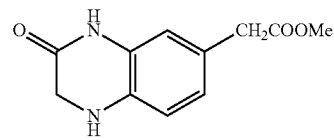

In an inert nitrogen atmosphere, a suspension of methyl 2-(4-(2-methoxy-2-oxoethyl)-2-nitrophenylamino)acetate (2 g, 7.09 mmol, 1.00 equiv), 10% Palladium carbon (1 g) and HCO$_2$NH$_4$ (6.7 g, 106.35 mmol, 15.00 equiv) in ethanol (60 mL) was stirred overnight at room temperature. The solids were filtered out. The filtrate was concentrated under vacuum. The residue was dissolved in EtOAc (100 ml), washed with water, dried over Na$_2$SO$_4$ and concentrated under vacuum. This resulted in 1.5 g of methyl 2-(3-oxo-1,2,3,4-tetrahydroquinoxalin-6-yl)-acetate as a white solid.

MS (ESI): m/z: 221 (M+1).

Step (iii) Synthesis of 2-(3-oxo-3,4-dihydroquinoxalin-6-yl)acetic acid

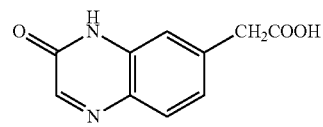

3% H$_2$O$_2$ (6.78 g, 2.00 equiv) was added to a solution of 2-(3-oxo-1,2,3,4-tetrahydroquinoxalin-6-yl)acetic acid (600 mg, 2.91 mmol, 1.00 equiv) in 8% sodium hydroxide (7.50 g, 5.00 equiv) solution and the resulting solution was heated to reflux for 2 hours. To this hot solution was added slowly acetic acid until pH 3-4. The resulting solution was cooled to room temperature and the precipitated product was collected by filtration and washed with water. The product was dried in an oven under reduced pressure. This resulted in 510 mg of 2-(3-oxo-1,2,3,4-tetrahydroquinoxalin-6-yl)acetic acid as a yellow solid.

MS (ES, m/z): 205 (M+1); $^1$H-NMR (DMSO-$d_6$, 300 MHz): δ 12.439 (br, 1H), 8.148 (s, 1H), 7.717-7.746 (d, 1H, J=8.7 Hz), 7.207-7.224 (m, 2H), 3.710 (s, 2H).

Example 15-a 2-(3-oxo-3,4-dihydro-2H-benzo[b][1,4]oxazin-6-yl)acetic acid

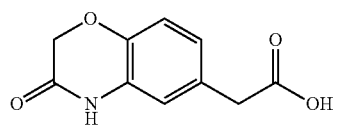 [SMILES: O=C(O)Cc1ccc2c(c1)NC(=O)CO2]

Step (i) Synthesis of 2-(4-hydroxy-3-nitrophenyl)acetic acid

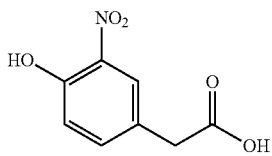

Into a 250-mL 3-necked round-bottom flask, was placed a solution of 2-(4-hydroxyphenyl)acetic acid (30 g, 197.37 mmol, 1.00 equiv) in acetic acid (100 mL). A solution of HNO$_3$(65%) (19 g, 301.59 mmol, 1.53 equiv) in acetic acid (25 mL) was then added dropwise with stirring while the temperature not exceeding 10° C. The resulting solution was stirred for 1 h at 15° C. The solids were collected by filtration and washed with 3×50 mL of water. This resulted in 20 g of 2-(4-hydroxy-3-nitrophenyl)acetic acid as a yellow solid.

Step (ii) Synthesis of methyl 2-(4-hydroxy-3-nitrophenyl)acetate

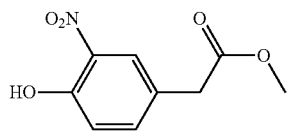

Into a 500-mL 3-necked round-bottom flask, was placed a solution of 2-(4-hydroxy-3-nitrophenyl)acetic acid (10 g, 50.76 mmol, 1.00 equiv) in methanol (50 mL). Thionyl chloride (12 g, 100.84 mmol, 1.99 equiv) was then added dropwise at 0° C. The resulting solution was stirred for 2 h at room temperature. The reaction was then quenched by the addition of 2 mL of water. The resulting mixture was concentrated under vacuum. This resulted in 10 g of methyl 2-(4-hydroxy-3-nitrophenyl) acetate as a yellow solid.

Step (iii) Synthesis of ethyl 2-(4-(2-methoxy-2-oxoethyl)-2-nitrophenoxy)acetate

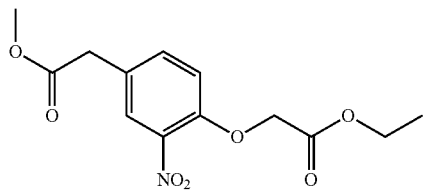 [SMILES: CCOC(=O)COc1ccc(CC(=O)OC)cc1[N+](=O)[O-]]

Into a 250-mL 3-necked round-bottom flask, was placed a suspension of methyl 2-(4-hydroxy-3-nitrophenyl)acetate (5 g, 23.70 mmol, 1.00 equiv) and Cs$_2$CO$_3$ (15.45 g, 47.39 mmol, 2.00 equiv) in tetrahydrofuran (100 mL). This was followed by the dropwise addition of a solution of ethyl 2-bromoacetate (4.75 g, 28.44 mmol, 1.20 equiv) in tetrahydrofuran (20 mL) with stirring at room temperature. The resulting solution was heated under reflux for 2 hr. The reaction mixture was cooled to room temperature and diluted with 50 mL of water. The resulting solution was extracted with 3×50 mL of ethyl acetate. The combined organic layers were dried over anhydrous sodium sulfate and concentrated under vacuum. This resulted in 3 g of methyl 2-(4-(2-ethoxy-2-oxoethoxy)-3-nitrophenyl)acetate as a pale yellow solid.

Step (iv) Synthesis of methyl 2-(3-oxo-3,4-dihydro-2H-benzo[b][1,4]oxazin-6-yl)acetate

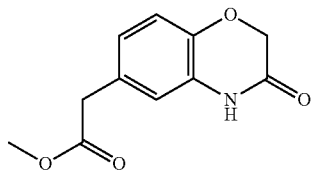 [SMILES: COC(=O)Cc1ccc2c(c1)NC(=O)CO2]

Into a 250-mL 3-necked round-bottom flask, was placed a solution of methyl 2-(4-(2-ethoxy-2-oxoethoxy)-3-nitrophenyl)acetate (3 g, 10.10 mmol, 1.00 equiv) in HOAc (30 mL). This was followed by the addition of iron (1.7 g, 30.36 mmol, 3.01 equiv) in several portions. The resulting solution was stirred for 2 h under reflux. The solids were filtered out. The reaction was then diluted with 50 mL of water. The resulting solution was extracted with 3×50 mL of ethyl acetate. The combined organic layers combined were washed with 3×30 mL of brine, dried over anhydrous sodium sulfate and concentrated under vacuum. This resulted in 1.5 g of methyl 2-(3-oxo-3,4-dihydro-2H-benzo[b][1,4]oxazin-6-yl)acetate as a light yellow solid.

Step (v) Synthesis of 2-(3-oxo-3,4-dihydro-2H-benzo[b][1,4]oxazin-6-yl)acetic acid

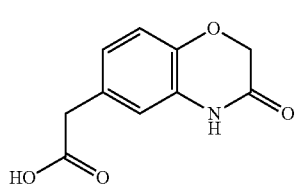 [SMILES: O=C(O)Cc1ccc2c(c1)NC(=O)CO2]

Into a 100-mL round-bottom flask, was placed a solution of methyl 2-(3-oxo-3,4-dihydro-2H-benzo[b][1,4]oxazin-6-yl)acetate (2 g, 9.05 mmol, 1.00 equiv) in methanol (20 mL). Then a solution of sodium hydroxide (720 mg, 18.00 mmol, 1.99 equiv) in water (20 mL) was added. The resulting solution was stirred for 3 h at room temperature. The resulting mixture was concentrated under vacuum, diluted with 30 mL of H$_2$O. The pH value of the resulting solution was adjusted to 2-3 and then extracted with 5×50 mL of ethyl acetate. The combined organic layers were washed with brine, dried over anhydrous sodium sulfate and concentrated under vacuum. The residue was applied onto a silica gel column and eluted with ethyl acetate/petroleum ether (1:2). This resulted in 1 g of 2-(3-oxo-3,4-dihydro-2H-benzo[b][1,4]oxazin-6-yl)acetic acid as a yellow solid.

LC-MS (ES−, m/z): 206 (M−1)−; 1H-NMR (DMSO-d6, 300 MHz): δ 12.290 (br, 1H), 10.707 (s, 1H), 6.793-6.910 (m, 3H), 4.559 (s, 2H), 3.490 (s, 2H).

Example 16-a 2-(3,3-difluoro-1-(4-methoxybenzyl)-2-oxoindolin-6-yl)acetic acid

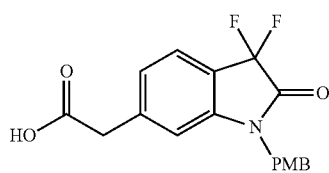

Step (i) Synthesis of
6-bromo-3,3-difluoroindolin-2-one

Into a 50-mL 3-necked round-bottom flask purged and maintained with an inert atmosphere of nitrogen, was placed a solution of 6-bromo-2,3-dihydro-1H-indole-2,3-dione (2.5 g, 11.06 mmol, 1.00 equiv) in dichloromethane (15 mL). This was followed by the addition of DAST (6.26 g, 38.84 mmol, 3.51 equiv) dropwise with stirring at 0° C. The resulting solution was stirred for 5 h at 25° C. The resulting solution was quenched with 150 mL of aqueous saturated NaHCO$_3$. The resulting aqueous solution was extracted with 3×150 mL of dichloromethane. The organic layers were combined and dried over anhydrous sodium sulfate, concentrated under vacuum. The residue was applied onto silica gel column and eluted with Petroleum ether:Ethyl acetate=50:1-25:1 to give 1.95 g (71%) of 6-bromo-3,3-difluoro-2,3-dihydro-1H-indol-2-one as a yellow solid.

$^1$H-NMR (CDCl$_3$, 300 MHz): δ 7.91 (s, 1H), 7.43-7.40 (d, J=8.1 Hz, 1H), 7.34-7.32 (d, J=8.1 Hz, 1H), 7.13 (s, 1H).

Step (ii) Synthesis of 6-bromo-3,3-difluoro-1-(4-methoxybenzyl)indolin-2-one

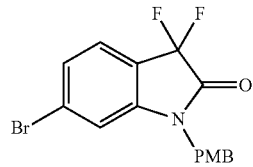

Into a solution of 6-bromo-3,3-difluoro-2,3-dihydro-1H-indol-2-one (1.36 g, 5.48 mmol, 1.00 equiv) in N,N-dimethylformamide (5 mL) was added potassium carbonate (2.28 g, 16.50 mmol, 3.01 equiv). then 1-(bromomethyl)-4-methoxybenzene (1.328 g, 6.60 mmol, 1.20 equiv) was added at room temperature. The resulting solution was stirred for 1 h at 25° C. The resulting mixture was quenched with 50 mL of H$_2$O. The resulting aqueous solution was extracted with 2×80 mL of ethyl acetate. The organic layers were combined. The resulting organic layer was washed with 3×100 mL of brine and dried over anhydrous sodium sulfate and concentrated under vacuum. The residue was applied onto a silica gel column and eluted with ethyl acetate/petroleum ether (1:50-1:20). This resulted in 1.7 g (84%) of 6-bromo-3,3-difluoro-1-[(4-methoxyphenyl)methyl]-2,3-dihydro-1H-indol-2-one as a white solid.

$^1$H-NMR (DMSO-d$_6$, 300 MHz): δ 7.70-7.67 (d, J=7.8 Hz, 1H), 7.53 (s, 1H), 7.45-7.42 (d, J=7.8 Hz, 1H), 7.31-7.28 (d, J=8.7 Hz, 1H), 6.95-6.92 (d, J=8.4 Hz, 1H), 4.38 (s, 2H), 3.73 (s, 1H).

Step (iii) Synthesis of tert-butyl 2-(3,3-difluoro-1-(4-methoxybenzyl)-2-oxoindolin-6-yl)acetate

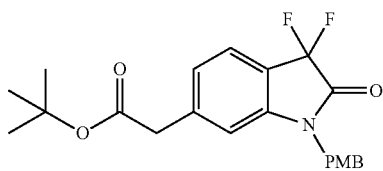

Into a solution of 6-bromo-3,3-difluoro-1-[(4-methoxyphenyl)methyl]-2,3-dihydro-1H-indol-2-one (700 mg, 1.90 mmol, 1.00 equiv) in degassed tetrahydrofuran (20 mL) was added Pd$_2$(dba)$_3$ (262 mg, 0.29 mmol, 0.15 equiv), X-Phos (242 mg, 0.51 mmol, 0.27 equiv). Then (2-tert-butoxy-2-oxoethyl)zinc(II) bromide (1.48 g, 5.68 mmol, 2.99 equiv) was added. The resulting solution was stirred overnight at 70° C. under nitrogen atmosphere and concentrated under vacuum. The residue was applied onto a silica gel column and eluted with ethyl acetate/petroleum ether (1/20). This resulted in 400 mg (52%) of tert-butyl 2-[3,3-difluoro-1-[(4-methoxyphenyl)methyl]-2-oxo-2,3-dihydro-1H-indol-6-yl]acetate as a off-white solid.

Step (iv) Synthesis of 2-(3,3-difluoro-1-(4-methoxybenzyl)-2-oxoindolin-6-yl)acetic acid

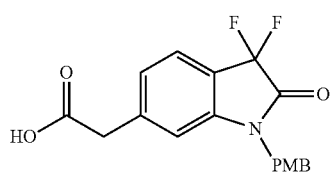

Into a solution of tert-butyl 2-[3,3-difluoro-1-[(4-methoxyphenyl)methyl]-2-oxo-2,3-dihydro-1H-indol-6-yl]acetate (380 mg, 0.94 mmol, 1.00 equiv) in dichloromethane (20 mL) was added trifluoroacetic acid (5 mL). The resulting solution was stirred overnight at 35° C. The resulting mixture was concentrated under vacuum. The residue was triturated with hexane/ether (5/1). This resulted in 300 mg (crude) of 2-[3,3-difluoro-1-[(4-methoxyphenyl)methyl]-2-oxo-2,3-dihydro-1H-indol-6-yl]acetic acid as a dark-grey solid.

MS (ES, m/z): 348 (M+1).

Example 17-a 2-(2,2-dimethyl-3-oxo-3,4-dihydro-2H-benzo[b][1,4]thiazin-6-yl)acetic acid

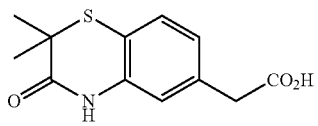 [SMILES: CC1(C)Sc2ccc(CC(=O)O)cc2NC1=O]

Step (i) Synthesis of ethyl 2-((4-bromo-2-nitrophenyl)thio)-2-methylpropanoate

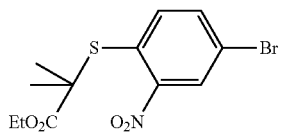

$K_2CO_3$ (5.8 g, 41.97 mmol, 2.50 equiv) was added to a solution of 4-bromo-1-fluoro-2-nitrobenzene (3.7 g, 16.82 mmol, 1.00 equiv) in DMF (50 mL), then ethyl 2-methyl-2-sulfanylpropanoate (3.5 g, 23.61 mmol, 1.40 equiv) was added. The reaction mixture was stirred for 4 h at 30° C. The solution was diluted with 200 mL of EA and filtered and washed with 5×20 mL of brine. The organic layer was dried over anhydrous sodium sulfate and concentrated in vacuo. The residue was purified by flash column with petroleum ether:EtOAc 100:1 to 20:1. This resulted in 4 g (68%) of ethyl 2-[(4-bromo-2-nitrophenyl)sulfanyl]-2-methylpropanoate as a white solid. $^1$H-NMR (DMSO-$d_6$, 300 MHz): 1.23-1.32 (m, 6H), 1.52-2.0 (m, 10H), 4.1-4.21 (m, 3H), 7.42 (d, J=12 Hz, 1H), 7.62 (d, J=12 Hz, 1H), 8.00 (s, 1H).

Step (ii) Synthesis of 6-bromo-2,2-dimethyl-2H-benzo[b][1,4]thiazin-3(4H)-one

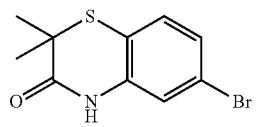

To a solution of ethyl 3-(4-bromo-2-nitrophenyl)-2,2-dimethylpropanoate (4 g, 12.11 mmol, 1.00 equiv) in acetic acid (50 mL) was added Fe powder (6.4 g, 114.29 mmol, 9.43 equiv) in small portions. The resulting solution was stirred for 2 h at 80° C. The mixture was diluted with 200 mL of EtOAc and filtered. The organic layer was concentrated under vacuum. The residue was purified by flash column with petroleum ether:ethyl acetate (20:1). This resulted in 2.1 g (64%) of 6-bromo-2,2-dimethyl-3,4-dihydro-2H-1,4-benzothiazin-3-one as a oil. $^1$H-NMR (DMSO-$d_6$, 300 MHz) δ 1.51 (s, 6H), 7.05 (s, 1H), 7.13-7.19 (m, 2H), 8.64 (s, 1H).

Step (iii) Synthesis of 6-bromo-2,2-dimethyl-4-((2-(trimethylsilyl)ethoxy)methyl)-2H-benzo[b][1,4]thiazin-3(4H)-one

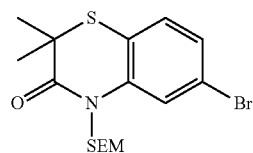 [SMILES: CC1(C)Sc2ccc(Br)cc2N(COCC[Si](C)(C)C)C1=O]

To a solution of 6-bromo-2,2-dimethyl-3,4-dihydro-2H-1,4-benzothiazin-3-one (2.6 g, 9.55 mmol, 1.00 equiv) in THF (30 mL), was added NaH (573 mg, 23.88 mmol, 2.50 equiv). After 30 min, SEMCl (3.2 g, 19.16 mmol, 2.01 equiv) was added. The resulting solution was stirred for 3 h at room temperature. The reaction was quenched by 10 mL of $H_2O$. The mixture was extracted with 3×20 mL of ethyl acetate. The organic layer was dried over $Na_2SO_4$ and concentrated. The residue was purified by silica column with petroleum: ethyl acetate=100:1. This resulted in 3.8 g (99%) of 6-bromo-2,2-dimethyl-4-[[2-(trimethylsilyl)ethoxy]methyl]-3,4-dihydro-2H-1,4-benzothiazin-3-one as oil.

Step (iv) Synthesis of tert-butyl 2-(2,2-dimethyl-3-oxo-4-((2-(trimethylsilyl)ethoxy)methyl)-3,4-dihydro-2H-benzo[b][1,4]thiazin-6-yl)acetate

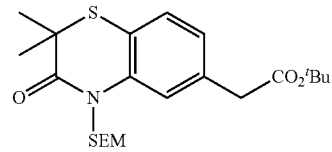 [SMILES: CC(C)(C)OC(=O)Cc1ccc2c(c1)N(COCC[Si](C)(C)C)C(=O)C(C)(C)S2]

A solution of 6-bromo-2,2-dimethyl-4-[[2-(trimethylsilyl)ethoxy]methyl]-3,4-dihydro-2H-1,4-benzothiazin-3-one (800 mg, 1.99 mmol, 1.00 equiv), tert-butyl 2-(bromozincio)acetate (2.08 g, 7.99 mmol, 4.02 equiv), Pd2 (dba)3 (274 mg, 0.30 mmol, 0.15 equiv), Xphos (286 mg, 0.60 mmol, 0.30 equiv) in THF (40 mL) was stirred overnight at 70° C. The mixture was diluted with 100 mL of EtOAc and filtered. The organic layer was concentrated under vacuum. The residue was purified by silica column with PE:EA (20:1). This resulted in 880 mg of tert-butyl 2-(2,2-dimethyl-3-oxo-4-[[2-(trimethylsilyl)ethoxy]methyl]-3,4-dihydro-2H-1,4-benzothiazin-6-yl)acetate as yellow oil.

$^1$H-NMR (DMSO-$d_6$, 300 MHz) δ 0.95 (t, J=7.8 Hz, 2H), 1.46 (s, 15H), 3.54 (s, 2H), 3.66 (t, J=7.8 Hz, 2H), 5.38 (s, 2H), 6.98 (d, J=6.9 Hz, 1H), 7.25 (d, J=8.1 Hz, 1H), 7.43 (s, 1H).

Step (v) Synthesis of 2-(2,2-dimethyl-3-oxo-3,4-dihydro-2H-benzo[b][1,4]thiazin-6-yl)acetic acid

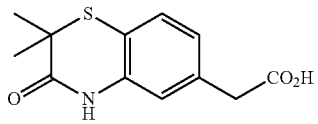 [SMILES: CC1(C)Sc2ccc(CC(=O)O)cc2NC1=O]

To a solution of tert-butyl 2-(2,2-dimethyl-3-oxo-4-[[2-(trimethylsilyl)ethoxy]methyl]-3,4-dihydro-2H-1,4-benzothiazin-6-yl)acetate (200 mg, 0.46 mmol, 1.00 equiv) in DCM (4 mL), was added TFA (2 mL) at 0° C. The resulting solution was stirred for 2 h at room temperature. The solution was concentrated. The residue was washed with PE and Et$_2$O. This resulted in 108 mg (94%) of 2-(2,2-dimethyl-3-oxo-3,4-dihydro-2H-1,4-benzothiazin-6-yl)acetic acid as a yellow solid. MS (ES, m/z): 252 (M+1).

Example 18-a 2-(2,2-dimethyl-1,1-dioxido-3-oxo-3,4-dihydro-2H-benzo[b][1,4]thiazin-6-yl)acetic acid

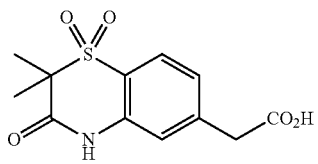 [SMILES: CC1(C)C(=O)Nc2cc(CC(=O)O)ccc2S1(=O)=O]

Step (i) Synthesis of tert-butyl 2-(2,2-dimethyl-1,1-dioxido-3-oxo-4-((2-(trimethylsilyl)ethoxy)methyl)-3,4-dihydro-2H-benzo[b][1,4]thiazin-6-yl)acetate

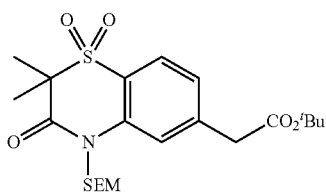 [SMILES: CC(C)(C)OC(=O)Cc1ccc2c(c1)N(COCC[Si](C)(C)C)C(=O)C(C)(C)S2(=O)=O]

To a solution of tert-butyl 2-(2,2-dimethyl-3-oxo-4-((2-(trimethylsilyl)ethoxy)methyl)-3,4-dihydro-2H-benzo[b][1,4]thiazin-6-yl)acetate (200 mg, 0.46 mmol, 1.00 equiv) in CH$_3$CN (2 mL) and DCM (2 mL), was added RuCl$_3$ (0.58 mg). Then a solution of NaIO$_4$ (289 mg, 1.35 mmol, 2.96 equiv) in H$_2$O (4 mL) was added dropwise at 0° C. The resulting solution was stirred for 30 min at 0° C. The mixture was extracted with 3×10 mL of EtOAc. The organic layer was washed with 3*5 mL of brine and concentrated. The residue was purified by Prep-TLC with PE:EtOAc=10:1. This resulted in 150 mg (70%) of tert-butyl 2-(2,2-dimethyl-1,1-dioxido-3-oxo-4-((2-(trimethylsilyl)ethoxy)methyl)-3,4-dihydro-2H-benzo[b][1,4]thiazin-6-yl)acetate as colorless oil.

Step (ii) Synthesis of 2-(2,2-dimethyl-1,1-dioxido-3-oxo-3,4-dihydro-2H-benzo[b][1,4]thiazin-6-yl) acetic acid

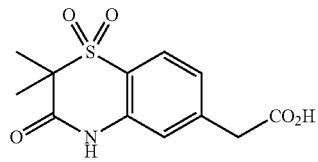 [SMILES: CC1(C)C(=O)Nc2cc(CC(=O)O)ccc2S1(=O)=O]

To a solution of tert-butyl 2-(2,2-dimethyl-1,1-dioxido-3-oxo-4-((2-(trimethylsilyl)ethoxy)methyl)-3,4-dihydro-2H-benzo[b][1,4]thiazin-6-yl)acetate (150 mg, 0.32 mmol, 1.00 equiv) in DCM (5 mL), was added TFA (2 mL). The resulting solution was stirred for 3 h at room temperature. The mixture was concentrated. The residue was triturated with PE. The resulting solid was collected by filtration and dried under vacuum. This resulted in 100 mg of 2-(2,2-dimethyl-1,1-dioxido-3-oxo-3,4-dihydro-2H-benzo[b][1,4]thiazin-6-yl)acetic acid as a yellow solid.

Example 19-a 2-(2-oxoindolin-5-yl)acetic acid

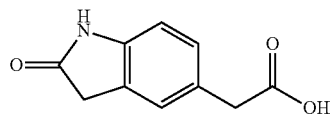 [SMILES: O=C(O)Cc1ccc2c(c1)CC(=O)N2]

Step (i) Synthesis of tetramethyl 2,2'-(4-nitro-1,3-phenylene)dimalonate

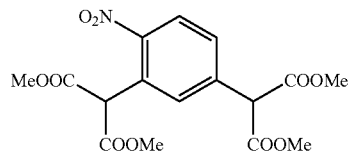 [SMILES: COC(=O)C(C(=O)OC)c1ccc([N+](=O)[O-])c(C(C(=O)OC)C(=O)OC)c1]

Into a 500-mL 3-necked round-bottom flask purged and maintained with an inert atmosphere of nitrogen, was placed a solution of sodium hydride (18.88 g, 786.67 mmol, 5.50 equiv) in DMSO (300 mL) at 0° C. This was followed by the addition of 1,3-dimethyl propanedioate (61.36 g, 464.45 mmol, 3.25 equiv) dropwise with stirring at 0° C. After stirred for 5 min at 0° C., to this was added 2,4-difluoro-1-nitrobenzene (22.756 g, 143.04 mmol, 1.00 equiv) dropwise with stirring at 0° C. The resulting solution was stirred overnight at 100° C. in an oil bath. The reaction was then quenched by the addition of NH$_4$Cl. The resulting solution was extracted with ethyl acetate (3×300 mL). The organic combined layers were washed with brine (1×200 mL), dried over anhydrous sodium sulfate and concentrated under vacuum. The residue was applied onto a silica gel column and eluted with ethyl acetate/petroleum ether (0:1-1:2). This resulted in 20 g (36%) of 1,3-dimethyl 2-[3-(1,3-dimethoxy-1,3-dioxopropan-2-yl)-4-nitrophenyl]propanedioate as a light yellow solid.

Step (ii) Synthesis of
2,2'-(4-nitro-1,3-phenylene)diacetic acid

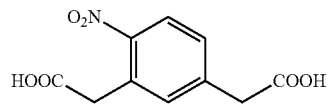

Into a 250-mL round-bottom flask, was placed a solution of 1,3-dimethyl 2-[3-(1,3-dimethoxy-1,3-dioxopropan-2-yl)-4-nitrophenyl]propanedioate (20 g, 52.18 mmol, 1.00 equiv) in methanol (40 mL). This was followed by the addition of a solution of sodium hydroxide (8.355 g, 208.89 mmol, 4.00 equiv) in water (20 mL) dropwise with stirring. The resulting solution was stirred for 1 h at 75° C. in an oil bath. The pH value of the solution was adjusted to 1 with hydrochloric acid aqueous. The resulting solution was extracted with ethyl acetate (3×100 mL) and the organic layers combined. The resulting mixture was washed with brine (1×100 mL), dried over anhydrous sodium sulfate and concentrated under vacuum. The residue was applied onto a silica gel column and eluted with ethyl acetate/petroleum ether (0:1-1:5). This resulted in 1.3 g (10%) of 2,2'-(4-nitro-1,3-phenylene)diacetic acid Step (iii) Synthesis of 2-(2-oxoindolin-5-yl)acetic acid

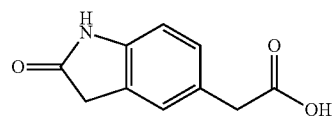 [SMILES: O=C(O)Cc1ccc2c(c1)CC(=O)N2]

Into a 100-mL round-bottom flask, was placed a solution of 2,2'-(4-nitro-1,3-phenylene)diacetic acid (1.2 g, 5.02 mmol, 1.00 equiv) in acetic acid (50 mL). This was followed by the addition of iron (1.1238 g, 20.12 mmol, 4.00 equiv) in portions. The resulting solution was stirred for 1 h at 100° C. in an oil bath. The solids were filtered out. The resulting mixture was concentrated under vacuum. This resulted in 0.56 g (58%) of 2-(2-oxoindolin-5-yl)acetic acid.

Further examples of the acid intermediates of formula (a), which can be prepared by substantially similar procedures as described above or procedures known in the art, include:

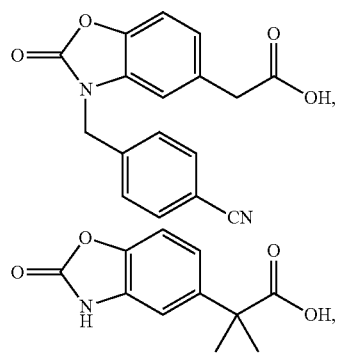

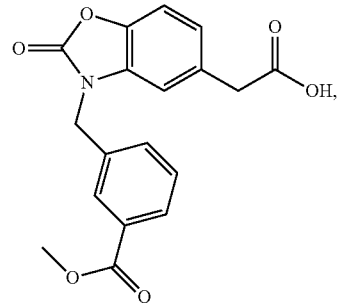

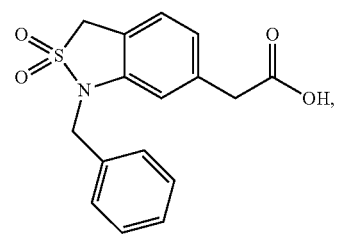

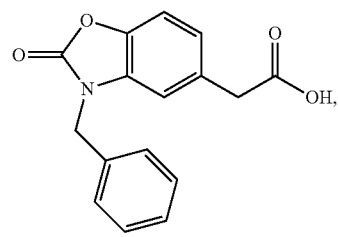

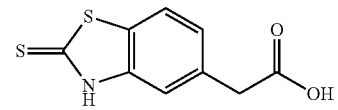

Following are the non-limiting examples of the reactant b:

Example 1-b tert-butyl 2-(3-((S)-2-((S)-3-((tert-butyldimethylsilyl)oxy)pyrrolidin-1-yl)-1-(methylamino)ethyl)phenoxy)acetate

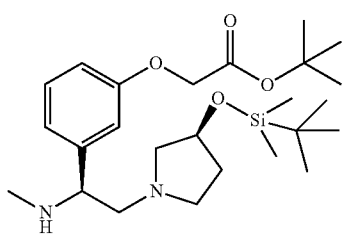 [SMILES: CN[C@H](CN1CC[C@H](O[Si](C)(C)C(C)(C)C)C1)c1cccc(OCC(=O)OC(C)(C)C)c1]

Step (i): Synthesis of tert-butyl 2-(3-formylphenoxy)acetate

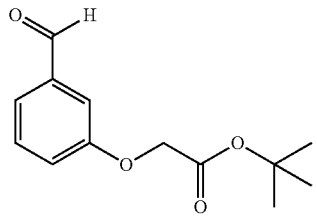 [SMILES: CC(C)(C)OC(=O)COc1cccc(C=O)c1]

A mixture of 3-hydroxybenzaldehyde (20.0 g, 0.163 moles), tert-butyl bromoacetate (26 ml, 0.18 moles) and potassium carbonate (57 g, 0.4 moles) in DMF (270 ml) was stirred at room temperature for 4 hours. Thereafter, DMF was removed in vacuo; water was added to the reaction mixture and it was extracted with ethyl acetate (2×500 ml). The combined organic layer was washed with saturated brine solution and the combined organic layer was dried over sodium sulphate and concentrated in vacuo to give crude product. The residue was purified by flash chromatography using silica gel 230-400 mesh as stationary phase and 30% ethyl acetate in n-hexane as eluent to obtain the titled compound (26.1 g).

$^1$H-NMR (400 MHz, DMSO-$d_6$): δ 9.98 (s, 1H), 7.55-7.52 (m, 2H), 7.39 (s, 1H), 7.38 (m, 1H), 4.76 (s, 2H), 1.43 (s, 9H).

Step (ii): Synthesis of tert-butyl 2-(3-vinylphenoxy)acetate

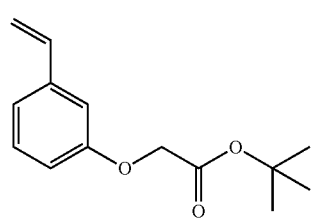 [SMILES: C=Cc1cccc(OCC(=O)OC(C)(C)C)c1]

To a suspension of NaH (26 g, 0.11 moles) in THF (300 ml) at 0° C. was added methytriphenylphophonium bromide (45 g, 0.12 mol) in portions and stirred for 1 h. To this mixture was added dropwise a solution of 2-(3-formylphenoxy)acetonitrile (43 g, 0.12 moles) in THF (100 ml) at 0° C. The reaction mixture was stirred at 25° C. for 2 hours.

Thereafter the reaction mixture was poured into crushed ice then partitioned with ethyl acetate (500 ml); the combined organic layer was dried over sodium sulphate and concentrated in vacuo to give crude product. The residue was purified by flash chromatography using silica gel 230-400 as stationary phase and 30% ethyl acetate in n-hexane as eluent to obtain the titled compound (12 g).

$^1$H-NMR (400 MHz, DMSO-$d_6$): δ 7.32-7.27 (m, 1H), 7.25-7.0 (m, 2H), 6.82-6.65 (m, 2H), 5.82 (d, J=17.6 Hz, 1H), 5.23 (d, J=19.6 Hz, 1H), 4.66 (s, 2H), 1.42 (s, 9H).

Step (iii): Synthesis of (S)-tert-butyl 2-(3-(1,2-dihydroxyethyl)phenoxy)acetate

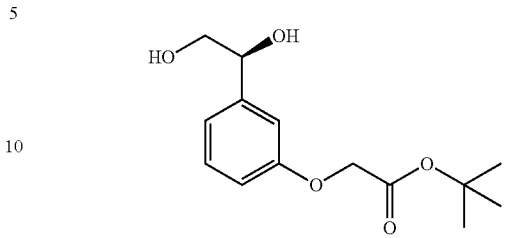

At 0° C., to a mixture of tert-butyl alcohol (250 ml), water (250 ml), and AD-mix-alpha (Aldrich™ (84 g) was added tert-butyl2-(3-vinylphenoxy)acetate (12 g, 0.05 moles) and the resultant mixture was stirred for 3.5 hours at room temperature. Sodium sulphite (96 g, 0.07 moles) was added and the reaction mixture stirred for another hour at room temperature. The reaction mixture was poured into ethyl acetate (500 ml); the aqueous layer was extracted with ethyl acetate (2×500 ml). The combined organic layer was washed with saturated brine solution, dried over sodium sulphate and concentrated in vacuo to obtain the crude product which was purified by flash chromatography using silica gel 230-400 mesh as stationary phase and 50% ethyl acetate in n-hexane as eluent to obtain the titled compound (7.6 g).

$^1$H-NMR (400 MHz, DMSO-$d_6$): δ 7.22-7.20 (m, 1H), 6.93-6.72 (m, 3H), 5.75 (s, 1H) 5.21 (m, 1H), 4.67 (m, 1H), 4.60 (s, 1H), 4.72-4.50 (m, 1H), 1.42 (s, 9H).

Step (iv): Synthesis of (S)-tert-butyl 2-(3-(oxiran-2-yl)phenoxy)acetate

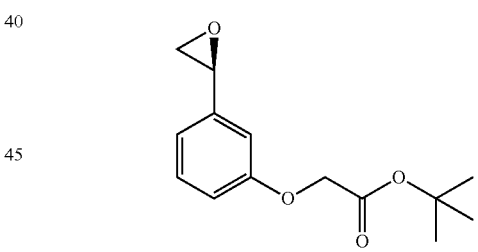

To a solution of (S)-tert-butyl 2-(3-(1,2-dihydroxyethyl)phenoxy)acetate (5 g, 0.01 moles) in DCM (50 ml); trimethylorthoacetate (5.7 ml, 0.04 moles) and chlorotrimethylsilane (5.7 ml, 0.04 moles) were added at room temperature. The reaction was stirred at room temperature under nitrogen for 1 hour, and then the solvent was removed in vacuo. Potassium carbonate (3.31 g, 0.02 moles) and methanol (10 ml) were added, and the reaction was stirred at room temperature under nitrogen for 3 hours. The reaction was then poured into saturated ammonium chloride solution (50 ml) and extracted with dichloromethane (2×200 ml). The combined organic layer was washed with saturated brine solution, dried over sodium sulphate and concentrated in vacuo to obtain the crude product which was purified by flash chromatography using silica gel 230-400 mesh as stationary phase and 30% ethyl acetate in n-hexane as eluent to obtain the titled compound (1.7 g).

¹H-NMR (400 MHz, DMSO-d₆): δ 7.28-7.24 (m, 1H), 6.92-6.85 (m, 3H), 4.64 (s, 2H), 3.89 (m, 1H), 2.81 (m, 1H), 1.42 (s, 9H).

Step (v): Synthesis of tert-butyl 2-(3-((S)-2-((S)-3-((tert-butyldimethylsilyl)oxy) pyrrolidin-1-yl)-1-(methyl amino)ethyl)phenoxy)acetate

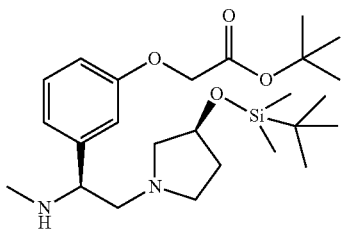 [SMILES: CN[C@H](CN1CC[C@H](O[Si](C)(C)C(C)(C)C)C1)c1cccc(OCC(=O)OC(C)(C)C)c1]

To a stirred solution of (S)-3-(oxiran-2-yl) benzonitrile (6 g, 41.3 mmol) in ethanol (60 ml); (S)-3-(tert-butyldimethylsilyloxy) pyrrolidine (12.5 g, 62.1 mmol) was added. The reaction was heated to reflux for 5 hours. Then ethanol was removed in vacuo. The crude reaction mixture was then dissolved in diethyl ether (120 ml), cooled to 0° C. and flushed with nitrogen. Triethylamine (24 ml, 132.16 mmol) was added followed by methanesulphonyl chloride (4.5 ml, 57.8 mmol) at 0° C. and reaction was stirred at 0° C. for half an hour. Some more triethylamine (12 ml, 82.6 mmol) was added, the reaction was warmed to room temperature over half an hour, then an aqueous solution of methyl amine (40% w/w) (72 ml, 826 mmol) and water (35 ml) were added. After stirring at room temperature under nitrogen for 16 hours, layers were separated and the aqueous layer was extracted with diethyl ether (3×200 ml). The combined organic layer was washed with 10% sodium bicarbonate solution (100 ml), water (100 ml) and brine (100 ml), dried over sodium sulphate and concentrated in vacuo to give crude product as yellow oil. The residue was purified by flash chromatography using silica gel 230-400 mesh as the stationary phase and 10% MeOH in DCM as eluent to obtain the titled compound (1.5 g).

Example 2-b 3-((S)-2-((S)-3-((tert-butyldimethylsilyl)oxy)pyrrolidin-1-yl)-1-(methylamino)ethyl)-5-fluorobenzonitrile Step (i) Synthesis of 3-fluoro-5-vinylbenzonitrile

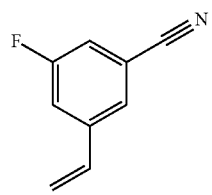

Into a 100-mL 3-necked round-bottom flask purged and maintained with an inert atmosphere of nitrogen, was placed a solution of 3-bromo-5-fluorobenzonitrile (5 g, 25.00 mmol, 1.00 equiv) in ethanol (50 mL). To the solution were added TEA (5.05 g, 49.91 mmol, 2.00 equiv), Pd(dppf)Cl₂ (918 mg, 0.05 equiv), and potassium vinyltrifluoroborate (9.98 g, 82.53 mmol, 3.00 equiv). The resulting solution was stirred for 3 hours at 80° C. in an oil bath. The resulting mixture was concentrated under vacuum. The resulting solution was diluted with 80 mL of ethyl acetate. The resulting mixture was washed with brine (2×30 mL), dried over with Na₂SO₄ and concentrated. The residue was applied onto a silica gel column and eluted with ethyl acetate/petroleum ether (1:100-1:10). This resulted in 4.21 g of 3-ethenyl-5-fluorobenzonitrile as a white solid.

Step (ii): Synthesis of (S)-3-(1,2-dihydroxyethyl)-5-fluorobenzonitrile

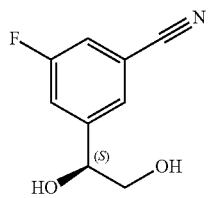

Into a 50-mL round-bottom flask, was placed a solution of 3-ethenyl-5-fluorobenzonitrile (1 g, 6.80 mmol, 1.00 equiv) in water/t-BuOH (v/v=1:1, 50 mL). To the solution was added AD-mix alpha (10 g). The resulting solution was stirred for 24 hours at room temperature. The resulting solution was diluted with 100 mL of water. The resulting solution was extracted with ethyl acetate (3×30 mL) and the organic layers combined. The resulting mixture was washed with brine (2×30 mL), dried over sodium sulfate and concentrated under vacuum. The resulting crude solid was washed with PE. This resulted in 1.3 g (crude) of 3-[(1S)-1,2-dihydroxyethyl]-5-fluorobenzonitrile as a white solid.

LC-MS: (ES, m/z): 182 (M+1).

Step (iii): Synthesis of (S)-3-fluoro-5-(oxiran-2-yl)benzonitrile

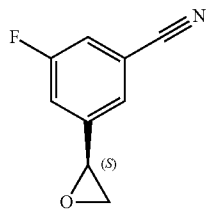

Into a 100-mL 3-necked round-bottom flask purged and maintained with an inert atmosphere of nitrogen, was placed a solution of 3-[(1S)-1,2-dihydroxyethyl]-5-fluorobenzonitrile (4.4 g, 24.29 mmol, 1.00 equiv) and CH₃C(OCH₃)₃ (13.25 g) in dichloromethane (50 mL). TMSCl (14.58 g, 134.20 mmol, 5.53 equiv) was added dropwise at 0° C. The resulting solution was stirred for 5 hours at room temperature. The resulting mixture was concentrated under vacuum. The residue was diluted in MeOH (50 mL). To the mixture was added potassium carbonate (16.77 g, 121.5 mmol, 5.00 equiv), in portions at 0° C. The resulting solution was allowed to react, with stirring, for an additional 1.5 hours at room temperature. The solids were filtered out. The filtrate was concentrated and then dissolved in DCM (100 mL), washed with water (3×30 mL), then dried over with Na₂SO₄. The resulting mixture was concentrated under vacuum. The residue was purified by silica gel column with ethyl acetate/petroleum ether (1:50-1:20). This resulted in 0.8 g (20%) of 3-fluoro-5-[(2S)-oxiran-2-yl]benzonitrile as a white solid.

Step (iv): 3-((S)-2-((S)-3-((tert-butyldimethyl silyl)oxy)pyrrolidin-1-yl)-1-hydroxyethyl)-5-fluorobenzonitrile

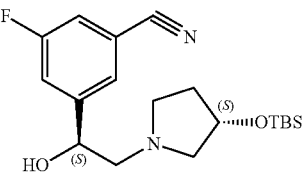

Into a 50-mL round-bottom flask, was placed a solution of 3-fluoro-5-[(2S)-oxiran-2-yl]benzonitrile (800 mg, 4.90 mmol, 1.00 equiv) in ethanol (20 mL). To the mixture was added (3S)-3-[(tert-butyldimethylsilyl)oxy]pyrrolidine (1.97 g, 9.78 mmol, 1.99 equiv). The resulting solution was stirred for 3 h at 80° C. The resulting mixture was concentrated under vacuum. The residue was applied onto a silica gel column and eluted with petroleum ether/ethyl acetate (100:1)-dichloromethane/methanol (50:1). This resulted in 0.8 g (45%) of 3-[(1S)-2-[(3S)-3-[(tert-butyldimethylsilyl)oxy]pyrrolidin-1-yl]-1-hydroxyethyl]-5-fluorobenzonitrile as yellow oil. LC-MS: (ES, m/z): 365 (M+1).

Step (v): Synthesis of 3-((S)-2-((S)-3-((tert-butyldimethyl silyl)oxy)pyrrolidin-1-yl)-1-(methylamino)ethyl)-5-fluorobenzonitrile

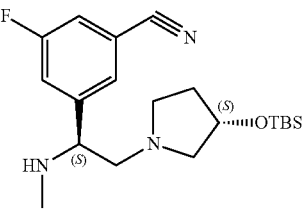

Into a 100-mL 3-necked round-bottom flask, was placed a solution of 3-[(1S)-2-[(3S)-3-[(tert-butyldimethylsilyl)oxy]pyrrolidin-1-yl]-1-hydroxyethyl]-5-fluorobenzonitrile (800 mg, 2.19 mmol, 1.00 equiv) and TEA (1.8 g, 17.79 mmol, 8.11 equiv) in dichloromethane (20 mL). To the solution was added MsCl (1.22 g, 10.70 mmol, 4.88 equiv) dropwise at 0° C. The solution was stirred for 1 hour at room temperature. Then to this was added MeNH₂ aqueous (30%, 5 mL) dropwise with stirring. The resulting solution was stirred overnight at room temperature. The resulting solution was extracted with dichloromethane (2×20 mL). The combined organic layers were washed with brine (1×20 mL), dried over anhydrous sodium sulfate and concentrated under vacuum. The residue was applied onto a silica gel column and eluted with dichloromethane/methanol (1:0-50:1). This resulted in 0.55 g (66%) of 3-[(1S)-2-[(3S)-3-[(tert-butyldimethylsilyl)oxy]pyrrolidin-1-yl]-1-(methylamino)ethyl]-5-fluorobenzonitrile as yellow oil. LC-MS: (ES, m/z): 378 (M+1).

Example 3-b 2-(3-(2-((S)-3-((tert-butyldimethylsilyl)oxy)pyrrolidin-1-yl)-1-methylamino)ethyl) phenoxy) acetonitrile

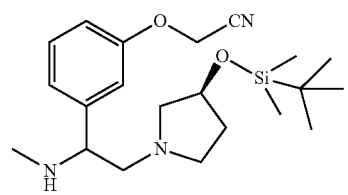 [SMILES: CNC(CN1CC[C@H](O[Si](C)(C)C(C)(C)C)C1)c1cccc(OCC#N)c1]

Step (i) Preparation of 2-(3-formylphenoxy)acetonitrile

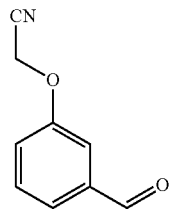 [SMILES: N#CCOc1cccc(C=O)c1]

3-Hydroxybenzaldehyde (5.0 g, 0.04 moles), bromoacetonitrile (6.4 g, 0.05 mol) and potassium carbonate (15.18 g, 0.11 mol) in DMF (50 ml) were placed in a 2 neck round bottom flask under nitrogen inlet. The reaction mixture stirred at room temperature for 6 h. Thereafter the reaction mixture was concentrated under reduced pressure, treated with water; and extracted with ethyl acetate (2×200 ml). The combined organic layer was washed with saturated brine solution; dried over sodium sulphate and concentrated under reduced pressure to give the crude product which was purified by Flash chromatography using silica gel 230-400 mesh and 20% ethyl acetate in n-hexane as eluent to obtain 2-(3-formylphenoxy)acetonitrile (2.1 g)

¹H-NMR (400 MHz, DMSO-d₆): δ 10.01 (s, 1H), 7.67-7.43 (m, 4H), 5.29 (s, 2H).

Step (ii): Preparation of 2-(3-vinylphenoxy)acetonitrile

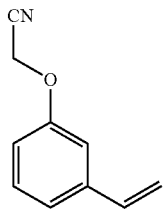

To a suspension of NaH (13.3 g, 0.55 mol) in THF (200 ml) at 0° C. was added methytriphenyl phosphonium bromide (53.6 g, 0.15 mol) in portions and stirred for 1 h. To this mixture was added dropwise a solution 2-(3-formylphenoxy) acetonitrile (19.8 g, 0.12 moles) in THF (100 ml) drop wise at 0° C. The reaction mixture was stirred at 25° C. for 2 h. The reaction mixture was poured in to crushed ice and the mixture was then extracted with ethyl acetate (500 ml). The organic layer was dried over sodium sulphate and concentrated under reduced pressure to get the crude product which was purified by flash chromatography using silica gel 230-400 mesh and 20% ethyl acetate in n-hexane as eluent to obtain 2-(3-vinylphenoxy)acetonitrile (8.0 g)

$^1$H-NMR (400 MHz, DMSO-d$_6$): δ 7.36-7.18 (m, 3H), 7.16-6.90 (m, 1H), 5.89 (d, J=17.7 Hz, 1H), 5.31 (d, J=11 Hz, 1H), 5.19 (s, 2H).

Step (iii): Preparation of 2-(3-(oxiran-2-yl)phenoxy)acetonitrile

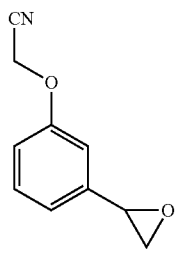 [SMILES: N#CCOc1cccc(C2CO2)c1]

m-Chloroperbenzoic acid (7.2 g, 41.8 moles) and (40 ml) 10% aqueous saturated NaHCO$_3$ was added to a solution of 2-(3-vinylphenoxy)acetonitrile (1.9 g, 11.9 moles) in dichloromethane (40 ml). The reaction mixture was stirred at room temperature under nitrogen for 2 h. Thereafter the reaction mixture was concentrated under reduced pressure. It was diluted with 10% aqueous Na$_2$S$_2$O$_3$ solution and extracted with dichloromethane (2×200 ml). The organic layer was washed with saturated NaHCO$_3$ solution; dried over sodium sulphate and concentrated under reduced pressure to get the crude product which was purified by flash chromatography using silica gel 230-400 mesh and 20% ethyl acetate in n-hexane as eluent to obtain 2-(3-(oxiran-2-yl)phenoxy)acetonitrile (0.82 g).

$^1$H-NMR (400 MHz, DMSO-d$_6$): δ 7.38 (m, 1H), 7.03-6.97 (m, 3H), 5.17 (s, 2H), 3.94-3.93 (m, 1H), 3.13-3.12 (m, 1H), 2.86-2.84 (m, 1H).

Step (iv): Preparation of —(S)-3-(tert-butyldimethylsilyloxy) pyrrolidine from (S)-pyrrolidin-3-ol

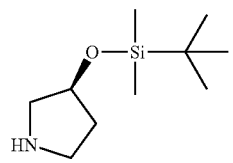

Imidazole (4.85 g, 0.07 moles) and tert-butyldimethylsilyl chloride (8.6 g, 0.05 moles) were added to a solution of (S)-pyrrolidin-3-ol (2.5 g, 0.02 moles) in dichloromethane (30 ml) at 20-35° C. under nitrogen and stirred for 3 h. The reaction was then diluted with dichloromethane (100 ml). The organic layer was washed with water; saturated aqueous sodium bicarbonate and brine. The organic layer was dried over sodium sulphate and concentrated under reduced pressure to get the product as yellow oil (5.1 g).

$^1$H-NMR (400 MHz, DMSO-d$_6$): δ 5.30 (bs, 1H), 4.35-4.31 (m, 1H), 2.90-2.84 (m, 2H), 2.76-2.70 (m, 1H), 2.57-2.54 (m, 1H), 1.85-1.77 (m, 1H), 1.57-1.50 (m, 1H), 0.90 (s, 9H), 0.14 (s, 6H).

Step (v): Preparation of—2-(3-(2-((S)-3-((tert-butyldimethylsilyl)oxy)pyrrolidin-1-yl)-1-(methylamino)ethyl)phenoxy)acetonitrile

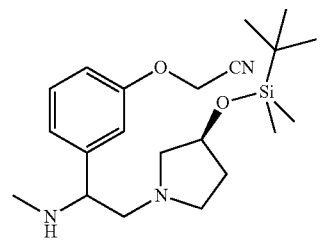 [SMILES: CNC(CN1CC[C@H](O[Si](C)(C)C(C)(C)C)C1)c1cccc(OCC#N)c1]

(S)-3-(tert-butyldimethylsilyloxy)pyrrolidine (2.57 g, 12.8 moles) was added to a stirred solution of 2-(3-(oxiran-2-yl)phenoxy)acetonitrile (1.6 g, 9.14 moles) in ethanol (60 ml). The reaction mixture was refluxed for 8 h and then concentrated under reduced pressure. The reaction mixture was then dissolved in diethyl ether (30 ml) and cooled to 0° C. Triethylamine (2.8 g, 27.42 moles) was added followed by methanesulphonyl chloride (1.36 g, 11.88 moles) at 0° C. and reaction was stirred at 0° C. for 30 minutes. Another portion of triethylamine (1.85 g, 18.28 moles) was added, the reaction was warmed to room temperature over 30 minutes, then an aqueous solution of methyl amine (40% w/w) (5.0 g, 161.8 moles) and water (10 ml) were added. After stirring at room temperature under nitrogen for 16 h, layers were separated and the aqueous layer was extracted with diethyl ether (3×200 ml). The organic layer was dried over sodium sulphate and concentrated under reduced pressure to get the crude product as yellow oil which was further purified by flash chromatography, using silica gel 230-400 mesh and 10% MeOH in DCM as the eluent to obtain 2-(3-(2-((S)-3-((tert-butyldimethylsilyl)oxy)pyrrolidin-1-yl)-1-(methylamino)ethyl)phenoxy)acetonitrile.

$^1$H-NMR (400 MHz, DMSO-d$_6$): δ 7.32-7.29 (m, 1H), 7.05-6.94 (m, 3H), 5.14 (s, 2H), 4.34 (s, 1H), 3.61-3.59 (s, 1H), 2.90-2.76 (m, 2H), 2.39-2.32 (m, 3H), 2.17-2.05 (m, 1H), 1.57-1.54 (m, 1H), 0.85-0.81 (m, 9H), 0.04 (s, 6H).

Example 4-b (3S)-1-(2-(methylamino)-2-(tetrahydro-2H-pyran-4-yl)ethyl)pyrrolidin-3-ol

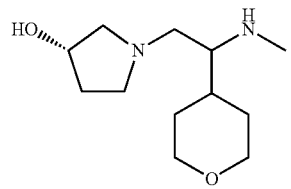

Step (i) Synthesis of 2-(((benzyloxy)carbonyl)amino)-2-hydroxyacetic acid

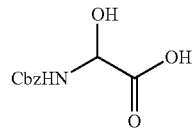

Into a 500-mL round-bottom flask, was placed a solution of benzyl carbamate (30 g, 198.47 mmol, 1.00 equiv) and 2-oxoacetic acid (22 g, 297.14 mmol, 1.20 equiv) in ether (300 mL). The resulting solution was stirred for 2 days at room temperature. The solids were collected by filtration. This resulted in the titled compound (30 g, 67%) as a white solid.

Step (ii) Synthesis of Methyl 2-[[(benzyloxy)carbonyl]amino]-2-methoxyacetate

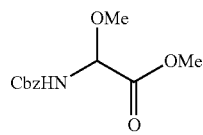 [SMILES: COC(=O)C(NC(=O)OCc1ccccc1)OC]

Into a 1000-mL round-bottom flask, was placed a solution of 2-[[(benzyloxy)carbonyl]amino]-2-hydroxyacetic acid (30 g, 133.22 mmol, 1.00 equiv) and sulfuric acid (30 mL) in methanol (300 mL). The resulting solution was stirred overnight at 25° C. The reaction mixture was cooled with an ice-cold water bath. The solids were collected by filtration. This resulted in 33 g (98%) of the title compound as a white solid.

LC-MS: (ES, m/z): 254 (M+1).

Step (iii) Synthesis of methyl 2-(((benzyloxy)carbonyl)amino)-2-(dimethoxyphosphoryl)acetate

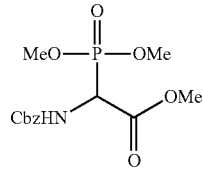 [SMILES: COC(=O)C(NC(=O)OCc1ccccc1)P(=O)(OC)OC]

Into a 500-mL round-bottom flask, was placed a solution of methyl 2-(benzyloxycarbonylamino)-2-methoxyacetate (33 g, 130.31 mmol, 1.00 equiv) in toluene (250 mL). This was followed by the dropwise addition of PCl$_3$ (18 g, 131.39 mmol, 1.00 equiv). The resulting solution was stirred for 16 h at 70° C. To this P(OMe)$_3$ (16.2 g, 130.65 mmol, 1.10 equiv) was added dropwise. The resulting solution was stirred for an additional 2 h at 70° C. The resulting mixture was concentrated in vacuo. The residue was diluted with 300 mL of ethyl acetate and the organic layer was washed with 3×250 mL of sodium bicarbonate solution and concentrated in vacuo. The crude product was re-crystallized from hexane-ethyl acetate (1:1). This resulted in 28 g (65%) of the title compound as a white solid.

Step (iv) Synthesis of methyl 2-(((benzyloxy)carbonyl)amino)-2-(dihydro-2H-pyran-4(3H)-ylidene)acetate

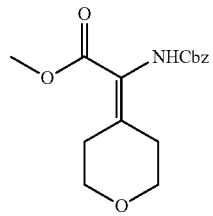 [SMILES: COC(=O)C(NC(=O)OCc1ccccc1)=C1CCOCC1]

A solution of methyl 2-(((benzyloxy)carbonyl)amino)-2-(dimethoxyphosphoryl)acetate (28 g, 84.59 mmol, 1.00 equiv) and 1,1,3,3-tetramethylguanidine (16.5 g, 143.25 mmol, 1.70 equiv) in ethyl acetate (150 mL) was stirred for 30 min at room temperature. To this reaction mixture, a solution of tetrahydropyran-4-one (16.5 g, 164.80 mmol, 1.95 equiv) in ethyl acetate (100 mL) was added. The resulting solution was stirred for 2 days at room temperature. The reaction was then quenched by the addition of 500 mL of 5% aqueous citric acid. The resulting solution was extracted with 3×200 mL of ethyl acetate and the combined organic layers were washed with 2×200 mL of brine and concentrated in vacuo. The residue was purified by column chromatography using silica gel as stationary phase and EtOAc: petroleum ether (1:8) as eluent. This resulted in the titled compound (22 g, 85%) as a white solid.

LC-MS: (ES, m/z): 306 (M+1).

Step (v) Synthesis of methyl 2-amino-2-(tetrahydro-2H-pyran-4-yl)acetate

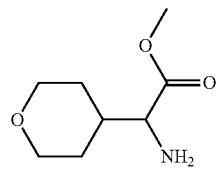

Under nitrogen atmosphere, palladium carbon (1 g) was added to a solution of methyl 2-[[(benzyloxy)carbonyl]amino]-2-(oxan-4-ylidene)acetate (10 g, 32.75 mmol, 1.00 equiv) in methanol (200 mL). The resulting solution was stirred overnight at 25° C. under hydrogen atmosphere. The catalyst was filtered off and the filtrate was concentrated in vacuo. This resulted in 5.5 g (97%) of the titled compound as a white solid.

LC-MS: (ES, m/z): 174 (M+1).

Step (vi) Synthesis of methyl 2-((tert-butoxycarbonyl)amino)-2-(tetrahydro-2H-pyran-4-yl)acetate

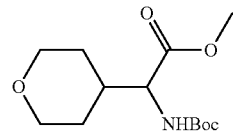 [SMILES: COC(=O)C(NC(=O)OC(C)(C)C)C1CCOCC1]

A mixture of methyl 2-amino-2-(oxan-4-yl)acetate (5.5 g, 31.75 mmol, 1.00 equiv), di-tert-butyl dicarbonate (7 g, 32.07 mmol, 1.03 equiv) and sodium carbonate (10.1 g, 95.28 mmol, 3.00 equiv) in H₂O/dioxane (80/80 mL) was stirred for 2 h at 25° C. and then diluted with 100 mL of water. The resulting solution was extracted with 200 ml of ethyl acetate and the combined organic layers were concentrated in vacuo. This resulted in 8 g (92%) of the titled compound as a white solid.

LC-MS: (ES, m/z): 274 (M+1).

Step (vii) Synthesis of 2-((tert-butoxycarbonyl) amino)-2-(tetrahydro-2H-pyran-4-yl)acetic acid

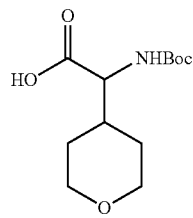

A solution of methyl 2-[[(tert-butoxy)carbonyl]amino]-2-(oxan-4-yl)acetate (8 g, 29.27 mmol, 1.00 equiv) and NaOH (2.2 g, 55.00 mmol, 1.82 equiv) in a mixture of methanol (20 mL) and H₂O (90 mL) was stirred for 2 h at 25° C. The organic solvent was removed in vacuo. The pH value of the aqueous layer was adjusted to 3 with 2N HCl. The resulting solution was extracted with 50 mL of EtOAc and the organic layer was washed with 2×20 mL of brine and concentrated in vacuo. This resulted in 5 g of the title compound as a white solid which was used in the next step without further purification.

Step (viii) Synthesis of tert-butyl (2-((S)-3-hydroxypyrrolidin-1-yl)-2-oxo-1-(tetrahydro-2H-pyran-4-yl)ethyl)carbamate

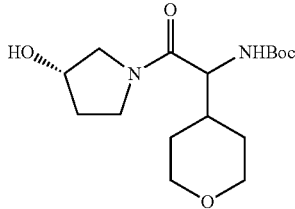 [SMILES: CC(C)(C)OC(=O)NC(C(=O)N1CC[C@H](O)C1)C1CCOCC1]

A solution of 2-[[(tert-butoxy)carbonyl]amino]-2-(oxan-4-yl)acetic acid (5 g, 19.28 mmol, 1.00 equiv), (3S)-pyrrolidin-3-ol (1.67 g, 19.17 mmol, 1.02 equiv), EDCI (3.67 g, 19.14 mmol, 1.06 equiv) and HOBT (2.6 g, 19.26 mmol, 1.02 equiv) in dichloromethane (80 mL) was stirred for 16 h at 25° C. The solids were filtered off and the filtrate was concentrated in vacuo. This resulted in 3 g (47%) of the title compound as a white solid.

LC-MS: (ES, m/z) 329 (M+1).

Step (ix) Synthesis of (3S)-1-(2-(methylamino)-2-(tetrahydro-2H-pyran-4-yl)ethyl)pyrrolidin-3-ol

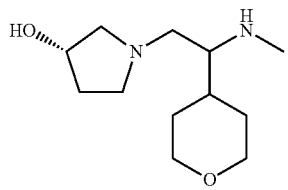 [SMILES: CNC(CN1CC[C@H](O)C1)C1CCOCC1]

To a solution of tert-butyl N-[2-[(3S)-3-hydroxypyrrolidin-1-yl]-1-(oxan-4-yl)-2-oxoethyl]carbamate (3 g, 9.14 mmol, 1.00 equiv) in tetrahydrofuran (50 mL), LiAlH₄ (2 g, 52.63 mmol, 5.76 equiv) was added portionwise. The resulting solution was stirred overnight at 65° C. The reaction was then quenched by the addition of ice-cold water. The solids were filtered off. The filtrate was extracted with 2×100 of ethyl acetate and the combined organic layers were dried over anhydrous sodium sulfate and concentrated in vacuo. This resulted in 1.4 g (67%) of the title compound as a light yellow solid.

LC-MS: (ES, m/z): 229 (M+1).

Example 5-b (3S)-1-[(2S)-2-(3-methoxyphenyl)-2-(methylamino) ethyl]pyrrolidin-3-ol

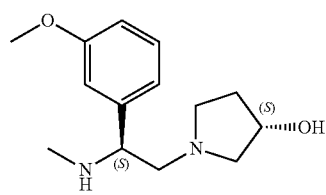

Step (i) Synthesis of 1-methoxy-3-vinylbenzene

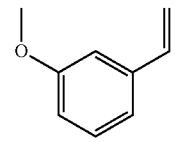

In an inert atmosphere of nitrogen, n-BuLi (2.5M) (22 mL, 1.10 equiv) was added dropwise with stirring to a solution of methyltriphenylphosphonium bromide (19.6 g, 54.90 mmol, 1.10 equiv) in tetrahydrofuran (100 mL) in a temperature range of −5 to 0° C. The suspension was stirred for 30 min at 0° C. A solution of 3-methoxybenzaldehyde (6.8 g, 49.95 mmol, 1.00 equiv) in tetrahydrofuran (5 mL) was added dropwise with stirring at 0° C. The resulting solution was stirred for 3 h at 25° C. The reaction was then quenched by the addition of sat. NH₄Cl. The resulting solution was extracted with 3×50 mL of ether and the combined organic layers were washed with 3×50 mL of brine, dried over anhydrous sodium sulfate and concentrated in vacuo. The residue was purified by column chromatography using silica gel as stationary phase and ethyl acetate/petroleum ether (1:50) as eluent. This resulted in 6 g (90%) of the title compound as a colorless oil.

Step (ii) Synthesis of (S)-1-(3-methoxyphenyl)ethane-1,2-diol

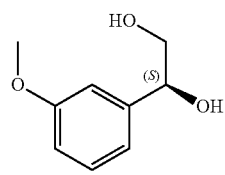

A suspension of AD-mix-alpha (25 g) in tert-Butanol/H$_2$O (40/40 mL) was stirred at 0° C. for 30 min. This was followed by the addition of 1-ethenyl-3-methoxybenzene (2.5 g, 18.63 mmol, 1.00 equiv) to it. The resulting solution was stirred for 16 h at 25° C. The reaction was then quenched by the addition of 20 g of Na$_2$SO$_3$ and then stirred for 1 h at 25° C. The resulting solution was extracted with 2×50 mL of ethyl acetate and the combined organic layers were washed with 2×30 mL of brine, dried over anhydrous sodium sulfate and concentrated in vacuo. The residue was purified by column chromatography using silica gel as a stationary phase and petroleum ether:EtOAc (3:1) to yield 2.9 g of the title compound as colorless oil.

Step (iii) Synthesis of (S)-2-(3-methoxyphenyl)oxirane

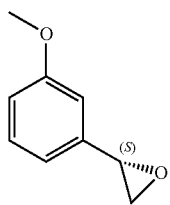

In an inert atmosphere of nitrogen, TMS-Cl (9.4 g, 86.64 mmol, 5.00 equiv) dropwise with stirring to a solution of (1S)-1-(3-methoxyphenyl)ethane-1,2-diol (2.9 g, 17.24 mmol, 1.00 equiv) in anhydrous dichloromethane (30 mL) at 25° C. Then CH$_3$C(OCH$_3$)$_3$ (10.4 g, 86.67 mmol, 5.00 equiv) was added dropwise at 25° C. and the reaction was stirred at 25° C. for 1.5 h. The solvent was removed in vacuo and the residue was dissolved in 60 ml of anhydrous methanol. To the solution was added potassium carbonate (4.8 g, 34.78 mmol, 2.00 equiv). The resulting mixture was stirred for 2 h at 25° C. and then quenched with sat NH$_4$Cl. The resulting solution was extracted with 2×50 mL of dichloromethane and the combined organic layers were washed with 2×25 mL of brine, dried over anhydrous sodium sulfate and concentrated in vacuo. The residue was purified by column chromatography using silica gel as stationary phase and ethyl acetate/petroleum ether (1:25) to yield 2 g of the title compound as colorless oil.

Step (iv) Synthesis of (S)-2-((S)-3-((tert-butyldimethylsilyl)oxy)pyrrolidin-1-yl)-1-(3-methoxyphenyl)-N-methylethanamine

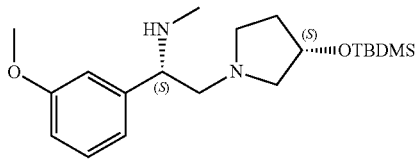

In an inert atmosphere of nitrogen, (3S)-3-[(tert-butyldimethylsilyl)oxy]pyrrolidine (4.02 g, 19.96 mmol, 1.50 equiv) was added to a solution of (2S)-2-(3-methoxyphenyl)oxirane (2 g, 13.32 mmol, 1.00 equiv) in anhydrous ethanol (100 mL). The reaction was refluxed for 8 h. Then the solvent was removed in vacuo and the residue was dissolved in ether (80 ml). To this TEA (4.04 g, 39.92 mmol, 3.00 equiv) was added dropwise at 0° C., followed by the addition of MsCl (1.98 g, 17.29 mmol, 1.30 equiv) dropwise at 0° C. Then the reaction was stirred at 0° C. for 1 h and at 25° C. for 1 h. To this reaction mixture CH$_3$NH$_2$ (aq, 40%) (21 mL, 20.00 equiv) was added followed by 20 mL of water. The resulting solution was stirred for 16 h at 25° C. The resulting solution was extracted with 100 mL of ether. The combined organic layers were washed with 3×25 mL of 10% sodium bicarbonate and 3×25 mL of water, dried over anhydrous sodium sulfate and concentrated in vacuo. The residue was purified by column chromatography using silica gel as stationary phase and DCM:MeOH (with 0.5% ammonia) (25:1) to yield 1.6 g of the title compound as colorless oil.

LC-MS: (ES, m/z): 366 (M+1).

Step (v) Synthesis of tert-butyl ((S)-2-((S)-3-((tert-butyldimethylsilyl)oxy)pyrrolidin-1-yl)-1-(3-methoxyphenyl)ethyl methyl)carbamate

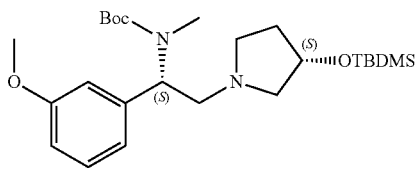

A solution of potassium carbonate (1.52 g, 11.01 mmol, 2.00 equiv) in water (20 mL) was added to a solution of [(1S)-2-[(3S)-3-[(tert-butyldimethylsilyl)oxy]pyrrolidin-1-yl]-1-(3-methoxyphenyl)ethyl](methyl)amine (1.6 g, 4.39 mmol, 1.00 equiv) in tetrahydrofuran (20 mL). This was followed by the addition of Boc$_2$O (1.3 g, 6.02 mmol, 1.10 equiv) at 0° C. The resulting solution was stirred for 16 h at 25° C. The resulting solution was extracted with 3×50 ml of ethyl acetate. The combined organic layers were washed with 2×20 mL of brine, dried and concentrated in vacuo. The residue was purified by column chromatography using silica gel as stationary phase and petroleum ether:EtOAc (15:1) to result in 2 g (98%) of the title compound as an off-white solid.

LC-MS: (ES, m/z): 466 (M+1).

Step (vi) Synthesis of (S)-2-((S)-3-hydroxypyrrolidin-1-yl)-1-(3-methoxyphenyl)-N-methylethanaminium 2,2,2-trifluoroacetate

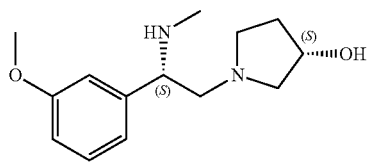

Trifluoroacetic acid (10 mL) was added to a solution of tert-butyl N-[(1S)-2-[(3S)-3-[(tert-butyldimethylsilyl)oxy]pyrrolidin-1-yl]-1-(3-methoxyphenyl)ethyl]-N-methylcarbamate (2 g, 4.30 mmol, 1.00 equiv) in dichloromethane (15 mL). The resulting solution was stirred for 5 h at 25° C. The resulting mixture was concentrated in vacuo and the residue was diluted with ether and n-hexane. The solids were collected by filtration and then washed with n-hexane. This resulted in 1 g (64%) of the title compound as an off-white solid.

LC-MS: (ES, m/z): 251 (M+1); $^1$H-NMR (300 MHz, CD$_3$OD): δ7.487-7.539 (m, 1H), 7.142-7.168 (m, 3H), 4.503-4.613 (m, 2H), 3.600-3.884 (br, 5H), 3.461-3.548 (m, 2H), 3.203-3.237 (m, 2H), 2.612 (s, 3H), 2.181-2.243 (m, 1H), 2.002-2.223 (m, 1H).

Example 6-b (3S)-1-[(2S)-2-(methylamino)-2-[3-(trifluoromethyl)phenyl]ethyl]pyrrolidin-3-ol

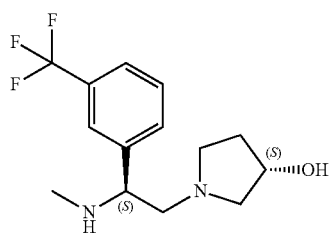

Step (i) Synthesis of 1-(trifluoromethyl)-3-vinylbenzene

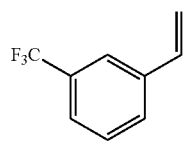

n-BuLi (30 mL) was added dropwise with stirring to a solution of 3-(trifluoromethyl) benzaldehyde (10 g, 57.43 mmol, 1.00 equiv) in tetrahydrofuran (100 mL) at 0° C. The resulting solution was stirred for 0.5 h at 0° C. To this was added a suspension of PPh$_3$CH$_3$Br (24.6 g, 68.86 mmol, 1.20 equiv) in tetrahydrofuran (250 mL) at 0° C. The resulting solution was stirred for 1 h at room temperature in an oil bath. The reaction was then quenched by the addition of Sat. NH$_4$Cl (50 mL). The resulting solution was extracted with 3×100 mL of ethyl acetate and the combined organic layers were washed with 1×100 mL of brine, dried over anhydrous sodium sulfate and concentrated in vacuo. The residue was applied onto a silica gel column eluting with petroleum ether. This resulted in 4 g (40%) of the title compound as colorless oil.

Step (ii) Synthesis of (S)-1-(3-(trifluoromethyl)phenyl)ethane-1,2-diol

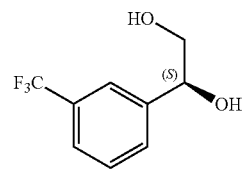

1-ethenyl-3-(trifluoromethyl)benzene (3.1 g, 18.01 mmol, 1.00 equiv) was added to a solution of AD-mix a (25 g) in tert-Butanol (90 mL) and water (90 mL) at 0° C. The resulting solution was stirred overnight at 0° C. in an ice/salt bath. Then the reaction was quenched by the addition of Na$_2$SO$_3$. After stirring for 1 h, the resulting solution was diluted with 25 mL of sodium bicarbonate; extracted with 2×100 mL of ethyl acetate; the combined organic layers were washed with 1×50 mL of brine and 1×50 mL of H$_2$O and concentrated in vacuo. The residue was purified by column chromatography using silica gel as stationary phase and dichloromethane/methanol (10:1-50:1) as eluent. This resulted in 3.1 g (84%) of the title compound as a colorless oil.

Step (iii) Synthesis of (S)-2-(3-(trifluoromethyl)phenyl)oxirane

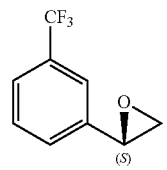

In an inert atmosphere of nitrogen, CH$_3$C(OCH$_3$)$_3$(5.4 g) and TMS-Cl (4.9 g) were added to a solution of (1S)-1-[3-(trifluoromethyl)phenyl]ethane-1,2-diol (3.1 g, 15.04 mmol, 1.00 equiv) in dichloromethane (60 mL) at 0° C. The reaction was stirred at 25° C. for 2 h. Thereafter the solvent was removed in vacuo, the crude product was dissolved in MeOH (20 mL) and then potassium carbonate (4.1 g) was added. The resulting solution was stirred at 25° C. for 0.5 h. The reaction was then poured into saturated ammonium chloride solution and extracted with dichloromethane. The combined organic layers were washed with brine and water, dried over Na$_2$SO$_4$ and concentrated in vacuo. The residue was further purified by column chromatography using silica gel as stationary phase and ethyl acetate/petroleum ether (1:5) as eluent to obtain 1.5 g (53%) of the title compound as colorless oil.

Step (iv) Synthesis of (S)-2-((S)-3-((tert-butyldimethylsilyl)oxy)pyrrolidin-1-yl)-N-methyl-1-(3-(trifluoromethyl)phenyl)ethanamine

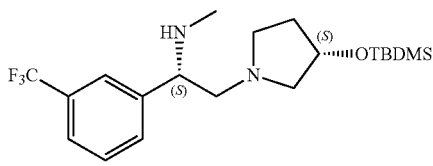

In an inert atmosphere of nitrogen, (3S)-3-[(tert-butyldimethylsilyl)oxy]pyrrolidine (322.3 mg, 1.60 mmol, 1.50 equiv) was added to a solution of (2S)-2-[3-(trifluoromethyl)phenyl]oxirane (201 mg, 1.07 mmol, 1.00 equiv) in ethanol (4 mL). The resulting solution was heated to reflux for 4 h. The solvent was removed in vacuo and the residue was diluted with 4 mL of ether. To this was added triethylamine (323 mg, 3.19 mmol, 2.99 equiv) at 0° C. The resulting solution was stirred for 0.5 h at room temperature. To the mixture was added MsCl (170 mg, 1.49 mmol, 1.40 equiv). After stirred for 1 h at 0° C., triethylamine (215 mg, 2.12 mmol, 2.00 equiv) was added. After stirred for 0.5 h at 25° C., a solution of $CH_3NH_2$ (2.22 g, 21.48 mmol, 20.00 equiv, 30%) in water (3 mL) was added. The resulting solution was stirred for 2 h at 25° C. The resulting solution was extracted with ether and the organic layers combined. The combined organic layers were washed with 10% sodium bicarbonate, water and brine. The mixture was dried over sodium sulfate and concentrated in vacuo. The residue further purified by column chromatography using silica gel as stationary phase and DCM/MeOH (30:1) as eluent to yield 200 mg of the title compound as colorless oil.

LC-MS: (ES, m/z): 403 (M+1)

Step (v) Synthesis of tert-butyl ((S)-2-((S)-3-((tert-butyldimethylsilyl)oxy)pyrrolidin-1-yl)-1-(3-(trifluoromethyl)phenyl)ethyl)(methyl)carbamate

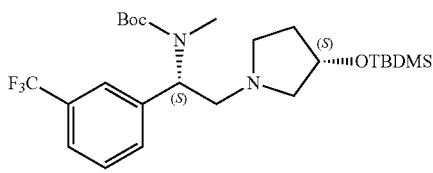

Sodium carbonate (109 mg, 1.03 mmol, 4.99 eq) was added to a solution of [(1S)-2-[(3S)-3-[(tert-butyldimethylsilyl)oxy]pyrrolidin-1-yl]-1-[3-(trifluoromethyl)phenyl]ethyl](methyl)amine (83 mg, 0.21 mmol, 1.00 equiv) in tetrahydrofuran/water (4/4 mL). After stirring for 15 min at room temperature, $Boc_2O$ (45 mg, 0.21 mmol, 1.00 eq.) was added. The resulting solution was stirred for 10 h at 25° C. in an oil bath. The organic solvent was removed in vacuo. The aqueous layer was extracted with 3×5 mL of ethyl acetate. The combined organic layers were washed with 3×10 mL of $H_2O$ and 3×10 mL of brine, dried over anhydrous sodium sulfate and concentrated in vacuo. This resulted in 100 mg (crude) of the title compound as a light yellow solid.

LC-MS: (ES, m/z): 503 (M+1).

Step (vi) Synthesis of (S)-1-((S)-2-(methylamino)-2-(3-(trifluoromethyl)phenyl)ethyl)pyrrolidin-3-ol

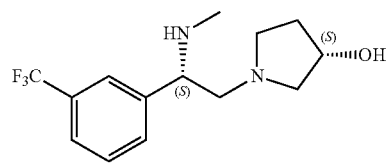

A solution of tert-butyl N-[(1S)-2-[(3S)-3-[(tert-butyldimethylsilyl)oxy]pyrrolidin-1-yl]-1-[3-(trifluoromethyl)phenyl]ethyl]-N-methylcarbamate (780 mg, 1.55 mmol, 1.00 equiv) in dichloromethane (5 mL) and trifluoroacetic acid (2.5 mL) was stirred for 2 h at 15° C. The solids were collected by filtration. The crude product was combined with the previous batches and purified by Prep-HPLC with the following conditions (1#-Pre-HPLC-016 (Waters)): Column, Xbridge Prep C18, 5 um, 19*150 mm; mobile phase, WATER WITH 0.05% $CF_3COOH$ and $CH_3CN$ (10.0% $CH_3CN$ up to 31.0% in 15 min, up to 100.0% in 2 min, down to 10.0% in 1 min); Detector, UV 254&220 nm. This resulted in 675 mg of the titled compound as a brown solid.

LC-MS: (ES, m/z): 289 (M+1); $^1$H-NMR (300 MHz, $CH_3OD$) 68.023 (1H, s), 7.913-7.938 (2H, m), 7.787-7.839 (1H, m), 4.868-4.893 (1H, m), 4.533-4.548 (1H, m), 4.025-4.048 (1H, m), 3.320-3.634 (4H, m), 2.630 (3H, s), 2.166-2.288 (1H, m), 2.016-2.226 (1H, m).

Example 7-b

(3S)-1-[(2S)-2-(3-fluorophenyl)-2-(methylamino)ethyl]pyrrolidin-3-ol

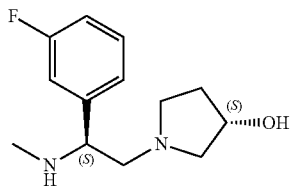

Step (i) Synthesis of 1-fluoro-3-vinylbenzene

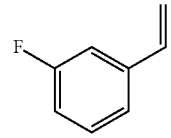

In an inert atmosphere of nitrogen, n-BuLi (2.4M) (69 mL, 1.10 equiv) was added to a suspension of $PPh_3CH_3Br$ (64.2 g, 179.83 mmol, 1.20 equiv) in tetrahydrofuran (300 mL) at 0° C. After stirring for 30 min, a solution of 3-fluorobenzaldehyde (18.6 g, 149.86 mmol, 1.00 equiv) in tetrahydrofuran (50 mL) was added dropwise. The resulting solution was stirred for 1.0 h at room temperature in an oil bath. The reaction was then quenched by the addition of saturated aqueous $NH_4Cl$. The resulting solution was extracted with ethyl acetate. The combined organic layers were washed with brine, dried over anhydrous sodium sulfate and concentrated in vacuo. The residue was purified further by column chromatography using silica gel as stationary phase and petroleum ether as eluent to get the titled compound 13 g (71%) as a colorless liquid.

$^1$H-NMR (CDCl$_3$, 400 MHz): 7.32-7.29 (m, 1H), 7.21-7.13 (m, 2H), 7.01-6.96 (m, 1H), 6.75-6.71 (q, J=10.8 Hz, 17.6 Hz, 1H), 5.79 (d, J=17.6 Hz, 1H), 5.33 (d, J=11.2 Hz, 1H).

Step (ii) Synthesis of (S)-1-(3-fluorophenyl)ethane-1,2-diol

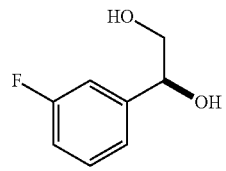 [SMILES: OC[C@@H](O)c1cccc(F)c1]

1-ethenyl-3-fluorobenzene (2.1 g, 17.19 mmol, 1.00 equiv) was added to a mixture of water (90 mL), t-BuOH (90 mL) and AD-Mix alpha (50 g) at 0° C. The resulting solution was stirred overnight at 0° C. The reaction was quenched with solid Na$_2$SO$_3$. After stirring for 1.0 hour at 25° C., the resulting solution was diluted with ethyl acetate. The organic layer was washed with brine, dried over anhydrous sodium sulfate and concentrated in vacuo. The residue was purified by column chromatography using silica gel as stationary phase and petroleum ether/EtOAc (1:1) as eluent to obtain 1.6 g (61%) of the titled compound as a white solid.

$^1$H-NMR (DMSO-d$_6$, 300 MHz): δ 7.93-7.32 (m, 1H), 7.20-7.13 (m, 2H), 7.09-7.02 (m, 1H), 5.38 (d, J=4.5 Hz, 1H), 4.76 (t, J=5.7 Hz, 1H), 4.76 (q, J=5.7 Hz, 9.9 Hz, 1H), 3.45 (t, J=5.7 Hz, 2H).

Step (iii) Synthesis of (S)-2-(3-fluorophenyl)oxirane

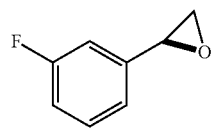

In an inert atmosphere of nitrogen, TMS-Cl (12.58 g, 115.80 mmol, 5.00 equiv) and CH$_3$C(OCH$_3$)$_3$ (13.85 g, 115.42 mmol, 5.00 equiv) were added to a solution of (1S)-1-(3-fluorophenyl)ethane-1,2-diol (3.6 g, 23.05 mmol, 1.00 equiv) in dichloromethane (40 mL) at 0° C. The resulting solution was stirred for 2.0 h at 25° C. The solvent was evaporated in vacuo. The residue was dissolved in dry methanol (50 mL) and then potassium carbonate (15.9 g, 115.22 mmol, 5.00 equiv) was added. The resulting solution was stirred for 1 hr at 25° C. The reaction was quenched by addition of saturated NH$_4$Cl. The resulting solution was extracted with dichloromethane. The combined organic layers were washed with brine and water, dried over anhydrous sodium sulfate and concentrated in vacuo. The residue was applied onto a silica gel column eluting with ethyl acetate/petroleum ether (1:30). This resulted in 2.38 g (75%) of the titled compound as light yellow oil.

Step (iv) Synthesis of (S)-2-((S)-3-((tert-butyldimethylsilyl)oxy)pyrrolidin-1-yl)-1-(3-fluorophenyl)-N-methylethanamine

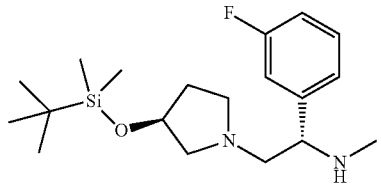 [SMILES: CN[C@H](CN1CC[C@H](O[Si](C)(C)C(C)(C)C)C1)c1cccc(F)c1]

In an inert atmosphere of nitrogen, a solution of (2S)-2-(3-fluorophenyl)oxirane (1.2 g, 8.69 mmol, 1.00 equiv) and (3S)-3-[(tert-butyldimethylsilyl)oxy]pyrrolidine (2.62 g, 13.01 mmol, 1.50 equiv) in ethanol (20 mL) was heated to reflux for 0.5 hr. The ethanol was removed in vacuo. The crude reaction mixture was then dissolved in 30 mL of Et$_2$O. Triethylamine (2.64 g, 26.14 mmol, 3.00 equiv) and MsCl (1.5 g, 13.04 mmol, 1.50 equiv) were added at 0° C. and stirred for 30 min. Another portion of triethylamine (1.76 g, 17.42 mmol, 2.00 equiv) was added. The reaction was warmed to room temperature over 30 min and then CH$_3$NH$_2$ (30% aq.) (18 g, 174.19 mmol, 20.00 equiv) and water (1.0 mL) were added. The resulting solution was allowed to react for 5.0 h at 25° C. The organic layers were separated and aqueous layer was extracted with 2×100 mL of ether. The combined organic layers were washed with 2×100 mL of sodium bicarbonate, 2×100 mL of water and 2×100 mL of brine, dried over anhydrous sodium sulfate and concentrated in vacuo. The residue was purified further by column chromatography using silica gel as stationary phase and dichloromethane/methanol (30:1) as eluent. This resulted in 1.9 g (62%) of the titled compound as yellow oil.

LC-MS: (ES, m/z): 353 (M+1).

Step (v) Synthesis of (S)-1-((S)-2-(3-fluorophenyl)-2-(methylamino)ethyl)pyrrolidin-3-ol

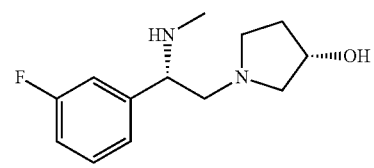 [SMILES: CN[C@H](CN1CC[C@H](O)C1)c1cccc(F)c1]

TBAF (1.0 M) (5.5 mL, 3.00 equiv) was added to a solution of [(1S)-2-[(3S)-3-[(tert-butyldimethylsilyl)oxy]pyrrolidin-1-yl]-1-(3-fluorophenyl)ethyl](methyl)amine (650 mg, 1.84 mmol, 1.00 equiv) in tetrahydrofuran (10 mL) at 0° C. The resulting solution was stirred for 1.0 h at room temperature. The solvent was removed in vacuo. The residue was purified by Flash-HPLC to give 360 mg (82%) the product (TFA salt) as yellow oil.

LC-MS: (ES, m/z): 239 (M+1); $^1$H-NMR (CD$_3$OD, 300 MHz): δ 7.67-7.60 (m, 1H), 7.46-7.32 (m, 3H), 4.74-4.69 (m, 1H), 4.53-4.50 (m, 1H), 3.96-3.82 (m, 2H), 3.59-3.49 (m, 1H), 3.42-3.36 (m, 1H), 3.32-3.25 (m, 2H), 2.62 (s, 3H), 2.25-2.16 (m, 1H), 2.06-2.01 (m, 1H).

Example 8-b (S)-1-((S)-2-(methylamino)-2-phenylethyl)pyrrolidin-3-ol

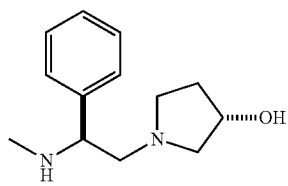

Step (i) Synthesis of (S)-2-(((benzyloxy)carbonyl)amino)-2-phenylacetic acid

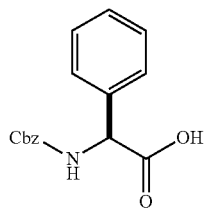

Into a 1000-mL round-bottom flask, were placed a solution of sodium hydroxide (16 g, 400.00 mmol, 2.01 equiv) in water (400 mL) and (S)-2-amino-2-phenylacetic acid (30 g, 198.68 mmol, 1.00 equiv). This was followed by the dropwise addition of Cbz-Cl (36 g, 210.53 mmol, 1.10 equiv) with stirring at 5° C. The resulting solution was stirred for 4 h at room temperature. The resulting solution was extracted with 2×200 ml of ethyl acetate. The pH value of the aqueous phase was adjusted to 3 with conc. hydrochloric acid. The resulting solids were collected by filtration. The solid was dried in an oven under reduced pressure. This resulted in 35 g (62%) of (S)-2-(benzyloxycarbonylamino)-2-phenylacetic acid as a white solid.

MS (ESI) m/z 286 (M+1).

Step (ii) Synthesis of benzyl ((S)-2-((S)-3-hydroxypyrrolidin-1-yl)-2-oxo-1-phenylethyl)carbamate

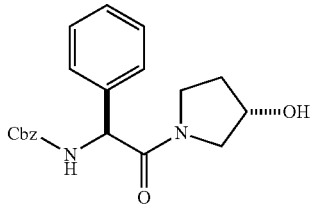

Into a 500-mL round-bottom flask, was placed a solution of (S)-2-(benzyloxycarbonylamino)-2-phenylacetic acid (10 g, 35.09 mmol, 1.00 equiv) in dichloromethane (200 mL). This was followed by the addition of DCC (8.7 g, 42.23 mmol, 1.20 equiv) at −10° C. To this was added HOBt (5.7 g, 42.22 mmol, 1.20 equiv) at −10° C. The resulting solution was stirred for 1 h at −10° C. To the mixture was added (S)-pyrrolidin-3-ol (3.66 g, 42.07 mmol, 0.33 equiv) at −10° C. The resulting solution was allowed to react, with stirring, for an additional 1 h at −10° C. The resulting solution was allowed to react, with stirring, overnight at 10° C. The solids were filtered out. The filtrate was washed with 1×100 mL of sat.NaHCO₃ and 1×200 mL of brine, dried over anhydrous sodium sulfate and concentrated under vacuum. The residue was applied onto a silica gel column and eluted with dichloromethane:CH3OH (50:1-20:1). This resulted in 6.7 g of benzyl (S)-2-((S)-3-hydroxypyrrolidin-1-yl)-2-oxo-1-phenylethylcarbamate as a white foamy solid.

MS(ESI) m/z: 355 (M+1).

Step (iii) Synthesis of (S)-1-((S)-2-(methylamino)-2-phenylethyl)pyrrolidin-3-ol

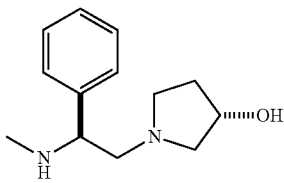

To a solution of LiAlH₄ (4.8 g, 126.32 mmol, 7.40 equiv) in tetrahydrofuran (100 mL) was added a solution of benzyl (S)-2-((S)-3-hydroxypyrrolidin-1-yl)-2-oxo-1-phenylethylcarbamate (6 g, 16.95 mmol, 1.00 equiv) in tetrahydrofuran (50 mL) at room temperature under N2. The resulting solution was heated under reflux overnight in an oil bath. The reaction was then quenched by the addition of 200 ML of water/ice. The solids were filtered out. The filtrate was extracted with 2×200 ML of ethyl acetate. The combined organic layers were dried over sodium sulfate and concentrated under vacuum. The residue was applied onto a Al2O3 column and eluted with EtOAc/Petroleum Ether (5:1) and then DCM/MeOH (80:1-20:1). This resulted in 3 g of (S)-1-((S)-2-(methylamino)-2-phenylethyl)pyrrolidin-3-ol as yellow oil.

MS (ESI) m/z: 221 (M+1).

Example 9-b (S)-1-phenyl-2-(pyrrolidin-1-yl)ethanamine

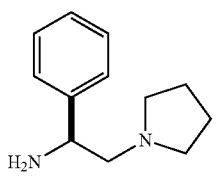

Step (i) Synthesis of (S)-benzyl (2-oxo-1-phenyl-2-(pyrrolidin-1-yl)ethyl)carbamate

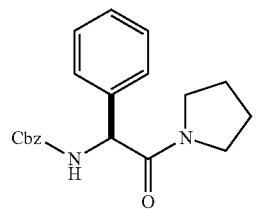

Into a 500-mL round-bottom flask, was placed a solution of (S)-2-(benzyloxycarbonylamino)-2-phenylacetic acid (10 g, 35.09 mmol, 1.00 equiv) in dichloromethane (200 mL). This was followed by the addition of DCC (8.7 g) at −10° C. To this was added HOBt (5.7 g) at −10° C. The resulting solution was stirred for 1 h at −10° C. To the mixture was added pyrrolidine (3 g, 42.25 mmol, 1.20 equiv) at −10° C. The resulting solution was allowed to react, with stirring, for an additional 1 h at −10° C. The resulting solution was allowed to react, with stirring, overnight at 10° C. The solids were filtered out. The filtrate was washed with 1×100 mL of NaHCO3, dried over anhydrous sodium sulfate and concentrated under vacuum. The residue was applied onto a silica gel column and eluted with ethyl acetate/petroleum ether (1:5) and then dichloromethane/methanol (50:1). This resulted in 10 g (84% yield) of (S)-benzyl 2-oxo-1-phenyl-2-(pyrrolidin-1-yl)ethylcarbamate as oil. MS (ESI) m/z: 339 (M+1).

Step (ii) Synthesis of (S)-benzyl (1-phenyl-2-(pyrrolidin-1-yl)ethyl)carbamate

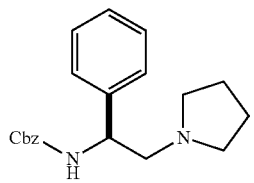

To a solution of LiAlH4 (4.8 g, 126.32 mmol, 7.40 equiv) in tetrahydrofuran (100 mL) was added a solution of benzyl (S)-2-((S)-3-hydroxypyrrolidin-1-yl)-2-oxo-1-phenylethylcarbamate (6 g, 16.95 mmol, 1.00 equiv) in tetrahydrofuran (50 mL) at room temperature under N2. The resulting solution was heated under reflux overnight in an oil bath. The reaction was then quenched by the addition of 200 ML of water/ice. The solids were filtered out. The filtrate was extracted with 2×200 ML of ethyl acetate. The combined organic layers were dried over sodium sulfate and concentrated under vacuum. The residue was applied onto a Al2O3 column and eluted with EtOAc/Petroleum Ether (5:1) and then DCM/MeOH (80:1-20:1). This resulted in 3 g of (S)-1-((S)-2-(methylamino)-2-phenylethyl)pyrrolidin-3-ol as yellow oil. MS (ESI) m/z: 221 (M+1).

Step (iii) Synthesis of (S)-1-phenyl-2-(pyrrolidin-1-yl)ethanamine

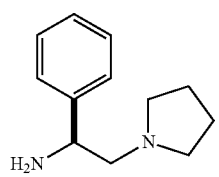

Into a 100-mL round-bottom flask, was placed a solution of (2S)-2-amino-2-phenyl-1-(pyrrolidin-1-yl)ethyl borinate (5 g, 22.92 mmol, 1.00 equiv) in aq. HCl (50 mL). The resulting solution was stirred overnight at 70° C. The resulting solution was extracted with 2×50 mL of ethyl acetate and the aqueous layers combined. The pH value of the aq. solution was adjusted to 10 with sodium hydroxide. The resulting solution was extracted with 3×50 mL of ethyl acetate. The combined organic layers were washed with 100 ml of brine, dried over anhydrous sodium sulfate and concentrated under vacuum. This resulted in 3 g (69% yield) of (1S)-1-phenyl-2-(pyrrolidin-1-yl)ethan-1-amine as yellow oil.

$^1$H NMR (DMSO-$d_6$, 400 MHz): δ 7.46-7.35 (m, 2H), 7.30-7.24 (m, 2H), 7.21-7.18 (m, 1H), 3.98-3.37 (m, 1H), 2.58-2.45 (m, 3H), 2.42-2.40 (m, 2H), 2.29 (dd, J=4.6 & 11.5 Hz, 1H), 2.31-2.27 (m, 1H), 2.00 (bs, 2H), 1.77-1.59 (m, 4H); MS (ES): m/z 191.4 (M+1).

Example 10-b (S)-2-((S)-3-((tert-butyldimethylsilyl)oxy)pyrrolidin-1-yl)-1-(3-(difluoromethoxy)phenyl)-N-methyl-ethanamine

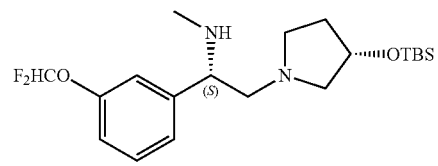

Step (i). Synthesis of 1-(difluoromethoxy)-3-iodobenzene

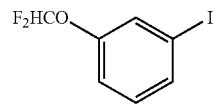

Into a 250-mL 3-necked round-bottom flask purged and maintained with an inert atmosphere of nitrogen, was placed a solution of 3-iodophenol (22 g, 100.00 mmol, 1.00 equiv) in N,N-dimethylformamide (100 mL). Then Cs2CO3 (65.2 g, 200.11 mmol, 2.00 equiv) and ClF2CCOONa (30.4 g, 200.00 mmol, 2.00 equiv) were added at room temperature. The resulting solution was stirred for 5.0 h at 100° C. The solids were filtered out and washed with 2×200 mL of EtOAc. The organic layers were combined and washed with 6×150 mL of brine. The mixture was dried over anhydrous sodium sulfate and concentrated under vacuum. The residue was applied onto a silica gel column and eluted with petroleum ether. This resulted in 15.5 g (57%) of 1-(difluoromethoxy)-3-iodobenzene as colorless oil.

Step (ii) Synthesis of 1-(difluoromethoxy)-3-vinylbenzene

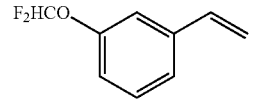

Into a 250-mL 3-necked round-bottom flask purged and maintained with an inert atmosphere of nitrogen, was placed a solution of potassium vinyltrifluoroborate (3.17 g, 23.67 mmol, 1.10 equiv) in tetrahydrofuran/H₂O (9/1) (60 mL), Ph₃P (338 mg, 0.06 equiv), PdCl₂ (75 mg, 0.02 equiv), Cs₂CO₃ (21 g, 64.45 mmol, 3.00 equiv). To this was added a solution of 1-(difluoromethoxy)-3-iodobenzene (5.81 g, 21.52 mmol, 1.00 equiv) in tetrahydrofuran/H₂O (9/1) (5 mL). The resulting solution was stirred for 24 h at 85° C. The reaction mixture was cooled and the solids were filtered out. The filtrate was extracted with 2×200 ml of petroleum ether and the organic layers combined and dried over anhydrous sodium sulfate and concentrated under vacuum. The residue was applied onto a silica gel column and eluted with petroleum ether. This resulted in 3.1 g (85%) of 1-(difluoromethoxy)-3-ethenylbenzene as yellow oil.

Step (iii) Synthesis of (S)-1-(3-(difluoromethoxy) phenyl)ethane-1,2-diol

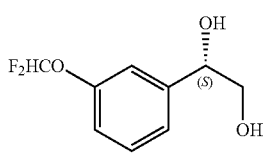

Into a 250-mL round-bottom flask purged and maintained with an inert atmosphere of nitrogen, was placed a solution of AD-Mix alpha (25.5 g) in tBuOH/H₂O (1:1) (148 mL). This was followed by the addition of a solution of 1-(difluoromethoxy)-3-ethenylbenzene (3.1 g, 18.22 mmol, 1.00 equiv) in tBuOH/H₂O (1:1) (10 mL) dropwise with stirring at 0° C. The resulting solution was stirred for 2-3 h at room temperature. The Na₂SO₃ was added at stirred for 1 h at room temperature. The resulting solution was extracted with 2×200 mL of ethyl acetate and the organic layers combined. The resulting mixture was washed with 2×200 mL of brine. The mixture was dried over sodium sulfate and concentrated under vacuum. The residue was applied onto a silica gel column and eluted with DCM/MeOH (200:1-150/1). This resulted in 3.05 g (82%) of (1S)-1-[3-(difluoromethoxy) phenyl]ethane-1,2-diol as yellow oil.

Step (iv) Synthesis of (S)-2-(3-(difluoromethoxy) phenyl)oxirane

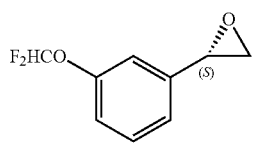

Into a 100-mL round-bottom flask purged and maintained with an inert atmosphere of nitrogen, was placed a solution of (1S)-1-[3-(difluoromethoxy)phenyl]ethane-1,2-diol (3.05 g, 14.94 mmol, 1.00 equiv) in dichloromethane (50 mL), CH₃C(OCH₃)₃(9.0 g, 75.00 mmol, 5.02 equiv). This was followed by the addition of TMSCl (8.2 g, 75.48 mmol, 5.05 equiv) dropwise with stirring at 0° C. After stirred for 5 h at room temperature, the mixture was concentrated. The residue was diluted in 50 mL of methanol. To this was added potassium carbonate (10.3 g, 74.52 mmol, 4.99 equiv) at 0° C. The resulting solution was stirred for 0.5 h at room temperature. The solids were filtrate out. The filtrate was concentrated under vacuum. The resulting solution was extracted with dichloromethane and the organic layers combined and dried over sodium sulfate and concentrated under vacuum. The residue was applied onto a silica gel column and eluted with ethyl acetate/petroleum ether (1:70-1:50). This resulted in 1.94 g (70%) of (2S)-2-[3-(difluoromethoxy)phenyl]oxirane as yellow oil.

Step (v). Synthesis of (S)-2-((S)-3-((tert-butyldimethylsilyl)oxy)pyrrolidin-1-yl)-1-(3-(difluoromethoxy)phenyl)-N-methylethanamine

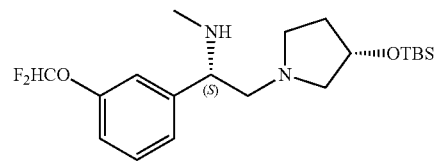

Into a 100-mL 3-necked round-bottom flask purged and maintained with an inert atmosphere of nitrogen, was placed a solution of (2S)-2-[3-(difluoromethoxy)phenyl]oxirane (390 mg, 2.10 mmol, 1.00 equiv) in ethanol (10 mL). This was followed by the addition of (3S)-3-[(tert-butyldimethylsilyl)oxy]pyrrolidine (625 mg, 3.10 mmol, 1.50 equiv). The resulting solution was heated to reflux for 2.0 h and then the solution was concentrated under vacuum. The residue was diluted in 10 mL of ether. To this was added triethylamine (629 mg, 6.21 mmol, 3.00 equiv). Then MsCl (358 mg, 3.11 mmol, 1.50 equiv) was added dropwise at 0° C. and stirred for 30 min. Then triethylamine (418 mg, 4.14 mmol, 2.00 equiv) and CH₃NH₂ (4.3 g, 41.4 mmol, 20 equiv, 30%) was added. The resulting solution was stirred for 24 h at 25° C. The reaction was then quenched by the addition of 20 mL of water. The resulting solution was extracted with ethyl acetate and the organic layers combined. The resulting mixture was washed with aqueous sodium bicarbonate, brine, dried over sodium sulfate and concentrated under vacuum. The residue was applied onto a silica gel column and eluted with DCM/MeOH (70:1-50:1) to obtain the title compound as yellow oil.

Example 11-b (S)-2-((S)-3-((tert-butyldimethylsilyl)oxy)pyrrolidin-1-yl)-N-methyl-1-(4-(trifluoromethoxy)phenyl) ethanamine

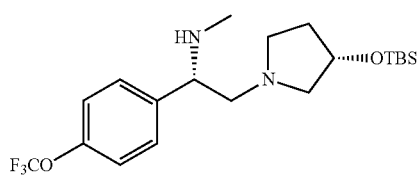 [SMILES: CN[C@H](CN1CC[C@H](O[Si](C)(C)C(C)(C)C)C1)c1ccc(OC(F)(F)F)cc1]

Step (i) Synthesis of 2-bromo-1-(4-(trifluoromethoxy)phenyl)ethanone

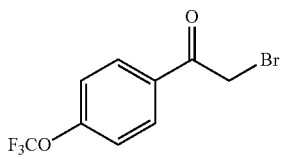 [SMILES: O=C(CBr)c1ccc(OC(F)(F)F)cc1]

Br$_2$ (15.2 g, 95.11 mmol, 1.20 equiv) was added dropwise to a solution of 1-[4-(trifluoromethoxy)phenyl]ethan-1-one (15 g, 73.48 mmol, 1.00 equiv) in ether (200 mL). The resulting solution was stirred for 5 h at room temperature. The reaction was then quenched by the addition of aqueous sodium thiosulfate pentahydrate. The resulting aqueous solution was extracted with 3×100 mL of ethyl acetate. The organic layers was combined and dried over Na2SO4 and concentrated under vacuum. The residue was applied onto a silica gel column with ethyl acetate/petroleum ether (1:70). This resulted in 11.4 g (55%) of 2-bromo-1-[4-(trifluoromethoxy)phenyl]ethan-1-one as a white solid.

Step (ii) Synthesis of (S)-2-bromo-1-(4-(trifluoromethoxy)phenyl)ethanol

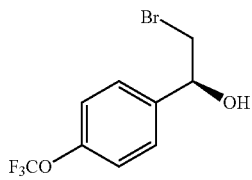

Into a 100-mL 3-necked round-bottom flask purged and maintained with an inert atmosphere of nitrogen, was placed (S)-Me-CBS (587 mg, 2.12 mmol, 0.10 equiv), a solution of N,N-diethylaniline borane (3.5 g, 21.44 mmol, 1.00 equiv) in MTBE (20 mL). The mixture was followed by the addition of a solution of 2-bromo-1-[4-(trifluoromethoxy)phenyl]ethan-1-one (6 g, 21.20 mmol, 1.00 equiv) in MTBE (60 mL) dropwise with stirring at 40° C. in 3 hr. After addition, continued to stirring 40° C. for 1 hr. The resulting solution was stirred for 14 h at room temperature. The reaction was quenched by the addition of 10 ml of methanol below 20° C. and then stirred for 30 min at room temperature. The resulting solution was added 60 ml of aqueous HCl (2.5N) below 20° C. and stirred for 30 min at room temperature. The resulting aqueous solution was extracted with 3×100 mL of ethyl acetate. The organic layers were combined and dried over anhydrous sodium sulfate and concentrated under vacuum. The residue was applied onto a silica gel column with ethyl acetate/petroleum ether (1:100). This resulted in 5.5 g (91%) of (1S)-2-bromo-1-[4-(trifluoromethoxy)phenyl]ethan-1-ol as a white solid.

Step (iii) Synthesis of (S)-2-(4-(trifluoromethoxy)phenyl)oxirane

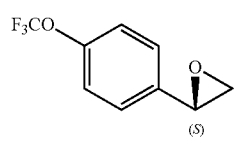

Potassium carbonate (5.2 g, 37.62 mmol, 2.00 equiv) was added to a solution of (1S)-2-bromo-1-[4-(trifluoromethoxy)phenyl]ethan-1-ol (5.4 g, 18.94 mmol, 1.00 equiv) in methanol (100 mL) in portions at 0° C. The resulting solution was stirred for 20 min at 0° C. The solids were filtered out. The resulting mixture was concentrated under vacuum. The residue was dissolved in EA. The resulting mixture was washed with 2×100 mL of bine. The organic layer was concentrated under vacuum. This resulted in 2.6 g (67%) of (2S)-2-[4-(trifluoromethoxy)phenyl]oxirane as a white solid.

Step (iv) Synthesis of (S)-2-((S)-3-((tert-butyldimethylsilyl)oxy)pyrrolidin-1-yl)-N-methyl-1-(4-(trifluoromethoxy)phenyl)ethanamine

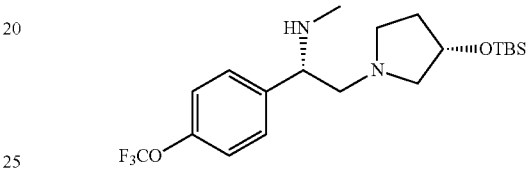

Into 250 ml round-bottom flash, a solution of (2S)-2-[4-(trifluoromethoxy)phenyl]oxirane (2.5 g, 12.25 mmol, 1.00 equiv) and (3S)-3-[(tert-butyldimethylsilyl)oxy]pyrrolidine (3.9 g, 19.37 mmol, 1.50 equiv) in ethanol (100 mL) was added. The resulting solution was allowed to react with stirring for overnight at reflux in oil bath. Then the mixture was concentrated and the residue was purified by silica-gel (DCM/MeOH=10/1) to afforded 4.1 g of (S)-2-((S)-3-(tert-butyldimethylsilyloxy)pyrrolidin-1-yl)-1-(4-(trifluoromethoxy)phenyl)ethanol which was dissolved in DCM (150 ml). triethylamine (5.05 g, 49.91 mmol, 2.00 equiv) was added. This resulting solution was followed by the addition of a solution of MsCl (2.28 g, 20.00 mmol, 5.00 equiv) in dichloromethane (50 mL) dropwise with stirring at 0° C. Then this resulting solution was allowed to react with stirring for 6 h at room temperature and added 40% aqueous CH$_3$NH$_2$ (3.1 g). The resulting solution was stirred for 14 h at room temperature. The resulting solution was extracted with 2×30 mL of ethyl acetate. The organic layers were combined and dried over anhydrous sodium sulfate and concentrated under vacuum. The residue was applied onto a silica gel column with dichloromethane/methanol (10:1). This resulted in 2.4 g (47%) of [(1S)-2-[(3S)-3-[(tert-butyldimethylsilyl)oxy]pyrrolidin-1-yl]-1-[4-(trifluoromethoxy)phenyl]ethyl](methyl) amine as yellow oil.

LC-MS (ES, m/z): 419 (M+1).

Example 12-b (S)-2-((S)-3-methoxypyrrolidin-1-yl)-N-methyl-1-phenylethanamine

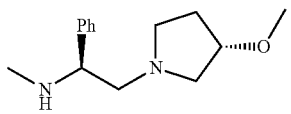

Step (i) Synthesis of (S)-2-(((benzyloxy)carbonyl) amino)-2-phenylacetic acid

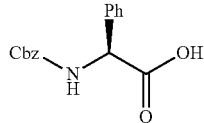 [SMILES: O=C(N[C@H](C(=O)O)c1ccccc1)OCc1ccccc1]

Into a solution of (2S)-2-amino-2-phenylacetic acid (10 g, 66.15 mmol, 1.00 equiv) in water (200 mL) was added aqueous sodium hydroxide (5.3 g, 132.50 mmol, 2.00 equiv) in water (100 ml). This followed by the addition of CbzCl (12.4 g, 72.69 mmol, 1.10 equiv) at 5° C. dropwise. The resulting solution was stirred for 3 h at room temperature. The resulting solution was extracted with ethyl acetate and the aqueous layers were combined. The pH value was adjusted to 3 with aqueous HCl (1 mol/L). The resulting aqueous solution was extracted with DCM/MeOH (10/1). The organic layers were combined and dried over anhydrous sodium sulfate, concentrated under vacuum. This resulted in 16.2 g (crude) (86%) of (2S)-2-[[(benzyloxy)carbonyl] amino]-2-phenylacetic acid as a white solid.

LC-MS (ES, m/z): 284 (M−1)⁻

Step (ii) Synthesis of benzyl ((S)-2-((S)-3-hydroxy-pyrrolidin-1-yl)-2-oxo-1-phenylethyl)carbamate

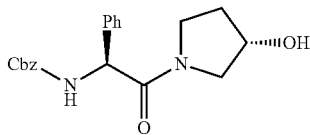 [SMILES: O=C(N[C@H](C(=O)N1CC[C@H](O)C1)c1ccccc1)OCc1ccccc1]

Into a solution of (2S)-2-[[(benzyloxy)carbonyl]amino]-2-phenylacetic acid (5.7 g, 19.98 mmol, 1.00 equiv) in dichloromethane (100 mL) was added DCC (4.94 g, 23.94 mmol, 1.20 equiv). This was followed by the addition of HOBt (3.24 g, 23.98 mmol, 1.20 equiv). The resulting solution was stirred for 30 min at room temperature. To this was added (3S)-pyrrolidin-3-ol (1.91 g, 21.92 mmol, 1.10 equiv) at 0° C. The resulting solution was stirred overnight at room temperature. The resulting mixture was washed with 2×50 mL of aqueous sat. sodium bicarbonate. The organic layers were separated and dried over anhydrous sodium sulfate, concentrated under vacuum. The residue was applied onto a silica gel column with dichloromethane/methanol (50:1). This resulted in 4.2 g (59%) of benzyl N-[(1S)-2-[(3S)-3-hydroxypyrrolidin-1-yl]-2-oxo-1-phenylethyl]carbamate as yellow oil.

LC-MS (ES, m/z): 355 (M+1).

Step (iii) Synthesis of benzyl ((S)-2-((S)-3-methoxypyrrolidin-1-yl)-2-oxo-1-phenylethyl)(methyl)carbamate

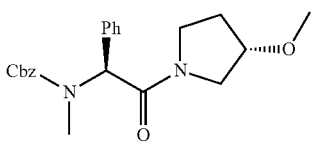 [SMILES: CO[C@H]1CCN(C(=O)[C@H](c2ccccc2)N(C)C(=O)OCc2ccccc2)C1]

Into a solution of benzyl N-[(1S)-2-[(3S)-3-hydroxypyrrolidin-1-yl]-2-oxo-1-phenylethyl]carbamate (1.1 g, 3.10 mmol, 1.00 equiv) in tetrahydrofuran (40 mL) was added sodium hydride (250 mg, 6.25 mmol, 2.01 equiv) portionwise at 0° C. in ice bath. The mixture was stirred for 10 min at room temperature. To this was added iodomethane (1.3 g, 9.15 mmol, 2.95 equiv) dropwise with stirring. The resulting solution was stirred for 2 h at 30° C. The reaction was then quenched by the addition of water/ice. The resulting aqueous solution was extracted with of ethyl acetate. The organic layers were combined and dried over anhydrous sodium sulfate, concentrated under vacuum. The residue was applied onto a silica gel column with ethyl acetate/petroleum ether (1:2). This resulted in 730 mg (61%) of benzyl N-[(1S)-2-[(3S)-3-methoxypyrrolidin-1-yl]-2-oxo-1-phenylethyl]-N-methylcarbamate as colorless oil.

LC-MS (ES, m/z): 383 (M+1)

Step (iv) Synthesis of (S)-1-((S)-3-methoxypyrrolidin-1-yl)-2-(methylamino)-2-phenylethanone

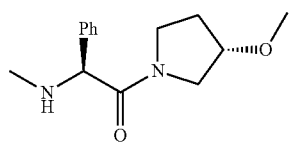

Into a solution of benzyl N-[(1S)-2-[(3S)-3-methoxypyrrolidin-1-yl]-2-oxo-1-phenylethyl]-N-methylcarbamate (580 mg, 1.52 mmol, 1.00 equiv) in methanol (20 mL) was added Palladium on carbon (290 mg, 10%) under nitrogen atmosphere. The resulting solution was hydrogenated overnight at 25° C. After the completion of the reaction, the reaction mixture was filtered. The filtrate was concentrated to dryness. This resulted in 300 mg (80%) of (2S)-1-[(3S)-3-methoxypyrrolidin-1-yl]-2-(methylamino)-2-phenylethan-1-one as a yellow solid.

LC-MS (ES, m/z): 249 (M+1).

Step (v) Synthesis of (S)-2-((S)-3-methoxypyrrolidin-1-yl)-N-methyl-1-phenylethanamine

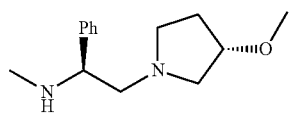

Into a solution of (2S)-1-[(3S)-3-methoxypyrrolidin-1-yl]-2-(methylamino)-2-phenylethan-1-one (300 mg, 1.21 mmol, 1.00 equiv) in tetrahydrofuran (25 mL) was added LiAlH₄ (184 mg, 4.85 mmol, 4.01 equiv) with stirring at 0° C. in ice bath. The resulting solution was stirred for 3 h at room temperature. The reaction was then quenched by the careful addition of water/ice at 0° C. The resulting aqueous solution was extracted with of ethyl acetate. The organic layers were combined and dried over anhydrous sodium sulfate, concentrated under vacuum. This resulted in 160 mg (57%) of [(1S)-2-[(3S)-3-methoxypyrrolidin-1-yl]-1-phenylethyl](methyl)amine as yellow oil.

LC-MS (ES, m/z): 235 (M+1).

Example 13-b 5-((S)-2-((S)-3-((tert-butyldimethylsilyl)oxy)pyrrolidin-1-yl)-1-(methylamino)ethyl)-2-fluorobenzonitrile

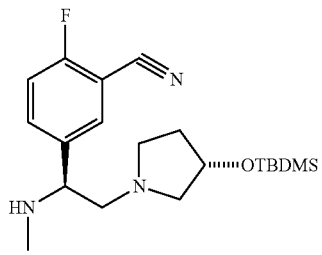 [SMILES: CN[C@H](CN1CC[C@H](O[Si](C)(C)C(C)(C)C)C1)c1ccc(F)c(C#N)c1]

Step (i) Synthesis of benzyl ((S)-1-(3-bromo-4-fluorophenyl)-2-((S)-3-((tert-butyldimethylsilyl)oxy)pyrrolidin-1-yl)ethyl)(methyl)carbamate

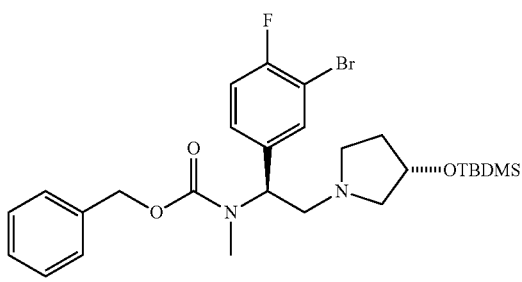 [SMILES: CN(C(=O)OCc1ccccc1)[C@H](CN1CC[C@H](O[Si](C)(C)C(C)(C)C)C1)c1ccc(F)c(Br)c1]

Into a 100-mL 3-necked round-bottom flask, was placed a solution of [(1S)-1-(3-bromo-4-fluorophenyl)-2-[(3S)-3-[(tert-butyldimethylsilyl)oxy]pyrrolidin-1-yl]ethyl](methyl)amine (2.4 g, 5.56 mmol, 1.00 equiv), obtained by following a suitable procedure(s) similar to that mentioned in example 8 by using appropriate starting materials; in EtOAc/H$_2$O (40/8 mL). This was followed by the addition of potassium carbonate (1 g, 7.24 mmol, 1.30 equiv) in portions at 0° C. Then Cbz-Cl (1.14 g, 6.68 mmol, 1.20 equiv) was added dropwise with stirring at 0° C. The resulting solution was stirred for 3 h at room temperature. The resulting solution was diluted with 10 mL of water. The resulting aqueous solution was extracted with 3×5 mL of ethyl acetate and the organic layers were combined. The organic layers were washed with 2×15 mL of brine and dried over anhydrous sodium sulfate and concentrated under vacuum. The residue was applied onto a silica gel column with ethyl acetate/petroleum ether (1:10-1:5). This resulted in 2.5 g (79%) of benzyl N-[(1S)-1-(3-bromo-4-fluorophenyl)-2-[(3S)-3-[(tert-butyldimethylsilyl)oxy]pyrrolidin-1-yl]ethyl]-N-methylcarbamate as yellow oil.

LC-MS (ES, m/z): 565, 567 (M+1).

Step (ii) Synthesis of benzyl ((S)-2-((S)-3-((tert-butyldimethylsilyl)oxy)pyrrolidin-1-yl)-1-(3-cyano-4-fluorophenyl)ethyl)(methyl)carbamate

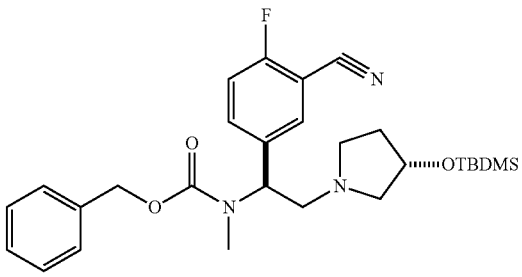 [SMILES: CN(C(=O)OCc1ccccc1)[C@H](CN1CC[C@H](O[Si](C)(C)C(C)(C)C)C1)c1ccc(F)c(C#N)c1]

Into a 50-mL round-bottom flask purged and maintained with an inert atmosphere of nitrogen, was placed a solution of benzyl N-[(1S)-1-(3-bromo-4-fluorophenyl)-2-[(3S)-3-[(tert-butyldimethylsilyl)oxy]pyrrolidin-1-yl]ethyl]-N-methylcarbamate (500 mg, 0.88 mmol, 1.00 equiv) in N,N-dimethylformamide (15 mL). Then Zn(CN)$_2$ (207 mg) was added. Following Pd(PPh$_3$)$_4$(1.02 g, 0.88 mmol, 0.98 equiv) was added. The resulting solution was stirred overnight at 95° C. in an oil bath. The reaction was then quenched by the addition of 20 mL of aqueous saturated FeSO$_4$. The resulting solids were filtered out. The filtrate was extracted with 3×10 mL of ethyl acetate and the organic layers were combined. The organic layers were washed with 1×20 mL of brine and dried over anhydrous sodium sulfate and concentrated under vacuum. The residue was applied onto a silica gel column with ethyl acetate/petroleum ether (1:10-1:8). This resulted in 350 mg (77%) of benzyl N-[(1S)-2-[(3S)-3-[(tert-butyldimethylsilyl)oxy]pyrrolidin-1-yl]-1-(3-cyano-4-fluorophenyl)ethyl]-N-methylcarbamate as yellow oil.

LC-MS (ES, m/z): 512 (M+1).

Step (iii) Synthesis of 5-((S)-2-((S)-3-((tert-butyldimethylsilyl)oxy)pyrrolidin-1-yl)-1-(methylamino)ethyl)-2-fluorobenzonitrile

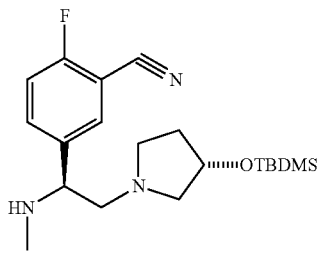

Into a 25-mL round-bottom flask, was placed a solution of benzyl N-[2-[(3S)-3-[(tert-butyldimethylsilyl)oxy]pyrrolidin-1-yl]-1-(3-cyano-4-fluorophenyl)ethyl]-N-methylcarbamate (180 mg, 0.35 mmol, 1.00 equiv) in ethyl acetate (15 mL). This was followed by addition of Palladium on carbon (60 mg, 10%). The resulting solution was hydrogenated at room temperature. After the completion of the reaction, the reaction mixture was filtered. The filtrate was concentrated under vacuum. The residue was applied onto Prep-TLC by DCM: MeOH (10:1). This resulted in 100 mg (75%) of 5-[2-[(3S)-3-[(tert-butyldimethylsilyl)oxy]pyrrolidin-1-yl]-1-(methylamino)ethyl]-2-fluorobenzonitrile as yellow oil. LC-MS (ES, m/z): 378 (M+1).

Example 14-b (S)-2-((S)-3-((tert-butyldimethylsilyl)oxy)pyrrolidin-1-yl)-1-(3,5-dimethylphenyl)-N-methylethanamine

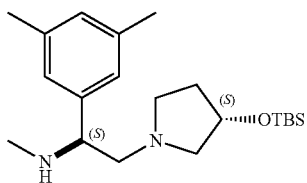

Step (i) Synthesis of 1-(3,5-dimethylphenyl)ethanone

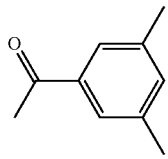

Into a 250-mL 4-necked round-bottom flask purged and maintained with an inert atmosphere of nitrogen, was placed Mg (3.2 g, 1.20 equiv) in tetrahydrofuran (100 mL). Then 2 mL of 1-bromo-3,5-dimethylbenzene and three grains of iodine were added. When the reaction was initiated, the rest of 1-bromo-3,5-dimethylbenzene (20 g, 108.07 mmol, 1.00 equiv) was added. The resulting solution was stirred for 2 h at 80° C. and then cooled to 25° C. To the solution, N-methoxy-N-methylacetamide (16.4 g, 159.04 mmol, 1.50 equiv) was added and the resulting solution was stirred for 2 h at 80° C. The reaction was then quenched by the addition of 50 mL of NH$_4$Cl aqueous and the solution was extracted with ethyl acetate (3×120 mL). The combined organic layers were washed with brine (3×100 mL), dried over anhydrous sodium sulfate and concentrated under vacuum to give of 15.18 g (95%) 1-(3,5-dimethylphenyl)ethan-1-one as yellow oil.

Step (ii) Synthesis of 2-bromo-1-(3,5-dimethylphenyl)ethanone

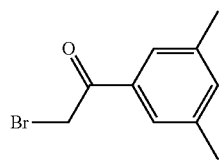

Into a 250-mL round-bottom flask purged and maintained with an inert atmosphere of nitrogen, was placed a solution of 1-(3,5-dimethylphenyl)ethan-1-one (13.04 g, 87.99 mmol, 1.00 equiv) and conc. H$_2$SO$_4$ aqueous (4.40 g) in acetic acid (50 ml). This was followed by the addition of NBS (17.23 g, 96.81 mmol, 1.10 equiv), in portions at 0° C. in 30 min. The resulting solution was stirred for 3 h at room temperature and quenched by the addition of 50 mL of NH$_4$Cl aqueous. The solution was extracted with ethyl acetate (3×50 mL). The combined organic layers were and washed with aq.Na$_2$S$_2$O$_3$ (3×50 mL), aq. NaHCO$_3$ (3×50 mL) and brine (3×50 mL). The organic solution was dried over anhydrous sodium sulfate and concentrated under vacuum. The residue was applied onto a silica gel column and eluted with ethylacetate:petroleum ether (1:80) to give of 11.3 g (57%) 2-bromo-1-(3,5-dimethylphenyl)ethan-1-one as a yellow solid.

Step (iii) Synthesis of (S)-2-bromo-1-(3,5-dimethylphenyl)ethanol

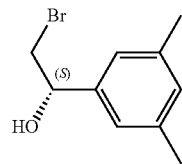

Into a 50-mL 3-necked round-bottom flask purged and maintained with an inert atmosphere of nitrogen, was placed a solution of 1-methyl-3,3-diphenyl-hexahydropyrrolo[1,2-c][1,3,2]oxazaborole (2.44 g, 8.80 mmol, 1.00 equiv) and N,N-diethylaniline borane (1.44 g, 8.83 mmol, 1.00 equiv) in MTBE (6 mL). This was followed by the addition of a solution of 2-bromo-1-(3,5-dimethylphenyl)ethan-1-one (2.00 g, 8.81 mmol, 1.00 equiv) in MTBE (6 mL) dropwise with stirring at 40° C. in 3 hr. The resulting solution was stirred for 1 h at 40° C. and cooled down to 25° C. The reaction was then quenched by the addition of 10 mL of methanol and the pH value of the solution was adjusted to 3-4 with hydrogen chloride aqueous (1 mol/L). The resulting solution was extracted with ethyl acetate (3×10 mL). The combined organic layers were washed with brine (3×10 mL), dried over anhydrous sodium sulfate and concentrated under vacuum to give of 2.15 g (crude) (1S)-2-bromo-1-(3,5-dimethylphenyl)ethan-1-ol as a yellow crystal.

Step (iv) Synthesis of (2S)-2-(3,5-dimethylphenyl)oxirane

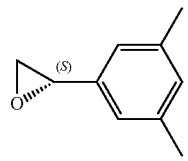

Into a 50-mL round-bottom flask, was placed a solution of (1S)-2-bromo-1-(3,5-dimethylphenyl)ethan-1-ol (1.18 g, 5.15 mmol, 1.00 equiv) in methanol (10 mL). To the solution was added potassium carbonate (1.42 g, 10.27 mmol, 1.99 equiv). The mixture was stirred for 1-2 h at 0° C. The solids were filtered out and the resulting mixture concentrated under vacuum. The residue was dissolved in 10 mL of ethyl acetate. The solution was washed with brine (3×10 mL), dried over anhydrous sodium sulfate and concentrated under vacuum to give of 0.748 g (98%) of (2S)-2-(3,5-dimethylphenyl)oxirane as yellow oil.

Step (v) Synthesis of (S)-2-((S)-3-((tert-butyldimethylsilyl)oxy)pyrrolidin-1-yl)-1-(3,5-dimethylphenyl)ethanol

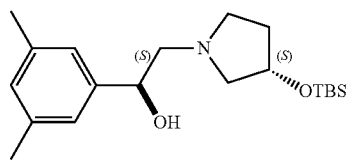

Into a 50-mL round-bottom flask, was placed a solution of (2S)-2-(3,5-dimethylphenyl)oxirane (750 mg, 5.06 mmol, 1.00 equiv) and (3S)-3-[(tert-butyldimethylsilyl)oxy]pyrrolidine (1.15 g, 5.71 mmol, 1.13 equiv) in ethanol (10 mL). The solution was stirred overnight at 80° C. The resulting mixture was concentrated under vacuum. The residue was dissolved in 40 mL of dichloromethane. The organic layer was washed with brine (3×10 mL), dried over anhydrous sodium sulfate and concentrated under vacuum. The residue was applied onto a silica gel column and eluted with dichloromethane/methanol (100:1) to give of 0.99 g (56%) (1S)-2-[(3S)-3-[(tert-butyldimethylsilyl)oxy]pyrrolidin-1-yl]-1-(3,5-dimethylphenyl)ethan-1-ol as yellow oil.

Step (vi) Synthesis of (S)-2-((S)-3-((tert-butyldimethylsilyl)oxy)pyrrolidin-1-yl)-1-(3,5-dimethylphenyl)-N-methylethanamine

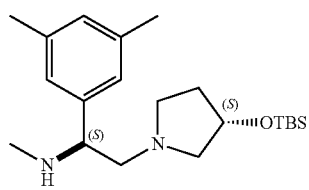

Into a 50-mL round-bottom flask, was placed a solution of (1S)-2-[(3S)-3-[(tert-butyldimethylsilyl)oxy]pyrrolidin-1-yl]-1-(3,5-dimethylphenyl)ethan-1-ol (990 mg, 2.83 mmol, 1.00 equiv) and TEA (1.43 g, 14.13 mmol, 4.99 equiv) in dichloromethane (15 mL). To the solution was added MsCl (0.97 g) and the mixture was stirred for 0.5 hour while the temperature was maintained at 0° C. Then to the solution was added 30% $CH_3NH_2$ aqueous (5.86 g, 56.7 mmol, 20 equiv) and the mixture was stirred overnight at room temperature. The resulting solution was extracted with dichloromethane (3×15 mL). The combined organic layers were washed with brine (3×15 mL), dried over $Na_2SO_4$ and concentrated under vacuum. The residue was applied onto a silica gel column and eluted with dichloromethane/methanol (100:1) to give of 0.68 g (66%) [(1S)-2-[(3S)-3-[(tert-butyldimethylsilyl)oxy]pyrrolidin-1-yl]-1-(3,5-dimethylphenyl)ethyl](methyl)amine as yellow oil.

LC-MS (ES, m/z): 363.3 (M+1).

Example 15-b 3-((S)-2-((S)-3-fluoropyrrolidin-1-yl)-1-(methylamino)ethyl)benzonitrile

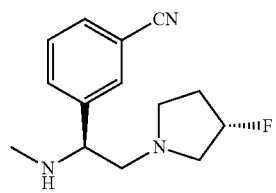 [SMILES: CN[C@H](CN1CC[C@H](F)C1)c1cccc(C#N)c1]

Step (i) Synthesis of (S)-1-(3-bromophenyl)-2-((S)-3-fluoropyrrolidin-1-yl)ethanol

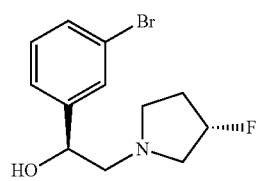

Into a 100 mL round-bottom flask, was placed a solution of (3S)-3-fluoropyrrolidine hydrochloride (2.12 g, 16.88 mmol, 1.00 equiv) in ethanol (25 mL). Then sodium carbonate (1.78 g, 16.79 mmol, 1.00 equiv) was added. The resulting solution was stirred at room temperature for 30 min and filtered. The filtrate was added (2S)-2-(3-bromophenyl)oxirane (3.35 g, 16.83 mmol, 1.00 equiv). The resulting solution was stirred at refluxing for 16 h in oil bath and concentrated to dryness. The residue was purified by column chromatography to get 2.93 g (60%) of the title compound as light yellow solid.

Step (ii) Synthesis of (S)-1-(3-bromophenyl)-2-((S)-3-fluoropyrrolidin-1-yl)-N-methylethanamine Into a 100 mL round-bottom flask, was placed a solution of (S)-1-(3-bromophenyl)-2-((S)-3-fluoropyrrolidin-1-yl)ethanol (1.25 g, 4.34 mmol, 1.00 equiv) in dichloromethane (30 mL). Then TEA (1.31 g, 13.02 mmol, 3.00 equiv) was added. Following MsCl (990 mg, 8.68 mmol, 2.00 equiv) was added dropwise at 0° C. The resulting solution was stirred for 30 min at 0° C. Then another part of TEA (0.88 g, 8.713 mmol, 2.00 equiv) was added. The resulting solution was stirred for 4 h at room temperature. Following $CH_3NH_2$ (aq) (4.48 g, 43.35 mmol, 9.99 equiv, 30%) was added dropwise. The resulting solution was stirred for 16 h at room temperature. The resulting mixture was concentrated under vacuum. The residue was applied onto a silica gel column with ethyl acetate: petroleum ether (1:2). This resulted in 1.1 g (84%) of the title compound as light yellow oil.

Step (iii) Synthesis of 3-((S)-2-((S)-3-fluoropyrrolidin-1-yl)-1-(methylamino)ethyl) benzonitrile

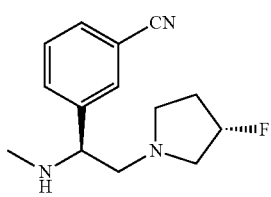 [SMILES: CN[C@H](CN1CC[C@H](F)C1)c1cccc(C#N)c1]

Into a 40-mL sealed tube, was placed a solution of [(1S)-1-(3-bromophenyl)-2-[(3S)-3-fluoropyrrolidin-1-yl]ethyl](methyl)amine obtained by following a procedure similar to that in Example 8, (1.0 g, 3.32 mmol, 1.00 equiv) in N,N-dimethylformamide (20 mL). Then Zn(CN)2 (387 mg, 3.31 mmol, 1.00 equiv) and Pd(PPh3)4 (382 mg, 0.33 mmol, 0.10 equiv) were added under nitrogen atmosphere. The resulting solution was stirred for 16 h at 100° C. under nitrogen atmosphere. The resulting mixture was concentrated under vacuum. The residue was applied onto a silica gel column with ethyl acetate/petroleum ether (1:1). This resulted in 570 mg (69%) of the titled compound as an off-white solid.

LC-MS (ES, m/z): 248 (M+1).

Example 16-b (S)-1-((S)-2-(3-(5-methyl-1,2,4-oxadiazol-3-yl)phenyl)-2-(methylamino)ethyl)pyrrolidin-3-ol

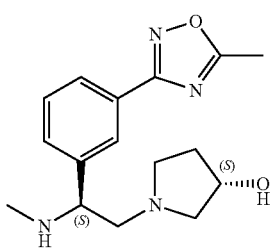

Step (i) Synthesis of benzyl ((S)-1-(3-bromophenyl)-2-((S)-3-((tert-butyldimethyl silyl)oxy)pyrrolidin-1-yl)ethyl)(methyl)carbamate

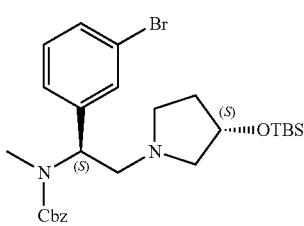

Into a 500-mL 3-necked round-bottom flask, was placed a solution of [(1S)-1-(3-bromophenyl)-2-[(3S)-3-[(tert-butyldimethylsilyl)oxy]pyrrolidin-1-yl]ethyl](methyl)amine (6.6 g, 15.96 mmol, 1.00 equiv) in ethyl acetate (200 mL). To the mixture was added a solution of potassium carbonate (2.8 g, 20.26 mmol, 1.29 equiv) in water (40 mL). This was followed by the addition of CbzCl (3.3 g, 19.34 mmol, 1.21 equiv) dropwise with stirring at 0° C. in 30 min. The resulting solution was stirred for 4 h at room temperature. The organic layer was separated and concentrated. The residue was applied onto a silica gel column and eluted with ethyl acetate/petroleum ether (1:50). This resulted in 8 g (92%) of benzyl N-[(1S)-1-(3-bromophenyl)-2-[(3S)-3-[(tert-butyldimethylsilyl)oxy]pyrrolidin-1-yl]ethyl]-N-methylcarbamate as green oil.

LC-MS (ES, m/z): 547 (M+1).

Step (ii) Synthesis of benzyl ((S)-2-((S)-3-((tert-butyldimethylsilyl)oxy)pyrrolidin-1-yl)-1-(3-cyanophenyl)ethyl)(methyl)carbamate

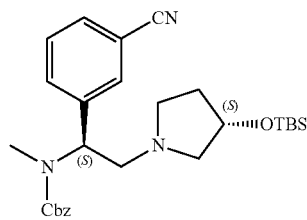

Into a 250-mL 3-necked round-bottom flask, was placed a solution of benzyl N-[(1S)-1-(3-bromophenyl)-2-[(3S)-3-[(tert-butyldimethylsilyl)oxy]pyrrolidin-1-yl]ethyl]-N-methylcarbamate (6 g, 10.96 mmol, 1.00 equiv) in N,N-dimethylformamide (110 mL). To the solution were added Zn(CN)2 (1.29 g, 1.00 equiv) and Pd(PPh3)4 (1.27 g, 1.10 mmol, 0.10 equiv) under nitrogen gas. The resulting solution was stirred for 12 hours at 80° C. in an oil bath. 100 mL of water was added to the mixture. The resulting solution was extracted with dichloromethane (2×100 mL) and the organic layers combined. The resulting mixture was washed with water (2×100 mL), dried over anhydrous sodium sulfate and concentrated under vacuum. The residue was applied onto a silica gel column and eluted with ethyl acetate/petroleum ether (1:10). This resulted in 4.5 g (83%) of benzyl N-[(1S)-2-[(3S)-3-[(tert-butyldimethylsilyl)oxy]pyrrolidin-1-yl]-1-(3-cyanophenyl)ethyl]-N-methylcarbamate as colorless oil.

LC-MS (ES, m/z): 494 (M+1)

Step (iii) Synthesis of benzyl ((S)-2-((S)-3-((tert-butyldimethylsilyl)oxy)pyrrolidin-1-yl)-1-(3-(N-hydroxycarbamimidoyl)phenyl)ethyl)(methyl)carbamate

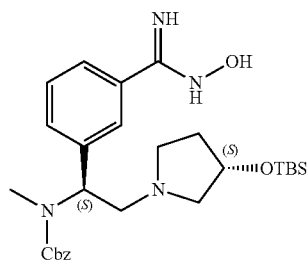

Into a 100-mL round-bottom flask, was placed a solution of benzyl N-[(1S)-2-[(3S)-3-[(tert-butyldimethylsilyl)oxy]pyrrolidin-1-yl]-1-(3-cyanophenyl)ethyl]-N-methylcarbamate (2.9 g, 5.87 mmol, 1.00 equiv) in ethanol (50 mL). To the solution were added NH$_2$OH.HCl (750 mg, 14.71 mmol, 2.50 equiv) and triethylamine (1.18 g, 11.66 mmol, 2.00 equiv). The resulting solution was stirred for 16 hours at 80° C. The resulting mixture was cooled to room temperature and concentrated under vacuum. This resulted in 4.8 g of benzyl N-[(1S)-2-[(3S)-3-[(tert-butyldimethylsilyl)oxy]pyrrolidin-1-yl]-1-[3-(N-hydroxycarbamimidoyl)phenyl]ethyl]-N-methylcarbamate as a white crude solid.

LC-MS (ES, m/z): 547 (M+1)

Step (iv) Synthesis of benzyl ((S)-2-((S)-3-hydroxypyrrolidin-1-yl)-1-(3-(5-methyl-1,2,4-oxadiazol-3-yl)phenyl)ethyl)(methyl)carbamate

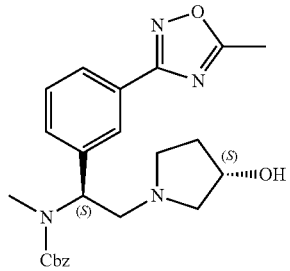

Into a 250-mL round-bottom flask purged and maintained with an inert atmosphere of nitrogen, was placed a solution of benzyl N-[(1S)-2-[(3S)-3-[(tert-butyldimethylsilyl)oxy]pyrrolidin-1-yl]-1-[3-(N-hydroxycarbamimidoyl)phenyl]ethyl]-N-methylcarbamate (4.8 g, 9.11 mmol, 1.00 equiv) in Toluene (70 mL). To the mixture was added acetic anhydride (4 g, 4.00 equiv). The resulting solution was stirred for 3 hours at room temperature. The resulting mixture was concentrated under vacuum. The residue was dissolved in tetrahydrofuran (50 mL). Then TBAF (7.2 g, 27.54 mmol, 5.00 equiv) was added. The resulting solution was allowed to react, with stirring, for an additional 36 hours at room temperature. The resulting mixture was concentrated under vacuum. The resulting solution was diluted with 250 mL of water and the resulting solution was extracted with dichloromethane (5×100 mL). The combined organic layers were dried over anhydrous sodium sulfate and concentrated under vacuum. This resulted in 2.78 g (70%) of benzyl N-[(1S)-2-[(3S)-3-hydroxypyrrolidin-1-yl]-1-[3-(5-methyl-1,2,4-oxadiazol-3-yl)phenyl]ethyl]-N-methylcarbamate as yellow crude oil.

LC-MS (ES, m/z): 437 (M+1).

Step (v) Synthesis of (S)-1-((S)-2-(3-(5-methyl-1,2,4-oxadiazol-3-yl)phenyl)-2-(methylamino)ethyl)pyrrolidin-3-ol

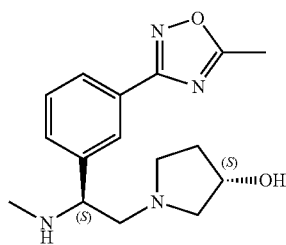

Into a 50-mL round-bottom flask, was placed a solution of benzyl N-[(1S)-2-[(3S)-3-hydroxypyrrolidin-1-yl]-1-[3-(5-methyl-1,2,4-oxadiazol-3-yl)phenyl]ethyl]-N-methylcarbamate (400 mg, 0.92 mmol, 1.00 equiv) in concentrated hydrogen chloride aqueous (10 mL). The resulting solution was stirred for 3 hours at 80° C. in an oil bath. The reaction mixture was cooled to room temperature. The resulting solution was washed with dichloromethane (4×20 mL) and the aqueous layer was concentrated under vacuum. The residue was diluted with 20 mL of methanol. The pH value of the solution was adjusted to 8-9 with ammonia. The resulting mixture was concentrated under vacuum. The residue was applied onto a silica gel column and eluted with dichloromethane/methanol (10/1). This resulted in 110 mg (40%) of (3S)-1-[(2S)-2-[3-(5-methyl-1,2,4-oxadiazol-3-yl)phenyl]-2-(methylamino)ethyl]pyrrolidin-3-ol as yellow oil.

LC-MS (ES, m/z): 303 (M+1).

Example 17-b (S)-1-((S)-2-(3-ethynylphenyl)-2-(methylamino)ethyl)pyrrolidin-3-ol

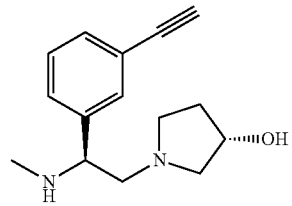 [SMILES: C#Cc1cccc([C@@H](CN2CC[C@H](O)C2)NC)c1]

Step (i) Synthesis of (S)-1-((S)-2-(3-bromophenyl)-2-(methylamino)ethyl)pyrrolidin-3-ol

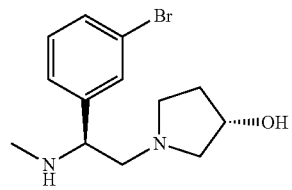 [SMILES: CN[C@H](CN1CC[C@H](O)C1)c1cccc(Br)c1]

To a solution of [(1S)-1-(3-bromophenyl)-2-[(3S)-3-[(tert-butyldimethylsilyl)oxy]pyrrolidin-1-yl]ethyl](methyl)amine (3 g, 7.26 mmol, 1.00 equiv) in methanol (25 mL). This was followed by the addition of hydrogen chloride aqueous (12N in water, 4 g) dropwise with stirring at 0° C. The resulting solution was stirred for 1 h at 20° C. The pH value of the solution was adjusted to 8 with saturated aqueous sodium bicarbonate. The resulting aqueous solution was extracted with DCM:MeOH (10:1, 5×20 mL) and the organic layers combined. The resulting organic layer was washed with brine (2×60 mL), dried over anhydrous sodium sulfate and concentrated under vacuum. This resulted in 2.8 g (crude) of (3S)-1-[(2S)-2-(3-bromophenyl)-2-(methylamino)ethyl]pyrrolidin-3-ol as brown crude oil.

LC-MS (ES, m/z): 299 (M+1).

Step (ii) Synthesis of (S)-1-((S)-2-(methylamino)-2-(3-((trimethyl silyl)ethynyl)phenyl)ethyl)pyrrolidin-3-ol

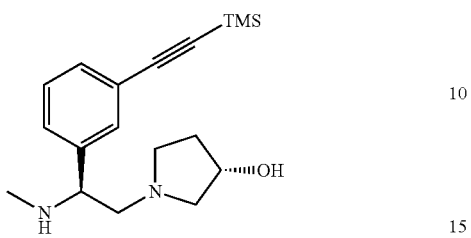

To a solution of (3S)-1-[(2S)-2-(3-bromophenyl)-2-(methylamino)ethyl]pyrrolidin-3-ol (2.8 g, 9.36 mmol, 1.00 equiv) in TEA (15 mL), were added ethynyltrimethylsilane (54 mg, 0.55 mmol, 0.03 equiv) and CuI (200 mg, 1.05 mmol, 0.02 equiv) under nitrogen. Following Pd(PPh$_3$)$_4$ (9.3 mg, 0.01 mmol) was added. The resulting solution was stirred for 40 h at 50° C. in an oil bath. The resulting mixture was concentrated under vacuum. The residue was purified by silica gel column and eluted with dichloromethane/methanol=20:1. This resulted in 1.3 g (44%) of (3S)-1-[(2S)-2-(methylamino)-2-[3-[2-(trimethyl silyl)ethynyl]phenyl]ethyl]pyrrolidin-3-ol as brown oil.

LC-MS (ES, m/z): 317 (M+1).

Step (iii) Synthesis of (S)-1-((S)-2-(3-ethynylphenyl)-2-(methylamino)ethyl)pyrrolidin-3-ol

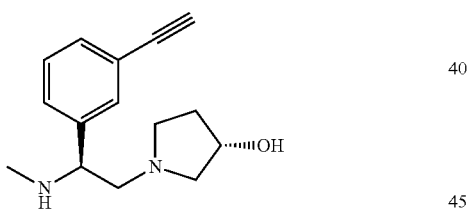

Into a 50-mL round-bottom flask, was placed a solution of (3S)-1-[(2S)-2-(methylamino)-2-[3-[2-(trimethylsilyl)ethynyl]phenyl]ethyl]pyrrolidin-3-ol (1.08 g, 3.41 mmol, 1.00 equiv) in methanol (15 mL). This was followed by the addition of potassium hydroxide in water (20%, 10 mL) dropwise with stirring at 0° C. The resulting solution was stirred for 2-3 h at 20° C. The pH value of the solution was adjusted to 8 with hydrogen chloride aqueous (2.5M). The resulting mixture was concentrated under vacuum and diluted with of water. The resulting aqueous solution was extracted with dichloromethane/methanol (10:1, 5×10 mL) and the organic layers combined. The resulting organic layer was washed with brine (2×30 mL), dried over anhydrous sodium sulfate and concentrated under vacuum. The residue was purified by Prep-TLC with dichloromethane/methanol/TEA (20:1:0.003, v/v/v). This resulted in 460 mg (55%) of (3S)-1-[(2S)-2-(3-ethynylphenyl)-2-(methylamino)ethyl]pyrrolidin-3-ol as yellow oil.

LC-MS (ES, m/z): 245 (M+1).

Example 18-b (S)-1-((S)-2-(methylamino)-2-(3-(5-(trifluoromethyl)-1,2,4-oxadiazol-3-yl)phenyl)ethyl)pyrrolidin-3-ol

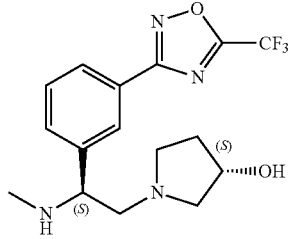

Step (i) Synthesis of benzyl ((S)-2-((S)-3-((tert-butyldimethylsilyl)oxy)pyrrolidin-1-yl)-1-(3-(5-(trifluoromethyl)-1,2,4-oxadiazol-3-yl)phenyl)ethyl)(methyl)carbamate

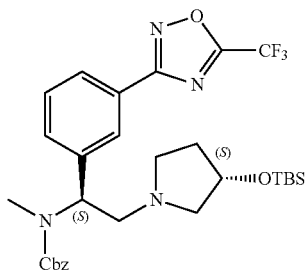

Into a 100-mL round-bottom flask, was placed a solution of benzyl N-[(1S)-2-[(3S)-3-[(tert-butyldimethylsilyl)oxy]pyrrolidin-1-yl]-1-[3-(N-hydroxycarbamimidoyl)phenyl]ethyl]-N-methylcarbamate (1 g, 1.90 mmol, 1.00 equiv) in pyridine (10 mL). To the solution was added (CF$_3$CO)$_2$O (1.2 g, 3.00 equiv). The resulting solution was stirred for 3 hours at 110° C. in an oil bath. The resulting mixture was concentrated under vacuum. The residue was purified by Prep-TLC with dichloromethane/methanol (10:1). This resulted in 0.39 g (34%) of benzyl N-[(1S)-2-[(3S)-3-[(tert-butyldimethylsilyl)oxy]pyrrolidin-1-yl]-1-[3-[5-(trifluoromethyl)-1,2,4-oxadiazol-3-yl]phenyl]ethyl]-N-methylcarbamate as yellow oil.

LC-MS (ES, m/z): 605 (M+1).

Step (ii) Synthesis of (S)-1-((S)-2-(methylamino)-2-(3-(5-(trifluoromethyl)-1,2,4-oxadiazol-3-yl)phenyl)ethyl)pyrrolidin-3-ol

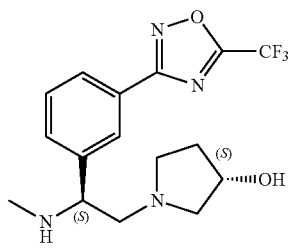

Into a 25-mL sealed tube, was placed a solution of benzyl N-[(1S)-2-[(3S)-3-[(tert-butyldimethylsilyl)oxy]pyrrolidin-1-yl]-1-[3-[5-(trifluoromethyl)-1,2,4-oxadiazol-3-yl]phenyl]ethyl]-N-methylcarbamate (1.4 g, 2.32 mmol, 1.00 equiv) in concentrated hydrogen chloride aqueous (15 mL). The resulting solution was stirred for 3 hours at 80° C. in an oil bath. The resulting mixture was concentrated under vacuum. The crude product (2 g) was purified by Flash-Prep-HPLC with the following conditions (IntelFlash-1): Column, C18 silica gel; mobile phase, 0.5% ammonia water/acetonitrile=100:1 increasing to 5% ammonia water/acetonitrile=100:45 within 30 min; Detector, UV 254 nm. This resulted in 0.8 g (97%) of (3S)-1-[(2S)-2-(methylamino)-2-[3-[5-(trifluoromethyl)-1,2,4-oxadiazol-3-yl]phenyl]ethyl]pyrrolidin-3-ol as yellow oil.

LC-MS (ES, m/z): 357 (M+1).

Example 19-b (S)-1-((S)-2-(methylamino)-2-(3-(thiazol-2-yl)phenyl)ethyl)pyrrolidin-3-ol

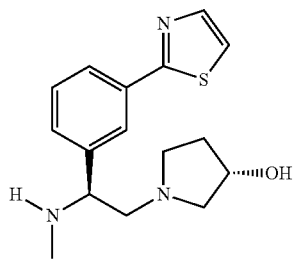 [SMILES: CN[C@H](CN1CC[C@H](O)C1)c1cccc(-c2nccs2)c1]

Step (i) Synthesis of benzyl ((S)-1-(3-bromophenyl)-2-((S)-3-((tert-butyldimethylsilyl)oxy) pyrrolidin-1-yl)ethyl)(methyl)carbamate

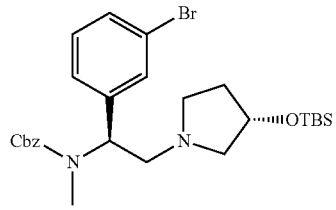 [SMILES: CN(C(=O)OCc1ccccc1)[C@H](CN1CC[C@H](O[Si](C)(C)C(C)(C)C)C1)c1cccc(Br)c1]

Into a 250-mL round-bottom flask, was placed a solution of [(1S)-1-(3-bromophenyl)-2-[(3S)-3-[(tert-butyldimethylsilyl)oxy]pyrrolidin-1-yl]ethyl](methyl)amine (6.2 g, 15.00 mmol, 1.00 equiv) in ethyl acetate:water (5:1) (60 mL). To it was added potassium carbonate (2.7 g, 19.54 mmol, 1.30 equiv) followed by benzyl chloroformate (3.1 g, 18.17 mmol, 1.21 equiv) dropwise at 5-10° C. in ice-water bath. The resulting solution was stirred for 2 hours at 25° C. and diluted with 50 ml of brine. The resulting aqueous solution was extracted with ethyl acetate (3×100 mL) and the organic layers combined and dried over anhydrous sodium sulfate and concentrated under vacuum. This resulted in 7.5 g (crude) of benzyl N-[(1S)-1-(3-bromophenyl)-2-[(3S)-3-[(tert-butyldimethylsilyl)oxy]pyrrolidin-1-yl]ethyl]-N-methylcarbamate as yellow oil.

LC-MS (ES, m/z): 549 (M+1).

Step (ii) Synthesis of benzyl ((S)-2-((S)-3-((tert-butyldimethylsilyl)oxy)pyrrolidin-1-yl)-1-(3-(4,4,5,5-tetramethyl-1,3,2-dioxaborolan-2-yl)phenyl)ethyl)(methyl)carbamate

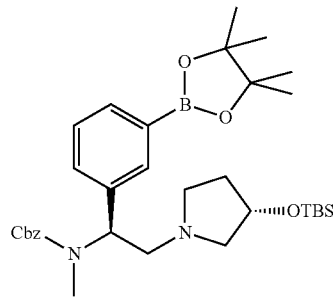 [SMILES: CN(C(=O)OCc1ccccc1)[C@H](CN1CC[C@H](O[Si](C)(C)C(C)(C)C)C1)c1cccc(B2OC(C)(C)C(C)(C)O2)c1]

Into a 250-mL 3-necked round-bottom flask purged and maintained with an inert atmosphere of nitrogen, was placed a solution of benzyl N-[(1S)-1-(3-bromophenyl)-2-[(3S)-3-[(tert-butyldimethylsilyl)oxy]pyrrolidin-1-yl]ethyl]-N-methylcarbamate (2.0 g, 3.65 mmol, 1.00 equiv) in 1,4-dioxane (100 mL). Then KOAc (720 mg, 7.34 mmol, 2.01 equiv) and 4,4,5,5-tetramethyl-2-(3,3,4,4-tetramethylborolan-1-yl)-1,3,2-dioxaborolane (1.85 g, 7.40 mmol, 2.03 equiv) were added. Following Pd(dppf)Cl$_2$ (530 mg, 0.72 mmol, 0.20 equiv) was added. The resulting solution was stirred overnight at 80° C. in an oil bath under nitrogen atmosphere. The resulting mixture was concentrated under vacuum. The residue was applied onto a silica gel column and eluted with ethyl acetate/petroleum ether (1:5). This resulted in 1.95 g (90%) of benzyl N-[(1S)-2-[(3S)-3-[(tert-butyldimethylsilyl)oxy]pyrrolidin-1-yl]-1-[3-(tetramethyl-1,3,2-dioxaborolan-2-yl)phenyl]ethyl]-N-methylcarbamate as yellow oil.

LC-MS (ES, m/z): 595 (M+1)

Step (iii) Synthesis of benzyl ((S)-2-((S)-3-((tert-butyldimethylsilyl)oxy)pyrrolidin-1-yl)-1-(3-(thiazol-2-yl)phenyl)ethyl)(methyl)carbamate

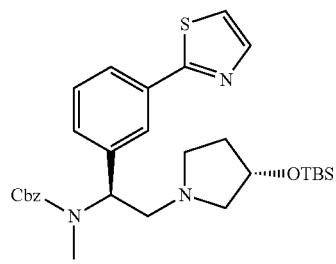 [SMILES: CN(C(=O)OCc1ccccc1)[C@H](CN1CC[C@H](O[Si](C)(C)C(C)(C)C)C1)c1cccc(-c2nccs2)c1]

Into a 250-mL 3-necked round-bottom flask purged and maintained with an inert atmosphere of nitrogen, was placed a solution of benzyl N-[(1S)-2-[(3S)-3-[(tert-butyldimethylsilyl)oxy]pyrrolidin-1-yl]-1-[3-(tetramethyl-1,3,2-dioxaborolan-2-yl)phenyl]ethyl]-N-methylcarbamate (1.9 g, 3.20 mmol, 1.00 equiv) in tetrahydrofuran:water (5:1) (120 mL). Then potassium carbonate (880 mg, 6.37 mmol, 1.99 equiv) and 2-bromo-1,3-thiazole (1.05 g, 6.40 mmol, 2.00 equiv)

were added. Following Pd(PPh$_3$)$_4$(740 mg, 0.64 mmol, 0.20 equiv) was added. The resulting solution was stirred overnight at 80° C. in an oil bath under nitrogen atmosphere. The resulting mixture was concentrated under vacuum. The residue was applied onto a silica gel column with ethyl acetate/petroleum ether (1:2). This resulted in 560 mg (32%) of benzyl N-[(1S)-2-[(3S)-3-[(tert-butyldimethylsilyl)oxy]pyrrolidin-1-yl]-1-[3-(1,3-thiazol-2-yl)phenyl]ethyl]-N-methylcarbamate as yellow oil.

LC-MS (ES, m/z): 552 (M+1).

Step (iv) Synthesis of (S)-1-((S)-2-(methylamino)-2-(3-(thiazol-2-yl)phenyl)ethyl)pyrrolidin-3-ol

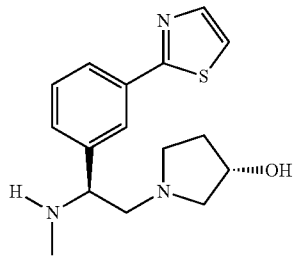 [SMILES: CN[C@H](CN1CC[C@H](O)C1)c1cccc(-c2nccs2)c1]

Into a 50-mL sealed tube, was placed a solution of benzyl N-[(1S)-2-[(3S)-3-[(tert-butyldimethylsilyl)oxy]pyrrolidin-1-yl]-1-[3-(1,3-thiazol-2-yl)phenyl]ethyl]-N-methylcarbamate (560 mg, 1.01 mmol, 1.00 equiv) in methanol (1 mL) and concentrated hydrogen chloride aqueous (6 mL). The resulting solution was stirred for 6 hours at 80° C. in an oil bath. The resulting solution was concentrated under vacuum and diluted with methanol. The PH value of the methanol solution was adjusted to 8 with ammonia water (30% in water). The resulting solution was concentrated and purified by silica gel column (dichloromethane/methanol=100/1). This resulted in 350 mg of (S)-1-((S)-2-(methylamino)-2-(3-(thiazol-2-yl)phenyl)ethyl)pyrrolidin-3-ol as yellow oil.

LC-MS (ES, m/z): 303 (M+1).

Example 20-b (3S)-1-(2-(3-(1,2,4-oxadiazol-3-yl)phenyl)-2-(methylamino)ethyl)pyrrolidin-3-ol

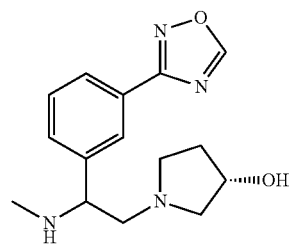 [SMILES: CNC(CN1CC[C@H](O)C1)c1cccc(-c2ncon2)c1]

Step (i) Synthesis of benzyl (1-(3-(1,2,4-oxadiazol-3-yl)phenyl)-2-((S)-3-((tert-butyldimethyl silyl)oxy)pyrrolidin-1-yl)ethyl)(methyl)carbamate

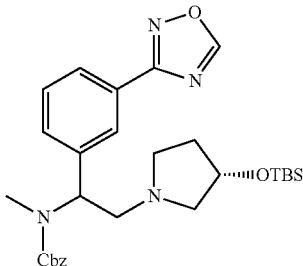 [SMILES: CN(C(=O)OCc1ccccc1)C(CN1CC[C@H](O[Si](C)(C)C(C)(C)C)C1)c1cccc(-c2ncon2)c1]

Into 50 ml round-bottom flash purged, was placed a solution of benzyl N-[(1S)-2-[(3S)-3-[(tert-butyldimethyl silyl)oxy]pyrrolidin-1-yl]-1-[3-(N-hydroxycarbamimidoyl)phenyl]ethyl]-N-methylcarbamate (300 mg, 0.56 mmol, 1.00 equiv) in trimethyl orthoformate (8 mL). Following boron trifluoride ethyl ether (2 drops) was added. The resulting solution was stirred for 2 hours at 80° C. The mixture was diluted with 40 mL of ethyl acetate and the result solution was washed with water (3×10 mL) and sodium bicarbonate (2×10 mL). The organic layer was dried and concentrated. The residue was purified by prep-TLC with petroleum ether/ethyl acetate=4:1. This resulted in 250 mg of benzyl N-[(1S)-2-[(3S)-3-[(tert-butyldimethylsilyl)oxy]pyrrolidin-1-yl]-1-[3-(1,2,4-oxadiazol-3-yl)phenyl]ethyl]-N-methylcarbamate as yellow oil.

LC-MS (ES, m/z): 537 (M+1).

Step (ii) Synthesis of (3S)-1-(2-(3-(1,2,4-oxadiazol-3-yl)phenyl)-2-(methylamino)ethyl) pyrrolidin-3-ol

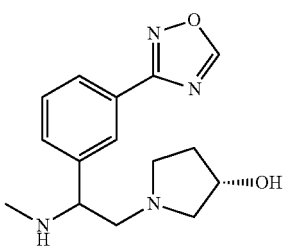 [SMILES: CNC(CN1CC[C@H](O)C1)c1cccc(-c2ncon2)c1]

Into 50 ml of sealed tube, was placed a solution of benzyl N-[(1S)-2-[(3S)-3-[(tert-butyldimethylsilyl)oxy]pyrrolidin-1-yl]-1-[3-(1,2,4-oxadiazol-3-yl)phenyl]ethyl]-N-methylcarbamate (1.5 g, 2.79 mmol, 1.00 equiv) in concentrated hydrochloride aqueous (30 mL). The resulting solution was stirred for 3 hours at 80° C. The mixture was concentrated under vacuum. The residue was dissolved in DCM (20 mL) and basified with Et$_3$N. The mixture was concentrated under vacuum. This resulted in 1.6 g (crude) of (3S)-1-[(2S)-2-(methylamino)-2-[3-(1,2,4-oxadiazol-3-yl)phenyl]ethyl]pyrrolidin-3-ol as a brown solid.

LC-MS (ES, m/z): 289 (M+1)

Example 21-b (S)-1-((S)-2-(3-(1H-imidazol-2-yl)phenyl)-2-(methylamino)ethyl)pyrrolidin-3-ol

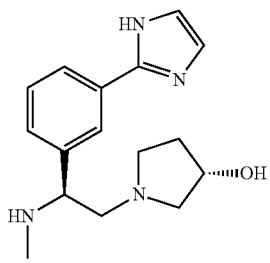 [SMILES: CN[C@H](CN1CC[C@H](O)C1)c1cccc(-c2ncc[nH]2)c1]

Step (i) Synthesis of N,N-dimethyl-1H-imidazole-1-sulfonamide

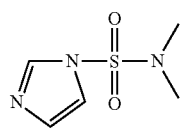

Into a 250-mL 3-necked round-bottom flask purged and maintained with an inert atmosphere of nitrogen, was placed a solution of 1H-imidazole (3 g, 44.07 mmol, 1.16 equiv) in dichloromethane (100 mL), TEA (4.15 g, 41.01 mmol, 1.08 equiv). This was followed by the addition of N,N-dimethylsulfamoyl chloride (5.46 g, 38.02 mmol, 1.00 equiv) dropwise with stirring at 0° C. The resulting solution was stirred for 20 h at room temperature. The solids were filtered out. The filtrate was washed with water (3×100 mL) and brine (1×100 mL). The organic layer was dried over anhydrous sodium sulfate and concentrated under vacuum. The residue was applied onto a silica gel column with dichloromethane/methanol (0-100/1). This resulted in 5.77 g (87%) of N,N-dimethyl-1H-imidazole-1-sulfonamide as light yellow oil.

LC-MS (ES, m/z): 176 (M+1).

Step (ii) Synthesis of 2-bromo-N,N-dimethyl-1H-imidazole-1-sulfonamide

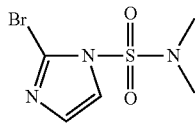

Into a 250-mL 3-necked round-bottom flask purged and maintained with an inert atmosphere of nitrogen, was placed a solution of N,N-dimethyl-1H-imidazole-1-sulfonamide (3.77 g, 21.52 mmol, 1.00 equiv) in tetrahydrofuran (50 mL). This was followed by the addition of n-BuLi (9.5 mL, 1.10 equiv, 2.5 N) dropwise with stirring at −78° C. The resulting solution was stirred for 30 min at −78° C. To this was added a solution of tetrabromomethane (7.86 g, 23.70 mmol, 1.10 equiv) in tetrahydrofuran (20 mL) dropwise with stirring at −78° C. The resulting solution was allowed to react, with stirring, for an additional 30 min at −78° C. The resulting solution was allowed to react, with stirring, for an additional 2 h at room temperature. The reaction was then quenched by the addition of 100 mL of water/ice. The resulting solution was extracted with ethyl acetate (4×70 mL) and the organic layers combined. The resulting mixture was washed with water (2×70 mL) and brine (2×70 mL). The mixture was dried over anhydrous sodium sulfate and concentrated under vacuum. The residue was applied onto a silica gel column with ethyl acetate/petroleum ether (0-1/1). This resulted in 3.47 g (63%) of 2-bromo-N,N-dimethyl-1H-imidazole-1-sulfonamide as a brown solid.

LC-MS (ES, m/z): 254 (M+1).

Step (iii) Synthesis of benzyl ((S)-2-((S)-3-((tert-butyldimethylsilyl)oxy)pyrrolidin-1-yl)-1-(3-(1-(N,N-dimethylsulfamoyl)-1H-imidazol-2-yl)phenyl)ethyl)(methyl)carbamate

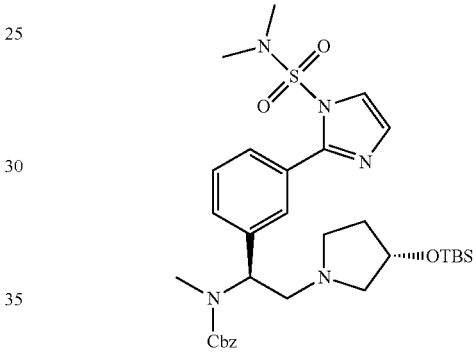

Into a 250-mL round-bottom flask purged and maintained with an inert atmosphere of nitrogen, was placed a solution of benzyl N-[(1S)-2-[(3S)-3-[(tert-butyldimethylsilyl)oxy]pyrrolidin-1-yl]-1-[3-(tetramethyl-1,3,2-dioxaborolan-2-yl)phenyl]ethyl]-N-methylcarbamate (2.0 g, 3.36 mmol, 1.00 equiv) in dioxane/H$_2$O (60/10 mL), 2-bromo-N,N-dimethyl-1H-imidazole-1-sulfonamide (1.27 g, 5.00 mmol, 1.50 equiv), potassium carbonate (930 mg, 6.73 mmol, 2.00 equiv), Pd(PPh$_3$)$_4$(770 mg, 0.67 mmol, 0.20 equiv). The resulting solution was stirred for 16 h at 80° C. in an oil bath. The reaction mixture was cooled. The reaction was then quenched by the addition of 100 mL of water/ice. The resulting solution was extracted with ethyl acetate (4×50 mL) and the organic layers combined. The resulting mixture was washed with brine (4×50 mL), dried over anhydrous sodium sulfate and concentrated under vacuum. The residue was applied onto a silica gel column with ethyl acetate/petroleum ether (0-1/1). This resulted in 1.1 g (51%) of benzyl N-[(1S)-2-[(3S)-3-[(tert-butyldimethylsilyl)oxy]pyrrolidin-1-yl]-1-[3-[1-(dimethylsulfamoyl)-1H-imidazol-2-yl]phenyl]ethyl]-N-methylcarbamate as yellow oil.

LC-MS (ES, m/z): 642 (M+1).

Step (iv) Synthesis of (S)-1-((S)-2-(3-(1H-imidazol-2-yl)phenyl)-2-(methylamino)ethyl)pyrrolidin-3-ol

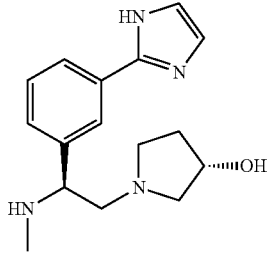 [SMILES: CN[C@H](CN1CC[C@H](O)C1)c1cccc(-c2ncc[nH]2)c1]

Into a 100-mL round-bottom flask, was placed a solution of benzyl N-[(1S)-2-[(3S)-3-hydroxypyrrolidin-1-yl]-1-[3-(1H-imidazol-2-yl)phenyl]ethyl]-N-methylcarbamate (1.1 g, 2.62 mmol, 1.00 equiv) in conc. hydrogen chloride aqueous (30 mL). The resulting solution was stirred for 2 h at 80° C. in an oil bath. The reaction mixture was cooled to room temperature. The resulting solution was washed with dichloromethane (4×20 mL) and the aqueous layer was concentrated under vacuum. This resulted in 800 mg of (3S)-1-[(2S)-2-[3-(1H-imidazol-2-yl)phenyl]-2-(methylamino)ethyl]pyrrolidin-3-ol as a brown crude solid.

LC-MS (ES, m/z): 287 (M+1).

Example 22-b (S)-1-((S)-2-(3-(but-1-yn-1-yl)phenyl)-2-(methylamino)ethyl)pyrrolidin-3-ol

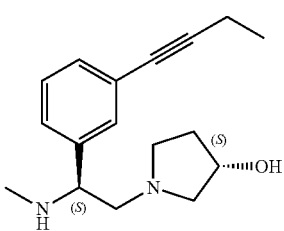

Step (i) Synthesis of (S)-1-(3-(but-1-yn-1-yl)phenyl)-2-((S)-3-((tert-butyldimethyl silyl)oxy)pyrrolidin-1-yl)-N-methylethanamine

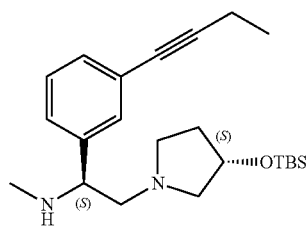

To a solution of [(1S)-1-(3-bromophenyl)-2-[(3S)-3-[(tert-butyldimethylsilyl)oxy]pyrrolidin-1-yl]ethyl](methyl)amine (2.5 g, 6.05 mmol, 1.00 equiv), Pd₂(dba)₃CHCl₃ (634 mg, 0.60 mmol, 0.10 equiv), PPh₃ (631 mg, 2.41 mmol, 0.40 equiv) and CuI (229 mg, 1.20 mmol, 0.20 equiv) in TEA (25 mL), was introduced but-1-yne (1.62 g, 29.95 mmol, 4.95 equiv). The resulting solution was stirred for 60 hours at 80° C. in a 50-mL sealed tube. The solution was concentrated and the residue was applied onto silica gel column (EA:PE=1:5). This resulted in 1.4 g (60%) of [(1S)-1-[3-(but-1-yn-1-yl)phenyl]-2-[(3S)-3-[(tert-butyldimethylsilyl)oxy]pyrrolidin-1-yl]ethyl](methyl)amine as yellow oil.

LC-MS (ES, m/z): 387 (M+1)

Step (ii) (S)-1-((S)-2-(3-(but-1-yn-1-yl)phenyl)-2-(methylamino)ethyl)pyrrolidin-3-ol

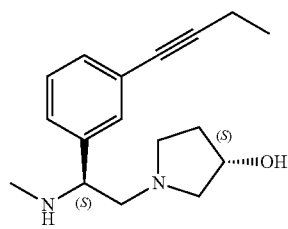

To a solution of [(1S)-1-[3-(but-1-yn-1-yl)phenyl]-2-[(3S)-3-[(tert-butyldimethylsilyl)oxy]pyrrolidin-1-yl]ethyl](methyl)amine (1.4 g, 3.62 mmol, 1.00 equiv) in methanol (60 mL), was added concentrated hydrogen chloride aqueous (10 mL) at 0° C. The resulting solution was stirred for 2 hour at 25° C. The resulting mixture was adjusted pH to 7 with saturated aqueous NaHCO₃. The mixture was concentrated under vacuum. The resulting aqueous phase was extracted with ethyl acetate. The combined organic layers were dried over Na₂SO₄ and concentrated under vacuum. The residue was applied on to prep-TLC (dichloromethane:methanol:ammonia=100:10:1). This resulted in 550 mg (56%) of (3S)-1-[(2S)-2-[3-(but-1-yn-1-yl)phenyl]-2-(methylamino)ethyl]pyrrolidin-3-ol as yellow oil.

LC-MS (ES, m/z): 273 (M+1).

Example 23-b 3-((S)-2-((S)-3-((tert-butyldimethylsilyl)oxy)pyrrolidin-1-yl)-1-(methylamino)ethyl)-N-(2,2,2-trifluoroethyl)benzamide

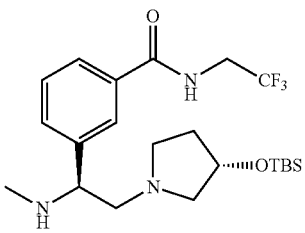 [SMILES: CN[C@H](CN1CC[C@H](O[Si](C)(C)C(C)(C)C)C1)c1cccc(C(=O)NCC(F)(F)F)c1]

Into a 100-mL round-bottom flask, was placed a solution of 3-[(1S)-2-[(3S)-3-[(tert-butyldimethylsilyl)oxy]pyrrolidin-1-yl]-1-(methylamino)ethyl]benzoic acid (2.04 g, 5.39 mmol, 1.00 equiv), CF₃CH₂NH₂ (2.67 g, 26.97 mmol, 5.00 equiv) and DIEA (2.09 g, 16.17 mmol, 3.00 equiv) in N,N-dimethylformamide (20 mL). To the solution was added HATU (2.26 g, 5.94 mmol, 1.10 equiv). The resulting solution was stirred for 1 hour at 25° C. The resulting solution was diluted with 100 mL of ethyl acetate. The resulting mixture was washed with water (3×50 mL), brine (3×50 mL), dried over anhydrous sodium sulfate and concentrated under vacuum. The residue was applied onto a silica gel column with dichloromethane/methanol (100:1). This resulted in 1.2 g (48%) of 3-[(1S)-2-[(3S)-3-[(tert-butyldimethylsilyl)oxy]pyrrolidin-1-yl]-1-(methylamino)ethyl]-N-(2,2,2-trifluoroethyl)benzamide as light brown oil.

LC-MS (ES, m/z): 460 (M+1)

Example 24-b 3-((S)-2-((S)-3-((tert-butyldimethylsilyl)oxy)pyrrolidin-1-yl)-1-(methylamino)ethyl)-N,N-dimethylbenzamide

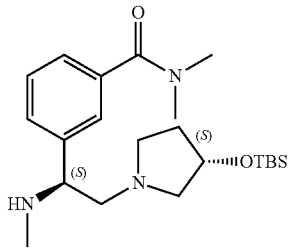

Step (i) Synthesis of ethyl 3-acetylbenzoate

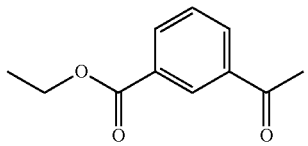

Into a 1-L round-bottom flask, was placed a solution of 3-acetylbenzoic acid (50 g, 304.58 mmol, 1.0 equiv) in ethanol (500 mL). This was followed by the addition of sulfuric acid (30 g, 305.88 mmol, 1.00 equiv, 98%) dropwise with stirring at 0° C. The resulting solution was stirred for 16 hours at 80° C. The resulting mixture was concentrated under vacuum. The residue was dissolved in 100 mL of H₂O. The resulting solution was extracted with ethyl acetate (3×200 mL) and the organic layers combined. The resulting mixture was washed with water (2×100 mL), brine (2×100 mL), dried over anhydrous sodium sulfate and concentrated under vacuum. This resulted in 53 g (crude) of ethyl 3-acetylbenzoate as brown oil.

Step (ii) Synthesis of ethyl 3-(2-bromoacetyl)benzoate

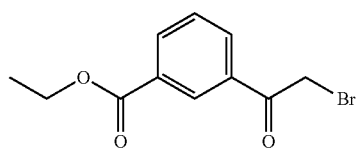

Into a 1000-mL round-bottom flask, was placed a solution of ethyl 3-acetylbenzoate (48 g, 249.73 mmol, 1.00 equiv) in MTBE (600 mL). To the solution was added PTAP (95.9 g, 255.05 mmol, 1.02 equiv). The resulting solution was stirred for 1.5 hours at 0° C. The resulting mixture was washed with saturated $Na_2S_2O_3$ aqueous (4×400 mL), water (3×300 mL) and brine (2×300 mL). The mixture was dried over anhydrous sodium sulfate and concentrated under vacuum. This resulted in 63.3 g (crude) of ethyl 3-(2-bromoacetyl)benzoate as brown oil.

Step (iii) Synthesis of (S)-ethyl 3-(2-bromo-1-hydroxyethyl)benzoate

Into a 250-mL round-bottom flask, was placed a solution of S-Met-CBS (9.2 g, 40.53 mmol, 0.50 equiv) and $DEA.BH_3$ (13.2 g, 80.98 mmol, 1.00 equiv) in MTBE (84 mL). This was followed by the addition of a solution of ethyl 3-(2-bromoacetyl)benzoate (22 g, 81.15 mmol, 1.00 equiv) in MTBE (20 mL) dropwise with stirring at 40° C. in 1 hour. The resulting solution was stirred for 8 hours at 25° C. The reaction was then quenched by the addition of 44 mL of methanol and 57 mL of hydrogen chloride aqueous (3N) at 0° C. The resulting solution was extracted with ethyl acetate (3×200 mL) and the organic layers combined. The resulting mixture was washed with water (3×100 mL), brine (3×100 mL), dried over anhydrous sodium sulfate and concentrated under vacuum. This resulted in 19.5 g (88%) of ethyl 3-[(1S)-2-bromo-1-hydroxyethyl]benzoate as yellow oil.

Step (iv) Synthesis of (S)-ethyl-(oxiran-2-yl)benzoate

Into a 250-mL round-bottom flask, was placed a solution of ethyl 3-[(1S)-2-bromo-1-hydroxyethyl]benzoate (12 g, 43.94 mmol, 1.00 equiv) in ethanol (120 mL). To the solution was added potassium carbonate (12 g, 86.82 mmol, 2.00 equiv). The resulting solution was stirred for 30 min at 0° C. The resulting solution was allowed to react, with stirring, for an additional 30 min at 25° C. The solids were filtered out. The resulting mixture was concentrated under vacuum. The residue was dissolved in 100 mL of ethyl acetate. The resulting mixture was washed with water (3×50 mL), brine (3×50 mL), dried over anhydrous sodium sulfate Step (v) Synthesis of ethyl 3-((S)-2-((S)-3-((tert-butyldimethylsilyl)oxy)pyrrolidin-1-yl)-1-hydroxyethyl)benzoate

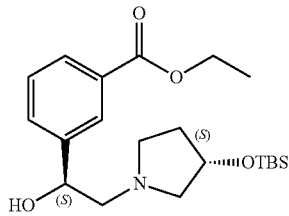

Into a 250-mL round-bottom flask, was placed a solution of ethyl 3-[(2S)-oxiran-2-yl]benzoate (5.9 g, 30.70 mmol, 1.00 equiv) in ethanol (60 mL). To the solution was added (3S)-3-[(tert-butyldimethylsilyl)oxy]pyrrolidine (7.5 g, 37.24 mmol, 1.20 equiv). The resulting solution was stirred for 15 hours at 70° C. in an oil bath. The resulting mixture was concentrated under vacuum. The residue was dissolved in 80 mL of ethyl acetate. The resulting mixture was washed with 0.5N hydrogen chloride aqueous (2×50 mL), water (3×30 mL) and brine (3×30 mL). The mixture was dried over anhydrous sodium sulfate and concentrated under vacuum. This resulted in 7.0 g (crude) of ethyl 3-[(1S)-2-[(3S)-3-[(tert-butyldimethylsilyl)oxy]pyrrolidin-1-yl]-1-hydroxyethyl]benzoate as brown oil.

LC-MS (ES, m/z): 394 (M+1).

Step (vi) Synthesis of ethyl 3-((S)-2-((S)-3-((tert-butyldimethylsilyl)oxy)pyrrolidin-1-yl)-1-(methylamino)ethyl)benzoate

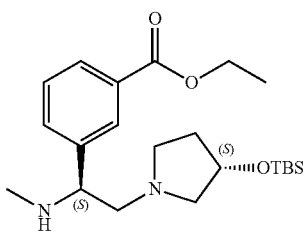

Into a 250-mL round-bottom flask, was placed a solution of ethyl 3-[(1S)-2-[(3S)-3-[(tert-butyldimethylsilyl)oxy]pyrrolidin-1-yl]-1-hydroxyethyl]benzoate (7.0 g, 17.78 mmol, 1.00 equiv) and TEA (9.1 g, 89.93 mmol, 5.00 equiv) in dichloromethane (70 mL). To the solution was added MsCl (6.2 g, 3.00 equiv) at 0° C. The mixture was stirred at 0° C. for 30 min, and stirred for 1 hour at 25° C. Then methanamine (37.2 g, 1.20 mol, 20.00 equiv) was added. The resulting solution was stirred for 20 hours at 30° C. The resulting solution was diluted with 100 mL of DCM. The resulting mixture was washed with water (3×50 mL) and brine (3×50 mL), dried over anhydrous sodium sulfate and concentrated under vacuum. This resulted in 8.1 g (crude) of ethyl 3-[(1S)-2-[(3S)-3-[(tert-butyldimethylsilyl)oxy]pyrrolidin-1-yl]-1-(methylamino)ethyl]benzoate as brown oil.

LC-MS (ES, m/z): 407 (M+1).

Step (vii) Synthesis of 3-((S)-2-((S)-3-((tert-butyldimethylsilyl)oxy)pyrrolidin-1-yl)-1-(methylamino)ethyl)benzoic acid

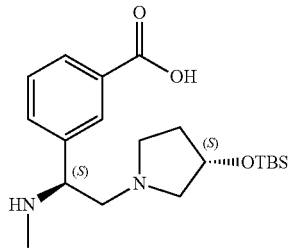

Into a 100-mL round-bottom flask, was placed a solution of ethyl 3-[(1S)-2-[(3S)-3-[(tert-butyldimethyl silyl)oxy]pyrrolidin-1-yl]-1-(methylamino)ethyl]benzoate (2.2 g, 5.41 mmol, 1.00 equiv) in methanol/H$_2$O (5/1) (12 mL). To the solution was added LiOH.H$_2$O (1.14 g, 27.17 mmol, 5.00 equiv). The resulting solution was stirred for 1 hour at 25° C. The resulting mixture was concentrated under vacuum. This resulted in 2.56 g (crude) of 3-[(1S)-2-[(3S)-3-[(tert-butyldimethylsilyl)oxy]pyrrolidin-1-yl]-1-(methylamino)ethyl]benzoic acid as yellow solid.

LC-MS (ES, m/z): 379 (M+1).

Step (viii) Synthesis of 3-((S)-2-((S)-3-((tert-butyldimethylsilyl)oxy)pyrrolidin-1-yl)-1-(methylamino)ethyl)-N,N-dimethylbenzamide

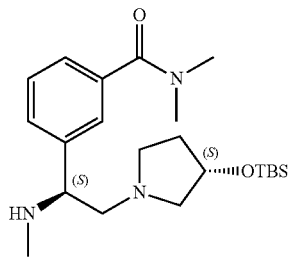

Into a 100-mL round-bottom flask, was placed a solution of 3-[(1S)-2-[(3S)-3-[(tert-butyldimethylsilyl)oxy]pyrrolidin-1-yl]-1-(methylamino)ethyl]benzoic acid (93.1 mg, 0.25 mmol, 1.00 equiv), NHMe$_2$.HCl (40 mg, 0.49 mmol, 2.00 equiv) and DIEA (95 mg, 0.74 mmol, 3.00 equiv) in N,N-dimethylformamide (4 mL). To the solution was added HATU (140 mg, 0.37 mmol, 1.50 equiv). The resulting solution was stirred for 1 h at 25° C.

The resulting solution was diluted with 50 mL of ethyl acetate and the organic layer was washed with brine (4×50 ml), dried over Na$_2$SO$_4$ and concentrated under vacuum. This resulted in 101.7 mg (crude) of 3-[(1S)-2-[(3S)-3-[(tert-butyldimethylsilyl)oxy]pyrrolidin-1-yl]-1-(methylamino)ethyl]-N,N-dimethylbenzamide as brown oil.

LC-MS (ES, m/z): 406 (M+1).

Example 25-b (S)-1-((S)-2-(methylamino)-2-(3-(5-(trifluoromethyl)-1,2,4-oxadiazol-3-yl)phenyl)ethyl) pyrrolidin-3-ol

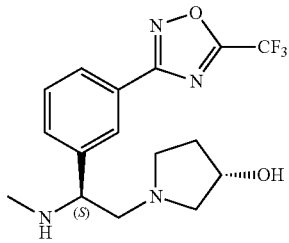

Step (i) Synthesis of 3-((S)-2-((S)-3-((tert-butyldimethylsilyl)oxy)pyrrolidin-1-yl)-1-(methylamino)ethyl)benzonitrile

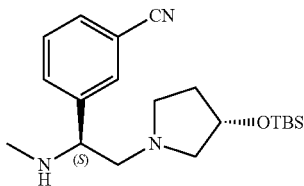

Into a 100-mL 3-necked round-bottom flask purged and maintained with an inert atmosphere of nitrogen, was placed a solution of [(1S)-1-(3-bromophenyl)-2-[(3S)-3-[(tert-butyldimethylsilyl)oxy]pyrrolidin-1-yl]ethyl](methyl)amine (20 g, 48.36 mmol, 1.00 equiv) in N,N-dimethylformamide (30 mL). To the solution were added Zn(CN)$_2$ (7.1 g, 60.68 mmol, 1.25 equiv) and Pd(PPh$_3$)$_4$(5.6 g, 4.84 mmol, 0.10 equiv). The resulting solution was stirred overnight at 100° C. in an oil bath. The reaction was then quenched by the addition of 50 mL of water. The resulting solution was extracted with ethyl acetate (5×10 mL), and the organic layers combined. The resulting mixture was washed with water (2×150 mL) and brine (3×100 mL), dried over anhydrous sodium sulfate and concentrated under vacuum. The residue was applied onto a silica gel column with dichloromethane/methanol (30:1). This resulted in 13 g (76%) of 3-[(1S)-2-[(3S)-3-[(tert-butyldimethylsilyl)oxy]pyrrolidin-1-yl]-1-(methylamino)ethyl]benzonitrile as a light yellow solid.

LC-MS (ES, m/z): 360 (M+1).

Step (ii) Synthesis of benzyl ((S)-2-((S)-3-((tert-butyldimethylsilyl)oxy)pyrrolidin-1-yl)-1-(3-cyanophenyl)ethyl)(methyl)carbamate

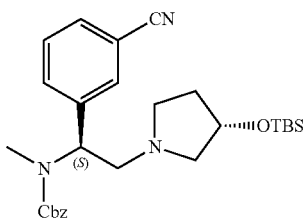

Into a 100-mL round-bottom flask, was placed a solution of 3-(2-[3-[(tert-butyldimethylsilyl)oxy]pyrrolidin-1-yl]-1-(methylamino)ethyl)benzonitrile (7 g, 19.47 mmol, 1.00 equiv) in ethyl acetate/water (50/10 mL). This was followed by the addition of potassium carbonate (3.5 g, 25.32 mmol, 1.30 equiv) for portions with stirring at 0° C. in a water/ice bath. The resulting solution was stirred for 20 min at 0° C. in a water/ice bath. Then benzyl carbonchloridate (4 g, 23.45 mmol, 1.20 equiv) was dropwised at 0° C. in a water/ice bath. Then it was warmed to 20° C. and stirred for 3 h at 20° C. The reaction was done, the resulting solution was extracted with ethyl acetate (3×100 mL) and the organic layers combined. The resulting solution was dried over anhydrous sodium sulfate and concentrated under vacuum. The residue was applied onto a silica gel column and eluted with ethyl acetate/petroleum ether (1:4). This resulted in 4 g (42%) of benzyl N-(2-[3-[(tert-butyldimethylsilyl)oxy]pyrrolidin-1-yl]-1-(3-cyanophenyl)ethyl)-N-methylcarbamate as yellow oil LC-MS (ES, m/z): 494 (M+1).

Step (iii) Synthesis of benzyl ((S)-2-((S)-3-((tert-butyldimethylsilyl)oxy)pyrrolidin-1-yl)-1-(3-(N-hydroxycarbamimidoyl)phenyl)ethyl)(methyl)carbamate

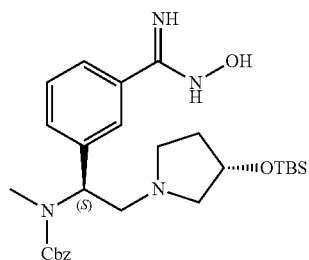

Into a 100-mL round-bottom flask, was placed a solution of benzyl N-(2-[3-[(tert-butyldimethylsilyl)oxy]pyrrolidin-1-yl]-1-(3-cyanophenyl)ethyl)-N-methylcarbamate (3.4 g, 6.89 mmol, 1.00 equiv) in ethanol (50 mL). To the solution were added NH$_2$OH HCl (1.2 g, 2.50 equiv) and triethylamine (1.4 g, 13.84 mmol, 2.00 equiv). The resulting solution was stirred for 12 h at 80° C. in an oil bath. The resulting mixture was concentrated under vacuum. This resulted in 5.1 g (crude) of benzyl N-(2-[3-[(tert-butyldimethylsilyl)oxy]pyrrolidin-1-yl]-1-[3-(N-hydroxycarbamimidoyl)phenyl]ethyl)-N-methylcarbamate as a solid.

LC-MS (ES, m/z): 527 (M+1).

Step (iv) Synthesis of benzyl ((S)-2-((S)-3-((tert-butyldimethylsilyl)oxy)pyrrolidin-1-yl)-1-(3-(5-(trifluoromethyl)-1,2,4-oxadiazol-3-yl)phenyl)ethyl)(methyl)carbamate

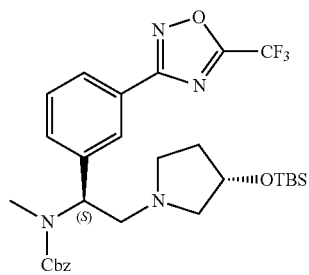

Into a 100-mL round-bottom flask, was placed a solution of benzyl N-(2-[3-[(tert-butyldimethylsilyl)oxy]pyrrolidin-1-yl]-1-[3-(N-hydroxycarbamimidoyl)phenyl]ethyl)-N-methylcarbamate (2 g, 3.80 mmol, 1.00 equiv) in pyridine (20 mL). To the solution was added (CF₃CO)₂O (2.4 g, 11.4 mmol, 3.00 equiv). The resulting solution was stirred for 3 h at 110° C. in an oil bath. The resulting mixture was concentrated under vacuum. The residue was applied onto a preparation TLC with dichloromethane/methanol (10:1). This resulted in 1.6 g (crude) of 1-[2-(methylamino)-2-[3-[5-(trifluoromethyl)-1,2,4-oxadiazol-3-yl]phenyl]ethyl]pyrrolidin-3-ol as yellow oil.

LC-MS (ES, m/z): 605 (M+1).

Step (v) Synthesis of (S)-1-((S)-2-(methylamino)-2-(3-(5-(trifluoromethyl)-1,2,4-oxadiazol-3-yl)phenyl)ethyl)pyrrolidin-3-ol

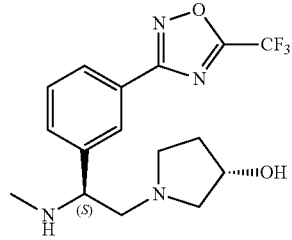

Into a 50-mL sealed tube, was placed a solution of benzyl N-[(1S)-2-[3-[(tert-butyldimethylsilyl)oxy]pyrrolidin-1-yl]-1-[3-[5-(trifluoromethyl)-1,2,4-oxadiazol-3-yl]phenyl]ethyl]-N-methylcarbamate (1.6 g, 2.56 mmol, 1.00 equiv) in methanol (50 mL). To the solution was added concentrated hydrogen chloride aqueous (8 mL). The resulting solution was stirred for 3 h at 80° C. in an oil bath. The resulting mixture was concentrated under vacuum. This resulted in 800 mg (87%) of 1-[2-(methylamino)-2-[3-[5-(trifluoromethyl)-1,2,4-oxadiazol-3-yl]phenyl]ethyl]pyrrolidin-3-ol as oil.

LC-MS (ES, m/z): 357 (M+1).

Example 26-b

N,N-diethyl-2-(3-((S)-2-((S)-3-hydroxypyrrolidin-1-yl)-1-(methylamino)ethyl)phenoxy) acetamide

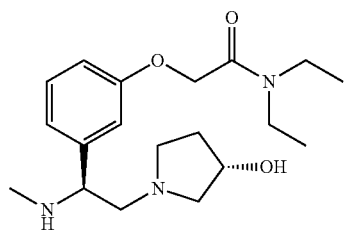 [SMILES: CCN(CC)C(=O)COc1cccc([C@@H](CN2CC[C@H](O)C2)NC)c1]

Into a 100-mL round-bottom flask, was placed a solution of 2-[3-[(1S)-2-[(3S)-3-hydroxypyrrolidin-1-yl]-1-(methylamino)ethyl]phenoxy]acetic acid (432 mg, 1.47 mmol, 1.00 equiv) in N,N-dimethylformamide (20 mL). To the solution were added DIEA (569 mg, 4.40 mmol, 3.00 equiv), NEt₃ (537 mg, 7.36 mmol, 5.00 equiv) and HATU (615 mg, 1.62 mmol, 1.10 equiv). The resulting solution was stirred for 1 h at 25° C. The resulting mixture was concentrated under vacuum. The residue was applied onto a silica gel column with dichloromethane/methanol (20:1). This resulted in 580 mg of N,N-diethyl-2-[3-[(1S)-2-[(3S)-3-hydroxypyrrolidin-1-yl]-1-(methylamino)ethyl]phenoxy]acetamide as light yellow oil.

LC-MS (ES, m/z): 350 (M+1)

Example 27-b (S)-1-((S)-2-(3-(5-ethyl-1,2,4-oxadiazol-3-yl)phenyl)-2-(methylamino)ethyl)pyrrolidin-3-ol

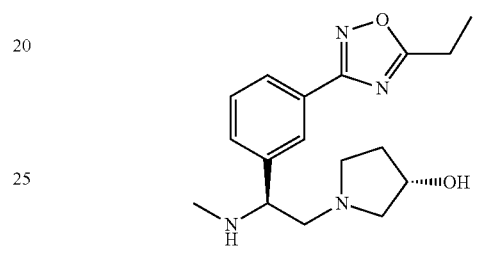

Step (i) Synthesis of benzyl ((S)-2-((S)-3-((tert-butyldimethylsilyl)oxy)pyrrolidin-1-yl)-1-(3-(5-ethyl-1,2,4-oxadiazol-3-yl)phenyl)ethyl)(methyl)carbamate

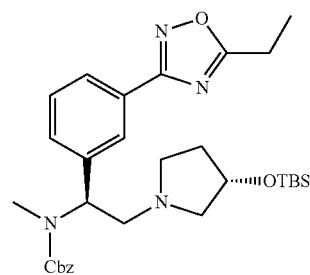 [SMILES: CCc1nc(-c2cccc([C@@H](CN3CC[C@H](O[Si](C)(C)C(C)(C)C)C3)N(C)C(=O)OCc3ccccc3)c2)no1]

Into a 100-mL round-bottom flask, was placed a solution of benzyl N-[(1S)-2-[(3S)-3-[(tert-butyldimethylsilyl)oxy]pyrrolidin-1-yl]-1-[3-(N-hydroxycarbamimidoyl)phenyl]ethyl]-N-methylcarbamate (2.3 g, 4.37 mmol, 1.00 equiv) in pyridine (30 mL). To the solution was added propanoyl propanoate (1.7 g, 13.06 mmol, 3.00 equiv). The resulting solution was stirred overnight at 110° C. The resulting mixture was concentrated under vacuum. The residue was applied onto a silica gel column with ethyl acetate/petroleum ether (0/100-1/30). This resulted in 1.2 g (49%) of benzyl N-[(1S)-2-[(3S)-3-[(tert-butyldimethylsilyl)oxy]pyrrolidin-1-yl]-1-[3-(5-ethyl-1,2,4-oxadiazol-3-yl)phenyl]ethyl]-N-methylcarbamate as orange oil.

LC-MS (ES, m/z): 565 (M+1)

Step (ii) Synthesis of (S)-1-((S)-2-(3-(5-ethyl-1,2,4-oxadiazol-3-yl)phenyl)-2-(methylamino)ethyl)pyrrolidin-3-ol

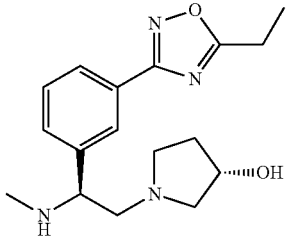 [SMILES: CCc1nc(-c2cccc([C@@H](CN3CC[C@H](O)C3)NC)c2)no1]

Into a 10-mL round-bottom flask, was placed a solution of [(1S)-2-[(3S)-3-[(tert-butyldimethylsilyl)oxy]pyrrolidin-1-yl]-1-[3-(5-ethyl-1,2,4-oxadiazol-3-yl)phenyl]ethyl](methyl)amine (230 mg, 0.53 mmol, 1.00 equiv) in concentrated hydrogen chloride aqueous (2 mL). The resulting solution was stirred for 2 h at room temperature. The resulting mixture was concentrated under vacuum. This resulted in 170 mg (crude) of (3S)-1-[(2S)-2-[3-(5-ethyl-1,2,4-oxadiazol-3-yl)phenyl]-2-(methylamino)ethyl]pyrrolidin-3-ol as a black solid.

LC-MS (ES, m/z): 317 (M+1).

Example 28-b (S)-1-((S)-2-(methylamino)-2-(3-(4-methylthiazol-2-yl)phenyl)ethyl)pyrrolidin-3-ol

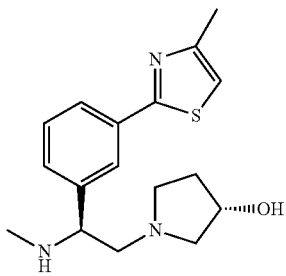 [SMILES: CN[C@H](CN1CC[C@H](O)C1)c1cccc(-c2nc(C)cs2)c1]

Step (i) Synthesis of benzyl ((S)-2-((S)-3-((tert-butyldimethylsilyl)oxy)pyrrolidin-1-yl)-1-(3-(4-methylthiazol-2-yl)phenyl)ethyl)(methyl)carbamate

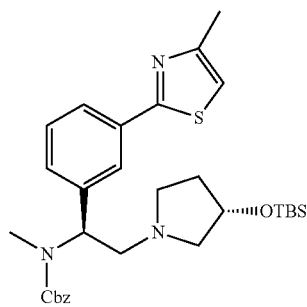 [SMILES: Cc1csc(-c2cccc([C@@H](CN3CC[C@H](O[Si](C)(C)C(C)(C)C)C3)N(C)C(=O)OCc3ccccc3)c2)n1]

Into a 50-mL round-bottom flask purged and maintained with an inert atmosphere of nitrogen, was placed a solution of benzyl N-[(1S)-2-[(3S)-3-[(tert-butyldimethylsilyl)oxy]pyrrolidin-1-yl]-1-[3-(tetramethyl-1,3,2-dioxaborolan-2-yl)phenyl]ethyl]-N-methylcarbamate (800 mg, 1.35 mmol, 1.00 equiv) in 1,4-dioxane:H2O (10/2 mL). To the solution were added 2-bromo-4-methyl-1,3-thiazole (358 mg, 2.01 mmol, 1.50 equiv), potassium carbonate (376 mg, 2.72 mmol, 2.00 equiv) and Pd(PPh$_3$)$_4$(316 mg, 0.27 mmol, 0.20 equiv). The resulting solution was stirred for 16 hours at 80° C. The resulting mixture was concentrated under vacuum. The residue was applied onto a silica gel column with ethyl acetate/petroleum ether (1:10). This resulted in 0.32 g (42%) of benzyl N-[(1S)-2-[(3S)-3-[(tert-butyldimethylsilyl)oxy]pyrrolidin-1-yl]-1-[3-(4-methyl-1,3-thiazol-2-yl)phenyl]ethyl]-N-methylcarbamate as yellow oil.

LC-MS (ES, m/z): 566 (M+1).

Step (ii) Synthesis of (S)-1-((S)-2-(methylamino)-2-(3-(4-methylthiazol-2-yl)phenyl)ethyl)pyrrolidin-3-ol

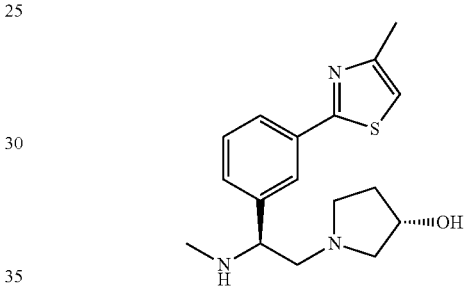

Into a 25-mL round-bottom flask, was placed a solution of benzyl N-[(1S)-2-[(3S)-3-[(tert-butyldimethylsilyl)oxy]pyrrolidin-1-yl]-1-[3-(4-methyl-1,3-thiazol-2-yl)phenyl]ethyl]-N-methylcarbamate (160 mg, 0.28 mmol, 1.00 equiv) in concentrated HCl aqueous (5 mL). The resulting solution was stirred for 2 h at 80° C. The resulting mixture was concentrated under vacuum. This resulted in 150 mg (crude) of (3S)-1-[(2S)-2-[3-(4-methyl-1,3-thiazol-2-yl)phenyl]-2-(methylamino)ethyl]pyrrolidin-3-ol as yellow oil.

LC-MS (ES, m/z): 318 (M+1).

Example 29-b (S)-1-((S)-2-(3-(5-methyl-1,3,4-thiadiazol-2-yl)phenyl)-2-(methylamino)ethyl)pyrrolidin-3-ol

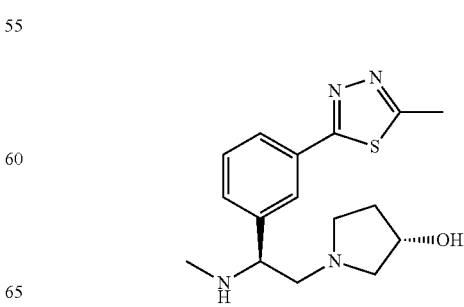

Step (i) Synthesis of 2-bromo-5-methyl-1,3,4-thiadiazole

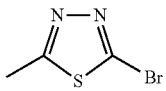

Into a 250-mL 3-necked round-bottom flask, HBr (20 ml, 10.00 equiv, 40%) was added. 5-methyl-1,3,4-thiadiazol-2-amine (2 g, 17.37 mmol, 1.00 equiv), water (20 ml) and CuBr (250 mg, 0.10 equiv) were added in sequence. A solution of sodium nitrite (1.2 g, 17.39 mmol, 1.00 equiv) in water (50 ml) was added dropwise with stirring at 0° C. in 30 mins. The reaction was stirred for additional 30 min at 25° C. The resulting solution was extracted with ethyl acetate (2×50 mL) and the organic layers combined. The resulting mixture was washed with sodium bicarbonate aqueous (2×40 mL), dried over anhydrous sodium sulfate and concentrated under vacuum. This resulted in 2.2 g (71%) of 2-bromo-5-methyl-1,3,4-thiadiazole as a yellow solid.

Step (ii) Synthesis of tert-butyl ((S)-2-((S)-3-((tert-butyldimethylsilyl)oxy)pyrrolidin-1-yl)-1-(3-(5-methyl-1,3,4-thiadiazol-2-yl)phenyl)ethyl)(methyl)carbamate

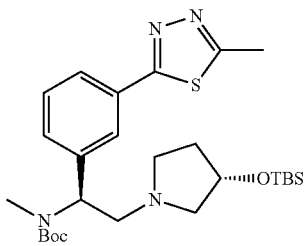 [SMILES: Cc1nnc(-c2cccc([C@@H](CN3CC[C@H](O[Si](C)(C)C(C)(C)C)C3)N(C)C(=O)OC(C)(C)C)c2)s1]

Into a 50-mL 3-necked round-bottom flask purged and maintained with an inert atmosphere of nitrogen, N,N-dimethylformamide (3 ml), tert-butyl (1R)-2-[(3S)-3-[(tert-butyldimethylsilyl)oxy]pyrrolidin-1-yl]-1-[3-(tetramethyl-1,3,2-dioxaborolan-2-yl)phenyl]ethyl N-methylcarbamate (300 mg, 0.53 mmol, 1.00 equiv), 2-bromo-5-methyl-1,3,4-thiadiazole (105.48 mg, 0.59 mmol, 1.10 equiv), tetrakis(triphenylphosphane) palladium (30 mg, 0.03 mmol, 0.05 equiv), potassium phosphate (228 mg, 1.07 mmol, 2.01 equiv) were added. The resulting solution was stirred for 16 h at 80° C. The resulting mixture was concentrated under vacuum. The residue was applied onto a silica gel column with dichloromethane/methanol (10;1). This resulted in 120 mg (42%) of tert-butyl (1R)-2-[(3S)-3-[(tert-butyldimethylsilyl)oxy]pyrrolidin-1-yl]-1-[3-(5-methyl-1,3,4-thiadiazol-2-yl)phenyl]ethyl N-methylcarbamate as light yellow oil.

LC-MS (ES, m/z): 533 (M+1)

Step (iii) Synthesis of (S)-1-((S)-2-(3-(5-methyl-1,3,4-thiadiazol-2-yl)phenyl)-2-(methylamino)ethyl)pyrrolidin-3-ol

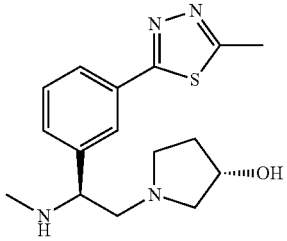

Into a 50-mL round-bottom flask, concentrated hydrogen chloride aqueous (1.2 ml) and tert-butyl (1R)-2-[(3S)-3-[(tert-butyldimethylsilyl)oxy]pyrrolidin-1-yl]-1-[3-(5-methyl-1,3,4-thiadiazol-2-yl)phenyl]ethyl N-methylcarbamate (120 mg, 0.22 mmol, 1.00 equiv) were added. The resulting solution was stirred for 30 min at 40° C. The pH value of the solution was adjusted to 8-9 with sodium bicarbonate. The resulting mixture was concentrated under vacuum. This resulted in 72 mg (crude) of (3S)-1-[(2S)-2-[3-(5-methyl-1,3,4-thiadiazol-2-yl)phenyl]-2-(methylamino)ethyl]pyrrolidin-3-ol as a yellow solid.

LC-MS (ES, m/z): 319 (M+1).

Example 30-b

(S)-1-((S)-2-(3-(1,3,4-oxadiazol-2-yl)phenyl)-2-(methylamino)ethyl)pyrrolidin-3-ol

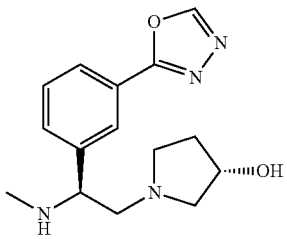 [SMILES: CN[C@H](CN1CC[C@H](O)C1)c1cccc(-c2nnco2)c1]

Step (i) Synthesis of benzyl ((S)-2-((S)-3-((tert-butyldimethylsilyl)oxy)pyrrolidin-1-yl)-1-(3-(hydrazinecarbonyl)phenyl)ethyl)(methyl)carbamate

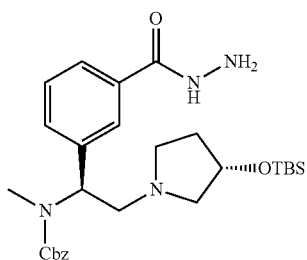 [SMILES: CN(C(=O)OCc1ccccc1)[C@H](CN1CC[C@H](O[Si](C)(C)C(C)(C)C)C1)c1cccc(C(=O)NN)c1]

Into a 500-mL round-bottom flask, was placed a solution of ethyl 3-[(1S)-1-[[(benzyloxy)carbonyl](methyl)amino]-

2-[(3S)-3-[(tert-butyldimethylsilyl)oxy]pyrrolidin-1-yl] ethyl]benzoate (5.6 g, 10.36 mmol, 1.00 equiv) in ethanol (100 mL). To the solution were added hydrazine (16.3 g, 508.66 mmol, 25.00 equiv). The resulting solution was stirred for 16 h at 80° C. in an oil bath. The resulting mixture was concentrated under vacuum. The resulting solution was diluted with 100 mL of ethyl acetate. The resulting mixture was washed with water (3×50 mL) and brine (3×50 mL). The mixture was dried over anhydrous sodium sulfate and concentrated under vacuum. This resulted in 6.0 g (crude) of benzyl N-[(1S)-2-[(3S)-3-[(tert-butyldimethylsilyl)oxy]pyrrolidin-1-yl]-1-[3-(hydrazinecarbonyl)phenyl]ethyl]-N-methylcarbamate as light yellow oil.

LC-MS (ES, m/z): 527 (M+1)

Step (ii) Synthesis of benzyl ((S)-1-(3-(1,3,4-oxadiazol-2-yl)phenyl)-2-((S)-3-((tert-butyldimethyl silyl) oxy)pyrrolidin-1-yl)ethyl)(methyl)carbamate

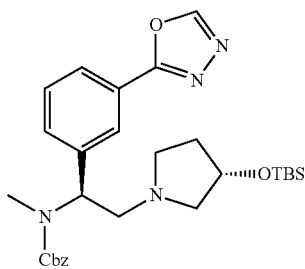 [SMILES: CN(C(=O)OCc1ccccc1)[C@H](CN1CC[C@H](O[Si](C)(C)C(C)(C)C)C1)c1cccc(-c2nnco2)c1]

Into a 100-mL round-bottom flask, was placed a solution of benzyl N-[(1S)-2-[(3S)-3-[(tert-butyldimethylsilyl)oxy pyrrolidin-1-yl]-1-[3-(hydrazinecarbonyl)phenyl]ethyl]-N-methylcarbamate (1.0 g, 1.90 mmol, 1.00 equiv) in CH(OCH$_3$)$_3$(15 mL). The resulting solution was stirred for 16 h at 100° C. in an oil bath. The resulting mixture was concentrated under vacuum. Purification by a silica gel column with dichloromethane:MeOH (100:0-100:1) resulted in 0.8 g (79%) of benzyl N-[(1S)-2-[(3S)-3-[(tert-butyldimethylsilyl)oxy]pyrrolidin-1-yl]-1-[3-(1,3,4-oxadiazol-2-yl)phenyl]ethyl]-N-methylcarbamate as light brown oil.

LC-MS (ES, m/z): 537 (M+1).

Step (iii) Synthesis of (S)-1-((S)-2-(3-(1,3,4-oxadiazol-2-yl)phenyl)-2-(methylamino)ethyl) pyrrolidin-3-ol

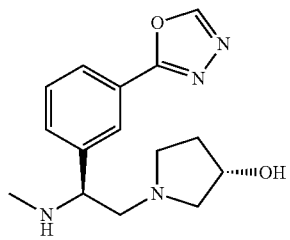 [SMILES: CN[C@H](CN1CC[C@H](O)C1)c1cccc(-c2nnco2)c1]

Into a 100-mL round-bottom flask, was placed a solution of benzyl N-[(1S)-2-[(3S)-3-[(tert-butyldimethylsilyl)oxy] pyrrolidin-1-yl]-1-[3-(1,3,4-oxadiazol-2-yl)phenyl]ethyl]-N-methylcarbamate (612 mg, 1.14 mmol, 1.00 equiv) in tetrahydrofuran (10 mL). To the mixture was added TBAF (2 mL, 2.28 mmol, 2.00 equiv, IM in THF). The resulting solution was stirred for 4 h at 25° C., then diluted with 20 mL of ethyl acetate. The resulting solution was washed with water (2×10 mL) and brine (2×10 mL), dried over anhydrous sodium sulfate and concentrated under vacuum. The residue was purified by Prep-TLC (dichloromethane:methanol=18: 1) to result in 244 mg product. A solution of the product (244 mg) in MeOH (10 mL) was hydrogenated in the presence of 20% Pd/C (40 mg) at 25° C. for 12 h. The mixture was filtered (through Celite) and washed with methanol. The solvent was evaporated to afford 168 mg (51%) of (3S)-1-[(2S)-2-(methylamino)-2-[3-(1,3,4-oxadiazol-2-yl)phenyl] ethyl]pyrrolidin-3-ol as light yellow oil.

LC-MS (ES, m/z): 289 (M+1).

Example 31-b (S)-1-((S)-2-(3-(1-(cyclopropylmethyl)-1H-imidazol-2-yl)phenyl)-2-(methylamino)ethyl)pyrrolidin-3-ol

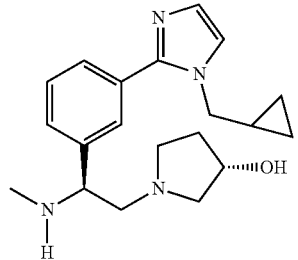 [SMILES: CN[C@H](CN1CC[C@H](O)C1)c1cccc(-c2nccn2CC2CC2)c1]

Step (i) Synthesis of 1-(cyclopropylmethyl)-1H-imidazole

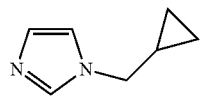

Into a 250-mL round-bottom flask purged and maintained with an inert atmosphere of nitrogen, was placed a solution of 1H-imidazole (3 g, 44.07 mmol, 1.00 equiv) and potassium hydroxide (11.8 g, 210.30 mmol, 5.00 equiv) in acetone (100 mL). The resulting solution was stirred for 30 min at 25° C. This was followed by the addition of (bromomethyl)cyclopropane (6.9 mL, 1.10 equiv) dropwise with stirring at 25° C. The resulting solution was allowed to react, with stirring, for an additional 30 min at 25° C. The resulting mixture was concentrated under vacuum. The resulting solution was diluted with 100/100 mL of dichloromethane/ H$_2$O. The pH value of the solution was adjusted to 2-4 with concentrated HCl aqueous (12 mol/L). The aqueous layer was separated and the pH value was adjusted to 9-10 by sodium hydroxide aqueous. The resulting solution was extracted with dichloromethane (2×150 mL) and the organic layers combined. The mixture was dried over anhydrous sodium sulfate and concentrated under vacuum. The residue was applied onto a silica gel column with petroleum ether/ ethyl acetate (1:2), This resulted in 3.19 g (59%) of 1-(cyclopropylmethyl)-1H-imidazole as yellow oil.

Step (ii) Synthesis of 1-(cyclopropylmethyl)-2-iodo-1H-imidazole

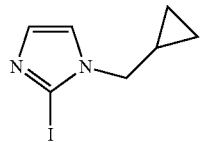

Into a 250-mL round-bottom flask purged and maintained with an inert atmosphere of nitrogen, was placed a solution of 1-(cyclopropylmethyl)-1H-imidazole (3.19 g, 26.11 mmol, 1.00 equiv) in tetrahydrofuran (100 mL). This was followed by the addition of n-BuLi (11.4 mL, 1.10 equiv) at −78° C. The resulting solution was stirred for 1 h at −78° C. To this was added a solution of $I_2$ (6.6 g, 26.09 mmol, 1.00 equiv) in tetrahydrofuran (30 mL) dropwise with stirring at −78° C. The resulting solution was allowed to react, with stirring, for an additional 1 h at 25° C. The reaction was then quenched by the addition of 10 mL of saturated $NH_4Cl$ aqueous. The resulting solution was extracted with ethyl acetate (2×100 mL) and the organic layers combined. The resulting mixture was washed with water (2×100 mL) and brine (2×100 mL). The mixture was dried over anhydrous sodium sulfate and concentrated under vacuum. The residue was applied onto a silica gel column with ethyl acetate/petroleum ether (1:7). This resulted in 5 g (77%) of 1-(cyclopropylmethyl)-2-iodo-1H-imidazole as yellow oil.
LC-MS (ES, m/z): 249 (M+1).

Step (iii) Synthesis of benzyl ((S)-2-((S)-3-((tert-butyldimethylsilyl)oxy)pyrrolidin-1-yl)-1-(3-(1-(cyclopropylmethyl)-1H-imidazol-2-yl)phenyl)ethyl)(methyl)carbamate

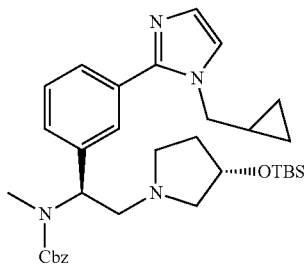 [SMILES: CN(C(=O)OCc1ccccc1)[C@H](CN1CC[C@H](O[Si](C)(C)C(C)(C)C)C1)c1cccc(-c2nccn2CC2CC2)c1]

Into a 100-mL round-bottom flask purged and maintained with an inert atmosphere of nitrogen, was placed a solution of benzyl N-[(1S)-2-[(3S)-3-[(tert-butyldimethylsilyl)oxy]pyrrolidin-1-yl]-1-[3-(tetramethyl-1,3,2-dioxaborolan-2-yl)phenyl]ethyl]-N-methylcarbamate (500 mg, 0.84 mmol, 1.00 equiv) in 1,4-dioxane/$H_2O$ (30/3 mL). To the solution were added 1-(cyclopropylmethyl)-2-iodo-1H-imidazole (230 mg, 0.93 mmol, 1.10 equiv), Pd(dppf)$Cl_2$ (62 mg, 0.08 mmol, 0.10 equiv), Potassium tert-butoxide (188 mg, 1.68 mmol, 2.00 equiv) and Xphos (80 mg, 0.17 mmol, 0.20 equiv). The resulting solution was stirred for 16 h at 90° C. The resulting mixture was concentrated under vacuum. The residue was purified by Prep-TLC. This resulted in 270 mg (55%) of benzyl N-[(1S)-2-[(3S)-3-[(tert-butyldimethylsi-lyl)oxy]pyrrolidin-1-yl]-1-[3-[1-(cyclopropylmethyl)-1H-imidazol-2-yl]phenyl]ethyl]-N-methylcarbamate as yellow oil.
LC-MS (ES, m/z): 589 (M+1).

Step (iv) Synthesis of (S)-1-((S)-2-(3-(1-(cyclopropylmethyl)-1H-imidazol-2-yl)phenyl)-2-(methylamino)ethyl)pyrrolidin-3-ol

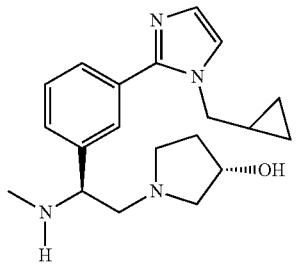 [SMILES: CN[C@H](CN1CC[C@H](O)C1)c1cccc(-c2nccn2CC2CC2)c1]

Into a 50-mL round-bottom flask, was placed a solution of benzyl N-[(1S)-2-[(3S)-3-[(tert-butyldimethylsilyl)oxy]pyrrolidin-1-yl]-1-[3-[1-(cyclopropylmethyl)-1H-imidazol-2-yl]phenyl]ethyl]-N-methylcarbamate (270 mg, 0.46 mmol, 1.00 equiv) in concentrated HCl aqueous (5 mL). The resulting solution was stirred for 2 h at 80° C. The resulting mixture was concentrated under vacuum. This resulted in 200 mg (crude) of (3S)-1-[(2S)-2-[3-[1-(cyclopropylmethyl)-1H-imidazol-2-yl]phenyl]-2-(methylamino)ethyl]pyrrolidin-3-ol as yellow oil.
LC-MS (ES, m/z): 341 (M+1).

Example 32-b (S)-1-((S)-2-(3-(3-methyl-1,2,4-oxadiazol-5-yl)phenyl)-2-(methylamino)ethyl)pyrrolidin-3-ol

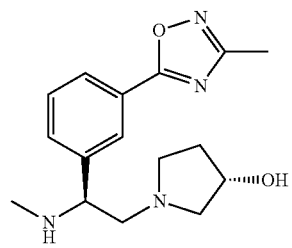

Step (i) Synthesis of benzyl ((S)-2-((S)-3-((tert-butyldimethylsilyl)oxy)pyrrolidin-1-yl)-1-(3-(3-methyl-1,2,4-oxadiazol-5-yl)phenyl)ethyl)(methyl)carbamate

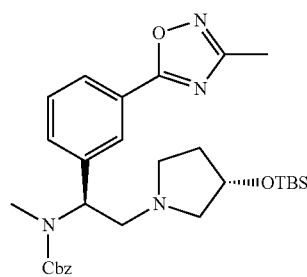

Into a 50-mL round-bottom flask, was placed a solution of ethyl 3-[(1S)-1-[[(benzyloxy)carbonyl](methyl)amino]-2-[(3S)-3-[(tert-butyldimethylsilyl)oxy]pyrrolidin-1-yl]ethyl]benzoate (1.0 g, 1.85 mmol, 1.00 equiv) in toluene (10 mL). To the solution were added (E)-N_ydroxyethenimidamide (2.74 g, 36.99 mmol, 20.00 equiv), potassium carbonate (1.27 g, 9.19 mmol, 4.97 equiv) and 4-dimethylaminopyridine (23 mg, 0.19 mmol, 0.10 equiv). The resulting solution was stirred for 24 hours at 110° C. in an oil bath. The resulting mixture was concentrated under vacuum. The residue was dissolved in 20 mL of ethyl acetate. The resulting mixture was washed with water (2×10 mL) and brine (2×10 mL). The mixture was dried over anhydrous sodium sulfate and concentrated under vacuum. The residue was applied onto a silica gel column with ethyl acetate/petroleum ether (1:100-1:5). This resulted in 0.796 g (78%) of benzyl N-[(1S)-2-[(3S)-3-[(tert-butyldimethylsilyl)oxy]pyrrolidin-1-yl]-1-[3-(3-methyl-1,2,4-oxadiazol-5-yl)phenyl]ethyl]-N-methylcarbamate as yellow oil.

LC-MS (ES, m/z): 551 (M+1).

Step (ii) Synthesis of (S)-1-((S)-2-(3-(3-methyl-1,2,4-oxadiazol-5-yl)phenyl)-2-(methylamino)ethyl)pyrrolidin-3-ol

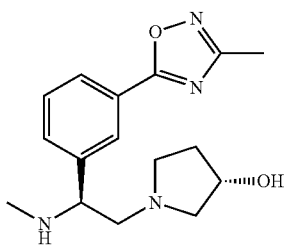

Into a 25-mL round-bottom flask, was placed a solution of benzyl N-[(1S)-2-[(3S)-3-[(tert-butyldimethylsilyl)oxy]pyrrolidin-1-yl]-1-[3-(3-methyl-1,2,4-oxadiazol-5-yl)phenyl]ethyl]-N-methylcarbamate (400 mg, 0.73 mmol, 1.00 equiv) in concentrated HCl aqueous (3 mL). The resulting solution was stirred for 1 hour at 70° C. in an oil bath. The resulting solution was diluted with 20 mL of water. The resulting mixture was washed with DCM (3×10 mL) and concentrated under vacuum. This resulted in 198 mg (crude) of (3S)-1-[(2S)-2-[3-(3-methyl-1,2,4-oxadiazol-5-yl)phenyl]-2-(methylamino)ethyl]pyrrolidin-3-ol as light yellow oil.

LC-MS (ES, m/z): 303 (M+1).

Example 33-b (S)-2-((S)-3-((tert-butyldimethylsilyl)oxy)pyrrolidin-1-yl)-N-ethyl-1-(3-(trifluoromethoxy)phenyl)ethanamine

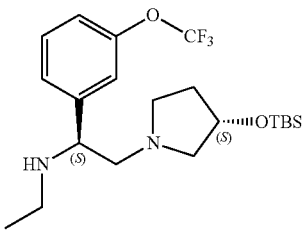

Into a 250-mL 3-necked round-bottom flask purged and maintained with an inert atmosphere of nitrogen, was placed a solution of (1S)-2-[(3S)-3-[(tert-butyldimethylsilyl)oxy]pyrrolidin-1-yl]-1-[3-(trifluoromethoxy)phenyl]ethan-1-ol (5 g, 12.33 mmol, 1.00 equiv) in dichloromethane (140 mL). This was followed by the addition of TEA (6.2 g, 61.27 mmol, 5.00 equiv) and MsCl (4.2 g, 36.84 mmol, 3.00 equiv) at 0° C. The mixture was stirred at 25° C. for 2 h. To the mixture was added ethanamine (7.9 g, 175.23 mmol, 10.00 equiv) dropwise with stirring at 0-5° C. The resulting solution was stirred for 18 h at 25° C. The resulting mixture was washed with water (3×50 mL) and brine (3×50 mL). The resulting mixture was concentrated under vacuum. The residue was applied onto a silica gel column with ethyl acetate/petroleum ether (1:4). This resulted in 4 g (75%) of [(1S)-2-[(3S)-3-[(tert-butyldimethylsilyl)oxy]pyrrolidin-1-yl]-1-[3-(trifluoromethoxy)phenyl]ethyl](ethyl)amine as light yellow oil LC-MS (ES, m/z): 433.3 (M+1).

Further examples of the amine intermediates of formula (b), as in Table 2, can be prepared by the following procedures substantially similar to those described previously, using suitable starting materials:

TABLE 2

| Ex No. | Amine intermediate of formula (b) | Analytical data |
|---|---|---|
| 34-b | 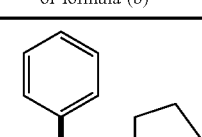 | ¹H-NMR (d₆-DMSO, 400 MHz): δ 7.36-7.28 (m, 4H), 7.24-7.22 (m, 1H), 3.55-3.51 (m, 1H), 2.66-2.61 (m, 1H). |
| 35-b |  | ¹H-NMR (d₆-DMSO, 400 MHz): δ 7.37-7.30 (m, 2H), 7.29-7.24 (m, 2H), 7.23-7.19 (m, 1H), 4.19-4.14 (m, 1H), 3.96-3.92 (m, 1H), 3.32 (bs, 2H), 2.80-2.76 (m, 1H), 2.69-2.65 (m, 1H), 2.43-2.38 (m, 1H), 2.32-2.26 (m, 2H), 2.00-1.91 (m, 2H), 1.56-1.49 (m, 1H). |

TABLE 2-continued

| Ex No. | Amine intermediate of formula (b) | Analytical data |
|---|---|---|
| 36-b | (S)-1-cyclohexyl-2-(pyrrolidin-1-yl)ethan-1-amine | $^1$H-NMR (400 MHz, CDCl$_3$ + d$_6$-DMSO): δ 3.32 (bs, 2H), 2.60-2.57 (m, 1H), 2.56-2.47 (m, 5H), 2.35-2.30 (m, 2H), 2.21-2.11 (m, 1H), 1.58-1.76 (m, 4H), 1.19-1.00 (m, 6H); MS (ES): m/z 197 (M + 1). |
| 37-b | (S)-1-(3-methoxyphenyl)-2-(pyrrolidin-1-yl)ethan-1-amine | $^1$H-NMR (d$_6$-DMSO, 400 MHz): δ 7.19 (t, J = 7.9 Hz, 1H), 6.96-6.91 (m, 2H), 6.77-6.75 (m, 1H), 3.95-3.92 (m, 1H), 3.73 (s, 3H), 2.45-2.40 (m, 2H), 2.33-2.36 (m, 2H), 1.93-1.81 (m, 2H); MS (ESI): m/z 221.2 (M + 1). |
| 38-b | (S)-1-(3-(benzyloxy)phenyl)-2-(pyrrolidin-1-yl)ethan-1-amine | $^1$H-NMR (d$_6$-DMSO, 400 MHz): δ 7.44-7.31 (m, 5H), 7.24-7.19 (m, 1H), 6.92-6.86 (m, 2H), 6.77 (d, J = 7.3 Hz, 1H), 5.08 (s, 2H), 4.62-4.58 (m, 1H), 2.38-2.29 (m, 2H), 1.65-1.59 (m, 4H), 1.34-1.24 (m, 4H); MS (ESI): m/z 298 (M + 1). |
| 39-b | (S)-1-(3-(benzyloxy)phenyl)-N-methyl-2-(pyrrolidin-1-yl)ethan-1-amine | $^1$H-NMR (d$_6$-DMSO, 400 MHz): δ 7.46-7.30 (m, 5H), 7.22 (t, J = 7.9 Hz, 1H), 7.0 (s, 1H), 6.87 (dd, J$_1$ = 2.6 Hz, J$_2$ = 8.0 Hz, 2H), 5.07 (s, 2H), 3.57-3.53 (m, 1H), 2.66 (t, J = 10.8 Hz, 1H), 2.57 (d, J = 5.2 Hz, 3H), 2.43-2.24 (m, 4H), 2.14 (s, 2H), 1.68 (s, 4H); MS (ES): m/z 311 (M + 1). |
| 40-b | (3S)-1-((S)-2-(methylamino)-2-(3-(trifluoromethoxy)phenyl)ethyl)pyrrolidin-3-ol | $^1$H-NMR: (CDCl$_3$): δ 7.75-7.52 (m, 4H), 4.84-4.58 (m, 1H), 4.53 (m, 2H), 4.15 (s, 1H), 4.07-3.95 (m, 2H), 3.62-3.42 (m, 4H), 2.63 (s, 3H), 2.27-2.16 (m, 1H), 2.06-2.01 (m, 1H); LC-MS: (ES, m/z): 305 (M + 1). |
| 41-b | (S)-3-(1-amino-2-(pyrrolidin-1-yl)ethyl)benzonitrile | $^1$H-NMR (d$_6$-DMSO, 400 MHz): δ 7.82-7.62 (m, 3H), 7.59-7.54 (m, 1H), 4.74 (t, J = 7.3 Hz, 1H), 2.50-2.49 (m, 4H), 2.33-2.18 (m, 2H), 1.83-1.56 (m, 4H); MS (ES): m/z 216.2 (M + 1) |
| 42-b | 1-(1-benzyl-1H-pyrazol-4-yl)-2-(pyrrolidin-1-yl)ethan-1-amine | $^1$H-NMR (d$_6$-DMSO, 400 MHz): δ 7.64 (s, 1H), 7.39 (s, 1H), 7.32-7.27 (m, 3H), 7.21-7.20 (m, 2H), 5.24 (s, 2H), 3.91-3.87 (m, 1H), 2.40-2.38 (m, 4H), 1.89-1.80 (m, 2H), 1.67-1.62 (m, 4H); MS (ES): m/z 271 (M + 1). |

Further examples of the amine intermediates of formula (b), as in Table 3, can be prepared by the following procedures substantially similar to those described previously, using suitable starting materials:

TABLE 3

| Example No./Structure/Characterization |
|---|
| Example No. 43-b<br>MS (ES): m/z 227 (M + 1) |
| Example No. 44-b<br>LC-MS (ES, m/z): 447 (M + 1) |
| Example No. 45-b<br>LC-MS (ES, m/z): 447 (M + 1) |
| Example No. 46-b<br>LC-MS (ES, m/z): 445 (M + 1) |
| Example No. 47-b<br>LC-MS (ES, m/z): 461 (M + 1) |

TABLE 3-continued

| Example No./Structure/Characterization |
|---|
| Example No. 48-b<br>LC-MS (ES, m/z): 459 (M + 1) |
| Example No. 49-b<br>LC-MS (ES, m/z): 319 (M + 1) |
| Example No. 50-b<br>LC-MS (ES, m/z): 433 (M + 1) |
| Example No. 51-b<br>LC-MS (ES, m/z): 371 (M + 1) |
| Example No. 52-b<br>LC-MS (ES, m/z): 349 (M + 1) |
| Example No. 53-b<br>LC-MS (ES, m/z): (M + 1) 487 |

TABLE 3-continued

Example No./Structure/Characterization

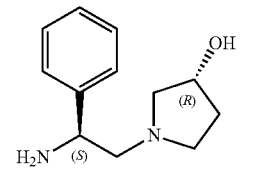

Example No. 54-b

LC-MS (ES, m/z): 207.1 (M + 1).

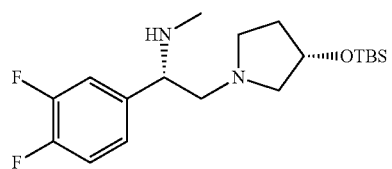

Example No. 55-b

LC-MS (ES, m/z): 371 (M + 1)

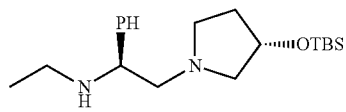

Example No. 56-b

LC-MS (ES, m/z): 349 (M + 1)

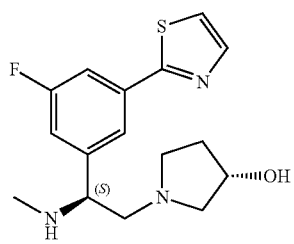

Example No. 57-b

LC-MS (ES, m/z): 322 (M + 1)

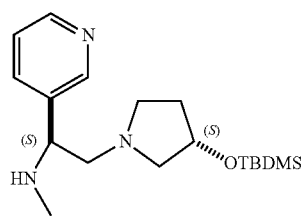

Example No. 58-b

LC-MS (ES, m/z): 336 (M + 1)

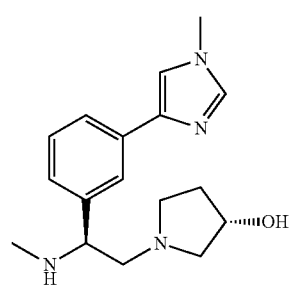

Example No. 59-b

LC-MS (ES, m/z): 301 (M + 1)

TABLE 3-continued

Example No./Structure/Characterization

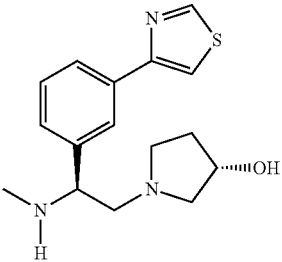

Example No. 60-b

LC-MS (ES, m/z): 304 (M + 1)

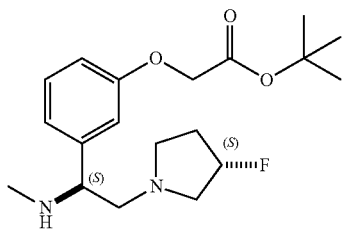

Example No. 61-b

LC-MS (ES, m/z): 353.2 (M + 1)

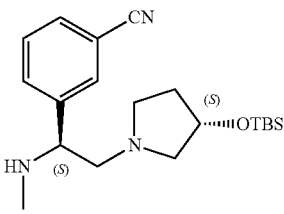

Example No. 62-b

LC-MS (ES, m/z): 360.2 (M + 1)

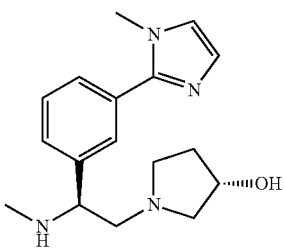

Example No. 63-b

LC-MS (ES, m/z): 301 (M + 1)

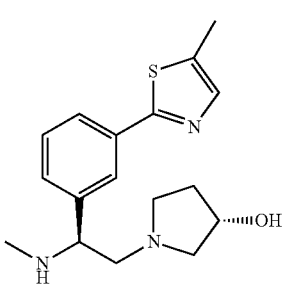

Example No. 64-b

LC-MS (ES, m/z): 318 (M + 1)

TABLE 3-continued

Example No./Structure/Characterization

Example No. 65-b

LC-MS (ES, m/z): 304 (M + 1)

Example No. 66-b

LC-MS (ES, m/z): 318 (M + 1)

Example No. 67-b

LC-MS (ES, m/z): 318 (M + 1)

Further examples of the amine intermediates of formula (b) which can be prepared by substantially similar procedures as described above, include:

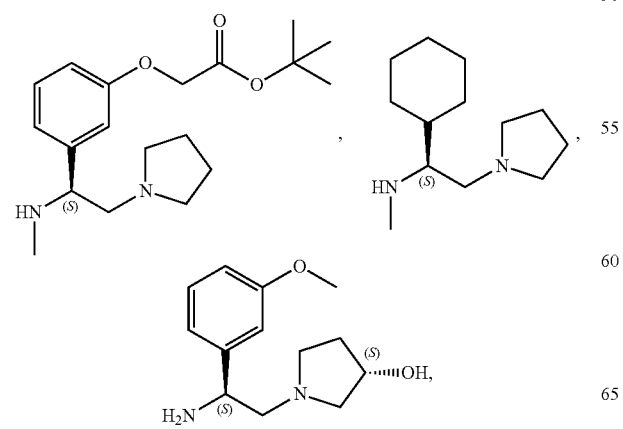

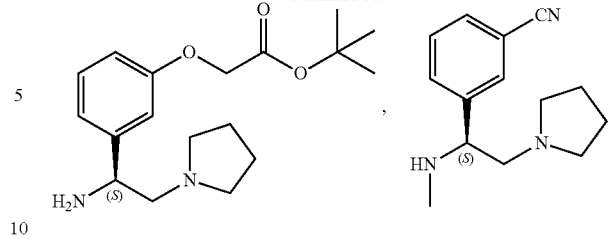

Following are the non-limiting examples of compounds of general formula (I)

Example 1

N—((S)-2-((S)-3-hydroxypyrrolidin-1-yl)-1-phenylethyl)-N-methyl-2-(2-oxoindolin-6-yl)acetamide

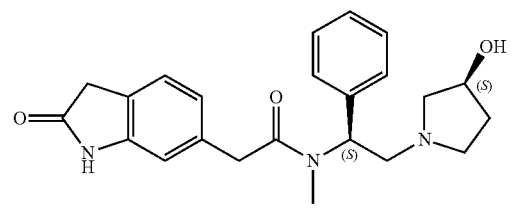

To a solution of 2-(2-oxoindolin-6-yl)acetic acid (4 g, 20.9 mmoles) in dichloromethane were added at room temperature, dicyclohexane carbodiimide (4.2 g, 20.9 mmoles) in DCM (30 mL) and 1-hydroxy benzo triazole (2.7 g, 20.9 mmoles) and the mixture was stirred at room temperature for 10 minutes. To this mixture was added (S)-1-((S)-2-(methylamino)-2-phenylethyl)pyrrolidin-3-ol (4.5 g, 20.9 mmoles) and the contents were allowed to stir for 12 h at room temperature. The reaction mixture was filtered and the filtrate was diluted with DCM (50 mL). The organic layer was washed with sat.NaHCO$_3$ solution (50 mL), brine solution (2×50 mL), dried over Na$_2$SO$_4$ and concentrated under reduced pressure to give the crude. The crude was purified by flash column chromatography over silica gel (230-400 mesh) using 10% MeOH in DCM to furnish the desired compound as a cream colour solid (3 g).

Melting point: 166-168° C.; $^1$H-NMR (400 MHz, DMSO-d$_6$): δ 10.43 (s, 1H), 7.42-7.26 (m, 5H), 7.18 (d, J=7.5 Hz, 1H), 6.89-6.81 (m, 2H), 5.93 (d, J=5.4 Hz, 1H), 4.96 (s, 1H), 4.26 (s, 1H), 3.88-3.84 (m, 1H), 3.74-3.70 (m, 1H), 3.49 (s, 2H), 3.14 (s, 1H), 2.92-2.76 (m, 6H), 2.45-2.40 (m, 2H), 2.06-1.98 (m, 1H), 1.58 (s, 1H); IR (KBr, cm$^{-1}$): 3325, 2938, 2793, 2769, 1713, 1618, 1462, 1383; MS (ESI): m/z 394.0 (M+1).

Example 2

N-[(1S)-2-[(3S)-3-hydroxypyrrolidin-1-yl]-1-phenylethyl]-2-(3-oxo-3,4-dihydro-2H-1,4-benzoxazin-6-yl)acetamide

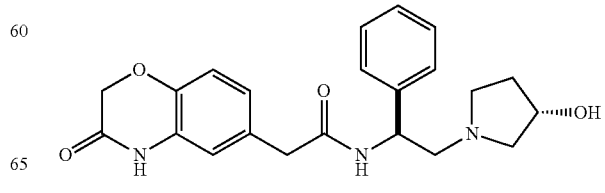

Into a 8-mL round-bottom flask, were placed 2-(3-oxo-3,4-dihydro-2H-1,4-benzoxazin-6-yl)acetic acid (50 mg, 0.24 mmol, 1.00 equiv), (3S)-1-[(2S)-2-amino-2-phenylethyl]pyrrolidin-3-ol (52.2 mg, 0.25 mmol, 1.05 equiv), EDCI (48.7 mg, 0.25 mmol, 1.05 equiv), HOBT (34.2 mg, 0.25 mmol, 1.05 equiv), DIEA (46.7 mg, 0.36 mmol, 1.50 equiv) and tetrahydrofuran (3 mL). The resulting solution was stirred overnight at 28° C. The crude product (100 mg) was directly purified by Prep-HPLC with the following conditions (Waters): Column, Xbridge Prep C18, 5 um, 19*150 mm; mobile phase, water with 0.03% $NH_3H_2O$ and $CH_3CN$ (15.0% $CH_3CN$ up to 34.0% in 8 min, up to 100.0% in 2 min, down to 15.0% in 2 min); Detector, UV 254&220 nm. This resulted in 61.4 mg (64%) of N-[(1S)-2-[(3S)-3-hydroxypyrrolidin-1-yl]-1-phenylethyl]-2-(3-oxo-3,4-dihydro-2H-1,4-benzoxazin-6-yl)acetamide as a white solid.

MS (ESI) m/z: 396 (M+1); $^1$H-NMR (DMSO-$d_6$, 400 MHz): δ 10.7 (s, 1H), 8.46 (d, 1H, J=8.4 Hz), 7.29 (m, 4H), 7.22 (m, 1H), 6.81-6.86 (m, 3H), 4.75-4.88 (br, 2H), 4.51 (s, 2H), 4.15 (br, 1H), 3.29-3.42 (m, 4H), 2.32-2.72 (m, 4H), 1.95 (m, 1H), 1.51 (m, 1H).

Example 3

N—((S)-2-((S)-3-hydroxypyrrolidin-1-yl)-1-phenylethyl)-N-methyl-2-(3-oxo-3,4-dihydroquinoxalin-6-yl)acetamide

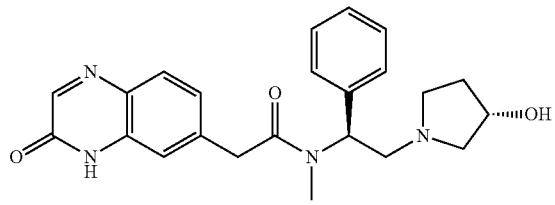 [SMILES: CN(C(=O)Cc1ccc2ncc(=O)[nH]c2c1)[C@H](CN1CC[C@H](O)C1)c1ccccc1]

A solution of 2-(3-oxo-3,4-dihydroquinoxalin-6-yl)acetic acid (50 mg, 0.24 mmol, 1.00 equiv) in tetrahydrofuran/DMF (1 mL/1 mL), EDCI (49.4 mg, 0.26 mmol) and HOBt (34.7 mg, 0.26 mmol, 1.05 equiv) was stirred for 30 min at room temperature. To this was then added (3S)-1-[(2S)-2-(methylamino)-2-phenylethyl]pyrrolidin-3-ol (56.6 mg, 0.26 mmol, 1.05 equiv). The resulting solution was allowed to react for an additional 3.0 h at 25° C. The solution was concentrated under vacuum. The residue was purified by Prep-HPLC with the following conditions (1#-Pre-HPLC-016 (Waters)): Column, Xbridge Prep C18, 5 um, 19*150 mm; mobile phase, WATER WITH 0.03% $NH_3H_2O$ and $CH_3CN$ (10.0% $CH_3CN$ up to 34.0% in 15 min, up to 100.0% in 2 min, down to 10.0% in 1 min); Detector, UV 254&220 nm. This resulted in N-[(1S)-2-[(3S)-3-hydroxypyrrolidin-1-yl]-1-phenylethyl]-N-methyl-2-(3-oxo-3,4-dihydroquinoxalin-6-yl)acetamide (45 mg) as a white solid.

LC-MS (ES, m/z) 407 (M+1); $^1$H-NMR (DMSO-$d_6$, 300 MHz): δ 12.43 (s, 1H), 8.14 (s, 1H), 7.74 (d, J=8.7 Hz, 1H), 7.38-7.22 (m, 7H), 5.88 (s, 1H), 4.84 (s, 1H), 4.20 (s, 1H), 3.99-3.82 (m, 2H), 2.75-2.60 (m, 4H), 2.75 (s, 3H), 1.95-1.93 (m, 1H), 1.55 (s, 1H).

Example 4

(S)-2-(2-oxo-2,3-dihydrobenzo[d]thiazol-5-yl)-N-(1-phenyl-2-(pyrrolidin-1-yl)ethyl)acetamide

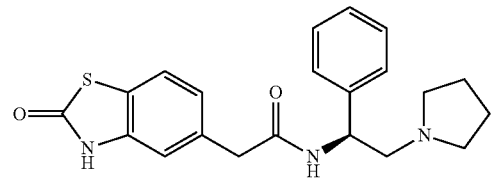 [SMILES: O=C(Cc1ccc2sc(=O)[nH]c2c1)N[C@H](CN1CCCC1)c1ccccc1]

Into a 8-mL vial, were placed a solution of 2-(2-oxo-2,3-dihydro-1,3-benzothiazol-5-yl)acetic acid (40 mg, 0.19 mmol, 1.00 equiv, obtained in scheme 6) in tetrahydrofuran (1 mL), (1S)-1-phenyl-2-(pyrrolidin-1-yl)ethan-1-amine (36 mg, 0.19 mmol, 0.99 equiv), EDCI (40 mg, 0.21 mmol, 1.09 equiv) and HOBt (28 mg, 0.21 mmol, 1.08 equiv). The resulting solution was stirred overnight at 25° C. The reaction was then quenched by the addition of 1 mL of sat. aq. $NaHCO_3$. The resulting solution was extracted with 8×2 mL of ethyl acetate. The combined organic layers were dried over anhydrous sodium sulfate and concentrated in vacuo to give crude product which was purified by Prep-TLC (MeOH/DCM=1/20). This resulted in 30 mg of the titled compound as a white solid.

LC-MS (ES, m/z) 382 (M+1); $^1$H-NMR (DMSO-$d_6$, 300 MHz): δ 11.823 (1H, s), 8.527 (1H, d, J=8.1 Hz), 7.457 (1H, d, J=8.4 Hz), 7.380-7.120 (5H, m), 7.036 (2H, d, J=5.1 Hz), 4.955-4.875 (1H, m), 3.550-3.440 (2H, m), 2.880-2.690 (1H, m), 2.680-2.550 (5H, m), 1.770-1.5 (4H, m).

Example 5

Synthesis of 2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide

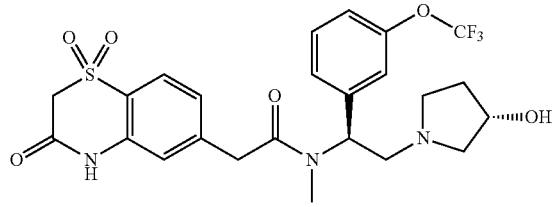

Into a 5-mL sealed tube purged and maintained with an inert atmosphere of nitrogen, was placed a solution of 2-(1,1,3-trioxo-3,4-dihydro-2H-1-[6],4-benzothiazin-6-yl)acetic acid (50 mg, 0.20 mmol, 1.00 equiv) in N,N-dimethylformamide (1 mL), EDCI (41.4 mg, 0.22 mmol, 1.10 equiv), HOBt (29.1 mg, 0.22 mmol, 1.10 equiv), triethylamine (20.8 mg, 0.21 mmol, 1.05 equiv). Then (3S)-1-[(2S)-2-(methylamino)-2-[3-(trifluoromethoxy)phenyl]ethyl]pyrrolidin-3-ol-2,2,2-trifluoroacetate (82.6 mg, 0.21 mmol, 1.05 equiv) were added at 0° C. The resulting solution was stirred for 2.0 h at 25° C. The resulting solution was diluted with 30 mL of dichloromethane, washed with 1×10 mL of sodium bicarbonate. The aqueous solution was extracted with 3×30 mL of dichloromethane. The combined organic layers were dried over anhydrous sodium sulfate and concentrated in vacuo. The crude product (70 mg) was purified by Prep-HPLC with the following conditions: Column, prep C18 5 um; 19*150 mm; mobile phase, 0.03% NH$_3$.H$_2$O and CH$_3$CN; ratio: 15%-60%; time; 10 min; Detector, UV 254 nm. This resulted in 25.7 mg (24%) of the title compound as a white solid.

LC-MS: (ES, m/z): 542 (M+1); $^1$H-NMR: (DMSO) δ 11.23 (d, J=10.5 Hz, 1H), 7.78-7.73 (m, 1H), 7.54-7.48 (m, 1H), 7.37-7.28 (m, 3H), 7.22-7.17 (m, 1H), 7.12 (s, 1H), 5.85 (s, 1H), 4.75-4.71 (m, 3H), 4.20 (s, 1H), 4.05-3.83 (m, 2H), 2.91-2.64 (m, 6H), 2.50-2.42 (m, 1H), 1.98-1.94 (m, 1H), 1.58-1.49 (m, 1H).

Example 6

N—((S)-1-(3-cyanophenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide

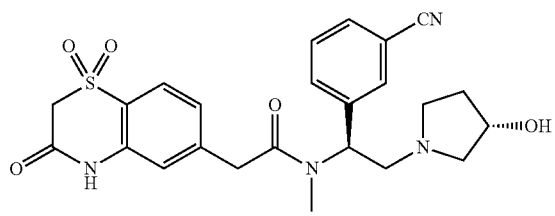 [SMILES: CN(C(=O)Cc1ccc2c(c1)NC(=O)CS2(=O)=O)[C@H](CN1CC[C@H](O)C1)c1cccc(C#N)c1]

Step (i) Synthesis of N—((S)-2-((S)-3-((tert-butyldimethylsilyl)oxy)pyrrolidin-1-yl)-1-(3-cyanophenyl)ethyl)-2-(1,1-dioxido-3-oxo-3,4-dihydro-2H-benzo[b][1,4]thiazin-6-yl)-N-methylacetamide

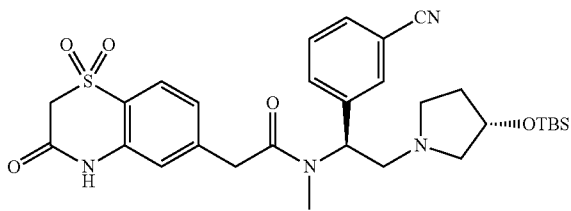 [SMILES: CN(C(=O)Cc1ccc2c(c1)NC(=O)CS2(=O)=O)[C@H](CN1CC[C@H](O[Si](C)(C)C(C)(C)C)C1)c1cccc(C#N)c1]

Into a 10-mL sealed tube, was placed a solution of 2-(1,1-dioxido-3-oxo-3,4-dihydro-2H-benzo[b][1,4]thiazin-6-yl)acetic acid (76.5 mg, 0.30 mmol, 1.00 equiv) in tetrahydrofuran (2 mL). Then EDCI (63.4 mg, 0.33 mmol, 1.10 equiv), HOBt (44.6 mg, 0.33 mmol, 1.10 equiv), 3-[(1S)-2-[(3S)-3-[(tert-butyldimethylsilyl)oxy]pyrrolidin-1-yl]-1-(methylamino)ethyl]benzonitrile (118.8 mg, 0.33 mmol, 1.10 equiv) were added at 0° C. The resulting solution was stirred for 2.0 h at 25° C. The resulting solution was diluted with 50 mL of dichloromethane. The resulting mixture was washed with 1×10 mL of sodium bicarbonate. The aqueous solution was extracted with 2×50 mL of dichloromethane. The combined organic layers were dried over anhydrous sodium sulfate and concentrated in vacuo. The residue was used in the next step without further purification.

Step (ii) Synthesis of N—((S)-1-(3-cyanophenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide

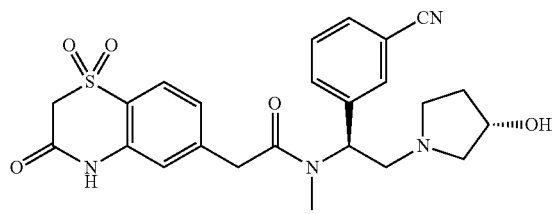 [SMILES: CN(C(=O)Cc1ccc2c(c1)NC(=O)CS2(=O)=O)[C@H](CN1CC[C@H](O)C1)c1cccc(C#N)c1]

Into a 50-mL round-bottom flask, was placed a solution of N—((S)-2-((S)-3-((tert-butyldimethyl silyl)oxy)pyrrolidin-1-yl)-1-(3-cyanophenyl)ethyl)-2-(1,1-dioxido-3-oxo-3,4-dihydro-2H-benzo[b][1,4]thiazin-6-yl)-N-methylacetamide (30 mg, 0.05 mmol, 1.00 equiv) in tetrahydrofuran (1 mL). Then TBAF (39.4 mg, 0.15 mmol, 3.00 equiv) was added. The resulting solution was stirred for 3.0 h at 25° C. The resulting mixture was concentrated in vacuo. The crude product (150 mg) was purified by Prep-HPLC with the following conditions: Column, prep C18 5 um; 19*150 mm; mobile phase, 0.05% NH$_5$O and CH$_3$CN; ratio: 10%-50%; time; 0-10 min; Detector, UV 254 nm. This resulted in 17.2 mg (71%) of the titled compound as a white solid.

LC-MS: (ES, m/z): 483 (M+1); $^1$H-NMR: (300 MHz, DMSO-d$_6$) δ 11.23 (s, 1H), 7.85-7.76 (m, 3H), 7.67-7.65 (m, 1H), 7.59-7.55 (m, 1H), 7.21-7.19 (m, 1H), 5.82-5.80 (m, 1H), 4.73-4.70 (m, 3H), 4.18 (s, 1H), 4.02-3.87 (m, 2H), 2.98-2.81 (m, 4H), 2.79-2.60 (m, 3H), 2.49-2.32 (m, 2H), 2.02-1.89 (m, 1H), 1.58-1.50 (m, 1H).

Example 7

Synthesis of N—((S)-2-((S)-3-hydroxypyrrolidin-1-yl)-1-phenylethyl)-N-methyl-2-(3-oxo-3,4-dihydro-2H-benzo[b][1,4]thiazin-6-yl)acetamide

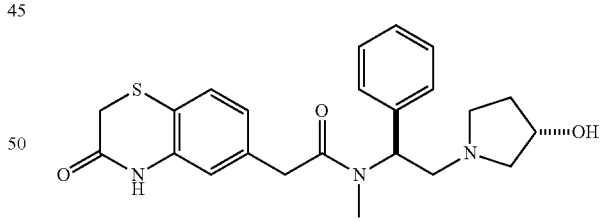

Into a 10-mL round-bottom flask, were placed a solution of 2-(3-oxo-3,4-dihydro-2H-1,4-benzothiazin-6-yl)acetic acid (Example 21-a, 20 mg, 0.09 mmol, 1.00 equiv) in tetrahydrofuran (1 mL), (3S)-1-[(2S)-2-(methylamino)-2-phenylethyl]pyrrolidin-3-ol (20 mg, 0.09 mmol, 1.01 equiv), EDCI (17.2 mg, 0.09 mmol, 1.00 equiv) and HOBT (12 mg, 0.09 mmol, 0.99 equiv). The resulting solution was stirred for 2 h at 25° C., diluted with 1 mL of water, extracted with 6×5 mL of dichloromethane. The combined organic layers were concentrated in vacuo. The crude product was purified by Prep-HPLC with the following conditions (Waters): Column, Xbridge Prep C18, 5 um, 19*150 mm; mobile phase, WATER WITH 0.03% NH$_3$H$_2$O and CH$_3$CN (10.0%

CH₃CN up to 34.0% in 15 min, up to 100.0% in 2 min, down to 10.0% in 1 min); Detector, UV 254 & 220 nm. This resulted in 23 mg of the titled compound as a white solid.

LC-MS (ES, m/z): 426 (M+1); ¹H-NMR (DMSO-d₆, 300 MHz) δ 1.5 (1H, s), 1.9 (1H, M), 2.5 (2H, m), 2.6 (8H, m), 3.6 (2H, m), 4.1 (1H, s), 4.5 (1H, s), 5.8 (1H, m), 6.8 (2H, m), 7.3 (6H, m), 10.5 (1H, s).

Example 8

2-(1,1-dioxido-3-oxo-2,3-dihydrobenzo[d]isothiazol-6-yl)-N—((S)-2-((S)-3-hydroxypyrrolidin-1-yl)-1-phenylethyl)-N-methylacetamide

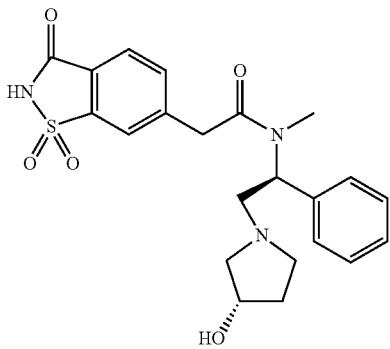 [SMILES: CN(C(=O)Cc1ccc2c(c1)S(=O)(=O)NC2=O)[C@H](CN1CC[C@H](O)C1)c1ccccc1]

Into a 10-mL round-bottom flask, were placed a solution of 2-(1,1-dioxido-3-oxo-2,3-dihydrobenzo[d]isothiazol-6-yl)acetic acid (30 mg, 0.12 mmol, 1.00 equiv) in tetrahydrofuran (1 ML), EDCI (26.3 mg, 0.14 mmol, 1.10 equiv), HOBt (18.5 mg, 0.14 mmol, 1.10 equiv), DIEA (24.1 mg, 0.19 mmol, 1.50 equiv) and (3S)-1-[(2S)-2-(methylamino)-2-phenylethyl]pyrrolidin-3-ol (30.1 mg, 0.14 mmol, 1.10 equiv). The resulting solution was stirred overnight at 25° C. The precipitate formed was collected by filtration, washed with dichloromethane and dried in an oven under reduced pressure. This resulted in 16.5 mg of the titled compound as a white solid.

LC-MS (ES, m/z) 444 (M+1); ¹H-NMR: (DMSO-d₆, 300 MHz) δ 9.864 (s, 1H), 9.355 (s, 1H), 7.236-7.967 (m, 8H), 6.146-6.178 (m, 1H), 5.461-5.548 (m, 1H), 3.866-4.079 (m, 3H), 3.686-3.606 (m, 3H), 3.606 (m, 1H), 2.894 (m, 3H), 2.273 (m, 1H), 1.764-2.082 (m, 2H).

Example 9

2-(2,2-dioxido-1,3-dihydrobenzo[c]isothiazol-6-yl)-N—((S)-2-((S)-3-hydroxypyrrolidin-1-yl)-1-(3-(trifluoromethyl)phenyl)ethyl)-N-methylacetamide

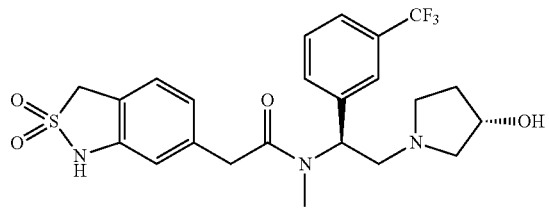 [SMILES: CN(C(=O)Cc1ccc2c(c1)NS(=O)(=O)C2)[C@H](CN1CC[C@H](O)C1)c1cccc(C(F)(F)F)c1]

Into a 10-mL sealed tube, was placed a solution of 2-(2,2-dioxido-1,3-dihydrobenzo[c]isothiazol-6-yl)acetic acid (34 mg, 0.15 mmol, 1.00 equiv) in N,N-dimethylformamide (1 mL). Then EDCI (32 mg, 0.17 mmol, 1.10 equiv), HOBt (22 mg, 0.16 mmol, 1.10 equiv), triethylamine (16 mg, 0.16 mmol, 1.05 equiv) and (3S)-1-[(2S)-2-(methylamino)-2-[3-(trifluoromethyl)phenyl]ethyl]pyrrolidin-3-ol 2,2,2-trifluoroacetic acid (62 mg, 0.15 mmol, 1.00 equiv) were added at 0° C. The resulting solution was stirred for 2.0 h at 25° C. The resulting solution was diluted with 20 mL of dichloromethane, washed with 1×10 mL of sodium bicarbonate. The aqueous solution was extracted with 2×30 mL of dichloromethane. The combined organic layers were dried over anhydrous sodium sulfate and concentrated in vacuo. The crude product (70 mg) was purified by Prep-HPLC with the following conditions: Column, prep C18 5 um; 19*150 mm; mobile phase, 0.03% NH₃. H₂O and CH₃CN; ratio: 10%-29%; time; 0-9 min; Detector, UV 254 nm. This resulted in 31.6 mg (40%) of the titled compound as an off-white solid.

LC-MS: (ES, m/z): 498 (M+1); ¹H-NMR: (300 MHz, DMSO-d₆) δ10.44-10.36 (m, 1H), 7.63-7.47 (m, 4H), 7.21-7.18 (m, 1H), 6.85-83 (m, 1H), 6.75 (s, 1H), 5.91-5.86 (m, 1H), 4.48 (s, 2H), 4.19 (s, 1H), 3.85-3.68 (m, 2H), 3.11-3.07 (m, 1H), 2.94-2.80 (m, 2H), 2.65-2.62 (m, 4H), 2.59 (s, 1H), 2.42-2.38 (m, 1H), 1.98-1.91 (m, 1H), 1.57-1.52 (m, 1H).

Example 10

5-(2-(((S)-2-((S)-3-hydroxypyrrolidin-1-yl)-1-phenylethyl)(methyl)amino)-2-oxoethyl)-1,3-dihydrobenzo[c]isothiazol-1-ium 2,2-dioxide 2,2,2-trifluoroacetate

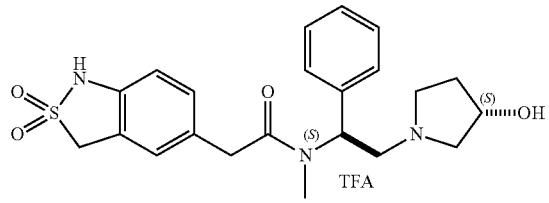

Into a 20-mL round-bottom flask, was placed a solution of 2-(2,2-dioxido-1,3-dihydrobenzo[c]isothiazol-5-yl)acetic acid (80 mg, 0.35 mmol, 1.00 equiv), HOBt (50 mg, 0.37 mmol, 1.05 equiv), EDCI (74 mg, 0.39 mmol, 1.05 equiv) and (S)-1-((S)-2-(methylamino)-2-phenylethyl)pyrrolidin-3-ol (74 mg, 0.34 mmol, 1.10 equiv) in tetrahydrofuran (5 mL). The resulting solution was stirred for 6 h at 25° C. The resulting mixture was concentrated in vacuo. The residue was purified by Prep-HPLC with the following conditions (1#-Pre-HPLC-016 (Waters)): Column, Xbridge Prep C18, 5 um, 19*150 mm; mobile phase, WATER WITH 0.05% TFA and CH₃CN (10.0% CH₃CN up to 30% in 15 min, up to 100.0% in 2 min, down to 10.0% in 1 min); Detector, UV 254&220 nm to result in 16.6 mg (11%) of the title compound as a white solid.

LC-MS: (ES, m/z) 430 (M+1); ¹H-NMR (DMSO-d₆, 300 MHz) δ 7.373-7.449 (m, 3H), 7.184-7.283 (m, 4H), 6.823-6.849 (m, 1H), 6.252-6.299 (m, 1H), 4.585 (s, 1H), 4.399 (s, 2H), 3.738-3.883 (m, 6H), 3.400-3.576 (m, 2H), 2.787 (s, 3H), 1.800-2.400 (br, 2H).

Example 11

N—((S)-1-(3-(difluoromethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide

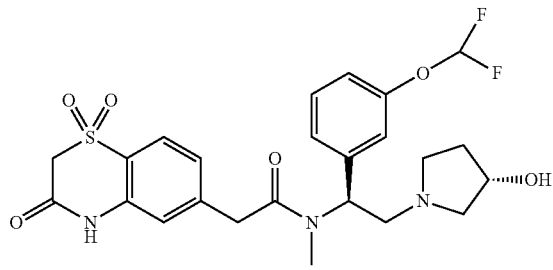 [SMILES: CN(C(=O)Cc1ccc2c(c1)NC(=O)CS2(=O)=O)[C@H](CN1CC[C@H](O)C1)c1cccc(OC(F)F)c1]

Step (i) Synthesis of N—((S)-2-((S)-3-((tert-butyldimethylsilyl)oxy)pyrrolidin-1-yl)-1-(3-(difluoromethoxy)phenyl)ethyl)-2-(1,1-dioxido-3-oxo-3,4-dihydro-2H-benzo[b][1,4]thiazin-6-yl)-N-methylacetamide

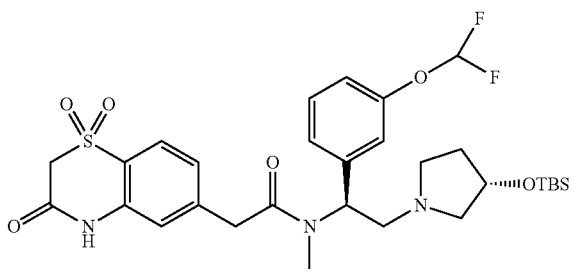 [SMILES: CN(C(=O)Cc1ccc2c(c1)NC(=O)CS2(=O)=O)[C@H](CN1CC[C@H](O[Si](C)(C)C(C)(C)C)C1)c1cccc(OC(F)F)c1]

Into a 100-mL 3-necked round-bottom flask purged and maintained with an inert atmosphere of nitrogen, was placed a solution of 2-(1,1-dioxido-3-oxo-3,4-dihydro-2H-benzo[b][1,4]thiazin-6-yl)acetic acid (482 mg, 1.89 mmol, 1.00 equiv) in N,N-dimethylformamide (15 mL). Then EDCI (397 mg, 2.07 mmol, 1.10 equiv) and HOBt (279 mg, 2.06 mmol, 1.10 equiv) was added at 0-5° C. The resulting solution was stirred for 20 min at 0° C. To this was added a solution of [(1S)-2-[(3S)-3-[(tert-butyldimethylsilyl)oxy]pyrrolidin-1-yl]-1-[3-(difluoromethoxy)phenyl]ethyl](methyl)amine (754 mg, 1.88 mmol, 1.00 equiv) in N,N-dimethylformamide (5 mL) at 0-50° C. The resulting solution was stirred for 2 h at 0-25° C. The reaction was then quenched by the addition of water. The resulting solution was extracted with ethyl acetate and the organic layers combined. The resulting mixture was washed with sodium bicarbonate (aq) and brine. The organic layers dried over anhydrous sodium sulfate and concentrated under vacuum. The residue was applied onto a silica gel column and eluted with dichloromethane/methanol (60/1-40/1). This resulted in 1.16 g (96%) of the titled compound as a yellow solid.

Step (ii) N—((S)-1-(3-(difluoromethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide

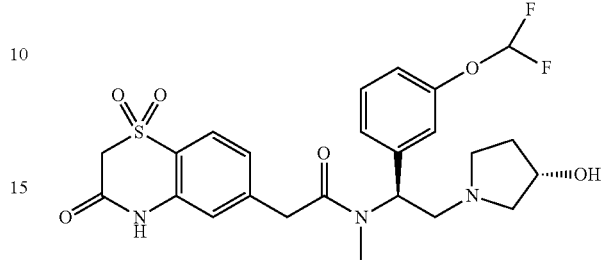

Into a 100-mL purged and maintained with an inert atmosphere of nitrogen, was placed a solution of N—((S)-2-((S)-3-((tert-butyldimethylsilyl)oxy)pyrrolidin-1-yl)-1-(3-(difluoromethoxy)phenyl)ethyl)-2-(1,1-dioxido-3-oxo-3,4-dihydro-2H-benzo[b][1,4]thiazin-6-yl)-N-methylacetamide, obtained in the previous step, (553 mg, 0.87 mmol, 1.00 equiv) in tetrahydrofuran (8 mL), TBAF.3H$_2$O (549 mg, 2.00 equiv). The resulting solution was stirred for 5 h at 25° C. The resulting mixture was concentrated under vacuum. The resulting solution was extracted with ethyl acetate and the organic layers combined and dried over anhydrous sodium sulfate and concentrated under vacuum. The crude product (300 mg) was purified by Prep-HPLC with the following conditions (Bridge): Column, RP C18 5 um; 19*150 mm; mobile phase, 0.03% NH$_3$. H$_2$O and CH$_3$CN; ratio: 20%-52%; time; 0-10 min; Detector, UV 254 nm. This resulted in 151 mg (34%) of the title compound as a white solid.

LC-MS (ES, m/z): 524 (M+1); $^1$H-NMR (CD$_3$OD, 300 MHz) δ 7.84 (d, J=8.0 Hz, 1H), 7.42-7.38 (m, 1H), 7.27 (d, J=8.0 Hz, 1H), 7.22-7.20 (m, 2H), 7.18-7.10 (m, 2H), 6.83 (t, J=74.0 Hz, 1H), 6.05-6.01 (m, 1H), 4.87 (s, 2H), 4.83 (s, 1H), 4.38-4.34 (m, 1H), 4.06-3.99 (m, 1H), 3.91-3.87 (m, 1H), 3.10-2.94 (m, 2H), 2.86 (s, 3H), 2.84-2.78 (m, 1H), 2.61-2.52 (m, 2H), 2.17-2.12 (m, 1H), 1.75-1.71 (m, 1H).

Example 12

2-(3,3-difluoro-2-oxoindolin-6-yl)-N—((S)-2-((S)-3-hydroxypyrrolidin-1-yl)-1-phenylethyl)-N-methylacetamide

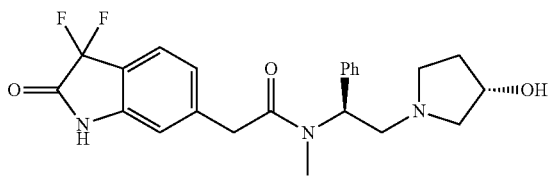 [SMILES: CN(C(=O)Cc1ccc2c(c1)NC(=O)C2(F)F)[C@H](CN1CC[C@H](O)C1)c1ccccc1]

Step (i) Synthesis of 2-(3,3-difluoro-1-(4-methoxy-benzyl)-2-oxoindolin-6-yl)-N—((S)-2-((S)-3-hydroxypyrrolidin-1-yl)-1-phenylethyl)-N-methylacetamide

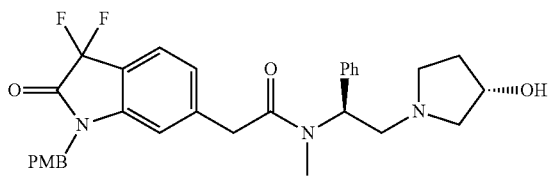

Into a 8-mL sealed tube, was placed 2-[3,3-difluoro-1-[(4-methoxyphenyl)methyl]-2-oxo-2,3-dihydro-1H-indol-6-yl]acetic acid (280 mg, 0.81 mmol, 1.00 equiv) in N,N-dimethylformamide (5 mL). This was following by addition of EDCI (310 mg, 1.62 mmol, 2.01 equiv) and HOBt (163 mg, 1.21 mmol, 1.50 equiv). The resulting solution was stirred for 30 mins at 0° C. Then (3S)-1-[(2S)-2-(methylamino)-2-phenylethyl]pyrrolidin-3-ol (178 mg, 0.81 mmol, 1.00 equiv) was added. The resulting solution was stirred for 2 h at 25° C. The resulting mixture was concentrated under vacuum. The residue was applied onto a silica gel column and eluted with dichloromethane/methanol/ammonia (50:1:1). This resulted in 330 mg (74%) of 2-[3,3-difluoro-1-[(4-methoxyphenyl)methyl]-2-oxo-2,3-dihydro-1H-indol-6-yl]-N-[(1S)-2-[(3S)-3-hydroxypyrrolidin-1-yl]-1-phenylethyl]-N-methylacetamide as brown oil.

Step (ii) Synthesis of 2-(3,3-difluoro-2-oxoindolin-6-yl)-N—((S)-2-((S)-3-hydroxypyrrolidin-1-yl)-1-phenylethyl)-N-methylacetamide

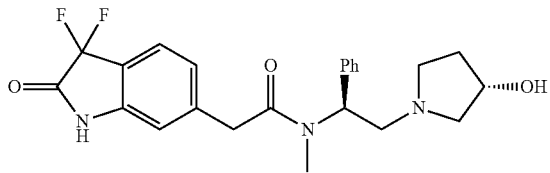 [SMILES: CN(C(=O)Cc1ccc2c(c1)NC(=O)C2(F)F)[C@H](CN1CC[C@H](O)C1)c1ccccc1]

Into a 50-mL round-bottom flask, was placed 2-[3,3-difluoro-1-[(4-methoxyphenyl)methyl]-2-oxo-2,3-dihydro-1H-indol-6-yl]-N-[(1S)-2-[(3S)-3-hydroxypyrrolidin-1-yl]-1-phenylethyl]-N-methylacetamide (300 mg, 0.55 mmol, 1.00 equiv) in CH3CN (8 mL) Then a solution of (NH4)2Ce(NO3)6 (900 mg, 1.64 mmol, 3.01 equiv) in water (4 mL) was added. The resulting solution was stirred for 1 h at 300° C. The resulting solids were filtered out and washed with ethyl acetate. The filtrate was concentrated under vacuum. The residue was applied onto a silica gel column and eluted with dichloromethane/methanol (100/1). This resulted in 13 mg (6%) of 2-(3,3-difluoro-2-oxo-2,3-dihydro-1H-indol-6-yl)-N-[(1S)-2-[(3S)-3-hydroxypyrrolidin-1-yl]-1-phenylethyl]-N-methylacetamide as a white solid.

MS (ES, m/z): 430 (M+1); $^1$H-NMR (DMSO-$d_6$, 300 MHz) δ 11.18 (s, 1H), 7.58 (d, J=7.5 Hz, 1H), 7.40-7.20 (m, 5H), 7.05 (d, J=7.8 Hz, 1H), 7.00-6.85 (m, 1H), 5.85 (s, 1H), 5.20-4.60 (m, 1H), 4.18 (s, 1H), 3.95 (d, J=14.7 Hz, 1H), 3.75 (d, J=15.9 Hz, 1H), 3.15-3.00 (m, 1H), 3.00-2.90 (m, 1H), 2.90-2.78 (m, 1H), 2.78-2.60 (m, 4H), 2.50-2.30 (m, 2H), 2.05-1.85 (m, 1H), 1.50 (bs, 1H); F-NMR: (DMSO-$d_6$, 300 MHz): −110 (s, 2F).

Example 13

2-(3,3-difluoro-2-oxoindolin-6-yl)-N—((S)-2-((S)-3-hydroxypyrrolidin-1-yl)-1-phenylethyl)acetamide

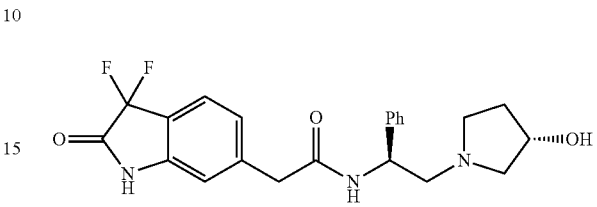

Step (i) Synthesis of 2-(3,3-difluoro-1-(4-methoxy-benzyl)-2-oxoindolin-6-yl)-N—((S)-2-((S)-3-hydroxypyrrolidin-1-yl)-1-phenylethyl)acetamide

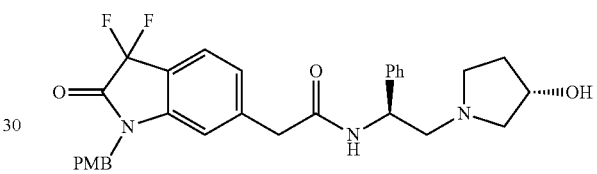

Into a solution of 2-[3,3-difluoro-1-[(4-methoxyphenyl)methyl]-2-oxo-2,3-dihydro-1H-indol-6-yl]acetic acid (300 mg, 0.86 mmol, 1.00 equiv) in N,N-dimethylformamide (3 mL) was added EDCI (332 mg, 1.73 mmol, 2.01 equiv), HOBt (175 mg, 1.30 mmol, 1.50 equiv). After stirring for 10 min, (3S)-1-[(2S)-2-amino-2-phenylethyl]pyrrolidin-3-ol (190 mg, 0.92 mmol, 1.07 equiv) was added. The resulting solution was stirred for 2 h at room temperature and concentrated under vacuum. The residue was applied onto a silica gel column with dichloromethane/methanol=50:1. This resulted in 370 mg (80%) of 2-[3,3-difluoro-1-[(4-methoxyphenyl)methyl]-2-oxo-2,3-dihydro-1H-indol-6-yl]-N-[(1S)-2-[(3S)-3-hydroxypyrrolidin-1-yl]-1-phenylethyl]acetamide as a white solid. MS (ES, m/z): 536 (M+1)

Step (ii) Synthesis of 2-(3,3-difluoro-2-oxoindolin-6-yl)-N—((S)-2-((S)-3-hydroxypyrrolidin-1-yl)-1-phenylethyl)acetamide

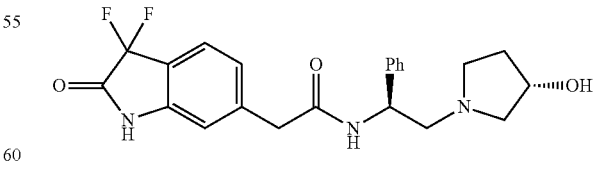

Into a solution of 2-[3,3-difluoro-1-[(4-methoxyphenyl)methyl]-2-oxo-2,3-dihydro-1H-indol-6-yl]-N-[(1S)-2-[(3S)-3-hydroxypyrrolidin-1-yl]-1-phenylethyl]acetamide (370 mg, 0.69 mmol, 1.00 equiv) in CH3CN (8 mL)/water (4 mL) was added (NH4)2Ce(NO3)6 (1.14 g, 2.08 mmol, 3.01 equiv). The resulting solution was stirred for 1 h at 30° C.

The resulting solids were filtered out. The filtrate was concentrated under vacuum. The residue was applied onto a silica gel column with dichloromethane/methanol (100/1). This resulted in 14.1 mg (5%) of 2-(3,3-difluoro-2-oxo-2,3-dihydro-1H-indol-6-yl)-N-[(1S)-2-[(3S)-3-hydroxypyrrolidin-1-yl]-1-phenylethyl]acetamide as a white solid. MS (ES, m/z): 416 (M+1); ¹H-NMR (DMSO-d6, 300 MHz) δ 11.17 (s, 1H), 8.58 (d, J=7.8 Hz, 1H), 7.54 (d, J=7.8 Hz, 1H), 7.48-7.18 (m, 5H), 7.05 (d, J=7.8 Hz, 1H), 6.97 (s, 1H), 4.89 (s, 1H), 4.16 (s, 1H), 3.63-3.42 (dd, J=14.4, 21.5 Hz, 2H), 2.84-2.59 (m, 3H), 2.46-2.30 (m, 2H), 2.05-1.85 (m, 1H), 1.50 (bs, 1H); F-NMR-(DMSO-d6, 300 MHz): −110 (s, 2F).

Example 14

2-(1,1-dioxido-3-oxo-3,4-dihydro-2H-benzo[b][1,4]thiazin-6-yl)-N-ethyl-N—((S)-2-((S)-3-hydroxypyrrolidin-1-yl)-1-(3-(trifluoromethoxy)phenyl)ethyl)acetamide

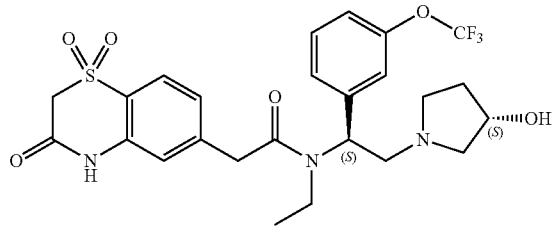

Step (i) Synthesis of N—((S)-2-((S)-3-((tert-butyldimethylsilyl)oxy)pyrrolidin-1-yl)-1-(3-(trifluoromethoxy)phenyl)ethyl)-2-(1,1-dioxido-3-oxo-3,4-dihydro-2H-benzo[b][1,4]thiazin-6-yl)-N-ethylacetamide

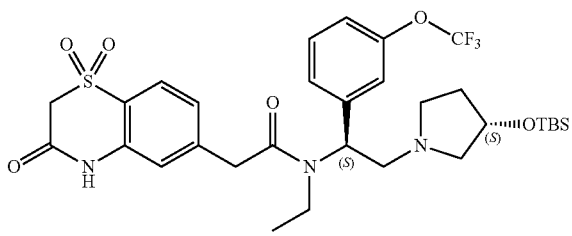

Into a 50-mL round-bottom flask purged and maintained with an inert atmosphere of nitrogen, was placed a solution of 2-(1,1-dioxido-3-oxo-3,4-dihydro-2H-benzo[b][1,4]thiazin-6-yl)acetic acid (62.0 mg, 0.24 mmol, 1.05 equiv) in N,N-dimethylformamide (10 mL). Then EDCI (67 mg, 0.35 mmol, 1.51 equiv) and HOBt (46 mg, 0.34 mmol, 1.47 equiv) were added at 0° C. After stirred for 5 min, [(1S)-2-[(3S)-3-[(tert-butyldimethylsilyl)oxy]pyrrolidin-1-yl]-1-[3-(trifluoromethoxy)phenyl]ethyl](ethyl)amine (100 mg, 0.23 mmol, 1.00 equiv) was added. The resulting solution was stirred for 2 h at room temperature. The resulting solution was diluted with 60 mL of ethyl acetate. The resulting mixture was washed with water (3×20 mL), brine (2×20 mL), 10% ammonia aqueous (4×20 mL) and brine (3×20 mL). The mixture was dried over anhydrous sodium sulfate and concentrated under vacuum. This resulted in 143 mg (crude) of the title compound as a light yellow solid. MS (ES, m/z): 670 (M+1).

Step (ii) Synthesis of 2-(1,1-dioxido-3-oxo-3,4-dihydro-2H-benzo[b][1,4]thiazin-6-yl)-N-ethyl-N—((S)-2-((S)-3-hydroxypyrrolidin-1-yl)-1-(3-(trifluoromethoxy)phenyl)ethyl)acetamide

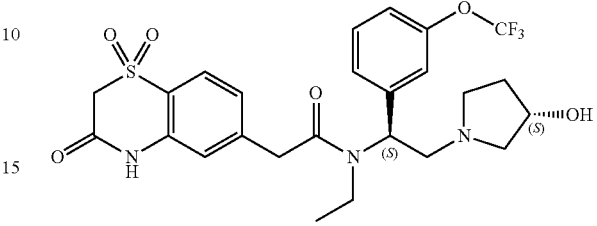

Into a 50-mL round-bottom flask, was placed a solution of N—((S)-2-((S)-3-((tert-butyldimethylsilyl)oxy)pyrrolidin-1-yl)-1-(3-(trifluoromethoxy)phenyl)ethyl)-2-(1,1-dioxido-3-oxo-3,4-dihydro-2H-benzo[b][1,4]thiazin-6-yl)-N-ethylacetamide (459 mg, 0.69 mmol, 1.00 equiv) in methanol (15 mL). This was followed by the addition of conc. HCl aqueous (1.5 mL) dropwise with stirring at 0° C. The resulting solution was stirred for 3 h at room temperature. The resulting mixture was concentrated under vacuum. The resulting solution was diluted with 50 mL of H₂O. The pH value of the solution was adjusted to 7-8 with saturated aqueous sodium bicarbonate. The resulting solution was extracted with dichloromethane (5×20 mL) and the organic layers combined. The resulting mixture was washed with brine (3×20 mL), dried over anhydrous sodium sulfate and concentrated under vacuum. The residue was purified by Flash-Prep-HPLC with the following conditions (IntelFlash-1): Column, C18; mobile phase, H₂O:MeCN=100:0 at 5 min, then increasing to H₂O:MeCN=50:50 within 40 min; Detector, UV 254 nm. That resulted in 25 mg of Synthesis of 2-(1,1-dioxido-3-oxo-3,4-dihydro-2H-benzo[b][1,4]thiazin-6-yl)-N-ethyl-N—((S)-2-((S)-3-hydroxypyrrolidin-1-yl)-1-(3-(trifluoromethoxy)phenyl)ethyl)acetamide as a white solid. MS (ES, m/z): 556 (M+1); 1H-NMR (DMSO, 400 Hz) δ 11.23 (s, 1H), 7.76-7.74 (m, 1H), 7.50-7.14 (m, 6H), 5.69 (m, 1H), 4.70-4.74 (m, 3H), 4.16 (m, 1H), 4.01-4.05 (m, 1H), 3.79-3.90 (m, 1H), 3.22-3.32 (m, 2H), 2.99 (m, 1H), 2.80-2.82 (m, 1H), 2.67-2.68 (m, 1H), 2.33-2.51 (m, 2H), 1.91-1.96 (m, 1H), 1.52 (m, 1H), 0.88-0.92 (m, 2H), 0.67-0.70 (m, 1H)

Example 15

2-(1,1-dioxido-3-oxo-3,4-dihydro-2H-benzo[b][1,4]thiazin-6-yl)-N—((S)-2-((S)-3-methoxypyrrolidin-1-yl)-1-(3-(trifluoromethoxy)phenyl)ethyl)-N-methylacetamide

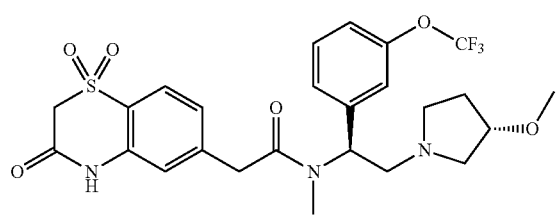 [SMILES: CO[C@H]1CCN(C[C@H](c2cccc(OC(F)(F)F)c2)N(C)C(=O)Cc2ccc3c(c2)NC(=O)CS3(=O)=O)C1]

Into a solution of 2-(1,1-dioxido-3-oxo-3,4-dihydro-2H-benzo[b][1,4]thiazin-6-yl)acetic acid (200 mg, 0.78 mmol, 1.10 equiv) in N,N-dimethylformamide (30 mL) was added EDCI (204 mg, 1.06 mmol, 1.49 equiv), HOBT (140 mg, 1.04 mmol, 1.45 equiv). Then [(1S)-2-[(3S)-3-methoxypyrrolidin-1-yl]-1-[3-(trifluoromethoxy)phenyl]ethyl](methyl)amine (227 mg, 0.71 mmol, 1.00 equiv) was added. The resulting solution was stirred for 6 h at room temperature. The reaction was then quenched by the addition 10 ml of water. The resulting aqueous solution was extracted with 3×30 mL of ethyl acetate. The organic layers was combined and dried over sodium sulfate and concentrated under vacuum. The residue was applied onto a silica gel column and eluted with dichloromethane/methanol (10:1). This resulted in 28.9 mg (7%) of 2-(1,1-dioxido-3-oxo-3,4-dihydro-2H-benzo[b][1,4]thiazin-6-yl)-N—((S)-2-((S)-3-methoxypyrrolidin-1-yl)-1-(3-(trifluoromethoxy)phenyl)ethyl)-N-methylacetamide as a white solid.

MS (ES, m/z): 556 (M+1); $^1$H-NMR (DMSO-$d_6$, 400 MHz) δ 11.23 (1, 1H), 7.76 (m, 7H), 5.82 (t, J=7.2 Hz, 1H), 4.70 (s, 2H), 3.99-3.81 (m, 3H), 3.32-2.33 (m, 12H), 1.99-1.91 (m. 1H), 1.63 (s, 1H).

Example 16

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-(2,2,2-trifluoroethyl)acetamide 2,2,2-trifluoroacetate

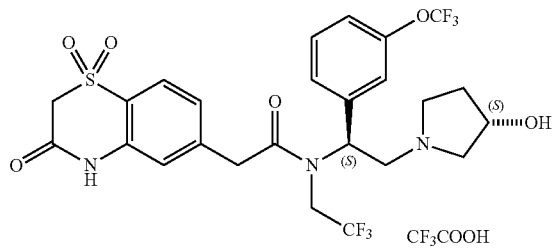

2,2-(1,1-dioxido-3-oxo-3,4-dihydro-2H-benzo[b][1,4]thiazin-6-yl)acetic acid (1 g, 3.92 mmol 1.00 equiv) was added into 10 ml of phosphoryl trichloride at room temperature. The resulting solution was stirred for 30 min at 85° C. in an oil bath. The resulting mixture was concentrated under vacuum. The crude product was dissolved in 5 ml THF. The resulting solution was added into a solution of [(1S)-2-[(3S)-3-[(tert-butyldimethyl silyl)oxy]pyrrolidin-1-yl]-1-[3-(trifluoromethoxy)phenyl]ethyl](2,2,2-trifluoroethyl)amine (1.9 g, 3.90 mmol, 1.00 equiv) in THF (10 mL), dropwised with stirring at 0° C. under nitrogen gas. The mixture was stirred for 2 hours at room temperature. Removing the solvent, the residue was purified by Prep-HPLC with the following conditions (waters): Column, SunFire Prep C18, 19*150 mm 5 um; Mobile phase: WATER WITH 0.05% TFA and MeCN (30% MeCN up to 70% in 30 min, up to 100% in 2 min); Detector, UV 254 nm. This resulted in 14 mg of the title compound as a white solid. LC-MS (ES, m/z): (M+1) 610; $^1$H-NMR (300 MHz, DMSO-d6): δ 11.20 (s, 1H), 7.76 (d, J=8.1 Hz, 1H), 7.39-7.55 (m, 4H), 7.08-7.15 (m, 2H), 5.57 (br, 1H), 4.72 (s, 2H), 4.41-4.58 (m, 3H) 3.78-4.16 (m, 5H), 3.65 (t, J=6.3 HZ, 1H), 2.02 (br, 1H), 1.70-1.80 (m, 1H), 1.55-1.64 (m, 2H), 1.22 (s, 1H);

Example 17

2-(1,1-dioxido-3-oxo-3,4-dihydro-2H-benzo[b][1,4]thiazin-6-yl)-N-(2-((S)-3-hydroxypyrrolidin-1-yl)-1-(tetrahydro-2H-pyran-4-yl)ethyl)-N-methylacetamide-2,2,2-trifluoroacetate

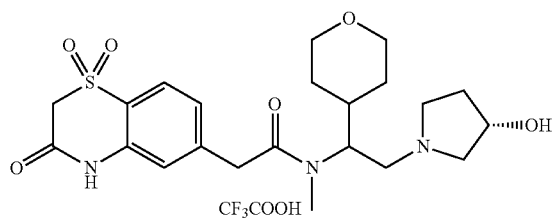

Into a solution of 2-(1,1-dioxido-3-oxo-3,4-dihydro-2H-benzo[b][1,4]thiazin-6-yl)acetic acid (127 mg, 0.50 mmol, 1.00 equiv) in N,N-dimethylformamide (5 mL) was added N-(3-dimethylaminopropyl)-N'-ethylcarbodiimide hydrochloride (105 mg, 0.55 mmol, 1.10 equiv), 1-Hydroxybenzotrizole (74 mg, 0.55 mmol, 1.10 equiv). The resulting solution was stirred for 30 min at 0° C. in a water/ice bath. Then (3S)-1-[2-(methylamino)-2-(oxan-4-yl)ethyl]pyrrolidin-3-ol (120 mg, 0.53 mmol, 1.05 equiv) was added. The resulting solution was allowed to react, with stirring, for an additional 2 h at room temperature. The resulting mixture was concentrated under vacuum. The crude product (150 mg) was purified by Flash-Prep-HPLC with the following conditions (IntelFlash-1): Column, C18 silica gel; mobile phase, CH3CN/0.5% aq TFA=1:100 increasing to CH3CN/0.5% aq TFA=35:100 within 22 min; Detector, UV 254 nm. This resulted in 60 mg (21%) of the title compound as a white solid.

MS (ES, m/z): 466 [M−CF$_3$COOH+H]$^+$; $^1$H-NMR (CD$_3$OD, 400 MHz) δ 7.82-7.84 (d, J=8 Hz, 1H), 7.22-7.24 (d, J=8 Hz, 1H), 7.12 (s, 1H), 4.71-4.88 (m, 1H), 4.56-4.69 (m, 1H), 4.43-4.45 (m, 1H), 3.78-4.01 (m, 5H), 3.42-3.67 (m, 5H), 3.19-3.22 (m, 1H), 3.02 (s, 3H), 1.92-2.45 (m, 2H), 1.67-1.88 (m, 2H), 1.35-1.45 (m, 2H), 1.21-1.25 (m, 1H).

Example 18

3-((S)-2-((S)-3-hydroxypyrrolidin-1-yl)-1-(N-methyl-2-(2-oxo-2,3-dihydrobenzo[d]thiazol-5-yl)acetamido)ethyl)benzoic acid

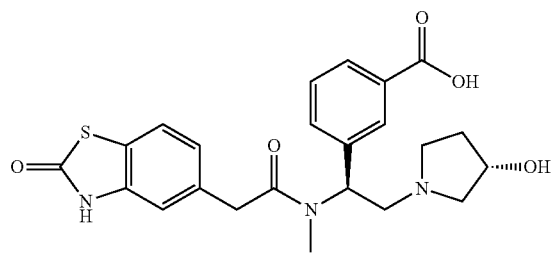

Into a 8.0 mL sealed tube, was placed a solution of N-[(1S)-2-[(3S)-3-[(tert-butyldimethylsil-yl)oxy]pyrrolidin-1-yl]-1-(3-cyanophenyl)ethyl]-N-methyl-2-(2-oxo-2,3-dihydro-1,3-benzothiazol-5-yl)a-cetamide (200 mg, 0.36 mmol, 1.00 equiv) in tetrahydrofuran (1.0 mL) and methanol (1.0 mL). Then water (2.0 mL) and potassium hydroxide (245.3 mg, 4.37 mmol, 12.04 equiv) were added. The resulting solution was stirred for 15 h at 75° C. and cooled to room temperature naturally. The pH value of the solution was adjusted to 2 with aqueous hydrogen chloride (2 mol/L) and concentrated under vacuum. The residue was purified by Prep-HPLC with the following conditions: Column, X-Bridge, C18, 15 cm; mobile phase, Water (contained 0.2% of $NH_4HCO_3$) and acetonitrile (5% acetonitrile up to 25% in 10 min, up to 100% in 1 min, down to 5% in 1 min); Detector, UV220/254 nm. This resulted in 70 mg (42%) of title compound as a white solid.

MS (ES, m/z): 456 (M+1); $^1$H-NMR (DMSO-$d_6$, 400 MHz) δ 7.85-7.84 (m, 2H), 7.53-7.44 (m, 3H), 7.10 (s, 1H), 7.04-6.95 (m, 1H), 5.91 (t, J=8.0 Hz, 1H), 4.21-4.17 (m, 1H), 3.87 (d, J=15.6 Hz, 1H), 3.73 (d, J=16.0 Hz, 1H), 3.16 (t, J=8.0 Hz, 1H), 2.84-2.72 (m, 3H), 2.62-2.54 (m, 3H), 2.47-2.39 (m, 2H), 1.98-1.93 (m, 1H), 1.54-1.45 (m, 1H)

Example 19

3-((S)-2-((S)-3-hydroxypyrrolidin-1-yl)-1-(N-methyl-2-(2-oxo-2,3-dihydrobenzo[d]thiazol-5-yl)acetamido)ethyl)benzamide

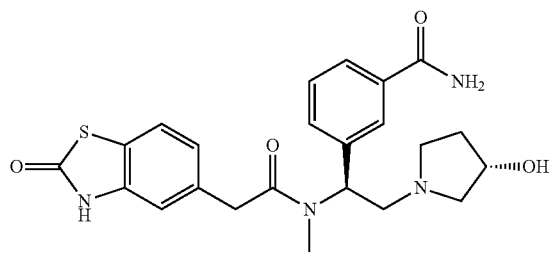

Into a 8.0 mL sealed tube, was placed a solution of N-[(1S)-2-[(3S)-3-[(tert-butyldimethylsilyl)ox-y]pyrrolidin-1-yl]-1-(3-cyanophenyl)ethyl]-N-methyl-2-(2-oxo-2,3-dihydro-1,3-benzothiazol-5-yl)aceta-mide (80 mg, 0.15 mmol, 1.00 equiv) in tetrahydrofuran (0.4 mL) and methanol (0.4 mL). Then water (0.8 mL) and potassium hydroxide (98.1 mg, 1.7 mmol, 12.04 equiv) were added. The resulting solution was stirred for 15 h at 50° C. and concentrated under vacuum. The residue was purified by Prep-HPLC with the following conditions: Column, X-Bridge, C18, 15 cm; mobile phase, Water (contained 0.2% of $NH_4HCO_3$) and acetonitrile (7% acetonitrile up to 25% in 10 min, up to 100% in 1 min, down to 7% in 1 min); Detector, UV220/254 nm. This resulted in 32 mg (48%) of 3-((S)-2-((S)-3-hydroxypyrrolidin-1-yl)-1-(N-methyl-2-(2-oxo-2,3-dihydrobenzo[d]thiazol-5-yl)acetamido)ethyl)benzamide as a white solid. MS (ES, m/z): 455 (M+1); $^1$H-NMR (DMSO-$d_6$, 300 MHz) δ 11.80-11.79 (m, 1H), 7.97 (s, 1H), 7.80-7.73 (m, 2H), 7.45-7.32 (m, 4H), 7.08-6.95 (m, 2H), 5.88-5.82 (m, 1H), 4.92-4.83 (m, 1H), 4.18-4.05 (m, 1H), 3.86-3.81 (m, 1H), 3.70-3.64 (m, 1H), 3.08 (t, J=11.4 Hz, 1H), 2.82-2.55 (m, 6H), 2.38-2.22 (m, 3H), 1.95-1.82 (m, 1H), 1.48-1.35 (m, 1H)

Example 20

(S)-2-(3-benzyl-2-oxo-2,3-dihydrobenzo[d]oxazol-5-yl)-N-(1-(3-hydroxyphenyl)-2-(pyrrolidin-1-yl)ethyl)acetamide

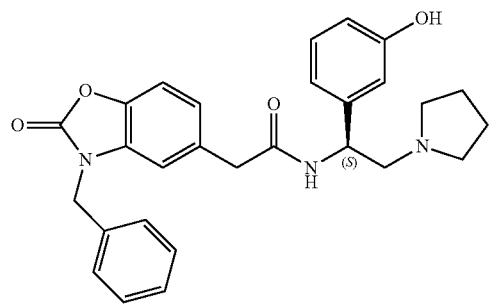

Hydrogenolysis of (S)-2-(3-benzyl-2-oxo-2,3-dihydrobenzo[d]oxazol-5-yl)-N-(1-(3-(benzyloxy)phenyl)-2-(pyrrolidin-1-yl)ethyl)acetamide in methanol at room temperature afforded the title compound in 64% yield as a while solid.

Melting point: 104-106° C.; $^1$H-NMR (400 MHz, DMSO-$d_6$): δ 12.00 (bs, 1H), 9.36 (bs, 1H), 8.45 (d, J=8.0 Hz, 1H), 7.42-7.33 (m, 6H), 7.13-7.07 (m, 3H), 6.74 (d, J=7.5 Hz, 2H), 6.66 (d, J=9.1 Hz, 1H), 5.04 (s, 2H), 4.84 (d, J=5.9 Hz, 1H), 3.50 (d, J=5.9 Hz, 2H), 2.72 (s, 1H), 2.59-2.38 (m, 4H), 1.66 (bs, 4H); IR (KBr, cm$^1$): 3275, 3064, 2970, 1774, 1659, 1589, 1550, 1492, 1466, 1384, 1350; MS (ESI) m/z: 472.0 (M+1).

Example 21

N—((S)-1-(3-(1H-tetrazol-5-yl)phenyl)-2-((S)-3-hydroxypyrrolidin-1-yl)ethyl)-N-methyl-2-(1-methyl-2,2-dioxido-1,3-dihydrobenzo[c]isothiazol-6-yl)acetamide

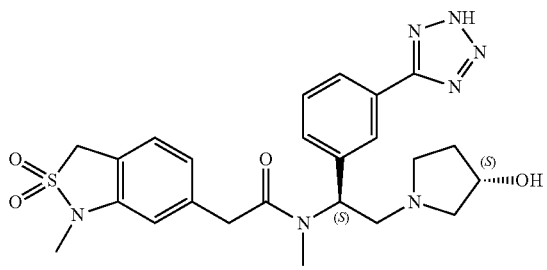

The title compound was obtained as white solid by treating N—((S)-1-(3-cyanophenyl)-2-((S)-3-hydroxypyrrolidin-1-yl)ethyl)-N-methyl-2-(1-methyl-2,2-dioxido-1,3-dihydrobenzo[c]isothiazol-6-yl)acetamide with sodium azide following standard procedure known in the literature.

$^1$H-NMR (400 MHz, DMSO-$d_6$): δ 7.92 (s, 1H), 7.86 (d, J=7.9 Hz, 1H), 7.35-7.31 (m, 1H), 7.24 (d, J=7.4 Hz, 1H), 7.17 (d, J=7.3 Hz, 1H), 6.95 (d, J=7.3 Hz, 1H), 6.76 (s, 1H), 5.93-5.89 (m, 1H), 4.61 (bs, 1H), 4.60 (s, 2H), 4.17-4.16 (m, 1H), 3.81-3.71 (m, 2H), 3.22-3.15 (m, 2H), 3.12-3.09 (m, 2H), 2.97 (s, 3H), 2.74 (s, 3H), 2.45-2.32 (m, 1H), 2.31-2.29

(m, 1H), 1.97-1.92 (m, 1H), 1.53-1.50 (m, 1H); IR (Neat, cm¹): 2978, 1641, 1402, 1321, 1217, 1139, 1056; MS (ESI) m/z: 512 (M+1).

Example 22

2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetic acid

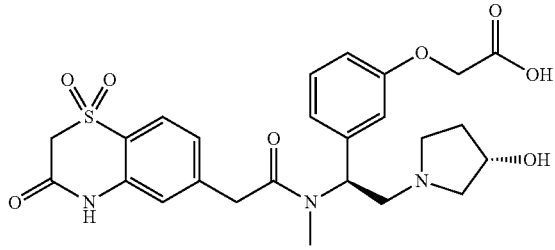 [SMILES: CN(C(=O)Cc1ccc2c(c1)NC(=O)CS2(=O)=O)[C@H](CN1CC[C@H](O)C1)c1cccc(OCC(=O)O)c1]

Step (i) Synthesis of tert-butyl 2-(3-((S)-2-((S)-3-((tert-butyldimethylsilyl)oxy)pyrrolidin-1-yl)-1-(2-(1,1-dioxido-3-oxo-3,4-dihydro-2H-benzo[b][1,4]thiazin-6-yl)-N-methylacetamido)ethyl)phenoxy)acetate

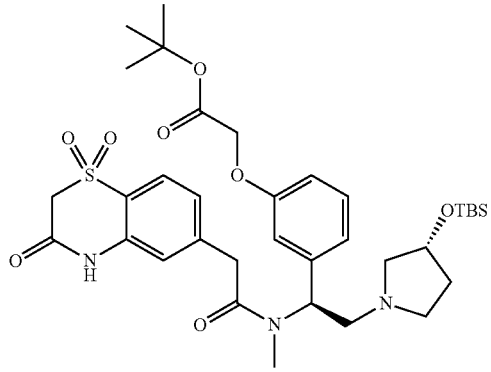 [SMILES: CN(C(=O)Cc1ccc2c(c1)NC(=O)CS2(=O)=O)[C@H](CN1CC[C@@H](O[Si](C)(C)C(C)(C)C)C1)c1cccc(OCC(=O)OC(C)(C)C)c1]

Into a 50-mL round-bottom flask purged and maintained with an inert atmosphere of nitrogen, was placed a solution of 2-(1,1-dioxido-3-oxo-3,4-dihydro-2H-benzo[b][1,4]thiazin-6-yl)acetic acid (300 mg, 1.18 mmol, 1.10 equiv) in N,N-dimethylformamide (10 mL). This was followed by the addition of EDCI (309 mg, 1.61 mmol, 1.50 equiv) at 0-5° C. To this was added HOBT (217 mg, 1.61 mmol, 1.50 equiv) at 0-5° C. To the mixture was added tert-butyl 2-[3-[(1S)-2-[(3S)-3-[(tert-butyldimethylsilyl)oxy]pyrrolidin-1-yl]-1-(methylamino)ethyl]phenoxy]acetate (500 mg, 1.08 mmol, 1.00 equiv). The resulting solution was stirred for 3 h at room temperature. The resulting solution was diluted with 150 mL of ethyl acetate. The resulting mixture was washed with 3×50 mL of water and 2×50 mL of brine. The resulting mixture was washed with 3×50 mL of 10% ammonia and 3×50 mL of brine. The mixture was dried over anhydrous sodium sulfate and concentrated under vacuum. This resulted in 700 mg (93%) of the title compound as a light yellow crude solid.

Step (ii) Synthesis of methyl 2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetate

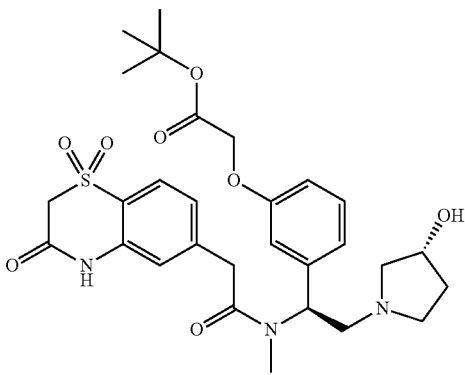 [SMILES: CN(C(=O)Cc1ccc2c(c1)NC(=O)CS2(=O)=O)[C@H](CN1CC[C@@H](O)C1)c1cccc(OCC(=O)OC(C)(C)C)c1]

Into a 50-mL round-bottom flask, was placed a solution of tert-butyl 2-(3-((S)-2-((S)-3-((tert-butyldimethylsilyl)oxy)pyrrolidin-1-yl)-1-(2-(1,1-dioxido-3-oxo-3,4-dihydro-2H-benzo[b][1,4]thiazin-6-yl)-N-methylacetamido)ethyl)phenoxy)acetate (400 mg, 0.57 mmol, 1.00 equiv) in methanol (15 mL). This was followed by the addition of conc. HCl (1.5 mL) dropwise with stirring at 0-5° C. The resulting solution was stirred for 2 h at room temperature. The resulting mixture was concentrated under vacuum. This resulted in 366 mg (118%) of the title compound as a light yellow crude solid which was used in the next step without further purification.

Step (iii) Synthesis of 2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetic acid

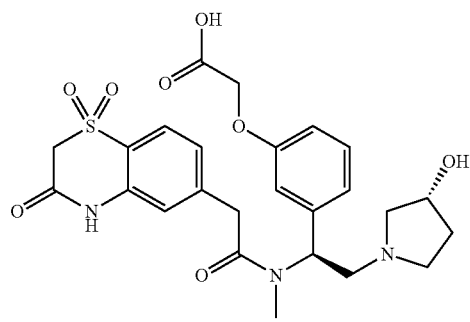 [SMILES: CN(C(=O)Cc1ccc2c(c1)NC(=O)CS2(=O)=O)[C@H](CN1CC[C@@H](O)C1)c1cccc(OCC(=O)O)c1]

Into a 50-mL round-bottom flask, was placed a solution of methyl 2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetate (100 mg, 0.18 mmol, 1.00 equiv) in methanol/water (15 mL/2.5 mL). This was followed by the addition of LiOH.H₂O (77 mg, 1.84 mmol, 10.00 equiv), in portions at 0° C. in ice/salt bath. The resulting solution was stirred for 2 h at 25° C. The resulting mixture was concentrated under vacuum. The resulting solution was diluted with 60 mL of H₂O. The resulting solution was washed with ethyl acetate (3×30 mL)

and the pH value of the solution was adjusted to 2-3 with conc. hydrogen chloride aqueous. The resulting mixture was concentrated under vacuum. The crude product (170 mg) was purified by Prep-HPLC with the following conditions (x-bridge): Column (5 nm 19*150 mm); mobile phase, 0.2% NH₄HCO₃ solution and CH₃CN, 3% CH₃CN up to 20% in 10 min; Detector, 220 nm&254 nm. 20 mg product was obtained. This resulted in 20 mg (21%) of the title compound as a white solid.

MS (ES, m/z): 532.1 (M+1); ¹H-NMR (400 MHz, DMSO-d₆) δ 11.47 (brs, 1H), 7.71-7.77 (m, 1H), 7.13-7.27 (m, 3H), 6.79-6.88 (m, 3H), 5.79-5.83 (m, 1H), 4.69 (s, 2H), 4.59-4.62 (m, 2H), 4.18-4.19 (m, 1H), 3.81-3.88 (m, 2H), 3.14 (t, J=11.2 Hz, 1H), 2.74-2.89 (m, 5H), 2.65-2.68 (m, 1H), 2.41-2.43 (m, 2H), 1.95-2.00 (m, 1H), 1.53-1.56 (m, 1H).

Example 23

3-((S)-2-((S)-3-hydroxypyrrolidin-1-yl)-1-(N-methyl-2-(2-oxoindolin-6-yl)acetamido)ethyl) benzoic acid

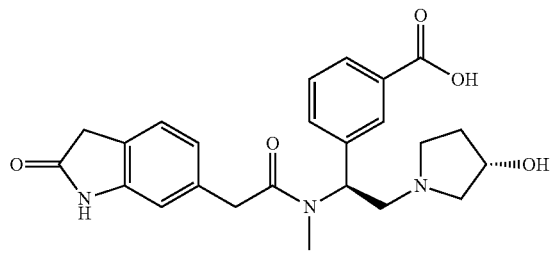 [SMILES: CN(C(=O)Cc1ccc2c(c1)NC(=O)C2)[C@H](CN1CC[C@H](O)C1)c1cccc(C(=O)O)c1]

Into a 8.0 mL sealed tube, was placed a solution of N—((S)-2-((S)-3-((tert-butyldimethylsilyl)oxy)pyrrolidin-1-yl)-1-(3-cyanophenyl)ethyl)-N-methyl-2-(2-oxoindolin-6-yl)acetamide (200 mg, 0.38 mmo, 1.00 equiv) in Conc. HCl (2.0 mL). The resulting solution was stirred for 5 h at 100° C. and concentrated under vacuum. The residue was purified by Prep-TLC and eluted with dichloromethane-methanol (3:1). This resulted in 60 mg (37%) of the title compound as a off-white solid. MS (ES, m/z): 438 (M+1); ¹H-NMR (DMSO-d₆, 300 MHz) δ 10.31 (s, 1H), 7.87-7.84 (m, 2H), 7.53-7.45 (m, 2H), 7.11 (d, J=7.5 Hz, 1H), 6.82-6.74 (m, 2H), 5.98-5.96 (m, 1H), 5.08-5.02 (m, 1H), 4.28-4.20 (m, 1H), 3.83-3.78 (m, 1H), 3.70-3.59 (m, 1H), 3.43 (s, 2H), 2.98-2.80 (m, 3H), 2.71 (s, 3H), 2.65-2.58 (m, 2H), 2.08-1.92 (m, 1H), 1.66-1.44 (m, 1H)

Example 24

3-((S)-2-((S)-3-hydroxypyrrolidin-1-yl)-1-(N-methyl-2-(2-oxoindolin-6-yl)acetamido)ethyl) benzamide

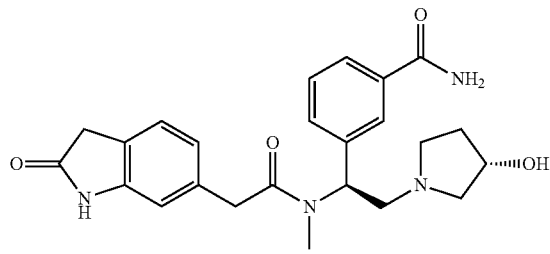 [SMILES: CN(C(=O)Cc1ccc2c(c1)NC(=O)C2)[C@H](CN1CC[C@H](O)C1)c1cccc(C(N)=O)c1]

Step (i) Synthesis of 3-((S)-2-((S)-3-((tert-butyldimethylsilyl)oxy)pyrrolidin-1-yl)-1-(N-methyl-2-(2-oxoindolin-6-yl)acetamido)ethyl)benzamide

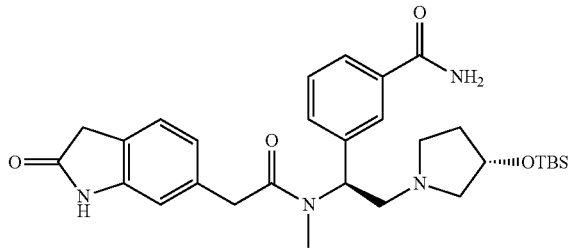 [SMILES: CN(C(=O)Cc1ccc2c(c1)NC(=O)C2)[C@H](CN1CC[C@H](O[Si](C)(C)C(C)(C)C)C1)c1cccc(C(N)=O)c1]

Into a 8.0 mL sealed tube, was placed a solution of N-[(1R)-2-[(3S)-3-[(tert-butyldimethylsilyl)ox-y]cyclopen-tyl]-1-(3-cyanophenyl)ethyl]-N-methyl-2-(2-oxo-2,3-di-hydro-1H-indol-6-yl)acetamide (150 mg, 0.28 mmol, 1.00 equiv) in DMSO (2.0 mL). Then potassium carbonate (11.7 mg, 0.08 mmol, 0.30 equiv) was added. This was followed by the addition of hydrogen peroxide (30% in water, 0.15 mL) dropwise with stirring at 0-10° C. The resulting solution was stirred for 3 h at 18° C. and diluted with 20 mL of water. The resulting aqueous solution was extracted with 3×10 mL of ethyl acetate and the organic layers combined. The resulting organic layer was washed with 2×20 mL of brine, then dried over anhydrous sodium sulfate and concentrated under vacuum. This resulted in 120 mg of the title compound as a light yellow solid which was used in the next step without further purification. MS (ES, m/z): 437 (M+1).

Step (ii) Synthesis of 3-((S)-2-((S)-3-hydroxypyrro-lidin-1-yl)-1-(N-methyl-2-(2-oxoindolin-6-yl)acet-amido)ethyl)benzamide

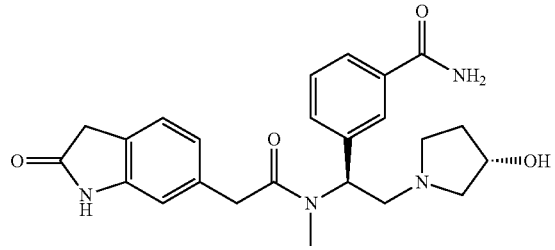 [SMILES: CN(C(=O)Cc1ccc2c(c1)NC(=O)C2)[C@H](CN1CC[C@H](O)C1)c1cccc(C(N)=O)c1]

Into a 8.0 mL sealed tube, was placed a solution of 3-((S)-2-((S)-3-((tert-butyldimethyl silyl)oxy)pyrrolidin-1-yl)-1-(N-methyl-2-(2-oxoindolin-6-yl)acetamido)ethyl)ben-zamide (110 mg, 0.20 mmol, 1.00 equiv) in methanol (1.0 mL) and Conc. hydrogen chloride (0.25 mL). The resulting solu-tion was stirred for 30 min at 18° C. and concentrated under vacuum. The residue was purified by Prep-HPLC with the following conditions: Column, X-Bridge, C18, 15 cm; mobile phase, Water (contained 0.2% of NH₄HCO₃) and acetonitrile (5% acetonitrile up to 28% in 10 min, up to 100% in 1 min, down to 5% in 1 min); Detector, UV220/254 nm. This resulted in 13 mg (15%) of title compound as a white solid.

MS (ES, m/z): 437 (M+1); ¹H-NMR (DMSO-d₆, 300 MHz) δ 10.35 (s, 1H), 8.95 (s, 1H), 7.85 (s, 2H), 7.47-7.32 (m, 3H), 7.06 (d, J=6.0 Hz, 1H), 6.78-6.65 (m, 2H), 5.93-

5.82 (m, 1H), 4.95-4.80 (m, 1H), 4.19-4.05 (m, 1H), 3.80-3.52 (m, 2H), 3.42 (s, 2H), 3.14-3.02 (m, 1H), 2.95-2.67 (m, 2H), 2.65 (s, 3H), 2.55 (s, 1H), 2.38-2.22 (m, 1H), 2.05-1.75 (m, 1H), 1.56-1.32 (m, 1H).

Example 25

N—((S)-1-(3-cyanophenyl)-2-((S)-3-fluoropyrrolidin-1-yl)ethyl)-N-methyl-2-(2-oxoindolin-6-yl)acetamide

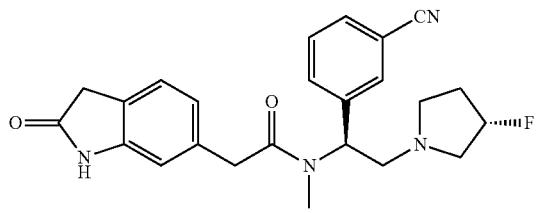 [SMILES: CN(C(=O)Cc1ccc2c(c1)NC(=O)C2)[C@H](CN1CC[C@H](F)C1)c1cccc(C#N)c1]

Into a 25-mL round-bottom flask, was placed a solution of 2-(2-oxo-2,3-dihydro-1H-indol-6-yl)acetic acid (155 mg, 0.81 mmol, 1.00 equiv) in N,N-dimethylformamide (5 mL). Then EDCI (186 mg, 0.97 mmol, 1.20 equiv) and HOBt (132 mg, 0.98 mmol, 1.20 equiv) were added. The resulting solution was stirred for 20 mins at room temperature. Following 3-[(1S)-2-[(3S)-3-fluoropyrrolidin-1-yl]-1-(methylamino)ethyl]benzonitrile (200 mg, 0.81 mmol, 1.00 equiv) was added. The resulting solution was stirred for 1 h at room temperature. The resulting mixture was concentrated under vacuum. The resulting solution was diluted with of ethyl acetate. The resulting ethyl acetate layer was washed with aqueous sat. sodium bicarbonate and brine. The ethyl acetate layer was dried over anhydrous sodium sulfate and concentrated under vacuum. The residue was purified onto prep-TLC (dichloromethane:MeOH=15:1). This resulted in 160 mg (49%) of the title compound as a white solid.

MS (ES, m/z): 443 (M+23); $^1$H-NMR (DMSO, 300 MHz): δ 10.33 (s, 1H), 7.81-7.67 (m, 2H), 7.67-7.50 (m, 2H), 7.18-7.07 (m, 1H), 6.88-6.78 (m, 1H), 6.78-6.67 (m, 1H), 5.90-5.77 (m, 1H), 5.29-4.99 (m, 2H), 3.95-3.65 (m, 2H), 3.42 (s, 2H), 3.15-3.00 (m, 1H), 2.93-2.79 (m, 3H), 2.79-2.33 (m, 5H), 2.18-1.92 (m, 1H), 1.92-1.70 (m, 1H).

Example 26

N—((S)-1-(3-(2-amino-2-oxoethoxy)phenyl)-2-((S)-3-hydroxypyrrolidin-1-yl)ethyl)-N-methyl-2-(2-oxoindolin-6-yl)acetamide

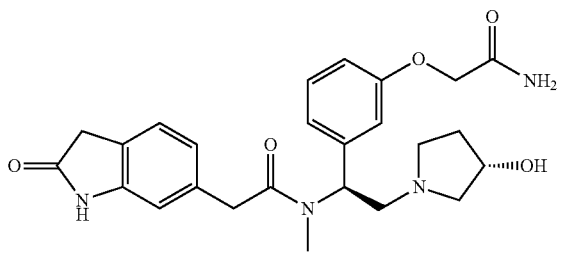 [SMILES: CN(C(=O)Cc1ccc2c(c1)NC(=O)C2)[C@H](CN1CC[C@H](O)C1)c1cccc(OCC(N)=O)c1]

Into a 25-mL round-bottom flask purged and maintained with an inert atmosphere of nitrogen, was placed a solution of 2-(3-((S)-2-((S)-3-hydroxypyrrolidin-1-yl)-1-(N-methyl-2-(2-oxoindolin-6-yl)acetamido)ethyl)phenoxy)acetic acid (100 mg, 0.21 mmol, 1.00 equiv) in N,N-dimethylformamide (6 mL). To the mixture were added HATU (90 mg, 0.24 mmol, 1.10 equiv) and DIEA (83 mg, 0.64 mmol, 5.00 equiv). The resulting solution was stirred for 5 min at room temperature. Then AcONH$_4$ (33 mg, 0.43 mmol, 10.00 equiv) was added. The resulting solution was allowed to react, with stirring, for an additional 3 h at room temperature. The resulting mixture was concentrated and the crude product (100 mg) was purified by Prep-HPLC with the following conditions (prep HPLC): Column, X-bridge, 19*150 nm; mobile phase, water with 0.05% ammonia and CH$_3$CN (5% CH$_3$CN up to 19% in 12 min, up to 100% in 2 min, down to 5% in 2 min); Detector, UV 254 nm&220 nm. 20 mg product was obtained. This resulted in 20 mg (20%) of the title compound as a white solid. MS (ES, m/z): 467.1 (M+1); $^1$H-NMR (DMSO-d$_6$, 400 MHz) δ 10.32-10.36 (m, 1H), 7.54 (s, 1H), 7.40 (s, 1H), 7.25 (t, J=8.4 Hz, 1H), 7.12 (t, J=7.6, 1H), 6.80-6.89 (m, 5H), 5.82-5.87 (m, 1H), 4.91 (s, 2H), 4.35-4.38 (m, 2H), 4.20 (brs, 1H), 3.76-3.82 (m, 1H), 3.59-3.67 (m, 1H), 3.43-3.45 (m, 2H), 3.15 (brs, 1H), 2.64-2.82 (m, 6H), 2.33-2.52 (m, 2H), 1.95-2.00 (m, 1H), 1.52-1.54 (m, 1H).

Example 27

N—((S)-2-((S)-3-hydroxypyrrolidin-1-yl)-1-(3-(2-(methylsulfonamido)-2-oxoethoxy)phenyl)ethyl)-N-methyl-2-(2-oxoindolin-6-yl)acetamide

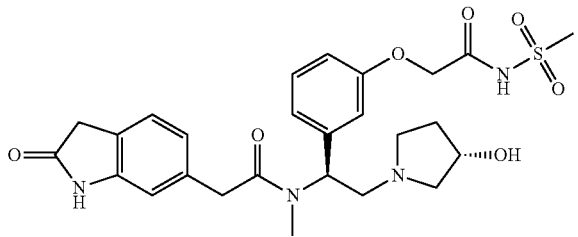 [SMILES: CN(C(=O)Cc1ccc2c(c1)NC(=O)C2)[C@H](CN1CC[C@H](O)C1)c1cccc(OCC(=O)NS(C)(=O)=O)c1]

Into a 25-mL round-bottom flask purged and maintained with an inert atmosphere of nitrogen, was placed a solution of 2-(3-((S)-2-((S)-3-hydroxypyrrolidin-1-yl)-1-(N-methyl-2-(2-oxoindolin-6-yl)acetamido)ethyl)phenoxy)acetic acid (100 mg, 0.21 mmol, 1.00 equiv) in N,N-dimethylformamide (5 mL). To the mixture were added HATU (90 mg, 0.24 mmol, 1.10 equiv) and DIEA (83 mg, 0.64 mmol, 5.00 equiv). The resulting solution was stirred for 5 min at room temperature. Then methanesulfonamide (160 mg, 1.68 mmol, 7.86 equiv) was added. The resulting solution was allowed to react, with stirring, for an additional 2 h at room temperature. The crude product (100 mg) was purified by Prep-HPLC with the following conditions (Waters): Column, X-bridge, 19*150 nm; mobile phase, water with 0.05% ammonia and CH$_3$CN (5% CH$_3$CN up to 25% in 12 min, up to 100% in 2 min, down to 5% in 2 min; Detector, UV 254 nm&220 nm. 30 mg product was obtained. This resulted in 30 mg (26%) of the title compound as a white solid.

MS (ES, m/z): 545.1 (M+1); $^1$H-NMR (300 MHz, DMSO-d$_6$) δ10.33 (s, 1H), 7.31 (t, J=7.8 Hz, 1H), 7.22 (d, J=7.5 Hz, 1H), 6.72-7.04 (m, 6H), 5.99-6.03 (m, 1H), 5.23-5.31 (m, 1H), 4.34-4.44 (m, 3H), 3.61-3.80 (m, 3H), 3.31-3.43 (m, 3H), 3.04-3.23 (m, 3H), 2.90-2.93 (m, 3H), 2.65-2.85 (m, 3H), 2.10-2.12 (m, 1H), 1.75-1.78 (m, 1H).

Example 28

3-((S)-2-((S)-3-fluoropyrrolidin-1-yl)-1-(N-methyl-2-(2-oxoindolin-6-yl)acetamido)ethyl) benzoic acid

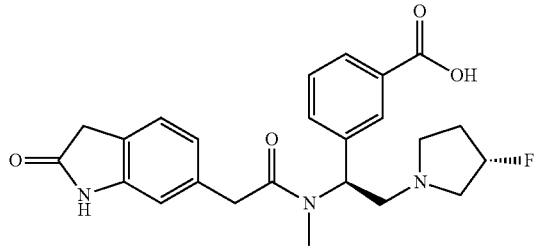 [SMILES: CN(C(=O)Cc1ccc2c(c1)NC(=O)C2)[C@H](CN1CC[C@H](F)C1)c1cccc(C(=O)O)c1]

Into a 8-mL sealed tube, was placed a solution of N—((S)-1-(3-cyanophenyl)-2-((S)-3-fluoropyrrolidin-1-yl)ethyl)-N-methyl-2-(2-oxoindolin-6-yl)acetamide (200 mg, 0.48 mmol, 1.00 equiv) in conc hydrogen chloride (4 mL). The resulting solution was stirred for 1.5 h at 100° C. After cooling to room temperature, the reaction mixture was concentrated to dryness. The residue was applied onto prep-TLC (dichloromethane:MeOH=10:1). This resulted in 11 mg of the title compound as a light yellow solid.

MS (ES, m/z): 440 (M+1); $^1$H-NMR (DMSO-$d_6$, 300 MHz): δ 10.44 (s, 1H), 7.90-7.67 (m, 2H), 7.45-7.30 (m, 2H), 7.09 (d, J=7.8 Hz, 1H), 6.88-6.65 (m, 2H), 6.00-5.80 (m, 1H), 5.29-5.01 (m, 1H), 3.86-3.65 (m, 2H), 3.47-3.38 (m, 2H), 3.20-3.10 (m, 1H), 3.02-2.56 (m, 7H), 2.40-2.27 (m, 1H), 2.15-1.96 (m, 1H), 1.96-1.70 (m, 1H); F-NMR (DMSO-$d_6$, 400 MHz) δ 167 (s).

Example 29

2-(3-((S)-2-((S)-3-fluoropyrrolidin-1-yl)-1-(N-methyl-2-(2-oxoindolin-6-yl)acetamido)ethyl) phenoxy)acetic acid

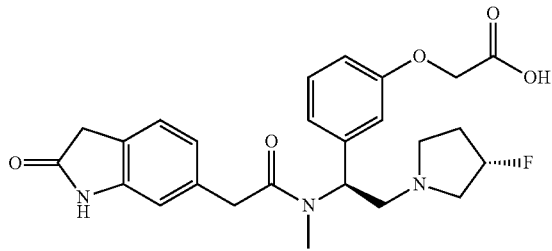 [SMILES: CN(C(=O)Cc1ccc2c(c1)NC(=O)C2)[C@H](CN1CC[C@H](F)C1)c1cccc(OCC(=O)O)c1]

Step (i) Synthesis of tert-butyl 2-(3-((S)-2-((S)-3-fluoropyrrolidin-1-yl)-1-(N-methyl-2-(2-oxoindolin-6-yl)acetamido)ethyl)phenoxy)acetate

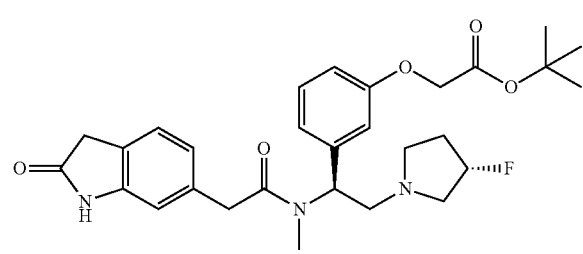 [SMILES: CN(C(=O)Cc1ccc2c(c1)NC(=O)C2)[C@H](CN1CC[C@H](F)C1)c1cccc(OCC(=O)OC(C)(C)C)c1]

Into a 25-mL round-bottom flask, was placed a solution of 2-(2-oxo-2,3-dihydro-1H-indol-6-yl)acetic acid (250 mg, 1.31 mmol, 1.00 equiv) in N,N-dimethylformamide (10 mL). To the solution were added EDCI (204 mg, 1.06 mmol, 1.50 equiv), HOBt (144 mg, 1.07 mmol, 1.50 equiv) and tert-butyl 2-(3-[2-[(3S)-3-fluoropyrrolidin-1-yl]-1-(methylamino)ethyl]phenoxy) acetate (136 mg, 0.39 mmol, 1.00 equiv). The resulting solution was stirred for 2 h at 25° C. The resulting solution was diluted with 50 mL of dichloromethane. The resulting mixture was washed with ammonia (10%) (1×20 mL), H$_2$O (3×20 mL) and (3×20 mL). The mixture was dried over anhydrous sodium sulfate and concentrated under vacuum. This resulted in 430 mg of tert-butyl 2-[3-[(1S)-2-[(3S)-3-fluoropyrrolidin-1-yl]-1-[N-methyl-2-(2-oxo-2,3-dihydro-1H-indol-6-yl)acetamido]ethyl]phenoxy]acetate as brown crude oil.

Step (ii) Synthesis of 2-(3-((S)-2-((S)-3-fluoropyrrolidin-1-yl)-1-(N-methyl-2-(2-oxoindolin-6-yl)acetamido)ethyl)phenoxy)acetic acid

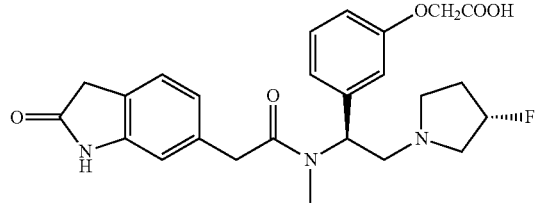

Into a 25-mL round-bottom flask, was placed a solution of tert-butyl 2-[3-[(1S)-2-[(3S)-3-fluoropyrrolidin-1-yl]-1-[N-methyl-2-(2-oxo-2,3-dihydro-1H-indol-6-yl)acetamido] ethyl]phenoxy]acetate (100 mg, 0.19 mmol, 1.00 equiv) in dichloromethane (5 mL). To the mixture was added trifluoroacetic acid (1 mL). The resulting solution was stirred for 3 h at 25 degree C. The resulting mixture was concentrated under vacuum. The crude product (80 mg) was purified by Prep-HPLC with the following conditions (prep-HPLC): Column, X-bridge prep C18; mobile phase, water and CH$_3$CN (10% CH$_3$CN up to 80% in 10 min, up to 100% in 1 min, down to 10% in 1 min); Detector, 254&220. 17.3 mg product was obtained. This resulted in 17.3 mg (19%) of 2-[3-[(1S)-2-[(3S)-3-fluoropyrrolidin-1-yl]-1-[N-methyl-2-(2-oxo-2,3-dihydro-1H-indol-6-yl)acetamido]ethyl]phenoxy]acetic acid as a white solid. MS (ES, m/z): 470 (M+1); $^1$H-NMR (DMSO-$d_6$, 300 MHz) δ 10.34 (s, 1H), 7.22-7.26 (m, 1H), 7.09-7.18 (m, 1H), 6.79-6.87 (m, 4H), 6.72-6.73 (m, 1H), 5.79-5.83 (m, 1H), 5.08-5.23 (m, 1H), 4.62 (s, 2H), 3.65-3.77 (m, 2H), 3.43 (s, 2H), 3.06-3.12 (m, 1H), 2.71-2.86 (m, 6H), 2.65-2.67 (m, 1H), 2.33-2.36 (m, 1H), 2.01-2.08 (m, 1H), 1.75-1.90 (m, 1H)

Example 30

N—((S)-1-(3-(2-amino-2-oxoethoxy)phenyl)-2-((S)-3-fluoropyrrolidin-1-yl)ethyl)-N-methyl-2-(2-oxoindolin-6-yl)acetamide

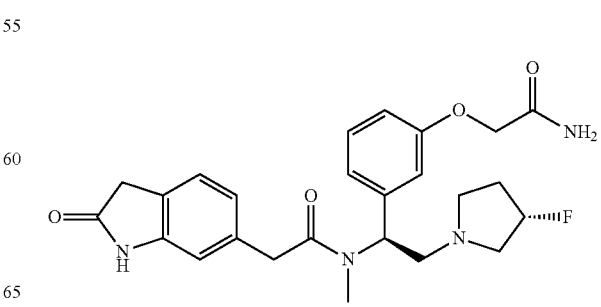

Into a 10-mL round-bottom flask, was placed a solution of 2-(3-((S)-2-((S)-3-fluoropyrrolidin-1-yl)-1-(N-methyl-2-(2-oxoindolin-6-yl)acetamido)ethyl)phenoxy)acetic acid (100 mg, 0.21 mmol, 1.00 equiv) in N,N-dimethylformamide (3 mL), HATU (89 mg, 0.23 mmol, 1.10 equiv), DIEA (137 mg, 1.06 mmol, 5.00 equiv), ammonia aqueous (1.5 mL). The resulting solution was stirred for 18 h at 25° C. The resulting mixture was concentrated under vacuum. The crude product (3 mL) was purified by Prep-HPLC with the following conditions (Prep-HPLC): Column, X-bridge prep C18; mobile phase, water and CH$_3$CN (10% CH$_3$CN up to 80% in 10 min, up to 100% in 1 min, down to 10% in 1 min); Detector, 254&220. 9 mg product was obtained. This resulted in 9 mg of the title compound as a white solid.

MS (ES, m/z): 469 (M+1); $^1$H-NMR (DMSO-d$_6$, 400 MHz) δ 10.32 (s, 1H), 7.53 (s, 1H), 7.40 (s, 1H), 7.23-7.27 (m, 1H), 7.09-7.11 (m, 1H), 6.81-6.89 (m, 4H), 6.72-6.73 (m, 1H), 5.80-5.84 (m, 1H), 5.08-5.23 (m, 1H), 4.38 (s, 1H), 3.65 (m, 2H), 3.42-3.44 (m, 2H), 3.06-3.11 (m, 1H), 2.66-2.95 (m, 7H), 7.40 (s, 1H), 2.31-2.40 (m, 1H), 1.65-2.18 (m, 2H)

Example 31

3-((S)-2-((S)-3-hydroxypyrrolidin-1-yl)-1-(N-methyl-2-(3-oxo-3,4-dihydroquinoxalin-6-yl)acetamido)ethyl)benzoic acid

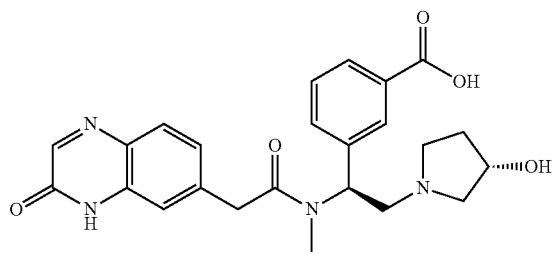 [SMILES: CN(C(=O)Cc1ccc2ncc(=O)[nH]c2c1)[C@H](CN1CC[C@H](O)C1)c1cccc(C(=O)O)c1]

Into a 8-mL vial, was placed a solution of N—((S)-2-((S)-3-((tert-butyldimethylsilyl)oxy)pyrrolidin-1-yl)-1-(3-cyanophenyl)ethyl)-N-methyl-2-(3-oxo-3,4-dihydroquinoxalin-6-yl)acetamide (100 mg, 0.18 mmol, 1.00 equiv) in conc. HCl (2 ml). The resulting solution was stirred overnight at 75° C. in an oil bath. The resulting mixture was concentrated under vacuum. The residue was purified by Prep-HPLC with the following conditions: Column, X-Bridge, C18, 15 cm; mobile phase, Water (contained 0.5% of ammonium bicarbonate) and CH$_3$CN (5% acetonitrile up to 32% in 12 min, up to 100% in 1 min, down 5% in 1 min); Detector, UV220/254 nm. This resulted in 8 mg of the title compound as a light yellow solid.

MS (ES, m/z): 451 (M+1); $^1$H-NMR (DMSO-d$_6$, 400 MHz): δ 12.09-12.49 (s, 1H), 8.13 (s, 1H), 7.85-7.67 (m, 3H), 7.55-7.44 (m, 2H), 7.22-7.21 (m, 2H), 5.91-5.87 (m, 1H), 4.64-4.91 (m, 1H), 4.16 (s, 1H), 3.83-4.00 (m, 2H), 3.13-3.07 (m, 1H), 2.86-2.64 (m, 6H), 2.48-2.34 (m, 2H), 1.96-1.91 (m, 1H), 1.53-1.50 (m, 1H).

Example 32

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzamide

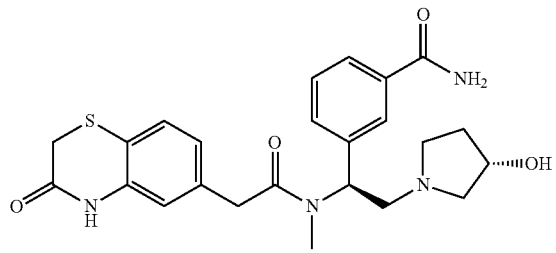 [SMILES: CN(C(=O)Cc1ccc2c(c1)NC(=O)CS2)[C@H](CN1CC[C@H](O)C1)c1cccc(C(N)=O)c1]

Into a 8.0 mL sealed tube, was placed a solution of N—((S)-2-((S)-3-((tert-butyldimethylsilyl)oxy)pyrrolidin-1-yl)-1-(3-cyanophenyl)ethyl)-N-methyl-2-(3-oxo-3,4-dihydro-2H-benzo[b][1,4]thiazin-6-yl)acetamide (60 mg, 0.11 mmol, 1.00 equiv) in tetrahydrofuran (0.4 mL) and methanol (0.4 mL). Then water (0.8 mL) and potassium hydroxide (59.6 mg, 1.06 mmol, 10.00 equiv) were added. The resulting solution was stirred for 7 hours at 50° C. and concentrated under vacuum. The residue was purified by Flash-Prep-HPLC with the following conditions (IntelFlash-1): Column, C18 silica gel; mobile phase, H$_2$O/MeCN=100:5 increasing to H$_2$O/MeCN=100:25 within 15 min; Detector, UV 254 nm. This resulted in 35 mg (70%) of 3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzamide as a white solid.

MS (ES, m/z): 533 (M+1); $^1$H-NMR (DMSO-d$_6$, 300 MHz): δ 10.49 (s, 1H), 7.96 (s, 1H), 7.72 (m, 2 h), 7.38-7.36 (m, 3H), 7.19 (d, J=7.8 Hz, 1H), 6.85-6.80 (m, 2H), 5.86-5.78 (m, 1H), 4.72-4.65 (m, 1H), 4.18-4.06 (m, 1H), 3.75-3.56 (m, 2H), 3.34 (s, 2H), 3.11-2.90 (m, 1H), 2.86-2.60 (m, 6H), 2.28-2.16 (m, 1H), 1.95-1.82 (m, 1H), 1.48-1.32 (m, 1H).

Example 33

N—((S)-1-(3-ethynylphenyl)-2-((S)-3-hydroxypyrrolidin-1-yl)ethyl)-N-methyl-2-(2-oxo-2,3-dihydrobenzo[d]thiazol-5-yl)acetamide

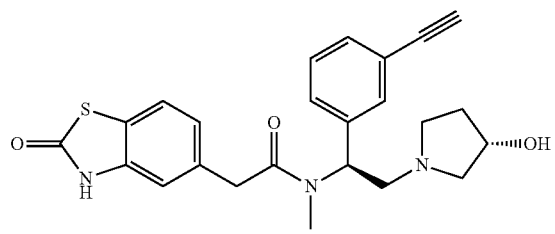 [SMILES: C#Cc1cccc([C@@H](CN2CC[C@H](O)C2)N(C)C(=O)Cc2ccc3sc(=O)[nH]c3c2)c1]

To a solution of 2-(2-oxo-2,3-dihydro-1,3-benzothiazol-5-yl)acetic acid (50 mg, 0.24 mmol, 1.10 equiv) in N,N-dimethylformamide (2 mL), were added EDCI (62.6 mg, 0.33 mmol, 1.51 equiv) and HOBt (44 mg, 0.33 mmol, 1.50 equiv). The resulting solution was stirred for 30 min at 20° C. This was followed by addition of a solution of (3S)-1-

[(2S)-2-(3-ethynylphenyl)-2-(methylamino)ethyl]pyrrolidin-3-ol (53 mg, 0.22 mmol, 1.00 equiv) in N,N-dimethylformamide (1 mL) dropwise with stirring. The resulting solution was allowed to react, with stirring, for an additional 1.5 h at 20° C. The reaction was concentrated and the residue was purified by Prep-HPLC with the following conditions: Column, X-Bridge, C18, 15 cm; mobile phase, Water (contained 0.5% of ammonium bicarbonate) and $CH_3CN$ (5% $CH_3CN$ up to 45% in 12 min, up to 100% in 1 min, down 10% in 1 min); Detector, UV220/254 nm. This resulted in 22.4 mg (24%) of the title compound as a off-white solid.

MS (ES, m/z): 436 (M+1), $^1$H-NMR (DMSO-$d_6$, 300 MHz): δ 7.49-7.64 (d, J=7.8 Hz, 1H), 7.37-7.33 (m, 4H), 7.08-7.00 (m, 2H), 5.84-5.78 (m, 1H), 4.18-4.17 (m, 2H), 3.89-3.70 (m, 2H), 3.09-3.00 (m, 1H), 2.81-2.69 (m, 5H), 2.42-2.35 (m, 2H), 2.12-1.83 (m, 1H), 1.59-1.41 (m, 1H).

Example 34

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(3-oxo-3,4-dihydroquinoxalin-6-yl)acetamide

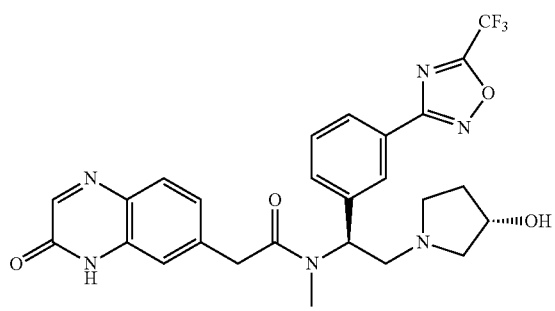 [SMILES: CN(C(=O)Cc1ccc2ncc(=O)[nH]c2c1)[C@H](CN1CC[C@H](O)C1)c1cccc(-c2noc(C(F)(F)F)n2)c1]

To a solution of 2-(3-oxo-3,4-dihydroquinoxalin-6-yl) acetic acid (70 mg, 0.34 mmol, 1.20 equiv) in N,N-dimethylformamide (3 mL), were added EDCI (60 mg, 0.31 mmol, 1.10 equiv) and HOBT (42 mg, 0.31 mmol, 1.10 equiv). The resulting solution was stirred for 10 min at room temperature. Then a solution of 1-[2-(methylamino)-2-[3-[5-(trifluoromethyl)-1,2,4-oxadiazol-3-yl]phenyl]ethyl]pyrrolidin-3-ol (100 mg, 0.28 mmol, 1.00 equiv) in N,N-dimethylformamide (2 mL) was added. The resulting solution was stirred for 3 hours at 20° C. The resulting mixture was concentrated under vacuum. The residue was purified by Prep-TLC with dichloromethane/methanol (10:1). This resulted in 41.4 mg (27%) of N-[(1S)-2-(3-hydroxypyrrolidin-1-yl)-1-[3-[5-(trifluoromethyl)-1,2,4-oxadiazol-3-yl]phenyl]ethyl]-N-methyl-2-(3-oxo-3,4-dihydroquinoxalin-6-yl)acetamide as a white solid.

MS (ES, m/z): 543 (M+1); $^1$H-NMR (DMSO-$d_6$, 300 MHz): δ 8.098 (s, 1H), 7.989-7.921 (m, 2H), 7.765-7.603 (m, 4H), 7.225-7.130 (m, 2H), 5.939-5.888 (m, 1H), 4.795-4.715 (m, 1H), 4.180 (s, 1H), 4.026-3.832 (m, 2H), 3.323-2.368 (m, 9H), 1.989-1.898 (m, 1H), 1.537-1.462 (m, 1H).

Example 35

N—((S)-2-((S)-3-hydroxypyrrolidin-1-yl)-1-(3-(5-methyl-1,2,4-oxadiazol-3-yl)phenyl)ethyl)-N-methyl-2-(2-oxoindolin-6-yl)acetamide

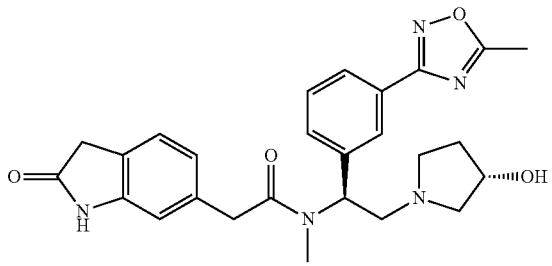 [SMILES: Cc1nc(-c2cccc([C@@H](CN3CC[C@H](O)C3)N(C)C(=O)Cc3ccc4c(c3)NC(=O)C4)c2)no1]

To a solution of 2-(2-oxo-2,3-dihydro-1H-indol-6-yl)acetic acid (44.89 mg, 0.23 mmol, 1.00 equiv) in N,N-dimethylformamide (2.0 mL), were added EDCI (67.41 mg, 0.35 mmol, 1.50 equiv) and HOBt (47.52 mg, 0.35 mmol, 1.50 equiv). The mixture was stirred for 20 min at 25. To this was added (3S)-1-[(2S)-2-[3-(5-methyl-1,2,4-oxadiazol-3-yl) phenyl]-2-(methylamino)ethyl]pyrrolidin-3-ol di-hydrochloride (80 mg, 0.21 mmol, 0.91 equiv) and triethylamine (172 mg, 1.70 mmol, 7.24 equiv). The resulting solution was stirred for 2 hours at 25° C., and then 20 mL of water/ice was added to quench the reaction. The resulting aqueous solution was extracted with dichloromethane (3×15 mL) and the organic layers combined. The resulting organic layers was washed with brine (1×20 mL), dried over anhydrous sodium sulfate and concentrated under vacuum. The residue was purified by Prep-HPLC with the following conditions: Column: X-Bridge, C18, 19*150 mm; mobile phase: Water (contained 0.2% of $NH_4HCO_3$) and acetonitrile (5% acetonitrile up to 45% in 10 min, up to 100% in 1 min, down to 5% in 1 min); Detector: UV220/254 nm. This resulted in 50 mg (46%) of the title compound as a white solid. MS (ES, m/z): 476 (M+1); $^1$H-NMR (DMSO-$d_6$, 300 MHz): δ 10.35 (s, 1H), 7.91-7.88 (m, 2H), 7.65-7.45 (m, 2H), 7.10 (d, J=7.2 Hz, 1H), 5.95-5.90 (m, 1H), 4.88 (d, J=3.9 Hz, 1H), 4.25-4.18 (m, 1H), 3.84-3.79 (m, 1H), 3.69-3.64 (m, 1H), 3.42 (s, 2H), 3.16-3.08 (m, 1H), 2.84-2.77 (m, 2H), 2.72 (s, 3H), 2.67 (s, 3H), 2.42-2.30 (m, 2H), 2.02-1.86 (m, 1H), 1.53-1.40 (m, 1H).

Example 36

N—((S)-2-((S)-3-hydroxypyrrolidin-1-yl)-1-(3-(thiazol-2-yl)phenyl)ethyl)-N-methyl-2-(2-oxoindolin-6-yl)acetamide

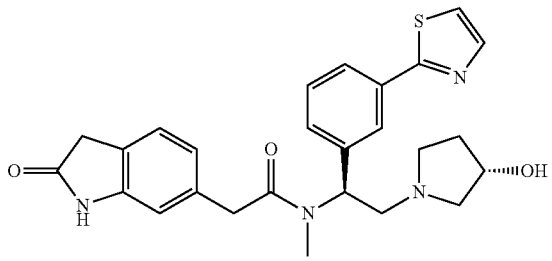 [SMILES: CN(C(=O)Cc1ccc2c(c1)NC(=O)C2)[C@H](CN1CC[C@H](O)C1)c1cccc(-c2nccs2)c1]

Into a 8-mL sealed tube, was placed a solution of 2-(2-oxo-2,3-dihydro-1H-indol-6-yl)acetic acid (40 mg, 0.21 mmol, 1.00 equiv) in N,N-dimethylformamide (3 mL). Then EDCI (45 mg, 0.23 mmol, 1.20 equiv) and HOBt (32 mg, 0.24 mmol, 1.20 equiv) were added. Following triethylamine (60 mg, 0.59 mmol, 3.00 equiv) was added. The resulting solution was stirred for 10 min at room temperature. Then (3S)-1-[(2S)-2-(methylamino)-2-[3-(1,3-thiazol-2-yl)phenyl]ethyl]pyrrolidin-3-ol (60 mg, 0.20 mmol, 1.00 equiv) was added. The resulting solution was allowed to react, with stirring, for an additional 2 hours at room temperature. The resulting mixture was concentrated under vacuum and the residue was purified by prep-HPLC with the following conditions: Column, X-Bridge, C18, 15 cm; mobile phase, water (contained 0.5% ammonium bicarbonate) and acetonitrile (10% acetonitrile up to 45% in 12 mins, up to 100% in 1 min, down to 10% in 1 min); detector, UV220/254 nm. This resulted in 10 mg of the title compound as a white solid.

MS (ES, m/z): 477 (M+1); $^1$H-NMR (CD$_3$OD-d$_4$, 300 MHz): δ 7.76-7.73 (m, 3H), 7.52-7.50 (m, 1H), 7.39-7.31 (m, 2H), 7.07-7.05 (m, 1H), 6.87-6.82 (m, 2H), 6.04-5.98 (m, 1H), 4.27-4.25 (m, 1H), 3.82-3.67 (m, 2H), 3.37-3.35 (m, 1H), 3.28-3.22 (m, 2H), 2.95-2.83 (m, 2H), 2.77-2.72 (m, 4H), 2.55-2.38 (m, 2H), 2.06-2.03 (m, 1H), 14.71-1.52 (m, 1H).

Example 37

N—((S)-1-(3-(but-1-yn-1-yl)phenyl)-2-((S)-3-hydroxypyrrolidin-1-yl)ethyl)-2-(2,2-dioxido-1,3-dihydrobenzo[c]isothiazol-6-yl)-N-methylacetamide

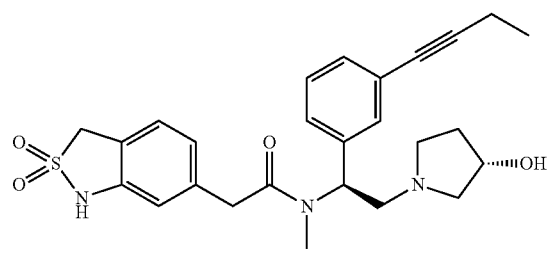 [SMILES: CCC#Cc1cccc([C@@H](CN2CC[C@H](O)C2)N(C)C(=O)Cc2ccc3c(c2)NS(=O)(=O)C3)c1]

Into a 25-mL round-bottom flask, was placed a solution of 2-(2,2-dioxido-1,3-dihydrobenzo[c]isothiazol-6-yl)acetic acid (70 mg, 0.31 mmol, 1.10 equiv) in N,N-dimethylformamide (10 mL), EDCI (84 mg, 0.44 mmol, 1.50 equiv), HOBT (60 mg, 0.44 mmol, 1.50 equiv). The resulting solution was stirred for 5 min at room temperature. Then (3S)-1-[(2S)-2-[3-(but-1-yn-1-yl)phenyl]-2-(methylamino)ethyl]pyrrolidin-3-ol (80 mg, 0.29 mmol, 1.00 equiv) was added. The resulting solution was allowed to react, with stirring, for an additional 3 h at room temperature. The resulting mixture was concentrated under vacuum. The residue was purified by Prep-TLC with dichloromethane/methanol (10/1). That resulted in 60 mg crude product. The crude product was purified by Prep-HPLC with the following conditions (Waters): Column, X-bridge Prep C18 19*150 nm; mobile phase, water with 0.08% NH$_4$HCO$_3$ and CH$_3$CN (10% CH$_3$CN up to 42% in 8 min, up to 100% in 1 min, down to 10% in 1 min); Detector, 254&220 nm. This resulted in 45 mg (32%) of the title compound as a white solid. MS (ES, m/z): 482 (M+1); $^1$H-NMR (300 MHz, DMSO-d$_6$): 7.17-7.31 (m, 5H), 6.84 (d, J=7.5 Hz, 1H), 6.73-6.75 (m, 1H), 5.77-5.83 (m, 1H), 4.47 (m, 2H), 4.18 (brs, 1H), 3.78-3.84 (m, 1H), 3.63-3.69 (m, 1H), 3.03-3.11 (m, 1H), 2.62-2.83 (m, 5H), 2.59 (s, 1H), 2.34-2.49 (m, 4H), 1.91-1.99 (m, 1H), 1.47 (brs, 1H), 1.16 (t, J=7.5 Hz, 3H).

Example 38

3-((S)-2-((S)-3-hydroxypyrrolidin-1-yl)-1-(N-methyl-2-(2-oxoindolin-6-yl)acetamido)ethyl)-N-(2,2,2-trifluoroethyl)benzamide

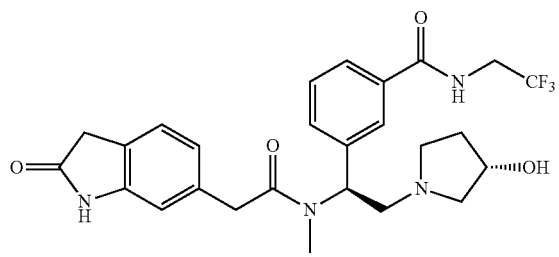 [SMILES: CN(C(=O)Cc1ccc2c(c1)NC(=O)C2)[C@H](CN1CC[C@H](O)C1)c1cccc(C(=O)NCC(F)(F)F)c1]

Step (i) Synthesis of 3-((S)-2-((S)-3-((tert-butyldimethylsilyl)oxy)pyrrolidin-1-yl)-1-(N-methyl-2-(2-oxoindolin-6-yl)acetamido)ethyl)-N-(2,2,2-trifluoroethyl)benzamide

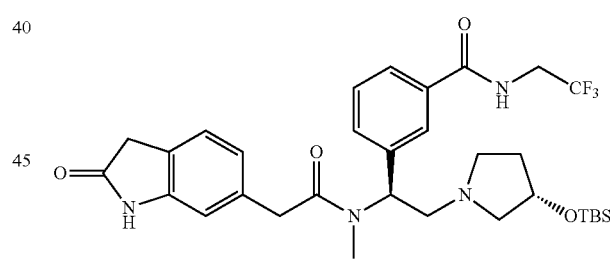

Into a 5-mL vial, was placed a solution of 3-[(1S)-2-[(3S)-3-[(tert-butyldimethylsilyl)oxy]pyrrolidin-1-yl]-1-(methylamino)ethyl]-N-(2,2,2-trifluoroethyl)benzamide (100 mg, 0.22 mmol, 1.00 equiv) in N,N-dimethylformamide (1 mL). To the solution were added 2-(2-oxo-2,3-dihydro-1H-indol-6-yl)acetic acid (42 mg, 0.22 mmol, 1.00 equiv), HOBt (44.2 mg, 0.33 mmol, 1.50 equiv) and EDCI (62.5 mg, 0.33 mmol, 1.50 equiv). The resulting solution was stirred for 1 hour at 25° C. The resulting solution was diluted with 20 mL of ethyl acetate. The resulting mixture was washed with ammonia (5%, 2×10 mL), brine (3×10 mL), dried over anhydrous sodium sulfate and concentrated under vacuum. This resulted in 139 of the title compound as yellow oil which was used without further purification. MS (ES, m/z): 633 (M+1).

Step (ii) Synthesis of 3-((S)-2-((S)-3-hydroxypyrrolidin-1-yl)-1-(N-methyl-2-(2-oxoindolin-6-yl)acetamido)ethyl)-N-(2,2,2-trifluoroethyl)benzamide

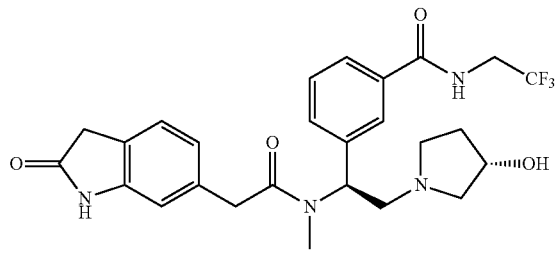 [SMILES: CN(C(=O)Cc1ccc2c(c1)NC(=O)C2)[C@H](CN1CC[C@H](O)C1)c1cccc(C(=O)NCC(F)(F)F)c1]

Into a 50-mL round-bottom flask, was placed a solution of 3-[(1S)-2-[(3S)-3-[(tert-butyldimethylsilyl)oxy]pyrrolidin-1-yl]-1-[N-methyl-2-(2-oxo-2,3-dihydro-1H-indol-6-yl)acetamido]ethyl]-N-(2,2,2-trifluoroethyl)benzamide (138.5 mg, 0.22 mmol, 1.00 equiv) in methanol (3 mL). To the solution was added conc. hydrogen chloride aqueous (0.3 mL). The resulting solution was stirred for 2 hours at 25° C. The resulting mixture was concentrated under vacuum. The crude product was purified by Prep-HPLC with the following conditions: Column, X-Bridge.prep C18 5 um OBD 19*150 mm; mobile phase, water with 0.5% $NH_3 \cdot H_2O$ and $CH_3CN$ (5% of $CH_3CN$ up to 52% in 8 mins); Detector, UV 254,220 nm. This resulted in 6 mg of the title compound as a white solid. MS (ES, m/z): 519 (M+1); $^1$H-NMR (400 MHz, DMSO-$d_6$): 10.35 (s, 1H), 9.13-9.09 (m, 1H), 7.8 (s, 2H), 7.49-7.46 (m, 2H), 7.10-7.13 (m, 1H), 6.83-6.73 (m, 2H), 5.94-5.89 (m, 1H), 5.20-5.13 (m, 1H), 4.91-4.89 (m, 1H), 4.20-4.08 (m, 3H), 3.84-3.80 (m, 1H), 3.67-3.3.63 (m, 1H), 3.42 (s, 2H), 3.12-3.08 (m, 1H), 2.85-2.81 (m, 2H), 2.76-2.74 (m, 2H), 2.63 (s, 1H), 2.52-2.50 (m, 2H), 1.98-1.95 (m, 1H), 1.52 (m, 1H).

Example 39

N,N-diethyl-3-((S)-2-((S)-3-hydroxypyrrolidin-1-yl)-1-(N-methyl-2-(2-oxoindolin-6-yl)acetamido)ethyl)benzamide

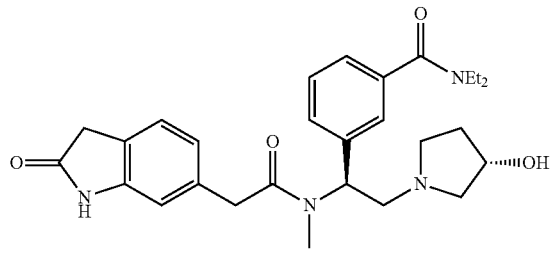

Into a 10-mL round-bottom flask purged and maintained with an inert atmosphere of nitrogen, was placed a solution of 3-[(1S)-2-[(3S)-3-hydroxypyrrolidin-1-yl]-1-[N-methyl-2-(2-oxo-2,3-dihydro-1H-indol-6-yl)acetamido]ethyl]benzoic acid (200 mg, 0.46 mmol, 1.00 equiv) in N,N-dimethylformamide (2 mL). To the mixture were added HATU (225 mg, 0.59 mmol, 1.20 equiv), DIEA (381 mg, 2.95 mmol, 6.00 equiv) and diethylamine (180 mg, 2.46 mmol, 5.00 equiv). The resulting solution was stirred for 6 hours at 25° C. The mixture was purified by Prep-HPLC with the following conditions (Waters): Column, X-bridge prep C18; mobile phase, water with 0.5% $NH_3H_2O$ and $CH_3CN$ (10% $CH_3CN$ up to 80% in 10 min, up to 100% in 1 min, down to 10% in 1 min); Detector, 254&220. This resulted in 5 mg of the title compound as a white solid. MS (ES, m/z): 493 (M+1); $^1$H-NMR (DMSO-$d_6$, 400 MHz): δ 10.33-10.36 (m, 1H), 7.33-7.41 (m, 2H), 7.20-7.24 (m, 2H), 7.10-7.19 (m, 1H), 6.74-6.81 (m, 2H), 5.88 (m, 1H), 4.70-4.90 (m, 1H), 4.17 (m, 1H), 3.77-3.81 (m, 1H), 3.64-3.68 (m, 1H), 3.40-3.41 (m, 4H), 3.04-3.10 (m, 3H), 2.70-2.79 (m, 5H), 2.33-2.38 (m, 2H), 1.93-1.96 (m, 1H), 1.51 (m, 1H), 1.00-1.14 (m, 6H).

Example 40

3-((S)-2-((S)-3-hydroxypyrrolidin-1-yl)-1-(N-methyl-2-(2-oxo-2,3-dihydrobenzo[d]thiazol-5-yl)acetamido)ethyl)-N,N-dimethylbenzamide-2,2,2-trifluoroacetate

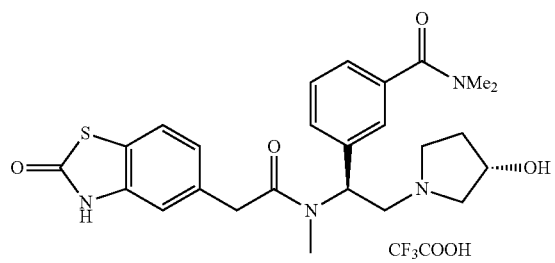 [SMILES: CN(C)C(=O)c1cccc([C@@H](CN2CC[C@H](O)C2)N(C)C(=O)Cc2ccc3sc(=O)[nH]c3c2)c1 ; "CF3COOH"]

Step (i) Synthesis of 3-((S)-2-((S)-3-((tert-butyldimethylsilyl)oxy)pyrrolidin-1-yl)-1-(N-methyl-2-(2-oxo-2,3-dihydrobenzo[d]thiazol-5-yl)acetamido)ethyl)-N,N-dimethylbenzamide

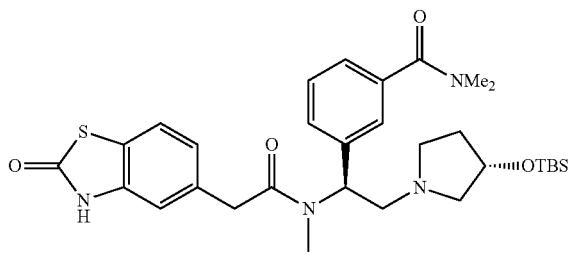 [SMILES: CN(C)C(=O)c1cccc([C@@H](CN2CC[C@H](O[Si](C)(C)C(C)(C)C)C2)N(C)C(=O)Cc2ccc3sc(=O)[nH]c3c2)c1]

Into a 8-mL sealed tube, was placed a solution of 3-[(1S)-2-[(3S)-3-[(tert-butyldimethylsilyl)oxy]pyrrolidin-1-yl]-1-(methylamino)ethyl]-N,N-dimethylbenzamide (100 mg, 0.25 mmol, 1.00 equiv) in N,N-dimethylformamide (3 mL). To the solution were added 2-(2-oxo-2,3-dihydro-1,3-benzothiazol-5-yl)acetic acid (52.3 mg, 0.25 mmol, 1.00 equiv), EDCI (73 mg, 0.38 mmol, 1.50 equiv) and 1H-1,2,3-benzotriazol-1-ol (51.3 mg, 0.38 mmol, 1.50 equiv). The resulting solution was stirred for 1 h at room temperature. The resulting mixture was diluted with 50 mL of ethyl acetate. Then the resulting solution was washed with ammonia (1×10 mL), brine (3×30 mL), dried over anhydrous sodium sulfate and concentrated under vacuum. This resulted in 80 mg (54%) of the title compound as orange oil. MS (ES, m/z): 597 (M+1).

Step (ii) Synthesis of 3-((S)-2-((S)-3-hydroxypyrrolidin-1-yl)-1-(N-methyl-2-(2-oxo-2,3-dihydrobenzo[d]thiazol-5-yl)acetamido)ethyl)-N,N-dimethylbenzamide 2,2,2-trifluoroacetate

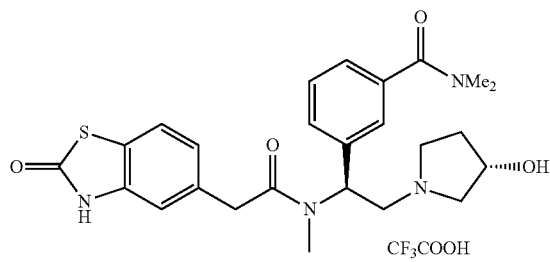 [SMILES: CN(C)C(=O)c1cccc([C@@H](CN2CC[C@H](O)C2)N(C)C(=O)Cc2ccc3sc(=O)[nH]c3c2)c1 ; "CF3COOH"]

Into a 25-mL round-bottom flask, was placed a solution of 3-[(1S)-2-[(3S)-3-[(tert-butyldimethylsilyl)oxy]pyrrolidin-1-yl]-1-[N-methyl-2-(2-oxo-2,3-dihydro-1,3-benzothiazol-5-yl)acetamido]ethyl]-N,N-dimethylbenzamide (80 mg, 0.13 mmol, 1.00 equiv) in methanol (2 mL). To the solution was added concentrated hydrogen chloride aqueous (0.2 mL). The resulting solution was stirred for 1 h at room temperature. The resulting mixture was concentrated under vacuum. The crude product was purified by Prep-HPLC with the following conditions (prep-HPLC): Column, X-bridge prep C18; mobile phase, water (0.5% TFA) and $CH_3CN$ (5% $CH_3CN$ up to 38% in 10 min, up to 100% in 1 min, down to 5% in 1 min); Detector, 254&220 nm. This resulted in 17 mg (26%) of the title compound as a white solid.

MS (ES, m/z): 483 (M+1); $^1$H-NMR (DMSO-$d_6$, 300 MHz): δ 11.89 (s, 1H), 10.08-9.61 (m, 1H), 7.58-6.91 (m, 7H), 6.28-6.13 (m, 1H), 5.63-5.43 (m, 1H), 4.52-4.33 (m, 1H), 4.18-4.02 (m, 1H), 3.93-3.57 (m, 5H), 3.08-2.91 (s, 3H), 2.83-2.61 (m, 6H), 2.42-2.23 (s, 1H), 2.13-1.72 (m, 1H).

Example 41

N—((S)-1-(3-(2-(diethylamino)-2-oxoethoxy)phenyl)-2-((S)-3-hydroxypyrrolidin-1-yl)ethyl)-N-methyl-2-(2-oxoindolin-6-yl)acetamide

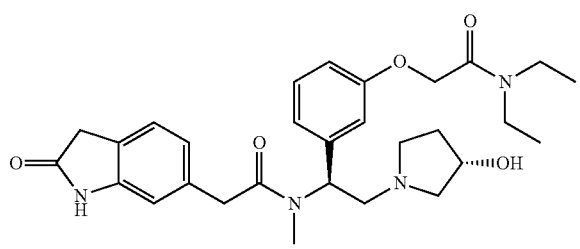 [SMILES: CCN(CC)C(=O)COc1cccc([C@@H](CN2CC[C@H](O)C2)N(C)C(=O)Cc2ccc3c(c2)NC(=O)C3)c1]

Into a 10-mL vial, was placed 2-(2-oxo-2,3-dihydro-1H-indol-6-yl)acetic acid (54.8 mg, 0.29 mmol, 1.00 equiv) in DMF (1 ml). To the solution were added HOBt (58.1 mg, 0.43 mmol, 1.50 equiv) and EDCI (82.2 mg, 0.43 mmol, 1.50 equiv), then followed by the addition of N,N-diethyl-2-[3-[(1S)-2-[(3S)-3-hydroxypyrrolidin-1-yl]-1-(methylamino)ethyl]phenoxy]acetamide (100.0 mg, 0.29 mmol, 1.00 equiv). After stirring for 1 h at 25 degree C., the resulting solution was concentrated under vacuum. The crude product was purified by Prep-HPLC with the following conditions: Column, X-Bridge prep C18; mobile phase, water with 0.5% $NH_3*H_2O$ and $CH_3CN$ (15% $CH_3CN$ up to 45% in 10 min, up to 100% in 1 min, down to 15% in 1 min); Detector, UV 254,220 nm. This resulted in 26 mg of the title compound as a white solid. MS (ES, m/z): 541 (M+1)$^1$H-NMR (DMSO-$d_6$, 300 MHz): 10.35-10.31 (m, 1H), 7.24-7.20 (t, J=8.0 Hz, 1H), 7.12-7.10 (d, J=7.2 Hz, 1H), 6.85-6.68 (m, 5H), 5.83-5.80 (m, 1H), 4.88 (s, 1H), 4.73 (s, 2H), 4.18 (s, 1H), 3.80-3.75 (m, 1H), 3.66-3.62 (m, 1H), 3.42 (s, 2H), 3.35-3.25 (m, 4H), 3.02 (t, 1H), 2.89-2.78 (m, 2H), 2.76-2.63 (m, 4H), 2.37-2.36 (s, 2H), 1.98-1.93 (m, 1H), 1.50 (m, 1H), 1.16-1.12 (t, J=7.2 Hz, 3H), 1.04-1.01 (t, J=7.2 Hz, 3H)

Example 42

N—((S)-1-(3-(2-(diethylamino)-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide

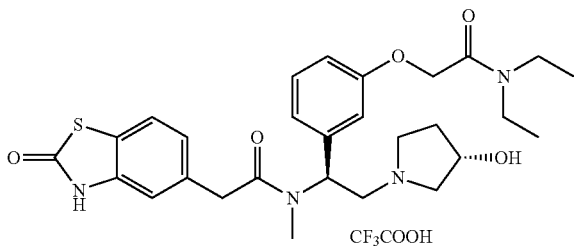 [SMILES: CCN(CC)C(=O)COc1cccc([C@@H](CN2CC[C@H](O)C2)N(C)C(=O)Cc2ccc3sc(=O)[nH]c3c2)c1 ; "CF3COOH"]

Into a 10-mL vial, was placed a solution of 2-(2-oxo-2,3-dihydro-1,3-benzothiazol-5-yl)acetic acid (60.0 mg, 0.29 mmol, 1.00 equiv) in N,N-dimethylformamide (1 mL). To the solution were added HOBt (58.1 mg, 0.43 mmol, 1.50 equiv) EDCI (82.2 mg, 0.43 mmol, 1.50 equiv), and N,N-diethyl-2-[3-[(1S)-2-[(3S)-3-hydroxypyrrolidin-1-yl]-1-(methylamino)ethyl]phenoxy]acetamide (100 mg, 0.29 mmol, 1.00 equiv). After stirring for 1 h at 25° C., the resulting solution was concentrated under vacuum. The crude product was purified by Prep-HPLC with the following conditions: Column, X-Bridge prep C18; mobile phase, water with 0.5% TFA and $CH_3CN$ (10% $CH_3CN$ up to 28% in 6 min, stay 28% in 5 min, up to 100% in 1 min, down to 10% in 1 min); Detector, UV 254,220 nm. This resulted in 15 mg of the title compound as a white solid. MS (ES, m/z): 541 [M+H−CF3COOH]$^+$ $^1$H-NMR: (DMSO-$d_6$, 300 MHz): δ 11.90 (s, 1H), 9.97-9.51 (m, 1H), 7.51-7.49 (d, J=8.0 Hz, 1H), 7.31-7.25 (m, 1H), 7.12-6.99 (m, 2H), 6.87-6.76 (m, 3H), 6.11 (brs, 1H), 5.58-5.49 (m, 1H), 4.76 (s, 2H), 4.48-4.41 (m, 1H), 4.07-3.98 (m, 1H), 3.89-3.49 (m, 5H), 3.37-3.18 (m, 5H), 2.74 (s, 3H), 2.34-1.84 (m, 2H), 1.16-1.12 (t, J=7.2 Hz, 3H), 1.05-1.01 (t, J=7.2 Hz, 3H)

Example 43

N—((S)-1-(3-fluoro-5-(thiazol-2-yl)phenyl)-2-((S)-3-hydroxypyrrolidin-1-yl)ethyl)-N-methyl-2-(2-oxoindolin-6-yl)acetamide

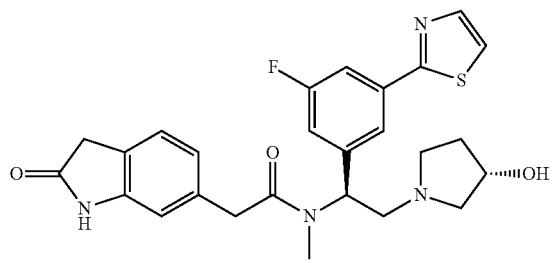 [SMILES: CN(C(=O)Cc1ccc2c(c1)NC(=O)C2)[C@H](CN1CC[C@H](O)C1)c1cc(F)cc(-c2nccs2)c1]

Into a 8-mL round-bottom flask, was placed a solution of (S)-1-((S)-2-(3-fluoro-5-(thiazol-2-yl)phenyl)-2-(methylamino)ethyl)pyrrolidin-3-ol (60 mg, 0.14 mmol, 1.00 equiv) in N,N-dimethylformamide (2 mL). To the solution were added 2-(2-oxo-2,3-dihydro-1H-indol-6-yl)acetic acid (35.3 mg, 0.18 mmol, 1.10 equiv), EDCI (48.4 mg, 0.25 mmol, 1.50 equiv), HOBt (34 mg, 0.25 mmol, 1.50 equiv) and TEA (51 mg, 0.50 mmol, 3.00 equiv). The resulting solution was stirred for 2 hours at room temperature. The resulting mixture was concentrated under vacuum. The residue was purified with Prep-HPLC with the following conditions (X-bridge Prep-HPLC): Column, Prep C18 19*150 mm; mobile phase, water with 0.5% $NH_3*H_2O$ and $CH_3CN$ (5% $CH_3CN$ up to 35% in 10 min, up to 100% in 1 min, down to 5% in 1 min); Detector, 254&220 nm. This resulted in 28.5 mg (41%) of the title compound as a white solid.

MS (ES, m/z): 495 (M+1); $^1$H-NMR: (300 MHz, $d_6$-DMSO): δ 10.33 (s, 1H), 7.96 (s, 1H), 7.85 (s, 1H), 7.65 (s, 2H), 7.41-7.12 (m, 2H), 6.84-6.80 (m, 2H), 5.90 (s, 1H), 4.87 (s, 1H), 4.19 (s, 1H), 3.83-3.67 (m, 2H), 3.42 (s, 2H), 3.18-3.06 (m, 1H), 2.87-2.63 (m, 5H), 2.40-2.27 (m, 2H), 2.02-1.95 (m, 1H), 1.53-1.48 (m, 1H).

Example 44

N—((S)-2-((S)-3-hydroxypyrrolidin-1-yl)-1-(3-(2-methyl-2H-tetrazol-5-yl)phenyl)ethyl)-N-methyl-2-(2-oxoindolin-6-yl)acetamide

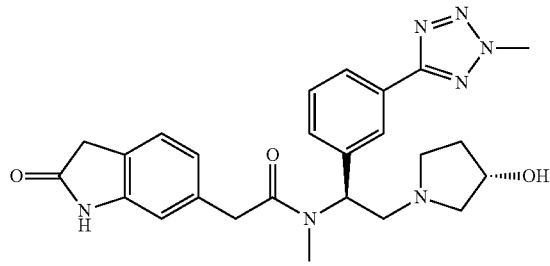 [SMILES: CN(C(=O)Cc1ccc2c(c1)NC(=O)C2)[C@H](CN1CC[C@H](O)C1)c1cccc(-c2nnn(C)n2)c1]

Into a 8-mL, was placed a solution of (3S)-1-[(2S)-2-[3-(2-methyl-2H-1,2,3,4-tetrazol-5-yl)phenyl]-2-(methylamino)ethyl]pyrrolidin-3-ol (160 mg, 0.53 mmol, 1.00 equiv) and 2-(2-oxo-2,3-dihydro-1H-indol-6-yl)acetic acid (101 mg, 0.53 mmol, 1.00 equiv) in N,N-dimethylformamide (2 mL). To the solution were added EDC (152 mg) and 1H-1,2,3-benzotriazol-1-ol (107 mg, 0.79 mmol, 1.50 equiv). The resulting solution was stirred for 2 hours at room temperature. The resulting mixture was concentrated under vacuum. The crude product (100 mg) was purified by Prep-HPLC with the following conditions (X-bridge): Column, prep C18 19*150 mm; mobile phase, water with 0.5% ammonia and $CH_3CN$ (10% $CH_3CN$ up to 45% in 10 min; up to 100% in 1 min; down to 10% in 1 min); Detector, 254,220. This resulted in 17 mg of the title compound as a white solid.

MS (ES, m/z): 476 (M+1); $^1$H-NMR (300 MHz, DMSO-$d_6$): δ 10.366 (1H, s), 7.943-7.972 (2H, d, J=8.7 Hz), 7.475-7.537 (2H, m), 7.095-7.121 (1H, d, J=7.8 Hz), 6.800-6.840 (2H, m), 5.95 (1H, m), 4.907-4.921 (1H, d, J=4.2 Hz), 4.431 (3H, s), 4.19 (1H, m), 3.801-3.852 (1H, d, J=15.3 Hz), 3.642-3.693 (1H, d, J=15.3 Hz), 3.394-3.423 (2H, s), 3.142 (1H, m), 2.731-2.829 (5H, m), 2.652 (1H, s), 2.383-2.425 (2H, m), 1.94 (1H, m), 1.55 (1H, m).

The following examples 45-228 were prepared by following suitable procedure(s) similar to that mentioned in above examples 1-44, by taking appropriate starting materials:

Example 45

N—((S)-2-((S)-3-hydroxypyrrolidin-1-yl)-1-phenylethyl)-2-(3-methyl-2-oxo-2,3-dihydrobenzo[d]oxazol-5-yl)acetamide

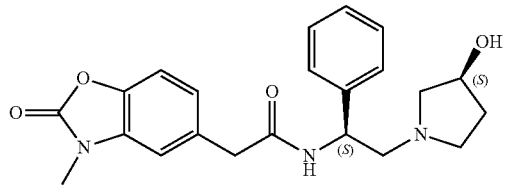

Melting point: 105-106° C.; $^1$H-NMR (400 MHz, DMSO-$d_6$): δ 8.49 (d, J=8.0 Hz, 1H), 7.30-7.29 (m, 3H), 7.24-7.20 (m, 2H), 7.09 (s, 1H), 7.04-7.03 (m, 1H), 4.89-4.88 (bs, 2H), 4.66 (bs, 1H), 4.12 (bs, 1H), 3.55-3.50 (m, 2H), 3.29 (s, 3H), 2.73 (d, J=8.0 Hz, 2H), 2.55-2.54 (m, 2H), 2.30 (bs, 2H), 1.91-1.90 (m, 1H), 1.49-1.48 (m, 1H); IR (KBr, $cm^{-1}$): 3286, 2945, 1766, 1651, 1494, 1384; MS (ESI): m/z 396 (M+1).

Example 46

(S)-2-(3-(3-cyanobenzyl)-2-oxo-2,3-dihydrobenzo[d]oxazol-5-yl)-N-(1-phenyl-2-(pyrrolidin-1-yl)ethyl)acetamide

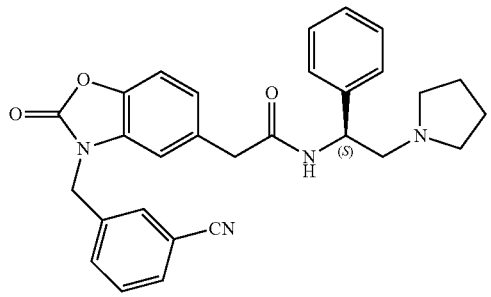

Melting point: 109-110° C.; $^1$H-NMR (400 MHz, DMSO-$d_6$): δ 8.48 (bs, 1H), 7.9 (s, 1H), 7.79 (d, J=7.3 Hz, 1H), 7.67 (d, J=7.6 Hz, 1H), 7.57 (m, 1H), 7.29-7.21 (m, 6H), 7.11 (s, 1H), 7.06 (d, J=8.2 Hz, 1H), 5.07 (s, 2H), 4.92 (m, 1H), 3.52 (s, 2H), 2.63-2.54 (m, 2H), 2.50 (bs, 4H), 1.63 (bs, 4H); IR (KBr, cm$^{-1}$): 3293, 3061, 2962, 2794, 2230, 1769, 1643, 1385, 1246; MS (ESI): m/z 481.22 (M+1).

Example 47

(S)—N-methyl-2-(2-oxo-1,2-dihydroquinolin-6-yl)-N-(1-phenyl-2-(pyrrolidin-1-yl)ethyl)acetamide

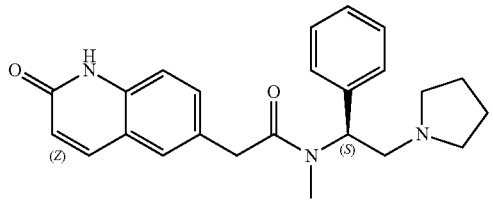

$^1$H-NMR (400 MHz, DMSO-$d_6$): δ 11.69 (bs, 1H), 7.83 (d, J=9.8 Hz, 1H), 7.47 (s, 1H), 7.40-7.23 (m, 7H), 6.48 (d, J=9.8 Hz, 1H), 5.93-5.90 (m, 1H), 3.91-3.98 (m, 1H), 3.78-3.74 (m, 1H), 3.18 (s, 1H), 2.74 (s, 3H), 2.67 (s, 1H), 2.51-2.50 (m, 4H), 1.64 (bs, 4H); IR (KBr, cm$^{-1}$): 3447, 2963, 1655, 1430, 1365, 1265, 1120; MS (ESI) m/z: 390 (M+1).

Example 48

N—((S)-2-((S)-3-hydroxypyrrolidin-1-yl)-1-phenylethyl)-N-methyl-2-(2-oxo-1,2-dihydroquinolin-6-yl)acetamide

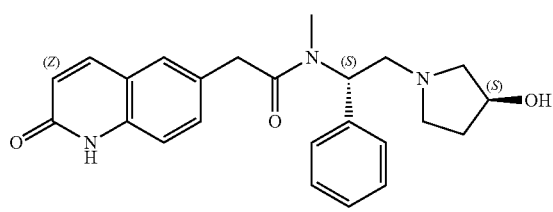

$^1$H-NMR (400 MHz, DMSO-$d_6$): δ 11.69 (bs, 1H), 7.85 (d, J=9.8 Hz, 1H), 7.47 (s, 1H), 7.39-7.23 (m, 7H), 6.47 (d, J=9.3 Hz, 1H), 5.92 (bs, 1H), 4.70 (bs, 1H), 4.15 (bs, 1H), 3.85-3.76 (m, 2H), 3.18-3.16 (m, 2H), 2.73 (bs, 3H), 2.63 (s, 2H), 2.51-2.50 (m, 2H), 1.90 (s, 1H), 1.50 (s, 1H); IR (KBr, cm$^{-1}$): 3333, 2905, 1219, 1109, 1026; MS (ESI) m/z: 406 (M+1).

Example 49

(S)—N-methyl-2-(2-oxo-1,2-dihydroquinolin-7-yl)-N-(1-phenyl-2-(pyrrolidin-1-yl)ethyl)acetamide

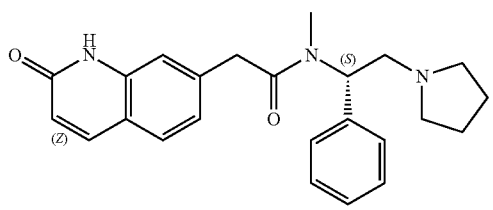

Melting point: 170-172° C.; $^1$H-NMR (400 MHz, DMSO-$d_6$): δ 11.70 (s, 1H), 7.86 (d, J=9.2 Hz, 1H), 7.57 (d, J=8 Hz, 1H), 7.35-7.25 (m, 5H), 7.19 (s, 1H), 7.06 (d, J=7.6 Hz, 1H), 6.44 (d, J=9.6 Hz, 1H), 6.0-5.80 (bs, 1H), 3.91-3.80 (m, 2H), 2.81 (s, 1H), 2.73 (s, 3H), 2.64 (s, 1H), 2.44 (s, 4H), 1.63 (s, 4H); IR (KBr, cm$^{-1}$): 2964, 2794, 1656, 1560, 1413, 1282, 1122; MS (ESI) m/z: 390 (M+1).

Example 50

(S)—N-methyl-2-(3-methyl-2,2-dioxido-1,3-dihydrobenzo[c]isothiazol-5-yl)-N-(1-phenyl-2-(pyrrolidin-1-yl)ethyl)acetamide

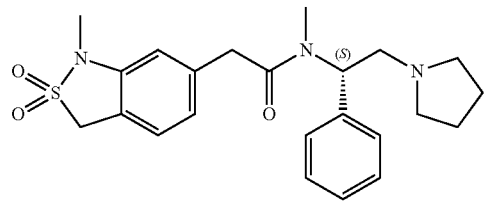

Melting point: 154-156° C.; $^1$H-NMR (400 MHz, DMSO-$d_6$): δ 7.34-7.22 (m, 6H), 6.91 (d, J=8.0 Hz, 1H), 6.75 (s, 1H), 5.87 (d, J=5.2 Hz, 1H), 4.61 (s, 2H), 3.86-3.74 (m, 2H), 3.32-3.08 (m, 1H), 2.98 (s, 3H), 2.74-3.63 (m, 3H), 2.57-2.43 (m, 5H), 1.59-1.65 (m, 4H); IR (KBr, cm$^{-1}$): 3329, 2926, 2850, 2791, 1625, 1585, 1500, 1444, 1400, 1323, 1205; MS (ESI) m/z: 428 (M+1).

Example 51

N—((S)-2-((R)-3-hydroxypyrrolidin-1-yl)-1-phenylethyl)-2-(2-oxo-1,2-dihydroquinolin-6-yl)acetamide

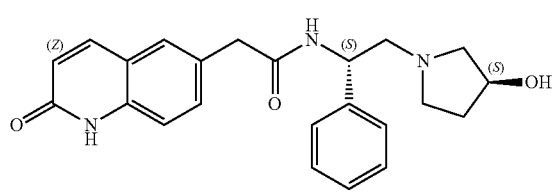

Melting point: 196-198° C.; $^1$H-NMR (400 MHz, DMSO-$d_6$): δ 11.67 (bs, 1H), 8.51 (bs, 1H), 7.78 (d, J=9.2 Hz, 1H), 7.48 (s, 1H), 7.40 (d, J=7.2 Hz, 1H), 7.30-7.22 (m, 6H), 6.45 (d, J=9.2 Hz, 1H), 4.97 (bs, 1H), 4.80-4.60 (bs, 1H), 4.19 (bs, 1H), 3.53 (q, J=12.5 Hz, 2H), 3.40 (d, J=6.8 Hz, 2H), 2.79-2.65 (m, 2H), 2.35 (bs, 2H), 1.96 (bs, 1H), 1.59 (bs, 1H); IR (KBr, cm$^{-1}$): 3032, 2806, 1660, 1604, 1546, 1425, 1382, 1261, 1220, 1153, 1095; MS (ESI) m/z: 392 (M+1).

Example 52

N—((S)-2-((S)-3-hydroxypyrrolidin-1-yl)-1-phenyl-ethyl)-N-methyl-2-(2-oxo-1,2-dihydroquinolin-7-yl)acetamide

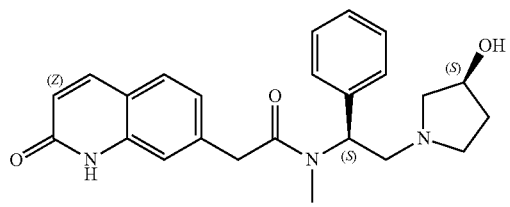

Melting point: 176-177° C.; $^1$H-NMR (400 MHz, DMSO-d$_6$): δ 11.70 (bs, 1H), 7.86 (d, J=9.2 Hz, 1H), 7.56 (d, J=7.6 Hz, 1H), 7.33-7.29 (bs, 1H), 7.19 (s, 1H), 7.06 (d, J=5.6 Hz, 1H), 6.44 (d, J=8.4 Hz, 1H), 5.84 (bs, 1H), 4.73-4.69 (bs, 1H), 4.15 (bs, 1H), 3.92-3.75 (m, 2H), 3.06-3.01 (m, 1H), 2.85 (bs, 1H), 2.63-2.72 (m, 3H), 2.50 (bs, 2H), 2.31 (bs, 2H), 1.91 (bs, 1H), 1.50 (bs, 1H); IR (KBr, cm$^{-1}$): 3338, 3184, 3057, 2964, 2918, 2769, 1666, 1631, 1415, 1346, 1274, 1138; MS (ESI) m/z: 406 (M+1).

Example 53

N—((S)-2-((S)-3-hydroxypyrrolidin-1-yl)-1-phenyl-ethyl)-N-2-dimethyl-2-(2-oxo-2,3-dihydrobenzo[d]oxazol-5-yl)propanamide

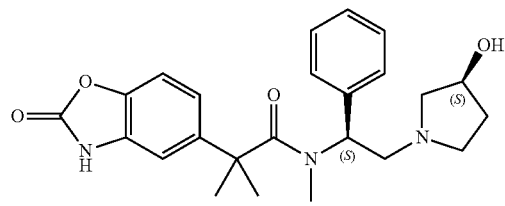

$^1$H-NMR (400 MHz, DMSO-d$_6$): δ 7.30-7.22 (m, 5H), 7.05-6.99 (m, 3H), 5.07-5.05 (m, 1H), 3.55-3.51 (m, 1H), 2.82-2.76 (m, 2H), 2.69-2.67 (m, 2H), 2.42-2.40 (d, J=10.4 Hz, 1H), 2.39-2.34 (m, 1H), 2.24-2.21 (m, 3H), 2.19 (s, 3H), 1.64-1.60 (bs, 1H), 1.49 (s, 6H); IR (KBr, cm$^{-1}$): 2972, 2798, 1776, 1496, 1467, 1388, 1350, 1257, 1147, 1147, 1074; MS (ESI) m/z: 424 (M+1).

Example 54

N—((S)-2-((S)-3-hydroxypyrrolidin-1-yl)-1-phenyl-ethyl)-2-(2-oxo-1,2-dihydroquinolin-7-yl)acetamide

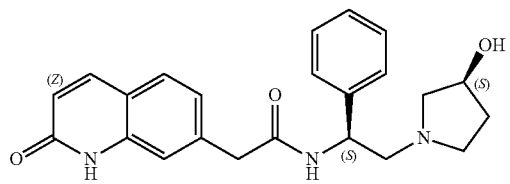

Melting point: 174-176° C.; $^1$H-NMR (400 MHz, DMSO-d$_6$): δ 11.72 (s, 1H), 8.54 (d, J=8.4 Hz, 1H), 7.84 (d, J=10.0 Hz, 1H), 7.55 (d, J=8.4 Hz, 1H), 7.30-7.27 (m, 4H), 7.24-7.19 (m, 2H), 7.11 (dd, J$_1$=1.2 Hz, J$_2$=8.0 Hz, 1H), 6.43 (dd, J$_1$=1.6 Hz, J$_2$=8.0 Hz, 1H), 4.89 (q, J=7.5 Hz, 1H), 4.7 (bs, 1H), 4.13-4.08 (m, 1H), 3.54 (q, J=13.6 Hz, 2H), 2.77-2.67 (m, 2H), 2.59-2.54 (m, 1H), 2.44-2.40 (m, 1H), 2.33-2.29 (m, 2H), 1.93-1.88 (m, 1H), 1.51-1.49 (m, 1H); IR (KBr, cm$^{-1}$): 3061, 2964, 2806, 1658, 1604, 1552, 1415, 1346, 1276, 1219, 1149; MS (ESI) m/z: 392 (M+1).

Example 55

N—((S)-2-((S)-3-hydroxypyrrolidin-1-yl)-1-phenyl-ethyl)-2-methyl-2-(2-oxo-2,3-dihydrobenzo[d]oxazol-5-yl)propanamide

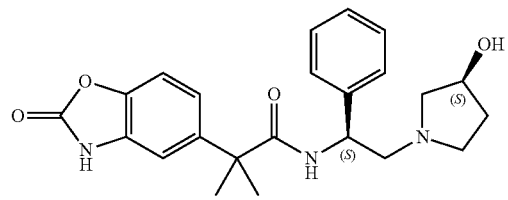

$^1$H-NMR (400 MHz, DMSO-d$_6$): δ 11.6 (bs, 1H), 7.52-7.50 (d, J=7.3 Hz, 1H), 7.28-7.24 (m, 6H), 7.28-7.17 (m, 2H), 4.93-4.90 (m, 1H), 4.09-4.12 (m, 1H), 2.94-2.67 (m, 4H), 2.54-2.30 (m, 3H), 1.95-1.90 (m, 1H), 1.52-1.48 (s, 3H), 1.47-1.43 (s, 3H); IR (KBr, cm$^{-1}$): 3305, 3084, 2929, 2810, 1766, 1664, 1494, 1467, 1259, 1159; MS (ESI) m/z: 410 (M+1).

Example 56

(S)-2-(2-oxo-2,3-dihydrobenzo[d]oxazol-5-yl)-N-(1-phenyl-2-(pyrrolidin-1-yl)ethyl) acetamide

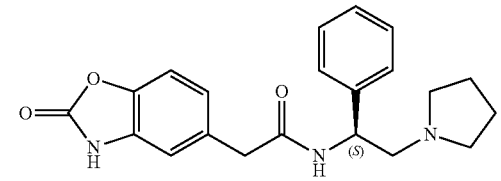

Melting point: 129-130° C.; $^1$H-NMR (400 MHz, DMSO-d$_6$): δ 12.0-11.0 (bs, 1H), 8.44 (d, J=8.0 Hz, 1H), 7.30-7.28 (m, 5H), 7.23-7.19 (m, 1H), 7.11 (m, 1H), 6.96-6.91 (m, 1H), 4.91-4.85 (m, 1H), 3.45 (s, 2H), 2.76-2.67 (m, 2H), 2.42 (bs, 4H), 1.62 (bs, 4H); IR (KBr, cm$^{-1}$): 3064, 2796, 1764, 1658, 1535, 1261; MS (ESI) m/z: 366.2 (M+1).

Example 57

N—((S)-2-((S)-3-hydroxypyrrolidin-1-yl)-1-phenylethyl)-2-(2-oxo-2,3-dihydrobenzo[d]oxazol-5-yl)acetamide

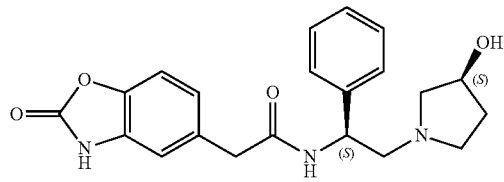

Melting point: 210-211° C.; $^1$H-NMR (400 MHz, DMSO-$d_6$): δ 11.5-11.0 (bs, 1H), 8.49 (d, J=8.3 Hz, 1H), 7.30-7.16 (m, 6H), 7.17 (d, J=8.0 Hz, 1H), 7.06 (s, 1H), 6.97 (d, J=7.3 Hz, 1H), 4.89 (q, J=8.5 Hz, 1H), 4.13 (bs, 1H), 3.52-3.42 (m, 2H), 2.76-2.68 (m, 2H), 2.60-2.50 (m, 2H), 2.43-2.40 (m, 1H), 2.33-2.30 (m, 1H), 1.96-1.91 (m, 1H), 1.50-1.40 (m, 1H); IR (KBr, cm$^{-1}$): 3420, 3120, 1640, 1339, 1219; MS (ESI) m/z: 382.0 (M+1).

Example 58

(S)-2-(3-benzyl-2-oxo-2,3-dihydrobenzo[d]oxazol-5-yl)-N-(1-(3-(4-methoxybenzyloxy)phenyl)-2-(pyrrolidin-1-yl)ethyl)acetamide

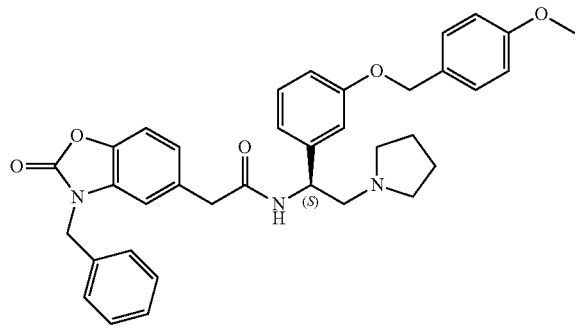

Melting point: 72-74° C.; $^1$H-NMR (400 MHz, DMSO-$d_6$): δ 8.45 (d, J=7.0 Hz, 1H), 7.36-7.39 (m, 7H), 7.31-7.25 (m, 1H), 7.21-7.17 (m, 1H), 7.11 (s, 1H), 7.06-7.04 (m, 1H), 6.95-6.93 (m, 3H), 6.85 (d, J=5.9 Hz, 2H), 4.97 (s, 2H), 4.94 (s, 2H), 4.90 (bs, 1H), 3.76 (s, 3H), 3.47 (s, 2H), 2.50 (bs, 4H), 2.45 (bs, 2H), 1.63 (bs, 4H); IR (KBr, cm$^{-1}$): 3313, 3034, 2962, 2794, 1774, 1664, 1610, 1585, 1514, 1492, 1465; MS (ESI) m/z: 591.8 (M+1).

Example 59

2-(3-(4-cyanobenzyl)-2-oxo-2,3-dihydrobenzo[d]oxazol-5-yl)-N—((S)-2-((S)-3-hydroxy pyrrolidin-1-yl)-1-phenylethyl)acetamide

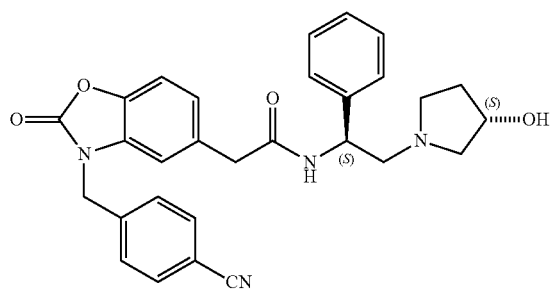

Melting point: 194-194° C.; $^1$H-NMR (400 MHz, DMSO-$d_6$): δ 8.47-8.45 (m, 1H), 7.84-7.82 (m, 2H), 7.53-7.51 (m, 2H), 7.31-7.21 (m, 6H), 7.08-7.06 (m, 2H), 5.20-5.18 (m, 2H), 4.90-4.80 (m, 1H), 4.71-4.61 (m, 1H), 4.13-4.20 (m, 1H), 3.50-3.38 (m, 4H), 2.80-2.71 (m, 2H), 2.67-2.33 (m, 2H), 1.91-1.89 (m, 1H), 1.50-1.50 (m, 1H); IR (Neat, cm$^{-1}$): 3304, 2943, 2230, 1768, 1495; MS (ESI): m/z 497 (M+1).

Example 60

N—((S)-2-((S)-3-hydroxypyrrolidin-1-yl)-1-phenylethyl)-2-(2-oxoindolin-6-yl)acetamide

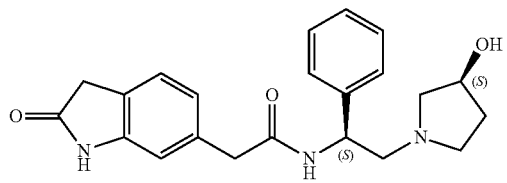

Melting point: 207-209° C.; $^1$H-NMR (400 MHz, DMSO-$d_6$): δ 10.35 (s, 1H), 8.49 (d, J=7.2 Hz, 1H), 7.37-7.22 (m, 5H), 7.08 (d, J=7.2 Hz, 1H), 6.81 (s, 2H), 4.90 (s, 1H), 4.84 (s, 1H), 4.16 (s, 1H), 3.47-3.32 (m, 4H), 2.77-2.67 (m, 3H), 2.50 (bs, 1H), 2.38 (bs, 2H), 1.95-1.91 (m, 1H), 1.53 (bs, 1H); IR (KBr, cm$^{-1}$): 3275, 3065, 2941, 2804, 1691, 1630, 1547; MS (ESI) m/z: 380.6 (M+1).

Example 61

(S)-2-(3-methyl-2-oxo-2,3-dihydrobenzo[d]oxazol-5-yl)-N-(1-phenyl-2-(pyrrolidin-1-yl)ethyl)acetamide

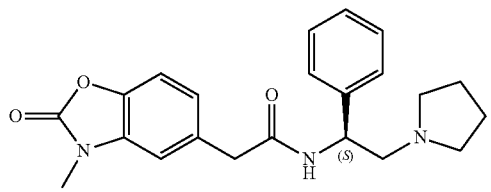

Melting point: 105-107° C.; $^1$H-NMR (400 MHz, DMSO-$d_6$): δ 8.49 (d, J=8.3 Hz, 1H), 7.30-7.29 (m, 4H), 7.27-7.20 (m, 2H), 7.09 (d, J=1.3 Hz, 1H), 7.03 (dd, $J_1$=1.6 Hz, $J_2$=8.3 Hz, 1H), 4.93-4.87 (m, 1H), 3.51 (d, J=2.4 Hz, 2H), 3.31 (s, 3H), 2.79-2.73 (m, 1H), 2.51 (bs, 1H), 2.50-2.44 (m, 4H), 1.64-1.23 (m, 4H); IR (KBr, cm$^{-1}$): 3286, 3061, 2954, 2794, 1764, 1649, 1535, 1494, 1384, 1064; MS (ESI) m/z: 380 (M+1).

Example 62

N-(1-(1-benzyl-1H-pyrazol-4-yl)-2-(pyrrolidin-1-yl)ethyl)-2-(2-oxo-2,3-dihydrobenzo[d]oxazol-5-yl)acetamide

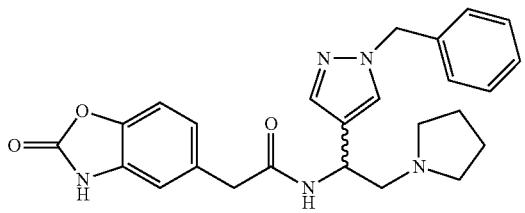 [SMILES: O=C(Cc1ccc2oc(=O)[nH]c2c1)NC(CN1CCCC1)c1cnn(Cc2ccccc2)c1]

$^1$H-NMR (400 MHz, DMSO-d$_6$): δ 11.52 (bs, 1H), 8.26 (d, J=8.32 Hz, 1H), 7.62 (s, 1H), 7.32-7.15 (m, 7H), 6.95 (d, J=8.32 Hz, 2H), 5.24 (s, 2H), 4.93-4.92 (m, 1H), 3.43 (s, 2H), 2.71-2.67 (m, 2H), 2.50-2.33 (m, 4H), 1.63 (bs, 4H); IR (KBr, cm$^{-1}$): 3064, 2962, 1774, 1656, 1496, 1261; MS (ESI) m/z: 446 (M+1).

Example 63

(S)-t-butyl-2-(3-(1-(2-(3-benzyl-2-oxo-2,3-dihydrobenzo[d]oxazol-5-yl)acetamido)-2-(pyrrolidin-1-yl)ethyl)phenoxy)acetate

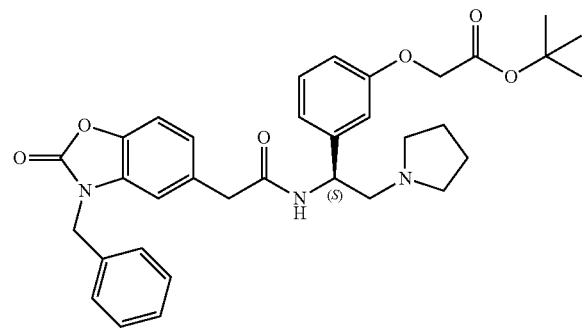

Melting point: 68-70° C.; $^1$H-NMR (400 MHz, DMSO-d$_6$): δ 8.50 (bs, 1H), 7.38-7.30 (m, 5H), 7.28-7.30 (m, 2H), 7.12 (s, 1H), 7.04 (d, J=8.3 Hz, 1H), 6.91 (bs, 2H), 6.76 (bs, 1H), 4.99 (bs, 3H), 4.60 (s, 2H), 3.49 (bs, 2H), 3.20-2.60 (m, 2H), 2.50 (bs, 4H), 1.68 (bs, 4H), 1.42 (s, 9H); IR (KBr, cm$^{-1}$): 3248, 2974, 2796, 1776, 1664, 1587, 1492, 1467, 1384, 1369, 1246; MS (ESI) m/z: 586.5 (M+1).

Example 64

(S)-2-(3-benzyl-2-oxo-2,3-dihydrobenzo[d]oxazol-5-yl)-N-(1-(3-(benzyloxy)phenyl)-2-(pyrrolidin-1-yl)ethyl)-N-methylacetamide

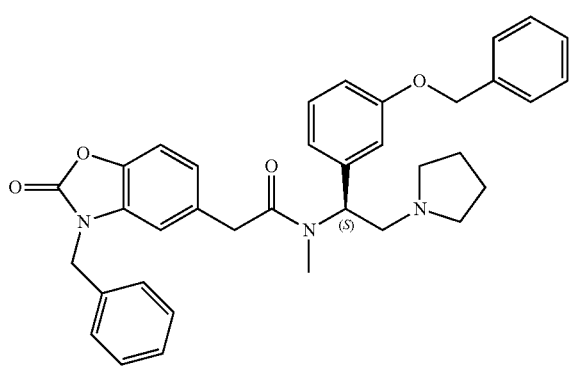

$^1$H-NMR (400 MHz, DMSO-d$_6$): δ 7.43-7.20 (m, 13H), 7.08 (s, 1H), 7.02 (d, J=8.2 Hz, 1H), 6.91 (d, J=7.0 Hz, 1H), 6.89-6.84 (m, 1H), 5.80-5.77 (m, 1H), 5.04-4.99 (m, 4H), 3.81-3.68 (m, 2H), 3.04-2.98 (m, 1H), 2.70 (s, 3H), 2.59 (s, 1H), 2.40 (bs, 4H), 1.60 (bs, 4H); IR (KBr, cm$^{-1}$): 2931, 2791, 1774, 1631, 1494, 1467, 1382, 1352, 1244, 1134; MS (ESI) m/z: 576 (M+1).

Example 65

N—((S)-1-cyclohexyl-2-((S)-3-hydroxypyrrolidin-1-yl)ethyl)-N-methyl-2-(2-oxoindolin-6-yl)acetamide

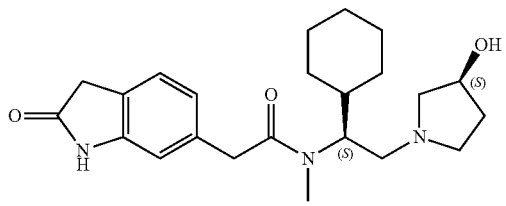

$^1$H-NMR (400 MHz, DMSO-d$_6$): δ 10.36 (s, 1H), 7.10 (d, J=7.3 Hz, 1H), 6.82-6.70 (m, 2H), 4.90 (bs, 1H), 4.39 (bs, 1H), 4.14 (s, 1H), 3.77-3.73 (m, 1H), 3.65 (s, 1H), 3.58-3.54 (m, 1H), 3.42 (s, 1H) 2.72 (s, 3H), 2.69-2.61 (m, 2H), 2.24-2.16 (m, 3H), 1.95-1.90 (m, 1H), 1.76-1.57 (m, 4H), 1.46-1.43 (m, 2H), 1.37-1.34 (m, 1H), 1.13-1.00 (m, 4H), 0.97-0.93 (m, 1H), 0.84-0.81 (m, 1H); IR (KBr, cm$^{-1}$): 3306, 3182, 2928, 2856, 2783, 1710, 1630, 1605, 1460; MS (ESI): m/z 400.4 (M+1).

Example 66

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide

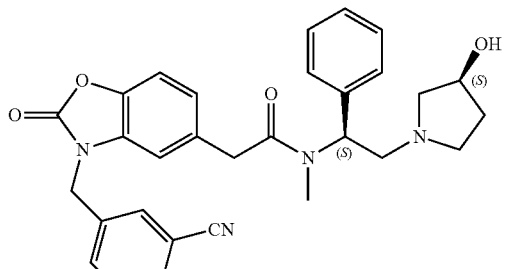

$^1$H-NMR (400 MHz, DMSO-d$_6$): δ 7.87 (s, 1H), 7.79 (d, J=7.69 Hz, 1H), 7.67 (d, J=8.05 Hz, 1H), 7.59-7.57 (m, 1H), 7.31-7.24 (m, 5H), 7.18 (d, J=6.96 Hz, 1H), 7.07 (d, J=10.9 Hz, 1H), 7.04-6.99 (m, 1H), 5.80 (m, 1H), 5.08 (s, 2H), 4.67 (d, J=8.42 Hz, 1H), 4.12 (bs, 1H), 3.84-3.68 (m, 2H), 2.99-2.80 (m, 2H), 2.70 (s, 2H), 2.60 (bs, 3H), 2.40-2.33 (m, 1H), 2.32-2.29 (m, 1H), 1.90-1.87 (m, 1H), 1.47-1.35 (m, 1H); IR (KBr, cm$^{-1}$): 3419, 2924, 2852, 2804, 2229, 1772, 1627, 1494, 1355, 1244, 1022, 754; MS (ESI): m/z 511 (M+1).

Example 67

N—((S)-1-cyclohexyl-2-((S)-3-hydroxypyrrolidin-1-yl)ethyl)-2-(2-oxo-2,3-dihydrobenzo[d]oxazol-5-yl)acetamide

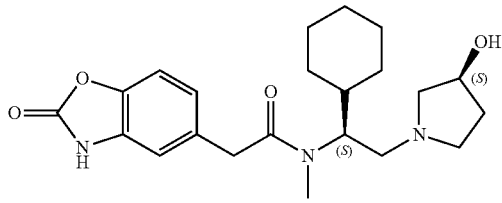

Melting point: 173-174° C.; $^1$H-NMR (400 MHz, DMSO-$d_6$): δ 11.5 (bs, 1H), 7.72 (s, J=8.24 Hz, 1H), 7.17 (d, J=7.94 Hz, 1H), 7.07 (s, 1H), 6.96 (d, J=7.94 Hz, 1H), 4.80 (bs, 1H), 4.12 (bs, 1H), 3.73 (bs, 1H), 3.41-3.37 (m, 2H), 2.65 (d, J=8.5 Hz, 1H), 2.43-2.23 (m, 4H), 1.92 (d, J=6.41 Hz, 1H), 1.59 (m, 7H), 1.2-1.08 (m, 6H); IR (KBr, cm$^{-1}$): 3065, 2797, 1765, 1649, 1535, 1262; MS (ESI): m/z 388 (M+1).

Example 68

(S)-tert-butyl-2-(3-(1-(2-(3-benzyl-2-oxo-2,3-dihydrobenzo[d]oxazol-5-yl)-N-methyl acetamido)-2-(pyrrolidin-1-yl)ethyl)phenoxy)acetate

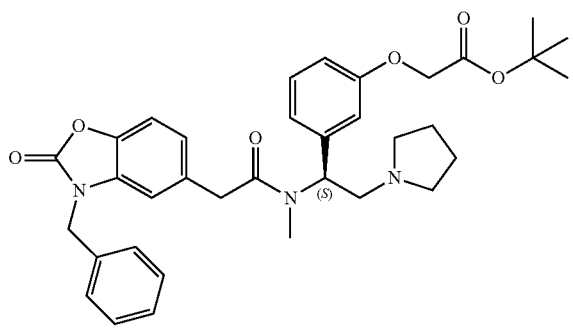

Melting point: 111-113° C.; $^1$H-NMR (400 MHz, DMSO-$d_6$): δ 7.35-7.26 (m, 6H), 7.22 (t, J=7.9 Hz, 1H), 7.07 (s, 1H), 7.05-7.01 (m, 1H), 6.86 (d, J=7.2 Hz, 1H), 6.79-6.73 (m, 2H), 5.79 (bs, 1H), 5.00 (s, 2H), 4.61 (s, 2H), 3.81-3.79 (m, 1H), 3.75-3.68 (m, 1H), 3.01 (bs, 1H), 2.89 (s, 1H), 2.71 (s, 3H), 2.61-2.54 (m, 2H), 2.49-2.33 (m, 2H), 1.61 (bs, 4H), 1.41 (s, 9H); IR (KBr, cm$^{-1}$): 3399, 2922, 2851, 1776, 1641, 1493, 1462, 1389, 1289; MS (ESI): m/z 600 (M+1).

Example 69

N—((S)-1-cyclohexyl-2-((S)-3-hydroxypyrrolidin-1-yl)ethyl)-2-(2-oxoindolin-6-yl)acetamide

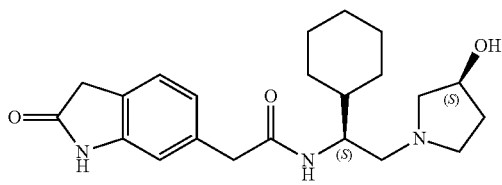

Melting point: 132-133° C.; $^1$H-NMR (400 MHz, DMSO-$d_6$): δ 10.32 (s, 1H), 7.63 (d, J=7.3 Hz, 1H), 7.07 (d, J=7.3 Hz, 1H), 6.91-6.81 (m, 2H), 4.86 (bs, 1H), 4.18 (bs, 1H), 3.78 (s, 1H), 3.46-3.31 (m, 4H), 2.68 (s, 2H), 2.21-2.19 (m, 4H), 1.96 (s, 1H), 1.67-1.60 (m, 6H), 1.52-0.97 (m, 6H); IR (KBr, cm$^{-1}$): 3262, 2928, 2853, 2799, 1703, 1632; MS (ESI): m/z 386 (M+1).

Example 70

N—((S)-1-cyclohexyl-2-((S)-3-hydroxypyrrolidin-1-yl)ethyl)-N-methyl-2-(2-oxo-2,3-dihydrobenzo[d]oxazol-5-yl)acetamide

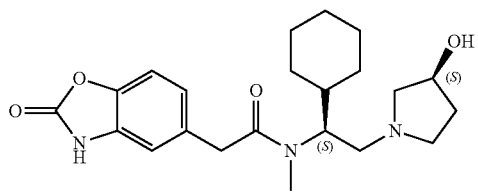

Melting point: 130-131° C.; $^1$H-NMR (400 MHz, DMSO-$d_6$): δ 11.5 (bs, 1H), 7.18 (d, J=7.8 Hz, 1H), 7.16 (s, 1H), 7.03-6.96 (m, 1H), 4.6 (bs, 1H), 4.3 (bs, 1H), 4.14 (bs, 1H), 3.8-3.6 (m, 4H), 2.73 (s, 3H), 2.7-2.6 (m, 2H), 2.2 (bs, 2H), 1.93-1.90 (m, 2H), 1.8-1.71 (m, 7H), 1.20-1.02 (m, 4H); IR (KBr, cm$^{-1}$): 2927, 2852, 1774, 1618, 1261; MS (ESI): m/z 402 (M+1).

Example 71

(S)—N-(1-(3-cyanophenyl)-2-(pyrrolidin-1-yl)ethyl)-N-methyl-2-(2-oxo-2,3-dihydrobenzo[d]oxazol-5-yl)acetamide

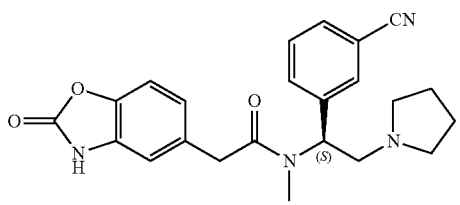

Melting point: 116-118° C.; $^1$H-NMR (400 MHz, DMSO-$d_6$): δ 11.5 (bs, 1H), 7.75-7.63 (m, 2H), 7.61-7.52 (m, 2H), 7.18 (d, J=8.0 Hz, 1H), 6.95-6.93 (m, 2H), 5.82-5.79 (m, 1H), 3.79-3.76 (m, 2H), 3.01-2.97 (m, 1H), 2.86-2.83 (m, 1H), 2.76 (s, 3H), 2.50 (bs, 4H), 1.6 (bs, 4H); IR (KBr, cm$^{-1}$): 2958, 2794, 2227, 1774, 1629, 1465, 1400, 1261; MS (ESI): m/z 405 (M+1).

Example 72

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)acetamide

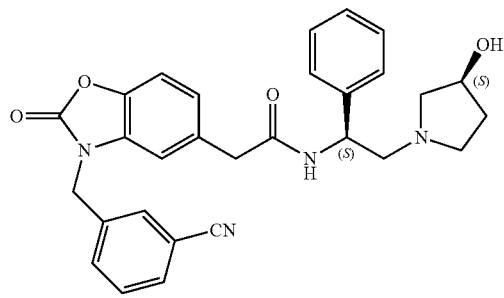

Melting point: 65-68° C.; ¹H-NMR (400 MHz, DMSO-d₆): δ 8.43 (d, J=8.3 Hz, 1H), 7.88 (s, 1H), 7.79 (d, J=7.8 Hz, 1H), 7.67 (d, J=8.1 Hz, 1H), 7.59-7.55 (m, 1H), 7.29-7.25 (m, 5H), 7.23-7.18 (m, 1H), 7.09-7.05 (m, 2H), 5.06 (s, 2H), 4.87-4.81 (m, 1H), 4.64 (d, J=4.3 Hz, 1H), 4.12-4.08 (m, 1H), 3.50-3.41 (m, 2H), 2.70-2.66 (m, 2H), 2.53-2.51 (m, 2H), 2.47-2.37 (m, 1H), 2.29-2.26 (m, 1H), 1.91-1.86 (m, 1H), 1.49-1.44 (m, 1H); IR (KBr, cm⁻¹): 3304, 3062, 2943, 2806, 2229, 1774, 1658, 1535, 1494, 1354, 1246; MS (ESI): m/z 497 (M+1).

Example 73

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide

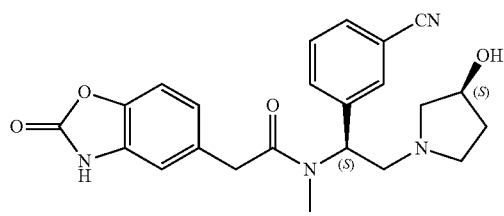

Melting point: 203-206° C.; ¹H-NMR (400 MHz, DMSO-d₆): δ 11.58 (bs, 1H), 7.74 (d, J=6.8 Hz, 1H), 7.70 (s, 1H), 7.62 (d, J=7.9 Hz, 1H), 7.58-7.53 (m, 1H), 7.20 (d, J=8.3 Hz, 1H), 7.02 (s, 1H), 6.95 (d, J=8.3 Hz, 1H), 5.86-5.82 (m, 1H), 4.90 (bs, 1H), 4.23-4.18 (m, 1H), 3.89-3.75 (m, 2H), 3.18-3.0 (m, 1H), 2.87-2.83 (m, 2H), 2.76 (s, 3H), 2.74-2.71 (m, 1H), 2.50-2.42 (m, 2H), 1.99-1.92 (m, 1H), 1.59-1.51 (m, 1H); IR (KBr, cm⁻¹): 3331, 2920, 2798, 2229, 1764, 1597, 1465, 1261, 1138; MS (ESI): m/z 421 (M+1).

Example 74

(S)-tert-butyl 2-(3-(2-(3-hydroxypyrrolidin-1-yl)-1-(2-(2-oxo-2,3-dihydrobenzo[d]oxazol-5-yl)acetamido)ethyl)phenoxy)acetate

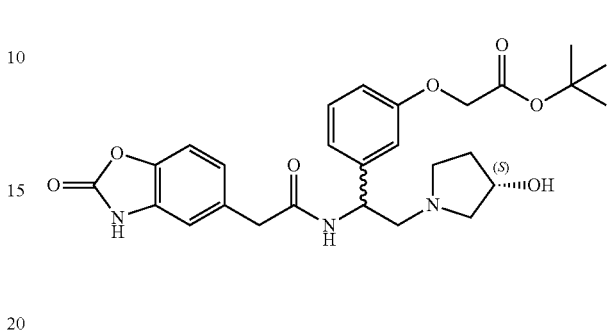

¹H-NMR (400 MHz, DMSO-d₆): δ 11.55 (bs, 1H), 8.47 (t, J=8.8 Hz, 1H), 7.22-7.15 (m, 2H), 7.06-6.70 (m, 5H), 4.88 (bs, 1H), 4.59 (d, J=2.0 Hz, 2H), 4.16 (bs, 1H), 3.53-3.40 (m, 2H), 3.18-3.14 (m, 1H), 2.84-2.60 (m, 3H), 2.40-2.35 (m, 2H), 1.96-1.86 (m, 1H), 1.58-1.52 (m, 1H), 1.42 (s, 9H); IR (KBr, cm⁻¹): 3288, 3055, 2974, 2808, 1764, 1656, 1492, 1467, 1369, 1261, 1153, 1087; MS (ESI): m/z 512 (M+1).

Example 75

2-(3-(4-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide

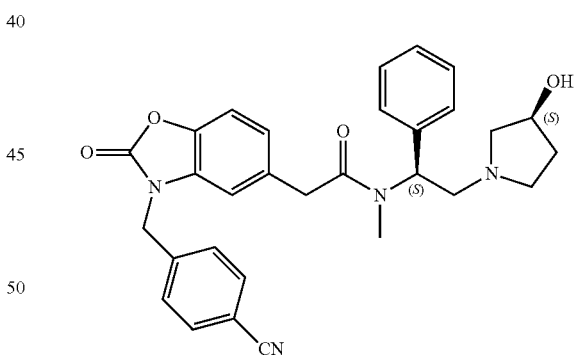

¹H-NMR (400 MHz, DMSO-d₆): δ 7.83 (d, J=8.3 Hz, 2H), 7.53 (d, J=8.3 Hz, 2H), 7.33-7.25 (m, 5H), 7.24-7.16 (m, 1H), 7.06-7.04 (m, 2H), 5.80 (m, 1H), 5.08 (s, 2H), 4.67 (d, J=8.42 Hz, 1H), 4.12 (bs, 1H), 3.84-3.68 (m, 2H), 2.99-2.80 (m, 2H), 2.70 (s, 2H), 2.60 (bs, 3H), 2.40-2.33 (m, 1H), 2.32-2.29 (m, 1H), 1.90-1.87 (m, 1H), 1.47-1.35 (m, 1H); IR (KBr, cm⁻¹): 3062, 2920, 2852, 2804, 2227, 1774, 1631, 1494, 1467, 1384, 1244, 1095; MS (ESI): m/z 511 (M+1).

Example 76

N-(1-(3-(cyanomethoxy)phenyl)-2-(3-hydroxypyrrolidin-1-yl)ethyl)-N-methyl-2-(2-oxo-2,3-dihydrobenzo[d]oxazol-5-yl)acetamide

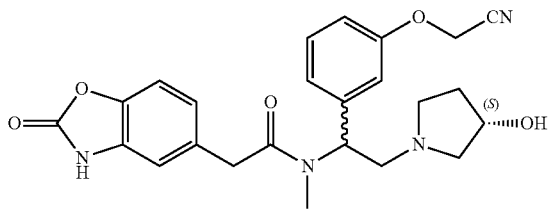

¹H-NMR (400 MHz, DMSO-d₆): δ 11.54 (bs, 1H), 7.35-7.31 (m, 1H), 7.30-7.20 (m, 1H), 7.17-6.90 (m, 5H), 5.82 (bs, 1H), 5.15-5.14 (s, 2H), 4.90 (bs, 1H), 4.68 (bs, 1H), 4.16-3.86 (bs, 1H), 3.82-3.72 (m, 2H), 3.29-3.17 (m, 1H), 2.96-2.78 (m, 2H), 2.73-2.62 (s, 3H), 2.5-2.37 (m, 2H), 1.98-1.94 (m, 1H), 1.60-1.40 (bs, 1H); IR (Neat, cm⁻¹): 2949, 2808, 1766, 1604, 1467, 1400, 1263, 1172, 1138, 1099; MS (ESI): m/z 451 (M+1).

Example 77 tert-butyl 2-(3-((S)-2-((R)-3-hydroxypyrrolidin-1-yl)-1-(N-methyl-2-(2-oxo-2,3-dihydro benzo [d]oxazol-5-yl)acetamido)ethyl)phenoxy)acetate

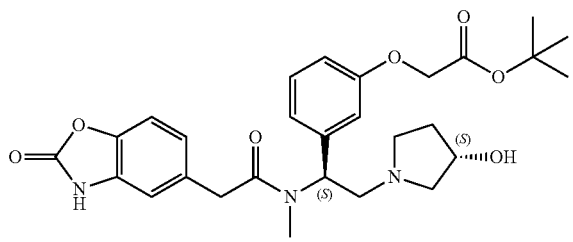

Melting point: 124-125° C.; ¹H-NMR (400 MHz, DMSO-d₆): δ 12.0-11.0 (bs, 1H), 7.26-7.17 (m, 2H), 7.04 (s, 1H), 6.96-6.95 (m, 1H), 6.88-6.86 (m, 1H), 6.83-6.80 (m, 1H), 6.77-6.74 (m, 2H), 5.84-5.80 (m, 1H), 4.83 (bs, 1H), 4.61 (s, 1H), 4.20-4.16 (m, 1H), 3.86-3.84 (m, 1H), 3.82-3.71 (m, 1H), 3.10-3.00 (m, 1H), 2.81-2.74 (m, 2H), 2.71 (s, 3H), 2.68-2.67 (m, 1H), 2.50-2.49 (m, 2H), 1.98-1.91 (m, 1H), 1.52-1.51 (m, 1H), 1.49 (s, 9H); IR (Neat, cm⁻¹): 3339, 2980, 2797, 1773, 1597, 1467; MS (ESI): m/z 526 (M+1).

Example 78

N—((S)-1-(3-cyanophenyl)-2-((S)-3-hydroxypyrrolidin-1-yl)ethyl)-N-methyl-2-(3-methyl-2-oxo-2,3-dihydrobenzo[d]oxazol-5-yl)acetamide

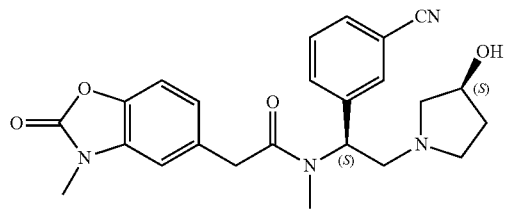

Melting point: 83-85° C.; ¹H-NMR (400 MHz, DMSO-d₆): δ 7.74 (d, J=6.8 Hz, 1H), 7.70 (s, 1H), 7.62 (d, J=7.9 Hz, 1H), 7.58-7.53 (m, 1H), 7.20 (d, J=8.3 Hz, 1H), 7.02 (s, 1H), 6.95 (d, J=8.3 Hz, 1H), 5.86-5.82 (m, 1H), 4.90 (bs, 1H), 4.23-4.18 (m, 1H), 3.89-3.75 (m, 2H), 3.31 (s, 3H), 3.18-3.0 (m, 1H), 2.87-2.83 (m, 2H), 2.76 (s, 3H), 2.74-2.71 (m, 1H), 2.50-2.42 (m, 2H), 1.99-1.92 (m, 1H), 1.59-1.51 (m, 1H); IR (Neat, cm⁻¹): 2943, 2802, 2227, 1776, 1631, 1479, 1384, 1265; MS (ESI): m/z 435 (M+1).

Example 79

N—((S)-1-(3-(1H-tetrazol-5-yl)phenyl)-2-((S)-3-hydroxypyrrolidin-1-yl)ethyl)-2-(2,2-dioxido-1,3-dihydrobenzo[c]isothiazol-6-yl)-N-methylacetamide

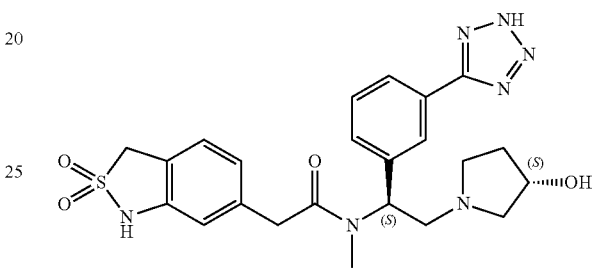

¹H-NMR (400 MHz, DMSO-d₆): δ 7.93 (s, 1H), 7.90 (d, J=7.3 Hz, 1H), 7.45-7.41 (m, 1H), 7.31 (s, 1H), 7.17 (d, J=7.8 Hz, 1H), 6.86 (d, J=7.8 Hz, 1H), 6.79 (s, 1H), 5.95 (m, 1H), 5.21 (bs, 1H), 4.40 (s, 2H), 4.23 (s, 1H), 3.81-3.71 (m, 2H), 3.22-3.15 (m, 2H), 3.12-3.09 (m, 2H), 2.74 (s, 3H), 2.45-2.32 (m, 1H), 2.31-2.29 (m, 1H), 1.97-1.92 (m, 1H), 1.53-1.50 (m, 1H); IR (Neat, cm⁻¹): 2926, 1708, 1641, 1583, 1444, 1402, 1309, 1136; MS (ESI) m/z: 498 (M+1).

Example 80

2-(3-((S)-2-((S)-3-hydroxypyrrolidin-1-yl)-1-(N-methyl-2-(1-methyl-2,2-dioxido-1,3-dihydrobenzo[c]isothiazol-6-yl)acetamido)ethyl)phenoxy)acetic acid

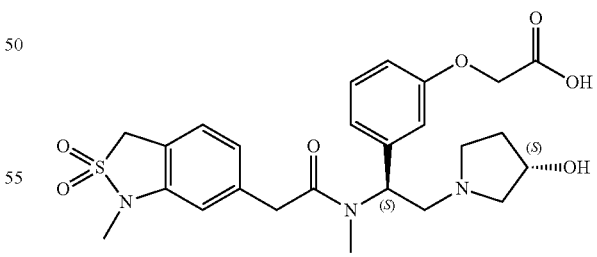

¹H-NMR (400 MHz, DMSO-d₆): δ 13.00 (s, 1H), 9.94-9.76 (m, 1H), 7.31-7.25 (m, 2H), 6.91-6.77 (m, 5H), 6.13-6.12 (m, 1H), 6.10 (s, 1H), 4.80-4.75 (s, 2H), 4.60-4.45 (s, 2H), 4.44 (d, 1H; J=28.3), 4.12-4.09 (m, 1H), 4.0-3.60 (m, 5H), 3.20-3.10 (s, 3H), 2.82-2.73 (m, 3H), 2.32-2.28 (m, 1H), 2.26-1.84 (m, 1H); IR (Neat, cm⁻¹): 2927, 1678, 1612, 1587, 1492, 1442, 1400, 1321, 1203, 1139; MS (ESI) m/z: 518 (M+1).

Example 81

(S)-methyl 3-((2-oxo-5-(2-oxo-2-(1-phenyl-2-(pyrrolidin-1-yl)ethylamino)ethyl)benzo[d]oxazol-3(2H)-yl)methyl)benzoate

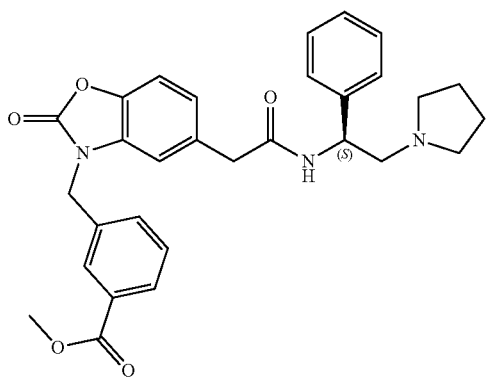

¹H-NMR (400 MHz, DMSO-d₆): δ 8.80-8.60 (m, 1H), 7.95 (s, 1H), 7.90 (d, J=7.8 Hz, 1H), 7.63 (d, J=7.5 Hz, 1H) 7.51 (t, J=7.8 Hz, 1H), 7.30-7.28 (m, 6H), 7.15 (s, 1H), 7.05 (d, J=8.33 Hz, 1H), 5.09 (m, 3H), 3.84 (s, 3H), 3.50 (s, 2H), 3.20 (m, 2H), 2.54-2.50 (m, 4H), 1.75 (bs, 4H); IR (KBr, cm⁻¹): 3360, 2951, 1776, 1722, 1658, 1492, 1286, 1203, 1107, 1020; MS (ESI) m/z: 514.0 (M+1).

Example 82

(S)-tert-butyl-2-(2-oxo-5-(2-oxo-2-(1-phenyl-2-(pyrrolidin-1-yl)ethylamino)ethyl)benzo[d]oxazol-3(2H)-yl)acetate

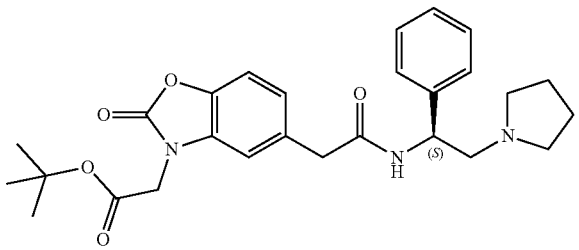

¹H-NMR (400 MHz, DMSO-d₆): δ 8.51 (bs, 1H), 7.30-7.05 (m, 8H), 4.92 (m, 1H), 4.58 (s, 2H), 3.52-3.37 (bs, 2H), 2.89-2.67 (m, 2H), 2.54-2.32 (m, 4H), 1.91-1.57 (m, 4H), 1.41 (s, 9H); IR (Neat, cm⁻¹): 2976, 1784, 1743, 1658, 1546, 1494, 1467, 1390, 1367, 1244, 1155; MS (ESI) m/z: 480 (M+1).

Example 83

(S)-2-(2-oxo-5-(2-oxo-2-(1-phenyl-2-(pyrrolidin-1-yl)ethylamino)ethyl) benzo[d]oxazol-3(2H)-yl)acetic acid hydrochloride

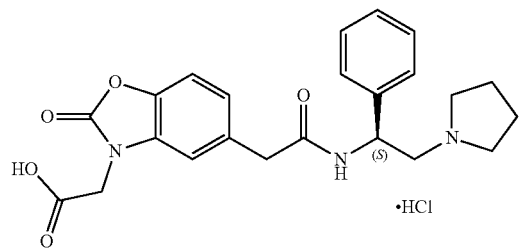

¹H-NMR (400 MHz, DMSO-d₆): δ 10.1 (bs, 1H), 8.90 (d, J=8.3 Hz, 1H), 7.2-7.4 (m, 7H), 7.06 (m, 1H), 5.25-5.29 (m, 1H), 4.26 (s, 2H), 3.61 (s, 2H), 3.53-3.38 (m, 4H), 3.32-3.06 (m, 2H), 2.32-1.90 (m, 4H); IR (Neat, cm⁻¹): 3030, 2601, 1778, 1670, 1535, 1496, 1467, 1390, 1357, 1246, 1219; MS (ESI) m/z: 424 (M+1).

Example 84

(S)—N-(1-(3-hydroxyphenyl)-2-(pyrrolidin-1-yl)ethyl)-2-(2-oxo-2,3-dihydrobenzo[d]oxazol-5-yl)acetamide

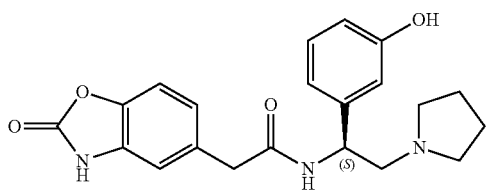

Melting point: 140-142° C.; ¹H-NMR (400 MHz, DMSO-d₆): δ 11.57 (bs, 1H), 9.33 (bs, 1H), 8.43 (bs, 1H), 7.17 (d, J=8.0 Hz, 1H), 7.08 (t, J=7.6 Hz, 1H), 6.99-6.95 (m, 2H), 6.73 (s, 1H), 6.69 (s, 1H), 6.62 (d, J=8.0 Hz, 1H), 4.82 (bs, 1H), 3.47 (d, J=5.9 Hz, 2H), 3.17 (d, J=5.2 Hz, 1H), 2.54 (bs, 4H), 2.44 (bs, 1H), 1.65 (bs, 4H); IR (KBr, cm⁻¹): 3066, 2972, 2823, 1764, 1658, 1589, 1546, 1500, 1467, 1382, 1263; MS (ESI) m/z: 382.4 (M+1).

Example 85

(S)-2-(3-(1-(2-(2-oxo-2,3-dihydrobenzo[d]oxazol-5-yl)acetamido)-2-(pyrrolidin-1-yl)ethyl)phenoxy)acetic acid hydrochloride

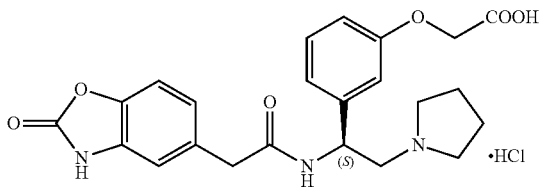

¹H-NMR (400 MHz, DMSO-d₆): δ 13.05 (bs, 1H), 11.60 (s, 1H), 10.20 (bs, 1H), 8.87 (d, J=8.6 Hz, 1H), 7.28-7.24 (m, 1H), 7.18 (d, J=8.3 Hz, 1H), 7.04-6.97 (m, 4H), 6.84-6.81 (m, 1H), 5.26-5.21 (m, 1H), 4.65 (s, 2H), 3.60 (s, 1H), 3.37-3.05 (m, 2H), 2.67-2.50 (m, 4H), 1.96-1.90 (m, 4H); IR (KBr, cm⁻¹): 3525, 3444, 2638, 1766, 1564, 1259, 1024, 792; MS (ESI) m/z: 440 (M+1).

Example 86

2-(5-(2-(((S)-2-((S)-3-hydroxypyrrolidin-1-yl)-1-phenylethyl)(methyl)amino)-2-oxoethyl)-2-oxobenzo[d]oxazol-3(2H)-yl)acetic acid

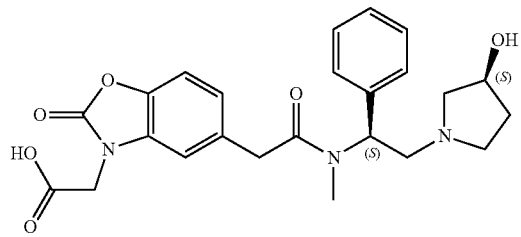

¹H-NMR (400 MHz, DMSO-d₆): δ 7.35-7.25 (m, 6H), 7.09-6.99 (m, 2H), 5.91-5.89 (m, 1H), 4.35 (bs, 2H), 4.19 (bs, 1H), 3.87-3.65 (m, 4H), 3.16-2.85 (m, 4H), 2.84-2.62 (m, 4H), 2.0-1.96 (m, 1H), 1.58-1.43 (m, 1H), 1.23-1.13 (m, 1H); IR (Neat, cm⁻¹): 3167, 2945, 1782, 1631, 1604, 1496, 1469, 1396, 1381, 1359, 1307; MS (ESI): m/z 454 (M+1).

Example 87

2-(3-(1-(N-methyl-2-(2-oxoindolin-6-yl)acetamido)-2-(pyrrolidin-1-yl)ethyl)phenoxy) acetic acid hydrochloride

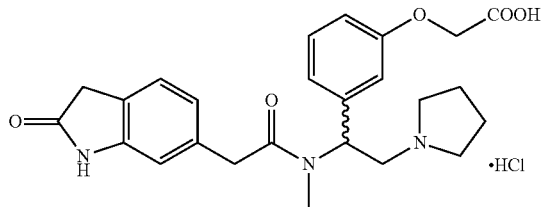 [SMILES: CN(C(=O)Cc1ccc2c(c1)NC(=O)C2)C(CN1CCCC1)c1cccc(OCC(=O)O)c1 ; Cl]

Melting point: 169-171° C.; ¹H-NMR (400 MHz, DMSO-d₆): δ 10.59 (s, 1H), 7.21 (t, J=7.0 Hz, 1H), 7.09 (d, J=7.6 Hz, 1H), 6.84-6.77 (m, 4H), 6.72 (s, 1H), 5.87-5.83 (m, 1H), 4.51 (s, 2H), 3.75 (d, J=5.6 Hz, 1H), 3.70 (s, 1H), 3.17 (s, 1H), 3.14-3.09 (m, 1H), 2.83-2.82 (m, 1H), 2.68 (s, 3H), 2.50 (bs, 4H), 2.44 (bs, 1H), 1.70 (bs, 4H); IR (KBr, cm⁻¹): 3018, 1699, 1629, 1215, 756, 669; MS (ESI): m/z 452 (M+1).

Example 88

3-((5-(2-(((S)-2-((S)-3-hydroxypyrrolidin-1-yl)-1-phenylethyl)(methyl)amino)-2-oxoethyl)-2-oxobenzo[d]oxazol-3(2H)-yl)methyl)benzamide

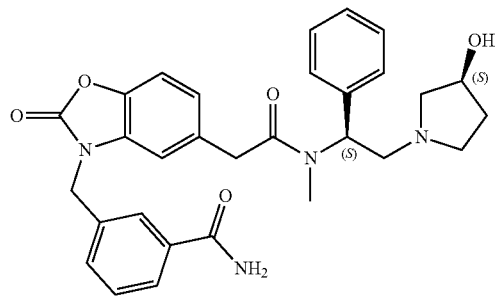

Melting point: 181-183° C.; ¹H-NMR (400 MHz, DMSO-d₆): δ 7.99 (s, 1H), 7.84 (s, 1H), 7.79 (d, J=7.33 Hz, 1H), 7.50-7.21 (m, 7H), 7.19-7.02 (m, 2H), 6.09 (bs, 1H), 5.81 (bs, 1H), 5.07 (s, 2H), 4.91 (bs, 1H), 4.56 (m, 1H), 4.03 (bs, 1H), 3.83-3.71 (m, 2H), 2.69 (s, 4H), 2.67-2.53 (m, 3H), 2.29-2.0 (m, 2H), 1.98-1.72 (m, 1H), 1.33-1.29 (m, 1H); IR (KBr, cm⁻¹): 3375, 3034, 2927, 2723, 1768, 1666, 1494, 1384, 1246; MS (ESI): m/z 529 (M+1).

Example 89

(S)-2-(3-benzyl-2-oxo-2,3-dihydrobenzo[d]oxazol-5-yl)-N-(1-(3-hydroxyphenyl)-2-(pyrrolidin-1-yl)ethyl)-N-methylacetamide

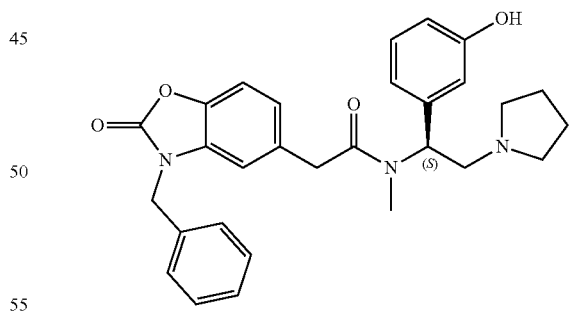

Melting point: 165-167° C.; ¹H-NMR (500 MHz, DMSO-d₆): δ 9.36 (bs, 1H), 7.36-7.27 (m, 6H), 7.12-7.02 (m, 3H), 6.68-6.61 (m, 3H), 5.76 (s, 1H), 5.00 (s, 2H), 3.79-3.69 (m, 2H), 2.71 (s, 2H), 2.65-2.64 (m, 1H), 2.43-2.36 (bs, 2H), 2.51-2.49 (bs, 4H), 1.64-1.58 (bs, 4H); IR (KBr, cm⁻¹): 3523, 1770, 1620, 1492, 1454, 1390, 1357, 1271, 1244, 1016; MS (ESI): m/z 486.2 (M+1).

Example 90

(R)-2-(3-(1-(N-methyl-2-(2-oxo-2,3-dihydrobenzo[d]oxazol-5-yl)acetamido)-2-(pyrrolidin-1-yl)ethyl)phenoxy)acetic acid

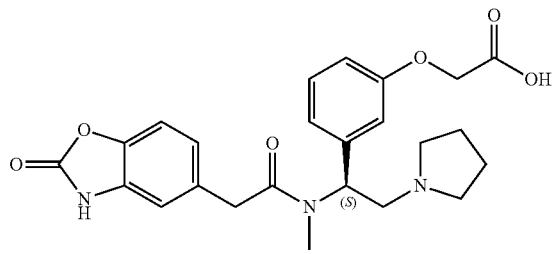

Melting point: 227-229° C.; $^1$H-NMR (400 MHz, DMSO-$d_6$): δ 13.03 (bs, 1H), 11.58 (s, 1H), 10.10 (bs, 1H), 7.30 (t, J=8.0 Hz, 1H), 7.19 (d, J=8.0 Hz, 1H), 7.05 (s, 1H), 6.97 (d, J=8.4 Hz, 1H), 6.88 (d, J=1.6 Hz, 1H), 6.86 (d, J=1.6 Hz, 1H), 6.82 (d, J=7.2 Hz, 1H), 6.10-6.07 (m, 1H), 4.65 (s, 2H), 4.05 (t, J=12.4 Hz, 1H), 3.94-3.78 (m, 2H), 3.63 (d, J=12.0 Hz, 2H), 3.52 (s, 1H), 3.16 (bs, 1H), 2.79 (s, 3H), 1.99 (bs, 4H); IR (KBr, cm$^{-1}$): 3477, 2949, 1759, 1612, 1462, 1265, 1172, 1074, 920, 781, 705; MS (ESI): m/z 454.3 (M+1).

Example 91

(S)-3-((2-oxo-5-(2-oxo-2-(1-phenyl-2-(pyrrolidin-1-yl)ethylamino)ethyl)benzo[d]oxazol-3(2H)-yl)methyl)benzamide

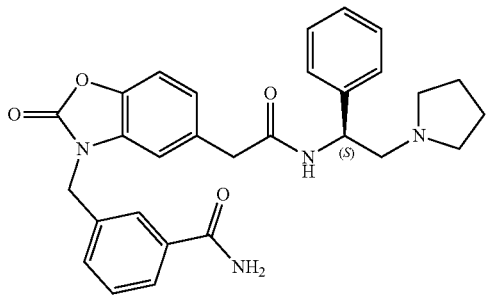

Melting point: 171-172° C.; $^1$H-NMR (400 MHz, DMSO-$d_6$): δ 8.61 (bs, 1H), 8.02 (bs, 1H), 7.85 (bs, 1H), 7.82 (d, J=7.3 Hz, 1H), 7.47 (bs, 1H), 7.45-7.40 (m, 2H), 7.39-7.23 (m, 6H), 7.11 (s, 1H), 7.05 (d, J=8.2 Hz, 1H), 5.03 (s, 2H), 4.95 (m, 1H), 3.49 (s, 2H), 2.91-2.74 (m, 2H), 2.50 (m, 2H), 1.67 (bs, 4H); IR (KBr, cm$^{-1}$): 3304, 3188, 3059, 2964, 2799, 1769, 1659, 1495, 1246; MS (ESI): m/z 499.0 (M+1).

Example 92

2-(3-(1-(2-(2-oxoindolin-6-yl)acetamido)-2-(pyrrolidin-1-yl)ethyl)phenoxy)acetic acid Melting point: 104-106° C.; $^1$H-NMR (400 MHz, DMSO-$d_6$): δ 13.00 (bs, 1H), 10.35 (s, 1H), 10.19 (bs, 1H), 8.85 (d, J=8.8 Hz, 1H), 7.26 (t, J=8.0 Hz, 1H), 7.09 (d, J=7.2 Hz, 1H), 7.0-7.06 (m, 2H), 6.85-6.81 (m, 2H), 6.75 (s, 1H), 5.23 (m, 1H), 4.63 (s, 2H), 3.56 (s, 3H), 3.53 (s, 2H), 3.44 (d, J=12.0 Hz, 2H), 3.30 (bs, 1H), 3.10 (bs, 1H), 1.98-1.88 (m, 4H); IR (KBr, cm$^{-1}$): 3020, 2401, 1535, 1217, 929, 759, 673; MS (ESI): m/z 438 (M+1).

Example 93

(S)—N-(1-(3-(2H-tetrazol-5-yl)phenyl)-2-(pyrrolidin-1-yl)ethyl)-N-methyl-2-(2-oxo-2,3-dihydrobenzo[d]oxazol-5-yl)acetamide Melting point: 240-242° C.; $^1$H-NMR (400 MHz, DMSO-$d_6$): δ 11.57 (s, 1H), 10.1 (bs, 1H), 8.01 (d, J=7.0 Hz, 2H), 7.98 (s, 1H), 7.65-7.62 (m, 1H), 7.45 (d, J=7.0 Hz, 1H), 7.17 (d, J=7.6 Hz, 1H), 7.07-6.98 (m, 1H), 6.24 (d, J=10.2 Hz, 1H), 4.20-4.13 (m, 2H), 3.99-3.82 (m, 2H), 2.85 (s, 3H), 2.50 (bs, 4H), 2.0 (bs, 4H); IR (KBr, cm$^{-1}$): 3373, 3035, 1778, 1629, 1550, 1467, 1388, 1269, 1103; MS (ESI): m/z 448 (M+1).

Example 94

(S)-2-(3-(2-(3-hydroxypyrrolidin-1-yl)-1-(N-methyl-2-(2-oxo-2,3-dihydrobenzo[d]oxazol-5-yl)acetamido)ethyl)phenoxy)acetic acid triflouro acetate ¹H-NMR (400 MHz, DMSO-d₆): δ 13.10 (bs, 1H), 11.60 (s, 1H), 9.80-9.60 (m, 1H), 7.30 (m, 1H), 7.20 (d, J=8.3 Hz, 1H), 6.99 (s, 1H), 6.95-6.76 (m, 4H), 6.18-6.05 (m, 1H), 5.50 (bs, 1H), 4.64 (s, 2H), 4.42 (bs, 1H), 4.20-3.60 (m, 5H), 3.50-3.20 (m, 3H), 2.73 (s, 3H), 2.30-2.20 (m, 1H), 1.90-1.80 (m, 1H); IR (KBr, cm⁻¹): 3062, 1766, 1672, 1469, 1265, 1199, 1134, 1095; MS (ESI): m/z 470 (M+1).

Example 95

(S)-2-(3-(2-(3-hydroxypyrrolidin-1-yl)-1-(N-methyl-2-(2-oxoindolin-6-yl) acetamido)ethyl)phenoxy) acetic acid hydrochloride

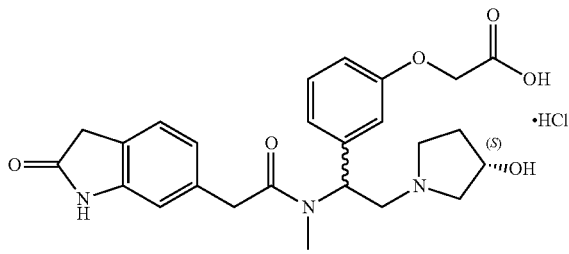

¹H-NMR (400 MHz, DMSO-d₆): δ 13.10 (bs, 1H), 10.35 (s, 1H), 9.90-9.65 (m, 1H), 7.30-7.27 (m, 1H) 7.12 (d, J=7.4 Hz, 1H), 6.86 (d, J=8.3 Hz, 1H), 6.81-6.70 (m, 4H), 6.2-6.13 (m, 1H), 5.50 (bs, 1H), 4.63 (s, 2H), 4.42 (s, 1H), 4.15-4.10 (m, 1H), 3.85-3.60 (m, 5H), 3.40-4.20 (m, 4H), 2.70 (s, 3H), 2.30-2.20 (m, 1H), 1.90-1.80 (m, 1H); IR (KBr, cm⁻¹): 3238, 2951, 1678, 1631, 1452, 1462, 1203, 1136; MS (ESI): m/z 468 (M+1).

Example 96

2-(3-((S)-2-((R)-3-hydroxypyrrolidin-1-yl)-1-(N-methyl-2-(2-oxo-2,3-dihydrobenzo[d]oxazol-5-yl) acetamido)ethyl)phenoxy)acetic acid

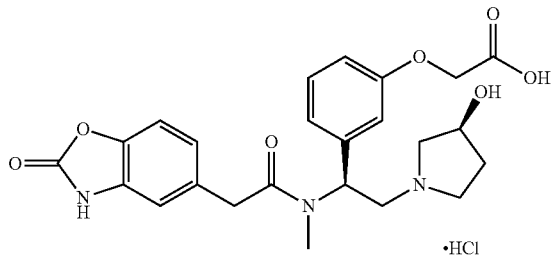 [SMILES: CN(C(=O)Cc1ccc2oc(=O)[nH]c2c1)[C@H](CN1CC[C@H](O)C1)c1cccc(OCC(=O)O)c1 ; Cl]

Melting point: 95-96° C.; ¹H-NMR (400 MHz, DMSO-d₆): δ 13.00 (bs, 1H), 11.60 (bs, 1H), 9.84 (bs, 1H), 7.31-7.27 (m, 1H), 7.21 (d, J=7.8 Hz, 1H), 7.00 (s, 1H), 6.96 (d, J=8.3 Hz, 1H), 6.88 (d, J=8.3 Hz, 1H), 6.82-6.75 (m, 2H), 6.11 (d, J=10.7 Hz, 1H), 5.50 (bs, 1H), 4.65 (s, 2H), 4.47 (s, 1H), 4.40-4.02 (m, 1H), 3.99-3.98 (m, 1H), 3.82 (s, 3H), 3.43-3.18 (m, 2H), 2.74 (s, 2H), 2.32-2.27 (m, 1H), 2.20-1.83 (m, 2H); IR (Neat, cm⁻¹): 2959, 1756, 1611, 1468, 1219; MS (ESI): m/z 470.2 (M+1).

Example 97

2-(5-(2-(((S)-1-cyclohexyl-2-((S)-3-hydroxypyrrolidin-1-yl)ethyl)(methyl)amino)-2-oxoethyl)-2-oxobenzo[d]oxazol-3(2H)-yl)acetic acid

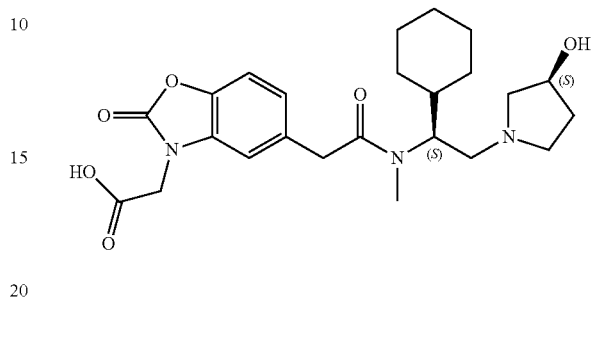

Melting point: 233-234° C.; ¹H-NMR (400 MHz, DMSO-d₆): δ 7.18 (d, J=8.2 Hz, 1H), 6.9-6.8 (m, 2H), 4.45 (s, 1H), 4.2-4.19 (m, 3H), 3.69-3.04 (m, 8H), 2.68 (s, 3H), 2.36-2.01 (m, 1H), 1.69-1.53 (m, 5H), 1.37-1.07 (m, 6H), 0.94-0.90 (m, 1H), 0.88-0.69 (m, 1H); IR (KBr, cm⁻¹): 3290, 2929, 2852, 1768, 1620, 1620, 1496, 1377, 1246, 1101, 1024; MS (ESI): m/z 460 (M+1).

Example 98

Methyl 4-((5-(2-(((S)-2-((S)-3-hydroxypyrrolidin-1-yl)-1-phenylethyl)(methyl)amino)-2-oxoethyl)-2-oxobenzo[d]oxazol-3(2H)-yl)methyl)benzoate

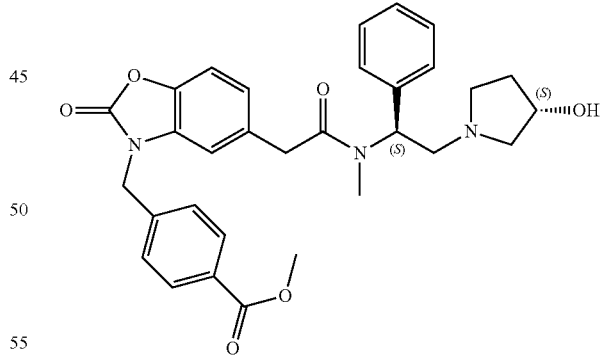

¹H-NMR (400 MHz, DMSO-d₆): δ 7.94 (d, J=7.8 Hz, 2H), 7.47 (d, J=7.8 Hz, 2H), 7.30-7.20 (m, 6H), 7.04 (s, 2H), 5.80 (bs, 1H), 5.11 (s, 2H), 4.65 (bs, 1H), 4.15 (bs, 1H), 3.83 (s, 3H), 3.80-3.60 (m, 2H), 3.0-2.60 (m, 7H), 2.45-2.25 (m, 2H), 1.90 (bs, 1H), 1.50 (bs, 1H); IR (KBr, cm⁻¹): 3420, 3032, 2949, 2800, 1774, 1720, 1612, 1495, 1385, 1280, 1244; MS (ESI): m/z 544 (M+1).

Example 99

N—((S)-1-(3-(2H-tetrazol-5-yl)phenyl)-2-((S)-3-hydroxypyrrolidin-1-yl)ethyl)-N-methyl-2-(2-oxo-2,3-dihydrobenzo[d]oxazol-5-yl)acetamide

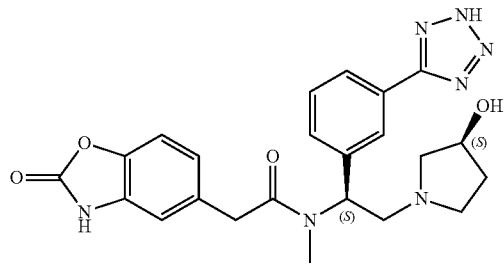

Melting point: 228-230° C.; $^1$H-NMR (400 MHz, DMSO-$d_6$): δ 11.59 (bs, 1H), 7.97-7.93 (m, 2H), 7.55-7.52 (m, 1H), 7.33 (d, J=7.9 Hz, 1H), 7.18 (d, J=8.3 Hz, 1H), 7.05 (s, 1H), 6.97 (d, J=7.9 Hz, 1H), 6.18-6.16 (m, 1H), 5.47-5.40 (m, 1H), 4.40 (s, 1H), 3.94-3.86 (m, 1H), 3.83 (s, 2H), 3.59-3.56 (m, 1H), 3.43-3.31 (m, 3H), 3.18-3.16 (m, 1H), 2.78 (s, 3H), 2.18-2.14 (m, 1H), 1.83-1.82 (m, 1H); IR (KBr, cm$^{-1}$): 3064, 2725, 1766, 1629, 1560, 1467, 1392, 1265; MS (ESI): m/z 464 (M+1).

Example 100

(S)-2-(3-(2-(3-hydroxypyrrolidin-1-yl)-1-(2-(2-oxoindolin-6-yl)acetamido)ethyl)phenoxy)acetic acid hydrochloride

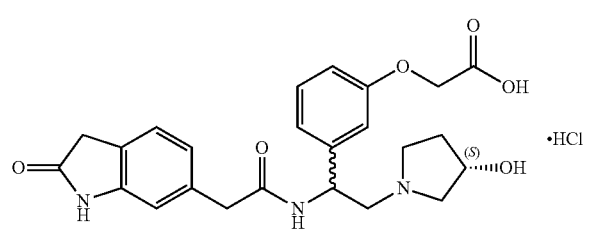

$^1$H-NMR (400 MHz, DMSO-$d_6$): δ 10.43 (s, 1H), 8.47 (t, J=8.8 Hz, 1H), 7.21 (d, J=2.0 Hz, 1H), 7.19 (d, J=1.4 Hz, 1H), 6.88-6.73 (m, 5H), 4.90-4.87 (m, 1H), 4.57 (d, J=2.4 Hz, 2H), 4.18-4.15 (m, 1H), 3.46-3.36 (m, 4H), 2.84-2.54 (m, 4H), 2.50-2.40 (m, 2H), 1.97-1.88 (m, 1H), 1.53-1.45 (m, 1H); IR (KBr, cm$^{-1}$): 3334, 2922, 1726, 1535, 1467, 1379, 1251, 1016; MS (ESI): m/z 454 (M+1).

Example 101

(S)-2-(3-(2-(3-hydroxypyrrolidin-1-yl)-1-(2-(2-oxo-2,3-dihydrobenzo[d]oxazol-5-yl)acetamido)ethyl)phenoxy)acetic acid

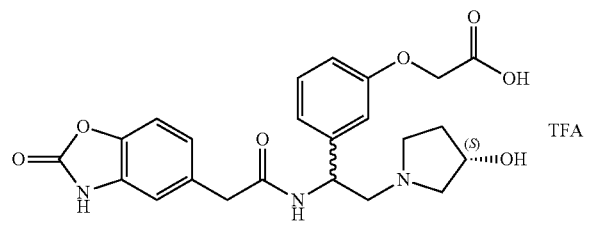

$^1$H-NMR (400 MHz, DMSO-$d_6$): δ 13.1 (bs, 1H), 11.6 (s, 1H), 10.0-9.6 (m, 1H), 8.7 (t, J=8.8 Hz, 1H) 7.3-6.8 (m, 7H), 5.5 (bs, 1H), 5.27 (s, 1H), 4.6 (s, 2H), 4.4 (d, J=15.6 Hz, 1H), 3.60-3.14 (m, 6H), 2.23 (bs, 1H), 1.98-1.80 (m, 2H), 1.58-1.54 (m, 1H); IR (KBr, cm$^1$): 3059, 2966, 1764, 1678, 1599, 1493, 1441, 1263, 1201, 1139, 1085; MS (ESI): m/z 456 (M+1).

Example 102

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide

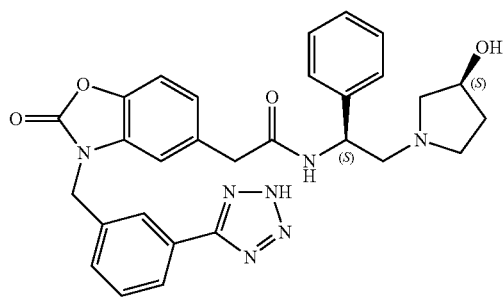

Melting point: 235-237° C.; $^1$H-NMR (400 MHz, DMSO-$d_6$): δ 8.62 (d, J=8.8 Hz, 1H), 7.97 (s, 1H), 7.93 (d, J=7.9 Hz, 1H), 7.46-7.42 (m, 1H), 7.34 (d, J=7.8 Hz, 1H), 7.31-7.29 (m, 5H), 7.27-7.23 (m, 1H), 7.09 (s, 1H), 7.03 (d, J=8.3 Hz, 1H), 5.12-5.09 (m, 1H), 5.06 (s, 2H), 4.25 (d, J=2.9 Hz, 1H), 4.23 (s, 1H), 3.49 (s, 2H), 3.16-3.03 (m, 4H), 2.96-2.93 (m, 1H), 2.92-2.80 (m, 1H), 2.01-1.96 (m, 1H), 1.67-1.64 (m, 1H); IR (KBr, cm$^{-1}$): 3379, 3028, 1764, 1658, 1546, 1494, 1357, 1246; MS (ESI): m/z 540 (M+1).

Example 103

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide

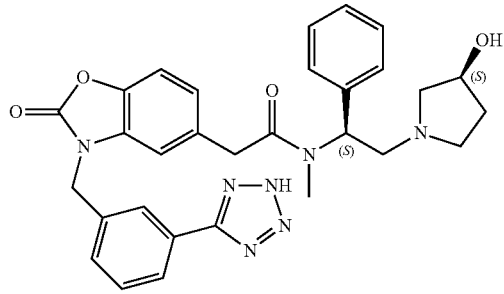

Melting point: 123-125° C.; $^1$H-NMR (400 MHz, DMSO-$d_6$): δ 8.0-7.80 (m, 2H), 7.40-7.20 (m, 8H), 7.10-7.0 (m, 2H), 5.80 (m, 1H), 5.08 (s, 2H), 4.67 (d, J=8.42 Hz, 1H), 4.12 (bs, 1H), 3.84-3.68 (m, 2H), 2.99-2.80 (m, 2H), 2.70 (s, 2H), 2.60 (bs, 3H), 2.40-2.33 (m, 1H), 2.32-2.29 (m, 1H), 1.90-1.87 (m, 1H), 1.47-1.35 (m, 2H); IR (KBr, cm$^{-1}$): 3138, 1766, 1641, 1494, 1390, 1244, 1091, 1016; MS (ESI): m/z 554 (M+1).

Example 104

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide

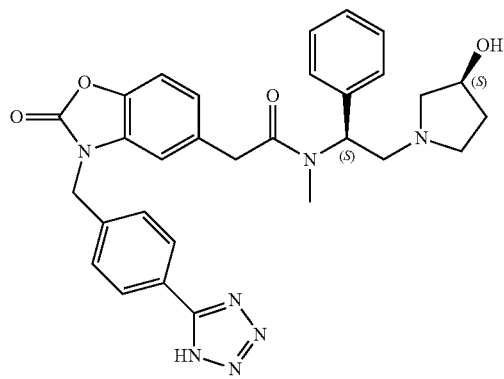

Melting point: 218-220° C.; $^1$H-NMR (400 MHz, DMSO-d$_6$): δ 7.83 (d, J=8.3 Hz, 2H), 7.53 (d, J=8.3 Hz, 2H), 7.33-7.25 (m, 5H), 7.24-7.16 (m, 1H), 7.06-7.04 (m, 2H), 5.80 (m, 1H), 5.08 (s, 2H), 4.67 (d, J=8.42 Hz, 1H), 4.12 (bs, 1H), 3.84-3.68 (m, 2H), 2.99-2.80 (m, 2H), 2.70 (s, 2H), 2.60 (bs, 3H), 2.40-2.33 (m, 1H), 2.32-2.29 (m, 1H), 1.90-1.87 (m, 1H), 1.47-1.35 (m, 2H); IR (Neat, cm$^{-1}$): 2920, 1764, 1629, 1492, 1390, 1346, 1219, 1089, 1012; MS (ESI): m/z 554 (M+1).

Example 105

(R)—N-(1-(3-((2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide

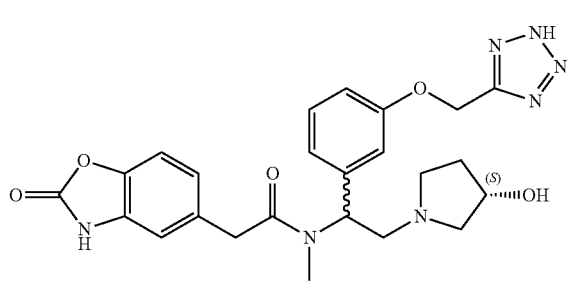

$^1$H-NMR (400 MHz, DMSO-d$_6$): δ 11.8-11.6 (bs, 1H), 7.28-7.26 (m, 1H), 7.24-7.20 (m, 1H), 7.02-6.98 (m, 5H), 6.81-6.80 (m, 1H), 6.0-5.98 (m, 1H), 5.26-5.24 (m, 3H), 4.35-4.27 (bs, 1H), 3.89-3.78 (m, 2H), 3.45-3.29 (m, 4H), 3.06-2.69 (m, 4H), 2.19-2.17 (m, 1H), 1.86 (m, 1H);

IR (Neat, cm$^{-1}$): 3039, 2723, 1757, 1629, 1467, 1392, 1292, 1267, 1236, 1168, 1101; MS (ESI): m/z 494 (M+1).

Example 106

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide

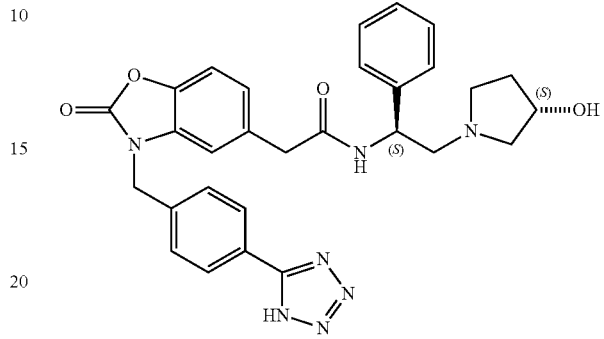

Melting point: 296-297° C.; $^1$H-NMR (400 MHz, DMSO-d$_6$): δ 8.01-7.98 (m, 2H), 7.39-7.42 (m, 2H), 7.35-7.26 (m, 6H), 7.08-7.03 (m, 2H), 5.19-5.16 (m, 1H), 5.02-4.98 (m, 2H), 4.40-4.33 (m, 1H), 3.64-3.53 (m, 2H), 3.35-3.25 (m, 3H), 3.17-3.15 (m, 2H), 3.05-3.01 (m, 1H), 2.09-2.04 (m, 1H), 1.78-1.75 (m, 1H); IR (Neat, cm$^{-1}$): 3242, 3061, 1766, 1494, 1011; MS (ESI): m/z 540 (M+1).

Example 107

N—((S)-1-(3-(2H-tetrazol-5-yl)phenyl)-2-((S)-3-hydroxypyrrolidin-1-yl)ethyl)-N-methyl-2-(3-methyl-2-oxo-2,3-dihydrobenzo[d]oxazol-5-yl)acetamide

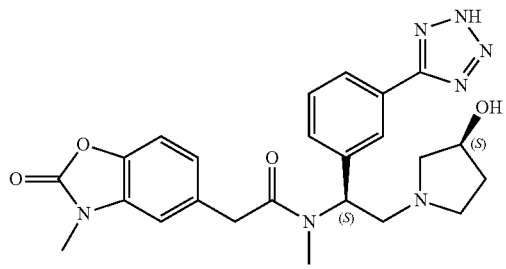

Melting point: 130-132° C.; $^1$H-NMR (400 MHz, DMSO-d$_6$): δ 7.97-7.93 (m, 2H), 7.55-7.52 (m, 1H), 7.33 (d, J=7.9 Hz, 1H), 7.18 (d, J=8.3 Hz, 1H), 7.05 (s, 1H), 6.97 (d, J=7.9 Hz, 1H), 6.18-6.16 (m, 1H), 5.47-5.40 (m, 1H), 4.40 (s, 1H), 3.94-3.86 (m, 1H), 3.83 (s, 2H), 3.60 (s, 3H), 3.59-3.56 (m, 1H), 3.43-3.31 (m, 3H), 3.18-3.16 (m, 1H), 2.78 (s, 3H), 2.18-2.14 (m, 1H), 1.83-1.82 (m, 1H); IR (Neat, cm$^{-1}$): 2964, 1774, 1641, 1479, 1384, 1267, 1219; MS (ESI): m/z 478 (M+1).

Example 108

N—((S)-1-(3-cyanophenyl)-2-((S)-3-fluoropyrrolidin-1-yl)ethyl)-N-methyl-2-(2-oxo-2,3-dihydrobenzo[d]oxazol-5-yl)acetamide

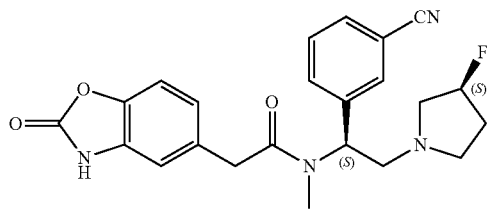

Melting point: 133-134° C.; $^1$H-NMR (400 MHz, DMSO-$d_6$): δ 11.5 (s, 1H), 7.75-7.53 (m, 4H), 7.17 (d, J=8.8 Hz, 1H), 6.98-6.94 (m, 2H), 5.83-5.81 (m, 1H), 5.20-5.0 (m, 1H), 3.83-3.80 (m, 2H), 2.88-2.81 (m, 4H), 2.76 (s, 3H), 2.42-2.46 (m, 2H), 2.1-2.0 (m, 1H), 1.98-1.80 (m, 1H); IR (Neat, cm$^{-1}$): 2927, 2852, 1774, 1618, 1261; MS (ESI): m/z 421 (M−1).

Example 109

N—((S)-1-(3-(2H-tetrazol-5-yl)phenyl)-2-((S)-3-fluoropyrrolidin-1-yl)ethyl)-N-methyl-2-(2-oxo-2,3-dihydrobenzo[d]oxazol-5-yl)acetamide

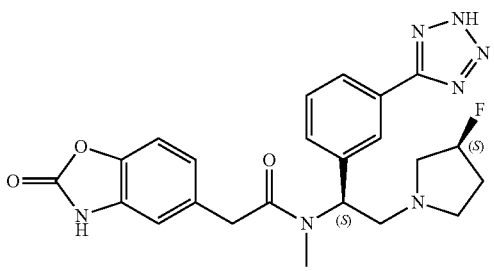

Melting point: 133-134° C.; $^1$H-NMR (400 MHz, DMSO-$d_6$): δ 11.59 (s, 1H), 10.2 (bs, 1H), 7.99 (d, J=7.8 Hz, 2H), 7.65 (d, J=7.8 Hz, 1H), 7.43 (d, J=7.8 Hz, 1H), 7.18 (d, J=7.9 Hz, 1H), 7.01-6.96 (m, 2H), 6.27 (m, 1H), 5.56-5.43 (m, 1H), 4.19 (s, 1H), 3.96-3.69 (m, 7H), 2.77 (s, 3H), 2.33 (bs, 2H); IR (Neat, cm$^{-1}$): 2980, 1764, 1678, 1467, 1205, 1265, 1138; MS (ESI): m/z 466 (M+1).

Example 110

N—((S)-1-(3-(2H-tetrazol-5-yl)phenyl)-2-((S)-3-hydroxypyrrolidin-1-yl)ethyl)-N-methyl-2-(2-oxoindolin-6-yl)acetamide

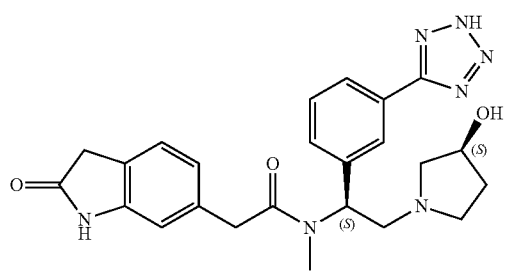

Melting point: 208-210° C.; $^1$H-NMR (400 MHz, DMSO-$d_6$): δ 10.35 (bs, 1H), 10.06 (bs, 1H), 9.93 (bs, 1H), 7.99 (d, J=7.8 Hz, 1H), 7.94 (s, 1H), 7.64-7.60 (m, 1H), 7.42 (d, J=7.8 Hz, 1H), 7.09 (d, J=7.8 Hz, 1H), 6.82 (d, J=7.8 Hz, 1H), 6.76 (s, 1H), 6.25-6.23 (m, 1H), 5.51 (bs, 1H), 4.45 (bs, 1H), 4.11 (bs, 1H), 3.79-3.77 (m, 4H), 3.73-3.42 (m, 4H), 2.76 (s, 3H), 2.32 (s, 1H), 2.08-1.90 (m, 1H); IR (Neat, cm$^{-1}$): 3053, 2752, 1689, 1629, 1483, 1460, 1400, 1271, 1246, 1116; MS (ESI): m/z 462 (M+1).

Example 111

N—((S)-1-(3-(2H-tetrazol-5-yl)phenyl)-2-((S)-3-hydroxypyrrolidin-1-yl)ethyl)-N-methyl-2-(1-methyl-2-oxoindolin-6-yl)acetamide

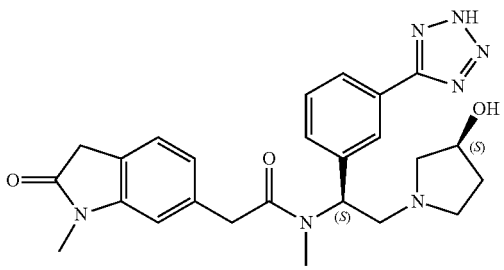

Melting point: 198-200° C.; $^1$H-NMR (400 MHz, DMSO-$d_6$): δ 9.99 (bs, 1H), 9.69 (bs, 1H), 7.99 (d, J=7.8 Hz, 1H), 7.94 (s, 1H), 7.64-7.60 (m, 1H), 7.42 (d, J=7.8 Hz, 1H), 7.09 (d, J=7.8 Hz, 1H), 6.82 (d, J=7.8 Hz, 1H), 6.76 (s, 1H), 6.25-6.23 (m, 1H), 5.51 (bs, 1H), 4.45 (bs, 1H), 4.11 (bs, 1H), 3.79-3.77 (m, 4H), 3.73-3.42 (m, 4H), 3.05 (s, 3H), 2.77 (s, 3H), 2.32 (s, 1H), 2.08-1.90 (m, 1H); IR (Neat, cm$^{-1}$): 3022, 2746, 1681, 1618, 1562, 1450, 1375, 1350, 1274, 1105; MS (ESI): m/z 476 (M+1).

Example 112

(R)—N-(1-(3-((2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide

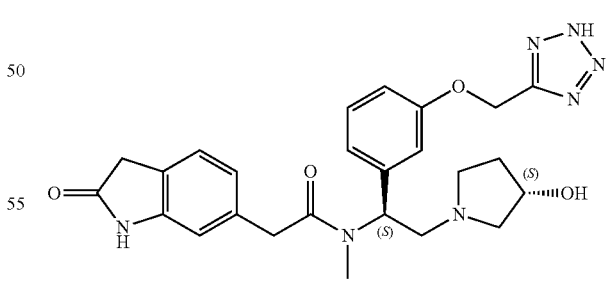

$^1$H-NMR (400 MHz, DMSO-$d_6$): δ 12.0 (bs, 1H), 10.38-10.35 (d, J=15.0 Hz, 1H), 7.23-7.21 (m, 1H), 7.09-6.95 (m, 1H), 6.95-6.80 (m, 5H), 5.87-5.85 (m, 1H), 5.13-5.08 (s, 2H), 4.26-4.23 (bs, 1H), 3.79-3.72 (m, 2H), 3.40-3.32 (bs, 2H), 3.16-2.63 (m, 6H), 2.63-2.59 (s, 3H), 1.99-1.90 (m, 2H), 1.6-1.55 (m, 1H); IR (Neat, cm$^{-1}$): 3053, 2953, 2773, 1703, 1643, 1589, 1492, 1462, 1413, 1269, 1043; MS (ESI): m/z 492 (M+1).

Example 113

N—((S)-1-(3-(2H-tetrazol-5-yl)phenyl)-2-((S)-3-fluoropyrrolidin-1-yl)ethyl)-N-methyl-2-(2-oxoindolin-6-yl)acetamide

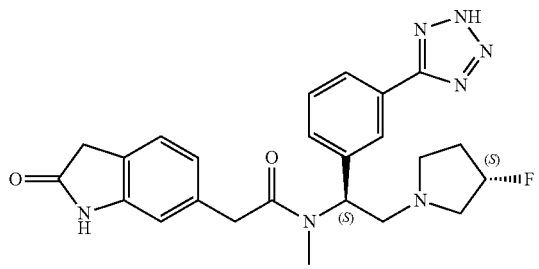

Melting point: 175-177° C.; ¹H-NMR (400 MHz, DMSO-d₆): δ 10.35 (s, 1H), 7.98 (d, J=7.8 Hz, 1H), 7.92 (s, 1H), 7.64 (d, J=7.8 Hz, 1H), 7.44 (d, J=7.8 Hz, 1H), 7.09 (d, J=7.8 Hz, 1H), 6.82 (d, J=7.8 Hz, 1H), 6.75 (s, 1H), 6.26-6.23 (m, 1H), 5.55-5.41 (m, 1H), 4.12 (s, 1H), 3.93-3.73 (m, 4H), 3.69-3.16 (m, 7H), 2.75 (s, 3H); MS (ESI): m/z 464 (M+1).

Example 114

(S)-2-(3-oxo-3,4-dihydro-2H-benzo[b][1,4]oxazin-6-yl)-N-(1-phenyl-2-(pyrrolidin-1-yl)ethyl)acetamide

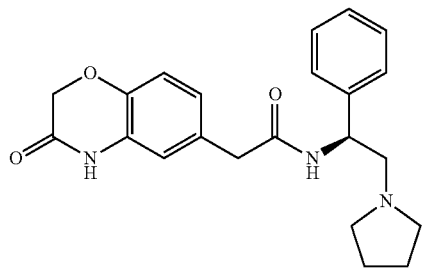 [SMILES: O=C1COc2ccc(CC(=O)N[C@H](CN3CCCC3)c3ccccc3)cc2N1]

MS (ESI): m/z 380 (M+1); ¹H-NMR (300 MHz, CD₃OD) δ 7.35-7.23 (m, 5H); 6.92-6.85 (m, 3H); 5.09-5.04 (m, 1H); 4.54 (s, 1H); 3.55 (s, 1H); 3.09-2.87 (m, 1H); 2.71-2.58 (m, 5H); 1.79 (s, 1H).

Example 115

(S)—N-methyl-2-(2-oxo-2,3-dihydrobenzo[d]thiazol-5-yl)-N-(1-phenyl-2-(pyrrolidin-1-yl)ethyl)acetamide

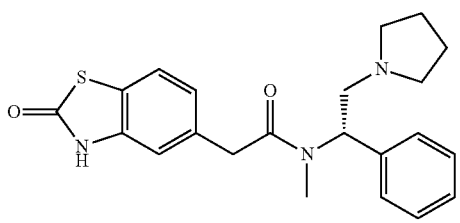 [SMILES: CN(C(=O)Cc1ccc2sc(=O)[nH]c2c1)[C@H](CN1CCCC1)c1ccccc1]

LC-MS (ES, m/z) 396 (M+1); ¹H-NMR (DMSO-d₆, 300 MHz) δ 11.736 (1H, s), 7.650-7.210 (6H, m), 7.160-6.920 (2H, m), 5.940-5.105 (1H, m), 3.970-3.680 (2H, m), 3.150-2.975 (1H, m), 2.860-2.615 (4H, m), 2.500-2.355 (3H, m), 2.180-2.005 (1H, m), 1.770-1.450 (4H, m).

Example 116

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide

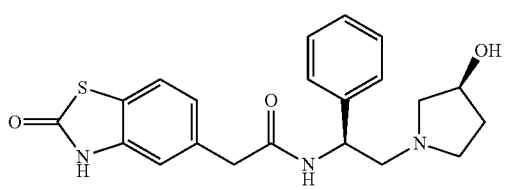 [SMILES: O=C(Cc1ccc2sc(=O)[nH]c2c1)N[C@H](CN1CC[C@H](O)C1)c1ccccc1]

LC-MS (ES, m/z) 382 (M+1).

Example 117

N—((S)-2-((S)-3-hydroxypyrrolidin-1-yl)-1-phenylethyl)-N-methyl-2-(2-oxo-2,3-dihydrobenzo[d]thiazol-5-yl)acetamide

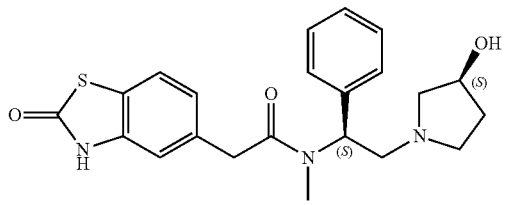

¹H-NMR (400 MHz, DMSO-d₆): δ 11.8 (bs, 1H), 7.49-7.47 (m, 1H), 7.35-7.23 (m, 5H), 7.08-7.01 (m, 2H), 5.86 (bs, 1H), 4.94-4.91 (m, 1H), 4.18 (bs, 1H), 3.87-3.70 (m, 2H), 3.29 (s, 1H), 2.75-2.62 (m, 6H), 2.50 (bs, 2H), 1.99-1.93 (bs, 1H), 1.51 (bs, 1H); IR (Neat, cm⁻¹): 3284, 2924, 2852, 2771, 1693, 1620, 1573, 1469, 1402, 1346, 1276; MS (ESI) m/z: 412 (M+1).

Example 118

N—((S)-2-((S)-3-hydroxypyrrolidin-1-yl)-1-phenylethyl)-2-(2-thioxo-2,3-dihydrobenzo[d]thiazol-5-yl)acetamide

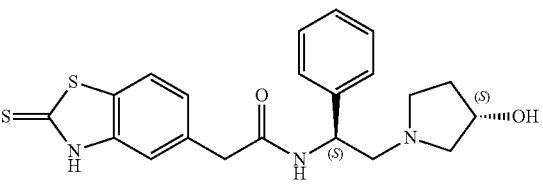

¹H-NMR (400 MHz, DMSO-d₆): δ 13.0 (bs, 1H), 8.56 (d, J=8.56 Hz, 1H), 7.57 (d, J=7.8 Hz, 1H), 7.30-7.17 (m, 7H), 4.93 (d, J=5.4 Hz, 1H), 4.17-4.15 (m, 1H), 3.54 (d, J=8.3 Hz, 2H), 2.81-2.50 (m, 5H), 2.42 (d, J=3.0 Hz, 1H), 1.9-1.85 (m, 1H), 1.6-1.55 (m, 1H); IR (Neat, cm$^{-1}$): 3240, 3030, 2930, 1658, 1529, 1452, 1365, 1323, 1261, 1157, 1082; MS (ESI) m/z: 414 (M+1).

Example 119

N—((S)-2-((S)-3-hydroxypyrrolidin-1-yl)-1-phenylethyl)-N-methyl-2-(2-thioxo-2,3-dihydrobenzo[d]thiazol-5-yl)acetamide

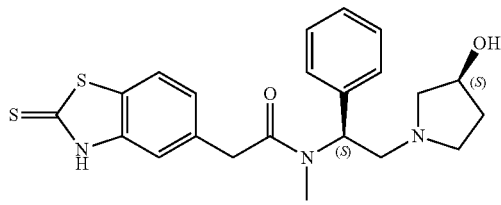

$^{1}$H-NMR (400 MHz, DMSO-d$_{6}$): 7.28-7.16 (m, 7H), 6.79-6.77 (m, 1H), 5.86 (bs, 1H), 4.16-4.01 (bs, 1H), 3.78-3.64 (m, 3H), 3.14-2.90 (m, 2H), 2.85-2.62 (m, 7H), 2.37-2.35 (m, 1H), 1.94-1.83 (bs, 1H), 1.59-1.55 (bs, 1H); IR (Neat, cm$^{-1}$): 3537, 2926, 2812, 1581, 1382, 1315, 1136; MS (ESI) m/z: 428 (M+1).

Example 120

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)-N-methylacetamide

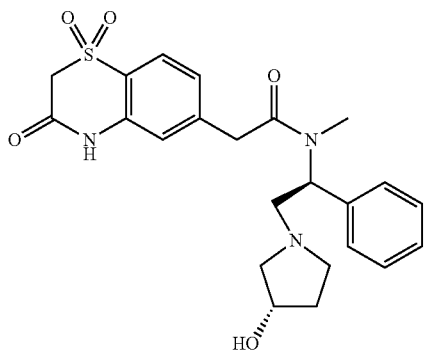 [SMILES: CN(C(=O)Cc1ccc2c(c1)NC(=O)CS2(=O)=O)[C@H](CN1CC[C@H](O)C1)c1ccccc1]

LC-MS (ES, m/z) 458 (M+1); $^{1}$H-NMR (DMSO-d$_{6}$, 300 MHz) δ 11.255 (s, 1H), 7.107-7.778 (m, 8H), 5.890-5.170 (m, 1H), 4.713 (s, 2H), 4.204 (s, 1H), 3.979-3.804 (m, 2H), 3.338-2.628 (m, 7H), 2.078-1.998 (m, 1H), 1.557-1.453 (m, 1H).

Example 121

(S)-2-(1,1-dioxido-3-oxo-3,4-dihydro-2H-benzo[b][1,4]thiazin-6-yl)-N-(1-phenyl-2-(pyrrolidin-1-yl)ethyl)acetamide

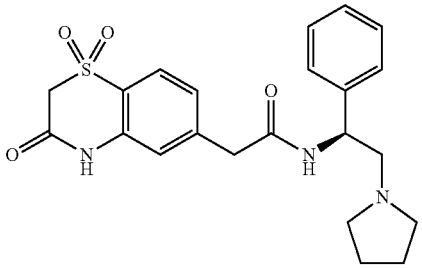 [SMILES: O=C1CS(=O)(=O)c2ccc(CC(=O)N[C@H](CN3CCCC3)c3ccccc3)cc2N1]

LC-MS (ES, m/z) 428 (M+1); $^{1}$H-NMR (DMSO-d$_{6}$, 300 MHz) δ 11.33 (br, s, 1H), 8.89-6.95 (m, 9H), 5.01-4.49 (m, 3H), 3.71-3.51 (m, 2H), 2.91-2.21 (m, 6H), 1.91-1.41 (m, 4H).

Example 122

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)acetamide

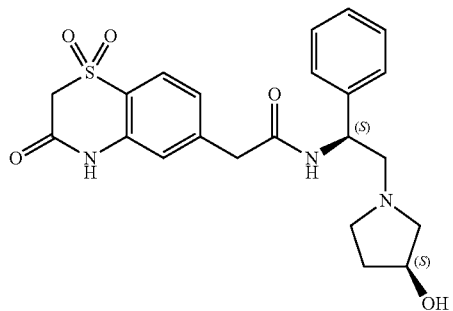

LC-MS (ES, m/z) 444 (M+1); $^{1}$H-NMR (DMSO-d$_{6}$, 400 MHz): δ 11.24 (s, 1H), 8.64 (d, 1H, J=8.4 Hz), 7.73 (d, 1H, J=8.4 Hz), 7.31 (d, 4H, J=4 Hz), 7.23 (d, 2H, J=7.6 Hz), 7.12 (s, 1H), 4.67-4.91 (m, 4H), 4.16 (bs, 1H), 3.52-3.62 (m, 2H), 2.63-2.78 (m, 3H), 2.27-2.36 (m, 1H), 1.94-1.99 (m, 1H), 1.53 (bs, 1H).

Example 123

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethyl)phenyl)ethyl)-N-methylacetamide

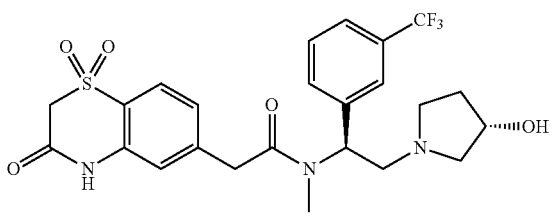 [SMILES: CN(C(=O)Cc1ccc2c(c1)NC(=O)CS2(=O)=O)[C@H](CN1CC[C@H](O)C1)c1cccc(C(F)(F)F)c1]

LC-MS: (ES, m/z): 526 (M+1);
¹H-NMR (DMSO-d₆, 300 MHz): δ 11.21 (d, J=12 Hz, 1H), 7.77-7.61 (m, 5H), 7.19 (d, J=6.6 Hz, 1H), 7.11 (s, 1H), 5.90-5.85 (m, 1H), 4.69 (s, 2H), 4.18 (s, 1H), 4.03-3.82 (m, 2H), 3.15-2.98 (m, 1H), 2.79-2.62 (m, 6H), 2.49-2.33 (m, 1H), 1.96-1.95 (m, 1H), 1.55 (s, 1H).

Example 124

2-(1,1-dioxido-3-oxo-3,4-dihydro-2H-benzo[b][1,4]thiazin-6-yl)-N—((S)-1-(3-fluoro phenyl)-2-((S)-3-hydroxypyrrolidin-1-yl)ethyl)-N-methylacetamide

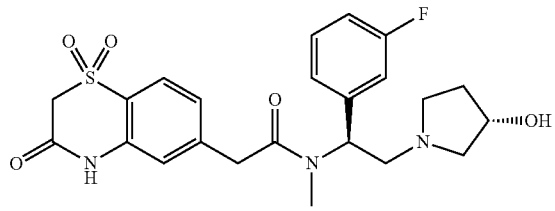 [SMILES: CN(C(=O)Cc1ccc2c(c1)NC(=O)CS2(=O)=O)[C@H](CN1CC[C@H](O)C1)c1cccc(F)c1]

LC-MS: (ES, m/z): 476 (M+1); ¹H-NMR (DMSO-d₆): 11.22 (d, J=9.9 Hz, 1H), 7.77-7.72 (m, 1H), 7.42-7.35 (m, 1H), 7.21-7.10 (m, 5H), 5.80 (s, 1H), 4.74-4.70 (m, 3H), 3.98 (s, 1H), 3.96-3.80 (m, 2H), 3.05-2.97 (m, 1H), 2.77-2.73 (m, 5H), 2.63 (s, 1H), 2.42-2.32 (m, 1H), 1.98-1.92 (m, 1H), 1.52 (s, 1H).

Example 125

N—((S)-1-cyclohexyl-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide

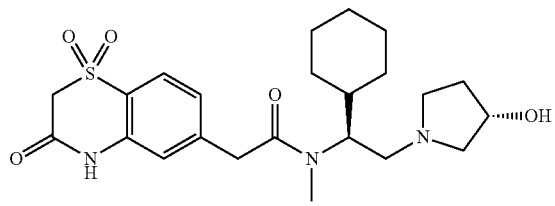 [SMILES: CN(C(=O)Cc1ccc2c(c1)NC(=O)CS2(=O)=O)[C@H](CN1CC[C@H](O)C1)C1CCCCC1]

LC-MS: (ES, m/z): 464 (M+1); ¹H-NMR: (DMSO-d6, 300 MHz): δ 11.23 (s, 1H), 7.77-7.71 (m, 1H), 7.21-7.13 (m, 1H), 7.13 (s, 1H), 4.71-4.69 (m, 1H), 4.39-4.31 (m, 1H), 3.90-3.70 (m, 2H), 2.78-2.50 (m, 7H), 2.31-2.16 (m, 3H), 1.95-1.89 (m, 1H), 1.78-1.41 (m, 7H), 1.22-1.07 (m, 3H), 1.05-0.82 (m, 2H).

Example 126

2-(1,1-dioxido-3-oxo-3,4-dihydro-2H-benzo[b][1,4]thiazin-6-yl)-N—((S)-2-((S)-3-hydroxy pyrrolidin-1-yl)-1-(3-methoxyphenyl)ethyl)-N-methylacetamide

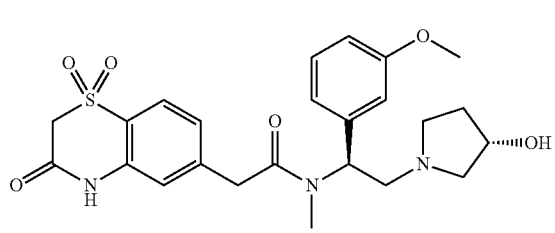 [SMILES: COc1cccc([C@@H](CN2CC[C@H](O)C2)N(C)C(=O)Cc2ccc3c(c2)NC(=O)CS3(=O)=O)c1]

LC-MS: (ES, m/z): 488 (M+1); ¹H-NMR (DMSO-d₆, 300 MHz): 11.23 (d, J=10.2 Hz, 1H), 7.79-7.74 (m, 1H), 7.31-7.18 (m, 2H), 7.13 (s, 1H), 6.90-6.82 (m, 3H), 5.81-5.78 (m, 1H), 4.72 (s, 2H), 4.20 (s, 1H), 3.98-3.81 (m, 2H), 3.74 (s, 3H), 3.07-3.00 (m, 2H), 2.89-2.77 (m, 4H), 2.66 (s, 1H), 2.52-2.33 (m, 1H), 1.99-1.97 (m, 1H), 1.55 (s, 1H).

Example 127

(S)-2-(3-oxo-3,4-dihydro-2H-benzo[b][1,4]thiazin-6-yl)-N-(1-phenyl-2-(pyrrolidin-1-yl)ethyl)acetamide

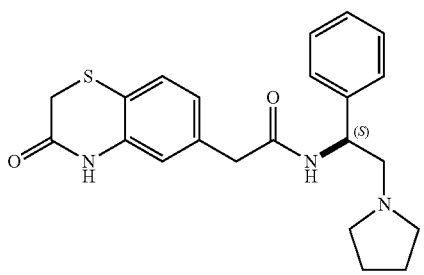

LC-MS (ES, m/z): 396 (M+1); ¹H-NMR (DMSO-d₆, 300 MHz) δ 10.56 (s, 1H), 8.51 (d, 1H, J=8.7 Hz), 7.20-7.31 (m, 6H), 8.62-8.69 (m, 2H), 4.90 (bs, 1H), 3.42 (bs, 4H), 2.73-2.76 (m, 1H), 2.45-2.68 (m, 5H), 1.65 (m, 4H).

Example 128

N—((S)-2-((S)-3-hydroxypyrrolidin-1-yl)-1-phenyl-ethyl)-2-(3-oxo-3,4-dihydro-2H-benzo[b][1,4]thiazin-6-yl)acetamide

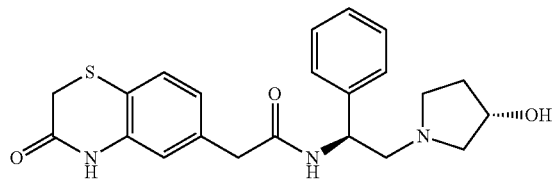 [SMILES: O=C1CSc2ccc(CC(=O)N[C@H](CN3CC[C@H](O)C3)c3ccccc3)cc2N1]

¹H-NMR (DMSO-d₆, 300 MHz): δ 10.576 (1H, s), 8.523 (1H, d, J=8.1 Hz), 7.370-7.175 (6H, m), 6.985-6.820 (2H, m), 4.985-4.820 (1H, m), 4.815-4.650 (1H, m), 4.235-4.095 (1H, m), 3.520-3.380 (4H, m), 2.850-2.675 (2H, m), 2.672-2.585 (1H, m), 2.460-2.375 (1H, m), 2.370-2.250 (1H, m), 2.040-1.850 (1H, m), 1.590-1.435 (1H, m).

Example 129

(S)—N-methyl-2-(3-oxo-3,4-dihydro-2H-benzo[b][1,4]thiazin-6-yl)-N-(1-phenyl-2-(pyrrolidin-1-yl)ethyl)acetamide

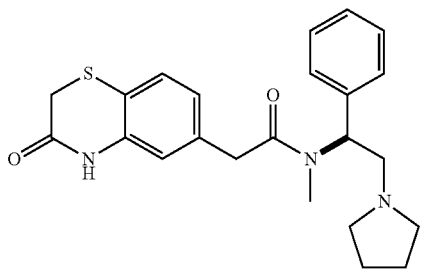

LC-MS (ES, m/z): 410 (M+1); ¹H-NMR (DMSO-d₆, 300 MHz) δ 10.57 (s, 1H), 7.23-7.35 (m, 6H), 6.89 (s, 2H), 5.87 and 5.12 (2 bs, 1H), 3.63-3.79 (m, 2H), 3.46 (s, 2H), 2.64-3.08 (m, 6H), 2.35-2.45 (m, 3H), 1.67 (bs, 4H).

Example 130

N-(2-((S)-3-hydroxypyrrolidin-1-yl)-1-(tetrahydro-2H-pyran-4-yl)ethyl)-N-methyl-2-(3-oxo-3,4-dihydro-2H-benzo[b][1,4]thiazin-6-yl)acetamide

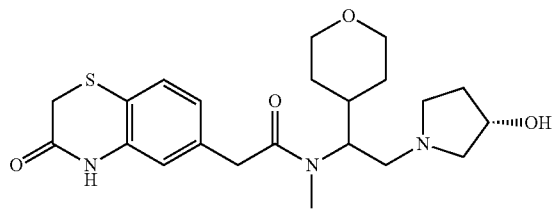 [SMILES: CN(C(=O)Cc1ccc2c(c1)NC(=O)CS2)C(CN1CC[C@H](O)C1)C1CCOCC1]

LC-MS: (ES, m/z): 434 (M+1); ¹H-NMR (DMSO-d₆, 300 MHz): 1.2-1.5 (3H, br), 1.5-1.7 (3H, m), 19-2.5 (6H, br), 2.7 (3H, m), 3.2-3.8 (8H, br), 4.1 (1H, m), 4.4 (1H, m), 4.7 (1H, m), 6.8 (2H, d, J=4.8 Hz), 7.2 (1H, m), 10.5 (1H, m).

Example 131

N—((S)-2-((S)-3-hydroxypyrrolidin-1-yl)-1-(3-methoxyphenyl)ethyl)-N-methyl-2-(3-oxo-3,4-dihydro-2H-benzo[b][1,4]thiazin-6-yl)acetamide

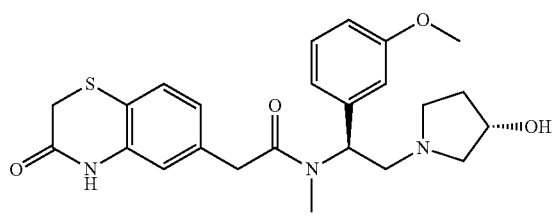 [SMILES: COc1cccc([C@@H](CN2CC[C@H](O)C2)N(C)C(=O)Cc2ccc3c(c2)NC(=O)CS3)c1]

LC-MS: (ES, m/z): 456 (M+1); ¹H-NMR (DMSO-d₆, 300 MHz): δ 10.53 (d, J=5.4 Hz, 1H), 7.27-7.22 (m, 2H), 6.89-6.67 (m, 5H), 5.78 (s, 1H), 4.70 (s, 1H), 4.15 (s, 1H), 3.76-3.67 (m, 5H), 3.43 (s, 2H), 3.31 (d, J=7.2 Hz, 2H), 3.01-2.81 (m, 2H), 2.71 (s, 3H), 2.62 (s, 1H), 2.31-2.27 (m, 1H), 1.94-1.92 (m, 2H), 1.50 (s, 1H).

Example 132

N—((S)-2-((S)-3-hydroxypyrrolidin-1-yl)-1-(3-(trifluoromethyl)phenyl)ethyl)-N-methyl-2-(3-oxo-3,4-dihydro-2H-benzo[b][1,4]thiazin-6-yl)acetamide

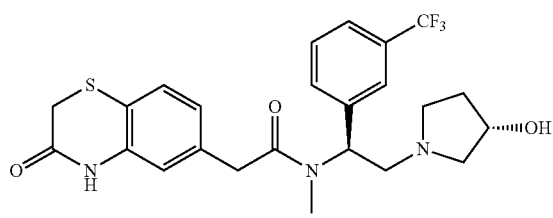 [SMILES: CN(C(=O)Cc1ccc2c(c1)NC(=O)CS2)[C@H](CN1CC[C@H](O)C1)c1cccc(C(F)(F)F)c1]

LC-MS: (ES, m/z): 494 (M+1); ¹H-NMR (DMSO-d₆, 300 MHz): δ 11.52 (d, J=7.5 Hz, 1H), 7.63-7.55 (m, 4H), 7.24 (d, J=8.4 Hz, 1H), 6.87 (d, J=6.6 Hz, 2H), 5.85 (s, 1H), 4.71 (s, 1H), 4.16 (s, 1H), 3.81-3.64 (m, 2H), 3.41-3.32 (m, 2H), 3.30 (s, 2H), 3.06-2.82 (m, 3H), 2.74 (s, 3H), 2.67 (s, 1H), 2.50-2.27 (m, 1H), 1.96-1.92 (m, 1H), 1.52-1.50 (m, 1H).

Example 133

N—((S)-1-(3-fluorophenyl)-2-((S)-3-hydroxypyrrolidin-1-yl)ethyl)-N-methyl-2-(3-oxo-3,4-dihydro-2H-benzo[b][1,4]thiazin-6-yl)acetamide

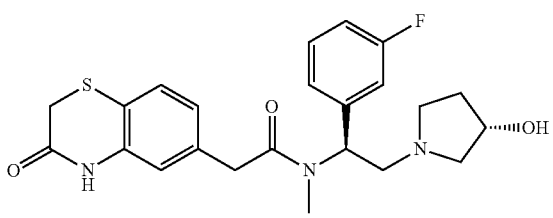 [SMILES: CN(C(=O)Cc1ccc2c(c1)NC(=O)CS2)[C@H](CN1CC[C@H](O)C1)c1cccc(F)c1]

LC-MS: (ES, m/z): 444 (M+1); ¹H-NMR (DMSO-d₆, 300 MHz): δ10.53 (d, J=6.6 Hz, 1H), 7.41-7.34 (m, 1H), 7.26-7.23 (m, 1H), 7.13-7.07 (m, 3H), 6.88-6.84 (m, 2H), 5.82 (d, J=9.0 Hz, 1H), 6.70 (d, J=3.3 Hz, 1H), 4.15 (s, 1H), 3.78-3.63 (m, 2H), 3.42 (s, 2H), 3.01-2.90 (m, 1H), 2.85-2.81 (m, 1H), 2.73 (s, 3H), 2.62-2.56 (m, 1H), 2.50-2.28 (m, 1H), 1.93-1.89 (m, 1H), 1.62-1.58 (m, 1H).

Example 134

N—((S)-2-((S)-3-hydroxypyrrolidin-1-yl)-1-(3-(trifluoromethoxy)phenyl)ethyl)-N-methyl-2-(3-oxo-3,4-dihydro-2H-benzo[b][1,4]thiazin-6-yl)acetamide

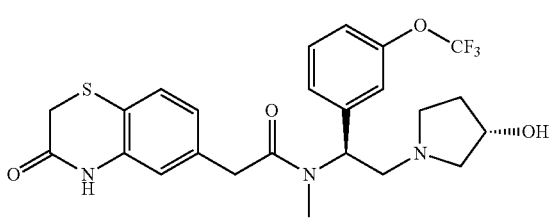 [SMILES: CN(C(=O)Cc1ccc2c(c1)NC(=O)CS2)[C@H](CN1CC[C@H](O)C1)c1cccc(OC(F)(F)F)c1]

LC-MS: (ES, m/z): 510 (M+1); ¹H-NMR: (DMSO-d₆, 300 MHz): δ 10.54 (d, J=6.0 Hz, 1H), 7.52-7.46 (m, 1H), 7.36-7.24 (m, 4H), 6.89-6.87 (m, 2H), 5.86-5.80 (m, 1H), 4.72-4.71 (m, 1H), 4.16 (s, 1H), 3.80-3.65 (m, 2H), 3.45 (s, 2H), 3.07-2.99 (m, 1H), 2.86-2.81 (m, 2H), 2.76 (s, 2H), 2.71-2.62 (m, 2H), 2.42-2.41 (m, 1H), 2.36-2.29 (m, 1H), 1.98-1.94 (m, 1H), 1.58-1.49 (m, 1H).

Example 135

2-(1-benzyl-2,2-dioxido-1,3-dihydrobenzo[c]isothiazol-6-yl)-N—((S)-2-((S)-3-hydroxypyrrolidin-1-yl)-1-phenylethyl)-N-methylacetamide

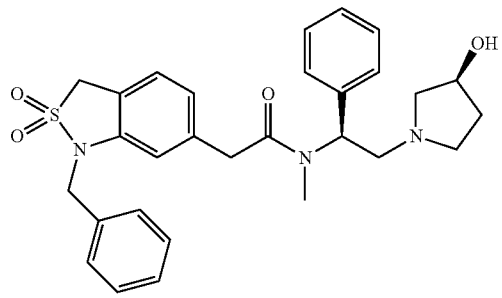 [SMILES: CN(C(=O)Cc1ccc2c(c1)N(Cc1ccccc1)S(=O)(=O)C2)[C@H](CN1CC[C@H](O)C1)c1ccccc1]

$^1$H-NMR (400 MHz, DMSO-d$_6$): δ 7.41-7.35 (m, 2H), 7.33-7.21 (m, 8H), 7.08 (d, J=6.9 Hz, 1H), 6.89-6.84 (m, 1H), 6.58-6.55 (m, 1H), 5.78-5.73 (bs, 1H), 4.93 (bs, 1H), 4.71-4.69 (m, 4H), 4.13 (bs, 1H), 3.71-3.58 (m, 2H), 3.39-3.28 (m, 2H), 2.84-2.77 (m, 1H), 2.62 (s, 3H), 2.54-2.48 (m, 2H), 2.31-2.28 (m, 1H), 1.90-1.89 (m, 1H), 1.49 (bs, 1H); IR (KBr, cm$^{-1}$): 3414, 2928, 2799, 1624, 1450, 1323, 1202, 1142, 1099; MS (ESI) m/z: 520 (M+1).

Example 136

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide

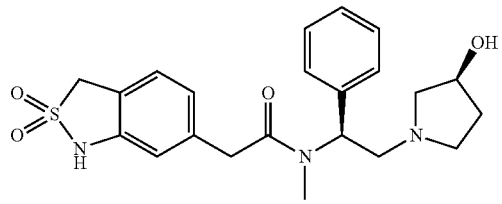 [SMILES: CN(C(=O)Cc1ccc2c(c1)NS(=O)(=O)C2)[C@H](CN1CC[C@H](O)C1)c1ccccc1]

Melting point: 232-234° C.; $^1$H-NMR (400 MHz, DMSO-d$_6$): δ 10.30 (bs, 1H), 7.35-7.26 (m, 5H), 7.24-7.18 (m, 1H), 6.85-6.82 (m, 1H), 6.75-6.73 (m, 1H), 5.87-5.83 (m, 1H), 5.10 (t, J=7.6 Hz, 1H), 4.47 (s, 2H) 4.21-4.16 (m, 1H), 3.81-3.77 (m, 1H), 3.69-3.65 (m, 1H), 3.16-3.05 (m, 1H), 2.85-2.81 (m, 1H), 2.78-2.64 (m, 4H), 2.61 (s, 1H), 2.42-2.32 (m, 2H), 2.01-1.91 (m, 1H), 1.56-1.49 (m, 1H); IR (KBr, cm$^{-1}$): 3294, 2938, 2787, 1612, 1450, 1313, 1196, 1134, 1091; MS (ESI) m/z: 428 (M+1).

Example 137

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-propylacetamide

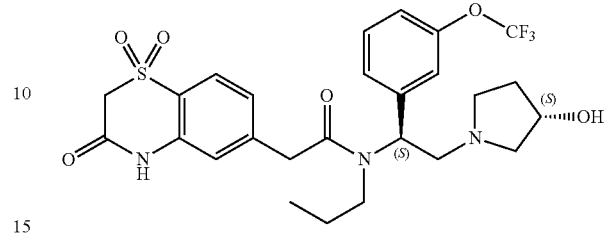

MS (ES, m/z): 570 (M+1); $^1$H-NMR: (DMSO-d$_6$, 400 MHz): δ 11.23 (s, 1H), 7.74-7.76 (m, 1H), 7.45-7.49 (m, 1H), 7.27-7.39 (m, 3H), 7.19-7.21 (m, 1H), 7.12 (s, 1H), 5.64 (m, 1H), 4.70-4.73 (m, 3H), 3.77-4.16 (m, 3H), 2.64-3.17 (m, 6H), 2.33-2.45 (m, 2H), 1.90-1.95 (m, 1H), 1.04-1.51 (m, 3H), 0.52-0.73 (m, 3H).

Example 138

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isopropylacetamide

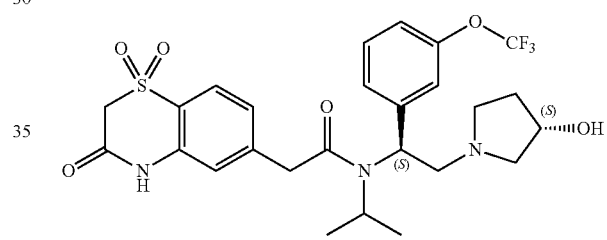

LC-MS: (ES, m/z): 570 (M+1); $^1$H-NMR: (DMSO-d$_6$, 400 MHz): δ 11.24 (s, 1H), 7.73-7.77 (m, 1H), 7.30-7.50 (m, 4H), 7.16-7.28 (m, 2H), 7.09 (s, 1H), 4.73-4.76 (m, 1H), 4.70 (s, 2H), 4.18 (m, 2H), 3.89 (s, 2H), 3.30 (m, 1H), 2.61-2.85 (m, 4H), 2.40-2.49 (m, 1H), 1.93-1.99 (m, 1H), 1.53-1.55 (m, 1H), 1.23-1.31 (m, 3H), 1.06-1.09 (m, 2H), 0.80 (m, 1H).

Example 139

N-cyclopropyl-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide

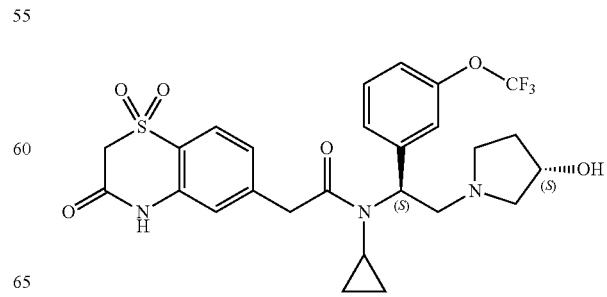

LC-MS (ES, m/z): 568 (M+1); ¹H-NMR (DMSO-d₆, 400 MHz) δ 11.24 (s, 1H), 7.77 (d, J=8 Hz, 1H), 7.44 (m, 1H), 7.30 (m, 1H), 7.23 (m, 3H), 7.14 (m, 1H), 5.44 (s, 1H), 4.75-4.71 (m, 3H), 4.15-3.98 (m, 3H), 3.30-3.27 (m, 2H), 3.00 (m, 1H), 2.74 (m, 3H), 2.39-2.33 (m, 2H), 1.95 (m, 1H), 1.55 (m, 1H), 0.84-0.71 (m, 3H), 0.38 (s, 1H)

Example 140

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isobutylacetamide

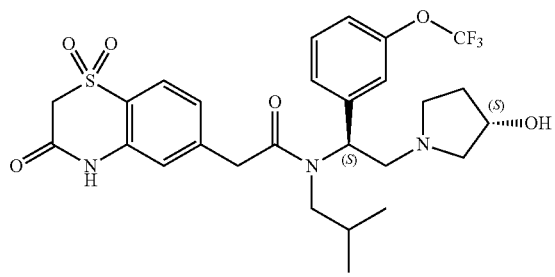

MS (ES, m/z): 584 (M+1); ¹H-NMR: (DMSO-d₆, 400 MHz) δ 11.23 (m, 1H), 7.77-7.73 (m, 1H), 7.49-7.39 (m, 3H), 7.26-7.11 (m, 3H), 5.32-5.15 (m, 1H), 4.75-4.70 (m, 3H), 3.90-3.01 (m, 3H), 2.75-2.67 (m, 3H), 2.41-2.38 (m, 2H), 1.92 (m, 1H), 1.54-1.52 (m, 2H), 0.79-0.72 (m, 4H), 0.63-0.61 (m, 1H), 0.36-0.34 (m, 1H)

Example 141

N-(cyclopropylmethyl)-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide

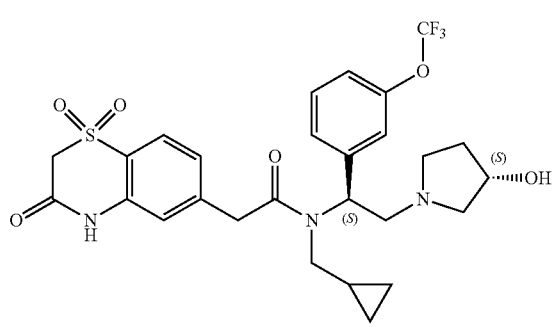

MS (ES, m/z): 582 (M+1); ¹H-NMR (CDCl₃, 400 MHz): δ 11.23 (m, 1H), 7.76-7.74 (m, 1H), 7.50-7.13 (m, 6H), 5.32-5.15 (m, 1H), 4.74-4.71 (m, 3H), 4.17-3.90 (m, 3H), 3.33-3.10 (m, 4H) 2.85-2.79 (m, 2H), 2.40 (m, 2H), 1.95-1.93 (m, 1H), 1.53-1.52 (m, 1H), 0.88-0.65 (m, 1H), 0.38-0.08 (m, 4H).

Example 142

2-(1,1-dioxido-3-oxo-3,4-dihydro-2H-benzo[b][1,4]thiazin-6-yl)-N—((S)-2-((S)-3-hydroxypyrrolidin-1-yl)-1-(4-(trifluoromethoxy)phenyl)ethyl)-N-methylacetamide

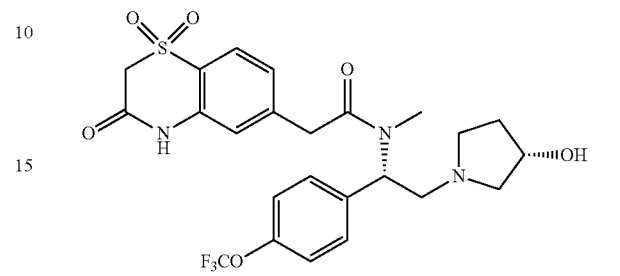

MS (ES, m/z): 542 (M+1); ¹H-NMR (DMSO-d₆, 400 MHz) δ 11.236 (s, 1H), 7.774-7.097 (m, 7H), 5.827 (s, 1H), 4.744-4.707 (m, 3H), 4.177 (s, 1H), 3.989-3.805 (m, 2H), 3.028-2.333 (m, 9H), 2.079 (m, 1H), 1.979-1.962 (m, 1H).

Example 143

2-(2,2-dimethyl-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide

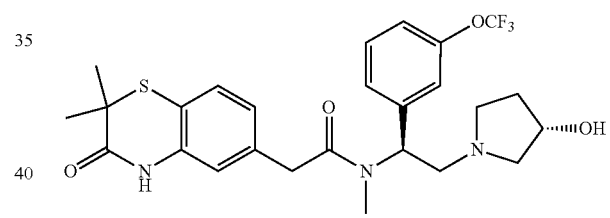

MS (ES, m/z): 538 (M+1); ¹H-NMR (DMSO-d6, 300 MHz) δ1.34 (s, 6H), 1.50-1.52 (m, 1H), 1.90-1.95 (m, 1H), 2.30-2.33 (m, 1H), 2.46-2.50 (m, 3H), 2.60-2.85 (m, 4H), 2.99-3.04 (m, 1H), 3.70 (q, J=12 Hz, 2H), 4.15 (s, 1H), 4.71 (s, 1H), 5.81 (m, 1H), 6.88-7.48 (m, 7H), 10.52 (s, 1H).

Example 144

2-(1,1-dioxido-3-oxo-3,4-dihydro-2H-benzo[b][1,4]thiazin-6-yl)-N—((S)-2-((S)-3-hydroxy pyrrolidin-1-yl)-1-(3-(2,2,2-trifluoroethoxy)phenyl)ethyl)-N-methylacetamide

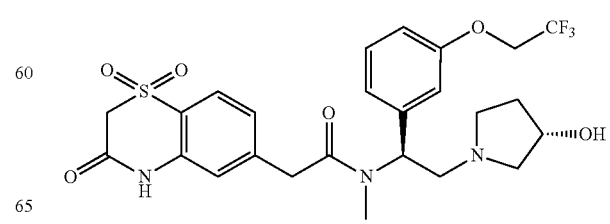

MS (ES, m/z): 556 (M+1); ¹H-NMR (300 MHz, DMSO-d₆) δ 11.20 (s, 1H), 7.75 (d, J=8.1, 1H), 7.32 (t, J=8.4, 1H), 7.18 (d, J=8.7, 1H), 7.16 (s, 1H), 6.95-7.10 (m, 3H), 5.77-5.83 (m, 1H), 4.70-4.80 (m, 5H), 4.17 (s, 1H), 3.78-3.98 (m, 2H), 3.04-3.12 (m, 1H), 2.50-3.00 (m, 6H), 2.33-2.50 (m, 2H), 1.92-1.98 (m, 1H), 1.53 (s, 1H).

Example 145

2-(1,1-dioxido-3-oxo-3,4-dihydro-2H-benzo[b][1,4]thiazin-6-yl)-N—((S)-2-((S)-3-hydroxy pyrrolidin-1-yl)-1-(m-tolyl)ethyl)-N-methylacetamide

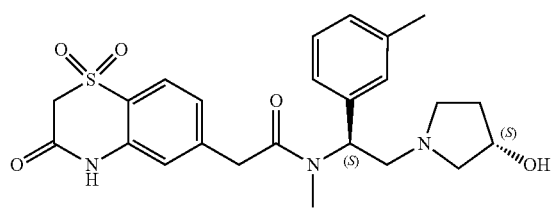

MS (ES, m/z): 472 (M+1); ¹H-NMR (DMSO-d₆, 400 MHz) δ 11.20-11.23 (m, 1H), 7.73-7.77 (m, 1H), 7.20-7.26 (m, 2H), 7.05-7.16 (m, 4H), 5.78-5.79 (m, 1H), 4.70-4.74 (m, 3H), 4.17 (m, 1H), 3.79-3.96 (m, 2H), 3.09 (m, 1H), 2.82 (m, 1H), 2.73 (s, 3H), 2.63-2.67 (m, 1H), 2.41 (m, 3H), 2.33 (s, 3H), 1.98 (m, 1H), 1.50 (m, 1H).

Example 146

2-(1,1-dioxido-3-oxo-3,4-dihydro-2H-benzo[b][1,4]thiazin-6-yl)-N—((S)-1-(4-fluoro-3-(trifluoromethoxy)phenyl)-2-((S)-3-hydroxypyrrolidin-1-yl)ethyl)-N-methylacetamide

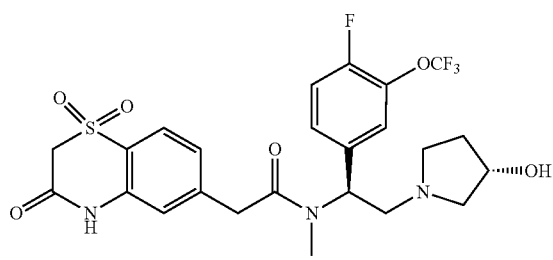 [SMILES: CN(C(=O)Cc1ccc2c(c1)NC(=O)CS2(=O)=O)[C@H](CN1CC[C@H](O)C1)c1ccc(F)c(OC(F)(F)F)c1]

MS (ES, m/z): 559.9 (M+1); ¹H-NMR (300 MHz, DMSO-d₆) δ 11.20 (s, 1H), 7.71 (d, J=7.8 Hz, 1H), 7.32-7.50 (m, 3H), 7.13 (d, J=8.1 Hz, 1H), 7.04 (s, 1H), 5.73 (t, J=6.6 Hz, 1H), 4.65-4.71 (m, 3H), 4.12 (s, 1H), 3.75-3.96 (m, 2H), 2.73 (brs, 1H), 2.44-2.68 (m, 6H), 2.33-2.40 (m, 2H), 1.86-1.93 (m, 1H), 1.45 (brs, 1H).

Example 147

N—((S)-1-(3,5-dimethylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide

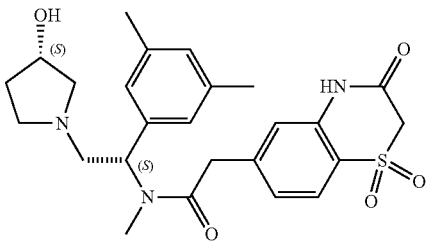

MS (ES, m/z): 486.12; ¹H-NMR (DMSO, 300 MHz) δ 11.19 (s, 1H), 7.731-7.71 (m, 1H), 7.18-7.16 (m, 1H), 7.07 (m, 1H), 6.84-6.79 (m, 3H), 5.71 (m, 0.8H), 4.95 (m, 0.2H), 4.71-4.65 (m, 3H), 4.13 (m, 1H), 3.91-3.78 (m, 2H), 3.15-2.19 (m, 15H), 1.95-1.85 (m, 1H), 1.48-1.42 (m, 1H)

Example 148

2-(2,2-dimethyl-1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide

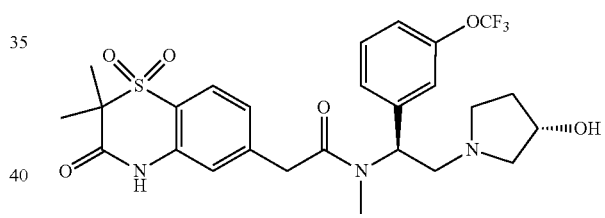

MS (ES, m/z): 570 (M+1); ¹H-NMR (DMSO-d₆, 300 MHz): δ 11.21 (s, 1H), 7.75-7.17 (m, 6H), 7.04 (s, 1H), 5.77 (t, J=8 Hz, 0.8H), 5.14 (t, J=8 Hz, 0.2H), 4.70 (s, 1H), 4.12 (s, 1H), 3.92 (q, J=12 Hz, 2H), 3.04 (br, 1H), 2.99-2.67 (m, 6H), 2.45-2.26 (m, 1H), 1.92-1.85 (m, 1H), 1.47 (s, 7H).

Example 149

2-(1,1-dioxido-3-oxo-3,4-dihydro-2H-benzo[b][1,4]thiazin-6-yl)-N—((S)-1-(3-fluoro-5-(2,2,2-trifluoroethoxy)phenyl)-2-((S)-3-hydroxypyrrolidin-1-yl)ethyl)-N-methylacetamide

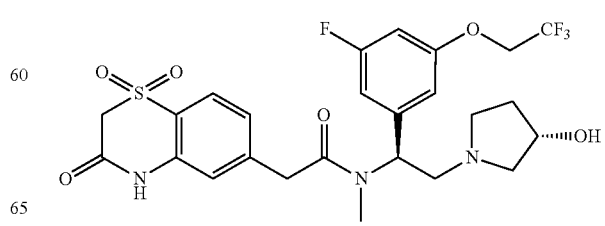

MS (ES, m/z): 573.9 (M+1); ¹H-NMR (300 MHz, DMSO-d₆) δ 11.20 (s, 1H), 7.75 (d, J=8.4 Hz, 1H), 7.15-7.20 (m, 1H), 7.09 (s, 1H), 6.78-6.95 (m, 3H), 5.73 (brs, 1H), 4.69-4.84 (m, 5H), 4.15 (brs, 1H), 3.79-3.98 (m, 2H), 3.29 (s, 1H), 2.96-3.01 (m, 1H), 2.63-2.79 (m, 5H), 2.26-2.35 (m, 2H), 1.52-1.98 (m, 1H), 1.48 (m, 1H).

Example 150

N—((S)-1-(3-cyclopropylphenyl)-2-((S)-3-hydroxy-pyrrolidin-1-yl)ethyl)-2-(1,1-dioxido-3-oxo-3,4-dihydro-2H-benzo[b][1,4]thiazin-6-yl)-N-methylacetamide

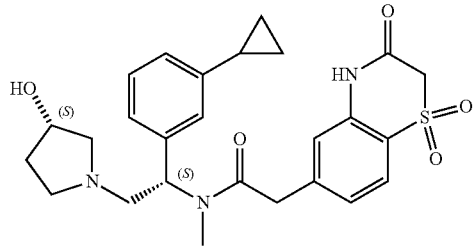

MS (ES, m/z): 498 (M+1); ¹H-NMR (DMSO-d₆, 300 MHz) δ 11.16 (m, 1H), 7.73-7.68 (m, 1H), 7.18-6.87 (m, 6H), 5.78-5.71 (m, 0.7H), 5.08-5.02 (m, 0.2H), 4.70-4.66 (m, 3H), 4.13 (m, 1H), 3.92-3.80 (m, 2H), 3.06-2.23 (m, 8H), 1.92-1.81 (m, 2H), 1.49 (m, 1H), 0.90-0.87 (m, 2H), 0.60-0.55 (m, 2H).

Example 151

N—((S)-1-(3-cyanophenyl)-2-((S)-3-hydroxypyrrolidin-1-yl)ethyl)-N-methyl-2-(2-oxo-2,3-dihydrobenzo[d]thiazol-5-yl)acetamide

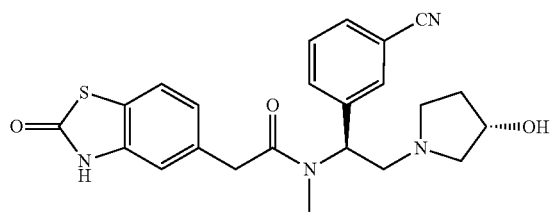 [SMILES: CN(C(=O)Cc1ccc2sc(=O)[nH]c2c1)[C@H](CN1CC[C@H](O)C1)c1cccc(C#N)c1]

MS (ES, m/z): 437 (M+1); ¹H-NMR (DMSO-d₆, 400 MHz) δ 11.84 (s, 1H), 7.76-7.73 (m, 2H), 7.65-7.46 (m, 3H), 7.07-7.01 (m, 2H), 5.85-5.81 (m, 0.8H), 5.18 (m, 0.2H), 4.89-4.70 (m, 1H), 4.18 (s, 1H), 3.92-3.74 (m, 2H), 3.12-2.56 (m, 7H), 2.40-2.33 (m, 2H), 1.97-1.94 (m, 1H), 1.42-1.49 (s, 1H).

Example 152

N—((S)-1-(3-cyanophenyl)-2-((S)-3-hydroxypyrrolidin-1-yl)ethyl)-N-methyl-2-(3-oxo-3,4-dihydro-2H-benzo[b][1,4]thiazin-6-yl)acetamide

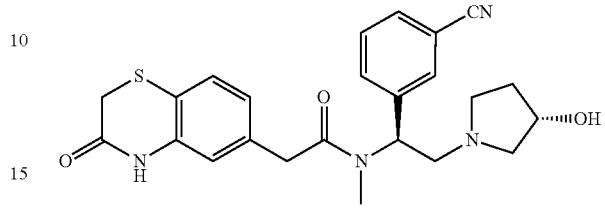

MS (ES, m/z): 451 (M+1); ¹H-NM (CD₃OD, 300 MHz) δ 7.67-7.64 (m, 3H), 7.56-7.50 (m, 1H), 6.98-6.91 (m, 2H), 6.02 (t, J=5.2 Hz, 1H), 4.36-4.32 (m, 1H), 3.82 (q, J=15.6 Hz, 2H), 3.43 (s, 2H), 3.28-3.22 (m, 1H), 2.95-2.90 (m, 2H), 2.82 (s, 3H), 2.76-2.72 (m, 1H), 2.54-2.46 (m, 2H), 2.15-2.02 (m, 1H), 1.73-1.62 (m, 1H).

Example 153

N—((S)-1-(3-cyanophenyl)-2-((S)-3-hydroxypyrrolidin-1-yl)ethyl)-N-methyl-2-(3-oxo-3,4-dihydro-2H-benzo[b][1,4]oxazin-6-yl)acetamide

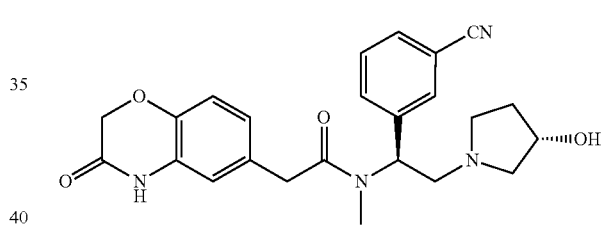

MS (ES, m/z): 435 (M+1); ¹H-NMR (CD₃OD, 400 MHz) δ 7.75-7.58 (m, 4H), 6.95-6.89 (m, 3H), 6.33-6.31 (d, J=10.8 Hz, 1H), 4.60-4.58 (m, 3H), 4.14-4.06 (m, 1H), 3.87-3.46 (m, 7H), 2.83-2.80 (m, 3H), 2.31-2.11 (m, 2H).

Example 154

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzoic acid

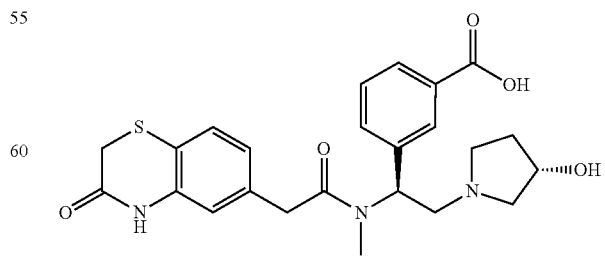

MS (ES, m/z): 470 (M+1); ¹H-NMR (DMSO-d₆, 300 MHz) δ 10.46 (s, 1H), 7.74 (d, J=13.5 Hz, 2H), 7.46-7.38

(m, 2H), 7.20-7.16 (m, 1H), 6.84-6.79 (m, 2H), 5.80 (dd, J=6.0 Hz, J=9.6 Hz, 1H), 4.67 (m, 1H), 4.11 (m, 1H), 3.72 (d, J=15.3 Hz, 1H), 3.59 (d, J=15.6 Hz, 1H), 3.39 (s, 2H), 3.04 (t, J=5.9 Hz, 1H), 2.82-2.54 (m, 6H), 2.30-2.25 (m, 1H), 1.92-1.80 (m, 1H), 1.48-1.35 (m, 1H)

Example 155

3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)benzoic acid

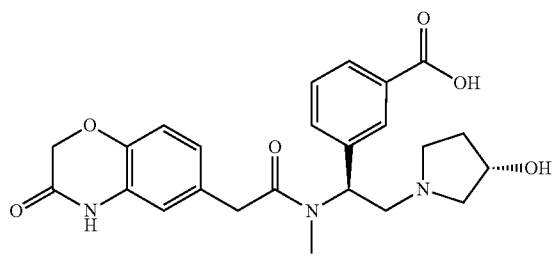 [SMILES: CN(C(=O)Cc1ccc2c(c1)NC(=O)CO2)[C@H](CN1CC[C@H](O)C1)c1cccc(C(=O)O)c1]

MS (ES, m/z): 454 (M+1); $^1$H-NMR (DMSO-d$_6$, 400 MHz) δ 10.72 (s, 1H), 7.84 (s, 2H), 7.51-7.42 (m, 2H), 6.88-6.80 (m, 3H), 5.88 (m, 1H), 4.53 (s, 2H), 4.18-4.16 (m, 1H), 3.73 (d, J=15.2 Hz, 1H), 3.62 (d, J=15.2 Hz, 1H), 3.11-3.08 (m, 1H), 2.86-2.81 (m, 3H), 2.80 (s, 3H), 2.62 (s, 1H), 2.46 (d, J=6.0 Hz, 1H), 2.37-2.34 (dd, J=4.0 Hz, J=4.4 Hz, 1H), 1.94 (m, 1H), 1.54-1.51 (m, 1H)

Example 156

N—((S)-1-(3-cyanophenyl)-2-((S)-3-hydroxypyrrolidin-1-yl)ethyl)-N-methyl-2-(2-oxoindolin-6-yl)acetamide

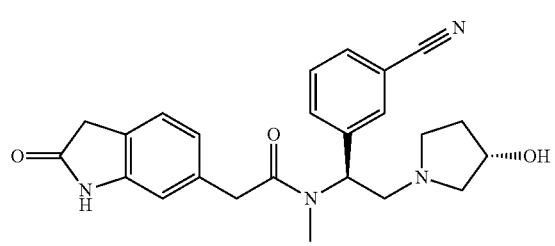 [SMILES: CN(C(=O)Cc1ccc2c(c1)NC(=O)C2)[C@H](CN1CC[C@H](O)C1)c1cccc(C#N)c1]

MS (ES, m/z): 419 (M+1); $^1$H-NMR $^1$H-NMR (CDCl$_3$, 300 MHz) δ 10.35 (s, 1H), 7.75-7.54 (m, 4H), 7.11 (d, J=6.3 Hz, 1H), 6.81-6.76 (m, 2H), 5.82 (t, J=6.0 Hz, 1H), 4.85 (d, J=3.6 Hz, 1H), 3.81-3.64 (m, 2H), 3.51-3.42 (m, 2H), 3.06-2.94 (m, 1H), 2.82-2.72 (m, 6H), 2.57 (s, 1H), 2.35-2.28 (m, 2H), 1.95-1.90 (m, 1H), 1.51-1.49 (m, 1H)

Example 157

N—((S)-2-((S)-3-hydroxypyrrolidin-1-yl)-1-phenylethyl)-2-(2-oxoindolin-5-yl)acetamide

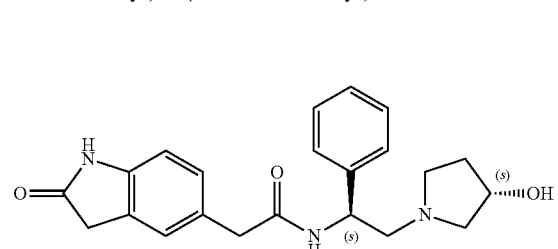

MS (ES, m/z): (M+1) 380
$^1$H-NMR (DMSO-d$_6$, 300 MHz) δ 10.28 (1H, s), 8.42-8.40 (1H, m), 7.29-7.19 (5H, m), 7.09-7.04 (2H, s) 6.71-6.69 (1H, m), 4.88-4.85 (1H, m), 4.66-4.65 (1H, m), 4.13-4.11 (1H, m), 3.43-3.32 (4H, m), 2.74-2.69 (2H, m), 2.57-2.47 (1H, m), 2.45-2.43 (1H, m), 2.29-2.25 (1H, m), 1.93-1.88 (1H, m), 1.57-1.47 (1H, m)

Example 158

N—((S)-1-(3-cyanophenyl)-2-((S)-3-hydroxypyrrolidin-1-yl)ethyl)-N-methyl-2-(3-oxo-3,4-dihydroquinoxalin-6-yl)acetamide

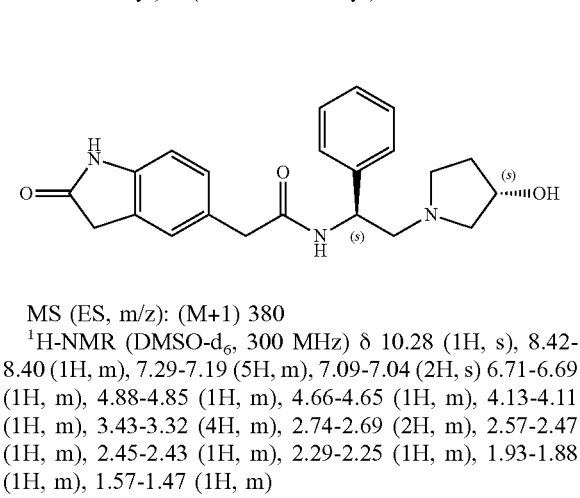

MS (ES, m/z): 432 (M+1); $^1$H-NMR (DMSO-d$_6$, 300 MHz) δ 12.262 (s, 1H), 9.353 (s, 1H), 8.122-7.525 (m, 4H), 7.198 (s, 2H), 5.835-5.710 (m, 1H), 4.830-4.622 (m, 1H), 4.150 (s, 1H), 4.021-3.830 (m, 2H), 3.154-2.270 (m, 9H), 1.998-1.854 (m, 1H), 1.587-1.375 (m, 1H)

Example 159

2-(3-((S)-2-((S)-3-hydroxypyrrolidin-1-yl)-1-(N-methyl-2-(2-oxoindolin-6-yl) acetamido)ethyl)phenoxy)acetic acid

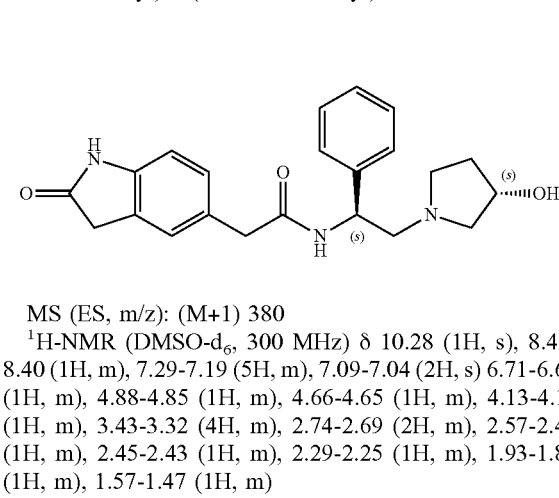

MS (ES, m/z): 467.9 (M+1); ¹H-NMR (DMSO-d₆, 300 MHz): δ 10.36-10.45 (m, 1H), 7.24 (d, J=8.8 Hz, 1H), 7.11 (d, J=7.6, 1H), 6.70-6.86 (m, 5H), 5.83-5.88 (m, 1H), 4.58 (s, 2H), 4.20-4.23 (m, 1H), 3.76-3.79 (m, 1H), 3.64-3.69 (m, 2H), 3.30-3.42 (s, 4H), 3.12-3.18 (m, 1H), 2.76-2.89 (m, 3H), 2.63-2.69 (m, 3H), 2.50-2.52 (m, 1H), 1.99-2.01 (m, 1H), 1.54-1.57 (m, 1H).

Example 160

3-((S)-2-((S)-3-hydroxypyrrolidin-1-yl)-1-(N-methyl-2-(2-oxo-2,3-dihydrobenzo[d]oxazol-5-yl)acetamido)ethyl)benzamide

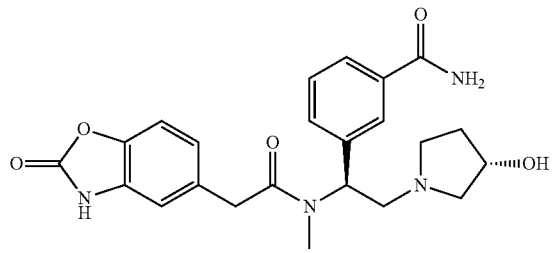

MS (ES, m/z): 439 (M+1); 1H-NMR (DMSO-d₆, 300 MHz) δ 11.35-11.69 (s, 1H), 8.00 (s, 1H), 7.77-7.74 (m, 2H), 7.42-7.39 (m, 3H), 7.21-7.17 (m, 1H), 7.05-6.96 (m, 2H), 5.92-5.87 (m, 0.8H), 5.12-5.25 (m, 1H), 5.09-4.89 (m, 1H), 4.18 (s, 1H), 3.89-3.84 (m, 1H), 3.72-3.67 (m, 1H), 3.17-3.09 (m, 1H), 2.85-2.62 (m, 6H), 2.39-2.36 (m, 2H), 1.99-1.92 (m, 1H), 1.42-1.59 (m, 1H)

Example 161

N—((S)-2-((S)-3-hydroxypyrrolidin-1-yl)-1-phenylethyl)-N-methyl-2-(2-oxoindolin-5-yl)acetamide

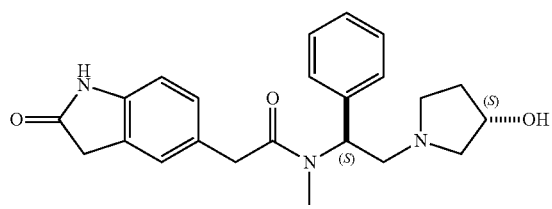

MS (ES, m/z): (M+1) 394; ¹H-NMR (DMSO-d₆, 300 MHz) δ 10.31 (1H, s), 7.36-7.22 (5H, m), 6.75-6.73 (2H, m), 5.86 (0.7H, m), 4.69 (0.2H, m), 4.16 (1H, m), 3.75-3.71 (1H, m), 3.64-3.60 (1H, m), 3.44 (2H, m), 3.09-2.89 (2H, m), 2.62-2.69 (4H, m), 2.49-2.51 (1H, m), 1.92-1.93 (1H, m), 1.52 (1H, m)

Example 162

N—((S)-2-((S)-3-fluoropyrrolidin-1-yl)-1-(3-(2-(methylsulfonamido)-2-oxoethoxy)phenyl)ethyl)-N-methyl-2-(2-oxoindolin-6-yl)acetamide

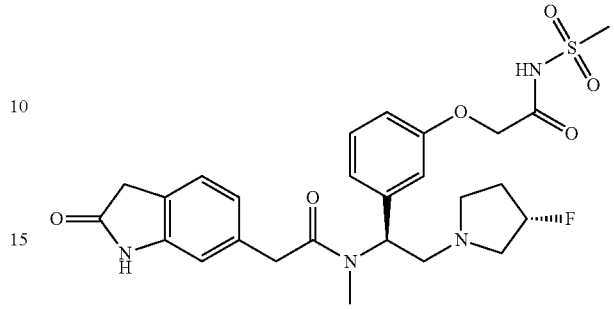

MS (ES, m/z): 547 (M+1); ¹H-NMR (DMSO-d₆, 400 MHz) δ 10.35 (s, 1H), 7.23-7.27 (m, 1H), 7.10-7.13 (m, 1H), 6.78-6.96 (m, 3H), 6.73 (s, 1H), 5.87-5.89 (m, 1H), 5.09-5.29 (m, 1H), 4.54 (s, 2H), 3.67-3.77 (m, 2H), 3.42 (s, 2H), 3.13 (s, 3H), 2.81-3.13 (m, 3H), 2.63-2.71 (m, 3H), 1.76-2.14 (m, 2H).

Example 163

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide

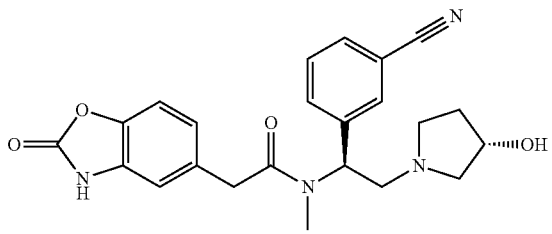 [SMILES: CN(C(=O)Cc1ccc2oc(=O)[nH]c2c1)[C@H](CN1CC[C@H](O)C1)c1cccc(C#N)c1]

MS (ES, m/z): 421 (M+1); ¹H-NMR (DMSO-d₆, 400 MHz) δ 11.56 (s, 1H), 7.76-7.71 (m, 2H), 7.64-7.62 (m, 1H), 7.59-7.54 (m, 1H), 7.22-7.17 (m, 1H), 7.03 (s, 1H), 6.99-6.95 (m, 1H), 5.85-5.13 (m, 1H), 5.05-4.66 (m, 1H), 4.60-5.02 (m, 1H), 4.17 (s, 1H), 3.90-3.72 (m, 2H), 3.33-3.00 (m, 1H), 2.85-2.60 (m, 6H), 2.42-2.36 (m, 2H), 1.55-1.41 (m, 1H).

Example 164

3-((S)-2-((S)-3-hydroxypyrrolidin-1-yl)-1-(N-methyl-2-(3-oxo-3,4-dihydroquinoxalin-6-yl)acetamido)ethyl)benzamide

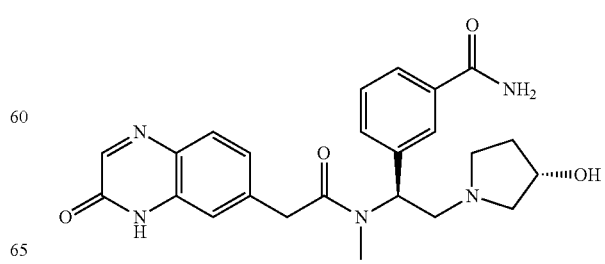

MS (ES, m/z): 450 (M+1); $^1$H-NMR (DMSO-d6, 300 MHz) δ 8.01-7.68 (m, 5H), 7.43-7.39 (m, 3H), 7.22-7.20 (m, 2H), 5.91-5.85 (m, 1H), 4.16 (s, 1H), 3.99-3.79 (m, 2H), 3.14-3.06 (m, 1H), 2.86-2.54 (m, 6H), 2.44-2.31 (m, 2H), 1.96-1.89 (m, 1H), 1.53-1.50 (m, 1H)

Example 165

3-((S)-2-((S)-3-fluoropyrrolidin-1-yl)-1-(N-methyl-2-(2-oxoindolin-6-yl)acetamido)ethyl)benzamide

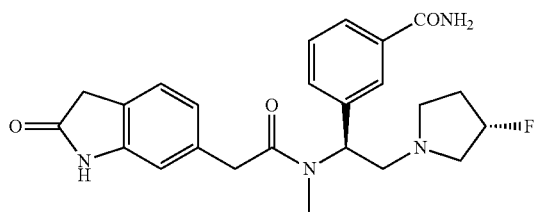 [SMILES: CN(C(=O)Cc1ccc2c(c1)NC(=O)C2)[C@H](CN1CC[C@H](F)C1)c1cccc(C(N)=O)c1]

MS (ES, m/z): 439 (M+1); $^1$H-NMR (DMSO-d$_6$, 300 MHz): δ 10.31 (s, 1H), 7.99 (s, 1H), 7.77 (s, 2H), 7.47-7.31 (m, 3H), 7.09 (d, J=7.2 Hz, 1H), 6.82 (d, J=7.2 Hz, 1H), 6.71 (s, 2H), 5.96-5.84 (m, 1H), 5.30-5.00 (m, 1H), 3.86-3.60 (m, 2H), 3.42 (s, 2H), 3.20-3.06 (m, 1H), 2.91-2.62 (m, 7H), 2.42-2.27 (m, 1H), 2.15-1.93 (m, 1H), 1.93-1.66 (m, 1H); $^{19}$F-NMR-(DMSO-d$_6$, 400 MHz) δ166 (s)

Example 166

2-(3-((S)-2-((S)-3-hydroxypyrrolidin-1-yl)-1-(N-methyl-2-(2-oxo-2,3-dihydrobenzo[d]thiazol-5-yl)acetamido)ethyl)phenoxy)acetic acid

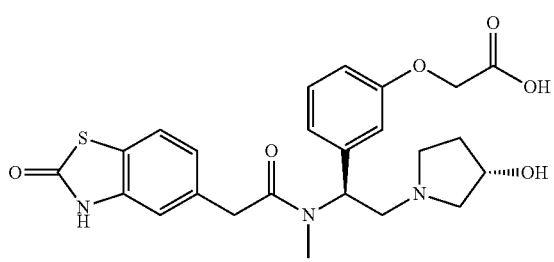 [SMILES: CN(C(=O)Cc1ccc2sc(=O)[nH]c2c1)[C@H](CN1CC[C@H](O)C1)c1cccc(OCC(=O)O)c1]

MS (ES, m/z): 486.00 (M+1); $^1$H-NMR (DMSO-d$_6$, 300 MHz) δ 12.51 (m, 1H), 7.49-7.46 (d, J=4.0 Hz, 1H), 7.26-7.22 (t, J=6.0 Hz, 1H), 7.06-7.01 (m, 2H), 6.87-6.79 (m, 3H), 5.88-5.85 (m, 1H), 5.10 (m, 1H), 4.60-4.58 (m, 2H), 4.22 (m, 1H), 3.85-3.74 (m, 2H), 3.32-3.17 (m, 1H), 2.95-2.70 (m, 3H), 2.68-2.65 (m, 3H), 2.54-2.50 (m, 1H), 2.01 (m, 1H), 1.57-1.56 (m, 1H).

Example 167

2-(3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)phenoxy)acetic acid

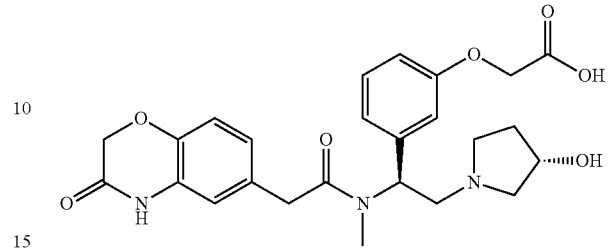

MS (ES, m/z): 484 (M+1); $^1$H-NMR (DMSO-d$_6$, 300 MHz) δ 10.87 (m, 1H), 7.25-7.20 (m, 1H), 6.88-6.74 (m, 6H), 5.83-5.79 (m, 0.8H), 5.07-5.01 (m, 0.2H), 4.57-4.53 (m, 4H), 4.18-4.15 (m, 1H), 3.72-3.60 (m, 2H), 3.10-3.04 (m, 1H), 2.91-2.83 (m, 1H), 2.79-2.73 (m, 1H), 2.70-2.64 (m, 2H), 2.55 (m, 1H), 2.38-2.33 (m, 1H), 2.50-2.51 (m, 1H), 1.93-1.98 (m, 1H), 1.51-1.53 (m, 1H).

Example 168

N—((S)-1-(3-(2-amino-2-oxoethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide

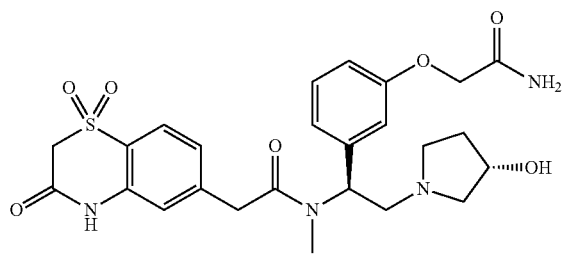 [SMILES: CN(C(=O)Cc1ccc2c(c1)NC(=O)CS2(=O)=O)[C@H](CN1CC[C@H](O)C1)c1cccc(OCC(N)=O)c1]

MS (ES, m/z): 531 (M+1); $^1$H-NMR (DMSO-d6,300 MHz): δ 11.19 (brs, 1H), 7.71-7.77 (m, 1H), 7.54 (brs, 1H), 7.40 (brs, 1H), 7.15-7.29 (m, 2H), 7.10 (s, 1H), 6.83-6.93 (m, 3H), 5.80-5.82 (m, 1H), 4.69-4.75 (m, 3H), 4.40-4.42 (m, 2H), 4.17 (brs, 1H), 3.77-3.96 (m, 2H), 2.96-3.06 (m, 1H), 2.65-2.85 (m, 5H), 2.32-2.45 (m, 2H), 1.92-1.99 (m, 1H), 1.51-1.53 (m, 1H)

Example 169

2-(3-((S)-2-((S)-3-hydroxypyrrolidin-1-yl)-1-(N-methyl-2-(2-oxoindolin-5-yl)acetamido)ethyl)phenoxy)acetic acid

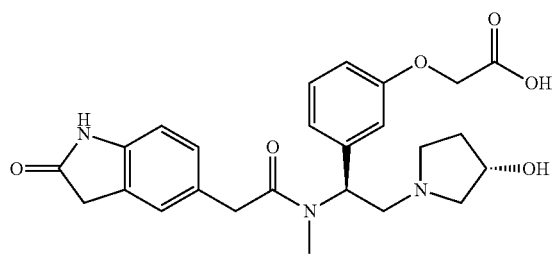 [SMILES: CN(C(=O)Cc1ccc2c(c1)CC(=O)N2)[C@H](CN1CC[C@H](O)C1)c1cccc(OCC(=O)O)c1]

MS (ES, m/z): 468 (M+1); ¹H-NMR (DMSO-d₆, 300 MHz) δ 10.31 (s, 1H), 7.25-7.21 (m, 1H), 7.06-7.02 (m, 2H), 6.86-6.73 (m, 4H), 5.84-5.80 (m, 1H), 4.59 (s, 1H), 4.15 (m, 1H), 3.75-3.60 (m, 2H), 3.54-3.32 (m, 2H), 3.10-3.04 (m, 1H), 2.94-2.87 (m, 1H), 2.75-2.50 (m, 5H), 2.37-2.31 (m, 1H), 1.97-1.91 (m, 1H), 1.76-1.52 (m, 1H).

Example 170

N—((S)-1-(3-(2-amino-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide

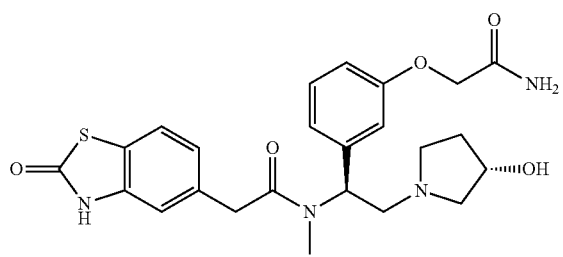 [SMILES: CN(C(=O)Cc1ccc2sc(=O)[nH]c2c1)[C@H](CN1CC[C@H](O)C1)c1cccc(OCC(N)=O)c1]

MS (ES, m/z): 485 (M+1); ¹H-NMR (DMSO-d₆, 400 MHz) δ 11.86 (brs, 1H), 7.54-7.40 (m, 3H), 7.28-7.24 (m, 1H), 7.09-7.02 (m, 2H), 6.90-6.84 (m, 3H), 5.85-5.81 (m, 1H), 5.14-4.73 (m, 1H), 4.40 (s, 2H), 4.18-4.17 (m, 1H), 3.90-3.70 (m, 2H), 3.10-2.66 (m, 6H), 2.39-2.35 (m, 2H), 1.97-1.93 (m, 1H), 1.53-1.51 (m, 1H).

Example 171

2-(3-((S)-2-((S)-3-hydroxypyrrolidin-1-yl)-1-(N-methyl-2-(3-oxo-3,4-dihydroquinoxalin-6-yl)acetamido)ethyl)phenoxy)acetic acid

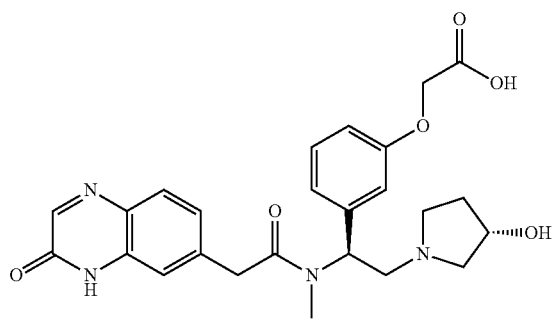 [SMILES: CN(C(=O)Cc1ccc2ncc(=O)[nH]c2c1)[C@H](CN1CC[C@H](O)C1)c1cccc(OCC(=O)O)c1]

MS (ES, m/z): 481 (M+1); ¹H-NMR (DMSO-d₆, 300 MHz) δ 8.13 (s, 1H), 7.72-7.68 (m, 1H), 7.25-7.17 (m, 3H), 6.87-6.78 (m, 3H), 5.85-5.80 (m, 0.8H), 5.13-5.08 (m, 0.2H), 4.55 (s, 2H), 4.17 (brs, 1H), 4.00-3.82 (m, 2H), 3.16-3.06 (m, 1H), 3.00-2.61 (m, 7H), 2.50-2.41 (m, 1H), 2.08-1.89 (m, 1H), 1.54-1.53 (m, 1H)

Example 172

2-(3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)phenoxy)acetic acid

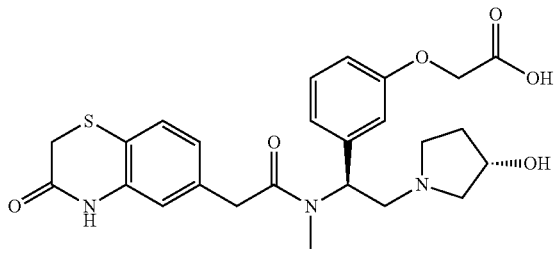 [SMILES: CN(C(=O)Cc1ccc2c(c1)NC(=O)CS2)[C@H](CN1CC[C@H](O)C1)c1cccc(OCC(=O)O)c1]

MS (ES, m/z): 500 (M+1); ¹H-NMR (DMSO-d₆, 400 MHz) δ 10.62 (s, 1H), 7.21-7.25 (m, 2H), 6.78-6.88 (m, 5H), 5.78-5.82 (m, 1H), 4.58 (s, 2H), 4.15-4.17 (m, 1H), 3.62-3.76 (m, 3H), 3.07-3.10 (m, 2H), 2.84-2.92 (m, 2H), 2.84 (m, 2H), 2.67-2.73 (s, 3H), 2.33-2.38 (m, 2H), 1.90-2.07 (m, 1H), 1.50 (m, 1H)

Example 173

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]oxazin-6-yl)acetamide

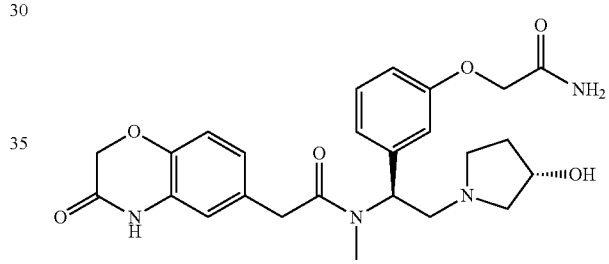

MS (ES, m/z): 483 (M+1); ¹H-NMR (DMSO-d₆, 300 MHz) δ 10.68-10.65 (m, 1H), 7.54 (s, 1H), 7.40 (s, 1H), 7.27-7.23 (m, 1H), 6.89-6.81 (m, 6H), 5.81-5.78 (m, 0.8H), 5.07-5.04 (m, 0.2H), 4.75-4.74 (m, 1H), 4.54 (s, 2H), 4.39 (s, 2H), 3.75-3.58 (m, 2H), 3.01-2.65 (m, 7H), 2.45-2.29 (m, 2H), 1.95-1.92 (m, 1H), 1.52-1.50 (m, 1H).

Example 174

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2-(methylsulfonamido)-2-oxoethoxy)phenyl)ethyl)-N-methylacetamide

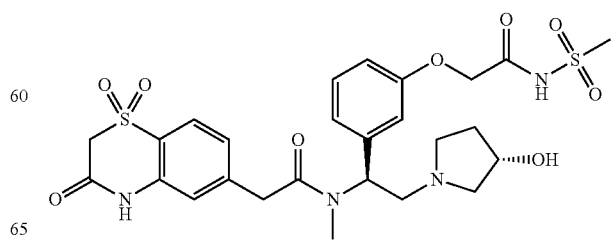

MS (ES, m/z): 609 (M+1); $^1$H-NMR (DMSO-d$_6$, 300 MHz): δ 11.21 (s, 1H), 7.72-7.77 (m, 1H), 7.12-7.29 (m, 4H), 6.74-6.82 (m, 3H), 5.98-6.01 (m, 1H), 5.28-5.32 (m, 1H), 4.70 (s, 2H), 4.25-4.42 (m, 3H), 3.81-3.98 (m, 3H), 3.07-3.32 (m, 3H), 2.90-2.94 (m, 4H), 3.81-3.86 (m, 3H), 2.10-2.28 (m, 1H), 1.75-1.78 (m, 1H).

Example 175

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]thiazin-6-yl)acetamide

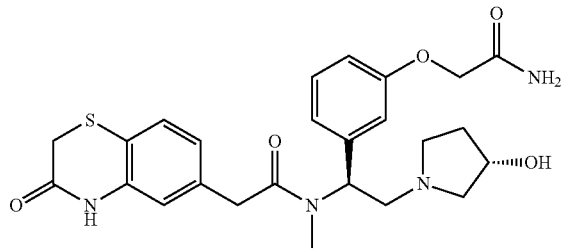 [SMILES: CN(C(=O)Cc1ccc2c(c1)NC(=O)CS2)[C@H](CN1CC[C@H](O)C1)c1cccc(OCC(N)=O)c1]

MS (ES, m/z): 499 (M+1); 1H-NMR (DMSO-d$_6$, 400 MHz): δ 10.54 (s, 1H), 7.55 (s, 1H), 7.41 (s, 1H), 7.27-7.24 (m, 2H), 6.89-6.83 (m, 5H), 5.81-5.78 (m, 1H), 4.72-4.71 (m, 1H), 4.40-4.30 (m, 2H), 4.15 (br, 1H), 3.78-3.61 (m, 2H), 3.44-3.26 (m, 2H), 3.05-2.65 (m, 7H), 2.51-2.28 (m, 2H), 1.87-1.97 (m, 1H), 1.50 (m, 1H).

Example 176

3-((S)-2-((S)-3-hydroxypyrrolidin-1-yl)-1-(N-methyl-2-(2-oxo-2,3-dihydrobenzo[d]oxazol-5-yl)acetamido)ethyl)benzoic acid

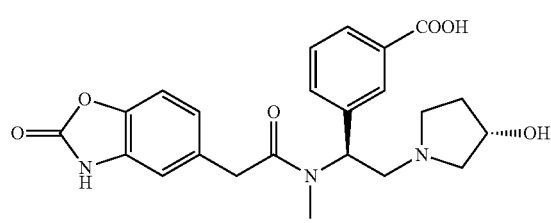 [SMILES: CN(C(=O)Cc1ccc2oc(=O)[nH]c2c1)[C@H](CN1CC[C@H](O)C1)c1cccc(C(=O)O)c1]

MS (ES, m/z): 440 (M+1); $^1$H-NMR (DMSO-d6, 300 MHz): δ 7.80 (m, 2H), 7.53-7.43 (m, 2H), 7.21-7.15 (m, 1H), 7.04-6.93 (m, 1H), 5.92-5.87 (m, 0.8H), 4.19-4.17 (s, 1H), 3.88-3.69 (m, 2H), 3.15-3.00 (m, 2H), 2.91-2.72 (m, 5H), 2.61 (s, 1H), 2.45-2.36 (m, 2H), 1.99-1.92 (m, 1H), 1.52-1.50 (m, 1H).

Example 177

3-((S)-2-((S)-3-hydroxypyrrolidin-1-yl)-1-(N-methyl-2-(2-oxoindolin-6-yl)acetamido)ethyl)-N-(methylsulfonyl)benzamide

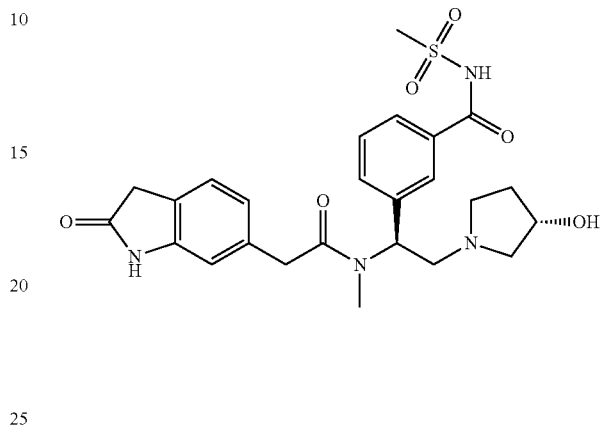

MS (ES, m/z): 515 (M+1); $^1$H-NMR (DMSO-d$_6$, 400 MHz): δ 10.34-10.30 (m, 1H), 7.87-7.86 (s, 2H), 7.36-7.27 (m, 2H), 7.14-7.12 (d, J=7.6 Hz, 1H), 6.08-5.97 (m, 1H), 5.10-5.35 (m, 1H), 4.41-4.15 (m, 1H), 3.79-3.74 (m, 2H), 3.43 (s, 2H). 3.07-2.98 (m, 2H), 2.94-2.92 (m, 4H), 2.73 (s, 2H), 2.67-2.64 (m, 3H), 2.11-2.08 (m, 1H), 1.76-1.67 (m, 1H).

Example 178

N—((S)-1-(3-ethynylphenyl)-2-((S)-3-hydroxypyrrolidin-1-yl)ethyl)-N-methyl-2-(3-oxo-3,4-dihydroquinoxalin-6-yl)acetamide

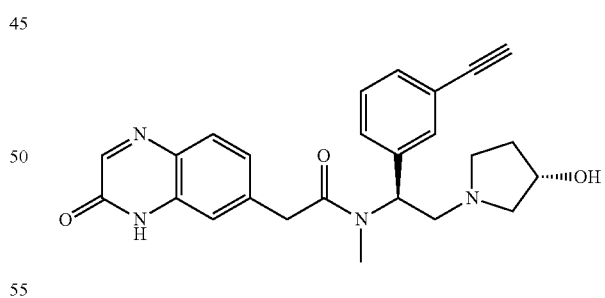

MS (ES, m/z): 431 (M+1); $^1$H-NMR (DMSO-d$_6$, 300 MHz): δ 12.48-12.32 (s, 1H), 8.13 (s, 1H), 7.73-7.70 (m, 1H), 7.38-7.35 (m, 4H), 7.21-7.20 (m, 2H), 5.69-5.95 (s, 1H), 4.65-4.90 (m, 1H), 4.19-4.16 (m, 2H), 4.00-3.89 (m, 2H), 3.12-2.94 (m, 1H), 2.92-2.75 (m, 5H), 2.62 (s, 1H), 2.21-2.31 (m, 2H), 2.12-1.92 (m, 1H), 2.52-2.41 (m, 1H).

Example 179

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxoindolin-6-yl)acetamide

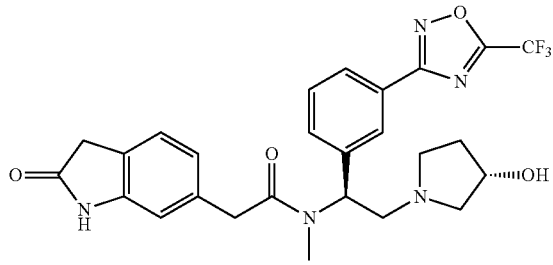 [SMILES: CN(C(=O)Cc1ccc2c(c1)NC(=O)C2)[C@H](CN1CC[C@H](O)C1)c1cccc(-c2noc(C(F)(F)F)n2)c1]

MS (ES, m/z): 530 (M+1); $^1$H-NMR (DMSO-d$_6$, 300 MHz): δ 10.35 (s, 1H), 7.97 (d, J=3 Hz, 1H), 7.60 (d, J=4.8 Hz, 2H), 7.08 (d, J=4.8 Hz, 1H), 6.83-6.79 (m, 2H), 5.96-5.24 (m, 1H), 4.88 (s, 1H), 4.19 (s, 1H), 3.84-3.65 (m, 2H), 3.42 (s, 2H), 3.16-2.40 (m, 9H), 2.00-1.93 (m, 1H), 1.54-1.49 (m, 1H).

Example 180

N—((S)-1-(3-ethynylphenyl)-2-((S)-3-hydroxypyrrolidin-1-yl)ethyl)-N-methyl-2-(2-oxoindolin-6-yl)acetamide

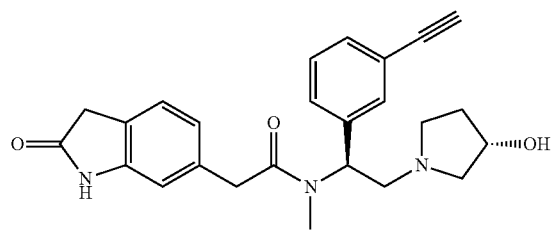 [SMILES: C#Cc1cccc([C@@H](CN2CC[C@H](O)C2)N(C)C(=O)Cc2ccc3c(c2)NC(=O)C3)c1]

MS (ES, m/z): 418 (M+1); $^1$H-NMR (DMSO-d$_6$, 300 MHz): δ 10.41-10.31 (m, 1H), 7.37-7.27 (m, 4H), 7.13-7.10 (d, J=6.9 Hz, 1H), 6.82-6.74 (m, 2H), 5.85-5.80 (m, 1H), 4.89-4.87 (d, J=4.2 Hz, 1H), 4.19-4.17 (m, 2H), 3.83-3.63 (m, 2H), 3.43 (s, 2H), 3.09-3.01 (m, 1H), 2.81-2.70 (m, 4H), 2.60-2.58 (m, 1H), 2.40-2.33 (m, 2H), 2.00-1.90 (m, 1H), 1.52-1.49 (m, 1H).

Example 181

2-(2,2-dioxido-1,3-dihydrobenzo[c]isothiazol-6-yl)-N—((S)-2-((S)-3-hydroxypyrrolidin-1-yl)-1-(3-(5-methyl-1,2,4-oxadiazol-3-yl)phenyl)ethyl)-N-methylacetamide

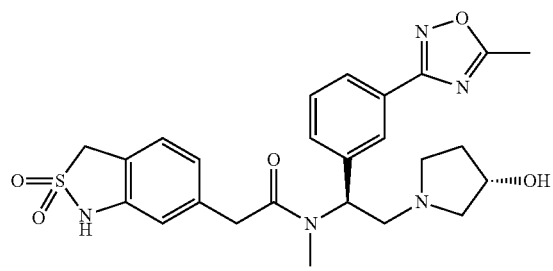 [SMILES: Cc1nc(-c2cccc([C@@H](CN3CC[C@H](O)C3)N(C)C(=O)Cc3ccc4c(c3)NS(=O)(=O)C4)c2)no1]

MS (ES, m/z): 512 (M+1); $^1$H-NMR (DMSO-d$_6$, 300 MHz): δ 7.89 (d, J=1.2 Hz, 1H), 7.53 (d, J=7.5 Hz, 1H), 7.20 (d, J=7.8 Hz, 1H), 6.86 (d, J=6.6 Hz, 1H), 6.75 (s, 1H), 5.95-5.85 (m, 0.8H), 5.25 (m, 0.2H), 4.45 (s, 2H), 4.24-4.13 (m, 1H), 3.75 (q, J=15.6 Hz, 2H), 3.11 (t, J=11.4 Hz, 1H), 2.95-2.35 (m, 11H), 2.04-1.86 (m, 1H), 1.60-1.45 (m, 1H).

Example 182

2-(2,2-dioxido-1,3-dihydrobenzo[c]isothiazol-6-yl)-N—((S)-1-(3-ethynylphenyl)-2-((S)-3-hydroxypyrrolidin-1-yl)ethyl)-N-methylacetamide

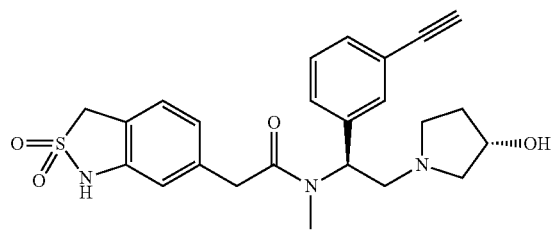 [SMILES: C#Cc1cccc([C@@H](CN2CC[C@H](O)C2)N(C)C(=O)Cc2ccc3c(c2)NS(=O)(=O)C3)c1]

MS (ES, m/z): 454 (M+1); $^1$H-NMR (DMSO-d$_6$, 300 MHz): δ 7.38-7.18 (m, 5H), 6.85-6.75 (m, 2H), 5.84-5.79 (m, 1H), 4.48 (s, 2H), 4.25-4.18 (m, 2H), 3.84-3.65 (m, 2H), 3.18-3.03 (m, 2H), 2.84-2.72 (m, 5H), 2.44-2.36 (m, 2H), 2.00-1.93 (m, 1H), 1.58-1.45 (m, 1H).

Example 183

N—((S)-2-((S)-3-hydroxypyrrolidin-1-yl)-1-(3-(5-methyl-1,2,4-oxadiazol-3-yl)phenyl)ethyl)-N-methyl-2-(2-oxo-2,3-dihydrobenzo[d]thiazol-5-yl)acetamide

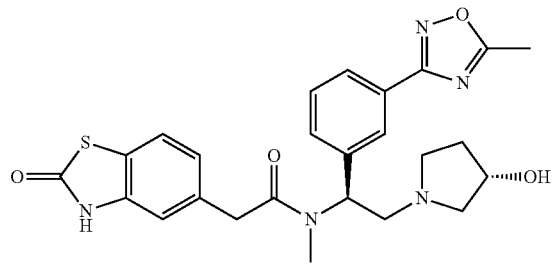 [SMILES: Cc1nc(-c2cccc([C@@H](CN3CC[C@H](O)C3)N(C)C(=O)Cc3ccc4sc(=O)[nH]c4c3)c2)no1]

MS (ES, m/z): 494 (M+1); $^1$H-NMR (DMSO-d$_6$, 300 MHz): δ 8.92-7.02 (m, 7H), 5.95-5.76 (m, 0.8H), 5.23 (m, 0.2H), 4.22-4.10 (m, 1H), 3.80 (q, J=15.6 Hz, 2H), 3.12 (t, J=11.4 Hz, 1H), 2.80-2.35 (m, 11H), 2.00-1.89 (m, 1H), 1.60-1.45 (m, 1H).

Example 184

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxo-2,3-dihydrobenzo[d]thiazol-5-yl)acetamide

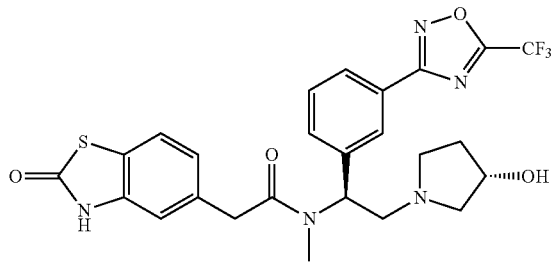 [SMILES: CN(C(=O)Cc1ccc2sc(=O)[nH]c2c1)[C@H](CN1CC[C@H](O)C1)c1cccc(-c2noc(C(F)(F)F)n2)c1]

MS (ES, m/z): 548 (M+1); ¹H-NMR (DMSO-d₆, 400 MHz): δ 11.84 (s, 1H), 7.99-7.93 (m, 2H), 7.62-7.41 (m, 3H), 7.04-7.00 (m, 2H), 5.95-5.91 (m, 1H), 4.91 (s, 1H), 4.19 (s, 1H), 3.92-3.78 (m, 2H), 3.17-2.40 (m, 9H), 1.98-1.92 (m, 1H), 1.54-1.51 (m, 1H).

Example 185

N—((S)-1-(3-(1,2,4-oxadiazol-3-yl)phenyl)-2-((S)-3-hydroxypyrrolidin-1-yl)ethyl)-N-methyl-2-(2-oxoindolin-6-yl)acetamide 2,2,2-trifluoroacetate

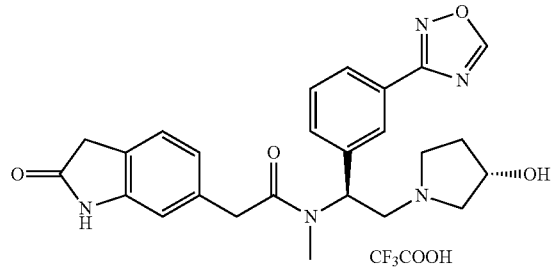 [SMILES: CN(C(=O)Cc1ccc2c(c1)NC(=O)C2)[C@H](CN1CC[C@H](O)C1)c1cccc(-c2ncon2)c1 ; "CF3COOH"]

MS (ES, m/z): 462 (M+1); ¹H-NMR (DMSO-d₆, 300 MHz): δ 10.40 (s, 1H), 9.95 (br, 0.5H), 9.75 (s, 1H), 9.60 (br, 0.3H), 8.02 (d, J=5.7 Hz, 1H), 7.90 (s, 1H), 7.62 (t, J=8.7 Hz, 1H), 7.43 (t, J=5.7 Hz, 1H), 7.11 (d, J=5.4 Hz, 1H), 6.81 (d, J=5.7 Hz, 1H), 6.75 (s, 1H), 6.25 (m, 1H), 5.70-5.40 (m, 1H), 4.52-3.21 (m, 13H), 2.74 (s, 3H), 2.35-1.82 (m, 3H).

Example 186

N—((S)-1-(3-(1,2,4-oxadiazol-3-yl)phenyl)-2-((S)-3-hydroxypyrrolidin-1-yl)ethyl)-2-(2,2-dioxido-1,3-dihydrobenzo[c]isothiazol-6-yl)-N-methylacetamide

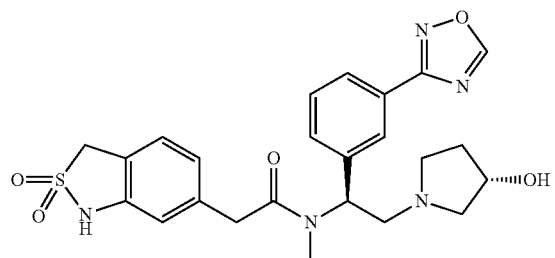

MS (ES, m/z): 498 (M+1); ¹H-NMR (DMSO-d₆, 300 MHz): δ 10.49 (s, 1H), 10.00 (br, 0.6H), 9.75 (s, 1H), 8.02 (d, J=7.5 Hz, 1H), 7.90 (s, 1H), 7.60 (t, J=7.8 Hz, 1H), 7.43 (m, 1H), 7.20 (d, J=7.8 Hz, 1H), 6.75 (s, 1H), 6.30-6.17 (m, 1H), 5.64-5.40 (m, 1H), 4.50 (s, 3H), 4.30-3.35 (m, 6H), 2.75 (s, 3H), 2.30-1.75 (m, 3H).

Example 187

2-(2,2-dioxido-1,3-dihydrobenzo[c]isothiazol-6-yl)-N—((S)-2-((S)-3-hydroxypyrrolidin-1-yl)-1-(3-(5-(trifluoromethyl)-1,2,4-oxadiazol-3-yl)phenyl)ethyl)-N-methylacetamide 2,2,2-trifluoroacetate

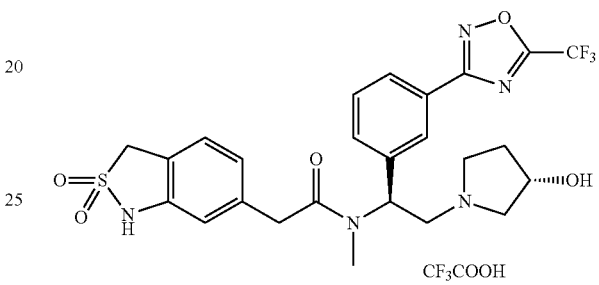

MS (ES, m/z): 566 (M+1); ¹H-NMR (DMSO-d₆, 400 MHz): δ 10.47 (d, J=4.5 Hz, 1H), 10.09 (s, 1H), 8.06 (d, J=6 Hz, 1H), 7.69 (d, J=4.5 Hz, 1H), 7.67-6.85 (m, 4H), 6.76 (s, 1H), 6.28-6.25 (m, 1H), 5.73-5.46 (s, 1H), 4.49-3.25 (m, 11H), 2.78 (s, 3H), 2.33-1.87 (m, 3H).

Example 188

N,N-diethyl-3-((S)-2-((S)-3-hydroxypyrrolidin-1-yl)-1-(N-methyl-2-(2-oxo-2,3-dihydrobenzo[d]thiazol-5-yl)acetamido)ethyl)benzamide

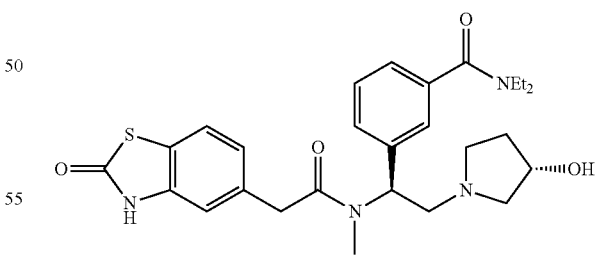

MS (ES, m/z): 511.23 (M+1); ¹H-NMR (300 MHz, DMSO-d₆): δ 7.45 (d, J=4.5 Hz, 1H), 7.40-7.33 (m, 2H), 7.24-7.19 (m, 2H), 7.07-7.00 (m, 2H), 5.87-5.85 (t, J=3 Hz, 1H), 4.88-4.77 (br, 1H), 3.88-3.71 (m, 2H), 3.32 (m, 2H), 3.11-3.10 (m, 3H), 2.92-2.79 (m, 4H), 2.49-2.23 (m, 2H), 2.04-1.95 (m, 1H), 1.54 (m, 1H), 1.24-0.99 (m, 6H)

Example 189

N—((S)-1-(3-(1,2,4-oxadiazol-3-yl)phenyl)-2-((S)-3-hydroxypyrrolidin-1-yl)ethyl)-N-methyl-2-(2-oxo-2,3-dihydrobenzo[d]thiazol-5-yl)acetamide 2,2,2-trifluoroacetate

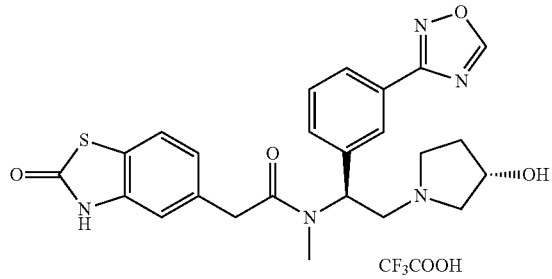 [SMILES: CN(C(=O)Cc1ccc2sc(=O)[nH]c2c1)[C@H](CN1CC[C@H](O)C1)c1cccc(-c2ncon2)c1 ; "CF3COOH"]

MS (ES, m/z): 480 (M+1); $^1$H-NMR (CD$_3$OD-d$_4$, 300 MHz): δ 9.32 (s, 1H), 8.11 (d, J=7.2 Hz, 1H), 7.95 (s, 1H), 7.60 (t, J=7.8 Hz, 1H), 7.50-7.10 (m, 4H), 6.40 (d, J=8.4 Hz, 1H), 4.60 (s, 1H), 4.35-3.50 (m, 7H), 2.82 (s, 3H), 2.50-2.00 (m, 2H).

Example 190

N—((S)-1-(3-(1,2,4-oxadiazol-3-yl)phenyl)-2-((S)-3-hydroxypyrrolidin-1-yl)ethyl)-N-methyl-2-(3-oxo-3,4-dihydroquinoxalin-6-yl)acetamide 2,2,2-trifluoroacetate

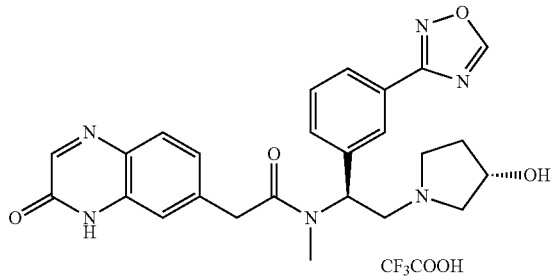 [SMILES: CN(C(=O)Cc1ccc2ncc(=O)[nH]c2c1)[C@H](CN1CC[C@H](O)C1)c1cccc(-c2ncon2)c1 ; "CF3COOH"]

MS (ES, m/z): 475 (M+1); $^1$H-NMR (CD$_3$OD-d$_4$, 300 MHz): δ 9.30 (s, 1H), 8.20 (s, 1H), 8.10 (d, J=7.5 Hz, 1H), 7.96 (s, 1H), 7.80 (d, J=8.1 Hz, 1H), 7.60 (t, J=7.8 Hz, 1H), 7.50-7.30 (m, 4H), 6.40 (d, J=8.7 Hz, 1H), 4.62 (s, 1H), 4.35-3.40 (m, 7H), 2.85 (s, 3H), 2.50-1.95 (m, 2H).

$^1$H-NMR (CD$_3$OD-d$_4$, 300 MHz): δ 9.30 (s, 1H), 8.20 (s, 1H), 8.10 (d, J=7.5 Hz, 1H), 7.96 (s, 1H), 7.80 (d, J=8.1 Hz, 1H), 7.60 (t, J=7.8 Hz, 1H), 7.50-7.30 (m, 4H), 6.40 (d, J=8.7 Hz, 1H), 4.62 (s, 1H), 4.35-3.40 (m, 7H), 2.85 (s, 3H), 2.50-1.95 (m, 2H).

Example 191

N—((S)-1-(3-(1H-imidazol-2-yl)phenyl)-2-((S)-3-hydroxypyrrolidin-1-yl)ethyl)-N-methyl-2-(2-oxo-2,3-dihydrobenzo[d]thiazol-5-yl)acetamide

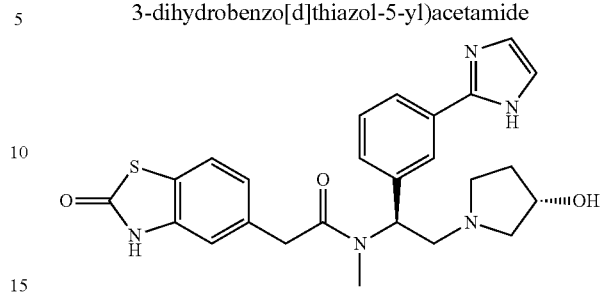

MS (ES, m/z): 478.18 (M+1); $^1$H-NMR (300 MHz, DMSO-d$_6$): δ 7.86-7.84 (m, 2H), 7.49-7.40 (m, 2H), 7.26-7.23 (m, 2H), 7.10 (s, 1H), 7.06-7.03 (m, 2H), 5.82-5.87 (m, 1H), 4.25-4.14 (br, 1H), 3.87 (m, 1H), 3.75 (d, 1H), 2.77 (m, 1H), 2.74 (m, 1H), 2.67 (m, 1H), 2.62 (m, 4H), 2.41-2.40 (m, 2H), 2.27-2.02 (m, 1H), 1.50-1.60 (m, 1H).

Example 192

N—((S)-2-((S)-3-hydroxypyrrolidin-1-yl)-1-(3-(thiazol-2-yl)phenyl)ethyl)-N-methyl-2-(2-oxo-2,3-dihydrobenzo[d]thiazol-5-yl)acetamide

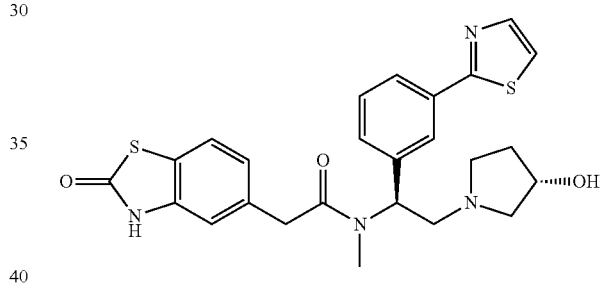

MS (ES, m/z): 495.1 (M+1); $^1$H-NMR (300 MHz, DMSO-d6): δ 11.90-11.82 (br, 1H), 7.92 (d, J=1.5 Hz, 1H), 7.85-7.78 (m, 3H), 7.48-7.39 (m, 3H), 7.10-7.03 (m, 2H), 5.87-5.85 (t, J=3 Hz, 1H), 4.88-4.77 (br, 1H), 3.85 (m, 2H), 2.83 (s, 1H), 2.80-2.77 (m, 5H), 2.73-2.64 (s, 1H), 2.04-1.95 (m, 1H), 1.54 (m, 1H).

Example 193

N—((S)-1-(3-cyano-5-fluorophenyl)-2-((S)-3-hydroxypyrrolidin-1-yl)ethyl)-N-methyl-2-(2-oxo-2,3-dihydrobenzo[d]thiazol-5-yl)acetamide hydrochloride

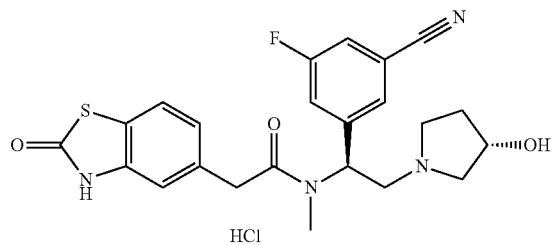 [SMILES: CN(C(=O)Cc1ccc2sc(=O)[nH]c2c1)[C@H](CN1CC[C@H](O)C1)c1cc(F)cc(C#N)c1 ; Cl]

MS (ES, m/z): 455 (M+1); ¹H-NMR (300 MHz, d6-DMSO): δ 11.90-11.88 (m, 1H), 9.95-10.05 (m, 1H), 7.89-7.87 (m, 1H), 7.58 (s, 1H), 7.43-7.58 (m, 2H), 7.08-7.04 (m, 1H), 6.14-6.11 (m, 1H), 5.58-5.48 (d, 1H), 4.49-4.41 (m, 1H), 3.95-3.82 (m, 5H), 3.56-3.43 (m, 3H), 3.27-3.17 (m, 2H), 2.83 (s, 3H), 2.49-2.33 (m, 1H), 1.91-1.87 (m, 1H).

Example 194

N—((S)-2-((S)-3-hydroxypyrrolidin-1-yl)-1-(3-(5-methyl-1,2,4-oxadiazol-3-yl)phenyl)ethyl)-N-methyl-2-(3-oxo-3,4-dihydroquinoxalin-6-yl)acetamide

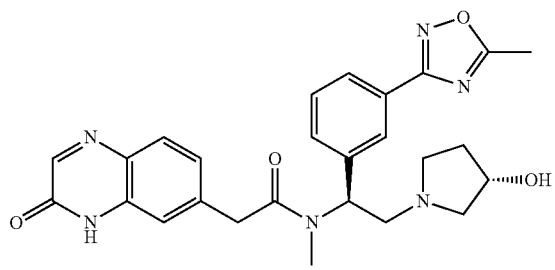 [SMILES: Cc1nc(-c2cccc([C@@H](CN3CC[C@H](O)C3)N(C)C(=O)Cc3ccc4ncc(=O)[nH]c4c3)c2)no1]

MS (ES, m/z): 489 (M+1); ¹H-NMR (300 MHz, DMSO-d6): δ 12.41 (brs, 1H), 8.11 (s, 1H), 7.86-7.91 (m, 2H), 7.64-7.73 (m, 1H), 7.51-7.54 (m, 2H), 7.21-7.23 (m, 2H), 5.87-5.93 (m, 1H), 4.70-4.85 (m, 1H), 4.17 (brs, 1H), 3.82-3.99 (m, 2H), 3.07-3.15 (m, 1H), 2.66-2.87 (m, 8H), 2.34-2.50 (m, 2H), 1.89-1.96 (m, 1H), 1.49-1.53 (m, 1H);

Example 195

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N-(2,2,2-trifluoroethyl)benzamide

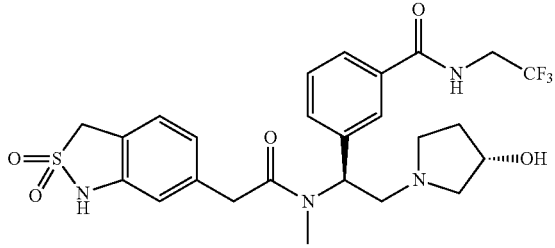 [SMILES: CN(C(=O)Cc1ccc2c(c1)NS(=O)(=O)C2)[C@H](CN1CC[C@H](O)C1)c1cccc(C(=O)NCC(F)(F)F)c1]

MS (ES, m/z): 555 (M+1); ¹H-NMR (DMSO-d6, 400 MHz): 10.50 (s, 1H), 9.13-9.09 (m, 1H), 7.80-7.77 (m, 2H), 7.48-7.44 (m, 2H), 7.20-7.18 (m, 1H), 6.86-6.73 (m, 2H), 5.92-5.88 (m, 1H), 5.20-5.15 (m, 1H), 4.47 (s, 2H), 4.19-4.08 (m, 3H), 3.84-3.80 (m, 1H), 3.69-3.65 (m, 1H), 3.12-3.09 (m, 1H), 2.87-2.74 (m, 2H), 2.72 (s, 3H), 2.63 (s, 1H), 2.45-2.36 (m, 2H), 2.00-1.95 (m, 1H), 1.54-1.53 (m, 1H).

Example 196

3-((S)-2-((S)-3-hydroxypyrrolidin-1-yl)-1-(N-methyl-2-(3-oxo-3,4-dihydroquinoxalin-6-yl)acetamido)ethyl)-N-(2,2,2-trifluoroethyl)benzamide

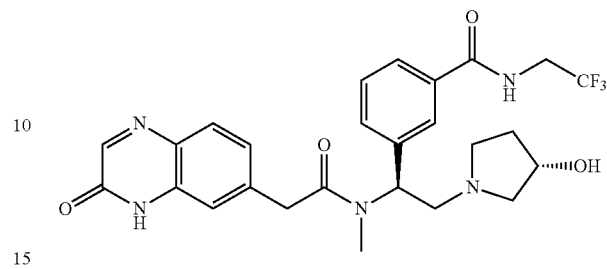

MS (ES, m/z): 532 (M+1); ¹H-NMR (DMSO-d6, 400 MHz): δ 12.39 (s, 1H), 9.11-9.10 (m, 1H), 8.12 (s, 1H), 7.80-7.70 (m, 3H), 7.49-7.47 (m, 2H), 7.22-7.20 (m, 2H), 5.90 (m, 1H), 4.79 (m, 1H), 4.16-4.10 (m, 3H), 4.08-3.81 (m, 2H), 3.17-3.01 (m, 1H), 2.92-2.85 (m, 2H), 2.83 (s, 2H), 2.75 (m, 2H), 2.46 (m, 2H), 1.92 (m, 1H), 1.51 (m, 1H).

Example 197

N—((S)-1-(3-cyano-5-fluorophenyl)-2-((S)-3-hydroxypyrrolidin-1-yl)ethyl)-N-methyl-2-(2-oxoindolin-6-yl)acetamide

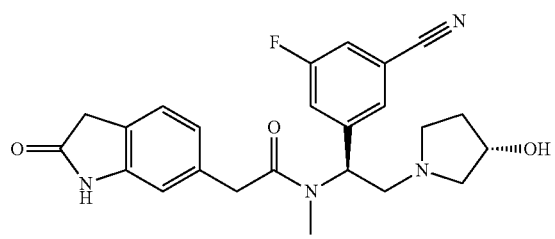 [SMILES: CN(C(=O)Cc1ccc2c(c1)NC(=O)C2)[C@H](CN1CC[C@H](O)C1)c1cc(F)cc(C#N)c1]

MS (ES, m/z): 438 (M+1); ¹H-NMR (300 MHz, DMSO-d6): δ 10.36 (s, 1H), 7.78-7.73 (m, 1H), 7.59-7.48 (m, 2H), 7.13-7.11 (d, 1H, J=7.5 Hz), 5.75 (s, 1H), 4.83 (s, 1H), 4.17 (s, 1H), 3.89-3.82 (m, 2H), 3.43 (s, 2H), 2.94-2.91 (m, 2H), 2.77 (m, 4H), 2.36-2.34 (m, 2H), 1.95-1.91 (m, 1H), 1.59-1.56 (m, 1H).

Example 198

N—((S)-1-(3-(1H-imidazol-2-yl)phenyl)-2-((S)-3-hydroxypyrrolidin-1-yl)ethyl)-N-methyl-2-(2-oxoindolin-6-yl)acetamide 2,2,2-trifluoroacetate

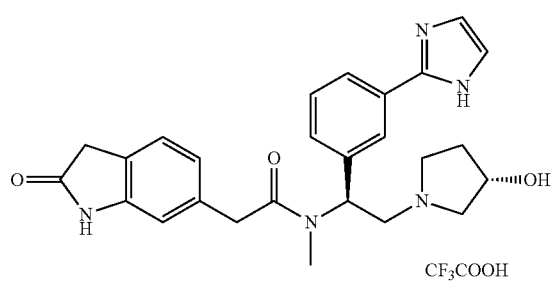 [SMILES: CN(C(=O)Cc1ccc2c(c1)NC(=O)C2)[C@H](CN1CC[C@H](O)C1)c1cccc(-c2ncc[nH]2)c1 ; "CF3COOH"]

MS (ES, m/z): 574.22 (M+1); $^1$H-NMR (300 MHz, DMSO-d$_6$): δ 7.84 (d, J=4.5 Hz, 1H), 7.70-7.58 (m, 4H), 7.44 (d, J=7.5 Hz, 1H), 7.11 (d, J=1.5 Hz, 1H), 6.8 (d, J=1.5 Hz, 1H), 6.75-6.72 (s, 1H), 6.2 (d, J=1.5 Hz, 1H), 4.46 (s, 2H), 3.76-3.55 (m, 4H), 3.39-3.36 (m, 4H), 2.88 (s, 3H), 2.46-1.96 (m, 2H).

Example 199

N—((S)-1-(3-cyano-5-fluorophenyl)-2-((S)-3-hydroxypyrrolidin-1-yl)ethyl)-2-(2,2-dioxido-1,3-dihydrobenzo[c]isothiazol-6-yl)-N-methylacetamide

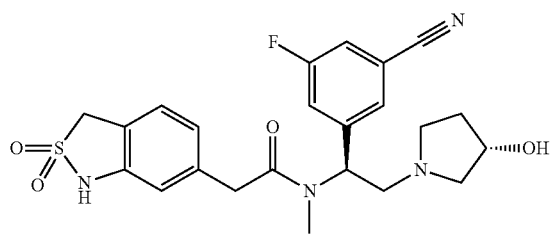 [SMILES: CN(C(=O)Cc1ccc2c(c1)NS(=O)(=O)C2)[C@H](CN1CC[C@H](O)C1)c1cc(F)cc(C#N)c1]

MS (ES, m/z): 473 (M+1); $^1$H-NMR (300 MHz, d$_6$-DMSO): δ 10.43 (brs, 1H), 7.78-7.75 (m, 1H), 7.61-7.49 (m, 2H), 7.21-7.18 (m, 1H), 6.85-6.82 (d, 1H, J=7.5 Hz), 6.73 (s, 1H), 5.79-5.74 (m, 1H), 4.85-4.75 (m, 1H), 4.47 (s, 2H), 4.17 (s, 1H), 3.84-3.68 (q, 2H), 2.97-2.88 (m, 2H), 2.78-2.60 (m, 5H), 2.38-2.35 (m, 2H), 1.99-1.94 (m, 1H), 1.54 (s, 1H).

Example 200

N—((S)-1-(3-cyano-5-fluorophenyl)-2-((S)-3-hydroxypyrrolidin-1-yl)ethyl)-N-methyl-2-(3-oxo-3,4-dihydroquinoxalin-6-yl)acetamide

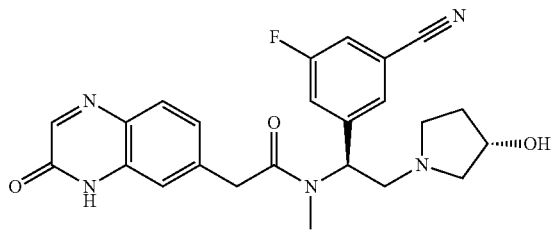 [SMILES: CN(C(=O)Cc1ccc2ncc(=O)[nH]c2c1)[C@H](CN1CC[C@H](O)C1)c1cc(F)cc(C#N)c1]

MS (ES, m/z): (M+1) 450; $^1$H-NMR (300 MHz, d6-DMSO): δ 8.15 (s, 1H), 7.89-7.85 (m, 2H), 7.58-7.51 (m, 2H), 7.18 (m, 2H), 5.78-5.74 (m, 1H), 4.79-4.71 (m, 1H), 4.16 (s, 1H), 4.03-3.83 (m, 2H), 3.93-3.87 (m, 1H), 2.81 (s, 4H), 2.75-2.64 (m, 1H), 2.41-2.32 (m, 2H), 1.91-1.87 (m, 1H), 1.63-1.58 (m, 1H).

Example 201

2-(1,1-dioxido-3-oxo-3,4-dihydro-2H-benzo[b][1,4]thiazin-6-yl)-N—((S)-1-(3-ethynyl phenyl)-2-((S)-3-hydroxypyrrolidin-1-yl)ethyl)-N-methylacetamide

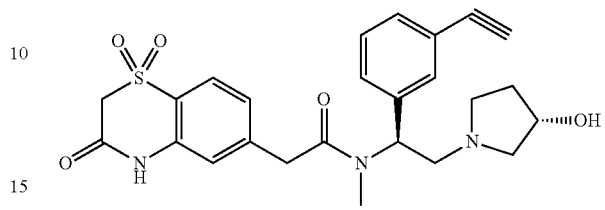

MS (ES, m/z): 482 (M+1); $^1$H-NMR (DMSO, 400 MHz): δ 11.20-11.22 (m, 1H), 7.72-7.77 (m, 1H), 7.35-7.44 (m, 4H), 7.17-7.21 (m, 1H), 7.10 (s, 1H), 5.79 (m, 1H), 4.70-4.73 (m, 3H), 4.17-4.22 (m, 2H), 3.80-3.99 (m, 2H), 2.93-3.14 (s, 1H), 2.76-2.79 (m, 4H), 2.62-2.71 (m, 2H), 2.33-2.43 (m, 2H), 1.93-2.08 (m, 1H), 1.40-1.60 (m, 1H).

Example 202

N—((S)-1-(3-(1H-imidazol-2-yl)phenyl)-2-((S)-3-hydroxypyrrolidin-1-yl)ethyl)-2-(2,2-dioxido-1,3-dihydrobenzo[c]isothiazol-6-yl)-N-methylacetamide

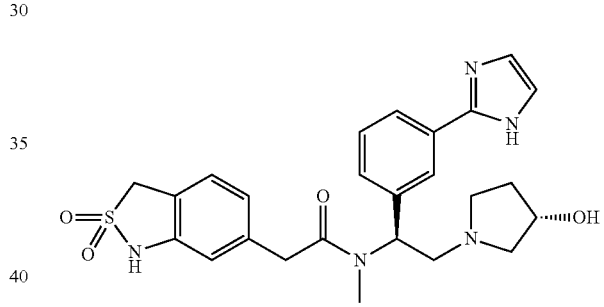

MS (ES, m/z): 496 (M+1); $^1$H-NMR (300 MHz, DMSO-d$_6$): δ 7.81-7.86 (m, 2H), 7.40 (t, J=7.8 Hz, 1H), 7.13-7.25 (m, 4H), 6.85 (d, J=7.8 Hz, 1H), 6.76 (s, 1H), 5.85-6.00 (m, 1H), 4.46 (s, 2H), 4.20 (brs, 1H), 3.81-3.86 (m, 1H), 3.60-3.69 (m, 1H), 2.95-3.20 (m, 1H), 2.80-2.85 (m, 1H), 2.73-2.78 (m, 4H), 2.66 (s, 1H), 2.38-2.49 (m, 2H), 1.90-2.10 (m, 1H), 1.50 (brs, 1H).

Example 203

N—((S)-1-(3-cyanophenyl)-2-((S)-3-hydroxypyrrolidin-1-yl)ethyl)-2-(2,2-dioxido-1,3-dihydrobenzo[c]isothiazol-6-yl)-N-methylacetamide

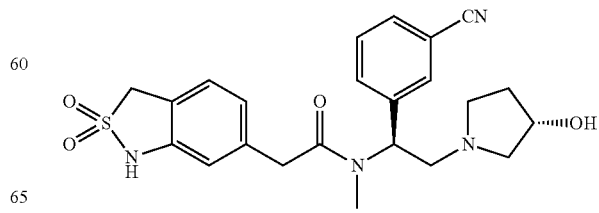

MS (ES, m/z): 455 (M+1); $^1$H-NMR (DMSO-$d_6$, 300 MHz): δ 7.80-7.69 (m, 2H), 7.69-7.46 (m, 2H), 7.20 (d, J=7.8 Hz, 1H), 6.83 (d, J=7.8 Hz, 1H), 6.73 (s, 1H), 5.88-5.74 (m, 1H), 4.47 (s, 2H), 4.18 (br s, 1H), 4.00-3.60 (m, 2H), 3.17-2.90 (m, 1H), 2.90-2.55 (m, 7H), 2.48-2.32 (m, 1H), 2.16-1.79 (m, 1H), 1.60-1.40 (m, 1H).

Example 204

N—((S)-1-(3-(but-1-yn-1-yl)phenyl)-2-((S)-3-hydroxypyrrolidin-1-yl)ethyl)-N-methyl-2-(2-oxoindolin-6-yl)acetamide

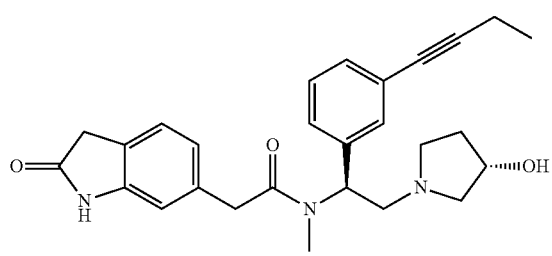 [SMILES: CCC#Cc1cccc([C@@H](CN2CC[C@H](O)C2)N(C)C(=O)Cc2ccc3c(c2)NC(=O)C3)c1]

MS (ES, m/z): 446 (M+1); $^1$H-NMR (DMSO-$d_6$, 300 MHz): δ 10.34 (m, 1H), 7.36-6.90 (m, 5H), 6.90-6.70 (m, 2H), 5.97-5.62 (m, 1H), 4.97-4.81 (m, 1H), 4.25-4.01 (br s, 1H), 3.87-3.55 (m, 2H), 3.42 (s, 2H), 3.20-2.86 (m, 1H), 2.83-2.62 (m, 5H), 2.48-2.22 (m, 4H), 2.01-1.84 (m, 1H), 1.65-1.40 (m, 1H), 1.29-1.08 (t, J=7.5 Hz, 3H).

Example 205

N—((S)-1-(3-(but-1-yn-1-yl)phenyl)-2-((S)-3-hydroxypyrrolidin-1-yl)ethyl)-N-methyl-2-(2-oxo-2,3-dihydrobenzo[d]thiazol-5-yl)acetamide

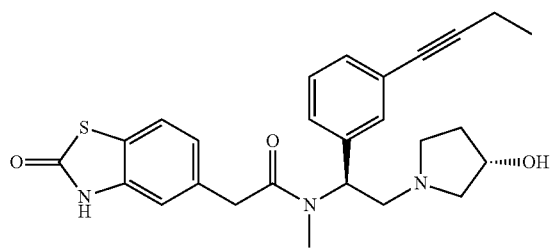 [SMILES: CCC#Cc1cccc([C@@H](CN2CC[C@H](O)C2)N(C)C(=O)Cc2ccc3sc(=O)[nH]c3c2)c1]

MS (ES, m/z): 464 (M+1); $^1$H-NMR (DMSO-$d_6$, 300 MHz): δ 7.47 (d, J=7.2 Hz, 1H), 7.38-7.15 (m, 4H), 7.12-6.97 (m, 2H), 5.90-5.73 (m, 1H), 4.24-4.01 (m, 1H), 3.92-3.58 (m, 2H), 3.20-2.96 (s, 1H), 2.80-2.55 (m, 6H), 2.45-2.30 (m, 4H), 1.99-1.82 (m, 1H), 1.58-1.45 (m, 1H), 1.21-1.12 (t, J=7.5 Hz, 3H).

Example 206

N—((S)-1-(3-(but-1-yn-1-yl)phenyl)-2-((S)-3-hydroxypyrrolidin-1-yl)ethyl)-N-methyl-2-(3-oxo-3,4-dihydroquinoxalin-6-yl)acetamide

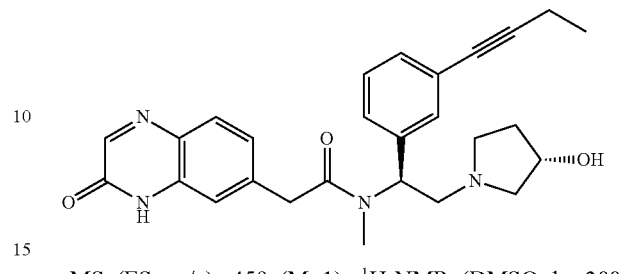

MS (ES, m/z): 459 (M+1); $^1$H-NMR (DMSO-$d_6$, 300 MHz): δ 8.12 (s, 1H), 7.73-7.70 (m, 1H), 7.28-7.19 (m, 6H), 5.79-5.78 (m, 1H), 4.79-4.67 (m, 1H), 4.14 (brs, 1H), 3.98-3.90 (m, 2H), 3.04-3.01 (m, 1H), 2.83-2.61 (m, 5H), 2.38-2.30 (m, 4H), 1.93-1.89 (m, 1H), 1.51 (brs, 1H), 1.18-1.13 (t, J=7.5 Hz, 3H).

Example 207

3-((S)-2-((S)-3-hydroxypyrrolidin-1-yl)-1-(N-methyl-2-(2-oxoindolin-6-yl)acetamido)ethyl)-N,N-dimethylbenzamide

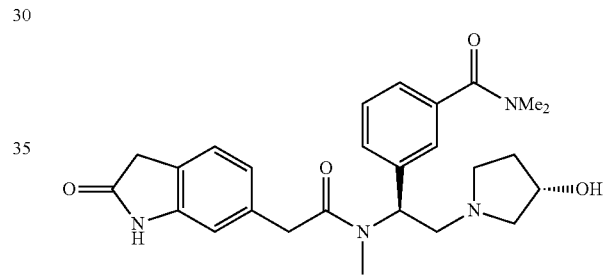

MS (ES, m/z): 465 (M+1); $^1$H-NMR (DMSO-$d_6$, 400 MHz): δ 7.46-7.44 (m, 2H), 7.36-7.31 (m, 2H), 7.21-7.19 (m, 1H), 6.94-6.92 (m, 2H), 6.10-6.08 (m, 1H), 4.39-4.36 (m, 1H), 3.90-3.76 (m, 2H), 3.50-3.48 (m, 1H), 3.33-3.30 (m, 2H), 3.12-3.10 (m, 3H), 3.03-2.90 (m, 5H), 2.84-2.76 (m, 4H), 2.64-2.50 (m, 2H), 2.16-2.13 (m, 1H), 1.73 (m, 1H)

Example 208

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-diethylbenzamide

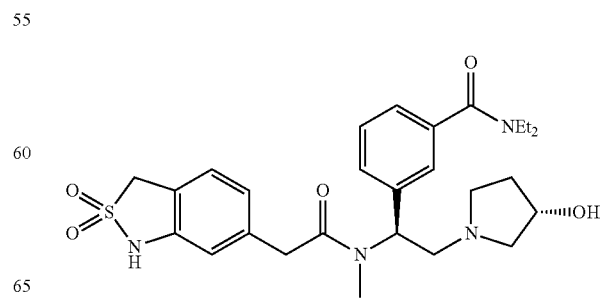

MS (ES, m/z): 529 (M+1); ¹H-NMR (DMSO-d₆, 400 MHz): δ 10.43 (brs, 1H), 7.42-7.33 (m, 2H), 7.25-7.20 (m, 3H), 6.85-6.83 (m, 1H), 6.75 (s, 1H), 5.89-5.85 (m, 1H), 4.48 (s, 2H), 4.19 (brs, 1H), 3.83-3.66 (m, 2H), 3.40 (m, 2H), 3.23-3.13 (m, 3H), 2.86-2.51 (m, 6H), 2.34-2.33 (m, 1H), 2.00-1.95 (m, 1H), 1.54 (brs, 1H), 1.14-1.01 (m, 6H).

Example 209

N,N-diethyl-3-((S)-2-((S)-3-hydroxypyrrolidin-1-yl)-1-(N-methyl-2-(3-oxo-3,4-dihydroquinoxalin-6-yl)acetamido)ethyl)benzamide 2,2,2-trifluoroacetate

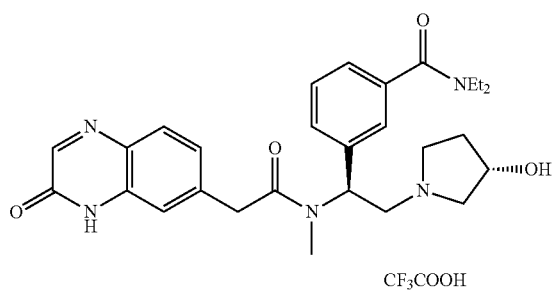

MS (ES, m/z): 620 [M+H—CF₃COOH]+; ¹H-NMR (D₂O, 300 MHz): δ 8.13 (s, 1H), 7.72-7.69 (d, J=8.4 Hz, 1H), 7.44-7.34 (m, 1H), 7.29-7.20 (m, 4H), 6.87 (s, 1H), 6.19-6.15 (m, 1H), 4.78-4.75 (m, 1H), 4.10-3.78 (m, 5H), 3.64-3.19 (m, 4H), 3.01-2.94 (m, 2H), 2.89 (s, 3H), 2.34-1.98 (m, 2H), 1.08-1.03 (t, J=7.2 Hz, 3H), 0.75-0.70 (t, J=7.2 Hz, 3H).

Example 210

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-dimethylbenzamide

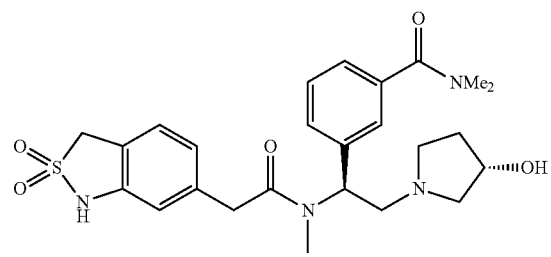 [SMILES: CN(C)C(=O)c1cccc([C@@H](CN2CC[C@H](O)C2)N(C)C(=O)Cc2ccc3c(c2)NS(=O)(=O)C3)c1]

MS (ES, m/z): 501 (M+1); ¹H-NMR (DMSO-d₆, 300 MHz): δ 7.40-7.38 (s, 2H), 7.36-7.34 (s, 2H), 7.20-7.18 (m, 1H), 6.84-6.83 (s, 1H), 6.74 (m, 1H), 5.86 (m, 1H), 4.47 (m, 2H), 4.18 (m, 1H), 3.82 (m, 1H), 3.78-3.67 (s, 1H), 3.08 (s, 1H), 3.05 (s, 3H), 2.98-2.85 (s, 3H), 2.82-2.80 (m, 2H), 2.83 (s, 3H), 2.51 (s, 1H), 2.43-2.36 (s, 2H), 1.92 (s, 1H), 1.42 (s, 1H) 1.12 (s, 1H).

Example 211

3-((S)-2-((S)-3-hydroxypyrrolidin-1-yl)-1-(N-methyl-2-(3-oxo-3,4-dihydroquinoxalin-6-yl)acetamido)ethyl)-N,N-dimethylbenzamide

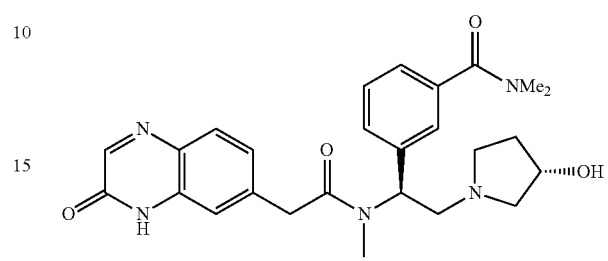

MS (ES, m/z): 478 (M+1); ¹H-NMR (DMSO-d₆, 300 MHz): 12.48-12.27 (m, 1H), 8.13 (s, 1H), 7.76-7.68 (m, 1H), 7.35-7.03 (m, 6H), 5.87 (m, 1H), 4.83-4.68 (m, 1H), 4.15 (s, 1H), 3.88-3.72 (m, 2H), 3.18-2.76 (m, 12H), 2.01-1.88 (m, 1H), 1.53 (s, 1H).

Example 212

N—((S)-1-(3-(1,2,4-oxadiazol-3-yl)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide2,2,2-trifluoroacetate

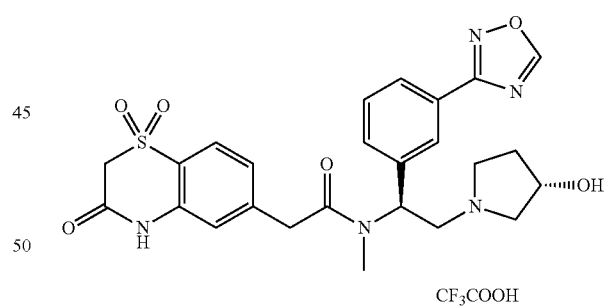

MS (ES, m/z): 526 [M+H—CF3COOH]+; ¹H-NMR (DMSO-d₆, 300 MHz): δ 11.30 (s, 1H), 9.75 (s, 1H), 8.05-8.02 (d, 1H), 7.91 (m, 1H), 7.58 (s, 1H), 7.78-7.77 (m, 1H), 7.75-7.66 (m, 1H), 7.64-7.61 (m, 1H), 7.27-7.21 (m, 1H), 7.17-7.11 (m, 1H), 6.26-6.22 (m, 1H), 5.58-5.48 (m, 1H), 4.72 (s, 2H), 4.51-4.42 (m, 1H), 4.25-4.17 (m, 1H), 3.95-3.82 (m, 5H), 3.70-3.52 (m, 2H), 2.80 (s, 3H), 2.49-2.27 (m, 1H), 2.30-2.26 (m, 2H).

Example 213

N—((S)-2-((S)-3-hydroxypyrrolidin-1-yl)-1-(3-(1-methyl-1H-imidazol-2-yl)phenyl)ethyl)-N-methyl-2-(2-oxoindolin-6-yl)acetamide

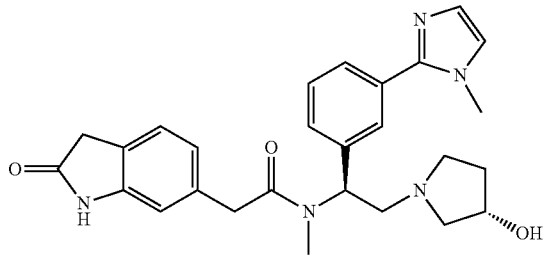 [SMILES: CN(C(=O)Cc1ccc2c(c1)NC(=O)C2)[C@H](CN1CC[C@H](O)C1)c1cccc(-c2nccn2C)c1]

MS (ES, m/z): 474 (M+1); ¹H-NMR (DMSO-d₆, 300 MHz): δ10.415 (1H, s), 7.590-6.760 (9H, m), 5.924 (1H, br), 4.894 (1H, m), 4.199 (1H, m), 3.823 (1H, m), 3.785 (3H, s), 3.703 (1H, m), 3.436-2.520 (11H, m), 1.990 (1H, m), 1.524 (1H, m).

Example 214

N—((S)-1-(3-(5-ethyl-1,2,4-oxadiazol-3-yl)phenyl)-2-((S)-3-hydroxypyrrolidin-1-yl)ethyl)-N-methyl-2-(2-oxoindolin-6-yl)acetamide

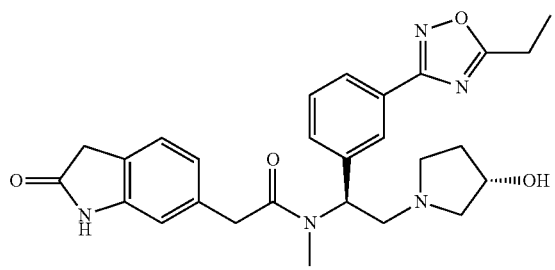 [SMILES: CCc1nc(-c2cccc([C@@H](CN3CC[C@H](O)C3)N(C)C(=O)Cc3ccc4c(c3)NC(=O)C4)c2)no1]

MS (ES, m/z): 490 (M+1); ¹H-NMR (DMSO-d₆, 300 MHz): δ10.41-10.28 (m, 1H), 7.93 (m, 2H), 7.61-7.43 (m, 1H), 7.14 (m, 1H), 608-6.75 (m, 2H), 5.93 (m, 1H), 4.95 (s, 1H), 4.13 (m, 1H), 3.83-3.58 (m, 2H), 3.34 (m, 2H), 3.11-2.92 (m, 3H), 2.83-2.59 (m, 6H), 2.51-2.33 (m, 2H), 1.92 (m, 1H), 1.31 (m, 3H).

Example 215

N—((S)-2-((S)-3-hydroxypyrrolidin-1-yl)-1-(3-(5-methylthiazol-2-yl)phenyl)ethyl)-N-methyl-2-(2-oxoindolin-6-yl)acetamide

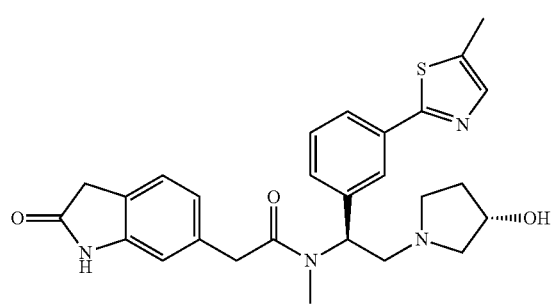 [SMILES: Cc1cnc(-c2cccc([C@@H](CN3CC[C@H](O)C3)N(C)C(=O)Cc3ccc4c(c3)NC(=O)C4)c2)s1]

MS (ES, m/z): 491 (M+1); ¹H-NMR (300 MHz, DMSO-d₆): δ 10.38 (s, 1H), 7.76-7.74 (d, J=8 Hz, 1H), 7.61-7.60 (d, J=4 Hz, 1H), 7.12-7.10 (d, J=8 Hz, 1H), 6.82 (t, J=6 Hz, 2H), 5.93-5.89 (m, 1H), 4.90-4.89 (s, 1H), 4.20 (s, 1H), 3.83-3.67 (m, 1H), 3.43 (s, 2H), 3.34 (s, 3H), 3.13-3.08 (m, 1H), 2.85-2.73 (m, 6H), 2.42-2.40 (m, 1H), 1.53 (m, 1H).

Example 216

N—((S)-2-((S)-3-hydroxypyrrolidin-1-yl)-1-(3-(thiazol-5-yl)phenyl)ethyl)-N-methyl-2-(2-oxoindolin-6-yl)acetamide

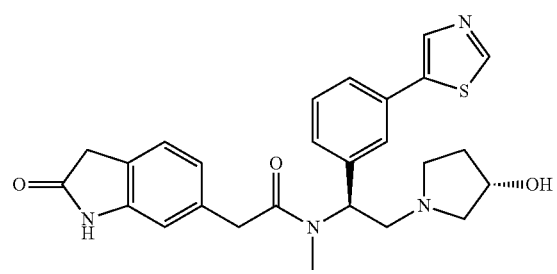 [SMILES: CN(C(=O)Cc1ccc2c(c1)NC(=O)C2)[C@H](CN1CC[C@H](O)C1)c1cccc(-c2cncs2)c1]

MS (ES, m/z): 477 (M+1); ¹H-NMR (300 MHz, DMSO-d₆): δ 10.40-10.30 (m, 1H), 9.08 (s, 1H), 8.23 (s, 1H), 7.63-7.7.55 (m, 1H), 7.48-7.37 (m, 2H), 7.32-7.22 (m, 1H), 7.15-7.05 (m, 1H), 6.86-6.75 (m, 2H), 5.94-5.80 (m, 1H), 4.95-4.85 (m, 1H), 4.25-4.10 (m, 1H), 3.91-3.62 (m, 2H), 3.45-3.40 (m, 2H), 3.18-3.00 (m, 1H), 2.87-2.71 (m, 5H), 2.63-2.59 (m, 1H), 2.46-2.35 (m, 2H), 2.05-1.89 (m, 1H), 1.60-1.45 (m, 1H).

Example 217

N—((S)-2-((S)-3-hydroxypyrrolidin-1-yl)-1-(3-(thiazol-4-yl)phenyl)ethyl)-N-methyl-2-(2-oxoindolin-6-yl)acetamide

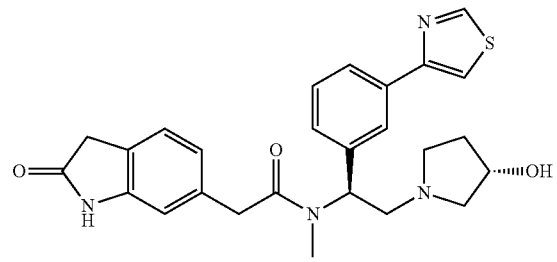 [SMILES: CN(C(=O)Cc1ccc2c(c1)NC(=O)C2)[C@H](CN1CC[C@H](O)C1)c1cccc(-c2cscn2)c1]

MS (ES, m/z): 477 (M+1); ¹H-NMR (300 MHz, DMSO-d₆): δ 10.40-10.30 (m, 1H), 9.20-9.19 (m, 1H), 8.12 (s, 1H), 7.82-7.91 (m, 2H), 7.48-7.37 (m, 1H), 7.28-7.18 (m, 1H), 7.15-7.05 (m, 1H), 6.86-6.75 (m, 2H), 5.97-5.85 (m, 1H), 4.95-4.85 (m, 1H), 4.25-4.10 (m. 1H), 3.91-3.62 (m, 2H), 3.45-3.40 (m, 2H), 3.18-3.00 (m, 1H), 2.87-2.71 (m, 5H), 2.63-2.59 (m, 1H), 2.46-2.35 (m, 2H), 2.05-1.89 (m, 1H), 1.60-1.45 (m, 1H).

Example 218

N—((S)-2-((S)-3-hydroxypyrrolidin-1-yl)-1-(3-(4-methylthiazol-2-yl)phenyl)ethyl)-N-methyl-2-(2-oxoindolin-6-yl)acetamide

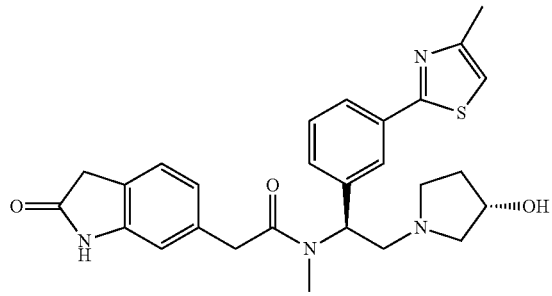 [SMILES: Cc1csc(-c2cccc([C@@H](CN3CC[C@H](O)C3)N(C)C(=O)Cc3ccc4c(c3)NC(=O)C4)c2)n1]

MS (ES, m/z): 491 (M+1); $^1$H-NMR (300 MHz, DMSO-$d_6$): δ 10.36 (m, 1H), 7.82-7.71 (m, 2H), 7.48-7.37 (m, 2H), 7.32 (s, 1H), 7.12-7.08 (m, 1H), 6.84-6.75 (m, 2H), 5.97-5.83 (m, 1H), 4.95-4.85 (m, 1H), 4.25-4.12 (m, 1H), 3.82-3.61 (m, 2H), 3.45-3.40 (m, 2H), 3.30 (s, 3H), 3.18-3.00 (m, 1H), 2.85-2.71 (m, 4H), 2.68-2.63 (m, 1H), 2.42 (s, 3H), 2.05-1.89 (m, 1H), 1.60-1.47 (m, 1H).

Example 219

N—((S)-2-((S)-3-hydroxypyrrolidin-1-yl)-1-(3-(2-methylthiazol-5-yl)phenyl)ethyl)-N-methyl-2-(2-oxoindolin-6-yl)acetamide

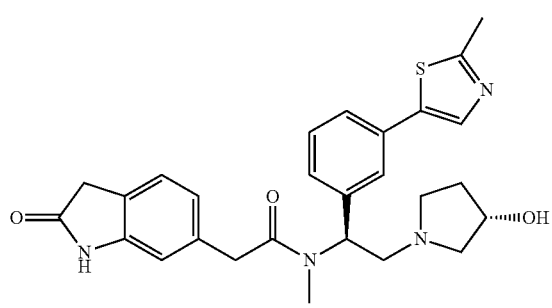 [SMILES: Cc1ncc(-c2cccc([C@@H](CN3CC[C@H](O)C3)N(C)C(=O)Cc3ccc4c(c3)NC(=O)C4)c2)s1]

MS (ES, m/z): 491 (M+1); $^1$H-NMR (400 MHz, DMSO-$d_6$): δ 10.37 (s, 1H), 7.88-7.94 (s, 1H), 7.50-7.51 (d, J=7.6 Hz, 1H), 7.37-7.41 (m, 2H), 7.21-7.27 (m, 1H), 7.07-7.15 (m, 1H), 6.79-6.85 (m, 1H), 5.85-5.89 (m, 1H), 4.88 (s, 1H), 4.20 (s, 1H), 3.68-3.87 (m, 2H), 3.43 (s, 2H), 3.32-3.34 (d, J=8 Hz, 1H), 3.07-3.12 (m, 1H), 2.88-2.90 (m, 2H), 2.74-2.81 (m, 2H), 2.68 (s, 3H), 2.59-2.64 (s, 1H), 2.42-2.51 (m, 2H), 1.96-2.00 (m, 1H), 1.54 (m, 1H).

Example 220

N—((S)-2-((S)-3-hydroxypyrrolidin-1-yl)-1-(3-(2-methylthiazol-4-yl)phenyl)ethyl)-N-methyl-2-(2-oxoindolin-6-yl)acetamide

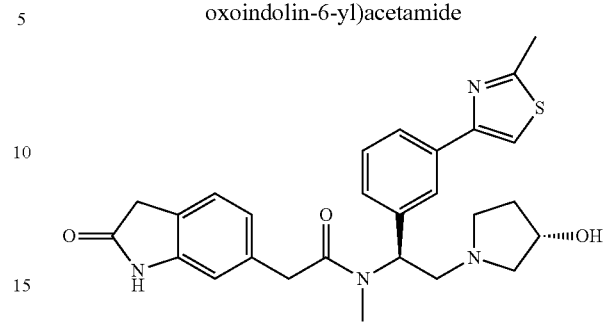

MS (ES, m/z): 491 (M+1); $^1$H-NMR (400 MHz, DMSO-$d_6$): δ 10.36 (m, 1H), 7.86-7.79 (m, 2H), 7.38 (s, 1H), 7.22-7.10 (m, 1H), 6.83-6.75 (m, 2H), 5.93-5.88 (m, 1H), 4.90-4.68 (m, 1H), 4.19 (m, 1H), 3.82-3.77 (m, 1H), 3.67-3.62 (m, 1H), 3.41-3.32 (m, 2H), 3.30-3.14 (m, 1H), 2.94-2.76 (m, 2H), 2.76-2.71 (m, 6H), 2.64 (m, 1H), 2.50-2.41 (m, 1H), 2.00-1.91 (m, 1H), 1.50 (m, 1H).

Example 221

N—((S)-2-((S)-3-hydroxypyrrolidin-1-yl)-1-(3-(5-methyl-1,3,4-thiadiazol-2-yl)phenyl)ethyl)-N-methyl-2-(2-oxoindolin-6-yl)acetamide

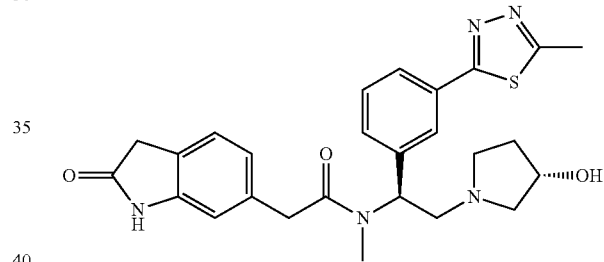

MS (ES, m/z): 492 (M+1); $^1$H-NMR (300 MHz, DMSO-$d_6$): δ 10.37 (brs, 1H), 7.83-7.77 (m, 2H), 7.52-7.46 (m, 2H), 7.13-7.11 (m, 1H), 6.84-6.77 (m, 2H), 5.94-4.71 (m, 1H), 4.25-4.14 (brs, 1H), 3.85-3.68 (m, 3H), 3.60-3.02 (m, 5H), 2.81-2.78 (m, 8H), 2.68-2.34 (m, 1H), 2.28-1.98 (m, 1H), 1.60-1.55 (m, 1H).

Example 222

N—((S)-2-((S)-3-hydroxypyrrolidin-1-yl)-1-(3-(1-methyl-1H-imidazol-5-yl)phenyl)ethyl)-N-methyl-2-(2-oxoindolin-6-yl)acetamide

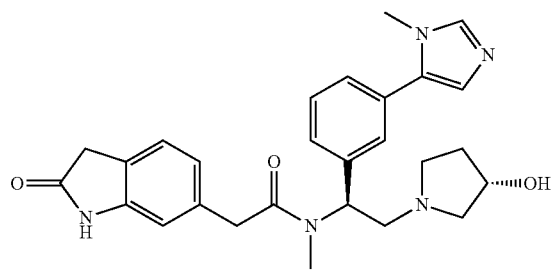 [SMILES: CN(C(=O)Cc1ccc2c(c1)NC(=O)C2)[C@H](CN1CC[C@H](O)C1)c1cccc(-c2cncn2C)c1]

MS (ES, m/z): 514 (M+1); $^1$H-NMR (300 MHz, DMSO-$d_6$): δ 10.41-10.28 (m, 1H), 7.74-7.63 (m, 1H), 7.48-7.31 (m, 2H), 7.31-7.19 (m, 2H), 7.14-7.03 (m, 1H), 7.03-6.91 (m, 1H), 6.88-6.70 (m, 2H), 5.98-5.80 (m, 1H), 4.95-4.85 (m, 1H), 4.25-4.08 (m, 1H), 3.89-3.58 (m, 5H), 3.46-3.37 (m, 2H), 3.16-2.97 (m, 1H), 2.90-2.80 (m, 2H), 2.79-2.72 (m, 3H), 2.62 (m, 1H), 2.46-1.31 (m, 2H), 2.03-1.88 (m, 1H), 1.62-1.49 (m, 1H).

Example 223

N—((S)-1-(3-(1,3,4-oxadiazol-2-yl)phenyl)-2-((S)-3-hydroxypyrrolidin-1-yl)ethyl)-N-methyl-2-(2-oxoindolin-6-yl)acetamide

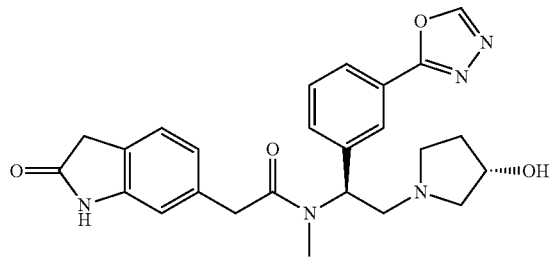 [SMILES: CN(C(=O)Cc1ccc2c(c1)NC(=O)C2)[C@H](CN1CC[C@H](O)C1)c1cccc(-c2nnco2)c1]

MS (ES, m/z): 462 (M+1); $^1$H-NMR (300 MHz, DMSO-$d_6$): δ 10.36 (s, 1H), 9.34 (s, 1H), 7.95-7.89 (m, 2H), 7.72-7.45 (m, 2H), 7.12-7.10 (d, J=7.5 Hz, 1H), 6.88-6.68 (m, 2H), 5.96-5.90 (m, 1H), 4.91-4.89 (d, J=3.9 Hz, 1H), 4.19 (brs, 1H), 3.84-3.65 (m, 2H), 3.42 (s, 2H), 3.18-3.03 (m, 1H), 2.89-2.74 (m, 6H), 2.51-2.40 (m, 2H), 1.98-1.93 (m, 1H), 1.53 (m, 1H).

Example 224

N—((S)-2-((S)-3-hydroxypyrrolidin-1-yl)-1-(3-(5-methyl-1,3,4-oxadiazol-2-yl)phenyl)ethyl)-N-methyl-2-(2-oxoindolin-6-yl)acetamide

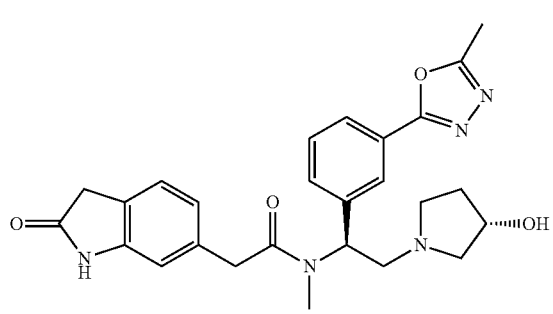 [SMILES: Cc1nnc(-c2cccc([C@@H](CN3CC[C@H](O)C3)N(C)C(=O)Cc3ccc4c(c3)NC(=O)C4)c2)o1]

MS (ES, m/z): 476 (M+1); $^1$H-NMR (300 MHz, DMSO-$d_6$): δ 10.36 (s, 1H), 7.90-7.84 (m, 2H), 7.72-7.40 (m, 2H), 7.12-7.07 (m, 1H), 6.83-6.70 (m, 2H), 5.96-5.90 (m, 1H), 4.91-4.89 (d, J=3.9 Hz, 1H), 4.19 (brs, 1H), 3.84-3.60 (m, 2H), 3.42 (s, 2H), 3.18-3.09 (m, 1H), 2.89-2.73 (m, 6H), 2.64 (s, 3H), 2.51-2.40 (m, 2H), 1.98-1.91 (m, 1H), 1.53 (m, 1H).

Example 225

N—((S)-2-((S)-3-hydroxypyrrolidin-1-yl)-1-(3-(1-methyl-1H-imidazol-4-yl)phenyl)ethyl)-N-methyl-2-(2-oxoindolin-6-yl)acetamide

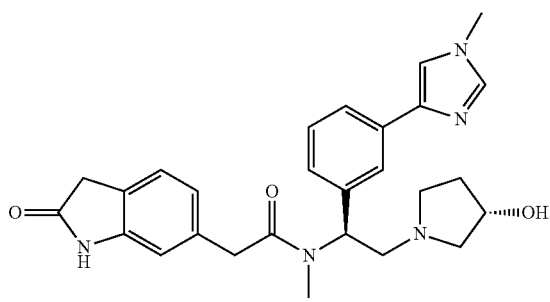 [SMILES: CN(C(=O)Cc1ccc2c(c1)NC(=O)C2)[C@H](CN1CC[C@H](O)C1)c1cccc(-c2cn(C)cn2)c1]

MS (ES, m/z): 474 (M+1); $^1$H-NMR (400 MHz, DMSO-$d_6$): δ 10.35-10.37 (s, 1H), 7.48-7.63 (m, 4H), 7.29-7.32 (t, 1H; J=15.6 HZ), 7.02-7.12 (m, 2H), 6.78-6.83 (m, 2H), 5.92-5.93 (s, 1H), 4.97 (s, 1H), 3.79-3.83 (m, 1H), 3.69-3.80 (m, 2H), 3.61-3.65 (m, 4H), 3.51 (m, 2H), 3.42 (s, 1H), 2.82-2.98 (m, 3H), 2.65-2.77 (m, 3H), 2.68 (s, 2H), 1.98-2.00 (m, 1H), 1.55 (m, 1H).

Example 226

N—((S)-1-(3-(1-(cyclopropylmethyl)-1H-imidazol-2-yl)phenyl)-2-((S)-3-hydroxy pyrrolidin-1-yl)ethyl)-N-methyl-2-(2-oxoindolin-6-yl)acetamide

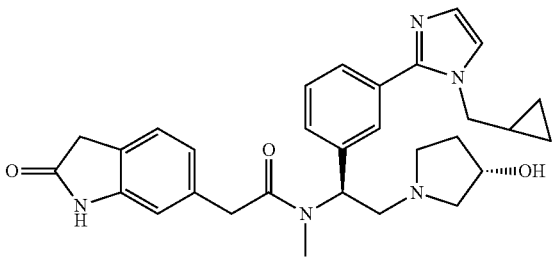 [SMILES: CN(C(=O)Cc1ccc2c(c1)NC(=O)C2)[C@H](CN1CC[C@H](O)C1)c1cccc(-c2nccn2CC2CC2)c1]

MS (ES, m/z): 514 (M+1); $^1$H-NMR (300 MHz, DMSO-$d_6$): δ 10.41 (s, 1H), 7.55-7.41 (m, 3H), 7.40-7.25 (m, 2H), 7.15-7.05 (m, 1H), 6.99 (m, 1H), 6.83-6.73 (m, 2H), 5.95-5.85 (m, 1H), 4.95-4.85 (m, 1H), 4.25-4.08 (m, 1H), 3.90-3.60 (m, 4H), 3.41 (s, 2H), 3.13-3.01 (m, 1H), 2.87-2.75 (m, 2H), 2.72 (s, 3H), 2.63 (m, 1H), 2.45-2.35 (m, 2H), 2.07-1.85 (m, 1H), 1.60-1.42 (m, 1H), 1.12-1.00 (m, 1H), 0.50-0.40 (m, 2H), 0.30-0.15 (m, 2H).

Example 227

N—((S)-2-((S)-3-hydroxypyrrolidin-1-yl)-1-(3-(3-methyl-1,2,4-oxadiazol-5-yl)phenyl)ethyl)-N-methyl-2-(2-oxoindolin-6-yl)acetamide

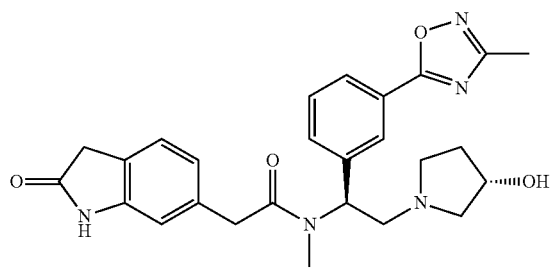 [SMILES: Cc1noc(-c2cccc([C@@H](CN3CC[C@H](O)C3)N(C)C(=O)Cc3ccc4c(c3)NC(=O)C4)c2)n1]

MS (ES, m/z): 476 (M+1); $^1$H-NMR (300 MHz, DMSO-$d_6$): δ 10.35 (s, 1H), 7.98-7.94 (m, 2H), 7.61 (m, 2H), 7.12-7.09 (m, 1H), 6.83-6.81 (m, 2H), 5.92 (m, 1H), 4.85 (s, 1H), 4.17 (brs, 1H), 3.84-3.70 (m, 2H), 3.42 (s, 2H), 3.12-3.05 (m, 1H), 2.81-2.63 (m, 6H), 2.49-2.42 (m, 5H), 1.99-1.931 (m, 1H), 1.52 (m, 1H).

Example 228

3-((S)-2-((S)-3-hydroxypyrrolidin-1-yl)-1-(N-methyl-2-(2-oxo-2,3-dihydrobenzo[d]thiazol-5-yl)acetamido)ethyl)-N-(2,2,2-trifluoroethyl)benzamide

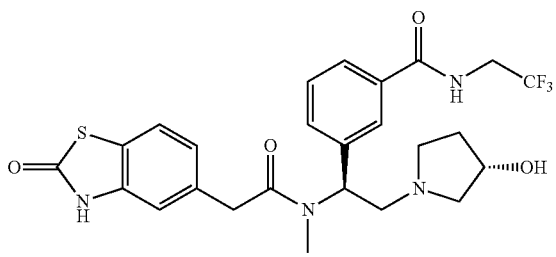 [SMILES: CN(C(=O)Cc1ccc2sc(=O)[nH]c2c1)[C@H](CN1CC[C@H](O)C1)c1cccc(C(=O)NCC(F)(F)F)c1]

MS (ES, m/z): 537 (M+1); $^1$H-NMR (400 MHz, DMSO-$d_6$): δ 11.82 (s, 1H), 9.13-9.10 (m, 1H), 7.81-7.79 (m, 2H), 7.48-7.45 (m, 3H), 7.08 (s, 1H), 7.04-7.01 (m, 1H), 5.92-5.88 (m, 1H), 5.20 (m, 1H), 4.68 (m, 1H), 4.18-4.05 (m, 3H), 3.92-3.88 (m, 1H), 3.86-3.70 (m, 1H), 3.15-3.09 (m, 1H), 2.84-2.80 (m, 2H), 2.76 (s, 2H), 2.74-2.63 (m, 1H), 2.43-2.33 (m, 2H), 1.98-1.93 (m, 1H), 1.52-1.51 (m, 1H).

Example 229

In Vitro Assay to Evaluate Potency of KOR Agonists of Formula (I) Using IP-One Assay The potency of the test compounds to the human KOR receptor was determined by performing dose-response experiments in COS-7 cells transiently transfected with the human KOR receptor cDNA using IP-One HTRF assay.

IP-One assay: One day following transfection cells were seeded in ½-area 96 well plates (Corning Costar, #675083) with 40,000 cells/well in DMEM medium supplemented with 10% fetal calf serum, 2 mM glutamine and 0.01 mg/ml gentamicin. The following day, media was aspirated and 50 μl Stimulation buffer (10 mM HEPES, 1 mM $CaCl_2$, 0.5 mM $MgCl_2$, 4.2 mM KCl, 146 mM NaCl, 5.5 mM glucose, 50 mM LiCl, 0.1% BSA, pH 7.4) were added to each well. Test compounds were dissolved in DMSO in various concentrations and 1 μl was added to each well to stimulate cells. Following an incubation of about 60 minutes at 37° C., 10 μL IP1-d2 (Cisbio) and 10 μl anti IP1-Cryptate (Cisbio) were added to each well. Plates were incubated at about 20-35° C. for a minimum of 60 minutes and counted on HTRF compatible Alpha-Fusion (Packard). Determinations were made in duplicates. EC50 values were calculated using AssayExplorer 3.2 (Symyx), a standard pharmacological data handling software. Using this protocol, various compounds as described in Table 4 defined above were found to exhibit KOR agonistic activity.

Using this protocol, various compounds as described herein were found to exhibit binding affinity towards KOR. For instance, examples 2, 5, 6, 7, 12, 15, 16, 18, 19, 20, 22, 23, 24, 25, 26, 29, 31, 32, 33, 34, 35, 37, 38, 39, 40, 41, 42, 43, 45, 46, 52, 53, 59, 55, 56, 57, 58, 62, 63, 64, 66, 67, 68, 69, 70, 71, 72, 73, 74, 75, 76, 77, 78, 79, 80, 82, 83, 84, 85, 86, 87, 88, 91, 92, 93, 94, 95, 96, 97, 98, 99, 100, 101, 102, 103, 104, 105, 106, 107, 108, 109, 110, 111, 113, 114, 115, 116, 117, 118, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 157, 158, 159, 160, 161, 162, 163, 164, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 198, 199, 200, 201, 203, 204, 205, 206, 207, 208, 209, 210, 211, 212, 213, 214, 215, 216, 217, 218, 219, 220, 221, 222, 223, 224, 225, 226, 227, and 228 as described herein, exhibited a KOR agonistic binding in-vitro $EC_{50}$ values of less than or equal to 50 nM; examples 1, 4, 21, 27, 36, 44, 48, 50, 61, 90, 112, 138, 197 and 202 as described herein exhibited a KOR agonistic binding in-vitro $EC_{50}$ values between 51-100 nM; examples 3, 9, 10, 17, 28, 47, 51, 89, 165 and 192 as described herein exhibited a KOR agonistic binding in-vitro EC50 values between 101 nM–1 μM; and examples 8, 11, 13, 14, 30 and 49 as described herein exhibited a KOR agonistic binding in-vitro $EC_{50}$ values greater than or equal to 1 μM.

Although the present application has been illustrated by certain of the preceding examples, it is not to be construed as being limited thereby; but rather, the present application encompasses the generic area as hereinbefore disclosed. Various modifications and embodiments can be made without departing from the spirit and scope thereof. For example, the following compounds are also included in the scope of the present application.

What is claimed is:
1. A method of alleviating pain or gastrointestinal dysfunction in a patient comprising administering to the patient a therapeutically effective amount of a compound selected from the group consisting of:
   N—((S)-2-((S)-3-hydroxypyrrolidin-1-yl)-1-phenylethyl)-N-methyl-2-(2-oxoindolin-6-yl)acetamide;
   N-[(1S)-2-[(3S)-3-hydroxypyrrolidin-1-yl]-1-phenylethyl]-2-(3-oxo-3,4-dihydro-2H-1,4-benzoxazin-6-yl)acetamide;
   N—((S)-2-((S)-3-hydroxypyrrolidin-1-yl)-1-phenylethyl)-N-methyl-2-(3-oxo-3,4-dihydroquinoxalin-6-yl)acetamide;
   (S)-2-(2-oxo-2,3-dihydrobenzo[d]thiazol-5-yl)-N-(1-phenyl-2-(pyrrolidin-1-yl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

N—((S)-1-(3-cyanophenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

N—((S)-2-((S)-3-hydroxypyrrolidin-1-yl)-1-phenylethyl)-N-methyl-2-(3-oxo-3,4-dihydro-2H-benzo[b][1,4]thiazin-6-yl)acetamide;

2-(1,1-dioxido-3-oxo-2,3-dihydrobenzo[d]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(trifluoromethyl)phenyl)ethyl)-N-methylacetamide;

5-(2-(((S)-2-((S)-3-hydroxypyrrolidin-1-yl)-1-phenylethyl)(methyl)amino)-2-oxoethyl)-1,3-dihydrobenzo[c]isothiazol-1-ium 2,2-dioxide 2,2,2-trifluoroacetate;

N—((S)-1-(3-(difluoromethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(3,3-difluoro-2-oxoindolin-6-yl)-N—((S)-2-((S)-3-hydroxypyrrolidin-1-yl)-1-phenylethyl)-N-methylacetamide;

2-(3,3-difluoro-2-oxoindolin-6-yl)-N—((S)-2-((S)-3-hydroxypyrrolidin-1-yl)-1-phenylethyl)acetamide;

2-(1,1-dioxido-3-oxo-3,4-dihydro-2H-benzo[b][1,4]thiazin-6-yl)-N-ethyl-N—((S)-2-((S)-3-hydroxypyrrolidin-1-yl)-1-(3-(trifluoromethoxy)phenyl) ethyl)acetamide;

2-(1,1-dioxido-3-oxo-3,4-dihydro-2H-benzo[b][1,4]thiazin-6-yl)-N—((S)-2-((S)-3-methoxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-(2,2,2-trifluoroethyl)acetamide 2,2,2-trifluoroacetate;

2-(1,1-dioxido-3-oxo-3,4-dihydro-2H-benzo[b][1,4]thiazin-6-yl)-N-(2-((S)-3-hydroxypyrrolidin-1-yl)-1-(tetrahydro-2H-pyran-4-yl)ethyl)-N-methylacetamide-2,2,2-trifluoroacetate;

3-((S)-2-((S)-3-hydroxypyrrolidin-1-yl)-1-(N-methyl-2-(2-oxo-2,3-dihydrobenzo[d]thiazol-5-yl)acetamido)ethyl)benzoic acid;

3-((S)-2-((S)-3-hydroxypyrrolidin-1-yl)-1-(N-methyl-2-(2-oxo-2,3-dihydrobenzo[d]thiazol-5-yl)acetamido)ethyl)benzamide;

(S)-2-(3-benzyl-2-oxo-2,3-dihydrobenzo[d]oxazol-5-yl)-N-(1-(3-hydroxyphenyl)-2-(pyrrolidin-1-yl)ethyl)acetamide;

N—((S)-1-(3-(1H-tetrazol-5-yl)phenyl)-2-((S)-3-hydroxypyrrolidin-1-yl)ethyl)-N-methyl-2-(1-methyl-2,2-dioxido-1,3-dihydrobenzo[c]isothiazol-6-yl)acetamide;

2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetic acid;

3-((S)-2-((S)-3-hydroxypyrrolidin-1-yl)-1-(N-methyl-2-(2-oxoindolin-6-yl)acetamido)ethyl) benzoic acid;

3-((S)-2-((S)-3-hydroxypyrrolidin-1-yl)-1-(N-methyl-2-(2-oxoindolin-6-yl)acetamido)ethyl) benzamide;

N—((S)-1-(3-cyanophenyl)-2-((S)-3-fluoropyrrolidin-1-yl)ethyl)-N-methyl-2-(2-oxoindolin-6-yl)acetamide;

N—((S)-1-(3-(2-amino-2-oxoethoxy)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(2-(methylsulfonamido)-2-oxoethoxy)phenyl)ethyl)-N-methyl-2-(2-oxoindolin-6-yl)acetamide;

3-((S)-2-((S)-3-fluoropyrrolidin-1-yl)-1-(N-methyl-2-(2-oxoindolin-6-yl)acetamido)ethyl) benzoic acid;

2-(3-((S)-2-((S)-3-fluoropyrrolidin-1-yl)-1-(N-methyl-2-(2-oxoindolin-6-yl)acetamido)ethyl) phenoxy)acetic acid;

N—((S)-1-(3-(2-amino-2-oxoethoxy)phenyl)-2-((S)-3-fluoropyrrolidin-1-yl)ethyl)-N-methyl-2-(2-oxoindolin-6-yl)acetamide;

3-((S)-2-((S)-3-hydroxypyrrolidin-1-yl)-1-(N-methyl-2-(3-oxo-3,4-dihydroquinoxalin-6-yl)acetamido)ethyl) benzoic acid;

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzamide;

N—((S)-1-(3-ethynylphenyl)-2-((S)-3-hydroxypyrrolidin-1-yl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(5-(trifluoromethyl)-1,2,4-oxadiazol-3-yl)phenyl) ethyl)-N-methyl-2-(3-oxo-3,4-dihydroquinoxalin-6-yl)acetamide;

N—((S)-2-((S)-3-hydroxypyrrolidin-1-yl)-1-(3-(5-methyl-1,2,4-oxadiazol-3-yl)phenyl)ethyl)-N-methyl-2-(2-oxoindolin-6-yl)acetamide;

N—((S)-2-((S)-3-hydroxypyrrolidin-1-yl)-1-(3-(thiazol-2-yl)phenyl)ethyl)-N-methyl-2-(2-oxoindolin-6-yl)acetamide;

N—((S)-1-(3-(but-1-yn-1-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

3-((S)-2-((S)-3-hydroxypyrrolidin-1-yl)-1-(N-methyl-2-(2-oxoindolin-6-yl)acetamido)ethyl)-N-(2,2,2-trifluoroethyl)benzamide;

N,N-diethyl-3-((S)-2-((S)-3-hydroxypyrrolidin-1-yl)-1-(N-methyl-2-(2-oxoindolin-6-yl)acetamido)ethyl)benzamide;

3-((S)-2-((S)-3-hydroxypyrrolidin-1-yl)-1-(N-methyl-2-(2-oxo-2,3-dihydrobenzo[d]thiazol-5-yl)acetamido) ethyl)-N,N-dimethylbenzamide 2,2,2-trifluoroacetate;

N—((S)-1-(3-(2-(diethylamino)-2-oxoethoxy)phenyl)-2-((S)-3-hydroxypyrrolidin-1-yl)ethyl)-N-methyl-2-(2-oxoindolin-6-yl)acetamide;

N—((S)-1-(3-(2-(diethylamino)-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-fluoro-5-(thiazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(2-methyl-2H-tetrazol-5-yl)phenyl)ethyl)-N-methyl-2-(2-oxoindolin-6-yl)acetamide;

N—((S)-2-((S)-3-hydroxypyrrolidin-1-yl)-1-phenylethyl)-2-(3-methyl-2-oxo-2,3-dihydrobenzo[d]oxazol-5-yl)acetamide;

(S)-2-(3-(3-cyanobenzyl)-2-oxo-2,3-dihydrobenzo[d]oxazol-5-yl)-N-(1-phenyl-2-(pyrrolidin-1-yl)ethyl)acetamide;

(S)—N-methyl-2-(2-oxo-1,2-dihydroquinolin-6-yl)-N-(1-phenyl-2-(pyrrolidin-1-yl)ethyl)acetamide;

N—((S)-2-((S)-3-hydroxypyrrolidin-1-yl)-1-phenyl-ethyl)-N-methyl-2-(2-oxo-1,2-dihydroquinolin-6-yl)acetamide;

(S)—N-methyl-2-(2-oxo-1,2-dihydroquinolin-7-yl)-N-(1-phenyl-2-(pyrrolidin-1-yl)ethyl)acetamide;

(S)—N-methyl-2-(3-methyl-2,2-dioxido-1,3-dihydrobenzo[c]isothiazol-5-yl)-N-(1-phenyl-2-(pyrrolidin-1-yl)ethyl)acetamide;

N—((S)-2-((R)-3-hydroxypyrrolidin-1-yl)-1-phenyl-ethyl)-2-(2-oxo-1,2-dihydroquinolin-6-yl)acetamide;

N—((S)-2-((S)-3-hydroxypyrrolidin-1-yl)-1-phenyl-ethyl)-N-methyl-2-(2-oxo-1,2-dihydroquinolin-7-yl)acetamide;

N—((S)-2-((S)-3-hydroxypyrrolidin-1-yl)-1-phenyl-ethyl)-N-2-dimethyl-2-(2-oxo-2,3-dihydrobenzo[d]oxazol-5-yl)propanamide;

N—((S)-2-((S)-3-hydroxypyrrolidin-1-yl)-1-phenyl-ethyl)-2-(2-oxo-1,2-dihydroquinolin-7-yl)acetamide;

N—((S)-2-((S)-3-hydroxypyrrolidin-1-yl)-1-phenyl-ethyl)-2-methyl-2-(2-oxo-2,3-dihydrobenzo[d]oxazol-5-yl)propanamide;

(S)-2-(2-oxo-2,3-dihydrobenzo[d]oxazol-5-yl)-N-(1-phenyl-2-(pyrrolidin-1-yl)ethyl) acetamide;

N—((S)-2-((S)-3-hydroxypyrrolidin-1-yl)-1-phenyl-ethyl)-2-(2-oxo-2,3-dihydrobenzo[d]oxazol-5-yl)acetamide;

(S)-2-(3-benzyl-2-oxo-2,3-dihydrobenzo[d]oxazol-5-yl)-N-(1-(3-(4-methoxybenzyloxy)phenyl)-2-(pyrrolidin-1-yl)ethyl)acetamide;

2-(3-(4-cyanobenzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-2-((S)-3-hydroxypyrrolidin-1-yl)-1-phenyl-ethyl)-2-(2-oxoindolin-6-yl)acetamide;

(S)-2-(3-methyl-2-oxo-2,3-dihydrobenzo[d]oxazol-5-yl)-N-(1-phenyl-2-(pyrrolidin-1-yl)ethyl)acetamide;

N-(1-(1-benzyl-1H-pyrazol-4-yl)-2-(pyrrolidin-1-yl)ethyl)-2-(2-oxo-2,3-dihydrobenzo[d]oxazol-5-yl)acetamide;

(S)-t-butyl-2-(3-(1-(2-(3-benzyl-2-oxo-2,3-dihydrobenzo[d]oxazol-5-yl)acetamido)-2-(pyrrolidin-1-yl)ethyl)phenoxy)acetate;

(S)-2-(3-benzyl-2-oxo-2,3-dihydrobenzo[d]oxazol-5-yl)-N-(1-(3-(benzyloxy)phenyl)-2-(pyrrolidin-1-yl)ethyl)-N-methylacetamide;

N—((S)-1-cyclohexyl-2-((S)-3-hydroxypyrrolidin-1-yl)ethyl)-N-methyl-2-(2-oxoindolin-6-yl)acetamide;

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide;

N—((S)-1-cyclohexyl-2-((S)-3-hydroxypyrrolidin-1-yl)ethyl)-2-(2-oxo-2,3-dihydrobenzo[d]oxazol-5-yl)acetamide;

(S)-tert-butyl-2-(3-(1-(2-(3-benzyl-2-oxo-2,3-dihydrobenzo[d]oxazol-5-yl)-N-methyl acetamido)-2-(pyrrolidin-1-yl)ethyl)phenoxy)acetate;

N—((S)-1-cyclohexyl-2-((S)-3-hydroxypyrrolidin-1-yl)ethyl)-2-(2-oxoindolin-6-yl)acetamide;

N—((S)-1-cyclohexyl-2-((S)-3-hydroxypyrrolidin-1-yl)ethyl)-N-methyl-2-(2-oxo-2,3-dihydrobenzo[d]oxazol-5-yl)acetamide;

(S)—N-(1-(3-cyanophenyl)-2-(pyrrolidin-1-yl)ethyl)-N-methyl-2-(2-oxo-2,3-dihydrobenzo[d]oxazol-5-yl)acetamide;

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

(S)-tert-butyl 2-(3-(2-(3-hydroxypyrrolidin-1-yl)-1-(2-(2-oxo-2,3-dihydro benzo[d]oxazol-5-yl)acetamido)ethyl)phenoxy)acetate;

2-(3-(4-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide;

N-(1-(3-(cyanomethoxy)phenyl)-2-(3-hydroxypyrrolidin-1-yl)ethyl)-N-methyl-2-(2-oxo-2,3-dihydrobenzo[d]oxazol-5-yl)acetamide;

tert-butyl 2-(3-((S)-2-((R)-3-hydroxypyrrolidin-1-yl)-1-(N-methyl-2-(2-oxo-2,3-dihydrobenzo[d]oxazol-5-yl)acetamido)ethyl)phenoxy)acetate;

N—((S)-1-(3-cyanophenyl)-2-((S)-3-hydroxypyrrolidin-1-yl)ethyl)-N-methyl-2-(3-methyl-2-oxo-2,3-dihydrobenzo[d]oxazol-5-yl)acetamide;

N—((S)-1-(3-(1H-tetrazol-5-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(3-((S)-2-((S)-3-hydroxypyrrolidin-1-yl)-1-(N-methyl-2-(1-methyl-2,2-dioxido-1,3-dihydrobenzo[c]isothiazol-6-yl)acetamido)ethyl)phenoxy) acetic acid;

(S)-methyl 3-((2-oxo-5-(2-oxo-2-(1-phenyl-2-(pyrrolidin-1-yl)ethylamino)ethyl)benzo[d]oxazol-3 (2H)-yl)methyl)benzoate;

(S)-tert-butyl 2-(2-oxo-5-(2-oxo-2-(1-phenyl-2-(pyrrolidin-1-yl)ethylamino) ethyl)benzo[d]oxazol-3 (2H)-yl)acetate;

(S)-2-(2-oxo-5-(2-oxo-2-(1-phenyl-2-(pyrrolidin-1-yl)ethylamino)ethyl)benzo[d]oxazol-3(2H)-yl)acetic acid hydrochloride;

(S)—N-(1-(3-hydroxyphenyl)-2-(pyrrolidin-1-yl)ethyl)-2-(2-oxo-2,3-dihydrobenzo[d]oxazol-5-yl)acetamide;

(S)-2-(3-(1-(2-(2-oxo-2,3-dihydrobenzo[d]oxazol-5-yl)acetamido)-2-(pyrrolidin-1-yl)ethyl)phenoxy)acetic acid hydrochloride;

2-(5-(2-((S)-2-((S)-3-hydroxypyrrolidin-1-yl)-1-phenylethyl)(methyl)amino)-2-oxoethyl)-2-oxobenzo[d]oxazol-3(2H)-yl)acetic acid;

2-(3-(1-(N-methyl-2-(2-oxoindolin-6-yl)acetamido)-2-(pyrrolidin-1-yl)ethyl)phenoxy)acetic acid hydrochloride;

3-((5-(2-((S)-2-((S)-3-hydroxypyrrolidin-1-yl)-1-phenylethyl)(methyl)amino)-2-oxoethyl)-2-oxobenzo[d]oxazol-3(2H)-yl)methyl)benzamide;

(S)-2-(3-benzyl-2-oxo-2,3-dihydrobenzo[d]oxazol-5-yl)-N-(1-(3-hydroxyphenyl)-2-(pyrrolidin-1-yl)ethyl)-N-methylacetamide;

(R)-2-(3-(1-(N-methyl-2-(2-oxo-2,3-dihydrobenzo[d]oxazol-5-yl)acetamido)-2-(pyrrolidin-1-yl)ethyl)phenoxy)acetic acid;

(S)-3-((2-oxo-5-(2-oxo-2-(1-phenyl-2-(pyrrolidin-1-yl)ethylamino)ethyl)benzo[d]oxazol-3(2H)-yl)methyl)benzamide;

2-(3-(1-(2-(2-oxoindolin-6-yl)acetamido)-2-(pyrrolidin-1-yl)ethyl)phenoxy)acetic acid;

(S)—N-(1-(3-(2H-tetrazol-5-yl)phenyl)-2-(pyrrolidin-1-yl)ethyl)-N-methyl-2-(2-oxo-2,3-dihydrobenzo[d]oxazol-5-yl)acetamide;

(S)-2-(3-(2-(3-hydroxypyrrolidin-1-yl)-1-(N-methyl-2-(2-oxo-2,3-dihydrobenzo[d]oxazol-5-yl)acetamido) ethyl)phenoxy)acetic acid triflouro acetate;

(S)-2-(3-(2-(3-hydroxypyrrolidin-1-yl)-1-(N-methyl-2-(2-oxoindolin-6-yl) acetamido) ethyl) phenoxy) acetic acid hydrochloride;

2-(3-((S)-2-((R)-3-hydroxypyrrolidin-1-yl)-1-(N-methyl-2-(2-oxo-2,3-dihydrobenzo[d]oxazol-5-yl)acetamido)ethyl)phenoxy)acetic acid;

2-(5-(2-((S)-1-cyclohexyl-2-((S)-3-hydroxypyrrolidin-1-yl)ethyl)(methyl)amino)-2-oxoethyl)-2-oxobenzo[d]oxazol-3(2H)-yl)acetic acid;

Methyl 4-((5-(2-(((S)-2-(((S)-3-hydroxypyrrolidin-1-yl)-1-phenylethyl)(methyl)amino)-2-oxoethyl)-2-oxobenzo[d]oxazol-3(2H)-yl)methyl)benzoate;

N—((S)-1-(3-(2H-tetrazol-5-yl)phenyl)-2-((S)-3-hydroxypyrrolidin-1-yl)ethyl)-N-methyl-2-(2-oxo-2,3-dihydrobenzo[d]oxazol-5-yl)acetamide;

(S)-2-(3-(2-(3-hydroxypyrrolidin-1-yl)-1-(2-(2-oxoindolin-6-yl)acetamido)ethyl)phenoxy)acetic acid hydrochloride;

(S)-2-(3-(2-(3-hydroxypyrrolidin-1-yl)-1-(2-(2-oxo-2,3-dihydrobenzo[d]oxazol-5-yl)acetamido)ethyl)phenoxy)acetic acid;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

(R)—N-(1-(3-((2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-1-(3-(2H-tetrazol-5-yl)phenyl)-2-((S)-3-hydroxypyrrolidin-1-yl)ethyl)-N-methyl-2-(3-methyl-2-oxo-2,3-dihydrobenzo[d]oxazol-5-yl)acetamide;

N—((S)-1-(3-cyanophenyl)-2-((S)-3-fluoropyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-fluoropyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-hydroxypyrrolidin-1-yl)ethyl)-N-methyl-2-(2-oxoindolin-6-yl)acetamide;

N—((S)-1-(3-(2H-tetrazol-5-yl)phenyl)-2-((S)-3-hydroxypyrrolidin-1-yl)ethyl)-N-methyl-2-(1-methyl-2-oxoindolin-6-yl)acetamide;

N—((S)-1-(3-((2H-tetrazol-5-yl)methoxy)phenyl)-2-((S)-3-hydroxypyrrolidin-1-yl)ethyl)-N-methyl-2-(2-oxoindolin-6-yl)acetamide;

N—((S)-1-(3-(2H-tetrazol-5-yl)phenyl)-2-((S)-3-fluoropyrrolidin-1-yl)ethyl)-N-methyl-2-(2-oxoindolin-6-yl)acetamide;

(S)-2-(3-oxo-3,4-dihydro-2H-benzo[b][1,4]oxazin-6-yl)-N-(1-phenyl-2-(pyrrolidin-1-yl)ethyl)acetamide;

(S)—N-methyl-2-(2-oxo-2,3-dihydrobenzo[d]thiazol-5-yl)-N-(1-phenyl-2-(pyrrolidin-1-yl)ethyl)acetamide;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

N—((S)-2-((S)-3-hydroxypyrrolidin-1-yl)-1-phenylethyl)-N-methyl-2-(2-oxo-2,3-dihydrobenzo[d]thiazol-5-yl)acetamide;

N—((S)-2-((S)-3-hydroxypyrrolidin-1-yl)-1-phenylethyl)-2-(2-thioxo-2,3-dihydrobenzo[d]thiazol-5-yl)acetamide;

N—((S)-2-((S)-3-hydroxypyrrolidin-1-yl)-1-phenylethyl)-N-methyl-2-(2-thioxo-2,3-dihydrobenzo[d]thiazol-5-yl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)-N-methylacetamide;

(S)-2-(1,1-dioxido-3-oxo-3,4-dihydro-2H-benzo[b][1,4]thiazin-6-yl)-N-(1-phenyl-2-(pyrrolidin-1-yl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethyl)phenyl)ethyl)-N-methylacetamide;

2-(1,1-dioxido-3-oxo-3,4-dihydro-2H-benzo[b][1,4]thiazin-6-yl)-N—((S)-1-(3-fluorophenyl)-2-((S)-3-hydroxypyrrolidin-1-yl)ethyl)-N-methylacetamide;

N—((S)-1-cyclohexyl-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-methoxyphenyl)ethyl)-N-methylacetamide;

(S)-2-(3-oxo-3,4-dihydro-2H-benzo[b][1,4]thiazin-6-yl)-N-(1-phenyl-2-(pyrrolidin-1-yl)ethyl)acetamide;

N—((S)-2-((S)-3-hydroxypyrrolidin-1-yl)-1-phenylethyl)-2-(3-oxo-3,4-dihydro-2H-benzo[b][1,4]thiazin-6-yl)acetamide;

(S)—N-methyl-2-(3-oxo-3,4-dihydro-2H-benzo[b][1,4]thiazin-6-yl)-N-(1-phenyl-2-(pyrrolidin-1-yl)ethyl)acetamide;

N-(2-((S)-3-hydroxypyrrolidin-1-yl)-1-(tetrahydro-2H-pyran-4-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-methoxyphenyl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethyl)phenyl)ethyl)-N-methyl-2-(3-oxo-3,4-dihydro-2H-benzo[b][1,4]thiazin-6-yl)acetamide;

N—((S)-1-(3-fluorophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethoxy)phenyl)ethyl)-N-methyl-2-(3-oxo-3,4-dihydro-2H-benzo[b][1,4]thiazin-6-yl)acetamide;

2-(1-benzyl-2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-propylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isopropylacetamide;

N-cyclopropyl-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isobutylacetamide;

N-(cyclopropylmethyl)-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(4-(trifluoromethoxy)phenyl)ethyl)-N-methylacetamide;

2-(2,2-dimethyl-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2,2,2-trifluoroethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(m-tolyl)ethyl)-N-methylacetamide;

2-(1,1-dioxido-3-oxo-3,4-dihydro-2H-benzo[b][1,4]thiazin-6-yl)-N—((S)-1-(4-fluoro-3-(trifluoromethoxy)phenyl)-2-((S)-3-hydroxypyrrolidin-1-yl)ethyl)-N-methylacetamide;

N—((S)-1-(3,5-dimethylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(2,2-dimethyl-1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-1-(3-fluoro-5-(2,2,2-trifluoroethoxy)phenyl)-2-((S)-3-hydroxypyrrolidin-1-yl)ethyl)-N-methylacetamide;

N—((S)-1-(3-cyclopropylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

N—((S)-1-(3-cyanophenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]oxazin-6-yl)acetamide;

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzoic acid;

3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)benzoic acid;

N—((S)-1-(3-cyanophenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-phenylethyl)-2-(2-oxoindolin-5-yl)acetamide;

N—((S)-1-(3-cyanophenyl)-2-((S)-3-hydroxypyrrolidin-1-yl)ethyl)-N-methyl-2-(3-oxo-3,4-dihydroquinoxalin-6-yl)acetamide;

2-(3-((S)-2-((S)-3-hydroxypyrrolidin-1-yl)-1-(N-methyl-2-(2-oxoindolin-6-yl)acetamido)ethyl)phenoxy)acetic acid;

3-((S)-2-((S)-3-hydroxypyrrolidin-1-yl)-1-(N-methyl-2-(2-oxo-2,3-dihydrobenzo[d]oxazol-5-yl)acetamido)ethyl)benzamide;

N—((S)-2-((S)-3-hydroxypyrrolidin-1-yl)-1-phenylethyl)-N-methyl-2-(2-oxoindolin-5-yl)acetamide;

N—((S)-2-((S)-3-fluoropyrrolidin-1-yl)-1-(3-(2-(methylsulfonamido)-2-oxoethoxy)phenyl)ethyl)-N-methyl-2-(2-oxoindolin-6-yl)acetamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

3-((S)-2-((S)-3-hydroxypyrrolidin-1-yl)-1-(N-methyl-2-(3-oxo-3,4-dihydroquinoxalin-6-yl)acetamido)ethyl)benzamide;

3-((S)-2-((S)-3-fluoropyrrolidin-1-yl)-1-(N-methyl-2-(2-oxoindolin-6-yl)acetamido)ethyl)benzamide;

2-(3-((S)-2-((S)-3-hydroxypyrrolidin-1-yl)-1-(N-methyl-2-(2-oxo-2,3-dihydrobenzo[d]thiazol-5-yl)acetamido)ethyl)phenoxy)acetic acid;

2-(3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(3-((S)-2-((S)-3-hydroxypyrrolidin-1-yl)-1-(N-methyl-2-(2-oxoindolin-5-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide;

2-(3-((S)-2-((S)-3-hydroxypyrrolidin-1-yl)-1-(N-methyl-2-(3-oxo-3,4-dihydroquinoxalin-6-yl)acetamido)ethyl)phenoxy)acetic acid;

2-(3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]oxazin-6-yl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2-(methylsulfonamido)-2-oxoethoxy)phenyl)ethyl)-N-methylacetamide;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]thiazin-6-yl)acetamide;

3-((S)-2-((S)-3-hydroxypyrrolidin-1-yl)-1-(N-methyl-2-(2-oxo-2,3-dihydrobenzo[d]oxazol-5-yl)acetamido)ethyl)benzoic acid;

3-((S)-2-((S)-3-hydroxypyrrolidin-1-yl)-1-(N-methyl-2-(2-oxoindolin-6-yl)acetamido)ethyl)-N-(methylsulfonyl)benzamide;

N—((S)-1-(3-ethynylphenyl)-2-((S)-3-hydroxypyrrolidin-1-yl)ethyl)-N-methyl-2-(3-oxo-3,4-dihydroquinoxalin-6-yl)acetamide;

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxoindolin-6-yl)acetamide;

N—((S)-1-(3-ethynylphenyl)-2-((S)-3-hydroxypyrrolidin-1-yl)ethyl)-N-methyl-2-(2-oxoindolin-6-yl)acetamide;

2-(2,2-dioxido-1,3-dihydrobenzo[c]isothiazol-6-yl)-N—((S)-2-((S)-3-hydroxypyrrolidin-1-yl)-1-(3-(5-methyl-1,2,4-oxadiazol-3-yl)phenyl)ethyl)-N-methylacetamide;

2-(2,2-dioxido-1,3-dihydrobenzo[c]isothiazol-6-yl)-N—((S)-1-(3-ethynylphenyl)-2-((S)-3-hydroxypyrrolidin-1-yl)ethyl)-N-methylacetamide;

N—((S)-2-((S)-3-hydroxypyrrolidin-1-yl)-1-(3-(5-methyl-1,2,4-oxadiazol-3-yl)phenyl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxo-2,3-dihydrobenzo[d]thiazol-5-yl)acetamide;

N—((S)-1-(3-(1,2,4-oxadiazol-3-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-(1,2,4-oxadiazol-3-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(5-(trifluoromethyl)-1,2,4-oxadiazol-3-yl)phenyl)ethyl)-N-methylacetamide 2,2,2-trifluoroacetate;

N,N-diethyl-3-((S)-2-((S)-3-hydroxypyrrolidin-1-yl)-1-(N-methyl-2-(2-oxo-2,3-dihydrobenzo[d]thiazol-5-yl)acetamido)ethyl)benzamide;

N—((S)-1-(3-(1,2,4-oxadiazol-3-yl)phenyl)-2-((S)-3-hydroxypyrrolidin-1-yl)ethyl)-N-methyl-2-(2-oxo-2,3-dihydrobenzo[d]thiazol-5-yl)acetamide 2,2,2-trifluoroacetate;

N—((S)-1-(3-(1,2,4-oxadiazol-3-yl)phenyl)-2-((S)-3-hydroxypyrrolidin-1-yl)ethyl)-N-methyl-2-(3-oxo-3,4-dihydroquinoxalin-6-yl)acetamide 2,2,2-trifluoroacetate;

N—((S)-1-(3-(1H-imidazol-2-yl)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(thiazol-2-yl)phenyl)ethyl)-N-methyl-2-(2-oxo-2,3-dihydrobenzo[d]thiazol-5-yl)acetamide;

N—((S)-1-(3-cyano-5-fluorophenyl)-2-((S)-3-hydroxypyrrolidin-1-yl)ethyl)-N-methyl-2-(2-oxo-2,3-dihydrobenzo[d]thiazol-5-yl)acetamide hydrochloride;

N—((S)-2-((S)-3-hydroxypyrrolidin-1-yl)-1-(3-(5-methyl-1,2,4-oxadiazol-3-yl)phenyl)ethyl)-N-methyl-2-(3-oxo-3,4-dihydroquinoxalin-6-yl)acetamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N-(2,2,2-trifluoroethyl)benzamide;

3-((S)-2-((S)-3-hydroxypyrrolidin-1-yl)-1-(N-methyl-2-(3-oxo-3,4-dihydroquinoxalin-6-yl)acetamido)ethyl)-N-(2,2,2-trifluoroethyl)benzamide;

N—((S)-1-(3-cyano-5-fluorophenyl)-2-((S)-3-hydroxypyrrolidin-1-yl)ethyl)-N-methyl-2-(2-oxoindolin-6-yl)acetamide;

N—((S)-1-(3-(1H-imidazol-2-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-cyano-5-fluorophenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-cyano-5-fluorophenyl)-2-((S)-3-hydroxypyrrolidin-1-yl)ethyl)-N-methyl-2-(3-oxo-3,4-dihydroquinoxalin-6-yl)acetamide;

2-(1,1-dioxido-3-oxo-3,4-dihydro-2H-benzo[b][1,4]thiazin-6-yl)-N—((S)-1-(3-ethynylphenyl)-2-((S)-3-hydroxypyrrolidin-1-yl)ethyl)-N-methylacetamide;

N—((S)-1-(3-(1H-imidazol-2-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-cyanophenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-(but-1-yn-1-yl)phenyl)-2-((S)-3-hydroxypyrrolidin-1-yl)ethyl)-N-methyl-2-(2-oxoindolin-6-yl)acetamide;

N—((S)-1-(3-(but-1-yn-1-yl)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-(but-1-yn-1-yl)phenyl)-2-((S)-3-hydroxypyrrolidin-1-yl)ethyl)-N-methyl-2-(3-oxo-3,4-dihydroquinoxalin-6-yl)acetamide;

3-((S)-2-((S)-3-hydroxypyrrolidin-1-yl)-1-(N-methyl-2-(2-oxoindolin-6-yl)acetamido)ethyl)-N,N-dimethylbenzamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-diethylbenzamide;

N,N-diethyl-3-((S)-2-((S)-3-hydroxypyrrolidin-1-yl)-1-(N-methyl-2-(3-oxo-3,4-dihydroquinoxalin-6-yl)acetamido)ethyl)benzamide 2,2,2-trifluoroacetate;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-dimethylbenzamide;

3-((S)-2-((S)-3-hydroxypyrrolidin-1-yl)-1-(N-methyl-2-(3-oxo-3,4-dihydroquinoxalin-6-yl)acetamido)ethyl)-N,N-dimethylbenzamide;

N—((S)-1-(3-(1,2,4-oxadiazol-3-yl)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide 2,2,2-trifluoroacetate;

N—((S)-2-((S)-3-hydroxypyrrolidin-1-yl)-1-(3-(1-methyl-1H-imidazol-2-yl)phenyl)ethyl)-N-methyl-2-(2-oxoindolin-6-yl)acetamide;

N—((S)-1-(3-(5-ethyl-1,2,4-oxadiazol-3-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(thiazol-5-yl)phenyl)ethyl)-N-methyl-2-(2-oxoindolin-6-yl)acetamide;

N—((S)-2-((S)-3-hydroxypyrrolidin-1-yl)-1-(3-(thiazol-4-yl)phenyl)ethyl)-N-methyl-2-(2-oxoindolin-6-yl)acetamide;

N—((S)-2-((S)-3-hydroxypyrrolidin-1-yl)-1-(3-(4-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(2-methylthiazol-5-yl)phenyl)ethyl)-N-methyl-2-(2-oxoindolin-6-yl)acetamide;

N—((S)-2-((S)-3-hydroxypyrrolidin-1-yl)-1-(3-(2-methylthiazol-4-yl)phenyl)ethyl)-N-methyl-2-(2-oxoindolin-6-yl)acetamide;

N—((S)-2-((S)-3-hydroxypyrrolidin-1-yl)-1-(3-(5-methyl-1,3,4-thiadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-5-yl)phenyl)ethyl)-N-methyl-2-(2-oxoindolin-6-yl)acetamide;

N—((S)-1-(3-(1,3,4-oxadiazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methyl-1,3,4-oxadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-4-yl)phenyl)ethyl)-N-methyl-2-(2-oxoindolin-6-yl)acetamide;

N—((S)-1-(3-(1-(cyclopropylmethyl)-1H-imidazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(3-methyl-1,2,4-oxadiazol-5-yl)phenyl)ethyl)-N-methyl-2-(2-oxoindolin-6-yl)acetamide; and 3-((S)-2-((S)-3-hydroxypyrrolidin-1-yl)-1-(N-methyl-2-(2-oxo-2,3-dihydrobenzo[d]thiazol-5-yl)acetamido)ethyl)-N-(2,2,2-trifluoroethyl)benzamide;

or a stereoisomer thereof or a pharmaceutically acceptable salt thereof.

2. A method of alleviating pain or gastrointestinal dysfunction in a patient suffering from diseases or disorders associated with and/or modulated by KOR agonists in a patient comprising administering to the patient a therapeutically effective amount of a compound selected from the group consisting of:

N—((S)-2-((S)-3-hydroxypyrrolidin-1-yl)-1-phenylethyl)-N-methyl-2-(2-oxoindolin-6-yl)acetamide;

N-[(1S)-2-[(3S)-3-hydroxypyrrolidin-1-yl]-1-phenylethyl]-2-(3-oxo-3,4-dihydro-2H-1,4-benzoxazin-6-yl)acetamide;

N—((S)-2-((S)-3-hydroxypyrrolidin-1-yl)-1-phenylethyl)-N-methyl-2-(3-oxo-3,4-dihydroquinoxalin-6-yl)acetamide;

(S)-2-(2-oxo-2,3-dihydrobenzo[d]thiazol-5-yl)-N-(1-phenyl-2-(pyrrolidin-1-yl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

N—((S)-1-(3-cyanophenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

N—((S)-2-((S)-3-hydroxypyrrolidin-1-yl)-1-phenylethyl)-N-methyl-2-(3-oxo-3,4-dihydro-2H-benzo[b][1,4]thiazin-6-yl)acetamide;

2-(1,1-dioxido-3-oxo-2,3-dihydrobenzo[d]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(trifluoromethyl)phenyl)ethyl)-N-methylacetamide;

5-(2-(((S)-2-((S)-3-hydroxypyrrolidin-1-yl)-1-phenylethyl)(methyl)amino)-2-oxoethyl)-1,3-dihydrobenzo[c]isothiazol-1-ium 2,2-dioxide 2,2,2-trifluoroacetate;

N—((S)-1-(3-(difluoromethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(3,3-difluoro-2-oxoindolin-6-yl)-N—((S)-2-((S)-3-hydroxypyrrolidin-1-yl)-1-phenylethyl)-N-methylacetamide;

2-(3,3-difluoro-2-oxoindolin-6-yl)-N—((S)-2-((S)-3-hydroxypyrrolidin-1-yl)-1-phenylethyl)acetamide;

2-(1,1-dioxido-3-oxo-3,4-dihydro-2H-benzo[b][1,4]thiazin-6-yl)-N-ethyl-N—((S)-2-((S)-3-hydroxypyrrolidin-1-yl)-1-(3-(trifluoromethoxy)phenyl) ethyl)acetamide;

2-(1,1-dioxido-3-oxo-3,4-dihydro-2H-benzo[b][1,4]thiazin-6-yl)-N—((S)-2-((S)-3-methoxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-(2,2,2-trifluoroethyl)acetamide 2,2,2-trifluoroacetate;

2-(1,1-dioxido-3-oxo-3,4-dihydro-2H-benzo[b][1,4]thiazin-6-yl)-N-(2-((S)-3-hydroxypyrrolidin-1-yl)-1-(tetrahydro-2H-pyran-4-yl)ethyl)-N-methylacetamide-2,2,2-trifluoroacetate;

3-((S)-2-((S)-3-hydroxypyrrolidin-1-yl)-1-(N-methyl-2-(2-oxo-2,3-dihydrobenzo[d]thiazol-5-yl)acetamido)ethyl)benzoic acid;

3-((S)-2-((S)-3-hydroxypyrrolidin-1-yl)-1-(N-methyl-2-(2-oxo-2,3-dihydrobenzo[d]thiazol-5-yl)acetamido)ethyl)benzamide;

(S)-2-(3-benzyl-2-oxo-2,3-dihydrobenzo[d]oxazol-5-yl)-N-(1-(3-hydroxyphenyl)-2-(pyrrolidin-1-yl)ethyl)acetamide;

N—((S)-1-(3-(1H-tetrazol-5-yl)phenyl)-2-((S)-3-hydroxypyrrolidin-1-yl)ethyl)-N-methyl-2-(1-methyl-2,2-dioxido-1,3-dihydrobenzo[c]isothiazol-6-yl)acetamide;

2-(3-((S)-1-(2-(1,1-dioxido-3-oxo-3,4-dihydro-2H-benzo[b][1,4]thiazin-6-yl)-N-methylacetamido)-2-((S)-3-hydroxypyrrolidin-1-yl)ethyl)phenoxy)acetic acid;

3-((S)-2-((S)-3-hydroxypyrrolidin-1-yl)-1-(N-methyl-2-(2-oxoindolin-6-yl)acetamido)ethyl) benzoic acid;

3-((S)-2-((S)-3-hydroxypyrrolidin-1-yl)-1-(N-methyl-2-(2-oxoindolin-6-yl)acetamido)ethyl) benzamide;

N—((S)-1-(3-cyanophenyl)-2-((S)-3-fluoropyrrolidin-1-yl)ethyl)-N-methyl-2-(2-oxoindolin-6-yl)acetamide;

N—((S)-1-(3-(2-amino-2-oxoethoxy)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(2-(methylsulfonamido)-2-oxoethoxy)phenyl)ethyl)-N-methyl-2-(2-oxoindolin-6-yl)acetamide;

3-((S)-2-((S)-3-fluoropyrrolidin-1-yl)-1-(N-methyl-2-(2-oxoindolin-6-yl)acetamido)ethyl) benzoic acid;

2-(3-((S)-2-((S)-3-fluoropyrrolidin-1-yl)-1-(N-methyl-2-(2-oxoindolin-6-yl)acetamido)ethyl) phenoxy)acetic acid;

N—((S)-1-(3-(2-amino-2-oxoethoxy)phenyl)-2-((S)-3-fluoropyrrolidin-1-yl)ethyl)-N-methyl-2-(2-oxoindolin-6-yl)acetamide;

3-((S)-2-((S)-3-hydroxypyrrolidin-1-yl)-1-(N-methyl-2-(3-oxo-3,4-dihydroquinoxalin-6-yl)acetamido)ethyl) benzoic acid;

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzamide;

N—((S)-1-(3-ethynylphenyl)-2-((S)-3-hydroxypyrrolidin-1-yl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(5-(trifluoromethyl)-1,2,4-oxadiazol-3-yl)phenyl) ethyl)-N-methyl-2-(3-oxo-3,4-dihydroquinoxalin-6-yl)acetamide;

N—((S)-2-((S)-3-hydroxypyrrolidin-1-yl)-1-(3-(5-methyl-1,2,4-oxadiazol-3-yl)phenyl)ethyl)-N-methyl-2-(2-oxoindolin-6-yl)acetamide;

N—((S)-2-((S)-3-hydroxypyrrolidin-1-yl)-1-(3-(thiazol-2-yl)phenyl)ethyl)-N-methyl-2-(2-oxoindolin-6-yl)acetamide;

N—((S)-1-(3-(but-1-yn-1-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

3-((S)-2-((S)-3-hydroxypyrrolidin-1-yl)-1-(N-methyl-2-(2-oxoindolin-6-yl)acetamido)ethyl)-N-(2,2,2-trifluoroethyl)benzamide;

N,N-diethyl-3-((S)-2-((S)-3-hydroxypyrrolidin-1-yl)-1-(N-methyl-2-(2-oxoindolin-6-yl)acetamido)ethyl)benzamide;

3-((S)-2-((S)-3-hydroxypyrrolidin-1-yl)-1-(N-methyl-2-(2-oxo-2,3-dihydrobenzo[d]thiazol-5-yl)acetamido)ethyl)-N,N-dimethylbenzamide 2,2,2-trifluoroacetate;

N—((S)-1-(3-(2-(diethylamino)-2-oxoethoxy)phenyl)-2-((S)-3-hydroxypyrrolidin-1-yl)ethyl)-N-methyl-2-(2-oxoindolin-6-yl)acetamide;

N—((S)-1-(3-(2-(diethylamino)-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-fluoro-5-(thiazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(2-methyl-2H-tetrazol-5-yl)phenyl)ethyl)-N-methyl-2-(2-oxoindolin-6-yl)acetamide;

N—((S)-2-((S)-3-hydroxypyrrolidin-1-yl)-1-phenylethyl)-2-(3-methyl-2-oxo-2,3-dihydrobenzo[d]oxazol-5-yl)acetamide;

(S)-2-(3-(3-cyanobenzyl)-2-oxo-2,3-dihydrobenzo[d]oxazol-5-yl)-N-(1-phenyl-2-(pyrrolidin-1-yl)ethyl)acetamide;

(S)—N-methyl-2-(2-oxo-1,2-dihydroquinolin-6-yl)-N-(1-phenyl-2-(pyrrolidin-1-yl)ethyl)acetamide;

N—((S)-2-((S)-3-hydroxypyrrolidin-1-yl)-1-phenylethyl)-N-methyl-2-(2-oxo-1,2-dihydroquinolin-6-yl)acetamide;

(S)—N-methyl-2-(2-oxo-1,2-dihydroquinolin-7-yl)-N-(1-phenyl-2-(pyrrolidin-1-yl)ethyl)acetamide;

(S)—N-methyl-2-(3-methyl-2,2-dioxido-1,3-dihydrobenzo[c]isothiazol-5-yl)-N-(1-phenyl-2-(pyrrolidin-1-yl)ethyl)acetamide;

N—((S)-2-((R)-3-hydroxypyrrolidin-1-yl)-1-phenylethyl)-2-(2-oxo-1,2-dihydroquinolin-6-yl)acetamide;

N—((S)-2-((S)-3-hydroxypyrrolidin-1-yl)-1-phenylethyl)-N-methyl-2-(2-oxo-1,2-dihydroquinolin-7-yl)acetamide;

N—((S)-2-((S)-3-hydroxypyrrolidin-1-yl)-1-phenylethyl)-N-2-dimethyl-2-(2-oxo-2,3-dihydrobenzo[d]oxazol-5-yl)propanamide;

N—((S)-2-((S)-3-hydroxypyrrolidin-1-yl)-1-phenylethyl)-2-(2-oxo-1,2-dihydroquinolin-7-yl)acetamide;

N—((S)-2-((S)-3-hydroxypyrrolidin-1-yl)-1-phenylethyl)-2-methyl-2-(2-oxo-2,3-dihydrobenzo[d]oxazol-5-yl)propanamide;

(S)-2-(2-oxo-2,3-dihydrobenzo[d]oxazol-5-yl)-N-(1-phenyl-2-(pyrrolidin-1-yl)ethyl) acetamide;

N—((S)-2-((S)-3-hydroxypyrrolidin-1-yl)-1-phenylethyl)-2-(2-oxo-2,3-dihydrobenzo[d]oxazol-5-yl)acetamide;

(S)-2-(3-benzyl-2-oxo-2,3-dihydrobenzo[d]oxazol-5-yl)-N-(1-(3-(4-methoxybenzyloxy)phenyl)-2-(pyrrolidin-1-yl)ethyl)acetamide;

2-(3-(4-cyanobenzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-2-((S)-3-hydroxypyrrolidin-1-yl)-1-phenylethyl)-2-(2-oxoindolin-6-yl)acetamide;

(S)-2-(3-methyl-2-oxo-2,3-dihydrobenzo[d]oxazol-5-yl)-N-(1-phenyl-2-(pyrrolidin-1-yl)ethyl)acetamide;

N-(1-(1-benzyl-1H-pyrazol-4-yl)-2-(pyrrolidin-1-yl)ethyl)-2-(2-oxo-2,3-dihydrobenzo[d]oxazol-5-yl)acetamide;

(S)-t-butyl-2-(3-(1-(2-(3-benzyl-2-oxo-2,3-dihydrobenzo[d]oxazol-5-yl)acetamido)-2-(pyrrolidin-1-yl)ethyl)phenoxy)acetate;

(S)-2-(3-benzyl-2-oxo-2,3-dihydrobenzo[d]oxazol-5-yl)-N-(1-(3-(benzyloxy)phenyl)-2-(pyrrolidin-1-yl)ethyl)-N-methylacetamide;

N—((S)-1-cyclohexyl-2-((S)-3-hydroxypyrrolidin-1-yl)ethyl)-N-methyl-2-(2-oxoindolin-6-yl)acetamide;

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide;

N—((S)-1-cyclohexyl-2-((S)-3-hydroxypyrrolidin-1-yl)ethyl)-2-(2-oxo-2,3-dihydrobenzo[d]oxazol-5-yl)acetamide;

(S)-tert-butyl-2-(3-(1-(2-(3-benzyl-2-oxo-2,3-dihydrobenzo[d]oxazol-5-yl)-N-methyl acetamido)-2-(pyrrolidin-1-yl)ethyl)phenoxy)acetate;

N—((S)-1-cyclohexyl-2-((S)-3-hydroxypyrrolidin-1-yl)ethyl)-2-(2-oxoindolin-6-yl)acetamide;

N—((S)-1-cyclohexyl-2-((S)-3-hydroxypyrrolidin-1-yl)ethyl)-N-methyl-2-(2-oxo-2,3-dihydrobenzo[d]oxazol-5-yl)acetamide;

(S)—N-(1-(3-cyanophenyl)-2-(pyrrolidin-1-yl)ethyl)-N-methyl-2-(2-oxo-2,3-dihydrobenzo[d]oxazol-5-yl)acetamide;

2-(3-(3-cyanobenzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

(S)-tert-butyl 2-(3-(2-(3-hydroxypyrrolidin-1-yl)-1-(2-(2-oxo-2,3-dihydro benzo[d]oxazol-5-yl)acetamido)ethyl)phenoxy)acetate;

2-(3-(4-cyanobenzyl)-2-oxo-2,3-dihydrobenzo[d]oxazol-5-yl)-N—((S)-2-((S)-3-hydroxypyrrolidin-1-yl)-1-phenylethyl)-N-methylacetamide;

N-(1-(3-(cyanomethoxy)phenyl)-2-(hydroxypyrrolidin-1-yl)ethyl)-N-methyl-2-(2-oxo-2,3-dihydrobenzo[d]oxazol-5-yl)acetamide;

tert-butyl 2-(3-((S)-2-((R)-3-hydroxypyrrolidin-1-yl)-1-(N-methyl-2-(2-oxo-2,3-dihydrobenzo[d]oxazol-5-yl)acetamido)ethyl)phenoxy)acetate;

N—((S)-1-(3-cyanophenyl)-2-((S)-3-hydroxypyrrolidin-1-yl)ethyl)-N-methyl-2-(3-methyl-2-oxo-2,3-dihydrobenzo[d]oxazol-5-yl)acetamide;

N—((S)-1-(3-(1H-tetrazol-5-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(3-((S)-2-((S)-3-hydroxypyrrolidin-1-yl)-1-(N-methyl-2-(1-methyl-2,2-dioxido-1,3-dihydrobenzo[c]isothiazol-6-yl)acetamido)ethyl)phenoxy) acetic acid;

(S)-methyl 3-((2-oxo-5-(2-oxo-2-(1-phenyl-2-(pyrrolidin-1-yl)ethylamino)ethyl)benzo[d]oxazol-3(2H)-yl)methyl)benzoate;

(S)-tert-butyl 2-(2-oxo-5-(2-oxo-2-(1-phenyl-2-(pyrrolidin-1-yl)ethylamino) ethyl)benzo[d]oxazol-3 (2H)-yl)acetate;

(S)-2-(2-oxo-5-(2-oxo-2-(1-phenyl-2-(pyrrolidin-1-yl)ethylamino)ethyl)benzo[d]oxazol-3(2H)-yl)acetic acid hydrochloride;

(S)—N-(1-(3-hydroxyphenyl)-2-(pyrrolidin-1-yl)ethyl)-2-(2-oxo-2,3-dihydrobenzo[d]oxazol-5-yl)acetamide;

(S)-2-(3-(1-(2-(2-oxo-2,3-dihydrobenzo[d]oxazol-5-yl)acetamido)-2-(pyrrolidin-1-yl)ethyl)phenoxy)acetic acid hydrochloride;

2-(5-(2-((S)-2-((S)-3-hydroxypyrrolidin-1-yl)-1-phenylethyl)(methyl)amino)-2-oxoethyl)-2-oxobenzo[d]oxazol-3(2H)-yl)acetic acid;

2-(3-(1-(N-methyl-2-(2-oxoindolin-6-yl)acetamido)-2-(pyrrolidin-1-yl)ethyl)phenoxy)acetic acid hydrochloride;

3-((5-(2-((S)-2-((S)-3-hydroxypyrrolidin-1-yl)-1-phenylethyl)(methyl)amino)-2-oxoethyl)-2-oxobenzo[d]oxazol-3(2H)-yl)methyl)benzamide;

(S)-2-(3-benzyl-2-oxo-2,3-dihydrobenzo[d]oxazol-5-yl)-N-(1-(3-hydroxyphenyl)-2-(pyrrolidin-1-yl)ethyl)-N-methylacetamide;

(R)-2-(3-(1-(N-methyl-2-(2-oxo-2,3-dihydrobenzo[d]oxazol-5-yl)acetamido)-2-(pyrrolidin-1-yl)ethyl)phenoxy)acetic acid;

(S)-3-((2-oxo-5-(2-oxo-2-(1-phenyl-2-(pyrrolidin-1-yl)ethylamino)ethyl)benzo[d]oxazol-3(2H)-yl)methyl)benzamide;

2-(3-(1-(2-(2-oxoindolin-6-yl)acetamido)-2-(pyrrolidin-1-yl)ethyl)phenoxy)acetic acid;

(S)—N-(1-(3-(2H-tetrazol-5-yl)phenyl)-2-(pyrrolidin-1-yl)ethyl)-N-methyl-2-(2-oxo-2,3-dihydrobenzo[d]oxazol-5-yl)acetamide;

(S)-2-(3-(2-(3-hydroxypyrrolidin-1-yl)-1-(N-methyl-2-(2-oxo-2,3-dihydrobenzo[d]oxazol-5-yl)acetamido)ethyl)phenoxy)acetic acid triflouro acetate;

(S)-2-(3-(2-(3-hydroxypyrrolidin-1-yl)-1-(N-methyl-2-(2-oxoindolin-6-yl) acetamido) ethyl) phenoxy) acetic acid hydrochloride;

2-(3-((S)-2-((R)-3-hydroxypyrrolidin-1-yl)-1-(N-methyl-2-(2-oxo-2,3-dihydrobenzo[d]oxazol-5-yl)acetamido)ethyl)phenoxy)acetic acid;

2-(5-(2-((S)-1-cyclohexyl-2-((S)-3-hydroxypyrrolidin-1-yl)ethyl)(methyl)amino)-2-oxoethyl)-2-oxobenzo[d]oxazol-3(2H)-yl)acetic acid;

Methyl 4-((5-(2-(((S)-2-((S)-3-hydroxypyrrolidin-1-yl)-1-phenylethyl)(methyl)amino)-2-oxoethyl)-2-oxobenzo[d]oxazol-3(2H)-yl)methyl)benzoate;

N—((S)-1-(3-(2H-tetrazol-5-yl)phenyl)-2-((S)-3-hydroxypyrrolidin-1-yl)ethyl)-N-methyl-2-(2-oxo-2,3-dihydrobenzo[d]oxazol-5-yl)acetamide;

(S)-2-(3-(2-(3-hydroxypyrrolidin-1-yl)-1-(2-(2-oxoindolin-6-yl)acetamido) ethyl)phenoxy)acetic acid hydrochloride;

(S)-2-(3-(2-(3-hydroxypyrrolidin-1-yl)-1-(2-(2-oxo-2,3-dihydrobenzo[d]oxazol-5-yl)acetamido)ethyl)phenoxy)acetic acid;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

2-(3-(3-(2H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)-N-methylacetamide;

(R)—N-(1-(3-(2H-tetrazol-5-yl)methoxy)phenyl)-2-(3-hydroxypyrrolidin-1-yl)ethyl)-N-methyl-2-(2-oxo-2,3-dihydrobenzo[d]oxazol-5-yl)acetamide;

2-(3-(4-(1H-tetrazol-5-yl)benzyl)-2-oxo-2,3-dihydrobenzo[d]oxazol-5-yl)-N—((S)-2-((S)-3-hydroxypyrrolidin-1-yl)-1-phenylethyl)acetamide;

N—((S)-1-(3-(2H-tetrazol-5-yl)phenyl)-2-((S)-3-hydroxypyrrolidin-1-yl)ethyl)-N-methyl-2-(3-methyl-2-oxo-2,3-dihydrobenzo[d]oxazol-5-yl)acetamide;

N—((S)-1-(3-cyanophenyl)-2-((S)-3-fluoropyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-fluoropyrrolidin-1-yl)ethyl)-N-methyl-2-(2-oxo-2,3-dihydrobenzo[d]oxazol-5-yl)acetamide;

N—((S)-1-(3-(2H-tetrazol-5-yl)phenyl)-2-((S)-3-hydroxypyrrolidin-1-yl)ethyl)-N-methyl-2-(2-oxoindolin-6-yl)acetamide;

N—((S)-1-(3-(2H-tetrazol-5-yl)phenyl)-2-((S)-3-hydroxypyrrolidin-1-yl)ethyl)-N-methyl-2-(1-methyl-2-oxoindolin-6-yl)acetamide;

N—((S)-1-(3-((2H-tetrazol-5-yl)methoxy)phenyl)-2-((S)-3-hydroxypyrrolidin-1-yl)ethyl)-N-methyl-2-(2-oxoindolin-6-yl)acetamide;

N—((S)-1-(3-(2H-tetrazol-5-yl)phenyl)-2-((S)-3-fluoropyrrolidin-1-yl)ethyl)-N-methyl-2-(2-oxoindolin-6-yl)acetamide;

(S)-2-(3-oxo-3,4-dihydro-2H-benzo[b][1,4]oxazin-6-yl)-N-(1-phenyl-2-(pyrrolidin-1-yl)ethyl)acetamide;

(S)—N-methyl-2-(2-oxo-2,3-dihydrobenzo[d]thiazol-5-yl)-N-(1-phenyl-2-(pyrrolidin-1-yl)ethyl)acetamide;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

N—((S)-2-((S)-3-hydroxypyrrolidin-1-yl)-1-phenylethyl)-N-methyl-2-(2-oxo-2,3-dihydrobenzo[d]thiazol-5-yl)acetamide;

N—((S)-2-((S)-3-hydroxypyrrolidin-1-yl)-1-phenylethyl)-2-(2-thioxo-2,3-dihydrobenzo[d]thiazol-5-yl)acetamide;

N—((S)-2-((S)-3-hydroxypyrrolidin-1-yl)-1-phenylethyl)-N-methyl-2-(2-thioxo-2,3-dihydrobenzo[d]thiazol-5-yl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)-N-methylacetamide;

(S)-2-(1,1-dioxido-3-oxo-3,4-dihydro-2H-benzo[b][1,4]thiazin-6-yl)-N-(1-phenyl-2-(pyrrolidin-1-yl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-phenylethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethyl)phenyl)ethyl)-N-methylacetamide;

2-(1,1-dioxido-3-oxo-3,4-dihydro-2H-benzo[b][1,4]thiazin-6-yl)-N—((S)-1-(3-fluorophenyl)-2-((S)-3-hydroxypyrrolidin-1-yl)ethyl)-N-methylacetamide;

N—((S)-1-cyclohexyl-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide 2-(1,1-dioxido-3-oxo-3,4-dihydro-2H-benzo[b][1,4]thiazin-6-yl)-N—((S)-2-((S)-3-hydroxypyrrolidin-1-yl)-1-(3-methoxyphenyl)ethyl)-N-methylacetamide;

(S)-2-(3-oxo-3,4-dihydro-2H-benzo[b][1,4]thiazin-6-yl)-N-(1-phenyl-2-(pyrrolidin-1-yl)ethyl)acetamide;

N—((S)-2-((S)-3-hydroxypyrrolidin-1-yl)-1-phenylethyl)-2-(3-oxo-3,4-dihydro-2H-benzo[b][1,4]thiazin-6-yl)acetamide;

(S)—N-methyl-2-(3-oxo-3,4-dihydro-2H-benzo[b][1,4]thiazin-6-yl)-N-(1-phenyl-2-(pyrrolidin-1-yl)ethyl)acetamide;

N-(2-((S)-3-hydroxypyrrolidin-1-yl)-1-(tetrahydro-2H-pyran-4-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-methoxyphenyl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethyl)phenyl)ethyl)-N-methyl-2-(3-oxo-3,4-dihydro-2H-benzo[b][1,4]thiazin-6-yl)acetamide;

N—((S)-1-(3-fluorophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

N—((S)-2-((S)-3-hydroxypyrrolidin-1-yl)-1-(3-(trifluoromethoxy)phenyl)ethyl)-N-methyl-2-(3-oxo-3,4-dihydro-2H-benzo[b][1,4]thiazin-6-yl)acetamide;

2-(1-benzyl-2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(2,2-dioxido-1,3-dihydrobenzo[c]isothiazol-6-yl)-N—((S)-2-((S)-3-hydroxypyrrolidin-1-yl)-1-phenylethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-propylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isopropylacetamide;

N-cyclopropyl-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-isobutylacetamide;

N-(cyclopropylmethyl)-2-(1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(4-(trifluoromethoxy)phenyl)ethyl)-N-methylacetamide;

2-(2,2-dimethyl-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2,2,2-trifluoroethoxy)phenyl)ethyl)-N-methylacetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(m-tolyl)ethyl)-N-methylacetamide;

2-(1,1-dioxido-3-oxo-3,4-dihydro-2H-benzo[b][1,4]thiazin-6-yl)-N—((S)-1-(4-fluoro-3-(trifluoromethoxy)phenyl)-2-((S)-3-hydroxypyrrolidin-1-yl)ethyl)-N-methylacetamide;

N—((S)-1-(3,5-dimethylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(2,2-dimethyl-1,1-dioxido-3-oxo-3,4-dihydro-2H-benzo[b][1,4]thiazin-6-yl)-N—((S)-2-((S)-3-hydroxypyrrolidin-1-yl)-1-(3-(trifluoromethoxy)phenyl)ethyl)-N-methylacetamide;

2-(1,1-dioxido-3-oxo-3,4-dihydro-2H-benzo[b][1,4]thiazin-6-yl)-N—((S)-1-(3-fluoro-5-(2,2,2-trifluoroethoxy)phenyl)-2-((S)-3-hydroxypyrrolidin-1-yl)ethyl)-N-methylacetamide;

N—((S)-1-(3-cyclopropylphenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

N—((S)-1-(3-cyanophenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]thiazin-6-yl)acetamide;

N—((S)-1-(3-cyanophenyl)-2-((S)-3-hydroxypyrrolidin-1-yl)ethyl)-N-methyl-2-(3-oxo-3,4-dihydro-2H-benzo[b][1,4]oxazin-6-yl)acetamide;

3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)benzoic acid;

3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)benzoic acid;

N—((S)-1-(3-cyanophenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-phenylethyl)-2-(2-oxoindolin-5-yl)acetamide;

N—((S)-1-(3-cyanophenyl)-2-((S)-3-hydroxypyrrolidin-1-yl)ethyl)-N-methyl-2-(3-oxo-3,4-dihydroquinoxalin-6-yl)acetamide;

2-(3-((S)-2-((S)-3-hydroxypyrrolidin-1-yl)-1-(N-methyl-2-(2-oxoindolin-6-yl)acetamido)ethyl)phenoxy)acetic acid;

3-((S)-2-((S)-3-hydroxypyrrolidin-1-yl)-1-(N-methyl-2-(2-oxo-2,3-dihydrobenzo[d]oxazol-5-yl)acetamido)ethyl)benzamide;

N—((S)-2-((S)-3-hydroxypyrrolidin-1-yl)-1-phenylethyl)-N-methyl-2-(2-oxoindolin-5-yl)acetamide;

N—((S)-2-((S)-3-fluoropyrrolidin-1-yl)-1-(3-(2-(methylsulfonamido)-2-oxoethoxy)phenyl) ethyl)-N-methyl-2-(2-oxoindolin-6-yl)acetamide;

N—((S)-1-(3-cyanophenyl)-2-((S)-3-hydroxypyrrolidin-1-yl)ethyl)-N-methyl-2-(2-oxo-2,3-dihydrobenzo[d]oxazol-5-yl)acetamide;

3-((S)-2-((S)-3-hydroxypyrrolidin-1-yl)-1-(N-methyl-2-(3-oxo-3,4-dihydroquinoxalin-6-yl)acetamido)ethyl)benzamide;

3-((S)-2-((S)-3-fluoropyrrolidin-1-yl)-1-(N-methyl-2-(2-oxoindolin-6-yl)acetamido)ethyl)benzamide;

2-(3-((S)-2-((S)-3-hydroxypyrrolidin-1-yl)-1-(N-methyl-2-(2-oxo-2,3-dihydrobenzo[d]thiazol-5-yl)acetamido)ethyl)phenoxy)acetic acid;

2-(3-((S)-2-((S)-3-hydroxypyrrolidin-1-yl)-1-(N-methyl-2-(3-oxo-3,4-dihydro-2H-benzo[b][1,4]oxazin-6-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide;

2-(3-((S)-2-((S)-3-hydroxypyrrolidin-1-yl)-1-(N-methyl-2-(2-oxoindolin-5-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-N-methyl-2-(2-oxo-2,3-dihydrobenzo[d]thiazol-5-yl)acetamide;

2-(3-((S)-2-((S)-3-hydroxypyrrolidin-1-yl)-1-(N-methyl-2-(3-oxo-3,4-dihydroquinoxalin-6-yl)acetamido)ethyl)phenoxy)acetic acid;

2-(3-((S)-2-((S)-3-hydroxypyrrolidin-1-yl)-1-(N-methyl-2-(3-oxo-3,4-dihydro-2H-benzo[b][1,4]thiazin-6-yl)acetamido)ethyl)phenoxy)acetic acid;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]oxazin-6-yl)acetamide;

2-(1,1-dioxido-3-oxo-3,4-dihydro-2H-benzo[b][1,4]thiazin-6-yl)-N—((S)-2-((S)-3-hydroxypyrrolidin-1-yl)-1-(3-(2-(methylsulfonamido)-2-oxoethoxy)phenyl)ethyl)-N-methylacetamide;

N—((S)-1-(3-(2-amino-2-oxoethoxy)phenyl)-2-((S)-3-hydroxypyrrolidin-1-yl)ethyl)-N-methyl-2-(3-oxo-3,4-dihydro-2H-benzo[b][1,4]thiazin-6-yl)acetamide;

3-((S)-2-((S)-3-hydroxypyrrolidin-1-yl)-1-(N-methyl-2-(2-oxo-2,3-dihydrobenzo[d]oxazol-5-yl)acetamido)ethyl)benzoic acid;

3-((S)-2-((S)-3-hydroxypyrrolidin-1-yl)-1-(N-methyl-2-(2-oxoindolin-6-yl)acetamido)ethyl)-N-(methylsulfonyl)benzamide;

N—((S)-1-(3-ethynylphenyl)-2-((S)-3-hydroxypyrrolidin-1-yl)ethyl)-N-methyl-2-(3-oxo-3,4-dihydroquinoxalin-6-yl)acetamide;

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxoindolin-6-yl)acetamide;

N—((S)-1-(3-ethynylphenyl)-2-((S)-3-hydroxypyrrolidin-1-yl)ethyl)-N-methyl-2-(2-oxoindolin-6-yl)acetamide;

2-(2,2-dioxido-1,3-dihydrobenzo[c]isothiazol-6-yl)-N—((S)-2-((S)-3-hydroxypyrrolidin-1-yl)-1-(3-(5-methyl-1,2,4-oxadiazol-3-yl)phenyl)ethyl)-N-methylacetamide;

2-(2,2-dioxido-1,3-dihydrobenzo[c]isothiazol-6-yl)-N—((S)-1-(3-ethynylphenyl)-2-((S)-3-hydroxypyrrolidin-1-yl)ethyl)-N-methylacetamide;

N—((S)-2-((S)-3-hydroxypyrrolidin-1-yl)-1-(3-(5-methyl-1,2,4-oxadiazol-3-yl)phenyl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(5-(trifluoromethyl)-1,2,4-oxadiazol-3-yl)phenyl)ethyl)-N-methyl-2-(2-oxo-2,3-dihydrobenzo[d]thiazol-5-yl)acetamide;

N—((S)-1-(3-(1,2,4-oxadiazol-3-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-(1,2,4-oxadiazol-3-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

2-(2,2-dioxido-1,3-dihydrobenzo[c]isothiazol-6-yl)-N—((S)-2-((S)-3-hydroxypyrrolidin-1-yl)-1-(3-(5-(trifluoromethyl)-1,2,4-oxadiazol-3-yl)phenyl)ethyl)-N-methylacetamide 2,2,2-trifluoroacetate;

N,N-diethyl-3-((S)-2-((S)-3-hydroxypyrrolidin-1-yl)-1-(N-methyl-2-(2-oxo-2,3-dihydrobenzo[d]thiazol-5-yl)acetamido)ethyl)benzamide;

N—((S)-1-(3-(1,2,4-oxadiazol-3-yl)phenyl)-2-((S)-3-hydroxypyrrolidin-1-yl)ethyl)-N-methyl-2-(2-oxo-2,3-dihydrobenzo[d]thiazol-5-yl)acetamide 2,2,2-trifluoroacetate;

N—((S)-1-(3-(1,2,4-oxadiazol-3-yl)phenyl)-2-((S)-3-hydroxypyrrolidin-1-yl)ethyl)-N-methyl-2-(3-oxo-3,4-dihydroquinoxalin-6-yl)acetamide 2,2,2-trifluoroacetate;

N—((S)-1-(3-(1H-imidazol-2-yl)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-2-((S)-3-hydroxypyrrolidin-1-yl)-1-(3-(thiazol-2-yl)phenyl)ethyl)-N-methyl-2-(2-oxo-2,3-dihydrobenzo[d]thiazol-5-yl)acetamide;

N—((S)-1-(3-cyano-5-fluorophenyl)-2-((S)-3-hydroxypyrrolidin-1-yl)ethyl)-N-methyl-2-(2-oxo-2,3-dihydrobenzo[d]thiazol-5-yl)acetamide hydrochloride;

N—((S)-2-((S)-3-hydroxypyrrolidin-1-yl)-1-(3-(5-methyl-1,2,4-oxadiazol-3-yl)phenyl)ethyl)-N-methyl-2-(3-oxo-3,4-dihydroquinoxalin-6-yl)acetamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N-(2,2,2-trifluoroethyl)benzamide;

3-((S)-2-((S)-3-hydroxypyrrolidin-1-yl)-1-(N-methyl-2-(3-oxo-3,4-dihydroquinoxalin-6-yl)acetamido)ethyl)-N-(2,2,2-trifluoroethyl)benzamide;

N—((S)-1-(3-cyano-5-fluorophenyl)-2-((S)-3-hydroxypyrrolidin-1-yl)ethyl)-N-methyl-2-(2-oxoindolin-6-yl)acetamide;

N—((S)-1-(3-(1H-imidazol-2-yl)phenyl)-2-((S)-3-hydroxypyrrolidin-1-yl)ethyl)-N-methyl-2-(2-oxoindolin-6-yl)acetamide 2,2,2-trifluoroacetate;

N—((S)-1-(3-cyano-5-fluorophenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-cyano-5-fluorophenyl)-2-((S)-3-hydroxypyrrolidin-1-yl)ethyl)-N-methyl-2-(3-oxo-3,4-dihydroquinoxalin-6-yl)acetamide;

2-(1,1-dioxido-3-oxo-3,4-dihydro-2H-benzo[b][1,4]thiazin-6-yl)-N—((S)-1-(3-ethynylphenyl)-2-((S)-3-hydroxypyrrolidin-1-yl)ethyl)-N-methylacetamide;

N—((S)-1-(3-(1H-imidazol-2-yl)phenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-(cyanophenyl)-2-((S)-3-hydroxypyrrolidin-1-yl)ethyl)-2-(2,2-dioxido-1,3-dihydrobenzo[c]isothiazol-6-yl)-N-methylacetamide;

N—((S)-1-(3-(but-1-yn-1-yl)phenyl)-2-((S)-3-hydroxypyrrolidin-1-yl)ethyl)-N-methyl-2-(2-oxoindolin-6-yl)acetamide;

N—((S)-1-(3-(but-1-yn-1-yl)phenyl)-2-((S)-3-hydroxypyrrolidin-1-yl)ethyl)-N-methyl-2-(2-oxo-2,3-dihydrobenzo[d]thiazol-5-yl)acetamide;

N—((S)-1-(3-(but-1-yn-1-yl)phenyl)-2-((S)-3-hydroxypyrrolidin-1-yl)ethyl)-N-methyl-2-(3-oxo-3,4-dihydroquinoxalin-6-yl)acetamide;

3-((S)-2-((S)-3-hydroxypyrrolidin-1-yl)-1-(N-methyl-2-(2-oxoindolin-6-yl)acetamido)ethyl)-N,N-dimethylbenzamide;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-diethylbenzamide;

N,N-diethyl-3-((S)-2-((S)-3-hydroxypyrrolidin-1-yl)-1-(N-methyl-2-(3-oxo-3,4-dihydroquinoxalin-6-yl)acetamido)ethyl)benzamide 2,2,2-trifluoroacetate;

3-((S)-1-(2-(2,2-dioxido-1,3-dihydrobenzo[c]isothiazol-6-yl)-N-methylacetamido)-2-((S)-3-hydroxypyrrolidin-1-yl)ethyl)-N,N-dimethylbenzamide;

3-((S)-2-((S)-3-hydroxypyrrolidin-1-yl)-1-(N-methyl-2-(3-oxo-3,4-dihydroquinoxalin-6-yl)acetamido)ethyl)-N,N-dimethylbenzamide;

N—((S)-1-(3-(1,2,4-oxadiazol-3-yl)phenyl)-2-((S)-3-hydroxypyrrolidin-1-yl)ethyl)-2-(1,1-dioxido-3-oxo-3,4-dihydro-2H-benzo[b][1,4]thiazin-6-yl)-N-methylacetamide 2,2,2-trifluoroacetate;

N—((S)-2-((S)-3-hydroxypyrrolidin-1-yl)-1-(3-(1-methyl-1H-imidazol-2-yl)phenyl)ethyl)-N-methyl-2-(2-oxoindolin-6-yl)acetamide;

N—((S)-1-(3-(5-ethyl-1,2,4-oxadiazol-3-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(thiazol-5-yl)phenyl)ethyl)-N-methyl-2-(2-oxoindolin-6-yl)acetamide;

N—((S)-2-((S)-3-hydroxypyrrolidin-1-yl)-1-(3-(thiazol-4-yl)phenyl)ethyl)-N-methyl-2-(2-oxoindolin-6-yl)acetamide;

N—((S)-2-((S)-3-hydroxypyrrolidin-1-yl)-1-(3-(4-methylthiazol-2-yl)phenyl)ethyl)-N-methyl-2-(2-oxoindolin-6-yl)acetamide;

N—((S)-2-((S)-3-hydroxypyrrolidin-1-yl)-1-(3-(2-methylthiazol-5-yl)phenyl)ethyl)-N-methyl-2-(2-oxoindolin-6-yl)acetamide;

N—((S)-2-((S)-3-hydroxypyrrolidin-1-yl)-1-(3-(2-methylthiazol-4-yl)phenyl)ethyl)-N-methyl-2-(2-oxoindolin-6-yl)acetamide;

N—((S)-2-((S)-3-hydroxypyrrolidin-1-yl)-1-(3-(5-methyl-1,3,4-thiadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-5-yl)phenyl)ethyl)-N-methyl-2-(2-oxoindolin-6-yl)acetamide;

N—((S)-1-(3-(1,3,4-oxadiazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(5-methyl-1,3,4-oxadiazol-2-yl)phenyl)ethyl)-N-methyl-2-(2-oxoindolin-6-yl)acetamide;

N—((S)-2-((S)-3-hydroxypyrrolidin-1-yl)-1-(3-(1-methyl-1H-imidazol-4-yl)phenyl)ethyl)-N-methyl-2-(2-oxoindolin-6-yl)acetamide;

N—((S)-1-(3-(1-(cyclopropylmethyl)-1H-imidazol-2-yl)phenyl)-2-((S)-3-hydroxypyrrolidin-1-yl)ethyl)-N-methyl-2-(2-oxoindolin-6-yl)acetamide;

N—((S)-2-((S)-3-hydroxypyrrolidin-1-yl)-1-(3-(3-methyl-1,2,4-oxadiazol-5-yl)phenyl)ethyl)-N-methyl-2-(2-oxoindolin-6-yl)acetamide; and 3-((S)-2-((S)-3-hydroxypyrrolidin-1-yl)-1-(N-methyl-2-(2-oxo-2,3-dihydrobenzo[d]thiazol-5-yl)acetamido)ethyl)-N-(2,2,2-trifluoroethyl)benzamide;

or a stereoisomer thereof or a pharmaceutically acceptable salt thereof.

3. The method according to claim 2, wherein pain is chronic pain or acute pain.

4. The method according to claim 2, wherein pain is selected from nociceptive pain, inflammatory pain, visceral pain, somatic pain, neuralgia, neuropathic pain, AIDS pain, cancer pain, phantom pain, psychogenic pain, pain resulting from hyperalgesia, pain caused by rheumatoid arthritis, migraine and allodynia.

5. The method according to claim 2, wherein gastrointestinal dysfunction is diarrhea, nausea, emesis, post-operative emesis, opioid-induced emesis, irritable bowel syndrome, opioid-bowel dysfunction, opioid induced constipation, ileus, including post-operative ileus, post-partum ileus and opioid-induced ileus, colitis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, distension, abdominal or epigastric pain and discomfort, non-ulcerogenic dyspepsia, gastritis, constipation, or delayed absorption of orally administered medications or nutritive substances.

6. A method of alleviating pain or gastrointestinal dysfunction in a patient according to claim 1 comprising administering to the patient a therapeutically effective amount of a pharmaceutical composition comprising the compound or a stereoisomer thereof or a pharmaceutically acceptable salt thereof.

7. The method according to claim 6, wherein pain is chronic pain or acute pain.

8. The method according to claim 6, wherein pain is selected from nociceptive pain, inflammatory pain, visceral pain, somatic pain, neuralgia, neuropathic pain, AIDS pain, cancer pain, phantom pain, psychogenic pain, pain resulting from hyperalgesia, pain caused by rheumatoid arthritis, migraine and allodynia.

9. The method according to claim 6, wherein gastrointestinal dysfunction is diarrhea, nausea, emesis, post-operative emesis, opioid-induced emesis, irritable bowel syndrome, opioid-bowel dysfunction, opioid induced constipation, ileus, including post-operative ileus, post-partum ileus and opioid-induced ileus, colitis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, distension, abdominal or epigastric pain and discomfort, non-ulcerogenic dyspepsia, gastritis, constipation, or delayed absorption of orally administered medications or nutritive substances.

* * * * *